(12) United States Patent
Kimura et al.

(10) Patent No.: US 7,935,815 B2
(45) Date of Patent: May 3, 2011

(54) IMIDAZOYL PYRIDINE COMPOUNDS AND SALTS THEREOF

(75) Inventors: Teiji Kimura, Tsukuba (JP); Noritaka Kitazawa, Tsukuba (JP); Toshihiko Kaneko, Tsukuba (JP); Nobuaki Sato, Tsukuba (JP); Koki Kawano, Tsukuba (JP); Koichi Ito, Tsukuba (JP); Mamoru Takaishi, Tsukuba (JP); Takeo Sasaki, Tsukuba (JP); Yu Yoshida, Tsukuba (JP); Toshiyuki Uemura, Tsukuba (JP); Takashi Doko, Tsukuba (JP); Daisuke Shinmyo, Tsukuba (JP); Daiju Hasegawa, Tsukuba (JP); Takehiko Miyagawa, London (GB); Hiroaki Hagiwara, Tsukuba (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 12/200,731

(22) Filed: Aug. 28, 2008

(65) Prior Publication Data

US 2009/0062529 A1    Mar. 5, 2009

Related U.S. Application Data

(60) Provisional application No. 60/935,824, filed on Aug. 31, 2007, provisional application No. 61/025,099, filed on Jan. 31, 2008, provisional application No. 61/051,751, filed on May 9, 2008.

(51) Int. Cl.
| | |
|---|---|
| *C07D 491/00* | (2006.01) |
| *C07D 513/00* | (2006.01) |
| *C07D 515/00* | (2006.01) |
| *C07D 265/36* | (2006.01) |
| *C07D 498/02* | (2006.01) |
| *C07D 487/00* | (2006.01) |
| *C07D 513/02* | (2006.01) |
| *C07D 515/02* | (2006.01) |
| *C07D 401/00* | (2006.01) |

(52) U.S. Cl. ........ 540/568; 544/105; 544/281; 546/119; 546/272.4

(58) Field of Classification Search .................. None
See application file for complete search history.

(56) References Cited

U.S. PATENT DOCUMENTS

| | | | |
|---|---|---|---|
| 3,470,167 A | 9/1969 | Sarkar | |
| 3,989,816 A | 11/1976 | Rajadhyaksha | |
| 4,910,200 A | 3/1990 | Curtze et al. | |
| 5,281,626 A | 1/1994 | Oinuma et al. | |
| 5,563,162 A | 10/1996 | Oku et al. | |
| 5,804,577 A | 9/1998 | Hebeisen et al. | |
| 5,985,856 A | 11/1999 | Stella et al. | |
| 6,235,728 B1 | 5/2001 | Golik et al. | |
| 6,306,870 B1 | 10/2001 | Bombrun et al. | |
| 7,053,087 B1 | 5/2006 | Beatch et al. | |
| 7,138,414 B2 | 11/2006 | Schoenafinger et al. | |
| 7,300,936 B2 | 11/2007 | Parker et al. | |
| 7,314,940 B2 | 1/2008 | Graczyk et al. | |
| 7,618,960 B2 | 11/2009 | Kimura et al. | |
| 7,667,041 B2 | 2/2010 | Kimura et al. | |
| 2001/0051642 A1 | 12/2001 | Ahn | |
| 2002/0128263 A1 | 9/2002 | Mutel et al. | |
| 2002/0183324 A1 | 12/2002 | Jacobson et al. | |
| 2003/0195201 A1 | 10/2003 | Bo et al. | |
| 2003/0208082 A1 | 11/2003 | Mutel et al. | |
| 2003/0225070 A1 | 12/2003 | Mutel et al. | |
| 2004/0006062 A1 | 1/2004 | Smallheer et al. | |
| 2004/0034096 A1 | 2/2004 | Jolidon et al. | |
| 2004/0038969 A1 | 2/2004 | Doherty et al. | |
| 2004/0063770 A1 | 4/2004 | Ahn et al. | |
| 2004/0087798 A1 | 5/2004 | Yamada | |
| 2004/0127494 A1 | 7/2004 | Parker et al. | |
| 2004/0127555 A1 | 7/2004 | Snow et al. | |
| 2004/0152743 A1 | 8/2004 | Schoenafinger et al. | |
| 2004/0192743 A1 | 9/2004 | Mjalli et al. | |
| 2004/0235864 A1 | 11/2004 | Graczyk et al. | |
| 2005/0070538 A1 | 3/2005 | Cheng et al. | |
| 2005/0131043 A1 | 6/2005 | Mutel et al. | |
| 2005/0187277 A1 | 8/2005 | Mjalli et al. | |

(Continued)

FOREIGN PATENT DOCUMENTS

DE    3541716 A1    5/1987

(Continued)

OTHER PUBLICATIONS

Official Action dated Jul. 4, 2008, which issued in corresponding Russian Patent Application No. 2006146070.
Official Action issued on Nov. 14, 2008, in corresponding Russian Patent Application No. 2006146070.
T. A. Comery, The Journal of Neuroscience, Sep. 28, 2005, 25(39): 8898-8902.
T. A. Comery et al., Society for Neuroscience Annual Meeting (2003), Abstracts, Program No. 525.21.
J. G. Varnes et al., Bioorganic & Medicinal Chemistry Letters, 14 (2004) 1645-1649.

(Continued)

*Primary Examiner* — James O Wilson
*Assistant Examiner* — Jeffrey H Murray
(74) *Attorney, Agent, or Firm* — Birch, Stewart, Kolasch & Birch, LLP

(57) ABSTRACT

A compound represented by the formula (I):

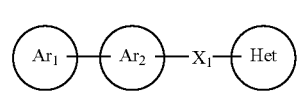

or a pharmacologically acceptable salt thereof, wherein $Ar_1$ represents an imidazolyl group or the like which may be substituted with a C1-6 alkyl group, $Ar_2$ represents a phenyl group or the like which may be substituted with a C1-6 alkoxy group, $X_1$ represents a double bond or the like and Het represents a triazolyl group or the like which may be substituted with a C1-6 alkyl group or the like, is effective as a therapeutic or prophylactic agent for a disease caused by Aβ.

7 Claims, No Drawings

U.S. PATENT DOCUMENTS

| | | | |
|---|---|---|---|
| 2006/0004013 A1 | 1/2006 | Kimura et al. | |
| 2007/0117798 A1 | 5/2007 | Kimura et al. | |
| 2007/0117839 A1 | 5/2007 | Kimura et al. | |
| 2007/0219181 A1* | 9/2007 | Kimura et al. | 514/211.09 |
| 2007/0249833 A1 | 10/2007 | Cheng et al. | |
| 2008/0070902 A1 | 3/2008 | Kimura et al. | |
| 2008/0085894 A1 | 4/2008 | Parker et al. | |
| 2008/0096892 A1 | 4/2008 | Cheng et al. | |
| 2008/0280948 A1 | 11/2008 | Baumann et al. | |
| 2009/0048213 A1 | 2/2009 | Kimura et al. | |
| 2009/0048448 A1 | 2/2009 | Kushida et al. | |
| 2009/0203916 A1 | 8/2009 | Kushida et al. | |
| 2009/0270623 A1 | 10/2009 | Shimomura et al. | |

FOREIGN PATENT DOCUMENTS

| | | |
|---|---|---|
| EP | 0219756 | 4/1987 |
| EP | 1 264 820 | 12/2002 |
| EP | 0 973 768 B1 | 7/2003 |
| EP | 1 757 591 A1 | 2/2007 |
| EP | 1808432 A | 7/2007 |
| EP | 1 953 151 A1 | 8/2008 |
| EP | 1 953 158 A1 | 8/2008 |
| GE | P 2006 3920 B | 5/2006 |
| GE | P-20084571 B | 12/2008 |
| JP | 52-1035 | 1/1977 |
| JP | 3-206042 A | 9/1991 |
| JP | 8283219 A | 10/1996 |
| JP | 9-132578 A | 5/1997 |
| JP | 10-510512 A | 10/1998 |
| JP | 11-228548 A | 8/1999 |
| JP | 3176365 B2 | 4/2001 |
| JP | 2001-508767 A | 7/2001 |
| JP | 2001-527083 A | 12/2001 |
| JP | 2003-206280 A | 7/2003 |
| JP | 11-513686 A | 9/2003 |
| JP | 2004-520292 A | 7/2004 |
| JP | 2004-531519 A | 10/2004 |
| JP | 2004-536084 A | 12/2004 |
| JP | 2005-518371 A | 6/2005 |
| JP | 2005-526807 A | 9/2005 |
| JP | 2005-531596 A | 10/2005 |
| JP | 2005-533092 A | 11/2005 |
| JP | 7-2780 A | 12/2005 |
| JP | 2006-502247 A | 1/2006 |
| JP | 2006-518738 A | 8/2006 |
| JP | 2007-504282 T | 3/2007 |
| JP | 2007-523903 A | 8/2007 |
| RU | 2001126135 A | 7/2003 |
| WO | WO-91/12237 A1 | 8/1991 |
| WO | WO 95/21832 A1 | 8/1995 |
| WO | WO-96/10559 A1 | 4/1996 |
| WO | WO 97/14417 A1 | 4/1997 |
| WO | WO-97/43287 | 11/1997 |
| WO | WO-98/03166 A1 | 1/1998 |
| WO | WO 98/09963 A1 | 3/1998 |
| WO | WO-98-24785 A1 | 6/1998 |
| WO | WO 99/55693 A2 | 11/1999 |
| WO | WO-00/07993 A1 | 2/2000 |
| WO | WO-00/50391 A1 | 8/2000 |
| WO | WO-00/51981 A1 | 9/2000 |
| WO | WO-01/68585 A1 | 9/2001 |
| WO | WO-01/81312 A2 | 11/2001 |
| WO | WO 03/022273 A1 | 3/2003 |
| WO | WO 03/027081 A2 | 4/2003 |
| WO | WO-03-053912 A1 | 7/2003 |
| WO | WO 03/062206 A2 | 7/2003 |
| WO | WO 03/074497 A1 | 9/2003 |
| WO | WO-03/082292 A1 | 10/2003 |
| WO | WO-03/101927 A1 | 12/2003 |
| WO | 2004/002478 A1 | 1/2004 |
| WO | WO-2004/007429 | 1/2004 |
| WO | WO-2004/007455 A1 | 1/2004 |
| WO | WO 2004/041776 A2 | 5/2004 |
| WO | WO 2004/089868 A1 | 10/2004 |
| WO | WO-2005/020921 A2 | 3/2005 |
| WO | WO-2005/063754 A1 | 7/2005 |
| WO | WO 2005/072731 A | 8/2005 |
| WO | WO 2005/087767 A1 | 9/2005 |
| WO | WO-2005/115990 A1 | 12/2005 |
| WO | WO 2006/018662 A2 | 2/2006 |
| WO | WO-2006/046575 A1 | 5/2006 |
| WO | WO-2006/112550 A2 | 10/2006 |
| WO | WO-2007/034282 A2 | 3/2007 |
| WO | WO-2007/060810 A1 | 5/2007 |
| WO | WO-2007/102580 A1 | 9/2007 |
| WO | WO2007102580 * | 9/2007 |
| WO | WO-2008/013213 A1 | 1/2008 |
| WO | WO-2008/097538 A1 | 8/2008 |
| WO | WO 2008/137102 A2 | 11/2008 |
| WO | WO-2008/137139 A1 | 11/2008 |
| WO | WO-2008/156580 A1 | 12/2008 |
| WO | WO-2009/020580 A1 | 2/2009 |

OTHER PUBLICATIONS

H. Stark et al., Pharmazie 52 (1997), vol. 6, pp. 419-423.
M. Kajbaf et al., Journal of Chromatography, 575 (1992) 75-85.
S. L. Marcus, Cancer Research, 45, 112-115, Jan. 1995.
H. L. Yale, J. Med. Chem., 1966, 9(1), 42-46.
Yuesong Gong et al.; Proceeding National Academy of Science, vol. 100, No. 18, pp. 10417-10422, Sep. 2, 2003.
Christoph Hock et al.; Neuron, vol. 38, No. 4, pp. 547-554, May 22, 2003.
Joseph T. Jarrett et al.; Biochemistry; vol. 32, No. 18, pp. 4693-4697, May 11, 1993.
George G. Glenner et al.; Biochemical and Biophysical Research Communications; vol. 120, No. 3, pp. 885-890, May 16, 1984.
Colin L. Masters et al.; Proceeding National Academy of Science; vol. 82, No. 12, pp. 4245-4249, Jun. 1985.
Gunnar K. Gouras et al.; American Journal of Pathology, vol. 156, No. 1, pp. 15-20, Jan. 2000.
D. Scheuner et al.; Nature Medicine, vol. 2, No. 8, pp. 864-870, Aug. 1996.
Mark S. Forman et al.; The Journal of Biological Chemistry; vol. 272, No. 51, pp. 32247-32253, Dec. 19, 1997.
Mark S. Shearman et al.; Biochemistry; vol. 39, No. 30, pp. 8698-8704, 2000.
Huw D. Lewis et al.; Biochemistry, vol. 42, No. 24, pp. 7580-7586, 2003.
Thomas A. Lanz et al., The Journal of Pharmacology and Experimental Therapeutics; vol. 39, No. 1, pp. 49-55, 2004.
Gwendolyn T. Wong et al.; The Journal of Biological Chemistry, vol. 279, No. 13, pp. 12876-12882, Mar. 26, 2004.
John P. Blass; Journal of Neuroscience Research, vol. 66, No. 1, pp. 851-856, 2001.
Genevieve Evin et al.; NeuroReport; vol. 13, No. 5, pp. 719-723, Apr. 16, 2002.
Osamu Yasuhara et al.; Neuroscience Letters, vol. 171, Nos. 1 and 2, pp. 63-66, 1994.
Jan T. Teller et al.; Nature Medicine, vol. 2, No. 1, pp. 93-95, Jan. 1996.
Takahiko Tokuda et al.; Annals Neurology, vol. 41, No. 2, pp. 271-273, Feb. 1997.
Yorihide Hayashi et al.; Brain Research; vol. 789, No. 2, pp. 307-314, 1998.
Helene Barelli et al.; Molecular Medicine, vol. 3, No. 10, pp. 695-707, Oct. 1997.
Michael E. Calhoun et al.; Proceeding National Academy of Science, vol. 96, No. 24, pp. 14088-14093, Nov. 23, 1999.
B. Dermaut et al.; Brain, vol. 124, No. 12, pp. 2383-2392, 2001.
P. Cras et al.; Acta Neuropathol, vol. 96, No. 3, pp. 253-260, 1998.
Martin C. Herzig et al.; Nature Neuroscience, vol. 7, No. 9, pp. 954-960, Sep. 2004.
Sjoerd G. Van Duinen et al.; Proceeding National Academy of Science, vol. 84, No. 16, pp. 5991-5994, Aug. 1987.
Efrat Levy et al.; Science, vol. 248, No. 4959, pp. 1124-1126, 1990.
Simon M. Laws et al.; Neurobiology of Aging, vol. 23, No. 1, pp. 55-58, 2002.
E. Vaucher et al.; Experimental Neurology, vol. 175, No. 2, pp. 398-406, 2002.
Dave Morgan et al.; Nature, vol. 408, No. 6815, pp. 982-985, Dec. 2000.

Paula M. Moran et al.; Proceeding National Academy of Science, vol. 92, No. 12, pp. 5341-5345, 2002.
Milla Koistinaho et al.; Proceeding National Academy of Science, vol. 99, No. 3, pp. 1610-1615, Feb. 5, 2002.
Fangyi Zhang et al.; The Journal of Neuroscience, vol. 17, No. 20, pp. 7655-7661, Oct. 15, 2997.
Marcin Sadowski et al.; Neurochemical Research, vol. 29, No. 6, pp. 1257-1266, Jun. 2004.
S. O'Riordan et al.; Neurology, vol. 59, No. 7, pp. 1108-1110, Oct. 2002.
Jochen Gehrmann et al.; Glia; vol. 15, No. 2, pp. 141-151, 1995.
Wanda F. Reynolds et al.; Experimental Neurology, vol. 155, No. 1, pp. 31-41, 1999.
Douglas H. Smith et al.; NeuroMolecular Medicine, vol. 4, No. 1 and 2, pp. 59-72, 2003.
Miho Matsubara-Tsutsui et al.; American Journal of Medical Genetics, vol. 114, No. 3, pp. 292-298, 2002.
Marina D. Kirkitadze et al.; Journal of Neuroscience Research, vol. 69, No. 5, pp. 567-577, 2002.
Bernd O. Evert at al.; The Journal of Neuroscience, vol. 21, No. 15, pp. 5389-5396, Aug. 1, 2001.
D.M.A. Mann et al.; Neuroscience Letters, vol. 109, No. 1 and 2, pp. 68-75, 1990.
James Primavera et al.; Journal of Alzheimer's Disease, vol. 1, No. 3, pp. 183-193, 1999.
Benoit I. Giasson et al.; NeuroMolecular Medicine, vol. 4, No. 1 and 2, pp. 49-58, 2003.
Eliezer Masliah et al.; Proceeding National Academy of Science; vol. 98, No. 21, pp. 12245-12250, Oct. 9, 2001.
Marta Barrachina et al.; Neurochemistry International; vol. 46, No. 3, pp. 253-260, 2005.
M.L. Schmidt et al.; Acta Neuropathol, vol. 95, No. 2, pp. 117-122, 1998.
H. Ito et al.; Neuropathology and Applied Neurobiology, vol. 17, No. 5, pp. 365-373, 1991.
S.M. Rosso et al.; Annals of the New York Academy of Science, vol. 920, pp. 115-119, 2000.
M. Tolnay et al.; Neuropathology and Applied Neurobiology, vol. 25, No. 4, pp. 295-305, 1999.
Lee-Way Jin et al.; American Journal of Pathology, vol. 164, No. 3, pp. 975-985, Mar. 2004.
Shoichi Sasaki et al.; Acta Neuropathol, vol. 97, No. 5, pp. 463-468, 1999.
A. Tamaoka et al.; Journal of Neurology, vol. 247, No. 8, pp. 633-635, 2000.
Ronald L. Hamilton et al.; Acta Neuropathol, vol. 107, No. 6, pp. 515-522, 2004.
Bradley J. Turner et al.; Neurochemical Research, vol. 29, No. 12, pp. 2281-2286, 2004.
Roy O. Weller; Journal of Neuropathology and Experimental Neurology, vol. 57, No. 10, pp. 885-894, Oct. 1998.
Gerald D. Silverberg et al.; Lancet Neurology, vol. 2, No. 8, pp. 506-511, Aug. 2003.
Roy O. Weller et al.; Annals of the New York Academy of Science, vol. 903, pp. 110-117, 2000.
H. Y. Yow et al.; Neuropathology and Applied Neurobiology; vol. 28, p. 149, 2002.
Roy O. Weller et al.; Annals of the New York Academy of Science, vol. 977, pp. 162-168, 2002.
Margaret J. Smith et al.; Annals of Neurology, vol. 49, No. 1, pp. 125-129, 2001.
Richard Crook et al.; Nature Medicine, vol. 4, No. 4, pp. 452-455, Apr. 1998.
Craig S. Atwood, Brain Research Review; vol. 43, No. 1, pp. 164-178, 2003.
Jonathan D. Lowenson et al.; Trends in Cardiovascular Medicine, vol. 4, No. 1, pp. 3-8, 1994.
Andrew B. Singleton et al.; vol. 123, No. 12, pp. 2467-2474, 2000.
W.F. Gattaz et al.; Journal of Neural Transmission, vol. 111, No. 5, pp. 591-601, 2004.
A. Assini et al.; Neurology, vol. 63, No. 5, pp. 828-831, 2004.
Guido R. Y. DeMeyer et al.; Circulation Research, vol. 90, No. 11, pp. 1197-1204, 2002.
Masahiko Kato et al., Chem. Pharm. Bull., 42 (12), 2546-2555 (1994).
W. J. Ross et al., Journal of Medicinal Chemistry, 1973, vol. 16, No. 4, pp. 347-352.
D. C. Guiroy et al., Acta Neuropathol (1991) 82: 87-92.
Office Action dated Sep. 16, 2008, that issued in connection with copending U.S. Appl. No. 11/594,150.
Office Action dated Jul. 11, 2008, that issued in connection with copending U.S. Appl. No. 11/136,355.
S. M. Catalano et al., "The Role of Amyloid-Beta Derived Diffusible Ligands (ADDLs) in Alzheimer's Disease," Current Topics in Medicinal Chemistry, vol. 6, 597-608 (2006).
Search Report issued May 27, 2009, in connection with Georgia Patent Application No. AP 2006 010709 (with English translation).
The International Search Report for International Appl. No. PCT/JP2008/053887, mailed Sep. 19, 2008.
An Office Action from Russian Patent Appl. No. 2008125426/04(030920), date Jun. 1, 2009.
An Office Action from U.S. Appl. No. 11/715,440, dated Jul. 16, 2009.
Office Action issued in Georgia Application No. 87447 on Oct. 1, 2009 (with translation).
Official Action issued Jan. 22, 2010, in Peruvian Patent Application No. 001480-2006.
Office Action issued Jan. 19, 2010, in copending U.S. Appl. No. 11/596,723.
Brocchini et al., "Preparation of piperazinedione-derivative inhibitors of plasminogen activator inhibitor," Database CA [Online] Chemical Abstracts Service, Columbus, Ohio, US, XP-002574973, retrieved from STN, Database accession No. 1995:994197, Abstract.
European Search Report dated Apr. 7, 2010 for corresponding Application No. 05743758.4.
European Search Report issued Aug. 4, 2010 in European Patent Application No. 06822806.3.
Extended European Search Report, dated Jan. 26, 2011, for European Application No. 07743622.8.
US Office Action, dated Feb. 15, 2011, for U.S. Appl. No. 12/301,421.
Chinese Office Action, dated Nov. 16, 2010, for Chinese Application No. 200780008382.0.
Chinese Office Action, dated Sep. 27, 2010, for Chinese Application No. 200780018255.9.
Extended European Search Report, dated Dec. 7, 2010, for European Application No. 07743623.6.
Chen et al., "Preparation of cyclosporine A nanoparticles by evaporative precipitation into aqueous solution," International Journal of Pharmaceutics, 242 (2002) 3-14.
Database Crossfire Beilstein, Beilstein Institut Zur Foerderung Der Chemischen Wissenschaften, Frankfurt Am Main, DE, XP-002574972, Database accession No. 4617764, Abstract, Jan. 2010.
European Search Report issued Oct. 13, 2010, in corresponding European Patent Application No. 07738023.6.
Lieberman et al., Tablets, Second Edition, Bioavailability in Tablet Technology, vol. 2, pp. 462-465 (1990).
Lipinski, Pharmaceutical Profiling in Drug Discovery for Lead Selection, pp. 93-125 (2004).
Office Action issued Apr. 11, 2008, in Pakistan Patent Application No. 1435/2006.
Office Action issued Feb. 11, 2009, in Singapore Patent Application No. 0803266-6.
Office Action issued Feb. 24, 2009, in Singapore Patent Application No. 0803192-4.
Office Action issued Mar. 12, 2010, in EA Patent Application No. 200870336/28.
Office Action issued Sep. 28, 2007, in Japanese Patent Application No. JP2006-513906.
Ono et al., "Synthesis and biological evaluation of (E)-3-styrylpyridine derivatives as amyloid imaging agents for Alzheimer's disease," Nuclear Medicine and Biology, 32 (2005) 329-335.
Ono et al., "Synthesis and biological evaluation of (E)-3-styrylpyridine derivatives as amyloid imaging agents for Alzheimer's disease," Nuclear Medicine and Biology, 32 (2005) 329-335.
Tietze et al., Detailed Organic Synthesis, Jan. 15, 1995, pp. 196-199.
Zyhuang et al., Structure-Activity Relationship of Imidazo[1,2-a]pyridines as Ligands for Detecting Beta-amyloid Plaques in the Brain, J. Med. Chem. (2003) 46, 237-243.

* cited by examiner

IMIDAZOYL PYRIDINE COMPOUNDS AND SALTS THEREOF

RELATED APPLICATIONS

The present application claims priority from U.S. provisional application Ser. No. 60/935,824 filed on Aug. 31, 2007, U.S. provisional application Ser. No. 61/025,099 filed on Jan. 31, 2008 and U.S. provisional application Ser. No. 61/051,751 filed on May 9, 2008, all of the contents of which are incorporated herein by reference.

BACKGROUND OF THE INVENTION

1. Filed of the Invention

The present invention relates to a pharmaceutical, more particularly, to a multi-cyclic cinnamide derivative effective for treatment of a neurodegenerative disease caused by amyloid-β (hereinafter referred to as Aβ) such as Alzheimer's disease or Down's syndrome and a medicine, in particular, a medicine for prevention or treatment of a disease caused by Aβ comprising the derivative as an active ingredient.

2. Description of Related Art

Alzheimer's disease is a disease characterized by degeneration and loss of neurons as well as formation of senile plaques and neurofibrillary degeneration. Currently, Alzheimer's disease is treated only with symptomatic treatment using a symptom improving agent typified by an acetylcholinesterase inhibitor, and a fundamental remedy to inhibit progression of the disease has not yet been developed. It is necessary to develop a method for controlling the cause of the onset of pathology in order to create a fundamental remedy for Alzheimer's disease.

It is assumed that Aβ-proteins as metabolites of amyloid precursor proteins (hereinafter referred to as APP) are highly involved in degeneration and loss of neurons and onset of symptoms of dementia (see Non-Patent Documents 1 and 2, for example). Main molecular species of Aβ-protein are Aβ40 consisting of 40 amino acids and Aβ42 with two amino acids added at the C-terminal. The Aβ40 and Aβ42 are known to have high aggregability (see Non-Patent Document 3, for example) and to be main components of senile plaques (see Non-Patent Documents 3, 4 and 5, for example). Further, it is known that the Aβ40 and Aβ42 are increased by mutation in APP and presenilin genes which is observed in familial Alzheimer's disease (see Non-Patent Documents 6, 7 and 8, for example). Accordingly, a compound that reduces production of Aβ40 and Aβ42 is expected as a progression inhibitor or prophylactic agent for Alzheimer's disease.

Aβ is produced by cleaving APP by β-secretase and subsequently by γ-secretase. For this reason, attempts have been made to create γ-secretase and β-secretase inhibitors in order to reduce Aβ production. Many of these secretase inhibitors already known are, for example, peptides and peptide mimetics such as L-685,458 (see Non-Patent Document 9, for example), LY-411,575 (see Non-Patent Documents 10, 11 and 12, for example) and LY-450,139 (see Non-Patent Documents 13, 14 and 15). Nonpeptidic compounds are, for example, MRK-560 (see Non-Patent Documents 16 and 17) and compounds having a plurality of aromatic rings as disclosed in Patent Document 1. However, the compound represented by the formula (VI) as disclosed in page 17 of the specification differs from the compound of the present invention in that the compound is limited to a compound having a 2-aminothiazolyl group as a main structure.

[Non-Patent Document 1] Klein W L, and seven others, Alzheimer's disease-affected brain: Presence of oligomeric Aβ ligands (ADDLs) suggests a molecular basis for reversible memory loss, Proceeding of the National Academy of Science USA, Sep. 2, 2003; 100(18), p. 10417-10422.

[Non-Patent Document 2] Nitsch R M, and sixteen others, Antibodies against β-amyloid slow cognitive decline in Alzheimer's disease, Neuron, May 22, 2003; 38, p. 547-554.

[Non-Patent Document 3] Jarrett J T, and two others, The carboxy terminus of the β amyloid protein is critical for the seeding of amyloid formation: Implications for the pathogenesis of Alzheimers' disease, Biochemistry, 1993, 32(18), p. 4693-4697.

[Non-Patent Document 4] Glenner G G, and one other, Alzheimer's disease: initial report of the purification and characterization of a novel cerebrovascular amyloid protein, Biochemical and Biophysical Research Communications, May 16, 1984, 120(3), p. 885-890.

[Non-Patent Document 5] Masters C L, and five others, Amyloid plaque core protein in Alzheimer disease and Down syndrome, Proceeding of the National Academy of Science USA, June, 1985, 82(12), p. 4245-4249.

[Non-Patent Document 6] Gouras G K, and eleven others, Intraneuronal Aβ42 accumulation in human brain, American Journal of Pathology, January, 2000, 156(1), p. 15-20.

[Non-Patent Document 7] Scheuner D, and twenty others, Secreted amyloid β-protein similar to that in the senile plaques of Alzheimer's disease is increased in vivo by the presenilin 1 and 2 and APP mutations linked to familial Alzheimer's disease, Nature Medicine, August, 1996, 2(8), p. 864-870.

[Non-Patent Document 8] Forman M S, and four others, Differential effects of the swedish mutant amyloid precursor protein on β-amyloid accumulation and secretion in neurons and nonneuronal cells, The Journal of Biological Chemistry, Dec. 19, 1997, 272(51), p. 32247-32253.

[Non-Patent Document 9] Shearman M S, and nine others, L-685, 458, an Aspartyl Protease Transition State Mimic, Is a Potent Inhibitor of Amyloid β-Protein Precursor γ-Secretase Activity, Biochemistry, Aug. 1, 2000, 39(30), p. 8698-8704.

[Non-Patent Document 10] Shearman M S, and six others, Catalytic Site-Directed γ-Secretase Complex Inhibitors Do Not Discriminate Pharmacologically between Notch S3 and β-APP Clevages, Biochemistry, Jun. 24, 2003, 42(24), p. 7580-7586.

[Non-Patent Document 11] Lanz T A, and three others, Studies of Aβ pharmacodynamics in the brain, cerebrospinal fluid, and plasma in young (plaque-free) Tg2576 mice using the γ-secretase inhibitor N2-[(2S)-2-(3,5-difluorophenyl)-2-hydroxyethanoyl]-N1-[(7S)-5-methyl-6-oxo-6,7-dihydro-5H-dibenzo[b,d]azepin-7-yl]-L-alaninamide (LY-411575), The Journal of Pharmacology and Experimental Therapeutics, April, 2004, 309(1), p. 49-55.

[Non-Patent Document 12] Wong G T, and twelve others, Chronic treatment with the γ-secretase inhibitor LY-411, 575 inhibits β-amyloid peptide production and alters lymphopoiesis and intestinal cell differentiation, The Journal of Biological Chemistry, Mar. 26, 2004, 279(13), p. 12876-12882.

[Non-Patent Document 13] Gitter B D, and ten others, Stereoselective inhibition of amyloid beta peptide secretion by LY450139, a novel functional gamma secretase inhibitor, Neurology of Aging 2004, 25, sup2, p. 571.

[Non-Patent Document 14] Lanz T A, and eighteen others, Concentration-dependent modulation of amyloid-β in vivo and in vitro using the γ-secretase inhibitor, LY-450139, The Journal of Pharmacology and Experimantal Therapeutics, November, 2006, 319(2) p. 924-933.

[Non-Patent Document 15] Siemers E R, and thirteen others, Effects of a γ-secretase inhibitor in a randomized study of patients with Alzheimer disease, Neurology, 2006, 66, p. 602-604.

[Non-Patent Document 16] Best J D, and nine others, In vivo characterization of Aβ (40) changes in brain and cerebrospinal fluid using the novel γ-secretase inhibitor N-[cis-4-[(4-chlorophenyl)sulfonyl]-4-(2,5-difluorophenyl)cyclohexyl]-1,1,1-trifluoromethanesulphonamide (MK-560) in the rat, The Journal of Pharmacology and Experimantal Therapeutics, May, 2006, 317(2) p. 786-790.

[Non-Patent Document 17] Best J D, and thirteen others The novel γ-secretase inhibitor N-[cis-4-[(4-chlorophenyl)sulfonyl]-4-(2,5-difluorophenyl)cyclohexyl]-1,1,1-trifluoromethanesulphonlamide (MK-560) reduces amylid plaque deposition without evidence notch-related pathology in the Tg2576 mouse, The Journal of Pharmacology and Experimantal Therapeutics, February, 2007, 320(2) p. 552-558.

[Patent Document 1] WO 2004/110350

BRIEF SUMMARY OF THE INVENTION

As described above, a compound that inhibits production of Aβ40 and Aβ42 from APP has been expected as a therapeutic or prophylactic agent for a disease caused by Aβ which is typified by Alzheimer's disease. However, a nonpeptidic compound having high efficacy which inhibits production of Aβ40 and Aβ42 has not yet been known. Accordingly, there is a need for a novel low-molecular-weight compound that inhibits production of Aβ40 and Aβ42.

As a result of extensive studies, the present inventors have found a nonpeptidic multi-cyclic compound that inhibits production of Aβ40 and Aβ42 from APP and thus found a prophylactic or therapeutic agent for a disease caused by Aβ which is typified by Alzheimer's disease. This finding has led to the accomplishment of the present invention.

Specifically, the present invention relates to the following 1) to 19):

1) A compound represented by the formula (I):

[Formula 1]

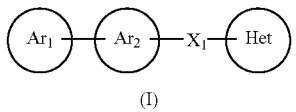

(I)

or a pharmacologically acceptable salt thereof, wherein $Ar_1$ represents an imidazolyl group which may be substituted with a C1-6 alkyl group, $Ar_2$ represents a phenyl group or a pyridinyl group, which may be substituted with 1 to 3 substituents selected from the group consisting of (1) a hydrogen atom, (2) a halogen atom, (3) a hydroxyl group and (4) a C1-6 alkoxy group, $X_1$ represents $-CR^1=CR^2-$ (wherein $R^1$ and $R^2$ are the same or different and each represent (1) a hydrogen atom, (2) a C1-6 alkyl group or (3) a halogen atom) and Het is monovalent or divalent and represents (1) a 5-membered aromatic heterocyclic group, (2) a 5-membered aromatic heterocyclic group condensed with a 6- to 14-membered non-aromatic hydrocarbon ring group or (3) a 5-membered aromatic heterocyclic group condensed with a 5- to 14-membered non-aromatic heterocyclic group, which may be substituted with 1 to 3 substituents selected from the following Substituent Group A1

[Substituent Group A1: (1) a hydrogen atom, (2) a halogen atom, (3) a hydroxyl group, (4) a cyano group, (5) a nitro group, (6) a C3-8 cycloalkyl group which may be substituted with 1 to 3 substituents selected from Substituent Group A2, (7) a C2-6 alkenyl group which may be substituted with 1 to 3 substituents selected from Substituent Group A2, (8) a C2-6 alkynyl group which may be substituted with 1 to 3 substituents selected from Substituent Group A2, (9) a C3-8 cycloalkoxy group, (10) a C3-8 cycloalkylthio group, (11) a formyl group, (12) a C1-6 alkylcarbonyl group which may be substituted with 1 to 3 substituents selected from Substituent Group A2, (13) a C1-6 alkylthio group which may be substituted with 1 to 3 substituents selected from Substituent Group A2, (14) a C1-6 alkylsulfinyl group which may be substituted with 1 to 3 substituents selected from Substituent Group A2, (15) a C1-6 alkylsulfonyl group which may be substituted with 1 to 3 substituents selected from Substituent Group A2, (16) a hydroxyimino group, (17) a C1-6 alkoxyimino group, (18) a C1-6 alkyl group which may be substituted with 1 to 3 substituents selected from Substituent Group A2, (19) a C1-6 alkoxy group which may be substituted with 1 to 3 substituents selected from Substituent Group A2, (20) an amino group which may be substituted with 1 or 2 substituents selected from Substituent Group A2, (21) a carbamoyl group which may be substituted with 1 or 2 substituents selected from Substituent Group A2, (22) a 6- to 14-membered aromatic hydrocarbon ring group which may be substituted with 1 to 3 substituents selected from Substituent Group A2, (23) a 5- to 14-membered aromatic heterocyclic group which may be substituted with 1 to 3 substituents selected from Substituent Group A2, (24) a 6- to 14-membered non-aromatic hydrocarbon ring group which may be substituted with 1 to 3 substituents selected from Substituent Group A2, (25) a 5- to 14-membered non-aromatic heterocyclic group which may be substituted with 1 to 3 substituents selected from Substituent Group A2, (26) a C2-6 alkenyloxy group, (27) a C2-6 alkynyloxy group, (28) a C3-8 cycloalkylsulfinyl group, (29) a C3-8 cycloalkylsulfonyl group, (30) —X-A (wherein X represents an imino group, —O— or —S— and A represents a 6- to 14-membered aromatic hydrocarbon ring group or a 5- to 14-membered aromatic heterocyclic group which may be substituted with 1 to 3 substituents selected from Substituent Group A2), (31) —CO-A (wherein A is as defined above), (32) =CH-A (wherein A is as defined above), (33) a carboxyl group, (34) a C1-6 alkoxycarbonyl group and (35) an azido group; Substituent Group A2: (1) a hydrogen atom, (2) a halogen atom, (3) a hydroxyl group, (4) a cyano group, (5) a nitro group, (6) a C3-8 cycloalkyl group, (7) a C2-6 alkenyl group, (8) a C2-6 alkynyl group, (9) a C3-8 cycloalkoxy group, (10) a C3-8 cycloalkylthio group, (11) a formyl group, (12) a C1-6 alkylcarbonyl group, (13) a C1-6 alkylthio group, (14) a C1-6 alkylsulfinyl group, (15) a C1-6 alkylsulfonyl group, (16) a hydroxyimino group, (17) a C1-6 alkoxyimino group, (18) a C1-6 alkyl group (wherein the C1-6 alkyl group may be substituted with 1 to 3 substituents selected from the group consisting of a halogen atom, a hydroxyl group, a C1-6 alkoxy group, a phenyl group which may be substituted with 1 to 3 halogen atoms and a pyridinyl group which may be substituted with 1 to 3 halogen atoms), (19) a C1-6 alkoxy group (wherein the C1-6 alkoxy group may be substituted with 1 to 3 substituents selected from the group consisting of a halogen atom, a hydroxyl group, a C1-6 alkoxy group, a phenyl group which may be substituted with 1 to 3 halogen atoms and a pyridinyl group which may be substituted with 1 to 3 halogen atoms), (20) an amino group which may be substituted with 1 or 2 C1-6 alkyl groups or C1-6 alkylcarbonyl groups, (21) a carbamoyl group which may be substituted with 1 or 2 C1-6 alkyl groups, (22) a 6- to 14-membered aromatic hydrocarbon ring group, (23) a 5- to 14-membered aromatic heterocyclic group, (24) a 6- to 14-membered non-aromatic hydrocarbon ring group, (25) a 5- to 14-membered non-aromatic heterocyclic group, (26) a C2-6 alkenyloxy group, (27) a C2-6 alkynyloxy group, (28) a C3-8 cycloalkylsulfinyl group, (29) a C3-8 cycloalkylsulfonyl group, (30) —X-A' (wherein X represents an imino group, —O—, —S— or —SO$_2$— and A' represents a 6- to 14-membered aromatic hydrocarbon ring group or a 5- to 14-membered aromatic heterocyclic group which may be substituted with 1 to 3 halogen atoms), (31) —CO-A' (wherein A' is as defined above) and (32) =CH-A' (wherein A' is as defined above)];

2) The compound or pharmacologically acceptable salt thereof according to 1) above, wherein the compound is represented by the formula (I-1), (I-2) or (I-3):

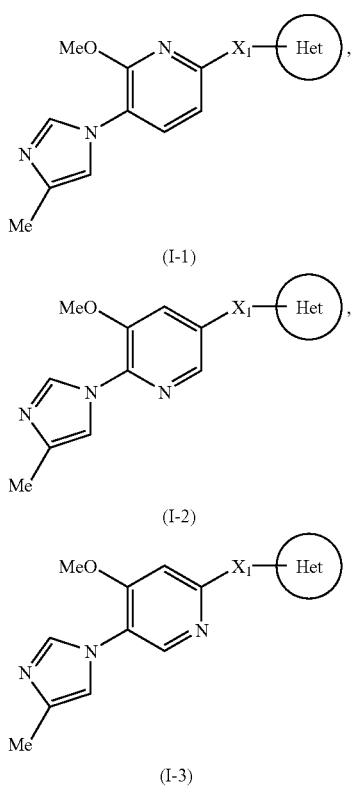

wherein $X_1$ and Het are as defined above;

3) The compound or pharmacologically acceptable salt thereof according to 1) above, wherein the compound is represented by the formula (I-1) or (I-3);

4) The compound or pharmacologically acceptable salt thereof according to 1) above, wherein the compound is represented by the formula (I-1);

5) The compound or pharmacologically acceptable salt thereof according to 1) above, wherein $X_1$ represents —CR$^1$=CR$^2$— (wherein R$^1$ and R$^2$ are the same or different and each represent a hydrogen atom or a fluorine atom;

6) The compound or pharmacologically acceptable salt thereof according to 1) above, wherein $X_1$ represents —CH=CH—;

7) The compound or pharmacologically acceptable salt thereof according to 1) above, wherein Het represents a triazolyl group which may be substituted with 1 or 2 substituents selected from Substituent Group A1;

8) The compound or pharmacologically acceptable salt thereof according to 1) above, wherein Het represents a group which may be substituted with 1 to 3 substituents selected from Substituent Group A1 and is represented by the following formula:

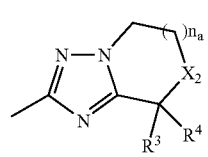

[Formula 3]

wherein R$^3$ and R$^4$ are the same or different and each represent a substituent selected from Substituent Group A1, or R$^3$ and R$^4$ are taken together with a carbon atom to which they are bonded to form =CH-A (wherein A represents a 6- to 14-membered aromatic hydrocarbon ring group or a 5- to 14-membered aromatic heterocyclic group which may be substituted with 1 to 3 substituents selected from Substituent Group A2), $X_2$ represents a methylene group which may be substituted with a substituent selected from Substituent Group A1, or an oxygen atom and $n_a$ represents an integer of 0 to 2;

9) The compound or pharmacologically acceptable salt thereof according to 1) above, wherein Het represents a group which may be substituted with 1 to 3 substituents selected from Substituent Group A1 and is represented by the following formula:

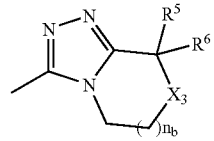

[Formula 4]

wherein R$^5$ and R$^6$ are the same or different and each represent a substituent selected from Substituent Group A1, $X_3$ represents a methylene group which may be substituted with a substituent selected from Substituent Group A1, or an oxygen atom and $n_b$ represents an integer of 0 to 2;

10) The compound or pharmacologically acceptable salt thereof according to 1) above, wherein Het represents a group which may be substituted with 1 to 3 substituents selected from Substituent Group A1 and is represented by the following formula:

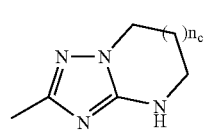

[Formula 5]

wherein $n_c$ represents an integer of 0 to 3;

11) The compound or pharmacologically acceptable salt thereof according to 6) above, wherein $n_c$ represents 0 or 2;
12) The compound or pharmacologically acceptable salt thereof according to 1) above, wherein Het represents a group which may be substituted with 1 to 3 substituents selected from Substituent Group A1 and is represented by the following formula:

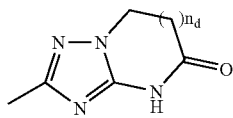

[Formula 6]

wherein $n_d$ represents an integer of 0 to 3;

13) The compound or pharmacologically acceptable salt thereof according to 1) above, wherein Het represents a group which may be substituted with 1 to 3 substituents selected from Substituent Group A1 and is represented by the following formulas:

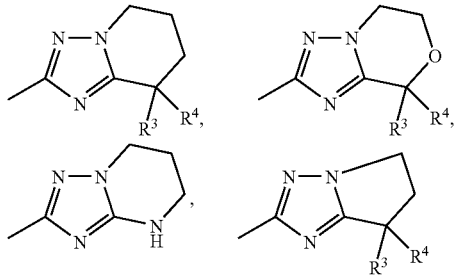

[Formula 7]

wherein $R^3$ and $R^4$ are as defined above;

The compound or pharmacologically acceptable salt thereof according to 1) above, wherein Substituent Group A1 is a group consisting of (1) a hydrogen atom, (2) a halogen atom, (3) a hydroxyl group, (4) a cyano group, (5) a C3-8 cycloalkyl group which may be substituted with 1 to 3 substituents selected from Substituent Group A2, (6) a C1-6 alkyl group which may be substituted with 1 to 3 substituents selected from Substituent Group A2, (7) a 6- to 14-membered aromatic hydrocarbon ring group which may be substituted with 1 to 3 substituents selected from Substituent Group A2, (8) a 5- to 14-membered aromatic heterocyclic group which may be substituted with 1 to 3 substituents selected from Substituent Group A2, (9) a 6- to 14-membered non-aromatic hydrocarbon ring group which may be substituted with 1 to 3 substituents selected from Substituent Group A2, (10) a 5- to 14-membered non-aromatic heterocyclic group which may be substituted with 1 to 3 substituents selected from Substituent Group A2, (11) —X-A (wherein X represents an imino group, —O— or —S— and A represents a 6- to 14-membered aromatic hydrocarbon ring group or a 5- to 14-membered aromatic heterocyclic group, which may be substituted with 1 to 3 substituents selected from Substituent Group A2), (12) =CH-A (wherein A represents a 6- to 14-membered aromatic hydrocarbon ring group or a 5- to 14-membered aromatic heterocyclic group, which may be substituted with 1 to 3 substituents selected from Substituent Group A2) and (13) an azido group;

The compound or pharmacologically acceptable salt thereof according to 1) above, wherein Substituent Group A2 is a group consisting of (1) a hydrogen atom, (2) a halogen atom, (3) a C1-6 alkyl group (wherein the C1-6 alkyl group may be substituted with 1 to 3 substituents selected from the group consisting of a halogen atom and a C1-6 alkoxy group) and (4) a C1-6 alkoxy group (wherein the C1-6 alkoxy group may be substituted with a halogen atom);

16) The compound or pharmacologically acceptable salt thereof according to 1) above, wherein the compound is selected from the following group:
1) (−)-8-(3-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine,
2) (−)-8-(4-isopropylphenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine,
3) (−)-8-(4-fluoro-2-methoxymethylphenyl)-2-{(E)-2-[3-methoxy-4-(4-methyl-1H-imidazol-1-yl)phenyl]vinyl}-5,6,7,8-tetrahydro-[1,2,4]triazolo[1,5-a]pyridine,
4) (−)-8-(2-fluorophenyl)-2-{(E)-2-[3-methoxy-4-(4-methyl-1H-imidazol-1-yl)phenyl]vinyl}-5,6,7,8-tetrahydro-[1,2,4]triazolo[1,5-a]pyridin-8-ol,
5) (+)-8-(3,5-difluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridin-8-ol,
6) 8-(4-fluorophenyl)-2-{(E)-2-[3-methoxy-4-(4-methyl-1H-imidazol-1-yl)phenyl]vinyl}-6-methyl-5,6,7,8-tetrahydro-[1,2,4]triazolo[1,5-a]pyridine,
7) 8-(4-fluorophenyl)-2-{(E)-2-[3-methoxy-4-(4-methyl-1H-imidazol-1-yl)phenyl]vinyl}-7-methyl-5,6,7,8-tetrahydro-[1,2,4]triazolo[1,5-a]pyridine,
8) (−)-2-{(E)-2-[3-methoxy-4-(4-methyl-1H-imidazol-1-yl)phenyl]vinyl}-7-phenyl-6,7-dihydro-5H-pyrrolo[1,2-b][1,2,4]triazole,
9) (−)-2-{(E)-2-[6-methoxy-5-(4-methyl-1H-imidazol-1-yl)pyridin-2-yl]vinyl}-8-(3,4,5-trifluorophenyl)-5,6,7,8-tetrahydro-[1,2,4]triazolo-[1,5-a]pyridine,
10) (−)-8-(3,4-difluorophenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine,
11) (−)-8-(4-fluorophenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine,
12) (−)-8-(3-chloro-4-fluorophenyl)-2-{(E)-2-[6-methoxy-5-(4-methyl-1H-imidazol-1-yl)pyridin-2-yl]vinyl}-5,6,7,8-tetrahydro[1,2,4]triazolo[1,5-a]pyridine,
13) (+)-8-(2,4,5-trifluorophenyl)-2-{(E)-2-[6-methoxy-5-(4-methyl-1H-imidazol-1-yl)pyridin-2-yl]vinyl}-5,6,7,8-tetrahydro[1,2,4]triazolo[1,5-a]pyridine,
14) (+)-8-(2,5-difluorophenyl)-2-{(E)-2-[6-methoxy-5-(4-methyl-1H-imidazol-1-yl)pyridin-2-yl]vinyl}-5,6,7,8-tetrahydro[1,2,4]triazolo[1,5-a]pyridine,
15) (−)-8-(2-bromo-4-fluorophenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine,
16) (−)-8-(2-chloro-4-fluorophenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine,
17) (+)-8-(3-fluorophenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine,
18) (−)-8-(2-chlorophenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine, 19) (−)-2-{(E)-2-[6-methoxy-5-(4-methyl-1H-imidazol-1-yl)pyridin-2-yl]vinyl}-8-(2-trifluoromethylphenyl)-5,6,7,8-tetrahydro-[1,2,4]triazolo[1,5-a]pyridine, 20) (+)-2-{(E)-2-[6-methoxy-5-(4-methyl-1H-imidazol-1-yl)pyridin-2-yl]vinyl}-8-(naphthalen-1-yl)-5,6,7,8-tetrahydro-[1,2,4]triazolo[1,5-a]pyridine, 21) (−)-2-{(E)-2-[6-methoxy-5-(4-methyl-1H-imidazol-1-yl)pyridin-2-yl]vinyl}-8-phenyl-5,6,7,8-tetrahydro-[1,2,4]triazolo[1,5-a]pyridine, 22) (−)-8-(4-chlorophenyl)-2-{(E)-2-[6-methoxy-5-(4-methyl-1H-imidazol-1-yl)pyridin-2-yl]vinyl}-8-phenyl-5,6,7,8-tetrahydro-[1,2,4]triazolo[1,5-a]pyridine, 23) (+)-8-(4-fluorophenyl)-2-{(E)-2-[5-methoxy-6-(4-methyl-1H-imidazol-1-yl)pyridin-3-yl]vinyl}-5,6,7,8-tetrahydro-[1,2,4]triazolo[1,5-a]pyridine, 24) (−)-8-(4-chlorophenyl)-2-{(E)-2-[5-methoxy-6-(4-methyl-1H-imidazol-1-yl)pyridin-3-yl]vinyl}-8-phenyl-5,6,7,8-tetrahydro-[1,2,4]triazolo[1,5-a]pyridine, 25) (+)-8-(3,4-difluorophenyl)-2-{(E)-2-[5-methoxy-6-(4-methyl-1H-imidazol-1-yl)pyridin-3-yl]vinyl}-5,6,7,8-tetrahydro-[1,2,4]triazolo[1,5-a]pyridine, 26) (−)-2-{(E)-2-[5-methoxy-6-(4-methyl-1H-imidazol-1-yl)pyridin-3-yl]vinyl}-8-(3,4,5-trifluorophenyl)-5,6,7,8-tetrahydro-[1,2,4]triazolo[1,5-a]pyridine-8-carbonitrile, 27) (−)-8-(4-chlorophenyl)-2-{(E)-2-[6-methoxy-5-(4-methyl-1H-imidazol-1-yl)pyridin-2-yl]vinyl}-5,6-dihydro-8H-[1,2,4]triazolo[5,1-c][1,4]oxazine, 28) (−)-8-(2,3-difluorophenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine, 29) (−)-8-(2-fluoro-3-methylphenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine, 30) (−)-8-(2-trifluoromethoxyphenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine, 31) (−)-8-(2-trifluoromethyl-4-fluorophenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine, 32) (−)-8-(2-difluoromethoxyphenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine, 33) (−)-8-(2-bromophenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine and 34) (−)-8-(3-fluoro-2-methylphenyl)-2-{(E)-2-[5-methoxy-6-(4-methyl-1H-imidazol-1-yl)pyridin-3-yl]vinyl}-8-(4-trifluoromethylphenyl)-5,6,7,8-tetrahydro-[1,2,4]triazolo[1,5-a]pyridine, 35) (−)-2-{(E)-2-[3-methoxy-4-(4-methyl-1H-imidazol-1-yl)phenyl]vinyl}-8-(2-trifluoromethylphenyl)-5,6,7,8-tetrahydro-[1,2,4]triazolo[1,5-a]pyridine, 36) (−)-2-{(E)-2-[3-methoxy-4-(4-methyl-1H-imidazol-1-yl)phenyl]vinyl}-7-(2-trifluoromethylphenyl)-6,7-dihydro-5H-pyrro[1,2-b][1,2,4]triazole, 37) (−)-8-(5-fluoro-2-trifluoromethylphenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine, 38) (5R,8S)-2-{(E)-2-[6-methoxy-5-(4-methyl-1H-imidazol-1-yl)pyridin-2-yl]vinyl}-5-methyl-8-(2-trifluoromethylphenyl)-5,6,7,8-tetrahydro-[1,2,4]triazolo[1,5-a]pyridine, 39) (S)-2-{(E)-2-[6-methoxy-5-(4-methyl-1H-imidazol-1-yl)pyridine-1-yl]vinyl}-7-(2-trifluoromethylphenyl)-6,7-dihydro-5H-pyrro[1,2-b][1,2,4]triazole, and 40) (S)-7-(5-fluoro-2-trifluoromethyphanyl)-2-{(E)-2-[6-methoxy-5-(4-methyl-1H-imidazol-1-yl)pyridine-1-yl]vinyl}-6,7-dihydro-5H-pyrro[1,2-b][1,2,4]triazole;

17) A medicine comprising the compound or pharmacologically acceptable salt thereof according to any of 1) to 16) above as an active ingredient;

18) The medicine according to 17) above for preventing or treating a disease caused by amyloid-β; and 19) The medicine according to 18) above, wherein the disease caused by amyloid-β is Alzheimer's disease, dementia, Down's syndrome or amyloidosis.

The compound of the general formula (I) or pharmacologically acceptable salt thereof according to the present invention and the prophylactic or therapeutic agent for a disease caused by Aβ according to the present invention are novel inventions that have not yet been described in any documents.

Meanings of symbols, terms and the like used in the present specification will be explained and the present invention will be described in detail below.

In the present specification, a structural formula of a compound may represent a certain isomer for convenience. However, the present invention includes all isomers and isomer mixtures such as geometric isomers which can be generated from the structure of a compound, optical isomers based on asymmetric carbon, stereoisomers and tautomers. The present invention is not limited to the description of a chemical formula for convenience and may include any one of the isomers or mixtures thereof. Accordingly, the compound of the present invention may have an asymmetric carbon atom in the molecule and exist as an optically active compound or racemate, and the present invention includes each of the optically active compound and the racemate without limitations. Although crystal polymorphs of the compound may be present, the compound is not limited thereto as well and may be present as a single crystal form or a mixture of single crystal forms. The compound may be an anhydride or hydrate.

The "disease caused by Aβ" refers to a wide variety of diseases such as Alzheimer's disease (see, for example, Klein W L, and seven others, Alzheimer's disease-affected brain: Presence of oligomeric Aβ ligands (ADDLs) suggests a molecular basis for reversible memory loss, Proceeding National Academy of Science USA, Sep. 2, 2003, 100(18), p. 10417-10422; Nitsch R M, and sixteen others, Antibodies against β-amyloid slow cognitive decline in Alzheimer's disease, Neuron, May 22, 2003, 38(4), p. 547-554: Jarrett J T, and two others, The carboxy terminus of the β amyloid protein is critical for the seeding of amyloid formation: Implications for the pathogenesis of Alzheimers' disease, Biochemistry, May 11, 1993, 32(18), p. 4693-4697; Glenner G G, and one other, Alzheimer's disease; initial report of the purification and characterization of a novel cerebrovascular amyloid protein, Biochemical and biophysical research communications, May 16, 1984, 120(3), p. 885-890; Masters C L, and six others, Amyloid plaque core protein in Alzheimer disease and Down syndrome, Proceeding National Academy of Science USA, June, 1985, 82(12), p. 4245-4249; Gouras G K, and eleven others, Intraneuronal Aβ42 accumulation in human brain, American journal of pathology, January, 2000, 156(1), p. 15-20; Scheuner D, and twenty others, Secreted amyloid β-protein similar to that in the senile plaques of Alzheimer's disease is increased in vivo by the presenilin 1 and 2 and APP mutations linked to familial Alzheimer's disease, Nature Medicine, August, 1996, 2(8), p. 864-870; Forman M S, and four others, Differential effects of the swedish mutant amyloid precursor protein on β-amyloid accumulation and secretion in neurons and nonneuronal cells, The journal of biological chemistry, Dec. 19, 1997, 272(51), p. 32247-32253), senile dementia (see, for example, Blass J P, Brain metabolism and brain disease: Is metabolic deficiency the proximate cause of Alzheimer dementia? Journal of Neuroscience Research, Dec. 1, 2001, 66(5), p. 851-856), frontotemporal dementia (see, for example, Evin G, and eleven others, Alternative transcripts of presenilin-1 associated with frontotemporal dementia, Neuroreport, Apr. 16, 2002, 13(5), p. 719-723), Pick's disease (see, for example, Yasuhara O, and three others, Accumulation of amyloid precursor protein in brain lesions of patients with Pick disease, Neuroscience Letters, Apr. 25, 1994, 171(1-2), p. 63-66), Down's syndrome (see, for example, Teller J K, and ten others, Presence of soluble amyloid β-peptide precedes amyloid plaque formation in Down's syndrome, Nature Medicine, January, 1996, 2(1), p. 93-95; Tokuda T, and six others, Plasma levels of amyloid β proteins Aβ1-40 and Aβ1-42(43) are elevated in Down's syndrome, Annals of Neurology, February, 1997, 41(2), p. 271-273), cerebral angiopathy (see, for example, Hayashi Y, and nine others, Evidence for presenilin-1 involvement in amyloid angiopathy in the Alzheimer's disease-affected brain, Brain Research, Apr. 13, 1998, 789(2), p. 307-314; Barelli H, and fifteen others, Characterization of new polyclonal antibodies specific for 40 and 42 amino acid-long amyloid β peptides: their use to examine the cell biology of presenilins and the immunohistochemistry of sporadic Alzheimer's disease and cerebral amyloid angiopathy cases, Molecular Medicine, October, 1997, 3(10), p. 695-707; Calhoun M E, and ten others, Neuronal overexpression of mutant amyloid precursor protein results in prominent deposition of cerebrovascular amyloid, Proceeding National Academy of Science USA, Nov. 23, 1999, 96(24), p. 14088-14093; Dermaut B, and ten others, Cerebral amyloid angiopathy is a pathogenic lesion in Alzheimer's Disease due to a novel presenilin-1 mutation, Brain, December, 2001, 124(12), p. 2383-2392), hereditary cerebral hemorrhage with amyloidosis (Dutch type) (see, for example, Cras P, and nine others, Presenile Alzheimer dementia characterized by amyloid angiopathy and large amyloid core type senile plaques in the APP 692Ala→Gly mutation, Acta Neuropathologica (Berl), September, 1998, 96(3), p. 253-260; Herzig M C, and fourteen others, Aβ is targeted to the vasculature in a mouse model of hereditary cerebral hemorrhage with amyloidosis, Nature Neuroscience, 2004, September, 7(9), p. 954-960; van Duinen S G, and five others, Hereditary cerebral hemorrhage with amyloidosis in patients of Dutch origin is related to Alzheimer disease, Proceeding National Academy of Science USA, August, 1987, 84(16), p. 5991-5994; Levy E, and eight others, Mutation of the Alzheimer's disease amyloid gene in hereditary cerebral hemorrhage, Dutch type, Science, Jun. 1, 1990, 248(4959), p. 1124-1126), cognitive impairment (see, for example, Laws S M, and seven others, Association between the presenilin-1 mutation Glu318Gly and complaints of memory impairment, Neurobiology of Aging, January-February, 2002, 23(1), p. 55-58), dysmnesia and learning disability (see, for example, Vaucher E, and five others, Object recognition memory and cholinergic parameters in mice expressing human presenilin 1 transgenes, Experimental Neurology, June 2002, 175(2), p. 398-406; Morgan D, and fourteen others, Aβ peptide vaccination prevents memory loss in an animal model of Alzheimer's disease, Nature, Dec. 21-28, 2000, 408(6815), p. 982-985; Moran P M, and three others, Age-related learning deficits in transgenic mice expressing the 751-amino acid isoform of human β-amyloid precursor protein, Proceeding National Academy of Science USA, Jun. 6, 1995, 92(12), p. 5341-5345), amyloidosis, cerebral ischemia (see, for example, Laws S M, and seven others, Association between the presenilin-1 mutation Glu318Gly and complaints of memory impairment, Neurobiology of Aging, January-February, 2002, 23(1), p. 55-58; Koistinaho M, and ten others, β-amyloid precursor protein transgenic mice that harbor diffuse Aβ deposits but do not form plaques show increased ischemic vulnerability: Role of inflammation, Proceeding National Academy of Science USA, Feb. 5, 2002, 99(3), p. 1610-1615; Zhang F, and four others, Increased susceptibility to ischemic brain damage in transgenic mice overexpressing the amyloid precursor protein, The journal of neuroscience, Oct. 15, 1997, 17(20), p. 7655-7661), vascular dementia (see, for example, Sadowski M, and six others, Links between the pathology of Alzheimer's disease and vascular dementia, Neurochemical Research, June, 2004, 29(6), p. 1257-1266), ophthalmoplegia (see, for example, O'Riordan S, and seven others, Presenilin-1 mutation (E280G), spastic paraparesis, and cranial MRI whitematter abnormalities, Neurology, Oct. 8, 2002, 59(7), p. 1108-1110), multiple sclerosis (see, for example, Gehrmann J, and four others, Amyloid precursor protein (APP) expression in multiple sclerosis lesions, Glia, October, 1995, 15(2), p. 141-51; Reynolds W F, and six others, Myeloperoxidase polymorphism is associated with gender specific risk for Alzheimer's disease, Experimental Neurology, January, 1999, 155(1), p. 31-41), head injury, skull injury (see, for example, Smith D H, and four others, Protein accumulation in traumatic brain injury, NeuroMolecular Medicine, 2003, 4(1-2), p. 59-72), apraxia (see, for example, Matsubara-Tsutsui M, and seven others, Molecular evidence of presenilin 1 mutation in familial early onset dementia, American journal of Medical Genetics, Apr. 8, 2002, 114(3), p. 292-298), prion disease, familial amyloid neuropathy, triplet repeat disease (see, for example, Kirkitadze M D, and two others, Paradigm shifts in Alzheimer's disease and other neurodegenerative disorders: the emerging role of oligomeric assemblies, Journal of Neuroscience Research, Sep. 1, 2002, 69(5), p. 567-577; Evert B O, and eight others, Inflammatory genes are upreglulated in expanded ataxin-3-expressing cell lines and spinocerebellar ataxia type 3 brains, The Journal of Neuroscience, Aug. 1, 2001, 21(15), p. 5389-5396; Mann D M, and one other, Deposition of amyloid (A4) protein within the brains of persons with dementing disorders other than Alzheimer's disease and Down's syndrome, Neuroscience Letters, Feb. 5, 1990, 109(1-2), p. 68-75), Parkinson's disease (see, for example, Primavera J, and four others, Brain accumulation of amyloid-β in Non-Alzheimer Neurodegeneration, Jornal of Alzheimer's Disease, October, 1999, 1(3), p. 183-193), Lewy body dementia (see, for example, Giasson B I, and two others, Interactions of amyloidogenic proteins. NeuroMolecular Medicine, 2003, 4(1-2), p. 49-58; Masliah E, and six others, β-amyloid peptides enhance α-synuclein accumulation and neuronal deficits in a trancgenic mouse model linking Alzheimer's disease and Parkinson's disease, Proceeding National Academy of Science USA, Oct. 9, 2001, 98(21), p. 12245-12250; Barrachina M, and six others, Amyloid-β deposition in the cerebral cortex in Dementia with Lewy bodies is accompanied by a relative increase in AβPP mRNA isoforms containing the Kunitz protease inhibitor, Neurochemistry International, February, 2005, 46(3), p. 253-260; Primavera J, and four others, Brain accumulation of amyloid-β in Non-Alzheimer Neurodegeneration, Jornal of Alzheimer's Disease, October, 1999, 1(3), p. 183-193), parkinsonism-dementia complex (see, for example, Schmidt M L, and six others, Amyloid plaques in Guam amyotrophic lateral sclerosis/parkinsonism-dementia complex contain species of Aβ similar to those found in the amyloid plaques of Alzheimer's disease and pathological aging, Acta Neuropathologica (Berl), February, 1998, 95(2), p. 117-122; Ito H, and three others, Demonstration of β amyloid protein-containing neurofibrillary tangles in parkinsonism-dementia complex on Guam, Neuropathology and applied neurobiology, October, 1991, 17(5), p. 365-373), frontotemporal dementia and parkinsonism linked to chromosome 17 (see, for example, Rosso S M, and three others, Coexistent tau and amyloid pathology in hereditary frontotemporal dementia with tau mutations, Annals of the New York academy of sciences, 2000, 920, p. 115-119), argyrophilic grain dementia (see, for example, Tolnay M, and four others, Low amyloid (Aβ) plaque load and relative predominance of diffuse plaques distinguish argyrophilic grain disease from Alzheimer's disease, Neuropathology and applied neurobiology, August, 1999, 25(4), p. 295-305), Niemann-Pick disease (see, for example, Jin L W, and three others, Intracellular accumulation of amyloidogenic fragments of amyloid-β precursor protein in neurons with Niemann-Pick type C defects is associated with endosomal abnormalities, American Journal of Pathology, March, 2004, 164(3), p. 975-985), amyotrophic lateral sclerosis (see, for example, Sasaki S, and one other, Immunoreactivity of β-amyloid precursor protein in amyotrophic lateral sclerosis, Acta Neuropathologica (Berl), May, 1999, 97(5), p. 463-468; Tamaoka A, and four others, Increased amyloid β protein in the skin of patients with amyotrophic lateral sclerosis, Journal of neurology, August, 2000, 247(8), p. 633-635; Hamilton R L, and one other, Alzheimer disease pathology in amyotrophic lateral sclerosis, Acta Neuropathologica, June, 2004, 107(6), p. 515-522; Turner B J, and six others, Brain β-amyloid accumulation in transgenic mice expressing mutant superoxide dismutase 1, Neurochemical Research, December, 2004, 29(12), p. 2281-2286), hydrocephalus (see, for example, Weller R O, Pathology of cerebrospinal fluid and interstitial fluid of the CNS: Significance for Alzheimer disease, prion disorders and multiple sclerosis, Journal of Neuropathology and Experimental Neurology, October, 1998, 57(10), p. 885-894; Silverberg G D, and four others, Alzheimer's disease, normal-pressure hydrocephalus, and senescent changes in CSF circulatory physiology: a hypothesis, Lancet neurology, August, 2003, 2(8), p. 506-511; Weller R O, and three others, Cerebral amyloid angiopathy: Accumulation of Aβ in interstitial fluid drainage pathways in Alzheimer's disease, Annals of the New York academy of sciences, April, 2000, 903, p. 110-117; Yow H Y, and one other, A role for cerebrovascular disease in determining the pattern of β-amyloid deposition in Alzheimer's disease, Neurology and applied neurobiology, 2002, 28, p. 149; Weller R O, and four others, Cerebrovasculardisease is a major factor in the failure of elimination of Aβ from the aging human brain, Annals of the New York academy of sciences, November, 2002, 977, p. 162-168), paraparesis (see, for example, O'Riordan S, and seven others, Presenilin-1 mutation (E280G), spastic paraparesis, and cranial MRI white-matter abnormalities, Neurology, Oct. 8, 2002, 59(7), p. 1108-1110; Matsubara-Tsutsui M, and seven others, Molecular evidence of presenilin 1 mutation in familial early onset dementia, American journal of Medical Genetics, Apr. 8, 2002, 114(3), p. 292-298; Smith M J, and eleven others, Variable phenotype of Alzheimer's disease with spastic paraparesis, Annals of Neurology, 2001, 49(1), p. 125-129; Crook R, and seventeen others, A variant of Alzheimer's disease with spastic pararesis and unusual plaques due to deletion of exon 9 of presenilin 1, Nature Medicine, April, 1998; 4(4), p. 452-455), progressive supranuclear palsy (see, for example, Barrachina M, and six others, Amyloid-β deposition in the cerebral cortex in Dementia with Lewy bodies is accompanied by a relative increase in AβPP mRNA isoforms containing the Kunitz protease inhibitor, Neurochemistry International, February, 2005, 46(3), p. 253-260; Primavera J, and four others, Brain accumulation of amyloid-β in Non-Alzheimer Neurodegeneration, Jornal of Alzheimer's Disease, October, 1999, 1(3), p. 183-193), intracerebral hemorrhage (see, for example, Atwood C S, and three others, Cerebrovascular requirement for sealant, anti-coagulant and remodeling molecules that allow for the maintenance of vascular integrity and blood supply, Brain Research Reviews, September, 2003, 43(1), p. 164-78; Lowenson J D, and two others, Protein aging: Extracellular amyloid formation and intracellular repair, Trends in cardiovascular medicine, 1994, 4(1), p. 3-8), convulsion (see, for example, Singleton A B, and thirteen others, Pathology of early-onset Alzheimer's disease cases bearing the Thr113-114ins presenilin-1 mutation, Brain, December, 2000, 123(Pt12), p. 2467-2474), mild cognitive impairment (see, for example, Gattaz W F, and four others, Platelet phospholipase A2 activity in Alzheimer's disease and mild cognitive impairment, Journal of Neural Transmission, 2004, May, 111(5), p. 591-601; Assini A, and fourteen others, Plasma levels of amyloid β-protein 42 are increased in women with mild cognitive impariment, Neurology, Sep. 14, 2004, 63(5), p. 828-831), arteriosclerosis (see, for example, De Meyer G R, and eight others, Platelet phagocytosis and processing of β-amyloid precursor protein as a mechanism of macrophage activation in atherosclerosis, Circulation Research, Jun. 14, 2002, 90(11), p. 1197-1204).

The "5-membered aromatic heterocyclic group", "6- to 14-membered aromatic hydrocarbon ring group", "5- to 14-membered aromatic heterocyclic group", "6- to 14-membered non-aromatic hydrocarbon ring group" and "5- to 14-membered non-aromatic heterocyclic group" in the compound represented by the formula (I) of the present invention which is effective for treatment or prevention of a disease caused by Aβ are defined as follows.

The "5-membered aromatic heterocyclic group" is a 5-membered aromatic heterocyclic group containing one or more hetero atoms selected from the group consisting of a nitrogen atom, a sulfur atom and an oxygen atom such as:

[Formula 8]

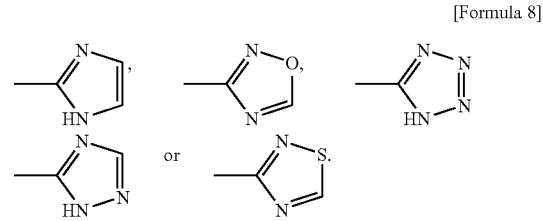

The "6- to 14-membered aromatic hydrocarbon ring group" refers to a monocyclic, bicyclic or tricyclic aromatic hydrocarbon ring group having 6 to 14 carbon atoms. Preferable examples of the group include 6- to 14-membered monocyclic, bicyclic, or tricyclic aromatic hydrocarbon ring groups such as a phenyl group, an indenyl group, a naphthyl group, an azulenyl group, a heptalenyl group, a biphenyl group, a fluorenyl group, a phenalenyl group, a phenanthrenyl group and an anthracenyl group.

The "5- to 14-membered aromatic heterocyclic group" refers to a monocyclic, bicyclic or tricyclic aromatic heterocyclic group having 5 to 14 carbon atoms. Preferable examples of the group include (1) nitrogen-containing aromatic heterocyclic groups such as a pyrrolyl group, a pyridyl group, a pyridazinyl group, a pyrimidinyl group, a pyrazinyl group, a pyrazolinyl group, an imidazolyl group, an indolyl group, an isoindolyl group, an indolizinyl group, a purinyl group, an indazolyl group, a quinolyl group, an isoquinolyl group, a quinolizinyl group, a phthalazinyl group, a naphthyridinyl group, a quinoxalinyl group, a quinazolinyl group, a cinnolinyl group, a pteridinyl group, an imidazotriazinyl group, a pyrazinopyridazinyl group, an acridinyl group, a phenanthridinyl group, a carbazolyl group, a perimidinyl group, a phenanthrolinyl group and a phenacyl group, (2) sulfur-containing aromatic heterocyclic groups such as a thienyl group and a benzothienyl group, (3) oxygen-containing aromatic heterocyclic groups such as a furyl group, a pyranyl group, a cyclopentapyranyl group, a benzofuranyl group and an isobenzofuranyl group and (4) aromatic heterocyclic groups containing two or more hetero atoms selected from the group consisting of a nitrogen atom, a sulfur atom and an oxygen atom such as a thiazolyl group, an isothiazolyl group, a benzothiazolinyl group, a benzothiadiazolyl group, a phenothiazinyl group, an isoxazolyl group, a furazanyl group, a phenoxazinyl group, a pyrazoloxazolyl group, an imidazothiazolyl group, a thienofuryl group, a furopyrrolyl group and a pyridooxazinyl group.

The "6- to 14-membered non-aromatic hydrocarbon ring group" refers to a cyclic aliphatic hydrocarbon group having 6 to 14 carbon atoms. Examples of the group include cyclic aliphatic hydrocarbon groups having 6 to 14 carbon atoms such as a cyclopropyl group, a cyclobutyl group, a cyclopentyl group, a cyclohexyl group, a cycloheptyl group, a cyclooctyl group, a spiro[3.4]octanyl group, a decanyl group, an indanyl group, a 1-acenaphthenyl group, a cyclopentacyclooctenyl group, a benzocyclooctenyl group, an indenyl group, a tetrahydronaphthyl group, a 6,7,8,9-tetrahydro-5H-benzocycloheptenyl group and a 1,4-dihydronaphthalenyl group.

The "5- to 14-membered non-aromatic heterocyclic group" 1) has 5 to 14 ring-forming atoms, 2) contains 1 to 5 hetero atoms such as a nitrogen atom, —O— or —S— in the ring-forming atoms, and 3) may contain one or more carbonyl groups, double bonds or triple bonds in the ring, and refers not only to a 5- to 14-membered non-aromatic monocyclic heterocyclic group but also to a saturated heterocyclic group condensed with an aromatic hydrocarbon ring group or a saturated hydrocarbon ring group or saturated heterocyclic group condensed with an aromatic heterocyclic group. Specific examples of the 5- to 14-membered non-aromatic heterocyclic group include an azetidinyl ring, a pyrrolidinyl ring, a piperidinyl ring, an azepanyl ring, an azocanyl ring, a tetrahydrofuranyl ring, a tetrahydropyranyl ring, a morpholinyl ring, a thiomorpholinyl ring, a piperazinyl ring, a thiazolidinyl ring, a dioxanyl ring, an imidazolinyl ring, a thiazolinyl ring, a 1,2-benzopyranyl ring, an isochromanyl ring, a chromanyl ring, an indolinyl ring, an isoindolinyl ring, an azaindanyl group, an azatetrahydronaphthyl group, an azachromanyl group, a tetrahydrobenzofuranyl group, a tetrahydrobenzothienyl group, a 2,3,4,5-tetrahydro-benzo[b]thienyl group, a 3,4-dihydro-2H-benzo[b][1,4]dioxepinyl group, an indan-1-onyl group, a 6,7-dihydro-5H-cyclopentapyrazinyl group, a 6,7-dihydro-5H-[1]pyridinyl group, a 6,7-dihydro-5H-[1]pyridinyl group, a 5,6-dihydro-4H-cyclopenta[b]thienyl group, a 4,5,6,7-tetrahydro-benzo[b]thienyl group, a 3,4-dihydro-2H-naphthale-1-onyl group, a 2,3-dihydro-isoindol-1-onyl group, a 3,4-dihydro-2H-isoquinolin-1-onyl group and a 3,4-dihydro-2H-benzo[1,4]oxapinyl group.

Substituent groups A1 and A2 refer to the following groups.

Substituent Group A1 refers to (1) a hydrogen atom, (2) a halogen atom, (3) a hydroxyl group, (4) a cyano group, (5) a nitro group, (6) a C3-8 cycloalkyl group which may be substituted with 1 to 3 substituents selected from Substituent Group A2, (7) a C2-6 alkenyl group which may be substituted with 1 to 3 substituents selected from Substituent Group A2, (8) a C2-6 alkynyl group which may be substituted with 1 to 3 substituents selected from Substituent Group A2, (9) a C3-8 cycloalkoxy group, (10) a C3-8 cycloalkylthio group, (11) a formyl group, (12) a C1-6 alkylcarbonyl group which may be substituted with 1 to 3 substituents selected from Substituent Group A2, (13) a C1-6 alkylthio group which may be substituted with 1 to 3 substituents selected from Substituent Group A2, (14) a C1-6 alkylsulfinyl group which may be substituted with 1 to 3 substituents selected from Substituent Group A2, (15) a C1-6 alkylsulfonyl group which may be substituted with 1 to 3 substituents selected from Substituent Group A2, (16) a hydroxyimino group, (17) a C1-6 alkoxyimino group, (18) a C1-6 alkyl group which may be substituted with 1 to 3 substituents selected from Substituent Group A2, (19) a C1-6 alkoxy group which may be substituted with 1 to 3 substituents selected from Substituent Group A2, (20) an amino group which may be substituted with 1 or 2 substituents selected from Substituent Group A2, (21) a carbamoyl group which may be substituted with 1 or 2 substituents selected from Substituent Group A2, (22) a 6- to 14-membered aromatic hydrocarbon ring group which may be substituted with 1 to 3 substituents selected from Substituent Group A2, (23) a 5- to 14-membered aromatic heterocyclic group which may be substituted with 1 to 3 substituents selected from Substituent Group A2, (24) a 6- to 14-membered non-aromatic hydrocarbon ring group which may be substituted with 1 to 3 substituents selected from Substituent Group A2, (25) a 5- to 14-membered non-aromatic heterocyclic group which may be substituted with 1 to 3 substituents selected from Substituent Group A2, (26) a C2-6 alkenyloxy group, (27) a C2-6 alkynyloxy group, (28) a C3-8 cycloalkylsulfinyl group, (29) a C3-8 cycloalkylsulfonyl group, (30) —X-A (wherein X represents an imino group, —O— or —S— and A represents a 6- to 14-membered aromatic hydrocarbon ring group or a 5- to 14-membered aromatic heterocyclic group which may be substituted with 1 to 3 substituents selected from Substituent Group A2), (31) —CO-A (wherein A is as defined above), (32) =CH-A (wherein A is as defined above), (33) a carboxyl group, (34) a C1-6 alkoxycarbonyl group or (35) an azido group.

Substituent Group A2 refers to (1) a hydrogen atom, (2) a halogen atom, (3) a hydroxyl group, (4) a cyano group, (5) a nitro group, (6) a C3-8 cycloalkyl group, (7) a C2-6 alkenyl group, (8) a C2-6 alkynyl group, (9) a C3-8 cycloalkoxy group, (10) a C3-8 cycloalkylthio group, (11) a formyl group, (12) a C1-6 alkylcarbonyl group, (13) a C1-6 alkylthio group, (14) a C1-6 alkylsulfinyl group, (15) a C1-6 alkylsulfonyl group, (16) a hydroxyimino group, (17) a C1-6 alkoxyimino group, (18) a C1-6 alkyl group (wherein the C1-6 alkyl group may be substituted with 1 to 3 substituents selected from the group consisting of a halogen atom, a hydroxyl group, a C1-6 alkoxy group, a phenyl group which may be substituted with 1 to 3 halogen atoms and a pyridinyl group which may be substituted with 1 to 3 halogen atoms), (19) a C1-6 alkoxy group (wherein the C1-6 alkoxy group may be substituted with 1 to 3 substituents selected from the group consisting of a halogen atom, a hydroxyl group, a C1-6 alkoxy group, a phenyl group which may be substituted with 1 to 3 halogen atoms and a pyridinyl group which may be substituted with 1 to 3 halogen atoms), (20) an amino group which may be substituted with 1 or 2 C1-6 alkyl groups or C1-6 alkylcarbonyl groups, (21) a carbamoyl group which may be substituted with 1 or 2 C1-6 alkyl groups, (22) a 6- to 14-membered aromatic hydrocarbon ring group, (23) a 5- to 14-membered aromatic heterocyclic group, (24) a 6- to 14-membered non-aromatic hydrocarbon ring group, (25) a 5- to 14-membered non-aromatic heterocyclic group, (26) a C2-6 alkenyloxy group, (27) a C2-6 alkynyloxy group, (28) a C3-8 cycloalkylsulfinyl group, (29) a C3-8 cycloalkylsulfonyl group, (30) —X-A' (wherein X represents an imino group, —O—, —S— or —SO$_2$— and A' represents a 6- to 14-membered aromatic hydrocarbon ring group or a 5- to 14-membered aromatic heterocyclic group which may be substituted with 1 to 3 halogen atoms), (31) —CO-A' (wherein A' is as defined above) or (32) =CH-A' (wherein A' is as defined above).

The "halogen atom" refers to a fluorine atom, a chlorine atom, a bromine atom, an iodine atom or the like and is preferably a fluorine atom, a chlorine atom or a bromine atom.

The "C3-8 cycloalkyl group" refers to a cyclic alkyl group having 3 to 8 carbon atoms. Preferable examples of the group include a cyclopropyl group, a cyclobutyl group, a cyclopentyl group, a cyclohexyl group, a cycloheptyl group and a cyclooctyl group.

The "C2-6 alkenyl group" refers to an alkenyl group having 2 to 6 carbon atoms. Preferable examples of the group include linear or branched alkenyl groups such as a vinyl group, an allyl group, a 1-propenyl group, an isopropenyl group, a 1-buten-1-yl group, a 1-buten-2-yl group, a 1-buten-3-yl group, a 2-buten-1-yl group and a 2-buten-2-yl group.

The "C2-6 alkynyl group" refers to an alkynyl group having 2 to 6 carbon atoms. Preferable examples of the group include linear or branched alkynyl groups such as an ethynyl group, a 1-propynyl group, a 2-propynyl group, a butynyl group, a pentynyl group and a hexynyl group.

The "C3-8 cycloalkoxy group" refers to a cyclic alkyl group having 3 to 8 carbon atoms in which one hydrogen atom is replaced by an oxygen atom. Preferable examples of the group include a cyclopropoxy group, a cyclobutoxy group, a cyclopentoxy group, a cyclohexoxy group, a cycloheptyloxy group and a cyclooctyloxy group.

The "C3-8 cycloalkylthio group" refers to a cyclic alkyl group having 3 to 8 carbon atoms in which one hydrogen atom is replaced by a sulfur atom. Preferable examples of the group include a cyclopropylthio group, a cyclobutylthio group, a cyclopentylthio group, a cyclohexylthio group, a cycloheptylthio group and a cyclooctylthio group.

The "C1-6 alkoxy group" refers to an alkyl group having 1 to 6 carbon atoms in which a hydrogen atom is replaced by an oxygen atom. Preferable examples of the group include a methoxy group, an ethoxy group, an n-propoxy group, an i-propoxy group, an n-butoxy group, an i-butoxy group, a sec-butoxy group, a tert-butoxy group, an n-pentoxy group, an i-pentoxy group, a sec-pentoxy group, a tert-pentoxy group, an n-hexoxy group, an i-hexoxy group, a 1,2-dimethylpropoxy group, a 2-ethylpropoxy group, a 1-methyl-2-ethylpropoxy group, a 1-ethyl-2-methylpropoxy group, a 1,1,2-trimethylpropoxy group, a 1,1,2-trimethylpropoxy group, a 1,1-dimethylbutoxy group, a 2,2-dimethylbutoxy group, a 2-ethylbutoxy group, a 1,3-dimethylbutoxy group, a 2-methylpentoxy group, a 3-methylpentoxy group and a hexyloxy group.

The "C1-6 alkylthio group" refers to an alkyl group having 1 to 6 carbon atoms in which one hydrogen atom is replaced by a sulfur atom. Preferable examples of the group include a methylthio group, an ethylthio group, an n-propylthio group, an i-propylthio group, an n-butylthio group, an i-butylthio group, a tert-butylthio group, an n-pentylthio group, an i-pentylthio group, a neopentylthio group, an n-hexylthio group and a 1-methylpropylthio group.

The "C1-6 alkylcarbonyl group" refers to an alkyl group having 1 to 6 carbon atoms in which one hydrogen atom is replaced by a carbonyl group. Preferable examples of the group include an acetyl group, a propionyl group and a butyryl group.

The "C1-6 alkylsulfinyl group" refers to an alkyl group having 1 to 6 carbon atoms in which one hydrogen atom is substituted with a sulfinyl group. Preferable examples of the group include a methylsulfinyl group, an ethylmethylsulfinyl group, an n-propylsulfinyl group, an i-propylsulfinyl group, an n-butylsulfinyl group, an i-butylsulfinyl group, a tert-butylsulfinyl group, an n-pentylsulfinyl group, an i-pentylsulfinyl group, a neopentylsulfinyl group, an n-hexylsulfinyl group and a 1-methylpropylsulfinyl group.

The "C1-6 alkylsulfonyl group" refers to an alkyl group having 1 to 6 carbon atoms in which one hydrogen atom is replaced by a sulfonyl group. Preferable examples of the group include a methanesulfonyl group and an ethanesulfonyl group.

The "C1-6 alkoxyimino group" refers to an imino group in which a hydrogen atom is replaced by a C1-6 alkoxy group. Preferable examples of the group include a methoxyimino group and an ethoxyimino group.

The "C1-6 alkyl group" refers to an alkyl group having 1 to 6 carbon atoms. Preferable examples of the group include linear or branched alkyl groups such as a methyl group, an ethyl group, an n-propyl group, an i-propyl group, an n-butyl group, an i-butyl group, a tert-butyl group, an n-pentyl group, an i-pentyl group, a neopentyl group, an n-hexyl group, a 1-methylpropyl group, an 1,2-dimethylpropyl group, a 1-ethylpropyl group, a 1-methyl-2-ethylpropyl group, a 1-ethyl-2-methylpropyl group, a 1,1,2-trimethylpropyl group, a 1-methylbutyl group, a 2-methylbutyl group, a 1,1-dimethylbutyl group, a 2,2-dimethylbutyl group, a 2-ethylbutyl group, a 1,3-dimethylbutyl group, a 2-methylpentyl group and a 3-methylpentyl group.

The "C2-6 alkenyloxy group" refers to an alkenyl group having 2 to 6 carbon atoms in which one hydrogen atom is replaced by an oxygen atom. Preferable examples of the group include linear or branched alkenyloxy groups such as a vinyloxy group, an allyloxy group, a 1-propenyloxy group, an isopropenyloxy group, a 1-buten-1-yloxy group, a 1-buten-2-yloxy group, a 1-buten-3-yloxy group, a 2-buten-1-yloxy group and a 2-buten-2-yloxy group.

The "C2-6 alkynyloxy group" refers to an alkynyl group having 2 to 6 carbon atoms in which one hydrogen atom is replaced by an oxygen atom. Preferable examples of the group include linear or branched alkynyloxy groups such as an ethynyloxy group, a 1-propynyloxy group, a 2-propynyloxy group, a butynyloxy group, a pentynyloxy group and a hexynyloxy group.

The "C3-8 cycloalkylsulfonyl group" refers to a cyclic alkyl group having 3 to 8 carbon atoms in which one hydrogen atom is replaced by a sulfonyl group. Preferable examples of the group include a cyclopropylsulfonyl group, a cyclobutylsulfonyl group, a cyclopentylsulfonyl group, a cyclohexylsulfonyl group, a cycloheptylsulfonyl group and a cyclooctylsulfonyl group.

The "C3-8 cycloalkylsulfinyl group" refers to a cyclic alkyl group having 3 to 8 carbon atoms in which one hydrogen atom is replaced by a sulfinyl group. Preferable examples of the group include a cyclopropylsulfinyl group, a cyclobutylsulfinyl group, a cyclopentylsulfinyl group, a cyclohexylsulfinyl group, a cycloheptylsulfinyl group and a cyclooctylsulfinyl group.

The "C1-6 alkoxycarbonyl group" refers to a carbonyl group in which a hydrogen atom is substituted with a C1-6 alkyl group. Preferable examples of the group include an ethoxycarbonyl group.

Examples of the pyridinyl group as $Ar_2$ which may be substituted with a hydroxyl group include a tautomer represented by the following formula:

[Formula 9]

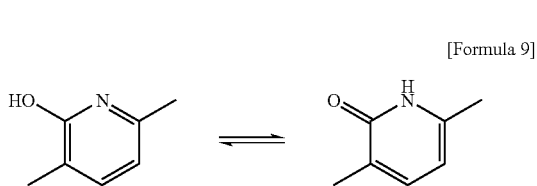

Examples of the "Het which is a group represented by the following formula":

[Formula 10]

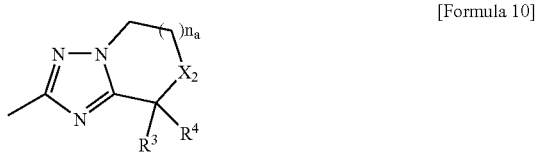

wherein $R^3$ and $R^4$ are the same or different and each represent a substituent selected from Substituent Group A1, or $R^3$ and $R^4$ are taken together with a carbon atom to which they are bonded to form =CH-A (wherein A represents a 6- to 14-membered aromatic hydrocarbon ring group or a 5- to 14-membered aromatic heterocyclic group which may be substituted with 1 to 3 substituents selected from Substituent Group A2), $X_2$ represents a methylene group or an oxygen atom and $n_a$ represents an integer of 0 to 2, include groups represented by the formulas:

[Formula 11]

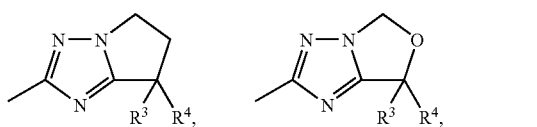

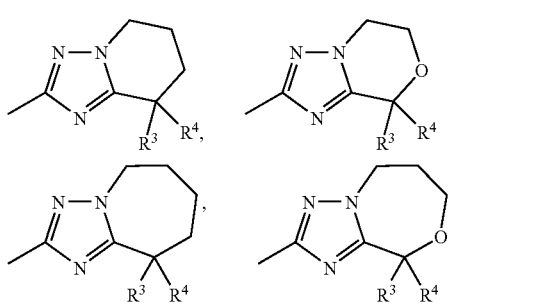

wherein $R^3$ and $R^4$ are the same or different and each represent a substituent selected from Substituent Group A1, or $R^3$ and $R^4$ are taken together with a carbon atom to which they are bonded to form =CH-A (wherein A represents a 6- to 14-membered aromatic hydrocarbon ring group or a 5- to 14-membered aromatic heterocyclic group which may be substituted with 1 to 3 substituents selected from Substituent Group A2).

Examples of the "Het represented by the following formula":

[Formula 12]

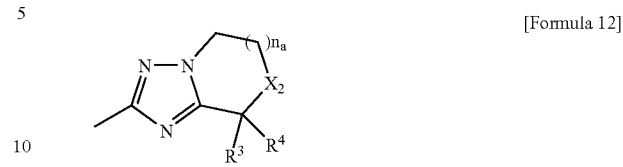

wherein $R^3$ and $R^4$ are taken together with a carbon atom to which they are bonded to form =CH-A, include:

[Formula 13]

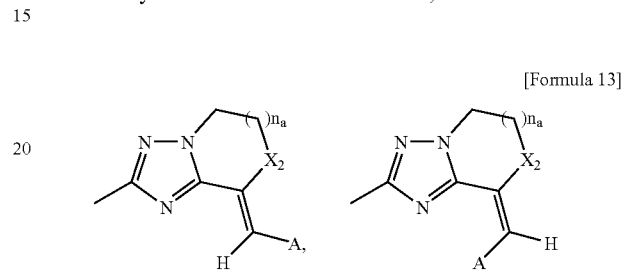

Examples of the "Het which is a group represented by the following formula":

[Formula 14]

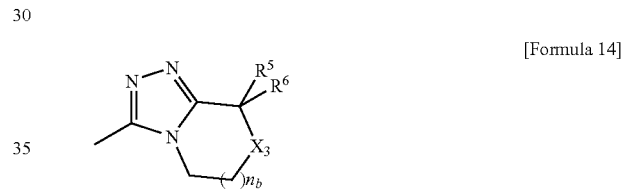

wherein $R^5$ and $R^6$ are the same or different and each represent a substituent selected from Substituent Group A1, $X_3$ represents a methylene group or an oxygen atom and $n_b$ represents an integer of 0 to 2, include:

[Formula 15]

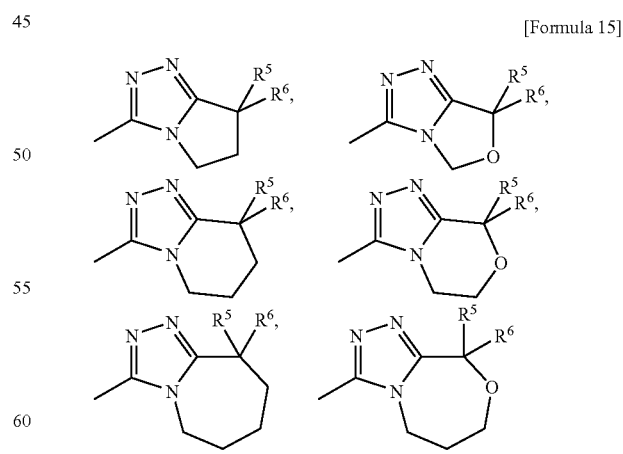

wherein $R^5$ and $R^6$ are the same or different and each represent a substituent selected from Substituent Group A1.

Examples of the "Het which is a group represented by the following formula":

[Formula 16]

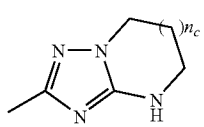

wherein $n_c$ represents an integer of 0 to 3, include:

[Formula 17]

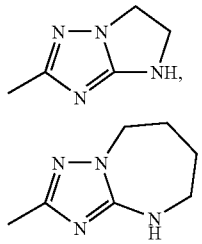 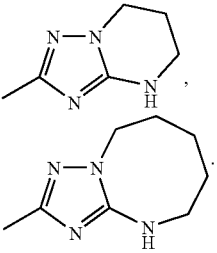

Examples of the "Het which is a group represented by the following formula":

[Formula 18]

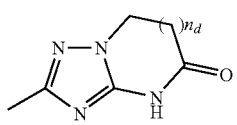

wherein $n_d$ represents an integer of 0 to 3, include:

[Formula 19]

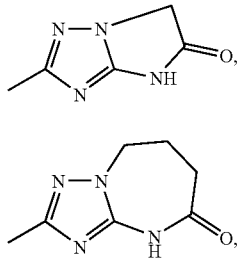 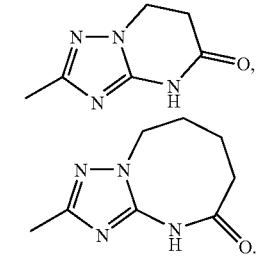

In the present invention, the "pharmacologically acceptable salt" is not particularly limited insofar as it is a pharmacologically acceptable salt formed with the compound of the general formula (I) which is a prophylactic or therapeutic agent for a disease caused by Aβ. Preferable specific examples of the salt include hydrohalides (such as hydrofluorides, hydrochlorides, hydrobromides and hydroiodides), inorganic acid salts (such as sulfates, nitrates, perchlorates, phosphates, carbonates and bicarbonates), organic carboxylates (such as acetates, oxalates, maleates, tartrates, fumarates and citrates), organic sulfonates (such as methanesulfonates, trifluoromethanesulfonates, ethanesulfonates, benzenesulfonates, toluenesulfonates and camphorsulfonates), amino acid salts (such as aspartates and glutamates), quaternary amine salts, alkali metal salts (such as sodium salts and potassium salts) and alkali earth metal salts (such as magnesium salts and calcium salts).

Next, the compound of the formula (I) of the present invention will be described.

In the compound of the formula (I) or pharmacologically acceptable salt thereof, $Ar_1$ is preferably an imidazolyl group substituted with a C1-6 alkyl group, and $Ar_1$ is more preferably an imidazolyl group substituted with a methyl group.

In the compound of the formula (I) or pharmacologically acceptable salt thereof, $Ar_2$ is preferably a pyridinyl group or a phenyl group which may be substituted with a halogen atom, a hydroxyl group or a C1-6 alkoxy group, $Ar_2$ is more preferably a phenyl group or a pyridinyl group, substituted with a C1-6 alkoxy group, $Ar_2$ is particularly preferably a phenyl group or a pyridinyl group, substituted with a methoxy group, and $Ar_2$ is most preferably a pyridinyl group substituted with a methoxy group.

In the compound of the formula (I) or pharmacologically acceptable salt thereof, $X_1$ is preferably —$CR^1$=$CR^2$—, wherein $R^1$ and $R^2$ are the same or different and each represent a hydrogen atom or a fluorine atom, and $X_1$ is most preferably —CH=CH—.

In the compound of the formula (I) or pharmacologically acceptable salt thereof, $Ar_1$ and Ar more preferably have the following structural formulas:

[Formula 20]

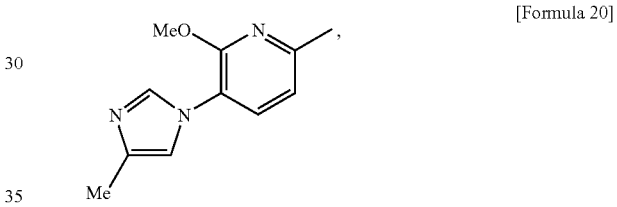

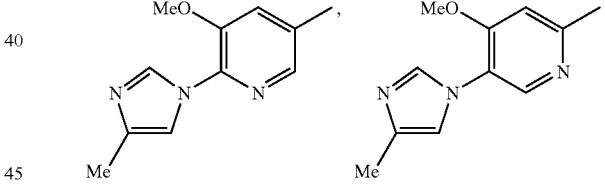

and most preferably have the following structural formulas:

[Formula 21]

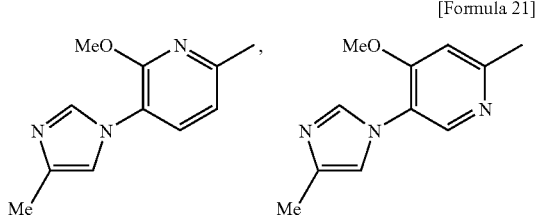

In the compound of the formula (I) or pharmacologically acceptable salt thereof, Het is preferably a triazolyl group which may be substituted with 1 or 2 substituents selected from Substituent Group A1, Het is preferably a group which may be substituted with 1 to 3 substituents selected from Substituent Group A1 and is represented by the following formula:

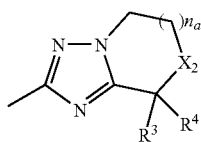

[Formula 22]

wherein $R^3$ and $R^4$ are the same or different and each represent a substituent selected from Substituent Group A1, or $R^3$ and $R^4$ are taken together with a carbon atom to which they are bonded to form =CH-A (wherein A represents a 6- to 14-membered aromatic hydrocarbon ring group or a 5- to 14-membered aromatic heterocyclic group which may be substituted with 1 to 3 substituents selected from Substituent Group A2), $X_2$ represents an oxygen atom or a methylene group which may be substituted with a substituent selected from Substituent Group A1 and $n_a$ represents an integer of 0 to 2, Het is preferably a group which may be substituted with 1 to 3 substituents selected from Substituent Group A1 and is represented by the following formula:

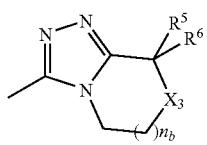

[Formula 23]

wherein $R^5$ and $R^6$ are the same or different and each represent a substituent selected from Substituent Group A1, $X_3$ represents a methylene group which may be substituted with a substituent selected from Substituent Group A1, or an oxygen atom and $n_b$ represents an integer of 0 to 2, Het is preferably a group which may be substituted with 1 to 3 substituents selected from Substituent Group A1 and is represented by the following formula:

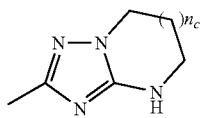

[Formula 24]

wherein $n_c$ represents an integer of 0 to 3, or

Het is preferably a group which may be substituted with 1 to 3 substituents selected from Substituent Group A1 and is represented by the following formula:

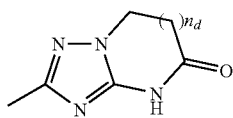

[Formula 25]

wherein $n_d$ represents an integer of 0 to 3,

Het is more preferably a group which may be substituted with 1 to 3 substituents selected from Substituent Group A1 and is represented by the following formula:

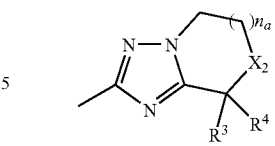

[Formula 26]

wherein $R^3$ and $R^4$ are the same or different and each represent a substituent selected from Substituent Group A1, or $R^3$ and $R^4$ are taken together with a carbon atom to which they are bonded to form =CH-A (wherein A represents a 6- to 14-membered aromatic hydrocarbon ring group or a 5- to 14-membered aromatic heterocyclic group which may be substituted with 1 to 3 substituents selected from Substituent Group A2), $X_2$ represents a methylene group which may be substituted with a substituent selected from Substituent Group A1, or an oxygen atom and $n_a$ represents an integer of 0 to 2, and Het is more preferably a group which may be substituted with 1 to 3 substituents selected from Substituent Group A1 and is represented by the following formula:

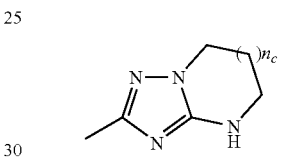

[Formula 27]

wherein $n_c$ represents an integer of 0 to 3, and

Het is most preferably a group which may be substituted with 1 to 3 substituents selected from Substituent Group A1 and is represented by the following formula:

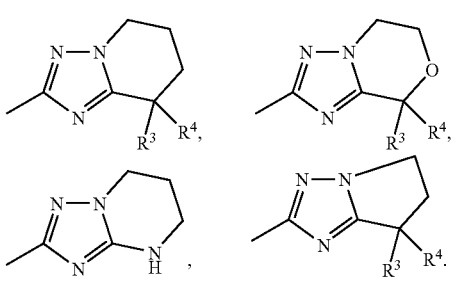

[Formula 28]

Substituent Group A1 is preferably a group consisting of (1) a hydrogen atom, (2) a halogen atom, (3) a hydroxyl group, (4) a cyano group, (5) a nitro group, (6) a C3-8 cycloalkyl group which may be substituted with 1 to 3 substituents selected from Substituent Group A2, (7) a C2-6 alkenyl group which may be substituted with 1 to 3 substituents selected from Substituent Group A2, (8) a C2-6 alkynyl group which may be substituted with 1 to 3 substituents selected from Substituent Group A2, (9) a C3-8 cycloalkoxy group, (10) a C3-8 cycloalkylthio group, (11) a formyl group, (12) a C1-6 alkylcarbonyl group which may be substituted with 1 to 3 substituents selected from Substituent Group A2, (13) a C1-6 alkylthio group which may be substituted with 1 to 3 substituents selected from Substituent Group A2, (14) a C1-6 alkylsulfinyl group which may be substituted with 1 to 3 substituents selected from Substituent Group A2, (15) a C1-6 alkylsulfonyl group which may be substituted with 1 to 3 substituents selected from Substituent Group A2, (16) a hydroxyimino group, (17) a C1-6 alkoxyimino group, (18) a C1-6 alkyl group which may be substituted with 1 to 3 substituents selected from Substituent Group A2, (19) a C1-6 alkoxy group which may be substituted with 1 to 3 substituents selected from Substituent Group A2, (20) an amino group which may be substituted with 1 or 2 substituents selected from Substituent Group A2, (21) a carbamoyl group which may be substituted with 1 or 2 substituents selected from Substituent Group A2, (22) a 6- to 14-membered aromatic hydrocarbon ring group which may be substituted with 1 to 3 substituents selected from Substituent Group A2, (23) a 5- to 14-membered aromatic heterocyclic group which may be substituted with 1 to 3 substituents selected from Substituent Group A2, (24) a 6- to 14-membered non-aromatic hydrocarbon ring group which may be substituted with 1 to 3 substituents selected from Substituent Group A2, (25) a 5- to 14-membered non-aromatic heterocyclic group which may be substituted with 1 to 3 substituents selected from Substituent Group A2, (26) a C2-6 alkenyloxy group, (27) a C2-6 alkynyloxy group, (28) a C3-8 cycloalkylsulfinyl group, (29) a C3-8 cycloalkylsulfonyl group, (30) —X-A (wherein X represents an imino group, —O— or —S— and A represents a 6- to 14-membered aromatic hydrocarbon ring group or a 5- to 14-membered aromatic heterocyclic group which may be substituted with 1 to 3 substituents selected from Substituent Group A2), (31) —CO-A (wherein A is as defined above), (32) =CH-A (wherein A is as defined above), (33) a carboxyl group, (34) a C1-6 alkoxycarbonyl group and (35) an azidoazido group.

Substituent Group A1 is more preferably a group consisting of (1) a hydrogen atom, (2) a halogen atom, (3) a hydroxyl group, (4) a cyano group, (5) a C3-8 cycloalkyl group which may be substituted with 1 to 3 substituents selected from Substituent Group A2, (6) a C1-6 alkyl group which may be substituted with 1 to 3 substituents selected from Substituent Group A2, (7) a 6- to 14-membered aromatic hydrocarbon ring group which may be substituted with 1 to 3 substituents selected from Substituent Group A2, (8) a 5- to 14-membered aromatic heterocyclic group which may be substituted with 1 to 3 substituents selected from Substituent Group A2, (9) a 6- to 14-membered non-aromatic hydrocarbon ring group which may be substituted with 1 to 3 substituents selected from Substituent Group A2, (10) a 5- to 14-membered non-aromatic heterocyclic group which may be substituted with 1 to 3 substituents selected from Substituent Group A2, (11) —X-A (wherein X represents an imino group, —O— or —S— and A represents a 6- to 14-membered aromatic hydrocarbon ring group or a 5- to 14-membered aromatic heterocyclic group which may be substituted with 1 to 3 substituents selected from Substituent Group A2), (12) =CH-A (wherein A represents a 6- to 14-membered aromatic hydrocarbon ring group or a 5- to 14-membered aromatic heterocyclic group which may be substituted with 1 to 3 substituents selected from Substituent Group A2) and (13) an azidoazido group.

When Substituent Group A1 is a 6- to 14-membered aromatic hydrocarbon ring group or a 5- to 14-membered aromatic heterocyclic group, Substituent Group A2 is preferably a group consisting of (1) a hydrogen atom, (2) a halogen atom, (3) a hydroxyl group, (4) a cyano group, (5) a nitro group, (6) a C3-8 cycloalkyl group, (7) a C2-6 alkenyl group, (8) a C2-6 alkynyl group, (9) a C3-8 cycloalkoxy group, (10) a C3-8 cycloalkylthio group, (11) a formyl group, (12) a C1-6 alkylcarbonyl group, (13) a C1-6 alkylthio group, (14) a C1-6 alkylsulfinyl group, (15) a C1-6 alkylsulfonyl group, (16) a hydroxyimino group, (17) a C1-6 alkoxyimino group, (18) a C1-6 alkyl group (wherein the C1-6 alkyl group may be substituted with 1 to 3 substituents selected from the group consisting of a halogen atom, a hydroxyl group, a C1-6 alkoxy group, a phenyl group which may be substituted with 1 to 3 halogen atoms and a pyridinyl group which may be substituted with 1 to 3 halogen atoms), (19) a C1-6 alkoxy group (wherein the C1-6 alkoxy group may be substituted with 1 to 3 substituents selected from the group consisting of a halogen atom, a hydroxyl group, a C1-6 alkoxy group, a phenyl group which may be substituted with 1 to 3 halogen atoms and a pyridinyl group which may be substituted with 1 to 3 halogen atoms), (20) an amino group which may be substituted with 1 or 2 C1-6 alkyl groups or C1-6 alkylcarbonyl groups, (21) a carbamoyl group which may be substituted with 1 or 2 C1-6 alkyl groups, (22) a 6- to 14-membered aromatic hydrocarbon ring group, (23) a 5- to 14-membered aromatic heterocyclic group, (24) a 6- to 14-membered non-aromatic hydrocarbon ring group, (25) a 5- to 14-membered non-aromatic heterocyclic group, (26) a C2-6 alkenyloxy group, (27) a C2-6 alkynyloxy group, (28) a C3-8 cycloalkylsulfinyl group, (29) a C3-8 cycloalkylsulfonyl group, (30) —X-A' (wherein X represents an imino group, —O—, —S— or —SO$_2$— and A' represents a 6- to 14-membered aromatic hydrocarbon ring group or a 5- to 14-membered aromatic heterocyclic group which may be substituted with 1 to 3 halogen atoms), (31) —CO-A' (wherein A' is as defined above) and (32) =CH-A' (wherein A' is as defined above);

more preferably a group consisting of (1) a hydrogen atom, (2) a halogen atom, (3) a nitro group, (4) a C1-6 alkylcarbonyl group, (5) a C1-6 alkylthio group, (6) a C1-6 alkyl sulfonyl group, (7) a C1-6 alkyl group (wherein the C1-6 alkyl group may be substituted with 1 to 3 substituents selected from the group consisting of a halogen atom, a hydroxyl group, a C1-6 alkoxy group, a phenyl group which may be substituted with 1 to 3 halogen atoms and a pyridinyl group which may be substituted with 1 to 3 halogen atoms), (8) a C1-6 alkoxy group (wherein the C1-6 alkoxy group may be substituted with 1 to 3 substituents selected from the group consisting of a halogen atom, a hydroxyl group, a C1-6 alkoxy group, a phenyl group which may be substituted with 1 to 3 halogen atoms and a pyridinyl group which may be substituted with 1 to 3 halogen atoms), (9) an amino group which may be substituted with 1 or 2 C1-6 alkyl groups or C1-6 alkylcarbonyl groups and (10) a 5- to 14-membered aromatic heterocyclic group; and most preferably a group consisting of (1) a hydrogen atom, (2) a halogen atom, (3) a C1-6 alkyl group (wherein the C1-6 alkyl group may be substituted with 1 to 3 substituents selected from the group consisting of a halogen atom and a C1-6 alkoxy group) and (4) a C1-6 alkoxy group (wherein the C1-6 alkoxy group may be substituted with a halogen atom).

When Substituent Group A1 is a 6- to 14-membered non-aromatic hydrocarbon ring group or a 5- to 14-membered non-aromatic heterocyclic group, Substituent Group A2 is preferably a group consisting of (1) a hydrogen atom, (2) a halogen atom, (3) a hydroxyl group, (4) a cyano group, (5) a nitro group, (6) a C3-8 cycloalkyl group, (7) a C2-6 alkenyl group, (8) a C2-6 alkynyl group, (9) a C3-8 cycloalkoxy group, (10) a C3-8 cycloalkylthio group, (11) a formyl group, (12) a C1-6 alkylcarbonyl group, (13) a C1-6 alkylthio group, (14) a C1-6 alkylsulfinyl group, (15) a C1-6 alkylsulfonyl group, (16) a hydroxyimino group, (17) a C1-6 alkoxyimino group, (18) a C1-6 alkyl group (wherein the C1-6 alkyl group may be substituted with 1 to 3 substituents selected from the group consisting of a halogen atom, a hydroxyl group, a C1-6 alkoxy group, a phenyl group which may be substituted with 1 to 3 halogen atoms and a pyridinyl group which may be substituted with 1 to 3 halogen atoms), (19) a C1-6 alkoxy group (wherein the C1-6 alkoxy group may be substituted with 1 to 3 substituents selected from the group consisting of a halogen atom, a hydroxyl group, a C1-6 alkoxy group, a phenyl group which may be substituted with 1 to 3 halogen atoms and a pyridinyl group which may be substituted with 1 to 3 halogen atoms), (20) an amino group which may be substituted with 1 or 2 C1-6 alkyl groups or C1-6 alkylcarbonyl groups, (21) a carbamoyl group which may be substituted with 1 or 2 C1-6 alkyl groups, (22) a 6- to 14-membered aromatic hydrocarbon ring group, (23) a 5- to 14-membered aromatic heterocyclic group, (24) a 6- to 14-membered non-aromatic hydrocarbon ring group, (25) a 5- to 14-membered non-aromatic heterocyclic group, (26) a C2-6 alkenyloxy group, (27) a C2-6 alkynyloxy group, (28) a C3-8 cycloalkylsulfinyl group, (29) a C3-8 cycloalkylsulfonyl group, (30) —X-A' (wherein X represents an imino group, —O—, —S— or —SO$_2$— and A' represents a 6- to 14-membered aromatic hydrocarbon ring group or a 5- to 14-membered aromatic heterocyclic group which may be substituted with 1 to 3 halogen atoms), (31) —CO-A' (wherein A' is as defined above) and (32) =CH-A' (wherein A' is as defined above); and more preferably a group consisting of (1) a hydrogen atom, (2) a C1-6 alkylcarbonyl group, (3) a C1-6 alkyl group (wherein the C1-6 alkyl group may be substituted with 1 to 3 substituents selected from the group consisting of a halogen atom, a hydroxyl group, a C1-6 alkoxy group, a phenyl group which may be substituted with 1 to 3 halogen atoms and a pyridinyl group which may be substituted with 1 to 3 halogen atoms), (4) a 6- to 14-membered aromatic hydrocarbon ring group, (5) —X-A' (wherein X represents an imino group, —O—, —S— or —SO$_2$— and A' represents a 6- to 14-membered aromatic hydrocarbon ring group or a 5- to 14-membered aromatic heterocyclic group which may be substituted with 1 to 3 halogen atoms) and (6) —CO-A' (wherein A' is as defined above).

The compound or pharmacologically acceptable salt, wherein the compound is at least one selected from the following group, for example, is particularly suitable and useful as a therapeutic or prophylactic agent for a disease caused by amyloid-β such as Alzheimer's disease, senile dementia, Down's syndrome or amyloidosis.

1) (−)-8-(3-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine,
2) (−)-8-(4-isopropylphenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine,
3) (−)-8-(4-fluoro-2-methoxymethylphenyl)-2-{(E)-2-[3-methoxy-4-(4-methyl-1H-imidazol-1-yl)phenyl]vinyl}-5,6,7,8-tetrahydro-[1,2,4]triazolo[1,5-a]pyridine,
4) (−)-8-(2-fluorophenyl)-2-{(E)-2-[3-methoxy-4-(4-methyl-1H-imidazol-1-yl)phenyl]vinyl}-5,6,7,8-tetrahydro-[1,2,4]triazolo[1,5-a]pyridin-8-ol,
5) (−)-8-(3,5-difluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridin-8-ol,
6) 8-(4-fluorophenyl)-2-{(E)-2-[3-methoxy-4-(4-methyl-1H-imidazol-1-yl)phenyl]vinyl}-6-methyl-5,6,7,8-tetrahydro-[1,2,4]triazolo[1,5-a]pyridine,
7) 8-(4-fluorophenyl)-2-{(E)-2-[3-methoxy-4-(4-methyl-1H-imidazol-1-yl)phenyl]vinyl}-7-methyl-5,6,7,8-tetrahydro-[1,2,4]triazolo[1,5-a]pyridine,
8) (−)-2-{(E)-2-[3-methoxy-4-(4-methyl-1H-imidazol-1-yl)phenyl]vinyl}-7-phenyl-6,7-dihydro-5H-pyrrolo[1,2-b][1,2,4]triazole,
9) (−)-2-{(E)-2-[6-methoxy-5-(4-methyl-1H-imidazol-1-yl)pyridin-2-yl]vinyl}-8-(3,4,5-trifluorophenyl)-5,6,7,8-tetrahydro-[1,2,4]triazolo-[1,5-a]pyridine,
10) (−)-8-(3,4-difluorophenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine,
11) (−)-8-(4-fluorophenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine,
12) (−)-8-(3-chloro-4-fluorophenyl)-2-{(E)-2-[6-methoxy-5-(4-methyl-1H-imidazol-1-yl)pyridin-2-yl]vinyl}-5,6,7,8-tetrahydro[1,2,4]triazolo[1,5-a]pyridine,
13) (+)-8-(2,4,5-trifluorophenyl)-2-{(E)-2-[6-methoxy-5-(4-methyl-1H-imidazol-1-yl)pyridin-2-yl]vinyl}-5,6,7,8-tetrahydro[1,2,4]triazolo[1,5-a]pyridine,
14) (+)-8-(2,5-difluorophenyl)-2-{(E)-2-[6-methoxy-5-(4-methyl-1H-imidazol-1-yl)pyridin-2-yl]vinyl}-5,6,7,8-tetrahydro[1,2,4]triazolo[1,5-a]pyridine,
15) (−)-8-(2-bromo-4-fluorophenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine,
16) (−)-8-(2-chloro-4-fluorophenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine,
17) (+)-8-(3-fluorophenyl)-2-{(E)-2-[6-methoxy-5-(4-methyl-1H-imidazol-1-yl)pyridin-2-yl]vinyl}-5,6,7,8-tetrahydro[1,2,4]triazolo[1,5-a]pyridine,
18) (−)-8-(2-chlorophenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine,
19) (−)-2-{(E)-2-[6-methoxy-5-(4-methyl-1H-imidazol-1-yl)pyridin-2-yl]vinyl}-8-(2-trifluoromethylphenyl)-5,6,7,8-tetrahydro-[1,2,4]triazolo[1,5-a]pyridine,
20) (+)-2-{(E)-2-[6-methoxy-5-(4-methyl-1H-imidazol-1-yl)pyridin-2-yl]vinyl}-8-(naphthalen-1-yl)-5,6,7,8-tetrahydro-[1,2,4]triazolo[1,5-a]pyridine,
21) (−)-2-{(E)-2-[6-methoxy-5-(4-methyl-1H-imidazol-1-yl)pyridin-2-yl]vinyl}-8-phenyl-5,6,7,8-tetrahydro-[1,2,4]triazolo[1,5-a]pyridine,
22) (−)-8-(4-chlorophenyl)-2-{(E)-2-[6-methoxy-5-(4-methyl-1H-imidazol-1-yl)pyridin-2-yl]vinyl}-8-phenyl-5,6,7,8-tetrahydro-[1,2,4]triazolo[1,5-a]pyridine,
23) (+)-8-(4-fluorophenyl)-2-{(E)-2-[5-methoxy-6-(4-methyl-1H-imidazol-1-yl)pyridin-3-yl]vinyl}-5,6,7,8-tetrahydro-[1,2,4]triazolo[1,5-a]pyridine,
24) (−)-8-(4-chlorophenyl)-2-{(E)-2-[5-methoxy-6-(4-methyl-1H-imidazol-1-yl)pyridin-3-yl]vinyl}-8-phenyl-5,6,7,8-tetrahydro-[1,2,4]triazolo[1,5-a]pyridine,
25) (+)-8-(3,4-difluorophenyl)-2-{(E)-2-[5-methoxy-6-(4-methyl-1H-imidazol-1-yl)pyridin-3-yl]vinyl}-5,6,7,8-tetrahydro-[1,2,4]triazolo[1,5-a]pyridine,
26) (−)-2-{(E)-2-[5-methoxy-6-(4-methyl-1H-imidazol-1-yl)pyridin-3-yl]vinyl}-8-(3,4,5-trifluorophenyl)-5,6,7,8-tetrahydro-[1,2,4]triazolo[1,5-a]pyridine-8-carbonitrile,
27) (−)-8-(4-chlorophenyl)-2-{(E)-2-[6-methoxy-5-(4-methyl-1H-imidazol-1-yl)pyridin-2-yl]vinyl}-5,6-dihydro-8H-[1,2,4]triazolo[5,1-c][1,4]oxazine,
28) (−)-8-(2,3-difluorophenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine,
29) (−)-8-(2-fluoro-3-methylphenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine,
30) (−)-8-(2-trifluoromethoxyphenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine, 31) (−)-8-(2-trifluoromethyl-4-fluorophenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine, 32) (−)-8-(2-difluoromethoxyphenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine, 33) (−)-8-(2-bromophenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine and 34) (−)-8-(3-fluoro-2-methylphenyl)-2-{(E)-2-[5-methoxy-6-(4-methyl-1H-imidazol-1-yl)pyridin-3-yl]vinyl}-8-(4-trifluoromethylphenyl)-5,6,7,8-tetrahydro-[1,2,4]triazolo[1,5-a]pyridine, 35) (−)-2-{(E)-2-[3-methoxy-4-(4-methyl-1H-imidazol-1-yl)phenyl]vinyl}-8-(2-trifluoromethylphenyl)-5,6,7,8-tetrahydro-[1,2,4]triazolo[1,5-a]pyridine, 36) (−)-2-{(E)-2-[3-methoxy-4-(4-methyl-1H-imidazol-1-yl)phenyl]vinyl}-7-(2-trifluoromethylphenyl)-6,7-dihydro-5H-pyrro[1,2-b][1,2,4]triazole, 37) (−)-8-(5-fluoro-2-trifluoromethylphenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine, 38) (5R,8S)-2-{(E)-2-[6-methoxy-5-(4-methyl-1H-imidazol-1-yl)pyridin-2-yl]vinyl}-5-methyl-8-(2-trifluoromethylphenyl)-5,6,7,8-tetrahydro-[1,2,4]triazolo[1,5-a]pyridine, 39) (S)-2-{(E)-2-[6-methoxy-5-(4-methyl-1H-imidazol-1-yl)pyridine-1-yl]vinyl}-7-(2-trifluoromethylphenyl)-6,7-dihydro-5H-pyrro[1,2-b][1,2,4]triazole, and 40) (S)-7-(5-fluoro-2-trifluoromethyphanyl)-2-{(E)-2-[6-methoxy-5-(4-methyl-1H-imidazol-1-yl)pyridine-1-yl]vinyl}-6,7-dihydro-5H-pyrro[1,2-b][1,2,4]triazole.

Methods for preparing the compound of the general formula (I) of the present invention will be described below.

The compound represented by the general formula (I):

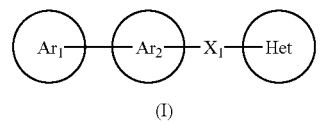

[Formula 29]

(I)

wherein $Ar_1$, $Ar_2$, $X_1$ and Het are as defined above, is synthesized according to a method such as the following General Preparation Method 1 to General Preparation Method 8, for example. It is obvious that, in order to prepare the compound of the present invention conveniently, the method comprises a protection reaction step and a deprotection reaction step appropriately, using a protecting group known to a person skilled in the art which is suitably selected for each step (see T. Greene et al., "Protective Groups in Organic Synthesis", John Wiley & Sons, Inc., New York, 1981). It is also obvious that, in order to prepare the compound of the present invention conveniently, all isomers and isomer mixtures such as geometric isomers which can be generated from the structure of the compound, optical isomers based on asymmetric carbon, stereoisomers, and tautomers can be prepared as a single compound by a technique known to a person skilled in the art which is suitable for each step such as fractional crystallization or column chromatography.

[General Preparation Method 1]

Typically used General Preparation Method 1 for the compound of the general formula (I) of the present invention will be described below.

[Formula 30]
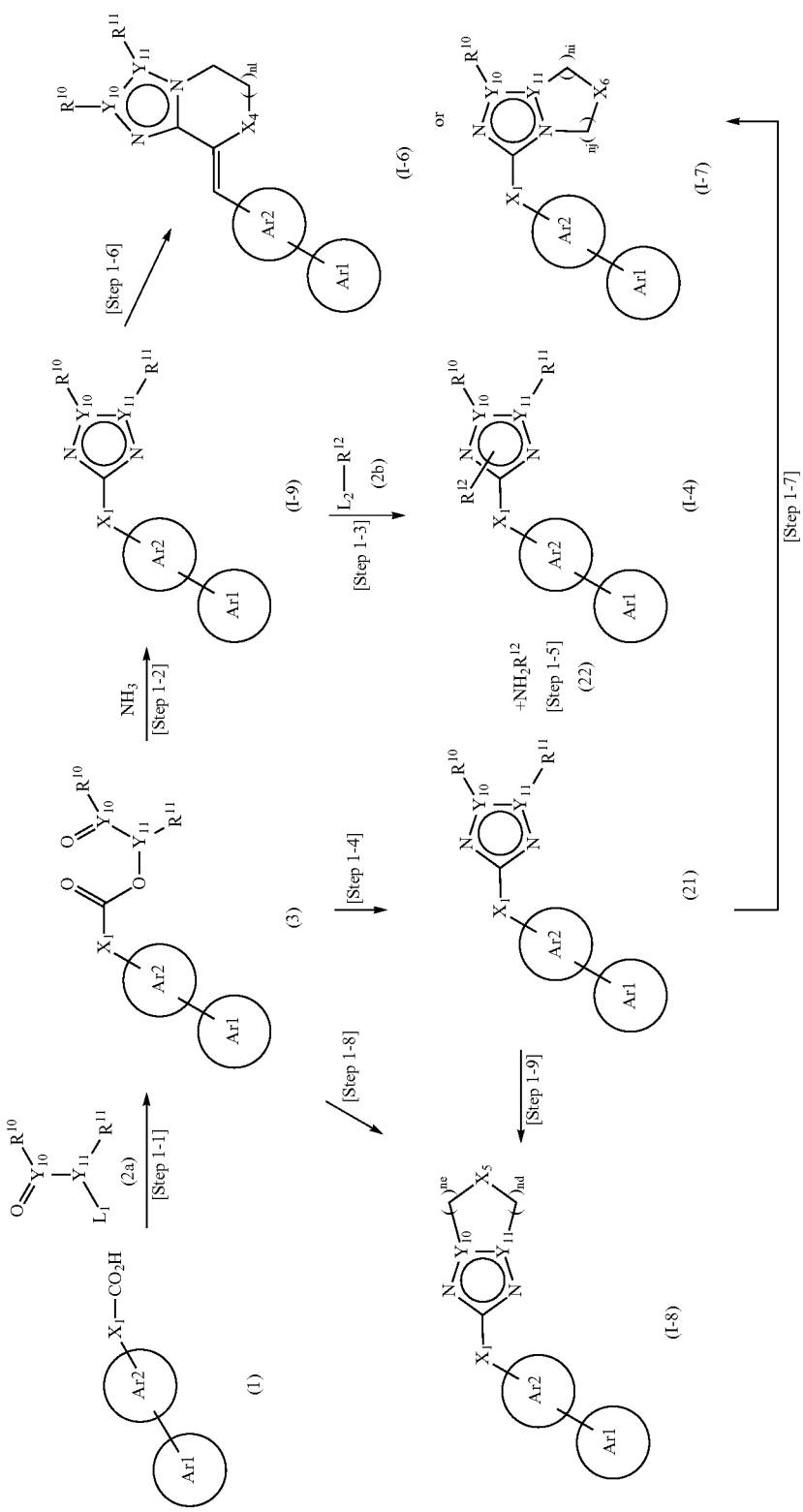

In the formula, the following partial structure (formula III-3, III-4, III-6, III-7 or III-8):

[Formula 31]

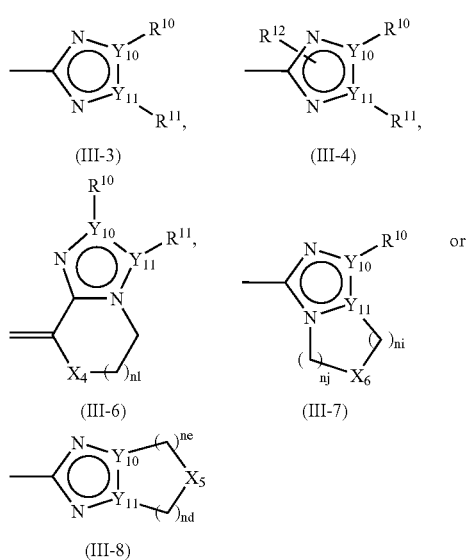

is a partial structure corresponding to the above-described Het, wherein $Ar_1$, $Ar_2$ and $X_1$ are as defined above; $X_5$, $X_6$, $Y_{10}$ and $Y_{11}$ are the same or different and each represent a carbon atom, a nitrogen atom or a sulfur atom; $R^{10}$, $R^{11}$ and $R^{12}$ are the same or different and represent groups selected from the above Substituent Group A1 which may optionally form a ring; $L_1$ represents a halogen atom such as a chlorine atom, a bromine atom or an iodine atom, a sulfonate group such as a methanesulfonate group, a p-toluenesulfonate group or a trifluoromethanesulfonate group, or a hydroxyl group; $L_2$ represents a halogen atom such as a chlorine atom, a bromine atom or an iodine atom, a sulfonate group such as a methanesulfonate group, a p-toluenesulfonate group or a trifluoromethanesulfonate group, a boronic acid group or a boronate group such as a boronic acid pinacol ester group; $X_4$ represents a carbon atom or an oxygen atom; nd, ne, ni and nj each represent an integer of 1 to 2; and nl represents an integer of 0 to 2.

The above General Preparation Method 1 includes a method of condensing a carboxylic acid compound (1) with a compound (2a) in Step 1-1 to convert the carboxylic acid compound (1) into an ester compound (3) and reacting the ester compound (3) with ammonia, an ammonium salt or formamide in Step 1-2 to prepare a compound of the general formula (I-9); a method of reacting the compound of the general formula (I-9) with a compound (2b) in Step 1-3 to prepare a compound of the general formula (I-4); a method of reacting the ester compound (3) with ammonia, an ammonium salt or formamide in Step 1-4 to convert the ester compound (3) into an oxazole compound (21) and then reacting the oxazole compound (21) with an amine compound (22) in Step 1-5 to prepare a compound of the general formula (I-4); a method of preparing a compound of the general formula (I-6) or a compound of the general formula (I-7) from the compound of the general formula (I-9) in Step 1-6; a method of preparing a compound of the general formula (I-6) or a compound of the general formula (I-7) from the oxazole compound (21) in Step 1-7; a method of preparing a compound of the general formula (I-8) from the ester compound (3) and ammonia, an ammonium salt or formamide in Step 1-8; and a method of preparing a compound of the general formula (I-8) from the oxazole compound (21) in Step 1-9.

[Preparation of Compound of General Formula (I-6) or Compound of General Formula (I-7)]

The compound of the general formula (I-6) or the compound of the general formula (I-7) can be prepared from a compound of the general formula (I-9) by intramolecular cyclization reaction according to Step 1-6. Specifically, Step 1-6 as an intramolecular cyclization reaction may employ a known method described in many documents such as N-alkylation reaction (see The Journal of Organic Chemistry, 1977, vol. 42, p. 3925, for example). The compound can also be prepared from an oxazole compound (21) by intramolecular cyclization reaction according to Step 1-7. Specifically, Step 1-7 may employ a method of forming a triazole or imidazole ring and cyclizing the second ring at the same time in the presence or absence of a nitrogen atom source (see The Chemistry of Heterocyclic Compounds. Imidazole and Derivatives, Part I, p. 33, Inters. Publish. 1953, for example).

Step 1-6 is preferably, for example, a method of stirring a compound of the general formula (I-9), wherein $X_1$ is —$CR^1$=$CR^{21}$— and $R^{21}$ represents a C1-6 alkyl group substituted with a halogen atom or a C1-6 alkoxy group substituted with a halogen atom, or $R^{11}$ represents a C1-6 alkyl group (wherein the C1-6 alkyl group is substituted with a halogen atom, a C1-6 alkoxy group substituted with a halogen atom or a C1-6 alkylamino group substituted with a halogen atom), in a solvent in the presence of 1.0 to 10.0 equivalents of a base with respect to the compound of the general formula (I-9). The base used varies according to the starting material and is not particularly limited. Preferable examples of the base include alkali metal hydrides (such as sodium hydride and lithium hydride), alkali metal salts (such as potassium carbonate, sodium carbonate and cesium carbonate), metal alkoxides (such as sodium methoxide and tert-butyl potassium) and organometallic salts (such as lithium diisopropyl amide and lithium hexamethyldisilazane). The solvent used varies according to the starting material, and is not particularly limited insofar as the solvent does not inhibit the reaction and allows the starting material to be dissolved therein to a certain extent. Preferable examples of the solvent include ether solvents such as tetrahydrofuran, 1,4-dioxane and diethyl ether; halogenated solvents such as methylene chloride, 1,2-dichloroethane and chloroform; polar solvents such as N,N-dimethylformamide and N-methylpyrrolidone; nonpolar solvents such as toluene and benzene; and a mixture thereof. The reaction temperature must be a temperature that can complete the reaction without promoting formation of an undesirable by-product, and is preferably −78° C. to 200° C., for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization.

Step 1-7 is preferably, for example, a method of stirring an oxazole compound (21), wherein $X_1$ is —$CR^1$=$CR^{21}$— and $R^{21}$ represents a C1-6 alkyl group substituted with a halogen atom or a C1-6 alkoxy group substituted with a halogen atom, or $R^{11}$ represents a C1-6 alkyl group (wherein the C1-6 alkyl group is substituted with a halogen atom, a C1-6 alkoxy group substituted with a halogen atom or a C1-6 alkylamino group substituted with a halogen atom), in a solvent in the presence of 1.0 to 100 equivalents of ammonia or an ammonium salt such as ammonium acetate with respect to the oxazole compound (21). Step 1-7 may also be a method of stirring an oxazole compound (21), wherein $X_1$ is —$CR^1$=$CR^{21}$— and $R^{21}$ represents a C1-6 alkyl group substituted with an amino group or a C1-6 alkoxy group substituted with an amino group, or $R^{11}$ represents a C1-6 alkyl group (wherein the C1-6 alkyl group is substituted with an amino group, a C1-6 alkoxy group substituted with an amino group or a C1-6 alkylamino group substituted with an amino group), in a solvent. The solvent used is not particularly limited insofar as the solvent does not inhibit the reaction and allows the starting material to be dissolved therein to a certain extent. Preferable examples of the solvent include nonpolar solvents such as toluene and benzene; alcohol solvents such as methanol and ethanol; organic acids such as acetic acid; water; and a mixture thereof. The reaction temperature must be a temperature that can complete the reaction without promoting formation of an undesirable by-product, and is preferably room temperature to 250° C., for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization.

[Preparation of Compound of General Formula (I-8)]

The compound of the general formula (I-8) can be prepared from an ester compound (3) according to Step 1-8 using ammonia, an ammonium salt or formamide as a nitrogen source, for example. The compound can also be prepared from an oxazole compound (21) according to Step 1-9 using ammonia, an ammonium salt or formamide as a nitrogen source, for example. Specifically, Step 1-8 or Step 1-9 varies according to the starting material and is not particularly limited insofar as the conditions are similar to those in this reaction. A known method described in many documents may be used for the reaction (see The Chemistry of Heterocyclic Compounds. Imidazole and Derivatives, Part I, p. 33, Inters. Publish. 1953, for example). The reaction is preferably a method of stirring an ester compound (3) or an oxazole compound (21) and 1.0 to 100.0 equivalents of ammonia or an ammonium salt such as ammonium acetate with respect to the ester compound (3) or the oxazole compound (21) in a solvent, for example. The solvent used is not particularly limited insofar as the solvent does not inhibit the reaction and allows the starting material to be dissolved therein to a certain extent. Preferable examples of the solvent include nonpolar solvents such as toluene and benzene; alcohol solvents such as methanol and ethanol; organic acids such as acetic acid; water; and a mixture thereof. Formamide may optionally be used as a nitrogen atom source and a solvent. The reaction temperature must be a temperature that can complete the reaction without promoting formation of an undesirable by-product, and is preferably room temperature to 250° C., for example. The yield may be improved when the reaction is performed using a tight container. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization.

[Preparation of Compound of General Formula (I-4)]

The compound of the general formula (I-4) can be prepared by reacting a compound of the general formula (I-9) with a compound of the general formula (2b) according to Step 1-3. Specifically, Step 1-3 may employ a known method described in many documents such as N-alkylation reaction (see The Journal of Organic Chemistry, 1977, vol. 42, p. 3925, for example) or N-arylation reaction (see The Journal of Organic Chemistry, 2001, vol. 66, p. 7892; Journal of Medicinal Chemistry, 1981, vol. 24, p. 1139; or Journal of Medicinal Chemistry, 1991, vol. 39, p. 2671, for example).

N-alkylation reaction is preferably, for example, a method of stirring a compound of the general formula (I-9) and 1.0 to 10.0 equivalents of a compound (2b), wherein $L_2$ represents a halogen atom such as a chlorine atom, a bromine atom or an iodine atom or a sulfonate group such as a methanesulfonate group, a p-toluenesulfonate group or a trifluoromethanesulfonate group, with respect to the compound of the general formula (I-9) in a solvent in the presence of 1.0 to 10.0 equivalents of a base with respect to the compound of the general formula (I-9). The base used varies according to the starting material and is not particularly limited. Preferable examples of the base include alkali metal hydrides (such as sodium hydride and lithium hydride), alkali metal salts (such as potassium carbonate, sodium carbonate and cesium carbonate) and metal alkoxides (such as sodium methoxide and potassium tert-butoxide). The solvent used varies according to the starting material, and is not particularly limited insofar as the solvent does not inhibit the reaction and allows the starting material to be dissolved therein to a certain extent. Preferable examples of the solvent include ether solvents such as tetrahydrofuran, 1,4-dioxane and diethyl ether; halogenated solvents such as methylene chloride, 1,2-dichloroethane and chloroform; polar solvents such as N,N-dimethylformamide and N-methylpyrrolidone; nonpolar solvents such as toluene and benzene; and a mixture thereof. The reaction temperature must be a temperature that can complete the reaction without promoting formation of an undesirable by-product, and is preferably 0° C. to 200° C., for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization.

N-arylation reaction may be i) Ullmann reaction, ii) a coupling reaction of an arylboronic acid derivative using a copper compound or iii) nucleophilic substitution reaction.

In the case of i) Ullmann reaction, there are no specific limitations to the reaction conditions. Ullmann reaction is preferably, for example, a method of stirring a compound of the general formula (I-9) and 1.0 to 10.0 equivalents of a compound (2b), wherein $L_2$ represents a halogen atom such as a chlorine atom, a bromine atom or an iodine atom, with respect to the compound of the general formula (I-9) in a solvent in the presence of 0.01 to 1.0 equivalent of a copper reagent such as copper, copper bromide or copper iodide with respect to the compound of the general formula (I-9) with 1.0 to 10.0 equivalents of a base added with respect to the compound of the general formula (I-9). The base used varies according to the starting material and is not particularly limited. Preferable examples of the base include alkali metal salts (such as potassium carbonate, sodium carbonate, potassium acetate, sodium acetate and cesium carbonate) and metal alkoxides (such as sodium methoxide and potassium tert-butoxide). The solvent used varies according to the starting material, the reagent and the like, and is not particularly limited insofar as the solvent does not inhibit the reaction and allows the starting material to be dissolved therein to a certain extent. Preferable examples of the solvent include ether solvents such as tetrahydrofuran, 1,4-dioxane and diethyl ether; halogenated solvents such as methylene chloride, 1,2-dichloroethane and chloroform; alcohol solvents such as amyl alcohol and isopropyl alcohol; polar solvents such as N,N-dimethylformamide and N-methylpyrrolidone; nonpolar solvents such as toluene, benzene and dichlorobenzene; and a mixture thereof. The reaction temperature must be a temperature that can complete the reaction without promoting formation of an undesirable by-product, and is preferably room temperature to 200° C., for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization.

The ii) coupling reaction of an arylboronic acid derivative using a copper compound is preferably, for example, a method of stirring a compound of the general formula (I-9) and 1.0 to 10.0 equivalents of a compound (2b), wherein $L_2$ represents a boronic acid group or a boronate group such as a boronic acid pinacol ester group, with respect to the compound of the general formula (I-9) in a solvent in the presence of 0.01 to 1.0 equivalent of a copper reagent such as copper, copper bromide or copper iodide with respect to the compound of the general formula (I-9) with 1.0 to 10.0 equivalents of a base added with respect to the compound of the general formula (I-9). The base used varies according to the starting material, the solvent used and the like, and is not particularly limited insofar as the base does not inhibit the reaction. Preferable examples of the base include organic bases such as triethylamine, pyridine and tetramethylethylenediamine; alkali metal salts such as potassium carbonate, sodium carbonate, potassium acetate, sodium acetate and cesium carbonate; and metal alkoxides such as sodium methoxide and potassium tert-butoxide. The copper reagent used varies according to the starting material and is not particularly limited. Preferable examples of the copper reagent include copper acetate and di-μ-hydroxo-bis[(N,N,N',N'-tetramethylethylenediamine)copper (II)]chloride. The solvent used varies according to the starting material, the reagent and the like, and is not particularly limited insofar as the solvent does not inhibit the reaction and allows the starting material to be dissolved therein to a certain extent. Preferable examples of the solvent include ether solvents such as tetrahydrofuran, 1,4-dioxane and diethyl ether; halogenated solvents such as methylene chloride, 1,2-dichloroethane and chloroform; polar solvents such as ethyl acetate, N,N-dimethylformamide and N-methylpyrrolidone; nonpolar solvents such as toluene, benzene and dichlorobenzene; and a mixture thereof. The reaction temperature must be a temperature that can complete the reaction without promoting formation of an undesirable by-product, and is preferably room temperature to 200° C., for example. Good results such as reduction in the reaction time and improvement of the yield can be achieved when the reaction is performed in an oxygen atmosphere or air stream. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization.

In iii) nucleophilic substitution reaction, a compound of the general formula (I-9) and 2.0 to 5.0 equivalents of a compound (2b), wherein $L_2$ represents a halogen atom such as a chlorine atom, a bromine atom or an iodine atom or a sulfonate group such as a methanesulfonate group, a p-toluenesulfonate group or a trifluoromethanesulfonate group, with respect to the compound of the general formula (I-9) are preferably stirred in a solvent in the presence or absence of 1.0 to 5.0 equivalents of a base with respect to the compound of the general formula (I-9), for example. The base used varies according to the starting material and is not particularly limited. Preferable examples of the base include sodium hydride, sodium hydroxide, potassium hydroxide, potassium carbonate, sodium carbonate, cesium carbonate, barium carbonate, pyridine, lutidine and triethylamine. The solvent used varies according to the starting material, and is not particularly limited insofar as the solvent does not inhibit the reaction and allows the starting material to be dissolved therein to a certain extent. Preferable examples of the solvent include acetonitrile, tetrahydrofuran, dimethyl sulfoxide, N,N-dimethylformamide and N-methylpyrrolidine. The base may optionally be used as a solvent. The reaction temperature must be a temperature that can complete the reaction without promoting formation of an undesirable by-product, and is preferably room temperature to 150° C., for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique or/and crystallization.

The compound of the general formula (I-4) can be prepared by reacting an oxazole compound (21) with an amine compound (22) according to Step 1-5. Specifically, Step 1-5 varies according to the starting material and is not particularly limited insofar as the conditions are similar to those in this reaction. A known method described in many documents may be used for the reaction (see Heterocyclic Compounds, vol. 5, Wiley, New York, N.Y. 1950, p. 214, for example). Preferably, an oxazole compound (21) and 1.0 to 100.0 equivalents of an amine compound (22) with respect to the oxazole compound (21) are stirred in a solvent, for example. The solvent used is not particularly limited insofar as the solvent does not inhibit the reaction and allows the starting material to be dissolved therein to a certain extent. Preferable examples of the solvent include ether solvents such as tetrahydrofuran, 1,4-dioxane and diethyl ether; halogenated solvents such as methylene chloride, 1,2-dichloroethane and chloroform; alcohol solvents such as amyl alcohol and isopropyl alcohol; polar solvents such as N,N-dimethylformamide and N-methylpyrrolidone; nonpolar solvents such as toluene, benzene and dichlorobenzene; organic acids such as acetic acid; water; and a mixture thereof. The amine compound (22) to be reacted may be used as a solvent. The reaction temperature must be a temperature that can complete the reaction without promoting formation of an undesirable by-product, and is preferably room temperature to 200° C., for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization.

[Preparation of Compound of General Formula (I-9)]

The compound of the general formula (I-1) can be prepared from an ester compound (3) according to Step 1-2 using ammonia, an ammonium salt or formamide as a nitrogen atom source, for example. Specifically, Step 1-2 varies according to the starting material and is not particularly limited insofar as the conditions are similar to those in this reaction. A known method described in many documents may be used for the reaction (see The Chemistry of Heterocyclic Compounds. Imidazole and Derivatives, Part I, p. 33, Inters. Publish. 1953, for example). The reaction is preferably a method of stirring an ester compound (3) and 1.0 to 100.0 equivalents of ammonia or an ammonium salt such as ammonium acetate with respect to the ester compound (3) in a solvent, for example. The solvent used is not particularly limited insofar as the solvent does not inhibit the reaction and allows the starting material to be dissolved therein to a certain extent. Preferable examples of the solvent include nonpolar solvents such as toluene and benzene; alcohol solvents such as methanol and ethanol; organic acids such as acetic acid; water; and a mixture thereof. Formamide may optionally be used as a nitrogen atom source and a solvent. The reaction temperature must be a temperature that can complete the reaction without promoting formation of an undesirable by-product, and is preferably room temperature to 250° C., for example. The yield may be improved when the reaction is performed using a tight container. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization.

[Preparation of Ester Compound (3)]

The ester compound (3) is prepared by condensation reaction of a carboxylic acid compound (1) with a compound (2a) according to Step 1-1. Specifically, Step 1-1 varies according to the starting material and is not particularly limited insofar as the conditions are similar to those in this reaction. A known method described in many documents may be used for the reaction. Preferable examples of the reaction include i) nucleophilic substitution reaction of a carboxylic acid compound (1) with a compound (2a), wherein $L_1$ represents a halogen atom such as a chlorine atom, a bromine atom or an iodine atom or a sulfonate group such as a methanesulfonate group, a p-toluenesulfonate group or a trifluoromethanesulfonate group (see Shin Jikken Kagaku Koza (New Courses in Experimental Chemistry), vol. 22, Yuki Gosei (Organic Synthesis) [IV], edited by The Chemical Society of Japan, Maruzen Co., Ltd., November 1992, p. 49-50, for example) and ii) dehydration condensation reaction of a carboxylic acid compound (1) with a compound (2a) (see Shin Jikken Kagaku Koza (New Courses in Experimental Chemistry), vol. 22, Yuki Gosei (Organic Synthesis) [IV], edited by The Chemical Society of Japan, Maruzen Co., Ltd., November 1992, p. 43-47, for example).

i) Nucleophilic substitution reaction is preferably, for example, a method of stirring a carboxylic acid compound (1) and 1.0 to 10.0 equivalents of a compound (2a) with respect to the carboxylic acid compound (1) in a solvent in the presence of 1.0 to 10.0 equivalents of a base with respect to the carboxylic acid compound (1). The base used varies according to the starting material and is not particularly limited. Preferable examples of the base include alkali metal hydroxides such as sodium hydroxide and lithium hydroxide; alkali metal carbonates such as sodium carbonate; alkali metal salts of alcohols such as sodium methoxide and potassium tert-butoxide; organic bases such as triethylamine, pyridine and diazabicyclononene; organic metals such as butyl lithium and lithium diisobutylamide; alkali metal hydrides such as sodium hydride; and alkali metal ammonium salts such as sodium amide. The solvent used varies according to the starting material and the base used, and is not particularly limited insofar as the solvent does not inhibit the reaction and allows the starting material to be dissolved therein to a certain extent. Preferable examples of the solvent include polar solvents such as nitromethane, acetonitrile, 1-methyl-2-pyrrolidone, N,N-dimethylformamide and dimethyl sulfoxide; ether solvents such as tetrahydrofuran, 1,4-dioxane and 1,2-dimethoxyethane; nonpolar solvents such as benzene, toluene and xylene; alcohol solvents such as ethanol and methanol; halogenated solvents such as chloroform and methylene chloride; water; and a mixed solvent thereof. The reaction temperature must be a temperature that can complete the reaction without promoting formation of an undesirable by-product, and is preferably −78 to 150° C., for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization.

ii) Dehydration condensation reaction is preferably, for example, a method of stirring a carboxylic acid compound (1) and 1.0 to 10.0 equivalents of a compound (2a) with respect to the carboxylic acid compound (1) in a solvent in the presence of 0.1 to 10.0 equivalents of a condensing agent with respect to the carboxylic acid compound (1). The condensing agent used varies according to the starting material and is not particularly limited. Preferable examples of the condensing agent include inorganic acids such as hydrochloric acid and sulfuric acid; organic acids such as p-toluenesulfonic acid and methanesulfonic acid; and 1,3-dicyclohexylcarbodiimide, 1-ethyl-3-(3'-dimethylaminopropyl)carbodiimide, benzotriazol-1-yloxytris(dimethylamino)phosphonium hexafluorophosphate, diethyl cyanophosphonate, bis(2-oxo-3-oxazolidinyl)phosphonic chloride and diphenylphosphoryl azide. Preferably, 1.0 to 5.0 equivalents of N-hydroxysuccinimide, N-hydroxybenzotriazole or dimethylaminopyridine may be added in order to make the reaction efficiently proceed, for example. The solvent used varies according to the starting material and the condensing agent used, and is not particularly limited insofar as the solvent does not inhibit the reaction and allows the starting material to be dissolved therein to a certain extent. Preferable examples of the solvent include halogenated solvents such as chloroform, methylene chloride and 1,2-dichloroethane; polar solvents such as tetrahydrofuran and N,N-dimethylformamide; and a mixed solvent thereof. The reaction temperature must be a temperature that can complete the reaction without promoting formation of an undesirable by-product, and is preferably ice-cold temperature to 150° C., for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique or/and crystallization.

[Preparation of Oxazole Compound (21)]

The oxazole compound (21) can be prepared by reacting an ester compound (3) with ammonia, an ammonium salt or formamide as a nitrogen atom source according to Step 1-4, for example. Specifically, Step 1-4 varies according to the starting material and is not particularly limited insofar as the conditions are similar to those in this reaction. A known method described in many documents may be used for the reaction (see Synthesis, 1998, vol. 9, p. 1298, for example). Preferably, an ester compound (3) and 1.0 to 100.0 equivalents of ammonia or an ammonium salt such as ammonium acetate with respect to the ester compound (3) are stirred in a solvent, for example. The solvent used is not particularly limited insofar as the solvent does not inhibit the reaction and allows the starting material to be dissolved therein to a certain extent. Preferable examples of the solvent include nonpolar solvents such as toluene and benzene; alcohol solvents such as methanol and ethanol; organic acids such as acetic acid;

water; and a mixture thereof. Formamide may optionally be used as a nitrogen atom source and a solvent. The reaction temperature must be a temperature that can complete the reaction without promoting formation of an undesirable by-product, and is preferably room temperature to 250° C., for example. The yield may be improved when the reaction is performed using a tight container. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization.

[Preparation of Compound (2b)]

The compound (2b) is commercially available or can be prepared by a method known to a person skilled in the art (see Shin Jikken Kagaku Koza (New Courses in Experimental Chemistry), vol. 19, Yuki Gosei (Organic Synthesis) [I], edited by The Chemical Society of Japan, Maruzen Co., Ltd., September 1992, p. 363-482; and Shin Jikken Kagaku Koza (New Courses in Experimental Chemistry), vol. 24, Yuki Gosei (Organic Synthesis) [VI], edited by The Chemical Society of Japan, Maruzen Co., Ltd., June 1992, p. 61-90, for example).

[Preparation of Compound (22)]

The compound (22) is commercially available or can be prepared by a method known to a person skilled in the art (see Shin Jikken Kagaku Koza (New Courses in Experimental Chemistry), vol. 20, Yuki Gosei (Organic Synthesis) [II], edited by The Chemical Society of Japan, Maruzen Co., Ltd., July 1992, p. 279-372, for example).

[Preparation of Compound (2a)]

The compound (2a) is commercially available or can be prepared by a method known to a person skilled in the art (see Shin Jikken Kagaku Koza (New Courses in Experimental Chemistry), vol. 19, Yuki Gosei (Organic Synthesis) [I], edited by The Chemical Society of Japan, Maruzen Co., Ltd., September 1992, p. 363-482; and Shin Jikken Kagaku Koza (New Courses in Experimental Chemistry), vol. 20, Yuki Gosei (Organic Synthesis) [II], edited by The Chemical Society of Japan, Maruzen Co., Ltd., July 1992, p. 1-110, for example).

[Preparation of Carboxylic Acid Compound (1)]

[Formula 32]
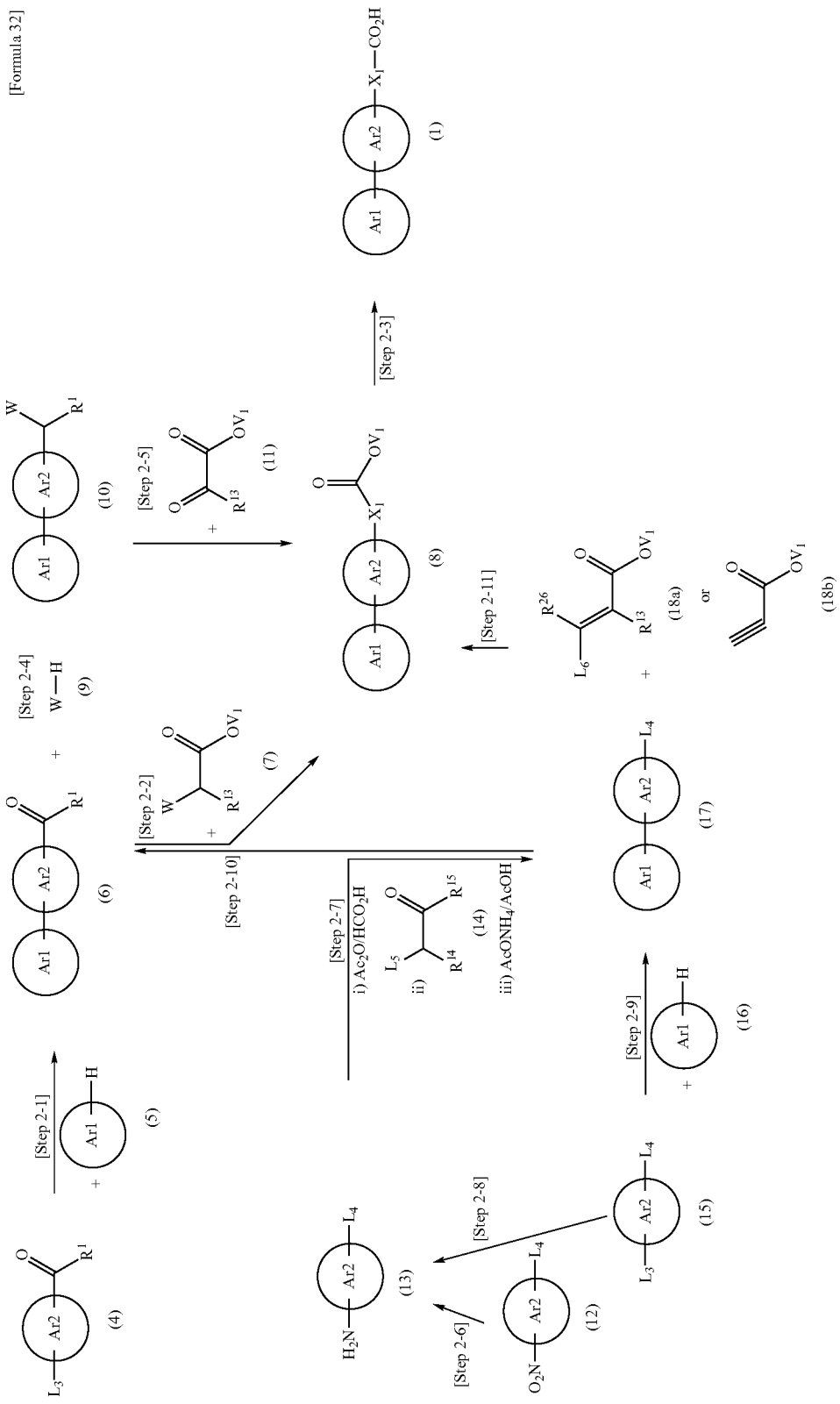

In the formula, $Ar_1$, $Ar_2$, $R^1$ and $X_1$ are as defined above; $V_1$ represents a protecting group for a carboxylic group such as a methyl group, an ethyl group, a benzyl group, an allyl group, a triphenylmethyl group, a tert-butyl group or a tert-butyldimethylsilyl group; $L_3$ and $L_6$ each represent a hydrogen atom, a halogen atom such as a fluorine atom, a chlorine atom, a bromine atom or an iodine atom, a sulfonate group such as a trifluoromethanesulfonate group, a trialkyltin group or a leaving group such as a boronic acid or boronate group; $L_4$ represents a formyl group, an alkanoyl group such as an acetyl group, an alkoxycarbonyl group such as a methyl ester group, a halogen atom such as a fluorine atom, a chlorine atom, a bromine atom or an iodine atom, a sulfonate group such as a trifluoromethanesulfonate group, a trialkyltin group or a boronic acid or boronate group; $L_5$ represents a halogen atom such as a fluorine atom, a chlorine atom, a bromine atom or an iodine atom or a sulfonate group such as a trifluoromethanesulfonate group; W represents a phosphate group such as a diethylphosphonyl group, a diphenylphosphonyl group or a bis(2,2,2-trifluoroethyl)phosphonyl group, a phosphonium salt such as triphenylphosphonium bromide or a silyl group such as a trimethylsilyl group; $R^{26}$ is as defined for the $R^1$; $R^{13}$ is as defined for the $R^2$; and $R^{14}$ and $R^{15}$ each represent a C1-6 alkyl group.

The carboxylic acid compound (1) is prepared by hydrolysis of an ester compound (8) according to Step 2-3. Specifically, Step 2-3 varies according to the starting material and is not particularly limited insofar as the conditions are similar to those in this reaction. A known method described in many documents may be used for the reaction (see Shin Jikken Kagaku Koza (New Courses in Experimental Chemistry), vol. 22, Yuki Gosei (Organic Synthesis) [IV], edited by The Chemical Society of Japan, Maruzen Co., Ltd., November 1992, p. 6-11, for example). Preferably, an ester compound (8) is stirred in a solvent in the presence of 1.0 to 100.0 equivalents of a base or acid with respect to the ester compound (8), for example. The base used varies according to the starting material and is not particularly limited. Preferable examples of the base include sodium hydride, sodium hydroxide, potassium hydroxide, potassium carbonate, sodium carbonate, cesium carbonate and barium carbonate. The acid used varies according to the starting material and is not particularly limited. Preferable examples of the acid include inorganic acids such as hydrochloric acid and sulfuric acid; organic acids such as trifluoroacetic acid and p-toluenesulfonic acid; and Lewis acids such as boron trichloride. The solvent used varies according to the starting material, and is not particularly limited insofar as the solvent does not inhibit the reaction and allows the starting material to be dissolved therein to a certain extent. Preferable examples of the solvent include alcohol solvents such as methanol, ethanol and ethylene glycol; ether solvents such as tetrahydrofuran; halogenated solvents such as dichloromethane and chloroform; water; and a mixed solvent thereof. In the case of acid hydrolysis, an organic acid such as acetic acid or formic acid may be used as a solvent. The reaction temperature must be a temperature that can complete the reaction without promoting formation of an undesirable by-product, and is preferably room temperature to 100° C., for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique or/and crystallization.

[Preparation of Ester Compound (8)]

The ester compound (8) can be prepared as shown by the above reaction formula, but the preparation is not limited thereto. Specifically, the ester compound (8) can be prepared by reacting a compound (4) with a compound (5) in Step 2-1 to obtain a carbonyl compound (6) and then condensing the carbonyl compound (6) by condensation reaction such as Horner-Emmons reaction, Wittig reaction or Peterson reaction in Step 2-2, for example. Alternatively, the ester compound (8) can be prepared by subjecting a carbonyl compound (6) as a starting material to Step 2-4 to prepare a compound (10) and condensing the compound (10) with a compound (11) by condensation reaction such as Horner-Emmons reaction, Wittig reaction or Peterson reaction in Step 2-5. Alternatively, the ester compound (8) can be prepared by forming $Ar_1$ in a compound (17) from an amino compound (13) as a starting material through three-stage reaction in Step 2-7 and then performing coupling reaction of the compound (17) with a compound (18a) or compound (18b) according to Step 2-11. The ester compound (8) can also be prepared by converting a compound (15) as a starting material into a compound (17) according to Step 2-9 and then subjecting the compound (17) to Step 2-11.

[Conversion of Carbonyl Compound (6) into Ester Compound (8) and Conversion of Compound (10) into Ester Compound (8)]

A carbonyl compound (6) can be converted into the ester compound (8) and a compound (10) can be converted into the ester compound (8) by a method known to a person skilled in the art. For example, the ester compound (8) can be prepared from a carbonyl compound (6) and a compound (7) according to Step 2-2. Alternatively, the ester compound (8) can be prepared from a compound (10) and a compound (11) according to Step 2-5. Specifically, coupling reaction in Step 2-2 or Step 2-5 varies according to the starting material and is not particularly limited insofar as the conditions are similar to those in this reaction. A method known to a person skilled in the art may be used for the reaction. Preferable examples of the method include Wittig reaction, Horner-Emmons reaction and Peterson reaction (see Shin Jikken Kagaku Koza (Courses in Experimental Chemistry), vol. 19, Yuki Gosei (Organic Synthesis) [I], edited by The Chemical Society of Japan, Maruzen Co., Ltd., June 1992, p. 57-85, for example).

In Wittig reaction, a compound (7) or compound (10), wherein W represents a phosphonium salt, and 0.5 to 2.0 equivalents of a carbonyl compound (6) or a compound (11) with respect to the compound (7) or compound (10) are preferably stirred in a solvent in the presence of 1.0 to 5.0 equivalents of a base with respect to the compound (7) or compound (10), for example. This reaction may be a method of first treating a compound (7) or compound (10) and a base to form a phosphorus ylide and then adding a carbonyl compound (6) or a compound (11) to the ylide; or a method of adding a base in the presence of a compound (7) or compound (10) and a carbonyl compound (6) or a compound (11). This reaction is preferably performed in the presence of a solvent from the viewpoint of handleability and stirring efficiency. The solvent used varies according to the starting material and the base used, and is not particularly limited insofar as the solvent does not inhibit the reaction and allows the starting material to be dissolved therein to a certain extent. Preferable examples of the solvent include polar solvents such as nitromethane, acetonitrile, 1-methyl-2-pyrrolidone, N,N-dimethylformamide and dimethyl sulfoxide; ether solvents such as tetrahydrofuran, 1,4-dioxane and 1,2-dimethoxyethane; nonpolar solvents such as benzene, toluene and xylene; alcohol solvents such as ethanol and methanol; halogenated solvents such as chloroform and methylene chloride; water; and a mixed solvent thereof. The base used varies according to the starting material and the solvent. Preferable examples of the base include alkali metal hydroxides such as sodium hydroxide and lithium hydroxide; alkali metal carbonates such as sodium carbonate; alkali metal salts of alcohols such as sodium methoxide and potassium tert-butoxide; organic bases such as triethylamine, pyridine and diazabicyclononene; organic metals such as butyl lithium and lithium diisobutylamide; and alkali metal hydrides such as sodium hydride. The reaction temperature must be a temperature that can complete the reaction without promoting formation of an undesirable by-product, and is preferably −78 to 150° C., for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization.

In Horner-Emmons reaction, a compound (7) or compound (10), wherein W represents a phosphate group, and 0.5 to 2.0 equivalents of a carbonyl compound (6) or a compound (11) with respect to the compound (7) or compound (10) are preferably stirred in a solvent in the presence of 1.0 to 5.0 equivalents of a base with respect to the compound (7) or compound (10), for example. This reaction may be a method of first treating a compound (7) or compound (10) and a base to form a carbanion and then adding a carbonyl compound (6) or a compound (11) to the carbanion; or a method of adding a base in the presence of a compound (7) or compound (10) and a carbonyl compound (6) or a compound (11). This reaction is preferably performed in the presence of a solvent from the viewpoint of handleability and stirring efficiency. The solvent used varies according to the starting material and the base used, and is not particularly limited insofar as the solvent does not inhibit the reaction and allows the starting material to be dissolved therein to a certain extent. Preferable examples of the solvent include polar solvents such as 1-methyl-2-pyrrolidone, N,N-dimethylformamide and dimethyl sulfoxide; ether solvents such as tetrahydrofuran, 1,4-dioxane and 1,2-dimethoxyethane; nonpolar solvents such as benzene, toluene and xylene; alcohol solvents such as ethanol and methanol; water; and a mixed solvent thereof. The base used varies according to the starting material and the solvent. Preferable examples of the base include alkali metal hydroxides such as sodium hydroxide and lithium hydroxide; alkali metal carbonates such as sodium carbonate; alkali metal salts of alcohols such as sodium methoxide and potassium tert-butoxide; organic bases such as triethylamine, pyridine and diazabicyclononene; organic metals such as butyl lithium and lithium diisobutylamide; alkali metal hydrides such as sodium hydride; and alkali metal ammonium salts such as sodium amide. The reaction temperature must be a temperature that can complete the reaction without promoting formation of an undesirable by-product, and is preferably −78 to 150° C., for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization.

In Peterson reaction, a compound (7) or compound (10), wherein W represents a silyl group, and 0.5 to 2.0 equivalents of a carbonyl compound (6) or a compound (11) with respect to the compound (7) or compound (10) are preferably stirred in a solvent in the presence of 1.0 to 5.0 equivalents of a base with respect to the compound (7) or compound (10), for example. This reaction may be a method of first treating a compound (7) or compound (10) and a base to form a carbanion and then adding a carbonyl compound (6) or a compound (11) to the carbanion; or a method of adding a base in the presence of a compound (7) or compound (10) and a carbonyl compound (6) or a compound (11). This reaction is preferably performed in the presence of a solvent from the viewpoint of handleability and stirring efficiency. The solvent used varies according to the starting material and the base used, and is not particularly limited insofar as the solvent does not inhibit the reaction and allows the starting material to be dissolved therein to a certain extent. Preferable examples of the solvent include polar solvents such as 1-methyl-2-pyrrolidone, N,N-dimethylformamide and dimethyl sulfoxide; ether solvents such as tetrahydrofuran, 1,4-dioxane and 1,2-dimethoxyethane; nonpolar solvents such as benzene, toluene and xylene; alcohol solvents such as ethanol and methanol; water; and a mixed solvent thereof. The base used varies according to the starting material and the solvent. Preferable examples of the base include alkali metal hydroxides such as sodium hydroxide and lithium hydroxide; alkali metal carbonates such as sodium carbonate; alkali metal salts of alcohols such as sodium methoxide and potassium tert-butoxide; organic bases such as triethylamine, pyridine and diazabicyclononene; organic metals such as butyl lithium and lithium diisobutylamide; alkali metal hydrides such as sodium hydride; and alkali metal ammonium salts such as sodium amide. The reaction temperature must be a temperature that can complete the reaction without promoting formation of an undesirable by-product, and is preferably −78 to 150° C., for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization.

[Conversion of Compound (17) into Ester Compound (8)]

A compound (17) can be converted into the ester compound (8) by a method known to a person skilled in the art. The ester compound (8) can be prepared from a compound (17) together with a compound (18a) or compound (18b) according to Step 2-11, for example. Specifically, the coupling reaction in Step 2-11 varies according to the starting material and is not particularly limited insofar as the conditions are similar to those in this reaction. A method known to a person skilled in the art may be used for the reaction. Preferable examples of the method include Mizoroki-Heck reaction (see R. F. Heck, "Org. Reactions.", 1982, vol. 27, p. 345, for example), Suzuki-Miyaura reaction (see A. Suzuki, "Chem. Rev.", 1995, vol. 95, p. 2457, for example), Sonogashira reaction (see K. Sonogashira, "Comprehensive Organic Synthesis", 1991, vol. 3, p. 521) and Stille coupling reaction (see J. K. Stille, "Angew. Chem. Int. Ed. Engl.", 1986, vol. 25, p. 508, for example).

In Mizoroki-Heck reaction, a halogen compound or triflate compound (17), wherein $L_4$ represents a chlorine atom, a bromine atom, an iodine atom or a sulfonate group such as a trifluoromethanesulfonate group, is preferably coupled with 1.0 to 5.0 equivalents of an alkene compound (18a; wherein $L_6$ is a hydrogen atom) with respect to the compound (17) in the presence of 0.01 to 0.2 equivalent of a transition metal catalyst with respect to the compound (17), for example. This reaction is preferably performed in the presence of a solvent from the viewpoint of handleability and stirring efficiency. The solvent used varies according to the starting material and the transition metal catalyst used, and is not particularly limited insofar as the solvent does not inhibit the reaction and allows the starting material to be dissolved therein to a certain extent. Preferable examples of the solvent include acetonitrile, tetrahydrofuran, 1,4-dioxane, 1,2-dimethoxyethane, benzene, toluene, xylene, 1-methyl-2-pyrrolidone and N,N-dimethylformamide. The reaction temperature must be a temperature that can complete the coupling reaction, and is preferably room temperature to 150° C. This reaction is performed preferably in an inert gas atmosphere, and more preferably in a nitrogen or argon atmosphere. The transition metal catalyst is preferably a palladium complex, for example, and more preferably a known palladium complex such as palladium (II) acetate, dichlorobis(triphenylphosphine)palladium (II), tetrakis(triphenylphosphine)palladium (0) or tris(dibenzylideneacetone)dipalladium (0). It is also preferable to appropriately add a phosphorus ligand (preferably triphenylphosphine, tri-o-tolylphosphine, tri-tert-butylphosphine or 2-(di-tert-butylphosphino)biphenyl, for example) in order to make the reaction efficiently proceed. A preferable result may be achieved in the presence of a base. The base used is not particularly limited insofar as the base is used in a coupling reaction similar to this reaction. Preferable examples of the base include triethylamine, N,N-diisopropylethylamine, N,N-dicyclohexylmethylamine and tetrabutylammonium chloride. Under preferable reaction conditions, the reaction is completed in 1 to 24 hours, and the progress of the reaction can be monitored by a known chromatography technique.

In Suzuki-Miyaura reaction, a halogen compound or trifluoromethanesulfonate compound (17), wherein $L_4$ represents a chlorine atom, a bromine atom, an iodine atom or a sulfonate group such as a trifluoromethanesulfonate group, is preferably coupled with 1.0 to 5.0 equivalents of a boronic acid compound or boronate compound (18a; wherein $L_6$ is a boronic acid or boronate group) with respect to the compound (17) in the presence of 0.01 to 0.5 equivalent of a transition metal catalyst with respect to the compound (17), for example. This reaction is preferably performed in the presence of a solvent from the viewpoint of handleability and stirring efficiency. The solvent used varies according to the starting material and the transition metal catalyst used, and is not particularly limited insofar as the solvent does not inhibit the reaction and allows the starting material to be dissolved therein to a certain extent. Preferable examples of the solvent include acetonitrile, tetrahydrofuran, 1,4-dioxane, 1,2-dimethoxyethane, benzene, toluene, xylene, 1-methyl-2-pyrrolidone, N,N-dimethylformamide, water and a mixed solvent thereof. The reaction temperature must be a temperature that can complete the coupling reaction, and is preferably room temperature to 200° C. This reaction is performed preferably in an inert gas atmosphere, and more preferably in a nitrogen or argon atmosphere. Under preferable reaction conditions, the reaction is completed in 1 to 24 hours, and the progress of the reaction can be monitored by a known chromatography technique. The transition metal catalyst is preferably a known palladium complex, and more preferably a known palladium complex such as palladium (II) acetate, dichlorobis(triphenylphosphine)palladium (II), tetrakis (triphenylphosphine)palladium (0), or tris(dibenzylideneacetone)dipalladium (0). A phosphorus ligand (preferably triphenylphosphine, tri-o-tolylphosphine, tricyclohexylphosphine, or tri-tert-butylphosphine, for example) may be appropriately added in order to make the reaction efficiently proceed. A quaternary ammonium salt, preferably tetrabutylammonium chloride or tetrabutylammonium bromide, for example, may also be appropriately added in order to make the reaction efficiently proceed. In this reaction, a preferable result may be achieved in the presence of a base. The base used at this time varies according to the starting material, the solvent used and the like, and is not particularly limited. Preferable examples of the base include sodium hydroxide, barium hydroxide, potassium fluoride, cesium fluoride, sodium carbonate, potassium carbonate, cesium carbonate and potassium phosphate. Under preferable reaction conditions, the reaction is completed in 1 to 24 hours, and the progress of the reaction can be monitored by a known chromatography technique. In this reaction, the desired ester compound (8) can be efficiently obtained even when the compound (18a) is a halide or a trifluoromethanesulfonate compound, wherein $L_6$ is a chlorine atom, a bromine atom, an iodine atom or a trifluoromethanesulfonate group, for example, and the compound (17) is a boronic acid compound or boronate compound, wherein $L_4$ is a boronic acid or boronate group, for example.

The reaction conditions in Sonogashira reaction vary according to the starting material, the solvent and the transition metal catalyst, and are not particularly limited insofar as the conditions are similar to those in this reaction. A method known to a person skilled in the art may be used for the reaction. Preferably, a compound (17), wherein $L_4$ represents a chlorine atom, a bromine atom, an iodine atom or a sulfonate group such as a trifluoromethanesulfonate group, and 1.0 to 5.0 equivalents of an alkyne compound (18b) with respect to the compound (17) are stirred in a solvent, for example. Preferable examples of the solvent used include acetonitrile, tetrahydrofuran, 1,4-dioxane, 1,2-dimethoxyethane, benzene, toluene, xylene, 1-methyl-2-pyrrolidone, N,N-dimethylformamide and dimethyl sulfoxide. More preferable examples of the solvent include tetrahydrofuran, 1,4-dioxane, 1-methyl-2-pyrrolidone and N,N-dimethylformamide. The reaction temperature must be a temperature that can complete the coupling reaction, and is preferably room temperature to 150° C. This reaction is performed preferably in an inert gas atmosphere, and more preferably in a nitrogen or argon atmosphere. Under preferable reaction conditions, the reaction is completed in 1 to 24 hours, and the progress of the reaction can be monitored by a known chromatography technique. The transition metal catalyst is preferably 0.01 to 0.5 equivalent with respect to the compound (17) of a known palladium complex, and more preferably a known palladium complex such as palladium (II) acetate, dichlorobis(triphenylphosphine)palladium (II), tetrakis(triphenylphosphine) palladium (0) or tris(dibenzylideneacetone)dipalladium (0). A phosphorus ligand (preferably triphenylphosphine, tri-o-tolylphosphine or tri-tert-butylphosphine, for example) may be appropriately added, for example, in order to make the reaction efficiently proceed. In the reaction, a metal halide or a quaternary ammonium salt, preferably copper (I) iodide, lithium chloride, tetrabutylammonium fluoride or silver (I) oxide, for example, may be added. A preferable result may be achieved in the presence of a base. The base used here is not particularly limited insofar as the base is used in a coupling reaction similar to this reaction. Preferable examples of the base include basic solvents such as diethylamine, triethylamine, N,N-diisopropylethylamine, piperidine and pyridine.

In Stille coupling reaction, a trialkyltin compound (17), wherein $L_4$ represents an alkyltin group, and 1.0 to 5.0 equivalents of a halide or a trifluoromethanesulfonate compound (18a), wherein $L_6$ represents a chlorine atom, a bromine atom, an iodine atom or a trifluoromethanesulfonate group, with respect to the compound (17) are preferably stirred in a solvent in the presence of 0.01 to 0.2 equivalent of a transition metal catalyst with respect to the compound (17), for example. It is preferable to appropriately use 0.1 to 5.0 equivalents of copper (I) halide or/and lithium chloride in order to make the reaction efficiently proceed. Preferable examples of the solvent used in this reaction include toluene, xylene, N,N-dimethylformamide, N,N-dimethylacetamide, 1-methyl-2-pyrrolidone and dimethyl sulfoxide. The reaction temperature must be a temperature that can complete the coupling reaction, and is preferably room temperature to 150° C. The preferable transition metal catalyst is a palladium complex, preferably a known palladium complex such as palladium (II) acetate, dichlorobis(triphenylphosphine)palladium (II), tetrakis(triphenylphosphine)palladium (0) or tris(dibenzylideneacetone)dipalladium (0), for example, and more preferably tetrakis(triphenylphosphine)palladium (0) or tris(dibenzylideneacetone)dipalladium (0), for example. This reaction is performed preferably in an inert gas atmosphere, and more preferably in a nitrogen or argon atmosphere. Under preferable reaction conditions, the reaction is completed in 1 to 24 hours, and the progress of the reaction can be monitored by a known chromatography technique.

[Preparation of Carbonyl Compound (6)]

The carbonyl compound (6) can be prepared from a compound (4) as a starting material according to Step 2-1, for example. Specifically, Step 2-1 varies according to the starting material and is not particularly limited insofar as the conditions are similar to those in this reaction. A method known to a person skilled in the art may be used for the reaction. For example, a compound (4) and 1.0 to 5.0 equivalents of a compound (5) with respect to the compound (4) are stirred in a solvent in the presence or absence of 1.0 to 5.0 equivalents of a base with respect to the compound (4) (see D. D. Davey et al., "J. Med. Chem.", 1991, vol. 39, p. 2671-2677). Preferable examples of the base used include sodium hydride, sodium hydroxide, potassium hydroxide, potassium carbonate, sodium carbonate, cesium carbonate, barium carbonate, pyridine, lutidine and triethylamine. The solvent used varies according to the starting material, and is not particularly limited insofar as the solvent does not inhibit the reaction and allows the starting material to be dissolved therein to a certain extent. Preferable examples of the solvent include acetonitrile, tetrahydrofuran, dimethyl sulfoxide, N,N-dimethylformamide and N-methylpyrrolidine. The base may optionally be used as a solvent. The reaction temperature must be a temperature that can complete the reaction without promoting formation of an undesirable by-product, and is preferably room temperature to 150° C., for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique or/and crystallization.

The carbonyl compound (6) can also be prepared from a compound (17) as a starting material according to Step 2-10, for example. Specifically, Step 2-10 varies according to the starting material and is not particularly limited insofar as the conditions are similar to those in this reaction. A method known to a person skilled in the art may be used for the reaction. For example, it is possible to use a two-stage method of converting a compound (17), wherein $L_4$ represents a chlorine atom, a bromine atom, an iodine atom or a sulfonate group such as a trifluoromethanesulfonate group, into a vinyl compound by Stille coupling reaction using 1.0 to 5.0 equivalents of a vinyltin compound with respect to the compound (17) and then oxidizing the carboxylic acid by ozone oxidation reaction (see S. S. Chandran et al., "Bioorg. Med. Chem. Lett.", 2001, vol. 11, p. 1493-1496, for example). It is also possible to use carbon monoxide insertion reaction using a transition metal catalyst (see T. Okano et al., "Bull. Chem. Soc. Jpn.", 1994, vol. 67, p. 2329-2332, for example).

[Preparation of Compound (4)]

The compound (4) is commercially available or can be obtained by a technique known to a person skilled in the art. If not commercially available, the preferable compound (4), wherein $L_3$ represents a fluorine atom, a chlorine atom or a bromine atom, can be obtained by oxidizing a corresponding alcohol compound by an oxidation reaction known to a person skilled in the art; or the carbonyl compound can be obtained by reducing a corresponding ester compound by a known reduction reaction.

[Preparation of Compound (5)]

The compound (5) used in this step is commercially available or can be obtained by a technique known to a person skilled in the art. (see M. Komoto et al., "Agr. Biol. Chem.", 1968, vol. 32, p. 983-987; or J. M. Kokosa et al., "J. Org. Chem.", 1983, vol. 48, p. 3605-3607, for example).

[Preparation of Compound (7)]

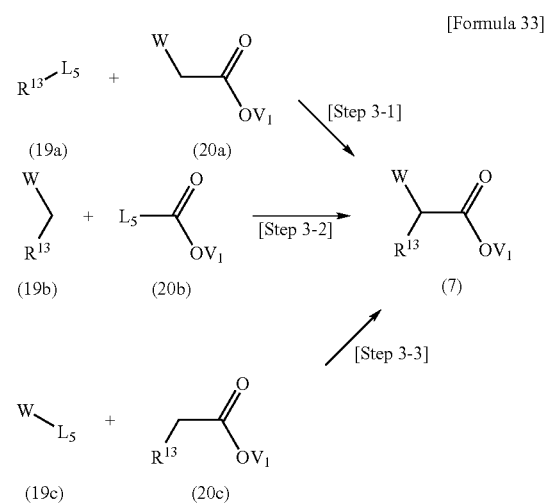

[Formula 33]

In the formula $R^{13}$, W, $L_5$ and $V_1$ are as defined above.

The above reaction formula shows an example of a method for preparing the phosphonate compound (7). Specifically, the phosphonate compound (7) is commercially available or can be obtained by a method shown in the above Step 3-1 to Step 3-3 and known to a person skilled in the art (see C. Patois et al., "Synth. Commun.", 1991, vol. 22, p. 2391; or J. A. Jackson et al., "J. Org. Chem.", 1989, vol. 20, p. 5556, for example). Step 3-1 is a step of obtaining the desired phosphonate compound (7) by stirring a phosphonate compound (20a) and 1.0 to 2.0 equivalents of an alkyl halide compound (19a) with respect to the phosphonate compound (20a) in a solvent in the presence of 1.0 to 1.5 equivalents of a base with respect to the phosphonate compound (20a) to introduce $R_{13}$, for example. Step 3-2 is a step of obtaining the desired phosphonate compound (7) by stirring a phosphonate compound (19b) and 1.0 to 2.0 equivalents of a halogenated formate compound (20b) with respect to the phosphonate compound (19b) in a solvent in the presence of 1.0 to 1.5 equivalents of a base with respect to the phosphonate compound (19b). Step 3-3 is a step of obtaining the desired phosphonate compound (7) by stirring a phosphonic acid halide compound (19c) and 1.0 to 2.0 equivalents of an ester compound (20c) with respect to the phosphonic acid halide compound (19c) in a solvent in the presence of 1.0 to 1.5 equivalents of a base with respect to the phosphonic acid halide compound (19c). The base used varies according to the starting material and is not particularly limited. Preferable examples of the base include sodium hydride, n-butyl lithium, lithium diisopropylamide, lithium bis(trimethylsilyl)amide and sodium bis(trimethylsilyl) amide. The solvent used varies according to the starting material, and is not particularly limited insofar as the solvent does not inhibit the reaction and allows the starting material to be dissolved therein to a certain extent. Preferable examples of the solvent include hexane, toluene, diethyl ether, tetrahydrofuran, N,N-dimethylformamide, hexamethylphosphoric triamide and a mixed solvent thereof. The reaction temperature must be a temperature that can complete the reaction without promoting formation of an undesirable by-product, and is preferably −78° C. to 100° C. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique or/and crystallization. The desired phosphonate compound (7) can be efficiently obtained by modification of $R_{13}$ by a technique known to a person skilled in the art.

The alkyl halide compound (19a), phosphonate compound (19b), phosphonic acid halide compound (19c), phosphonate compound (20a), halogenated formate compound (20b) and ester compound (20c) used in this step are commercially available or can be obtained by a technique known to a person skilled in the art.

[Preparation of Compound (10)]

The compound (10) can be prepared from a compound (6) and a compound (9) according to Step 2-4. Specifically, Step 2-4 varies according to the starting material and is not particularly limited insofar as the conditions are similar to those in this reaction. A method known to a person skilled in the art may be used for the reaction (see Journal of the American Chemistry, 1961, vol. 83, p. 173, for example). Preferably, a compound (6) and 1.0 to 10.0 equivalents of a compound (9) with respect to the compound (6) are stirred in a solvent in the presence of 1.0 to 10.0 equivalents of a base with respect to the compound (6), for example. The base used varies according to the starting material and is not particularly limited. Preferable examples of the base include organic bases such as 1,8-diazabicyclo[5,4,0]-7-undecene and diisopropylamine; and alkali metal salts such as potassium carbonate and sodium carbonate. The solvent used varies according to the starting material, and is not particularly limited insofar as the solvent does not inhibit the reaction and allows the starting material to be dissolved therein to a certain extent. Preferable examples of the solvent include hexane, toluene, diethyl ether, tetrahydrofuran, N,N-dimethylformamide, hexamethylphosphoric triamide and a mixed solvent thereof. The reaction temperature must be a temperature that can complete the reaction without promoting formation of an undesirable by-product, and is preferably −78° C. to 100° C. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique or/and crystallization.

[Preparation of Compound (9)]

The compound (9) used in this step is commercially available or can be obtained by a technique known to a person skilled in the art.

[Preparation of Compound (11)]

The compound (11) used in this step is commercially available or can be obtained by a technique known to a person skilled in the art.

[Preparation of Amine Compound (13)]

The amine compound (13) is commercially available or can be obtained by a technique known to a person skilled in the art. Preferably, the compound can be prepared from a nitro compound (12) as a starting material according to Step 2-6. Specifically, reduction reaction in Step 2-6 varies according to the starting material and is not particularly limited insofar as the conditions are similar to those in this reaction. A method known to a person skilled in the art may be used for the reaction (see Shin Jikken Kagaku Koza (New Courses in Experimental Chemistry), vol. 14, Yuki Kagobutsu No Gosei To Hannou (Synthesis and Reaction of Organic Compounds) [III], edited by The Chemical Society of Japan, Maruzen Co., Ltd., February 1978, p. 1333-1341, for example). The reaction is preferably a catalytic reduction method using a metal catalyst or a reduction method using a metal, for example. The catalytic reduction method is preferably performed in a hydrogen atmosphere at normal pressure to 100 atm. Preferable examples of the metal catalyst used in this reaction include platinum, platinum oxide, platinum black, Raney nickel and palladium-carbon. The solvent used in the present reaction varies according to the starting material, and is not particularly limited insofar as the solvent does not inhibit the reaction and allows the starting material to be dissolved therein to a certain extent. Preferable examples of the solvent include methanol, ethanol, diethyl ether, tetrahydrofuran, methylene chloride, chloroform and ethyl acetate. An acidic substance such as acetic acid or hydrochloric acid may be appropriately added in order to make the reaction efficiently proceed. The reduction method using a metal preferably employs zinc, iron or tin, for example, and is preferably performed under acidic conditions using hydrochloric acid, acetic acid or ammonium chloride, for example. The solvent used in the present reaction varies according to the starting material, and is not particularly limited insofar as the solvent does not inhibit the reaction and allows the starting material to be dissolved therein to a certain extent. Preferable examples of the solvent include methanol, ethanol and 2-propanol. The reaction temperature must be a temperature that can complete the reaction without promoting formation of an undesirable by-product, and is preferably room temperature to 100° C. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique or/and crystallization.

The preferable amine compound (13) can also be prepared from a compound (15) as a starting material which is commercially available or can be obtained by a technique known to a person skilled in the art, according to coupling reaction in Step 2-8. Specifically, the coupling reaction in Step 2-8 varies according to the starting material and is not particularly limited insofar as the conditions are similar to those in this reaction. A method known to a person skilled in the art may be used for the reaction. Preferably, for example, it is possible to use a two-stage method of performing coupling reaction of benzophenone imine using a transition metal catalyst and then performing a known benzophenone removal reaction treatment (see S. L. Buchwald et al., "Tetrahedron Lett.", 1997, vol. 38, p. 6367-6370; or J. F. Hartwig et al., "J. Am. Chem. Soc.", 1998, vol. 120, p. 827-828, for example). In the coupling reaction of benzophenone imine, a compound (15) and 1.0 to 10.0 equivalents of benzophenone imine with respect to the compound (15) are stirred in a solvent in the presence of 0.01 to 0.2 equivalent of a catalyst with respect to the compound (15). Preferable examples of the catalyst that can be used include known palladium complexes such as palladium (II) acetate, dichlorobis(triphenylphosphine)palladium (II), tetrakis(triphenylphosphine)palladium (0) and tris (dibenzylideneacetone)dipalladium (0); and known nickel catalysts such as (1,5-cyclooctadiene)nickel (0). Preferably, a phosphorus ligand such as triphenylphosphine, tri-o-tolylphosphine, tri-tert-butylphosphine, 2-(di-tert-butylphosphino)biphenyl, 2,2'-bis(diphenylphosphino)-1,1'-binaphthyl, 1,2-bis(diphenylphosphino)ethane or 1,1'-bis(diphenylphosphino)ferrocene may be appropriately added in order to make the reaction efficiently proceed, for example. A preferable result may be achieved in the presence of a base. The base used is not particularly limited insofar as the base is used in a coupling reaction similar to this reaction. Preferable examples of the base include sodium hydroxide, barium hydroxide, potassium fluoride, cesium fluoride, sodium carbonate, potassium carbonate, cesium carbonate, potassium phosphate and sodium tert-butoxide. The solvent used varies according to the starting material and the transition metal catalyst used, and is not particularly limited insofar as the solvent does not inhibit the reaction and allows the starting material to be dissolved therein to a certain extent. Preferable examples of the solvent include acetonitrile, tetrahydrofuran, 1,4-dioxane, 1,2-dimethoxyethane, benzene, toluene, xylene, 1-methyl-2-pyrrolidone and N,N-dimethylformamide. The reaction temperature must be a temperature that can complete the coupling reaction, and is preferably room temperature to 100° C., for example. This reaction is performed preferably in an inert gas atmosphere, and more preferably in a nitrogen or argon atmosphere. A method known to a person skilled in the art may be used for the treatment after the second stage (see T. W. Green, "Protective Groups in Organic Synthesis", John Wiley & Sons, Inc., 1981). An undesirable by-product can be removed by a technique known to a person skilled in the art such as a conventional chromatography technique or/and crystallization.

In the preferable amine compound (13), $L_4$ can be modified by a method known to a person skilled in the art, and a hydrogen atom in $L_4$ can be preferably converted into a halogen substituent (see Shin Jikken Kagaku Koza (New Courses in Experimental Chemistry), vol. 14, Yuki Kagobutsu No Gosei To Hannou (Synthesis and Reaction of Organic Compounds) [I], edited by The Chemical Society of Japan, Maruzen Co., Ltd., November 1977, p. 354-360, for example).

[Preparation of Nitro Compound (12)]

The nitro compound (12) is commercially available or can be obtained by a technique known to a person skilled in the art. If not commercially available, the preferable compound (12), wherein $L_4$ represents a fluorine atom, a chlorine atom, a bromine atom or an iodine atom, can be efficiently obtained from a corresponding precursor by a nitration reaction known to a person skilled in the art (see Shin Jikken Kagaku Koza (New Courses in Experimental Chemistry), vol. 14, Yuki Kagobutsu No Gosei To Hannou (Synthesis and Reaction of Organic Compounds) [III], edited by The Chemical Society of Japan, Maruzen Co., Ltd., February 1978, p. 1261-1300, for example).

[Preparation of Compound (17)]

The compound (17) can be obtained by a technique known to a person skilled in the art. Preferably, the compound (17) can be prepared i) from a compound (15) as a starting material according to Step 2-9 or ii) from an amine compound (13) as a starting material according to Step 2-7, for example.

In the case of i), Step 2-9 is performed by the same method as in the above Step 2-1.

In the case of ii), an amine compound (13) can be efficiently converted into the compound (17) in Step 2-7 by treating the amine compound (13) with a mixed solvent of acetic anhydride and formic acid in a first stage, condensing the compound with a compound (14) under basic conditions in a second stage, and heating the condensate with ammonium acetate and acetic acid in a third stage, for example. In the first stage, a compound (13) is stirred in a mixed solvent of 2.0 to 10.0 equivalents of acetic anhydride with respect to the compound (13) and 10.0 to 20.0 equivalents of formic acid with respect to the compound (13) at ice-cold temperature to 50° C. In the second stage, 1.0 to 5.0 equivalents of a base is preferably used with respect to the compound (13). Examples of the base include sodium hydride, sodium hydroxide, potassium hydroxide, lithium hydroxide, n-butyl lithium, lithium diisopropylamide, lithium bis(trimethylsilyl)amide and sodium bis(trimethylsilyl)amide. The solvent used in the present reaction varies according to the starting material, and is not particularly limited insofar as the solvent does not inhibit the reaction and allows the starting material to be dissolved therein to a certain extent. Preferable examples of the solvent include diethyl ether, tetrahydrofuran, dimethyl sulfoxide and N,N-dimethylformamide. Preferably, potassium iodide or sodium iodide may be added, for example, in order to make the reaction efficiently proceed. The reaction temperature must be a temperature that can complete the reaction without promoting formation of an undesirable by-product, and is preferably room temperature to 100° C., for example. In the third stage, the condensate is preferably treated in a mixture of 5.0 to 10.0 equivalents of ammonium acetate with respect to the compound (13) and 10.0 to 20.0 equivalents of acetic acid with respect to the compound (13) at 50 to 100° C. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique or/and crystallization.

The compound (14) used in the second stage of this step is commercially available or can be obtained by a technique known to a person skilled in the art. If not commercially available, the preferable compound (14) can be prepared from a corresponding carbonyl compound by a halogenation reaction known to a person skilled in the art (see Shin Jikken Kagaku Koza (New Courses in Experimental Chemistry), vol. 19, Yuki Gosei (Organic Synthesis) [I], edited by The Chemical Society of Japan, Maruzen Co., Ltd., June 1992, p. 363-482, for example).

$L_4$ in the compound (17) can be modified by a technique known to a person skilled in the art, and can be preferably converted into, for example, an iodine group (see S. L. Buchwald et al., "J. Am. Chem. Soc.", 2002, vol. 124, p. 14844-14845, for example), a lower alkyltin group (see J. Marti et al., "Synth. Commun.", 2000, vol. 30, p. 3023-3030, for example) or a boron group (see N. Miyaura et al., "J. Org. Chem.", 1995, vol. 60, p. 7508-7510, for example). The compounds (18a) and (18b) are commercially available or can be obtained by a technique known to a person skilled in the art.

The compound of the general formula (I-9), general formula (I-4) or general formula (I-6), wherein two of $R^{10}$, $R^{11}$ and $R^{12}$ form a ring, can be prepared from the compound (2a) as a starting material, wherein $R^{10}$ and $R^{11}$ form a ring, by the same method as above. When the method as above is performed using the compound (2a) as a starting material, wherein $R^{10}$ or $R^{11}$ represents an alkyl group substituted with a halogen atom such as a chlorine atom, a bromine atom or an iodine atom, the compound of the general formula (I-9), general formula (I-4) or general formula (I-6), wherein two of $R^{10}$, $R^{11}$ and $R^{12}$ form a ring, can be prepared in Step 1-2, Step 1-5, Step 1-6 or Step 1-7.

[General Preparation Method 2]

Typically used General Preparation Method 2 for the compound of the general formula (I) of the present invention will be described below.

[Formula 34]
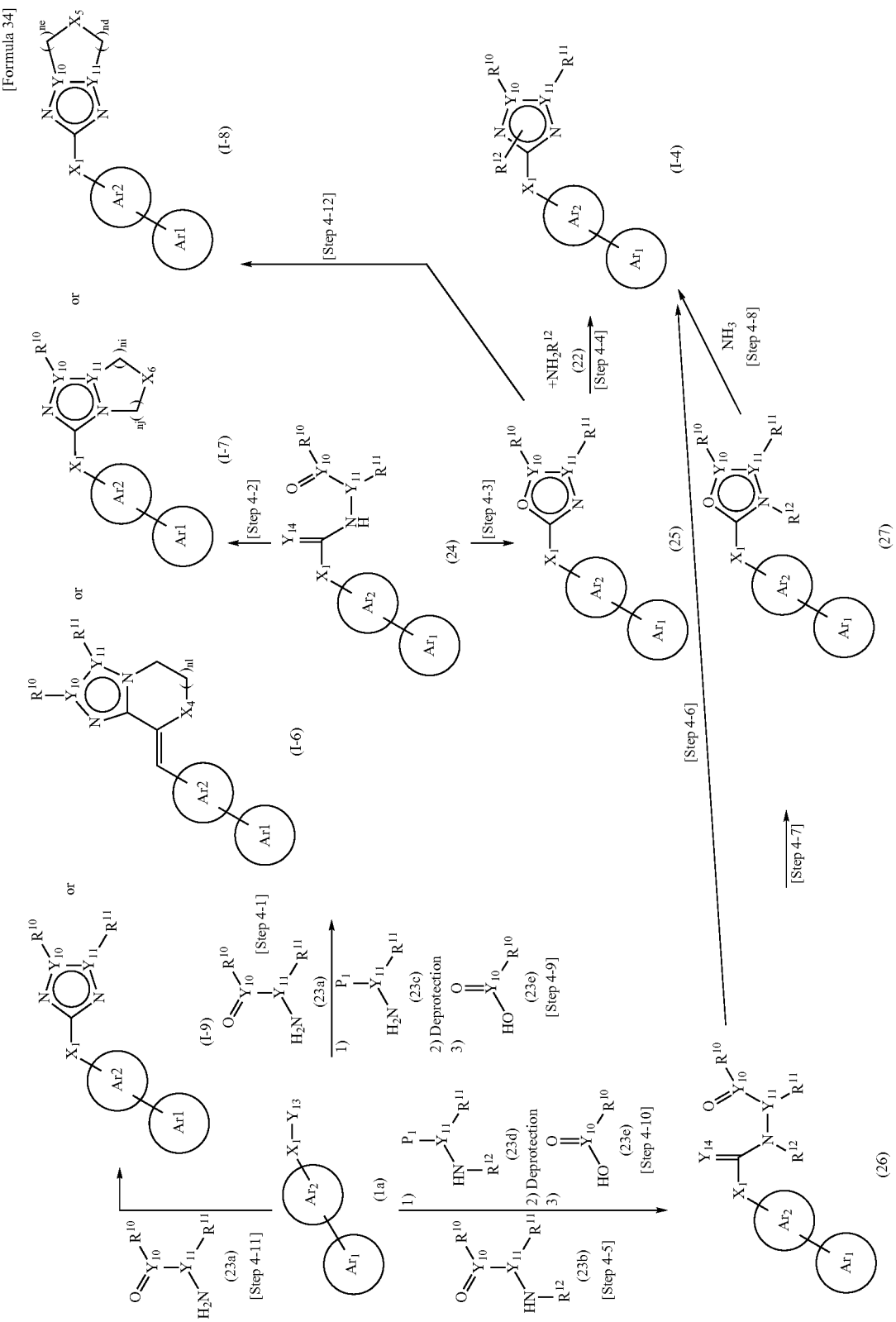

In the formula, the following partial structure (formula III-3, III-4, III-6, III-7 or III-8):

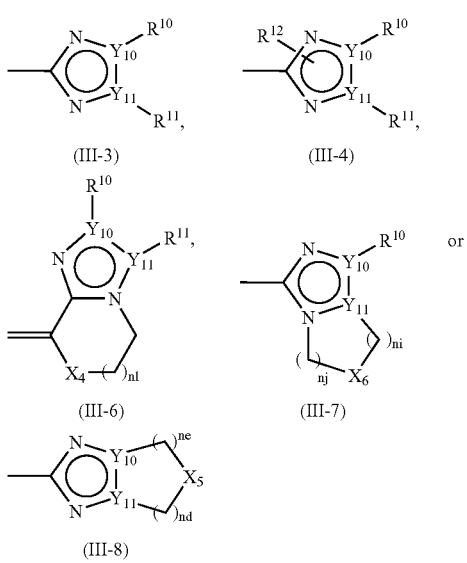

[Formula 35]

is a partial structure corresponding to the above-described Het, wherein $Ar_1$, $Ar_2$, $X_1$, $X_4$, $X_5$, $X_6$, $Y_{10}$, $Y_{11}$, $R^{10}$, $R^{11}$, $R^{12}$, nd, ne, ni, nj and ni are as defined above; $Y_{13}$ represents a carboxyl group, an ester group, a thioester group, a dithioester group, a nitrile group, a thioimino ether group or an iminoether group; $Y_{14}$ represents an oxygen atom, a nitrogen atom or a sulfur atom; and $P_1$ represents a protecting group for an amino group such as a methyl carbamate group, a benzyl carbamate group, a tert-butyl carbamate group, an allyl group, an acetyl group or a formyl group.

The above General Preparation Method 2 includes a method of reacting a compound (1a) with an amine compound (23a) or amine compound (23b) according to Step 4-1 or Step 4-5 to convert the compound (1a) into a compound (24) or compound (26), or converting a compound (1a) into a compound (24) or compound (26) according to Step 4-9 or Step 4-10 which is a three-stage reaction including deprotection, and further reacting the resulting compound (24) or compound (26) with ammonia, an ammonium salt or formamide in Step 4-2 or Step 4-6 to prepare a compound of the general formula (I-9), the general formula (I-4), the general formula (I-6), the general formula (I-7) or the general formula (I-8); a method of once converting a compound (24) or compound (26) into an oxazole compound (25) or a compound (27) by dehydration reaction in Step 4-3 or Step 4-7, and then reacting the oxazole compound (25) or the compound (27) with ammonia, an ammonium salt, formamide or an amine compound (22) in Step 4-4, Step 4-8 or Step 4-12 to prepare a compound of the general formula (I-9), the general formula (I-4), the general formula (I-6), the general formula (I-7) or the general formula (I-8); and a method of reacting a compound (1a) with an amine compound (23a) according to Step 4-11 to prepare a compound of the general formula (I-9), the general formula (I-6), the general formula (I-7) or the general formula (I-8).

[Preparation of Compound of General Formula (I-4)]

The compound of the general formula (I-4) can be prepared by i) reacting a compound (26) in the presence of an acid or base and optionally in the presence of ammonia, an ammonium salt, formamide or the like according to Step 4-6. The compound can also be prepared by ii) reacting a compound (25) or compound (27) with an amine compound (22), ammonia, an ammonium salt, formamide or the like according to Step 4-4 or Step 4-8.

The method i), specifically, Step 4-6 varies according to the starting material and is not particularly limited insofar as the conditions are similar to those in this reaction. A known method described in many documents may be used for the reaction (see Heterocyclic Compounds, Vol. 5, Wiley, New York, N.Y. 1957, p. 503; and Journal of Heterocyclic Chemistry, 1982, vol. 19, p. 193, for example). Preferably, a compound (26), wherein $Y_{14}$ represents an oxygen atom or a sulfur atom, is stirred in a solvent in the presence of 1.0 to 100.0 equivalents of ammonia, an ammonium salt such as ammonium acetate or ammonium carbonate or formamide with respect to the compound (26), for example. The solvent used is not particularly limited insofar as the solvent does not inhibit the reaction and allows the starting material to be dissolved therein to a certain extent. Preferable examples of the solvent include ether solvents such as tetrahydrofuran, 1,4-dioxane and diethyl ether; halogenated solvents such as methylene chloride, 1,2-dichloroethane and chloroform; alcohol solvents such as amyl alcohol and isopropyl alcohol; polar solvents such as N,N-dimethylformamide and N-methylpyrrolidone; nonpolar solvents such as toluene, benzene and dichlorobenzene; organic acids such as acetic acid; water; and a mixture thereof. Formamide may be used as a solvent. The reaction temperature must be a temperature that can complete the reaction without promoting formation of an undesirable by-product, and is preferably room temperature to 200° C., for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization.

Alternatively, a compound (26), wherein $Y_4$ represents a nitrogen atom, is stirred in a solvent in the presence or absence of 0.1 to 10 equivalents of an acid, base or organic salt with respect to the compound (26). Preferable examples of the acid, base or organic salt used include inorganic acids such as hydrochloric acid and sulfuric acid; organic acids, such as p-toluenesulfonic acid and methanesulfonic acid; organic bases such as pyridine and dimethylamino pyridine; and organic salts such as pyridinium p-toluenesulfonate and tetrabutylammonium hydroxide. The solvent used is not particularly limited insofar as the solvent does not inhibit the reaction and allows the starting material to be dissolved therein to a certain extent. Preferable examples of the solvent that can be used include ether solvents such as tetrahydrofuran, 1,4-dioxane and diethyl ether; halogenated solvents such as methylene chloride, 1,2-dichloroethane and chloroform; alcohol solvents such as methanol, ethanol, amyl alcohol and isopropyl alcohol; polar solvents such as N,N-dimethylformamide and N-methylpyrrolidone; nonpolar solvents such as toluene, benzene and dichlorobenzene; water; and a mixture thereof. The above acid, base or organic salt may be used as a solvent. The reaction temperature must be a temperature that can complete the reaction without promoting formation of an undesirable by-product, and is preferably room temperature to 200° C., for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization.

The method ii), specifically, Step 4-4 or Step 4-8 varies according to the starting material and is not particularly limited insofar as the conditions are similar to those in this reaction. A known method described in many documents may be used for the reaction (see Heterocyclic Compounds, vol. 5, Wiley, New York, N.Y. 1950, p. 214; and The Journal of Organic Chemistry, 1962, vol. 27, p. 3240, for example). For example, an oxazole compound (25) or a compound (27) and 1.0 to 100.0 equivalents of an amine compound (22), ammonia, an ammonium salt such as ammonium acetate or ammonium carbonate or formamide with respect to the compound (25) or compound (27) are stirred in a solvent. The solvent used is not particularly limited insofar as the solvent does not inhibit the reaction and allows the starting material to be dissolved therein to a certain extent. Preferable examples of the solvent include ether solvents such as tetrahydrofuran, 1,4-dioxane and diethyl ether; halogenated solvents such as methylene chloride, 1,2-dichloroethane and chloroform; alcohol solvents such as amyl alcohol and isopropyl alcohol; polar solvents such as N,N-dimethylformamide and N-methylpyrrolidone; nonpolar solvents such as toluene, benzene and dichlorobenzene; organic acids such as acetic acid; water; and a mixture thereof. The amine source to be reacted may be used as a solvent. The reaction temperature must be a temperature that can complete the reaction without promoting formation of an undesirable by-product, and is preferably room temperature to 200° C., for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization. The amine compound (22) used in this step is commercially available or can be obtained by a technique known to a person skilled in the art.

[Preparation of Compound of General Formula (I-9), General Formula (I-6), General Formula (I-7) and General Formula (I-8)]

The compound of the general formula (I-9), the general formula (I-6), the general formula (I-7) or the general formula (I-8) can be prepared by i) reacting a compound (24) or compound (25) in the presence of ammonia, an ammonium salt, formamide or the like according to Step 4-2 or Step 4-12. The compound can also be prepared by ii) reacting a compound (1a) with an amine compound (23a) according to Step 4-11.

The method i), specifically, Step 4-2 or Step 4-12 is the same method as in Step 4-6.

The method ii), specifically, Step 4-11 varies according to the starting material and is not particularly limited insofar as the conditions are similar to those in this reaction. A known method described in many documents may be used for the reaction (see Journal of the Chemical Society, 1962, p. 5149; and Journal of Medicinal Chemistry, 1983, vol. 26, p. 1187, for example). For example, a compound (1a), wherein $Y^{13}$ represents a nitrile group, a thioimino ether group or an imino ether group, and 1.0 to 5.0 equivalents of an amine compound (23a) with respect to the compound (1a) are stirred in a solvent. The solvent used is not particularly limited insofar as the solvent does not inhibit the reaction and allows the starting material to be dissolved therein to a certain extent. Preferable examples of the solvent include ether solvents such as tetrahydrofuran, 1,4-dioxane and diethyl ether; halogenated solvents such as methylene chloride, 1,2-dichloroethane and chloroform; alcohol solvents such as methanol, ethanol, butanol, amyl alcohol and isopropyl alcohol; polar solvents such as N,N-dimethylformamide and N-methylpyrrolidone; nonpolar solvents such as toluene, benzene and dichlorobenzene; organic acids such as acetic acid; water; and a mixture thereof. The yield may be improved when performing reaction in the presence of 1.0 to 10.0 equivalents of an organic amine such as triethylamine, diisopropylamine or pyridine or an alkali metal salt such as potassium carbonate or sodium carbonate with respect to the compound (1a). The reaction temperature must be a temperature that can complete the reaction without promoting formation of an undesirable by-product, and is preferably room temperature to 200° C., for example. Under preferable reaction conditions, the reaction is completed in 1 to 72 hours, and the progress of the reaction can be monitored by a known chromatography technique. An undesirable by-product can be removed by a technique known to a person skilled in the art such as a conventional chromatography technique, extraction or/and crystallization.

[Preparation of Compound (24) and Compound (26)]

The compound (24) or compound (26) can be prepared by reacting a compound (1a) with an amine compound (23a) or amine compound (23b) according to Step 4-1 or Step 4-5. Specifically, Step 4-1 or Step 4-5 varies according to the starting material and is not particularly limited insofar as the conditions are similar to those in this reaction. A known method described in many documents may be used for the reaction (see Shin Jikken Kagaku Koza (New Courses in Experimental Chemistry), vol. 22, Yuki Gosei (Organic Synthesis) [IV], edited by The Chemical Society of Japan, Maruzen Co., Ltd., November 1992, p. 137-163; and Organic Synthesis, 1941, I, p. 5, for example). For example, a compound (1a), wherein $Y_{13}$ represents a carboxyl group, and 1.0 to 10.0 equivalents of a compound (23a) or compound (23b) with respect to the compound (1a) are stirred in a solvent in the presence of 0.1 to 10.0 equivalents of a condensing agent with respect to the compound (1a). The condensing agent used varies according to the starting material and is not particularly limited. Preferable examples of the condensing agent include inorganic acids such as hydrochloric acid and sulfuric acid; organic acids such as p-toluenesulfonic acid and methanesulfonic acid, 1,3-dicyclohexylcarbodiimide, 1-ethyl-3-(3'-dimethylaminopropyl)carbodiimide, benzotriazol-1-yloxytris(dimethylamino)phosphonium hexafluorophosphate, diethyl cyanophosphonate and bis(2-oxo-3-oxazolidinyl)phosphonic chloride. Preferably, 1.0 to 5.0 equivalents of N-hydroxysuccinimide, N-hydroxybenzotriazole or dimethylaminopyridine may be added with respect to the compound (1a) in order to make the reaction efficiently proceed, for example. The solvent used varies according to the starting material and the condensing agent used, and is not particularly limited insofar as the solvent does not inhibit the reaction and allows the starting material to be dissolved therein to a certain extent. Preferable examples of the solvent include halogenated solvents such as chloroform, methylene chloride and 1,2-dichloroethane; and polar solvents such as tetrahydrofuran and N,N-dimethylformamide. The reaction temperature must be a temperature that can complete the reaction without promoting formation of an undesirable by-product, and is preferably ice-cold temperature to 150° C., for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique or/and crystallization.

Alternatively, a compound (1a), wherein $Y_{13}$ represents a cyano group, an imino ether group or a thioimino ether group, and 1.0 to 100.0 equivalents of an amine compound (23a) or amine compound (23b) with respect to the compound (1a) are stirred in a solvent. The solvent used is not particularly limited insofar as the solvent does not inhibit the reaction and allows the starting material to be dissolved therein to a certain extent. Preferable examples of the solvent include ether solvents such as tetrahydrofuran, 1,4-dioxane and diethyl ether; halogenated solvents such as methylene chloride, 1,2-dichloroethane and chloroform; alcohol solvents such as methanol, ethanol and isopropyl alcohol; polar solvents such as N,N-dimethylformamide and N-methylpyrrolidone; nonpolar solvents such as toluene, benzene and dichlorobenzene; organic acids such as acetic acid; organic bases such as pyridine; water; and a mixture thereof. The amine compound (23a) or amine compound (24b) may be used as a solvent. The yield may be improved when using 0.1 to 1.0 equivalent of an inorganic acid such as hydrochloric acid, a Lewis acid such as trifluoroborate or an organic acid such as p-toluenesulfonic acid with respect to the compound (1a) or when using 1.0 to 10.0 equivalents of an organic base such as triethylamine, pyridine or diisopropylethylamine with respect to the compound (1a). The reaction temperature must be a temperature that can complete the reaction without promoting formation of an undesirable by-product, and is preferably 0 to 200° C., for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization.

The compound (24) or compound (26) can also be prepared from a compound (1a) according to Step 4-9 or Step 4-10. Specifically, Step 4-9 or Step 4-10 consists of a three-stage reaction including a deprotection step. In a first stage, a compound (1a) is condensed with a compound (23c) or compound (23d) by dehydration. In a second stage, the protecting group is deprotected. In a third stage, the condensate is condensed with a compound (23e).

The first-stage condensation reaction may be performed by the same method as in Step 4-1. The second-stage deprotection reaction varies according to the starting material and is not particularly limited insofar as the conditions are similar to those in this reaction. A known method described in many documents may be used for the reaction (see T. W. Green, "Protective Groups in Organic Synthesis", John Wiley & Sons, Inc., 1999, p. 615-626). Preferably, the condensation compound in the first stage, wherein $P_1$ represents a tert-butyl carbamate group, is stirred in a solvent in the presence of 1.0 to 100.0 equivalents of an acid with respect to the compound, for example. Examples of the acid used include inorganic acids such as hydrochloric acid and sulfuric acid; and organic acids such as trifluoroacetic acid and methanesulfonic acid. The solvent used is not particularly limited insofar as the solvent does not inhibit the reaction and allows the starting material to be dissolved therein to a certain extent. Preferable examples of the solvent include ethyl acetate, methanol, ethanol, 1,4-dioxane, methylene chloride, chloroform, methanol, isopropyl alcohol, N,N-dimethylformamide and N-methylpyrrolidone. The reaction temperature must be a temperature that can complete the reaction without promoting formation of an undesirable by-product, and is preferably 0 to 100° C., for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization.

The third-stage condensation reaction may be performed by the same method as in Step 4-1.

[Preparation of Compound (1a)]

The compound (1a) can be prepared from a compound (4) or compound (17) by the same method as in the above Step 2-1 or Step 2-10.

[Preparation of Compound (25) and Compound (27)]

The compound (25) or compound (27) can be prepared from the compound (24) or compound (26) by dehydration reaction according to Step 4-3 or Step 4-7. Specifically, Step 4-3 or Step 4-7 varies according to the starting material and is not particularly limited insofar as the conditions are similar to those in this reaction. A known method described in many documents may be used for the reaction (see The Chemistry of Heterocyclic Compounds, 45; Wiley, New York, 1986, p. 1, for example). For example, the compound (24) or compound (26) is stirred in a solvent in the presence of 1.0 to 100.0 equivalents of a dehydration reagent with respect to the compound (24) or compound (26). The dehydration reagent used varies according to the starting material and is not particularly limited. Preferable examples of the dehydration reagent include phosphorus oxychloride, thionyl chloride, phosgene, triphosgene, carbonyldiimidazole, hydrochloric acid, sulfuric acid, p-toluenesulfonic acid, methanesulfonic acid, triphenylphosphine-carbon tetrachloride and triphenylphosphine-carbon tetrabromide. The solvent used is not particularly limited insofar as the solvent does not inhibit the reaction and allows the starting material to be dissolved therein to a certain extent. Preferable examples of the solvent include ether solvents such as tetrahydrofuran, 1,4-dioxane and diethyl ether; halogenated solvents such as methylene chloride, 1,2-dichloroethane and chloroform; polar solvents such as N,N-dimethylformamide and N-methylpyrrolidone; nonpolar solvents such as toluene, benzene and dichlorobenzene; and a mixture thereof. The dehydration reagent may be used as a solvent. The reaction temperature must be a temperature that can complete the reaction without promoting formation of an undesirable by-product, and is preferably 0 to 200° C., for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization.

[Preparation of Compound (23a), Compound (23b), Compound (23c), Compound (23d) and Compound (23e)]

The compound (23a), compound (23b), compound (23c), compound (23d) and compound (23e) are commercially available or can be obtained by a technique known to a person skilled in the art.

[General Preparation Method 3]

Typically used General Preparation Method 3 for the compound of the general formula (I) of the present invention will be described below.

[Formula 36]

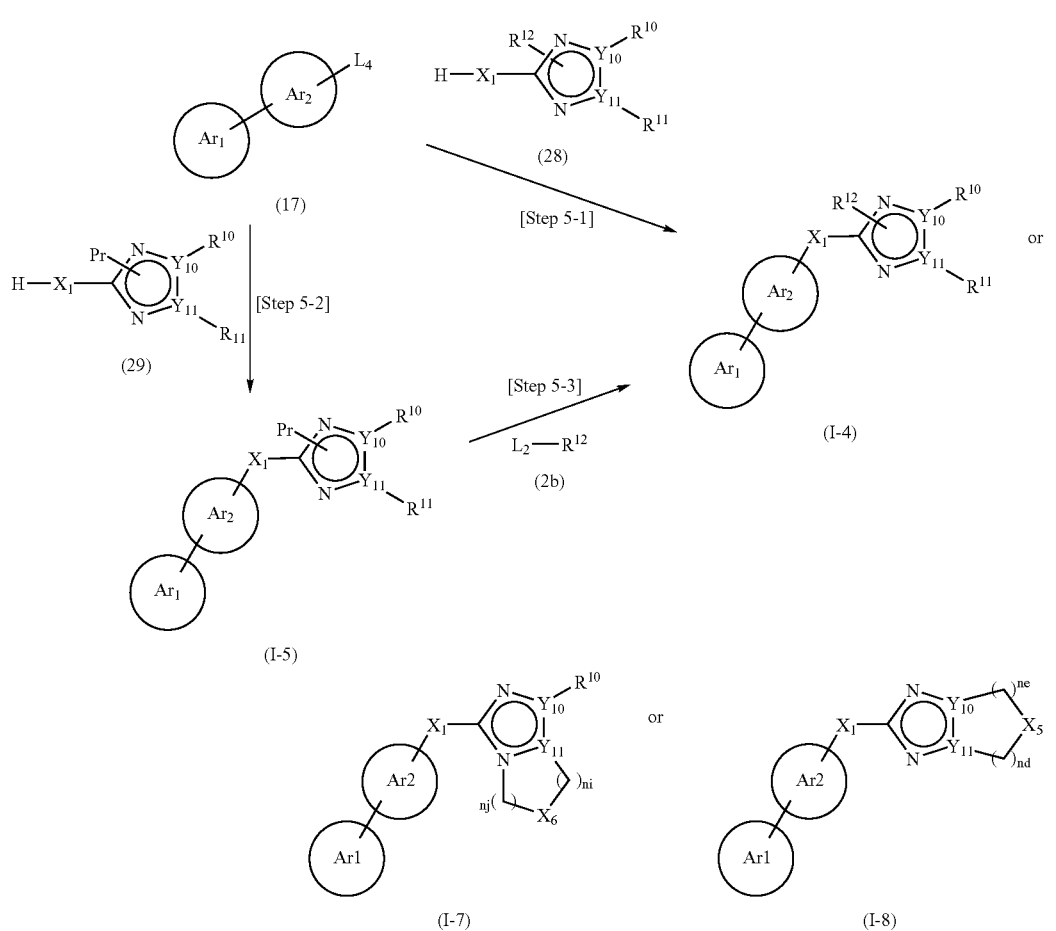

In the formula, the following partial structure (formula III-4, III-5, III-7 or III-8):

[Formula 37]

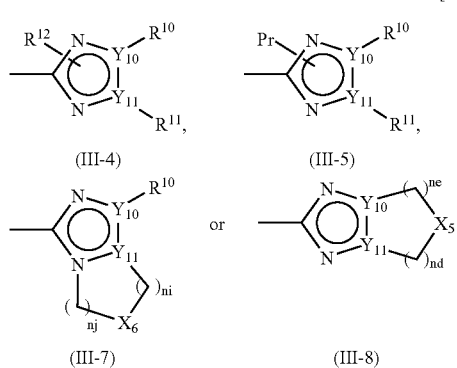

is a partial structure corresponding to the above-described Het, wherein $Ar_1$, $Ar_2$, $X_1$, $X_5$, $X_6$, $Y_{10}$, $Y_{11}$, $R^{10}$, $R^{11}$, $R^{12}$, $L_2$, $L_4$, nd, ne, ni and nj are as defined above; and Pr represents a protecting group for a heterocycle nitrogen atom such as a trityl group, a methoxymethyl group, a benzyl group or a methanesulfonic acid group.

The above General Preparation Method 3 includes a method of reacting a compound (17) with a heterocyclic compound (28) in Step 5-1 to prepare a compound of the general formula (I-4), the general formula (I-7) or the general formula (I-8); and a method of reacting a compound (17) with a heterocyclic compound (29) having a protecting group in Step 5-2 to once convert the compound (17) into a compound of the general formula (I-5) having a protecting group and then deprotecting the protecting group of the compound of the general formula (I-5) and subsequently reacting the compound with a compound (2b) in Step 5-3 to prepare a compound of the general formula (I-4), the general formula (I-7) or the general formula (I-8).

[Preparation of compounds of General Formula (I-4) and (I-5)]

The compound of the general formula (I-4) or (I-5) can be prepared by i) reacting a compound (17) with a compound (28) or compound (29) according to Step 5-1 or Step 5-2. The compound of the general formula (I-4) can also be prepared by ii) deprotecting the protecting group of the compound of the general formula (I-5) and then reacting the compound with a compound (2b) according to Step 5-3.

The method i), specifically, Step 5-1 or Step 5-2 varies according to the starting material and is not particularly limited insofar as the conditions are similar to those in this reaction. A known method described in many documents such as Mizoroki-Heck reaction (see R. F. Heck, "Org. Reactions.", 1982, vol. 27, p. 345, for example) or Sonogashira reaction (see K. Sonogashira, "Comprehensive Organic Synthesis", 1991, vol. 3, p. 521, for example) may be used for the reaction.

In Mizoroki-Heck reaction, a compound (17), wherein L₄ represents a chlorine atom, a bromine atom, an iodine atom or a sulfonate group such as a trifluoromethanesulfonate group, and 1.0 to 5.0 equivalents of a compound (28) or compound (29), wherein X₁ represents an alkenyl group, with respect to the compound (17) are stirred in a solvent in the presence of 0.01 to 0.5 equivalent of a transition metal catalyst with respect to the compound (17), for example. The transition metal catalyst used is preferably a palladium complex, for example, and more preferably a known palladium complex such as palladium (II) acetate, dichlorobis(triphenylphosphine)palladium (II), tetrakis(triphenylphosphine)palladium (0) or tris(dibenzylideneacetone)dipalladium (0). A phosphorus ligand such as triphenylphosphine, tri-o-tolylphosphine, tri-tert-butylphosphine or 2-(di-tert-butylphosphino)biphenyl may be preferably added, for example, in order to make the reaction efficiently proceed. A preferable result may be achieved in the presence of a base. The base used is not particularly limited insofar as the base is used in a coupling reaction similar to this reaction. Preferable examples of the base include triethylamine, N,N-diisopropylethylamine, N,N-dicyclohexylmethylamine and tetrabutylammonium chloride. The solvent used varies according to the starting material and the transition metal catalyst used, and is not particularly limited insofar as the solvent does not inhibit the reaction and allows the starting material to be dissolved therein to a certain extent. Preferable examples of the solvent include acetonitrile, tetrahydrofuran, 1,4-dioxane, 1,2-dimethoxyethane, benzene, toluene, xylene, 1-methyl-2-pyrrolidone and N,N-dimethylformamide. The reaction temperature must be a temperature that can complete the coupling reaction, and is preferably room temperature to 150° C., for example. This reaction is performed preferably in an inert gas atmosphere, and more preferably in a nitrogen or argon atmosphere, for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization.

In Sonogashira reaction, a compound (17), wherein L₄ represents a chlorine atom, a bromine atom, an iodine atom or a sulfonate group such as a trifluoromethanesulfonate group, and 1.0 to 5.0 equivalents of a compound (28) or compound (29), wherein X₁ represents an alkynyl group, with respect to the compound (17) are stirred in a solvent in the presence of 0.01 to 0.5 equivalent of a transition metal catalyst with respect to the compound (17), for example. The transition metal catalyst used is preferably a known palladium complex, for example, and more preferably a known palladium complex such as palladium (II) acetate, dichlorobis(triphenylphosphine)palladium (II), tetrakis(triphenylphosphine)palladium (0) or tris(dibenzylideneacetone)dipalladium (0). A phosphorus ligand such as triphenylphosphine, tri-o-tolylphosphine or tri-tert-butylphosphine may be preferably added, for example, in order to make the reaction efficiently proceed. In the reaction, a good result may be achieved when adding a metal halide or a quaternary ammonium salt, preferably copper (I) iodide, lithium chloride, tetrabutylammonium fluoride or silver (I) oxide, for example. A preferable result may be achieved in the presence of a base. The base used here is not particularly limited insofar as the base is used in a coupling reaction similar to this reaction. Preferable examples of the base include diethylamine, triethylamine, N,N-diisopropylethylamine, piperidine and pyridine. Preferable examples of the solvent used include acetonitrile, tetrahydrofuran, 1,4-dioxane, 1,2-dimethoxyethane, benzene, toluene, xylene, 1-methyl-2-pyrrolidone, N,N-dimethylformamide and dimethyl sulfoxide. More preferable examples of the solvent include tetrahydrofuran, 1,4-dioxane, 1-methyl-2-pyrrolidone and N,N-dimethylformamide. The reaction temperature must be a temperature that can complete the coupling reaction, and is preferably room temperature to 150° C., for example. This reaction is performed preferably in an inert gas atmosphere, and more preferably in a nitrogen or argon atmosphere, for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization.

The method ii), specifically, Step 5-3 consists of first-stage deprotection reaction and second-stage reaction with a compound (2b). The first-stage deprotection reaction varies according to the starting material and is not particularly limited insofar as the conditions are similar to those in this reaction. A known method described in many documents may be used for the reaction (see T. W. Green, "Protective Groups in Organic Synthesis", John Wiley & Sons, Inc., 1999, p. 615-626). Preferably, the compound of the general formula (I-5) is stirred in a solvent in the presence of 1.0 to 100.0 equivalents of an acid or base with respect to the compound of the general formula (I-5), for example. Preferable Examples of the acid used include inorganic acids such as hydrochloric acid and sulfuric acid; and organic acids such as trifluoroacetic acid, methanesulfonic acid and p-toluenesulfonic acid. Preferable examples of the base used include alkali metal hydroxides such as sodium hydroxide and potassium hydroxide; alkali metal carbonates such as potassium carbonate and sodium carbonate; and organic amines such as ammonia and methylamine. The solvent used is not particularly limited insofar as the solvent does not inhibit the reaction and allows the starting material to be dissolved therein to a certain extent. Preferable examples of the solvent include acetonitrile, tetrahydrofuran, 1,4-dioxane, 1,2-dimethoxyethane, ethyl acetate, methanol, ethanol, benzene, toluene, xylene, chloroform, methylene chloride, water and a mixed solvent thereof. The acid or base may be used as a solvent. The reaction temperature must be a temperature that can complete the deprotection reaction, and is preferably room temperature to 150° C., for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization. The second stage reaction of the compound (I-5) with the compound (2b) may be performed by the same method as in Step 1-3.

[Preparation of Compound (28)]

[Formula 38]

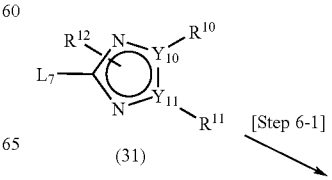

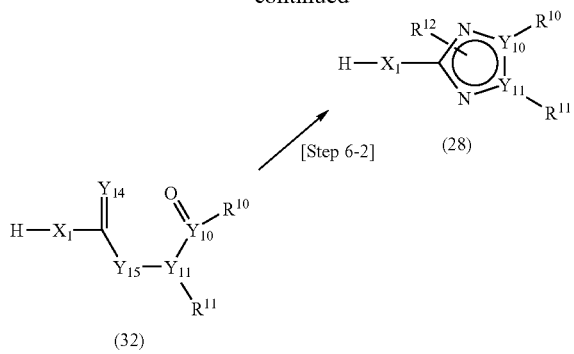

In the formula, $X_1$, $Y_{10}$, $Y_{11}$, $Y_{14}$, $R^{10}$, $R^{11}$ and $R^{12}$ are as defined above; $L_7$ represents a hydrogen atom, a halogen atom such as a chlorine atom, a bromine atom or an iodine atom, a sulfonate group such as a trifluoromethanesulfonate group, a trialkyltin group or a leaving group such as a boronic acid or boronate group; and $Y_{15}$ represents an oxygen atom, or a nitrogen atom which may be substituted with a substituent selected from the above Substituent Group A1.

The compound (28) can be prepared by i) condensing a compound (31) with an alkene or alkyne compound according to Step 6-1. The compound (28) can also be prepared by ii) cyclizing a compound (32) according to Step 6-2.

The method i), specifically, Step 6-1 varies according to the starting material and is not particularly limited insofar as the conditions are similar to those in this reaction. A known method described in many documents such as Mizoroki-Heck reaction (see R. F. Heck, "Org. Reactions.", 1982, vol. 27, p. 345, for example), Suzuki-Miyaura reaction (see A. Suzuki, "Chem. Rev.", 1995, vol. 95, p. 2457, for example), Sonogashira reaction (see K. Sonogashira, "Comprehensive Organic Synthesis", 1991, vol. 3, p. 521) or Stille coupling reaction (see J. K. Stille, "Angew. Chem. Int. Ed. Engl.", 1986, vol. 25, p. 508, for example) may be used for the reaction.

In Mizoroki-Heck reaction, a compound (31), wherein $L_7$ represents a chlorine atom, a bromine atom, an iodine atom or a sulfonate group such as a trifluoromethanesulfonate group, and 1.0 to 5.0 equivalents of an alkene compound, wherein the alkene compound refers to a compound having a double bond in the molecule, with respect to the compound (31) are stirred in a solvent in the presence of 0.01 to 0.2 equivalent of a transition metal catalyst with respect to the compound (31), for example. The transition metal catalyst used is preferably a palladium complex, for example, and more preferably a known palladium complex such as palladium (II) acetate, dichlorobis(triphenylphosphine)palladium (II), tetrakis(triphenylphosphine)palladium (0) or tris(dibenzylideneacetone)dipalladium (0). A phosphorus ligand such as triphenylphosphine, tri-o-tolylphosphine, tri-tert-butylphosphine or 2-(di-tert-butylphosphino)biphenyl may be preferably added, for example, in order to make the reaction efficiently proceed. A preferable result may be achieved in the presence of a base. The base used is not particularly limited insofar as the base is used in a coupling reaction similar to this reaction. Preferable examples of the base include triethylamine, N,N-diisopropylethylamine, N,N-dicyclohexylmethylamine and tetrabutylammonium chloride. The solvent used varies according to the starting material and the transition metal catalyst used, and is not particularly limited insofar as the solvent does not inhibit the reaction and allows the starting material to be dissolved therein to a certain extent. Preferable examples of the solvent include acetonitrile, tetrahydrofuran, 1,4-dioxane, 1,2-dimethoxyethane, benzene, toluene, xylene, 1-methyl-2-pyrrolidone and N,N-dimethylformamide. The reaction temperature must be a temperature that can complete the coupling reaction, and is preferably room temperature to 150° C., for example. This reaction is performed preferably in an inert gas atmosphere, and more preferably in a nitrogen or argon atmosphere, for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization.

In Suzuki-Miyaura reaction, a compound (31), wherein $L_7$ represents a chlorine atom, a bromine atom, an iodine atom or a sulfonate group such as a trifluoromethanesulfonate group, and 1.0 to 5.0 equivalents of an alkene or alkyne boronic acid or boronate compound, wherein the boronic acid or boronate compound refers to a boronic acid or boronate compound directly bonded to a double bond or triple bond, with respect to the compound (31) are stirred in a solvent in the presence of 0.01 to 0.5 equivalent of a transition metal catalyst with respect to the compound (31), for example. The transition metal catalyst used is preferably a known palladium complex, and more preferably a known palladium complex such as palladium (II) acetate, dichlorobis(triphenylphosphine)palladium (II), tetrakis(triphenylphosphine)palladium (0) or tris (dibenzylideneacetone)dipalladium (0). A phosphorus ligand such as triphenylphosphine, tri-o-tolylphosphine, tricyclohexylphosphine or tri-tert-butylphosphine may be preferably added, for example, in order to make the reaction efficiently proceed. A quaternary ammonium salt, preferably tetrabutylammonium chloride or tetrabutylammonium bromide, for example, may also be added in order to make the reaction efficiently proceed. In this reaction, a preferable result may be achieved in the presence of a base. The base used at this time varies according to the starting material, the solvent used and the like, and is not particularly limited. Preferable examples of the base include sodium hydroxide, barium hydroxide, potassium fluoride, cesium fluoride, sodium carbonate, potassium carbonate, cesium carbonate and potassium phosphate. The solvent used varies according to the starting material and the transition metal catalyst used, and is not particularly limited insofar as the solvent does not inhibit the reaction and allows the starting material to be dissolved therein to a certain extent. Preferable examples of the solvent include acetonitrile, tetrahydrofuran, 1,4-dioxane, 1,2-dimethoxyethane, benzene, toluene, xylene, 1-methyl-2-pyrrolidone, N,N-dimethylformamide, water and a mixed solvent thereof. The reaction temperature must be a temperature that can complete the coupling reaction, and is preferably room temperature to 200° C., for example. This reaction is performed preferably in an inert gas atmosphere, and more preferably in a nitrogen or argon atmosphere, for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization. The desired compound (28) can also be obtained from a combination of the boronic acid compound or boronate compound (31), wherein $L_7$ represents a boronic acid group or a boronate group, with a halogenated alkene compound or an enol trifluoromethanesulfonate compound by the same method as above.

In Sonogashira reaction, a compound (31), wherein $L_7$ represents a chlorine atom, a bromine atom, an iodine atom or a sulfonate group such as a trifluoromethanesulfonate group, and 1.0 to 5.0 equivalents of an alkyne compound, wherein the alkyne compound refers to a compound having HC≡C— in the molecule, with respect to the compound (31) are stirred in a solvent in the presence of 0.01 to 0.5 equivalent of a transition metal catalyst with respect to the compound (31), for example. The transition metal catalyst used is preferably a known palladium complex, for example, and more preferably a known palladium complex such as palladium (II) acetate, dichlorobis(triphenylphosphine)palladium (II), tetrakis (triphenylphosphine)palladium (0) or tris(dibenzylideneacetone)dipalladium (0). A phosphorus ligand such as triphenylphosphine, tri-o-tolylphosphine or tri-tert-butylphosphine may be preferably added, for example, in order to make the reaction efficiently proceed. In the reaction, a good result may be achieved when adding a metal halide or a quaternary ammonium salt, preferably copper (I) iodide, lithium chloride, tetrabutylammonium fluoride or silver (I) oxide, for example. A preferable result may be achieved in the presence of a base. The base used here is not particularly limited insofar as the base is used in a coupling reaction similar to this reaction. Preferable examples of the base include diethylamine, triethylamine, N,N-diisopropylethylamine, piperidine and pyridine. Preferable examples of the solvent used include acetonitrile, tetrahydrofuran, 1,4-dioxane, 1,2-dimethoxyethane, benzene, toluene, xylene, 1-methyl-2-pyrrolidone, N,N-dimethylformamide and dimethyl sulfoxide. More preferable examples of the solvent include tetrahydrofuran, 1,4-dioxane, 1-methyl-2-pyrrolidone and N,N-dimethylformamide. The reaction temperature must be a temperature that can complete the coupling reaction, and is preferably room temperature to 150° C., for example. This reaction is performed preferably in an inert gas atmosphere, and more preferably in a nitrogen or argon atmosphere, for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization.

In Stille coupling reaction, a compound (31), wherein $L_7$ represents a chlorine atom, a bromine atom, an iodine atom or a trifluoromethanesulfonate group, and 1.0 equivalent or more of a trialkyltin compound, wherein the trialkyltin compound refers to an alkyltin compound directly bonded to a double bond or triple bond, with respect to the compound (31) are stirred in a solvent in the presence of 0.01 to 0.2 equivalent of a transition metal catalyst with respect to the compound (31), for example. The transition metal catalyst used is preferably a palladium complex, for example, and more preferably a known palladium complex such as palladium (II) acetate, dichlorobis(triphenylphosphine)palladium (II), tetrakis(triphenylphosphine)palladium (0) or tris(dibenzylideneacetone)dipalladium (0). In order to make the reaction efficiently proceed, 0.1 to 5.0 equivalents of copper (I) halide or/and lithium chloride may be added. Preferable examples of the solvent used include toluene, xylene, N,N-dimethylformamide, N,N-dimethylacetamide, 1-methyl-2-pyrrolidone and dimethyl sulfoxide. The reaction temperature must be a temperature that can complete the coupling reaction, and is preferably room temperature to 150° C., for example. This reaction is performed preferably in an inert gas atmosphere, and more preferably in a nitrogen or argon atmosphere, for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization. The desired compound (28) can also be obtained from a combination of the tin compound (31), wherein $L_7$ represents a trialkyltin group, with a halogenated alkene compound or enol trifluoromethanesulfonate compound by the same method as above. The halogenated alkene compound refers to a compound of which the hydrogen atom bonded to the double bond in the molecule is replaced by a halogen atom. The enol trifluoromethanesulfonate compound refers to a compound of which the hydrogen atom of the enol ester group in the molecule is replaced by a trifluoromethanesulfonyl group.

The method ii), specifically, Step 6-2 may be performed by the same method as in Step 4-2 or Step 4-6.

[Preparation of Compound (31)]

The compound (31) is commercially available or prepared by a method known to a person skilled in the art. If not commercially available, the compound (31), wherein $L_7$ is a boronic acid group or a boronate group, can be prepared by a method known to a person skilled in the art, for example, although the method varies according to the starting material (see Shin Jikken Kagaku Koza (New Courses in Experimental Chemistry), vol. 22, Yuki Gosei (Organic Synthesis) [VI], edited by The Chemical Society of Japan, Maruzen Co., Ltd., September 1992, p. 61-90, for example). The compound (31), wherein $L_7$ is a trialkyltin group, can be prepared by a method known to a person skilled in the art, although the method varies according to the starting material (see Shin Jikken Kagaku Koza (New Courses in Experimental Chemistry), vol. 22, Yuki Gosei (Organic Synthesis) [VI], edited by The Chemical Society of Japan, Maruzen Co., Ltd., September 1992, p. 179-201, for example).

[Preparation of Compound (32)]

The compound (32) is commercially available or prepared by a method known to a person skilled in the art. If not commercially available, the compound (32) can be prepared by the same method as in Step 1-1 or Step 4-1, for example.

[Preparation of Compound (29)]

The compound (29) is commercially available or can be prepared by the same method as in the case of the compound (28) if not commercially available.

The compound of the general formula (I-7) or the general formula (I-8) can be prepared from the compound (28) or compound (29), wherein two of $R^{10}$, $R^{11}$ and $R^{12}$ form a ring, as a starting material by the same method as above.

[General Preparation Method 4]

Typically used General Preparation Method 4 for the compound of the general formula (I) of the present invention will be described below.

[Formula 39]

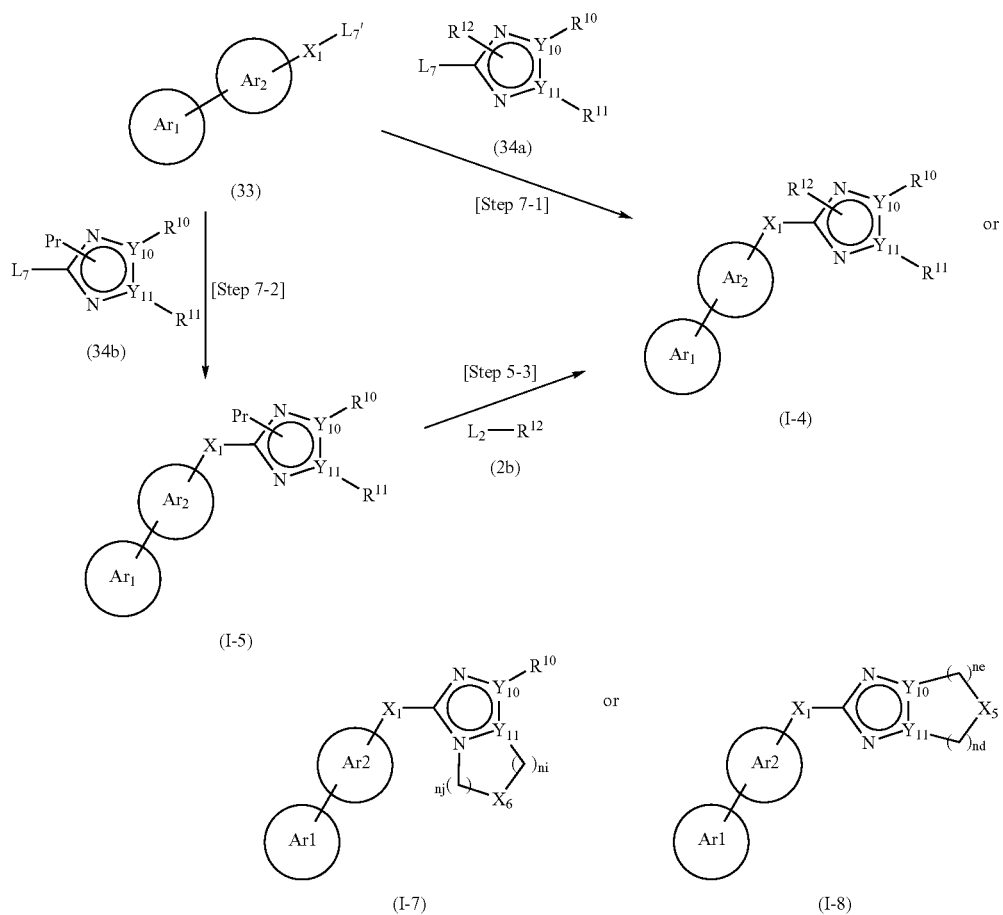

In the formula, the following partial structure (formula III-4, III-5, III-7 or III-8):

[Formula 40]

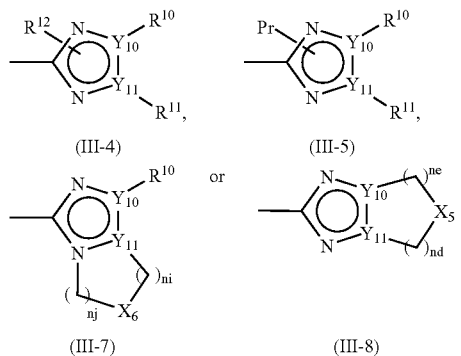

is a partial structure corresponding to the above-described Het, wherein $Ar_1$, $Ar_2$, $X_1$, $X_5$, $X_6$, $Y_{10}$, $Y_{11}$, $R^{10}$, $R^{11}$, $R^{12}$, $L_2$, Pr, nd, ne, ni and nj are as defined above; and $L_7$ and $L_7'$ each represent a halogen atom such as hydrogen, chlorine, bromine or iodine, a sulfonate group such as a trifluoromethanesulfonate group or a trialkyltin group or a leaving group such as a boron acid or boronate group.

The above General Preparation Method 4 includes a method of condensing a compound (33) with a heterocyclic compound (34a) in Step 7-1 to prepare a compound of the general formula (I-4), the general formula (I-7) or the general formula (I-8); and a method of condensing a compound (33) with a heterocyclic compound (34b) having a protecting group in Step 7-2 to convert the compound (33) into a compound of the general formula (I-5) having a protecting group and then deprotecting the protecting group of the compound of the general formula (I-5) and subsequently reacting the compound with a compound (2b) in Step 5-3 to prepare a compound of the general formula (I-4), the general formula (I-7) or the general formula (I-8).

[Preparation of Compound of General Formula (I-4) and Compound of General Formula (I-5)]

The compound of the general formula (I-4) or the compound of the general formula (I-5) can be prepared by reacting a compound (33) with a compound (34a) or compound (34b) according to Step 7-1 or Step 7-2. Specifically, Step 7-1 or Step 7-2 varies according to the starting material and is not particularly limited insofar as the conditions are similar to those in this reaction. A known method described in many documents may be used for the reaction. Preferable examples of the method include Mizoroki-Heck reaction (see R. F. Heck, "Org. Reactions.", 1982, vol. 27, p. 345, for example), Suzuki-Miyaura reaction (see A. Suzuki, "Chem. Rev.", 1995, vol. 95, p. 2457, for example), Sonogashira reaction (see K. Sonogashira, "Comprehensive Organic Synthesis", 1991, vol. 3, p. 521) and Stille coupling reaction (see J. K. Stille, "Angew. Chem. Int. Ed. Engl.", 1986, vol. 25, p. 508, for example).

In Mizoroki-Heck reaction, a compound (33), wherein $L_7'$ represents a hydrogen atom and $X_1$ represents an alkenyl group, and 0.5 to 5.0 equivalents of a compound (34a) or compound (34b), wherein $L_7$ represents a chlorine atom, a bromine atom, an iodine atom or a sulfonate group such as a trifluoromethanesulfonate group, with respect to the compound (33) are stirred in a solvent in the presence of 0.01 to 1.0 equivalent of a transition metal catalyst with respect to the compound (33), for example. The transition metal catalyst used is preferably a palladium complex, for example, and more preferably a known palladium complex such as palladium (II) acetate, dichlorobis(triphenylphosphine)palladium (II), tetrakis(triphenylphosphine)palladium (0) or tris(dibenzylideneacetone)dipalladium (0). A phosphorus ligand such as triphenylphosphine, tri-o-tolylphosphine, tri-tert-butylphosphine or 2-(di-tert-butylphosphino)biphenyl may be preferably added, for example, in order to make the reaction efficiently proceed. A preferable result may be achieved in the presence of a base. The base used is not particularly limited insofar as the base is used in a coupling reaction similar to this reaction. Preferable examples of the base include triethylamine, N,N-diisopropylethylamine, N,N-dicyclohexylmethylamine and tetrabutylammonium chloride. The solvent used varies according to the starting material and the transition metal catalyst used, and is not particularly limited insofar as the solvent does not inhibit the reaction and allows the starting material to be dissolved therein to a certain extent. Preferable examples of the solvent include acetonitrile, tetrahydrofuran, 1,4-dioxane, 1,2-dimethoxyethane, benzene, toluene, xylene, 1-methyl-2-pyrrolidone and N,N-dimethylformamide. The reaction temperature must be a temperature that can complete the coupling reaction, and is preferably room temperature to 150° C., for example. This reaction is performed preferably in an inert gas atmosphere, and more preferably in a nitrogen or argon atmosphere, for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization.

In Suzuki-Miyaura reaction, a compound (33), wherein $L_7'$ represents a boronic acid or boronate group, and 0.5 to 5.0 equivalents of a compound (34a) or compound (34b), wherein $L_7$ represents a chlorine atom, a bromine atom, an iodine atom or a sulfonate group such as a trifluoromethanesulfonate group, with respect to the compound (33) are stirred in a solvent in the presence of 0.01 to 1.0 equivalent of a transition metal catalyst with respect to the compound (33), for example. The transition metal catalyst used is preferably a known palladium complex, for example, and more preferably a known palladium complex such as palladium (II) acetate, dichlorobis(triphenylphosphine)palladium (II), tetrakis(triphenylphosphine)palladium (0) or tris(dibenzylideneacetone)dipalladium (0). A phosphorus ligand such as triphenylphosphine, tri-o-tolylphosphine, tricyclohexylphosphine or tri-tert-butylphosphine may be preferably added, for example, in order to make the reaction efficiently proceed. A good result may be achieved when appropriately adding a quaternary ammonium salt, preferably tetrabutylammonium chloride or tetrabutylammonium bromide, for example. In this reaction, a preferable result may be achieved in the presence of a base. The base used at this time varies according to the starting material, the solvent used and the like, and is not particularly limited. Preferable examples of the base include sodium hydroxide, barium hydroxide, potassium fluoride, cesium fluoride, sodium carbonate, potassium carbonate, cesium carbonate and potassium phosphate. The solvent used varies according to the starting material and the transition metal catalyst used, and is not particularly limited insofar as the solvent does not inhibit the reaction and allows the starting material to be dissolved therein to a certain extent. Preferable examples of the solvent include acetonitrile, tetrahydrofuran, 1,4-dioxane, 1,2-dimethoxyethane, benzene, toluene, xylene, 1-methyl-2-pyrrolidone, N,N-dimethylformamide, water and a mixed solvent thereof. The reaction temperature must be a temperature that can complete the coupling reaction, and is preferably room temperature to 200° C., for example. This reaction is performed preferably in an inert gas atmosphere, and more preferably in a nitrogen or argon atmosphere, for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization. The desired compound of the general formula (I-4) or general formula (I-5) can also be obtained from a combination of the compound (33), wherein $L_7'$ represents a chlorine atom, a bromine atom, an iodine atom or a sulfonate group such as a trifluoromethanesulfonate group, with the compound (34a) or compound (34b), wherein $L_7$ represents a boronic acid or boronate group, by the same method as above.

In Sonogashira reaction, an alkyne compound (33), wherein $L_7'$ represents a hydrogen atom, and $X_1$ represents an alkynyl group, and 0.5 to 5 equivalents of a compound (34a) or compound (34b), wherein $L_7$ represents a chlorine atom, a bromine atom, an iodine atom or a sulfonate group such as a trifluoromethanesulfonate group, with respect to the compound (33) are stirred in a solvent in the presence of 0.01 to 1.0 equivalent of a transition metal with respect to the compound (33), for example. The transition metal catalyst used is preferably a known palladium complex, for example, and more preferably a known palladium complex such as palladium (II) acetate, dichlorobis(triphenylphosphine)palladium (II), tetrakis(triphenylphosphine)palladium (0) or tris(dibenzylideneacetone)dipalladium (0). A phosphorus ligand such as triphenylphosphine, tri-o-tolylphosphine or tri-tert-butylphosphine may be preferably added, for example, in order to make the reaction efficiently proceed. In the reaction, a good result may be achieved when adding a metal halide or a quaternary ammonium salt such as preferably copper (I) iodide, lithium chloride, tetrabutylammonium fluoride or silver (I) oxide, for example. A preferable result may be achieved in the presence of a base. The base used here is not particularly limited insofar as the base is used in a coupling reaction similar to this reaction. Preferable examples of the base include diethylamine, triethylamine, N,N-diisopropylethylamine, piperidine and pyridine. Preferable examples of the solvent used include acetonitrile, tetrahydrofuran, 1,4-dioxane, 1,2-dimethoxyethane, benzene, toluene, xylene, 1-methyl-2-pyrrolidone, N,N-dimethylformamide, dimethyl sulfoxide and a mixture thereof. More preferable examples of the solvent include tetrahydrofuran, 1,4-dioxane, 1-methyl-2-pyrrolidone and N,N-dimethylformamide. The reaction temperature must be a temperature that can complete the coupling reaction, and is preferably room temperature to 150° C., for example. This reaction is performed preferably in an inert gas atmosphere, and more preferably in a nitrogen or argon atmosphere, for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization.

In Stille coupling reaction, a compound (33), wherein $L_7'$ represents a chlorine atom, a bromine atom, an iodine atom or a trifluoromethanesulfonate group, and 0.5 to 5 equivalents of a compound (34a) or compound (34b), wherein $L_7$ represents an alkyltin group, with respect to the compound (33) are stirred in a solvent in the presence of 0.01 to 1.0 equivalent of a transition metal catalyst with respect to the compound (33), for example. The transition metal catalyst used is preferably a known palladium complex such as palladium (II) acetate, dichlorobis(triphenylphosphine)palladium (II), tetrakis (triphenylphosphine)palladium (0) or tris(dibenzylideneacetone)dipalladium (0), for example, and more preferably tetrakis(triphenylphosphine)palladium (0) or tris (dibenzylideneacetone)dipalladium (0), for example. In order to make the reaction efficiently proceed, 0.1 to 5.0 equivalents of copper (I) halide or/and lithium chloride may be appropriately used. Preferable examples of the solvent used include toluene, xylene, N,N-dimethylformamide, N,N-dimethylacetamide, 1-methyl-2-pyrrolidone, dimethyl sulfoxide and a mixture thereof. The reaction temperature must be a temperature that can complete the coupling reaction, and is preferably room temperature to 150° C., for example. This reaction is performed preferably in an inert gas atmosphere, and more preferably in a nitrogen or argon atmosphere, for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization. The desired compound of the general formula (I-4) or general formula (I-5) can also be obtained from a combination of the compound (33), wherein $L_7'$ represents a trialkyltin group, with the compound (34a) or compound (35b), wherein $L_7$ represents a chlorine atom, a bromine atom, an iodine atom or a trifluoromethanesulfonate group, by the same method as above.

[Preparation of Compound (34a) and Compound (34b)]

The compound (34a) or compound (34b) can be prepared by the same method as in the case of the compound (31).

[Preparation of Compound (33)]

The compound (33) can be prepared from a compound (13) or compound (15) by the same method as in Step 2-7 or Step 2-9.

The compound of the general formula (I-7) or the general formula (I-8) can be prepared from the compound (34a) or compound (34b), wherein two of $R^{10}$, $R^{11}$ and $R^{12}$ form a ring, as a starting material by the same method as above.

[General Preparation Method 5]

Typically used General Preparation Method 5 for the compound of the general formula (I) of the present invention will be described below.

[Formula 41]

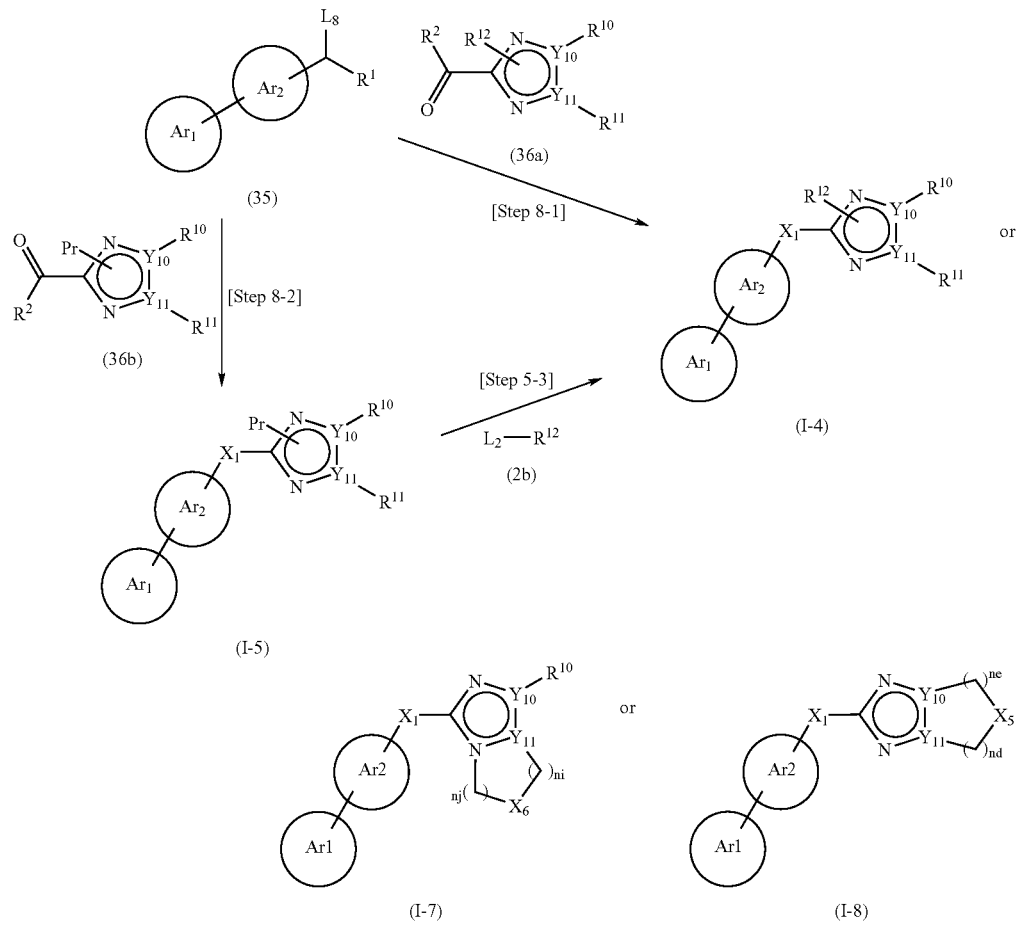

In the formula, the following partial structure (formula III-4, III-5, III-7 or III-8):

[Formula 42]

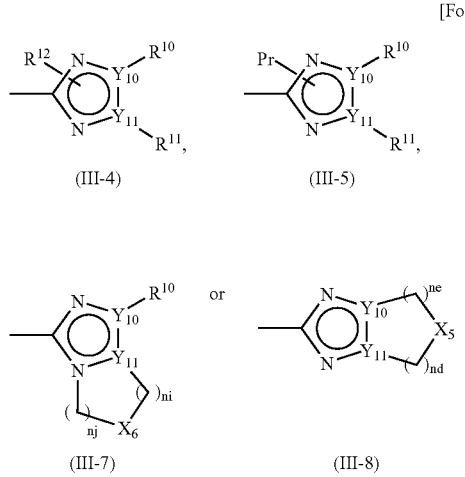

(III-4)    (III-5)

(III-7)    (III-8)

is a partial structure corresponding to the above-described Het, wherein $Ar_1$, $Ar_2$, $X_1$, $X_5$, $X_6$, $Y_{10}$, $Y_{11}$, $R_1$, $R_2$, $R^{10}$, $R^{11}$, $R^{12}$, $L_2$, Pr, nd, ne, ni and nj are as defined above; and $L_8$ represents a phosphite group such as a diethylphosphonyl group, a phosphonium salt such as triphenylphosphonium bromide or a silyl group such as a trimethylsilyl group.

The above General Preparation Method 5 is an example of a method of condensing a compound (35) with a heterocyclic compound (36a) in Step 8-1 to prepare a compound of the general formula (I-4), the general formula (I-7) or the general formula (I-8); or a method of reacting a compound (35) with a heterocyclic compound (36b) having a protecting group in Step 8-2 to once convert the compound (35) into a compound of the general formula (I-5) having a protecting group and then deprotecting the protecting group of the compound of the general formula (I-5) and subsequently reacting the compound with a compound (2b) in Step 5-3 to prepare a compound of the general formula (I-4), the general formula (I-7) or the general formula (I-8).

[Preparation of Compound of General Formula (I-4) and compound of General Formula (I-5)]

The compound of the general formula (I-4) or the compound of the general formula (I-5) can be prepared by reacting a compound (35) with a compound (36a) or (36b) according to Step 8-1 or Step 8-2. Specifically, Step 8-1 or Step 8-2 varies according to the starting material and is not particularly limited insofar as the conditions are similar to those in this reaction. A known method described in many documents such as Wittig reaction, Horner-Emmons reaction or Peterson reaction (see Shin Jikken Kagaku Koza (new Courses in Experimental Chemistry), vol. 19, Yuki Gosei (Organic Synthesis) [I], edited by The Chemical Society of Japan, Maruzen Co., Ltd., June 1992, p. 57-85, for example) may be used.

In Wittig reaction, a compound (35), wherein $L_8$ represents a phosphonium salt, and 0.5 to 2.0 equivalents of a carbonyl compound (36a) or a compound (36b) with respect to the compound (35) are stirred in a solvent in the presence of 1.0 to 5.0 equivalents of a base with respect to the compound (35), for example. This reaction may be a method of first reacting a compound (35) with a base to form a phosphorus ylide and then adding a carbonyl compound (36a) or a compound (36b) to the ylide; or a method of adding a base in the presence of a compound (35) and a carbonyl compound (36a) or a compound (36b). The base used varies according to the starting material and the solvent and is not particularly limited. Preferable examples of the base include alkali metal hydroxides such as sodium hydroxide and lithium hydroxide; alkali metal carbonates such as sodium carbonate; alkali metal salts of alcohols such as sodium methoxide and potassium tert-butoxide; organic bases such as triethylamine, pyridine and diazabicyclononene; organic metals such as butyl lithium and lithium diisobutylamide; and alkali metal hydrides such as sodium hydride. The solvent used varies according to the starting material and the base used, and is not particularly limited insofar as the solvent does not inhibit the reaction and allows the starting material to be dissolved therein to a certain extent. Preferable examples of the solvent used include polar solvents such as nitromethane, acetonitrile, 1-methyl-2-pyrrolidone, N,N-dimethylformamide and dimethyl sulfoxide; ether solvents such as tetrahydrofuran, 1,4-dioxane and 1,2-dimethoxyethane; nonpolar solvents such as benzene, toluene and xylene; alcohol solvents such as ethanol and methanol; halogenated solvents such as chloroform and methylene chloride; water; and a mixed solvent thereof. The reaction temperature must be a temperature that can complete the reaction without promoting formation of an undesirable by-product, and is preferably −78 to 150° C., for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization.

In Horner-Emmons reaction, a compound (35), wherein $L_8$ represents a phosphite group, is reacted with 0.5 to 2.0 equivalents of a carbonyl compound (36a) or a compound (36b) with respect to the compound (35) in a solvent in the presence of 1.0 to 5.0 equivalents of a base with respect to the compound (35), for example. This reaction may be a method of first treating a compound (35) and a base to form a carbanion and then adding a carbonyl compound (36a) or a compound (36b) to the carbanion; or a method of adding a base in the presence of a compound (35) and a carbonyl compound (36a) or a compound (36b). The base used varies according to the starting material and the solvent and is not particularly limited. Preferable examples of the base include alkali metal hydroxides such as sodium hydroxide and lithium hydroxide; alkali metal carbonates such as sodium carbonate; alkali metal salts of alcohols such as sodium methoxide and potassium tert-butoxide; organic bases such as triethylamine, pyridine and diazabicyclononene; organic metals such as butyl lithium and lithium diisobutylamide; alkali metal hydrides such as sodium hydride; and alkali metal ammonium salts such as sodium amide. The solvent used varies according to the starting material and the base used, and is not particularly limited insofar as the solvent does not inhibit the reaction and allows the starting material to be dissolved therein to a certain extent. Preferable examples of the solvent include polar solvents such as 1-methyl-2-pyrrolidone, N,N-dimethylformamide and dimethyl sulfoxide; ether solvents such as tetrahydrofuran, 1,4-dioxane and 1,2-dimethoxyethane; nonpolar solvents such as benzene, toluene and xylene; alcohol solvents such as ethanol and methanol; water; and a mixed solvent thereof. The reaction temperature must be a temperature that can complete the reaction without promoting formation of an undesirable by-product, and is preferably −78 to 150° C., for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization.

In Peterson reaction, a compound (35), wherein $L_8$ represents a silyl group, is reacted with 0.5 to 2.0 equivalents of a carbonyl compound (36a) or a compound (36b) with respect to the compound (35) in a solvent in the presence of 1.0 to 5.0 equivalents of a base with respect to the compound (35), for example. This reaction may be a method of first treating a compound (35) and a base to form a carbanion and then adding a carbonyl compound (36a) or a compound (36b) to the carbanion; or a method of adding a base in the presence of a compound (35) and a carbonyl compound (36a) or a compound (36b). The base used varies according to the starting material and the solvent and is not particularly limited. Preferable examples of the base include alkali metal hydroxides such as sodium hydroxide and lithium hydroxide; alkali metal carbonates such as sodium carbonate; alkali metal salts of alcohols such as sodium methoxide and potassium tert-butoxide; organic bases such as triethylamine, pyridine and diazabicyclononene; organic metals such as butyl lithium and lithium diisobutylamide; alkali metal hydrides such as sodium hydride; and alkali metal ammonium salts such as sodium amide. The solvent used varies according to the starting material and the base used, and is not particularly limited insofar as the solvent does not inhibit the reaction and allows the starting material to be dissolved therein to a certain extent. Preferable examples of the solvent include polar solvents such as 1-methyl-2-pyrrolidone, N,N-dimethylformamide and dimethyl sulfoxide; ether solvents such as tetrahydrofuran, 1,4-dioxane and 1,2-dimethoxyethane; nonpolar solvents such as benzene, toluene and xylene; alcohol solvents such as ethanol and methanol; water; and a mixed solvent thereof. The reaction temperature must be a temperature that can complete the reaction without promoting formation of an undesirable by-product, and is preferably −78 to 150° C., for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization.

[Preparation of Compound (36a) and Compound (36b)]

The compound (36a) and the compound (36b) are commercially available or can be prepared by a technique known to a person skilled in the art. If not commercially available, the compounds can be prepared by acylation of a compound (31), for example (see Shin Jikken Kagaku Koza (New Courses in Experimental Chemistry), vol. 21, Yuki Gosei (Organic Synthesis) [III], edited by The Chemical Society of Japan, Maruzen Co., Ltd., February 1991, p. 184-194, for example).

[Preparation of Compound (35)]

The compound (35) can be prepared from a compound (6) or compound (17) as a starting material by a known method described in many documents. Preferably, for example, i) the compound (35) as a Wittig reagent, wherein $L_8$ represents a phosphonium salt, can be prepared by halogenating a corresponding alcohol compound by a method known to a person skilled in the art (see Shin Jikken Kagaku Koza (New Courses in Experimental Chemistry), vol. 19, Yuki Gosei (Organic Synthesis) [I], edited by The Chemical Society of Japan, Maruzen Co., Ltd., June 1992, p. 430-438, for example), and then reacting the compound with an organophosphorus compound such as triphenylphosphine (see Organic Reaction, 1965, vol. 14, p. 270, for example). ii) The compound (35) as a Horner-Emmons reagent, wherein $L_8$ represents a phosphite, can be prepared by halogenating a corresponding alcohol compound by a method known to a person skilled in the art (see Shin Jikken Kagaku Koza (New Courses in Experimental Chemistry), vol. 19, Yuki Gosei (Organic Synthesis) [I], edited by The Chemical Society of Japan, Maruzen Co., Ltd., June 1992, p. 430-438, for example), and then reacting the compound with an alkyl phosphinite by Arbuzov reaction (see Chemical Review, 1981, vol. 81, p. 415, for example) or with a metal phosphonite by Becker reaction (see Journal of the American Chemical Society, 1945, vol. 67, p. 1180, for example). Alternatively, the Horner-Emmons reagent can be prepared from a corresponding carbonyl compound and a chlorophosphate in the presence of a base (see The Journal of Organic Chemistry, 1989, vol. 54, p. 4750, for example). iii) The compound (35) as a Peterson reagent, wherein $L_9$ represents a silyl group, can be prepared from a corresponding halogen compound and a trialkylsilyl chloride in the presence of a base (see Journal of Organometallic Chemistry, 1983, vol. 248, p. 51, for example).

The compound of the general formula (I-7) or the compound of the general formula (I-8) can be prepared from the compound (36a) or compound (36b), wherein two of $R^{10}$, $R^{11}$ and $R^{12}$ form a ring, as a starting material by the same method as above.

[General Preparation Method 6]

Typically used General Preparation Method 6 for the compound of the general formula (I) of the present invention will be described below.

[Formula 43]

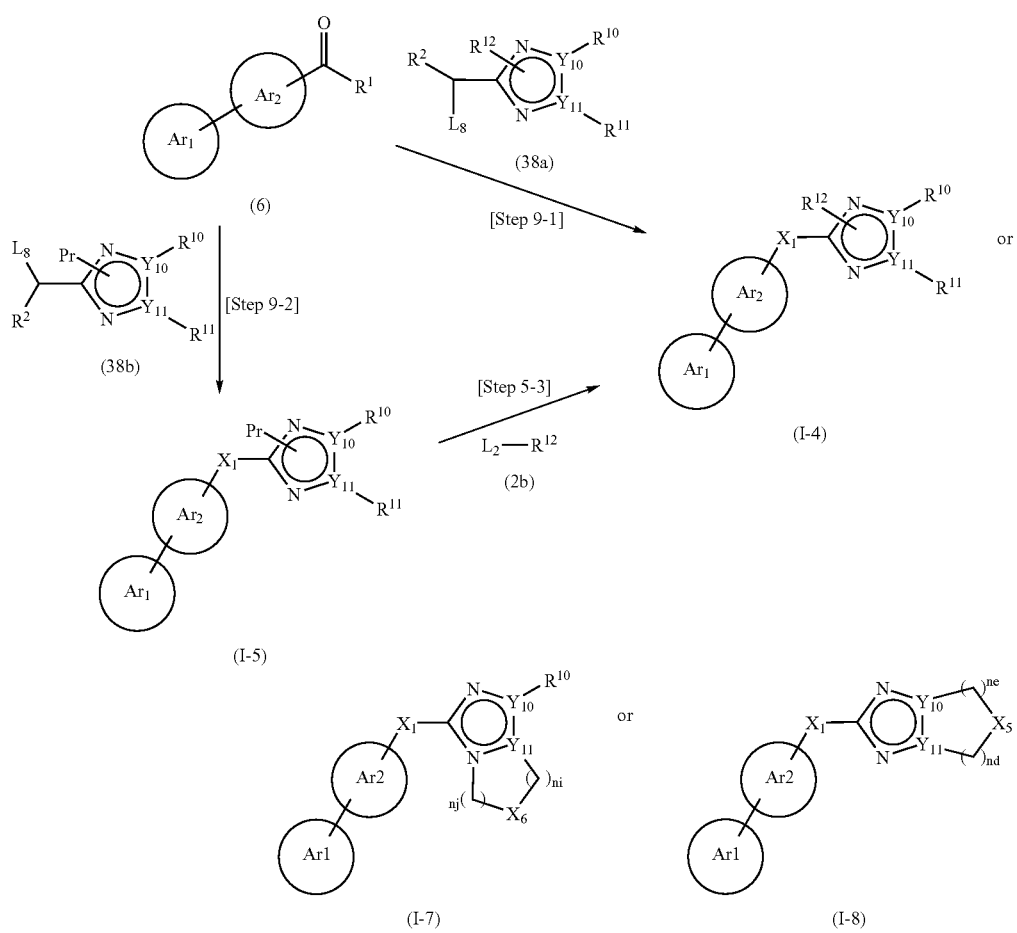

In the formula, the following partial structure (formula III-4, III-5, III-7 or III-8):

[Formula 44]

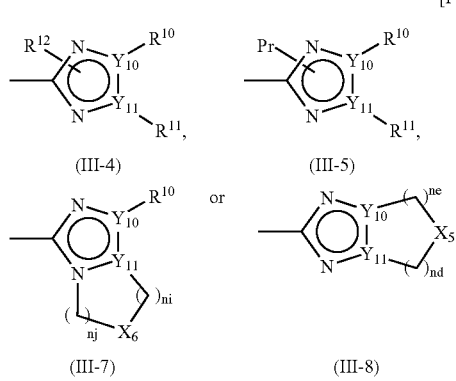

is a partial structure corresponding to the above-described Het, wherein $Ar_1$, $Ar_2$, $X_1$, $X_5$, $X_6$, $Y_{10}$, $Y_{11}$, $R_1$, $R_2$, $R^{10}$, $R^{11}$, $R^{12}$, $L_2$, $L_8$, Pr, nd, ne, ni and nj are as defined above.

The above General Preparation Method 6 is an example of a method of condensing a compound (6) with a heterocyclic compound (38a) in Step 9-1 to prepare a compound of the general formula (I-4), the general formula (I-7) or the general formula (I-8); or a method of condensing a compound (6) with a heterocyclic compound (36b) having a protecting group in Step 8-2 to once convert the compound (6) into a compound of the general formula (I-5) having a protecting group and then deprotecting the protecting group of the compound of the general formula (I-5) and subsequently reacting the compound with a compound (2b) in Step 5-3 to prepare a compound of the general formula (I-4), the general formula (I-7) or the general formula (I-8).

[Preparation of Compound of General Formula (I-4) and Compound of General Formula (I-5)]

The compound of the general formula (I-4) or general formula (I-5) can be prepared by reacting a compound (6) with a compound (38a) or compound (36b) according to Step 9-1 or Step 9-2. Specifically, Step 9-1 or Step 9-2 varies according to the starting material and is not particularly limited insofar as the conditions are similar to those in this reaction. A known method described in many documents such as Wittig reaction, Horner-Emmons reaction or Peterson reaction may be used for the reaction (see Jikken Kagaku Koza (Courses in Experimental Chemistry), vol. 19, Yuki Gosei (Organic Synthesis) [I], edited by The Chemical Society of Japan, Maruzen Co., Ltd., June 1992, p. 57-85, for example).

In Wittig reaction, a carbonyl compound (6) and 0.5 to 2.0 equivalents of a compound (38a) or compound (38b), wherein $L_8$ represents a phosphonium salt, with respect to the carbonyl compound (6) are stirred in a solvent in the presence of 1.0 to 5.0 equivalents of a base with respect to the carbonyl compound (6), for example. This reaction may be a method of first reacting a compound (38a) or compound (38b) with a base to form a phosphorus ylide and then adding a carbonyl compound (6) to the ylide; or a method of adding a base in the presence of a carbonyl compound (6) and a compound (38a) or compound (38b). The base used varies according to the starting material and the solvent and is not particularly limited. Preferable examples of the base include alkali metal hydroxides such as sodium hydroxide and lithium hydroxide; alkali metal carbonates such as sodium carbonate; alkali metal salts of alcohols such as sodium methoxide and potassium tert-butoxide; organic bases such as triethylamine, pyridine and diazabicyclononene; organic metals such as butyl lithium and lithium diisobutylamide; and alkali metal hydrides such as sodium hydride. The solvent used varies according to the starting material and the base used, and is not particularly limited insofar as the solvent does not inhibit the reaction and allows the starting material to be dissolved therein to a certain extent. Preferable examples of the solvent used include polar solvents such as nitromethane, acetonitrile, 1-methyl-2-pyrrolidone, N,N-dimethylformamide and dimethyl sulfoxide; ether solvents such as tetrahydrofuran, 1,4-dioxane and 1,2-dimethoxyethane; nonpolar solvents such as benzene, toluene and xylene; alcohol solvents such as ethanol and methanol; halogenated solvents such as chloroform and methylene chloride; water; and a mixed solvent thereof. The reaction temperature must be a temperature that can complete the reaction without promoting formation of an undesirable by-product, and is preferably −78 to 150° C., for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization.

In Horner-Emmons reaction, a carbonyl compound (6) and 0.5 to 2.0 equivalents of a compound (38a) or compound (38b), wherein $L_8$ represents a phosphite group, with respect to the carbonyl compound (6) are stirred in a solvent in the presence of 1.0 to 5.0 equivalents of a base with respect to the carbonyl compound (6), for example. This reaction may be a method of first treating a compound (38a) or compound (38b) and a base to form a carbanion and then adding a carbonyl compound (6) to the carbanion; or a method of adding a base in the presence of a carbonyl compound (6) and a compound (38a) or compound (38b). The base used varies according to the starting material and the solvent and is not particularly limited. Preferable examples of the base include alkali metal hydroxides such as sodium hydroxide and lithium hydroxide; alkali metal carbonates such as sodium carbonate; alkali metal salts of alcohols such as sodium methoxide and potassium tert-butoxide; organic bases such as triethylamine, pyridine and diazabicyclononene; organic metals such as butyl lithium and lithium diisobutylamide; alkali metal hydrides such as sodium hydride; and alkali metal ammonium salts such as sodium amide. The solvent used varies according to the starting material and the base used, and is not particularly limited insofar as the solvent does not inhibit the reaction and allows the starting material to be dissolved therein to a certain extent. Preferable examples of the solvent include polar solvents such as 1-methyl-2-pyrrolidone, N,N-dimethylformamide and dimethyl sulfoxide; ether solvents such as tetrahydrofuran, 1,4-dioxane and 1,2-dimethoxyethane; nonpolar solvents such as benzene, toluene and xylene; alcohol solvents such as ethanol and methanol; water; and a mixed solvent thereof. The reaction temperature must be a temperature that can complete the reaction without promoting formation of an undesirable by-product, and is preferably −78 to 150° C., for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization.

In Peterson reaction, a carbonyl compound (6) and 0.5 to 2.0 equivalents of a compound (38a) or compound (38b), wherein $L_8$ represents a silyl group, with respect to the carbonyl compound (6) are stirred in a solvent in the presence of 1.0 to 5.0 equivalents of a base with respect to the carbonyl compound (6), for example. This reaction may be a method of first treating a compound (38a) or compound (38b) and a base to form a carbanion and then adding a carbonyl compound (6) to the carbanion; or a method of adding a base in the presence of a carbonyl compound (6) and a compound (38a) or compound (38b). The base used varies according to the starting material and the solvent and is not particularly limited. Preferable examples of the base include alkali metal hydroxides such as sodium hydroxide and lithium hydroxide; alkali metal carbonates such as sodium carbonate; alkali metal salts of alcohols such as sodium methoxide and potassium tert-butoxide; organic bases such as triethylamine, pyridine and diazabicyclononene; organic metals such as butyl lithium and lithium diisobutylamide; alkali metal hydrides such as sodium hydride; and alkali metal ammonium salts such as sodium amide. The solvent used varies according to the starting material and the base used, and is not particularly limited insofar as the solvent does not inhibit the reaction and allows the starting material to be dissolved therein to a certain extent. Preferable examples of the solvent include polar solvents such as 1-methyl-2-pyrrolidone, N,N-dimethylformamide and dimethyl sulfoxide; ether solvents such as tetrahydrofuran, 1,4-dioxane and 1,2-dimethoxyethane; nonpolar solvents such as benzene, toluene and xylene; alcohol solvents such as ethanol and methanol; water; and a mixed solvent thereof. The reaction temperature must be a temperature that can complete the reaction without promoting formation of an undesirable by-product, and is preferably −78 to 150° C., for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization.

[Preparation of Compound (38a) and Compound (38b)]

The compound (38a) and the compound (38b) are commercially available or prepared by a technique known to a person skilled in the art. If not commercially available, for example, i) the compound (38a) or compound (38b) as a Wittig reagent, wherein $L_8$ represents a phosphonium salt, can be prepared by halogenating a corresponding alcohol compound by a method known to a person skilled in the art (see Shin Jikken Kagaku Koza (New Courses in Experimental Chemistry), vol. 19, Yuki Gosei (Organic Synthesis) [I], edited by The Chemical Society of Japan, Maruzen Co., Ltd., June 1992, p. 430-438, for example), and then reacting the compound with an organophosphorus compound such as triphenylphosphine (see Organic Reaction, 1965, vol. 14, p. 270, for example). ii) The compound (38a) or compound (38b) as a Horner-Emmons reagent, wherein $L_8$ represents a phosphite, can be prepared by halogenating a corresponding alcohol compound by a method known to a person skilled in the art (see Shin Jikken Kagaku Koza (New Courses in Experimental Chemistry), vol. 19, Yuki Gosei (Organic Synthesis) [I], edited by The Chemical Society of Japan, Maruzen Co., Ltd., June 1992, p. 430-438, for example), and then reacting the compound with an alkyl phosphinite by Arbuzov reaction (see Chemical Review, 1981, vol. 81, p. 415, for example) or with a metal phosphonite by Becker reaction (see Journal of the American Chemical Society, 1945, vol. 67, p. 1180, for example). Alternatively, the compound can be prepared from a corresponding carbonyl compound and a chlorophosphate in the presence of a base (see Journal of Organic Chemistry, 1989, vol. 54, p. 4750, for example). iii) The compound (38a) or compound (38b) as a Peterson reagent, wherein $L_9$ represents a silyl group, can be prepared from a corresponding halogen compound and a trialkylsilyl chloride (see Journal of Organometallic Chemistry, 1983, vol. 248, p. 51, for example).

The compound of the general formula (I-7) or the compound of the general formula (I-8) can be prepared from the compound (38a) or compound (38b), wherein two of $R^{10}$, $R^{11}$ and $R^{12}$ form a ring, as a starting material by the same method as above.

[General Preparation Method 7]

Typically used General Preparation Method 7 for the compound of the general formula (I) of the present invention will be described below.

[Formula 45]

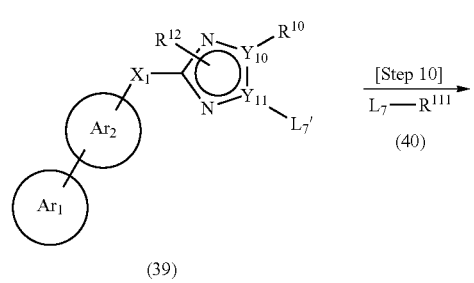
(39)

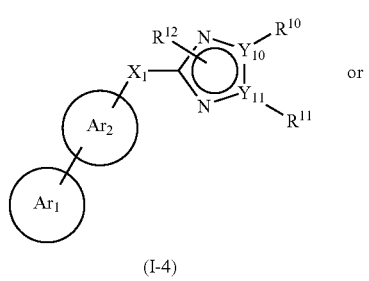
(I-4)

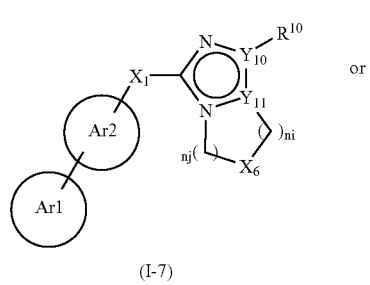
(I-7)

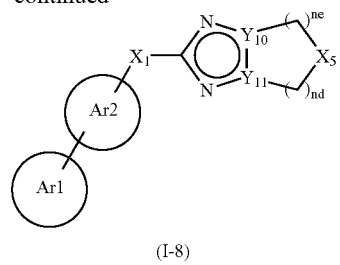
(I-8)

In the formula, the following partial structure (formula III-4, III-7 or III-8):

[Formula 46]

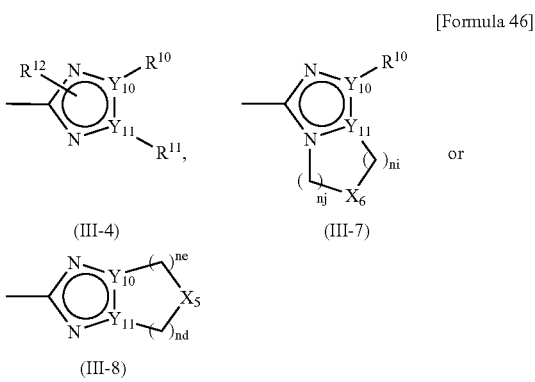

is a partial structure corresponding to the above-described Het, wherein $Ar_1$, $Ar_2$, $X_1$, $X_5$, $X_6$, $Y_{10}$, $Y_{11}$, $R^{10}$, $R^{11}$, $R^{12}$, $L_7$, $L_7'$, nd, ne, ni and nj are as defined above; and $R^{111}$ is as defined for $R^{11}$.

The above General Preparation Method 7 is an example of a method of condensing a compound (39) with a compound (40) in Step 10 to prepare a compound of the general formula (I-4), the general formula (I-7) or the general formula (I-8).

[Preparation of Compound of General Formula (I-4)]

The compound of the general formula (I-4) can be prepared by reacting a compound (39) with a compound (40) according to Step 10. Specifically, Step 10 varies according to the starting material and is not particularly limited insofar as the conditions are similar to those in this reaction. A known method described in many documents such as Mizoroki-Heck reaction (see R. F. Heck, "Org. Reactions.", 1982, vol. 27, p. 345, for example), Suzuki-Miyaura reaction (see A. Suzuki, "Chem. Rev.", 1995, vol. 95, p. 2457, for example), Sonogashira reaction (see K. Sonogashira, "Comprehensive Organic Synthesis", 1991, vol. 3, p. 521) or Stille coupling reaction (see J. K. Stille, "Angew. Chem. Int. Ed. Engl.", 1986, vol. 25, p. 508, for example) may be used for the reaction.

In Mizoroki-Heck reaction, a compound (39), wherein $L_7'$ represents a chlorine atom, a bromine atom, an iodine atom or a sulfonate group such as a trifluoromethanesulfonate group, and 1.0 to 5.0 equivalents of an alkene compound (40), wherein $L_7$ represents a hydrogen atom and $R^{111}$ represents a C1-6 alkenyl group which may be substituted with 1 to 3 substituents selected from the above Substituent Group A1, with respect to the compound (39) are stirred in a solvent in the presence of 0.01 to 0.2 equivalent of a transition metal catalyst with respect to the compound (39), for example. The transition metal catalyst used is preferably a palladium complex, for example, and more preferably a known palladium complex such as palladium (II) acetate, dichlorobis(triphenylphosphine)palladium (II), tetrakis(triphenylphosphine)palladium (0) or tris(dibenzylideneacetone)dipalladium (0). A phosphorus ligand such as triphenylphosphine, tri-o-tolylphosphine, tri-tert-butylphosphine or 2-(di-tert-butylphosphino)biphenyl may be preferably added, for example, in order to make the reaction efficiently proceed. A preferable result may be obtained in the presence of a base, and the base used is not particularly limited insofar as the base is used in a coupling reaction the same as this reaction. Preferable examples of the base include triethylamine, N,N-diisopropylethylamine, N,N-dicyclohexylmethylamine and tetrabutylammonium chloride. The solvent used varies according to the starting material and the transition metal catalyst used, and is not particularly limited insofar as the solvent does not inhibit the reaction and allows the starting material to be dissolved therein to a certain extent. Preferable examples of the solvent include acetonitrile, tetrahydrofuran, 1,4-dioxane, 1,2-dimethoxyethane, benzene, toluene, xylene, 1-methyl-2-pyrrolidone and N,N-dimethylformamide. The reaction temperature must be a temperature that can complete the coupling reaction, and is preferably room temperature to 150° C., for example. This reaction is performed preferably in an inert gas atmosphere, and more preferably in a nitrogen or argon atmosphere, for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization.

In Suzuki-Miyaura reaction, a compound (39), wherein $L_7'$ represents a chlorine atom, a bromine atom, an iodine atom or a sulfonate group such as a trifluoromethanesulfonate group, and 1.0 to 10.0 equivalents of a compound (40), wherein $L_7$ represents a boronic acid group or a boronate group, with respect to the compound (39) are stirred in a solvent in the presence of 0.01 to 0.5 equivalent of a transition metal catalyst with respect to the compound (39), for example. The transition metal catalyst used is preferably a known palladium complex, and more preferably a known palladium complex such as palladium (II) acetate, dichlorobis(triphenylphosphine)palladium (II), tetrakis(triphenylphosphine)palladium (0) or tris(dibenzylideneacetone)dipalladium (0). A phosphorus ligand such as triphenylphosphine, tri-o-tolylphosphine, tricyclohexylphosphine or tri-tert-butylphosphine may be preferably added, for example, in order to make the reaction efficiently proceed. A quaternary ammonium salt, preferably tetrabutylammonium chloride or tetrabutylammonium bromide, for example, may also be added in order to make the reaction efficiently proceed. In this reaction, a preferable result may be achieved in the presence of a base. The base used at this time varies according to the starting material, the solvent used and the like, and is not particularly limited. Preferable examples of the base include sodium hydroxide, barium hydroxide, potassium fluoride, cesium fluoride, sodium carbonate, potassium carbonate, cesium carbonate and potassium phosphate. The solvent used varies according to the starting material and the transition metal catalyst used, and is not particularly limited insofar as the solvent does not inhibit the reaction and allows the starting material to be dissolved therein to a certain extent. Preferable examples of the solvent include acetonitrile, tetrahydrofuran, 1,4-dioxane, 1,2-dimethoxyethane, benzene, toluene, xylene, 1-methyl-2-pyrrolidone, N,N-dimethylformamide, water and a mixed solvent thereof. The reaction temperature must be a temperature that can complete the coupling reaction, and is preferably room temperature to 200° C., for example. This reaction is performed preferably in an inert gas atmosphere, and more preferably in a nitrogen or argon atmosphere, for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization. The desired compound of the general formula (I-4) can also be obtained from a combination of the compound (39), wherein $L_7'$ represents a boronic acid group or a boronate group, with the compound (40), wherein $L_7$ represents a chlorine atom, a bromine atom, an iodine atom or a sulfonate group such as a trifluoromethanesulfonate group, by the same method as above.

In Sonogashira reaction, a compound (39), wherein $L_7'$ represents a chlorine atom, a bromine atom, an iodine atom or a sulfonate group such as a trifluoromethanesulfonate group, and 1.0 to 10 equivalents of an alkyne compound (40), wherein $L_7$ represents a hydrogen atom and $R^{111}$ represents a C1-6 alkynyl group which may be substituted with 1 to 3 substituents selected from the above Substituent Group A1, with respect to the compound (39) are stirred in a solvent in the presence of 0.01 to 0.5 equivalent of a transition metal catalyst with respect to the compound (39), for example. The transition metal catalyst used is preferably a known palladium complex, for example, and more preferably a known palladium complex such as palladium (II) acetate, dichlorobis(triphenylphosphine)palladium (II), tetrakis(triphenylphosphine)palladium (0) or tris(dibenzylideneacetone)dipalladium (0). A phosphorus ligand such as triphenylphosphine, tri-o-tolylphosphine or tri-tert-butylphosphine may be preferably added, for example, in order to make the reaction efficiently proceed. In the reaction, a good result may be achieved when adding a metal halide or a quaternary ammonium salt, preferably copper (I) iodide, lithium chloride, tetrabutylammonium fluoride or silver (I) oxide, for example. A preferable result may be obtained in the presence of a base, and the base used here is not particularly limited insofar as the base is used in a coupling reaction the same as this reaction. Preferable examples of the base include diethylamine, triethylamine, N,N-diisopropylethylamine, piperidine and pyridine. Preferable examples of the solvent used include acetonitrile, tetrahydrofuran, 1,4-dioxane, 1,2-dimethoxyethane, benzene, toluene, xylene, 1-methyl-2-pyrrolidone, N,N-dimethylformamide and dimethyl sulfoxide. More preferable examples of the solvent include tetrahydrofuran, 1,4-dioxane, 1-methyl-2-pyrrolidone and N,N-dimethylformamide. The reaction temperature must be a temperature that can complete the coupling reaction, and is preferably room temperature to 150° C., for example. This reaction is performed preferably in an inert gas atmosphere, and more preferably in a nitrogen or argon atmosphere, for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization.

In Stille coupling reaction, a compound (39), wherein $L_7'$ represents a chlorine atom, a bromine atom, an iodine atom or a trifluoromethanesulfonate group, and 1.0 equivalent or more of a compound (40), wherein $L_7$ represents a trialkyltin group, with respect to the compound (39) are stirred in a solvent in the presence of 0.01 to 0.2 equivalent of a transition metal catalyst with respect to the compound (39), for example. The transition metal catalyst used is preferably a palladium complex, for example, and more preferably a known palladium complex such as palladium (II) acetate, dichlorobis(triphenylphosphine)palladium (II), tetrakis(triphenylphosphine)palladium (0) or tris(dibenzylideneacetone)dipalladium (0). In order to make the reaction efficiently proceed, 0.1 to 5.0 equivalents of copper (I) halide or/and lithium chloride may be added. Preferable examples of the solvent used include toluene, xylene, N,N-dimethylformamide, N,N-dimethylacetamide, 1-methyl-2-pyrrolidone and dimethyl sulfoxide. The reaction temperature must be a temperature that can complete the coupling reaction, and is preferably room temperature to 150° C., for example. This reaction is performed preferably in an inert gas atmosphere, and more preferably in a nitrogen or argon atmosphere, for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization. The desired compound of the general formula (I-4) can also be obtained from a combination of the compound (39), wherein $L_7$' represents a trialkyltin group, with the compound (40), wherein $L_7$ represents a chlorine atom, a bromine atom, an iodine atom or a trifluoromethanesulfonate group, by the same method as above. The compound (40) is commercially available or can be prepared by a method known to a person skilled in the art.

[Preparation of Compound (39)]

The compound (39) can be prepared by a method in the above General Preparation Methods 1 to 6.

The compound of the general formula (I-7) or the general formula (I-8) can be prepared by the same method as above using, as a starting material, the compound (39), wherein $R^{10}$ and $R^{12}$ each represent an alkyl group substituted with an alkenyl group or an alkynyl group or an alkenyl group, an alkynyl group or an alkyl group substituted with a halogen atom and $L_7$' represents a chlorine atom, a bromine atom, an iodine atom, a sulfonate group such as a trifluoromethanesulfonate group, or a trialkyltin group, without use of the compound (40).

[General Preparation Method 8]

Typically used General Preparation Method 8 for the compound of the general formula (I) of the present invention will be described below.

[Formula 47]

(41)    [Step 12]    (42)

In the formula, the following partial structure (formula III-4, III-7 or III-8):

[Formula 48]

(III-4)    (III-7)    (III-8)

is a partial structure corresponding to the above-described Het, wherein $Ar_1$, $Ar_2$, $X_1$, $X_5$, $X_6$, $Y_{10}$, $Y_{11}$, $R^{10}$, $R^{11}$, $R^{12}$, $L_3$, nd, ne, ni and nj are as defined above.

The above General Preparation Method 8 is an example of a method of condensing a compound (41) with a compound (42) in Step 12 to prepare a compound of the general formula (I-4), the general formula (I-7) or the general formula (I-8).

[Preparation of Compound of General Formula (I-4)]

The compound of the general formula (I-4) can be prepared by condensing a compound (41) with a compound (42) according to Step 12. Specifically, Step 12 varies according to the starting material and is not particularly limited insofar as the conditions are similar to those in this reaction. For example, a known method described in many documents such as coupling reaction using a copper compound of an arylboronic acid derivative (see The Journal of Organic Chemistry, 2001, vol. 66, p. 7892, for example), Ullmann reaction (see Journal of Medicinal Chemistry, 1981, vol. 24, p. 1139, for example) or nucleophilic substitution reaction (see Journal of Medicinal Chemistry, 1991, vol. 39, p. 2671-2677, for example) may be used for the reaction.

The coupling reaction of an arylboronic acid derivative using a copper compound is, for example, a method of stirring a compound (41), wherein $L_3$ represents a boronic acid group or a boronate group, and 1.0 to 10.0 equivalents of a compound (42) with respect to the compound (41) in a solvent in the presence of 0.01 to 1.0 equivalent of a copper reagent such as copper, copper bromide or copper iodide with respect to the compound (41) by addition of 1.0 to 10.0 equivalents of a base with respect to the compound (41). The base used varies according to the starting material, the solvent used and the like, and is not particularly limited insofar as the base does not inhibit the reaction. Preferable examples of the base include organic bases such as triethylamine, pyridine and tetramethylethylenediamine; alkali metal salts such as potassium carbonate, sodium carbonate, potassium acetate, sodium acetate and cesium carbonate; and metal alkoxides such as sodium methoxide and potassium tert-butoxide. The copper reagent used varies according to the starting material and is not particularly limited. Preferable examples of the copper reagent include copper acetate and di-μ-hydroxo-bis[(N,N,N',N'-tetramethylethylenediamine)copper (II)]chloride. The solvent used varies according to the starting material, the reagent and the like, and is not particularly limited insofar as the solvent does not inhibit the reaction and allows the starting material to be dissolved therein to a certain extent. Preferable examples of the solvent include ether solvents such as tetrahydrofuran, 1,4-dioxane and diethyl ether; halogenated solvents such as methylene chloride, 1,2-dichloroethane and chloroform; polar solvents such as ethyl acetate, N,N-dimethylformamide and N-methylpyrrolidone; nonpolar solvents such as toluene, benzene and dichlorobenzene; and a mixture thereof. The reaction temperature must be a temperature that can complete the reaction without promoting formation of an undesirable by-product, and is preferably room temperature to 200° C., for example. Good results such as reduction in the reaction time and improvement of the yield may be achieved when the reaction is performed in an oxygen atmosphere or air stream. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization.

In Ullmann reaction, a compound (41), wherein $L_3$ represents a halogen atom such as a chlorine atom, a bromine atom or an iodine atom, and 1.0 to 10.0 equivalents of a compound (42) with respect to the compound (41) are stirred in a solvent in the presence of 0.01 to 1.0 equivalent of a copper reagent such as copper, copper bromide or copper iodide with respect to the compound (41) by addition of 1.0 to 10.0 equivalents of a base with respect to the compound (41), for example. The base used varies according to the starting material and is not particularly limited. Preferable examples of the base include alkali metal salts such as potassium carbonate, sodium carbonate, potassium acetate, sodium acetate and cesium carbonate; and metal alkoxides such as sodium methoxide and potassium tert-butoxide. The solvent used varies according to the starting material, the reagent and the like, and is not particularly limited insofar as the solvent does not inhibit the reaction and allows the starting material to be dissolved therein to a certain extent. Preferable examples of the solvent that can be used include ether solvents such as tetrahydrofuran, 1,4-dioxane and diethyl ether; halogenated solvents such as methylene chloride, 1,2-dichloroethane and chloroform; alcohol solvents such as amyl alcohol and isopropyl alcohol; polar solvents such as N,N-dimethylformamide and N-methylpyrrolidone; nonpolar solvents such as toluene, benzene and dichlorobenzene; and a mixture thereof. The reaction temperature must be a temperature that can complete the reaction without promoting formation of an undesirable by-product, and is preferably room temperature to 200° C., for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique, extraction or/and crystallization.

In nucleophilic substitution reaction, a compound (41), wherein $L_3$ represents a halogen atom such as a chlorine atom, a bromine atom or an iodine atom or a sulfonate group such as a methanesulfonate group, a p-toluenesulfonate group or a trifluoromethanesulfonate group, and 2.0 to 5.0 equivalents of a compound (42) with respect to the compound (41) are stirred in a solvent in the presence or absence of 1.0 to 5.0 equivalents of a base with respect to the compound (41), for example. The base used varies according to the starting material and is not particularly limited. Preferable examples of the base include sodium hydride, sodium hydroxide, potassium hydroxide, potassium carbonate, sodium carbonate, cesium carbonate, barium carbonate, pyridine, lutidine and triethylamine. The solvent used varies according to the starting material, and is not particularly limited insofar as the solvent does not inhibit the reaction and allows the starting material to be dissolved therein to a certain extent. Preferable examples of the solvent include acetonitrile, tetrahydrofuran, dimethyl sulfoxide, N,N-dimethylformamide and N-methylpyrrolidine. The base may optionally be used as a solvent. The reaction temperature must be a temperature that can complete the reaction without promoting formation of an undesirable by-product, and is preferably room temperature to 150° C., for example. Under preferable reaction conditions, the reaction is completed in 1 to 24 hours, and the progress of the reaction can be monitored by a known chromatography technique. An undesirable by-product can be removed by a technique known to a person skilled in the art such as a conventional chromatography technique or/and crystallization.

[Preparation of Compound (41)]

The compound (41) is prepared by the same method as in the above General Preparation Methods 1 to 7.

[Preparation of Compound (42)]

The compound (42) is commercially available or prepared by a method known to a person skilled in the art.

The compound of the general formula (I-7) or the general formula (I-8) can be prepared from the compound (41), wherein two of $R^{10}$, $R^{11}$ and $R^{12}$ form a ring, as a starting material by the same method as above.

General Preparation Methods 1 to 8 for the compound of the present invention described above in detail are methods for preparing a compound represented by the general formula (I-9), the general formula (I-4), the general formula (I-5), the general formula (I-6), the general formula (I-7) or the general formula (I-8), wherein Het falls within a part of the definition of Het in the general formula (I). However, the compound of the general formula (I), wherein Het falls within another part of the definition of Het, can be prepared almost in the same manner as in the above General Preparation Methods 1 to 8, or can be prepared by another method itself known to a person skilled in the art. The examples described later will provide reference to these Preparation Methods, and the compound of the general formula (I) can be easily prepared by a method itself known to a person skilled in the art based on these examples.

The compound of the general formula (I) or pharmacologically acceptable salt thereof according to the present invention is effective for prevention or treatment of a disease caused by Aβ and is excellent in terms of pharmacokinetics, toxicity, stability, absorption and the like.

A prophylactic or therapeutic agent for a disease caused by Aβ comprising the compound of the formula (I) or pharmacologically acceptable salt thereof according to the present invention as an active ingredient can be prepared by a conventional method. Preferable examples of the dosage form include tablets, powders, fine granules, granules, coated tablets, capsules, syrups, troches, inhalants, suppositories, injections, ointments, ophthalmic solutions, ophthalmic ointments, nasal drops, ear drops, cataplasms and lotions. The prophylactic or therapeutic agent can be prepared by using ingredients typically used such as an excipient, a binder, a lubricant, a colorant and a corrective, and ingredients used where necessary such as a stabilizer, an emulsifier, an absorbefacient, a surfactant, a pH adjuster, a preservative and an antioxidant, and can be prepared by blending ingredients generally used as materials for a pharmaceutical preparation. Examples of such ingredients include animal and vegetable oils such as soybean oil, beef tallow and synthetic glyceride; hydrocarbons such as liquid paraffin, squalane and solid paraffin; ester oils such as octyldodecyl myristate and isopropyl myristate; higher alcohols such as cetostearyl alcohol and behenyl alcohol; a silicone resin; silicone oil; surfactants such as polyoxyethylene fatty acid ester, sorbitan fatty acid ester, glycerin fatty acid ester, polyoxyethylene sorbitan fatty acid ester, polyoxyethylene hydrogenated castor oil and a polyoxyethylene-polyoxypropylene block copolymer; water-soluble polymers such as hydroxyethylcellulose, polyacrytic acid, a carboxyvinyl polymer, polyethylene glycol, polyvinylpyrrolidone and methylcellulose; lower alcohols such as ethanol and isopropanol; polyhydric alcohols such as glycerin, propylene glycol, dipropylene glycol and sorbitol; sugars such as glucose and sucrose; inorganic powders such as silicic anhydride, magnesium aluminum silicate and aluminum silicate; and purified water. Examples of the excipient used include lactose, corn starch, saccharose, glucose, mannitol, sorbitol, crystalline cellulose and silicon dioxide. Examples of the binder used include polyvinyl alcohol, polyvinyl ether, methylcellulose, ethylcellulose, gum arabic, tragacanth, gelatin, shellac, hydroxypropylmethylcellulose, hydroxypropylcellulose, polyvinylpyrrolidone, a polypropylene glycol-polyoxyethylene block copolymer and meglumine. Examples of the disintegrator used include starch, agar, gelatin powder, crystalline cellulose, calcium carbonate, sodium bicarbonate, calcium citrate, dextrin, pectin and carboxymethylcellulose calcium. Examples of the lubricant used include magnesium stearate, talc, polyethylene glycol, silica and hydrogenated vegetable oil. Examples of the colorant used include those permitted to be added to pharmaceuticals. Examples of the corrective used include cocoa powder, menthol, empasm, mentha oil, borneol and cinnamon powder.

For example, an oral preparation is prepared by adding an active ingredient compound or a salt thereof or a hydrate of the compound or salt, an excipient, and, where necessary, a binder, a disintegrant, a lubricant, a colorant and a corrective, for example, and then forming the mixture into powder, fine granules, granules, tablets, coated tablets or capsules, for example, by a conventional method. It is obvious that tablets or granules may be appropriately coated, for example, sugar coated, where necessary. A syrup or an injection preparation is prepared by adding a pH adjuster, a solubilizer and an isotonizing agent, for example, and a solubilizing agent, a stabilizer and the like where necessary by a conventional method. An external preparation may be prepared by any conventional method without specific limitations. As a base material, any of various materials usually used for a pharmaceutical, a quasi drug, a cosmetic or the like may be used. Examples of the base material include materials such as animal and vegetable oils, mineral oils, ester oils, waxes, higher alcohols, fatty acids, silicone oils, surfactants, phospholipids, alcohols, polyhydric alcohols, water-soluble polymers, clay minerals and purified water. A pH adjuster, an antioxidant, a chelator, a preservative and fungicide, a colorant, a flavor or the like may be added where necessary. Further, an ingredient having a differentiation inducing effect such as a blood flow enhancer, a bactericide, an antiphlogistic, a cell activator, vitamin, amino acid, a humectant or a keratolytic agent may be blended where necessary.

The dose of the therapeutic or prophylactic agent of the present invention varies according to the degree of symptoms, age, sex, body weight, mode of administration, type of salt and specific type of disease, for example. Typically, the compound of the formula (I) or pharmacologically acceptable salt thereof is orally administered to an adult at about 30 μg to 10 g, preferably 100 μg to 5 g, and more preferably 100 μg to 100 mg per day, or is administered to an adult by injection at about 30 μg to 1 g, preferably 100 μg to 500 mg, and more preferably 100 μg to 30 mg per day, in a single dose or several divided doses, respectively.

For prevention or treatment of a disease caused by Aβ such as Alzheimer's disease, senile dementia, Down's disease and amyloidosis, the compound represented by the formula (I) or a pharmacologically acceptable salt thereof according to the present invention may be used in combination with for compounds having mechanisms as described below.

For example, such compounds include cholinesterase inhibitors (e.g., donepezil, huperzine A, tacrine, rivastigmine, galantamine); AMPA receptor antagonists (e.g., 1,2-dihydropyridine compounds such as 3-(2-cyanophenyl)-5-(2-pyridyl)-1-phenyl-1,2-dihydropyridin-2-one); NMDA receptor antagonists (e.g., memantine); acetylcholine releasing stimulants (e.g., pramiracetam; aniracetam); calcium channel agonists (e.g., nefiracetam); free radical scavengers (e.g., EGb 761); platelet activating factor antagonists (e.g., EGb 761); platelet aggregation antagonists (e.g., EGb 761, triflusal); insulin sensitizers (e.g., rosiglitazone); peroxisome proliferator-activated receptor agonists (e.g., rosiglitazone); peroxisome proliferator-activated receptor gamma agonists (e.g., rosiglitazone); monoamine oxidase B inhibitors (e.g., rasagiline, selegiline, procaine); carnitine acetyltransferase stimulants (e.g., levacecarnine); NSAIDs (e.g., triflusal, cyclooxygenase-2 inhibitors, such as celecoxib); nerve growth factor agonists (e.g., xaliproden, FPF 1070); beta-amyloid inhibitors (e.g., tarenflurbil, tramiprosate, leuprorelin-D); immunomodulators (e.g., tarenflurbil, immune globulin, icosapentethyl ester); NF-kappa B inhibitors (e.g., tarenflurbil); thyrotropin releasing hormone agonists (e.g., taltirelin); dopamine D2 receptor antagonists (e.g., risperidone); serotonin 2 receptor antagonists (e.g., risperidone); muscarinic M1 receptor agonists (e.g., cevimeline); alpha 1 adrenoceptor agonists (e.g., modafinil); serotonin 3 receptor antagonists (e.g., alosetron); dopamine D2 receptor agonists (e.g., aripiprazole); dopamine D2 receptor antagonists (e.g., aripiprazole); serotonin 1A receptor agonists (e.g., aripiprazole); serotonin 2A receptor antagonists (e.g., aripiprazole); glucocorticoid antagonists (e.g., mifepristone); progesterone antagonists (e.g., mifepristone); HMG-CoA reductase inhibitors (e.g., atorvastatin, simvastatin); adenosine uptake inhibitors (e.g., propentofylline); phosphodiesterase inhibitors (e.g., propentofylline); acetylcholine receptor agonists (e.g., choline alfoscerate); membrane permeability enhancers (e.g., choline alfoscerate); cannabinoid 1 receptor antagonists (e.g., rimonabant); cannabinoid receptor agonists (e.g,. dronabinol); angiogenesis inhibitors (e.g., paclitaxel); immunosuppressants (e.g., paclitaxel); tubulin antagonists (e.g., paclitaxel); thromboxane A2 synthase inhibitors (e.g., triflusal); antioxidants (e.g., idebenone); alpha adrenoreceptor antagonists (e.g., nicergoline); estrogen agonists (e.g., conjugated estrogens, trilostane); 3-beta hydroxysteroid dehydrogenase inhibitors (e.g., trilostane); signal transduction pathway inhibitors (e.g., trilostane); melatonin receptor agonists (e.g., ramelteon); immunostimulants (e.g., immune globulin, icosapentethyl ester, procaine); HIV entry inhibitors (e.g., procaine); sodium channel antagonists (e.g., procaine); microtubule inhibitor (e.g., CPH 82); glycine NMDA agonists (e.g., cycloserine); adenosine A1 receptor antagonists (e.g., KW 3902); ATPase stimulants (e.g., triacetyluridine); mitochondrial function enhancers (e.g, triacetyluridine); growth hormone releasing factor agonists (e.g., tesamorelin); butylcholine esterase inhibitor (e.g., bisnorcymserine); alpha adrenergic receptor antagonists (e.g., nicergoline); NO synthase type II inhibitors (e.g., arundic acid); chelating agents (e.g., PBT 2); amyloid fibrillogenesis inhibitors (e.g., TTP488, PF 4494700); serotonin 4 receptor agonists (e.g., PRX 03140); serotonin 6 receptor antagonists (e.g., SB 742457); benzodiazepine receptor inverse agonists (e.g., radequinil); Ca channel antagonists (e.g., safinamide); nicotinic receptor agonists (e.g., ispronicline); and ACE inhibitor (e.g., CTS 21166).

Further, the above compounds include, for example, huperzine A, tacrine, rivastigmine, galantamine, pramiracetam, aniracetam, nefiracetam, EGb 761, rosiglitazone, rasagiline, levacecarnine, celecoxib, 3-(2-cyanophenyl)-5-(2-pyridyl)-1-phenyl-1,2-dihydropyridin-2-one, talampanel, becampanel, memantine, xaliproden, tarenflurbil, tramiprosate, leuprorelin-D, taltirelin, risperidone, cevimeline, modafinil, alosetron, aripiprazole, mifepristone, atorvastatin, propentofylline, choline alfoscerate, FPF 1070 (CAS Number 143637-01-8), rimonabant, dronabinol, docosahexaenoic acid, paclitaxel, triflusal, idebenone, nicergoline, conjugated estrogens, trilostane, simvastatin, selegiline, ramelteon, immune globulin, icosapentethyl ester, procaine, CPH 82, cycloserine, KW 3902 (CAS Number 136199-02-5), triacetyluridine, estrogen dementia therapeutics (e.g., MIGENIX, Vancouver, Canada), tesamorelin, bisnorcymserine, nicergoline, arundic acid, PBT 2, TTP488, PF 4494700, PRX 03140, SB 742457, radequinil, safinamide, ispronicline, CTS 21166, Bapineuzumab, NP 031112, (2S,3aS,7aS)-1{[(R,R)-2-Phenylcyclopropyl]carbonyl}-2-[(thiazolidin-3-yl)carbonyl]octahydro-1H-indole, citalopram, venlafaxine, levprorelin, prasterone, peptide T (CAS Number 53-43-0), besipiridine, lexipafant, stacofylline, SGS 742 (CAS Number 123690-78-8), T 588 (CAS Number 142935-03-3), nerispiridine, dexanabinol, sabcomeline, GTS 21 (CAS Number 156223-05-1), CX 516 (CAS Number 154235-83-3), ABT 089 (CAS Number 161417-03-4), anapsos, tesofensine, SIB 1553A (i.e., 4-[[2-(1-methyl-yl-2-pyrrolidinyl)ethyl]thia]phenol), ladostigil, radequinil, GPI 1485, ispronicline, arundic acid, MEM 1003 (i.e., 3-Isopropyl 5-(2-methoxyethyl) 4-(2-chloro-3-cyanophenyl)-2,6-dimethylpyridine-3,5-dicarboxylate), V 3381 (i.e., 2-(2,3-Dihydro-1H-inden-3-ylamino)acetamide hydrochloride), farampator, paliroden, prasterone-paladin, urocortin, DP b99 (i.e., 2,2'-(Ethylenedioxy)bis(2,1-phenylene)bis[N-[2-[2-(octyloxy)ethoxy]-2-oxoethyl]imino]bis(acetic acid)), capserod, DU 125530, bapineuzumab, AL 108 (i.e., L-Asparaginyl-L-alanyl-L-prolyl-L-valyl-L-seryl-L-isoleucyl-L-prolyl-L-glutamine), DAS 431, DEBIO 9902, DAR 100, mitoquinone, IPL 455903 (i.e., 5(S)-[3-(Cyclopentyloxy)-4-methoxyphenyl]-3(S)-(3-methylbenzyl)piperidin-2-one), E2CDS, PYM 50028, PBT 2, lecozotan, SB 742457, CX 717, AVE 1625 (i.e., 1-(bis(4-chlorophenyl)methyl)-3-((3,5-difluorophenyl)(methylsulfonyl)methylene)azetidine), LY 450139 (i.e., N2-[2(s)-Hydroxy-3-methylbutyryl]-N1-[3-methyl-2-oxo-2,3,4,5-tetrahydro-1H-3-benzazepin-1(S)-yl]-L-alaninamide), EM 1421 (i.e., 4,4'-[(2R,3S)-2,3-Dimethylbutane-1,4-diyl]bis(1,2-dimethoxybenzene), SRN 001, TTP 488, PRX 03140, dimebolin, glycine-proline-glutamate, C105, AL 208, MEM 3454, AC 1202, L 830982, LY 451395 (i.e., (R)—N-[2-[4-(methylsulfonamidomethyl)biphenyl-4-yl]propyl]propane-2-sulfonamide), MK 0249, LY 2062430, diethylnorspermine, neboglamine, S 18986, SA 4503 (CAS Number 165377-44-6), GRI 1, S 17092 (i.e., (2S,3aS,7aS)-1{[(R,R)-2-Phenylcyclopropyl]carbonyl}-2-[(thiazolidin-3-yl)carbonyl]octahydro-1H-indole), SL 251188, EUK 189, R 1450, 6,6-dimethyl-3-(2-hydroxyethyl)thio-1-(thiazol-2-yl)-6,7-dihydro-2-benzothiophen-4(5H)-one, CERE 110, dexefaroxan, CAD 106, HF 0220, HF 0420, EHT 0202, VP 025, MEM 1414, BGC 201259 (i.e., N,N-Dimethylcarbamic acid, 4-[1(S)-(methylamino)-3-(4-nitrophenoxy)propyl]phenyl ester), EN 100, ABT 834, ABT 239 (i.e., 4-[2-[2-[(2R)-2-Methylpyrrolidinyl]ethyl]-benzofuran-5-yl]benzonitrile), SGS 518, R 1500, C 9138, SSR 180711, alfatradiol, R 1577, T 817MA (i.e., 1-[3-[2-(1-Benzothien-5-yl)ethoxy]propyl]azetidin-3-olmaleate), CNP 1061 (i.e., 4-Methyl-5-(2-nitrooxyethyl) thiazole), KTX 0101 (i.e., sodium beta-hydroxybutyrate), GSK 189254 (i.e., 6-[3-Cyclobutyl-2,3,4,5-tetrahydro-1H-benzo[d]azepin-7-yloxy]-N-methylnicotinamide), AZD 1080, ACC 001, PRX 07034, midazolam, R-phenserine, AZD 103 (CAS Number 488-59-5), SN 522, NGX 267 (CAS Number 503431-81-0), N-PEP-12, RN 1219, FGLL, AVE 8112, EVT 101, NP 031112, MK 0752, MK 0952, LX 6171, PAZ 417, AV 965, PF 3084014, SYN 114, GSI 953, SAM 315, SAM 531, D-serine, leteprinim potassium, BR 16A (CAS Number 149175-77-9), RPR 107393 (CAS Number 190841-57-7), NXD 2858, REN 1654, CDD 0102, NC 1900 (CAS Number 132925-74-7), ciclosporin, NCX 2216 (i.e., (E)-4-(Nitrooxy)butyl 3-[4-[2-(2-fluorobiphenyl-4-yl)propanoyloxy]-3-methoxyphenyl]acrylate), NXD 3109, NXD 1191, ZSET 845 (i.e., 3,3-diphenylimidazo[1,2-a]pyridin-2-(3H)-one), ET 002, NT 13, RO 638695 (i.e., [1,6-(1,6-dioxohexyl)] dipyrrolidine-(2R)-carboxylic acid), bisnorcymserine, BA 1016, XD 4241, EUK 207 (i.e., (SP-5-13)-(acetato-κO)[13,16,19,22-tetraoxa-3,6-diazatricyclo[21.3.18,12]octacosa-1(27),2,6,8,10,12(28),23,25-octaene-27,28-diolato(2-)-κN3,κN6,κO27,κO28]manganese), LG 617 inhibitors, ZSET 1446, PAN 811, F 14413 (i.e., 2-[5-fluoro-2(S)-methoxy-2,3-dihydro-1,4-benzodioxin-2-yl]-4,5-dihydro-1H-imidazole), FP 7832 (i.e., N-[2-(5-methoxy-1-nitroso-1H-indol-3-yl)ethyl]acetamide), ARA 014418 (i.e., N-(4-methoxybenzyl)-N'-(5-nitro-1,3-thiazol-2-yl)urea), AZD 3102, KP 544 (i.e., 2-amino-5-(4-chlorophenylethynyl)-4-(4-trans-hydroxycyclohexylamino)pyrimidine), DP 155, 5-chloro-N-[3-[2-(dimethylamino)ethyl]-1H-indol-5-yl] naphthalene-2-sulfonamide, TAK 070, huperzine, N-[2-(3,5-dimethyladamant-1-yl)ethyl]acetamidine hydrochloride, 6-[4-[(dimethylamino)methyl]-5-ethyl-2-methoxyphenyl] pyridin-2-amine, 4,6-diphenyl-3-(4-(pyrimidin-2-yl)piperazin-1-yl)pyridazine, N-[(1S,2R)-3-(3,5-difluorophenyl)-1-hydroxy-1-[(5S,6R)-5-methyl-6-(neopentyloxy)morpholin-3-yl]propan-2-yl]acetamide hydrochloride, N-[(1R,2S)-3-(3,5-difluorophenyl)-1-hydroxy-1-[(2R,4R)-4-phenoxypyrrolidin-2-yl]propan-2-yl]-3-[(R)-2-(methoxymethyl)pyrrolidine-1-carbonyl]-5-methylbenzamide, R 1589, midafotel, phenserine, coluracetam, physostigmine, cipralisant, nitroflurbiprofen, PPI 1019 (i.e., (3α,5β,7α,12α)-trihydroxycholan-24-oyl-L-leucyl-L-valyl-L-phenylalanyl-L-phenylalanyl-L-alanine), dapsone, MDL 100453 (CAS Number 129938-34-7), NS 377, midaxifylline, propofol phosphate, metrifonate, ceronapril, tenilsetam, sufoxazine, seglitide, ebiratide, nebracetam, milacemide, iododoxorubicin, SM 10888 (CAS Number 129297-21-8), U 80816 (CAS Number 138554-11-7), YM 954 (CAS Number 132041-85-1), SUT 8701 (CAS Number 123577-73-1), apovincamine, FR 121196 (CAS Number 133920-65-7), LY 274614 (CAS Number 136109-04-1), CL 275838 (CAS Number 115931-65-2), igmesine, K 7259 (CAS Number 133667-88-6), vinconate, itasetron, CL 287663 (CAS Number 125109-98-0), WAY 100289 (CAS Number 136013-69-9), SR 46559A (CAS Number 137733-33-6), GYKI 46903 (CAS Number 142999-59-5), L 670548 (CAS Number 121564-89-4), Y 29794 (CAS Number 129184-48-1), AF 125 (CAS Number 7631-86-9), KFM 19 (CAS Number 133058-72-7), ST 796 (i.e., (S)-3-[3-(trifluoromethyl)benzoyl)amino]hexahydroazepin-2-one), RU 33965 (CAS Number 122321-05-5), SDZ 210086 (i.e., (−)-1',2(S)-Dimethylspiro[1,3-dioxolan-4,4'-piperidine]), L 689660 (CAS Number 144860-79-7), L 689560 (CAS Number 139051-78-8), ST 618 (i.e., 1-(6,7-Dimethoxy-1,2,3,4-tetrahydro-2-naphthyl)-4-hydroxy pyrrolidin-2-one), U 74500A (CAS Number 110101-65-0), GEA 857 (CAS Number 120493-42-7), BIBN 99 (CAS Number 145301-48-0), DX 9366, ONO 1603 (CAS Number 114668-76-7), MDL 102234 (CAS Number 137766-81-5), P 9939 (CAS Number 157971-37-4), PD 140532 (CAS Number 157971-39-6), azetirelin, MR 16728 (CAS Number 147614-21-9), dabelotine, MDL 102503 (i.e., 8-[1(R)-methyl-2-phenylethyl]-1,3-dipropyl-7H-xanthine), PD 141606 (i.e., (±)-(Z)-3-(3-Phenyl-2-propynyloxyimino)-1-azabicyclo[2.2.1]heptane), SNK 882 (CAS Number 152221-12-0), L 696986 (CAS Number 141553-45-9), tazomeline, LY 235959 (CAS Number 137433-06-8), 2-(2-thiooxopyrrolidin-1-yl)acetamide, AK 30 NGF, ABT 418 (CAS Number 147402-53-7), itameline, HUP 13, sibopirdine, KST 5452 (CAS Number 157998-88-4), TJ 54, U 92798 (i.e., 7-[4-[Bis(4-fluorophenyl)methyl]perhydro-1,4-diazepin-1-ylmethyl]-4-isopropyl-2-methoxy-2,4,6-cycloheptatrien-1-one), U 92032 (CAS Number 142223-92-5), 3-(sulfamoyloxy)estra-1,3,5(10)-trien-17-one, P 11012 (CAS Number 164723-36-8), A 82695 (CAS Number 147388-86-1), FR 76659 (CAS Number 116904-25-7), apaxifylline, CX 417, 7 MEOTA (CAS Number 5778-80-3), BU 4514N (CAS Number 151013-39-7), pregnenolone, mexidol, ST 857 (CAS Number 154755-63-2), RU 49041 (CAS Number 123828-80-8), RU 35929 (CAS Number 111711-47-8), P 878184, P 128 (CAS Number 157716-52-4), eurystatin A, eurystatin B, LK 12, NBI 108, NBI 107, NBI 117, L 705106, bacoside A+B, clausenamide, SM 21 (CAS Number 155156-22-2), alaptide, RS 17017 (i.e., 1-(4-Amino-5-chloro-2-methoxyphenyl)-5-(1-piperidinyl)-1-pentanone hydrochloride), AF 150(S) (i.e., (S)-[1-Methyl-piperidine-4-spiro-(2-methylthiazoline)]), RO 153505 (CAS Number 78771-13-8), PV 113 (i.e., 1,2,3,4-Tetrahydropyrrolo-[1,2-a]-pyrazine), arisugacin, A 98284 (i.e., 2(R)-(3-Methylisoxazol-5-yl) quinuclidine), AP 5 (CAS Number 136941-85-0), BD 1054, SDZ NDD 094 (i.e., bis-(2-(2-methylimidazol-1-yl]methyl)-pyridine-tris(hydrogen-fumarate), AZ 36041 (CAS Number 173324-76-0), quilostigmine, A 84543 (i.e., 3-[1-Methylpyrrolidin-2-(S)-ylmethoxy]pyridine fumarate), BTG 4247 (i.e., (2-[2-Chloroethoxy[4-(dimethylamino)phenyl]phosphoryl]-acetohydrazide), CGP 50068 (CAS Number 158647-49-5), cerebrocrast, desferrinordanoxamine, isolichenan, MHP 133 (i.e., 3-(N,N-dimethylcarbamoyloxy)-1-methyl-2-(4-phenyl-semicarbazonomethyl)pyridinium chloride), FR 152558 (CAS Number 151098-08-7), GVS 111 (CAS Number 157115-85-0), P 11149 (CAS Number 164724-79-2), PDC 008004, KST 2818 (CAS Number 158623-26-8), KST 5410 (CAS Number 158623-27-9), RU 52583 (CAS Number 123829-33-4), PD 151832 (CAS Number 149929-39-5), UCL 1199 (i.e., 4-[2-[(5-Nitropyridin-2-ylsulfanyl)ethyl]-1H-imidazole), isovanihuperzine A, SIB 1765F (CAS Number 179120-52-6), JWS USC 751X (i.e., 3-[[[2-[[(5-dimethylaminomethyl)-2-furanyl]methyl]thio]ethyl]amino]-4-nitropyridazine), GR 175737 (i.e., 3-(4-Chlorobenzyl)-5-[2-(1H-imidazol-4-yl)ethyl]-1,2,4-oxadiazole), KS 505A (CAS Number 131774-53-3), ZTTA 1 (i.e., N-benzyloxycarbonyl-thioprolyl-thioprolynal-dimethylaceta 1), AGN 190837 (CAS Number 136527-40-7), P 10358 (188240-59-7), WAY 131256 (CAS Number 174001-71-9), DBO 83 (i.e., 3-(6-chloropyridazin-3-yl)-diazabicyclo[3.2.1] octane dihydrochloride monohydrate), FUB 181 (CAS Number 152029-80-6), RJR 2557, WSU 2088, LVV-haemorphin-7, M 40 (i.e., galanin[1-12]-Pro3-(Ala-Leu)$_2$-Ala-NH$_2$), SIB 1757, SKF 74652 (i.e., [5-chloro-2-(4-methoxy phenyl)-3-benzofuranyl][4-[3-(diethylamino)-propoxy]phenyl]methanone), CGP 71982, SCH 57790 (i.e., 4-cyclohexyl-alpha-[4-[[4-methoxyphenyl]sulfinyl]phenyl]-1-piperazineacetonitrile), Putrescine-D-YiAbeta11, DU 14 (i.e., p-O-(sulfamoyl)-N-tetradecanoyl tyramine), CLZ 4, SL 340026, PPRT 424, ciproxifan, UR 1827 (i.e., 2-(1-benzylpiperidin-4-yl)-1-[4-(5-methylpyrimidin-4-ylamino)phenyl]-1-ethanone), caproctamine, TGS 20 (i.e., L-pyroglutamil-D-alanine amide), PG 9 (i.e., alpha-tropanyl 2-[(4-bromo) phenyl]propionate), TEI 3356 (i.e., (16S)-15-Deoxy-16-hydroxy-16-methyl-9-(O)-methano-DELTA6(9alpha)-prostaglandin I1), LY 392098 (i.e., Thiophene, 3-[(2-methylethyl-2)sulphonylaminopropyl-2]phenyl-4-yl-), PG 1000, DM 232, NEPP 11 (i.e., 12-iso-15-Deoxy-18-(4-methyl)phenyl-13,14-dihydro-delta7-prostaglandinA1 methyl ester), VA 100 (i.e., (2,3-Dihydro-2-[[(4-fluorobenzoyl) amino]ethyl]-1-methyl-5-phenyl-1H-1,4-benzodiazepine), VA 101 (i.e., (2,3-dihydro-2-[[(2-thienylcarbonyl)amino]ethyl]-1-methyl-5-phenyl-1H-1,4-benzodiazepine), NC 111585 (i.e., (3S)-1,3-Bis-[3-[(3-azabicylo[2.2.2]octanyl)-1,2,5-thiadiazol-4-yloxy]-1-propyn-1-yl]benzene, 2L-(+)-tartate), IN 201, imoproxifan, kanokodiol, picroside I, picroside II, DM 235 (i.e., 1-(4-Benzoylpiperazin-1-yl)propan-1-one), monoclonal antibody 10D5, JLK2, JLK 6, JLK 7, DAPT (i.e., N—[N-(3,5-difluorophenacetyl)-L-alanyl]-S-phenylglycine t-butyl ester), huperine X, SGS 111 (i.e., (S)-ethyl 2-[1-(2-phenylacetyl)pyrrolidine-2-carboxamido]acetate), NP 7557, C 9136, C 7617, R 1485, rofecoxib, velnacrine, montirelin, lazabemide, ORG 2766 (CAS Number 50913-82-1), sabeluzole, adafenoxate, CAS Number 9061-61-4, ipidacrine, bemesetron, idazoxan, linopirdine, selfotel, suritozole, milameline, xanomeline, TJ 960, fasoracetam, eptastigmine, ensaculin, zanapezil, posatirelin, zacopride, RS 86 (CAS Number 3576-73-6), ORG 5667 (CAS Number 37552-33-3), RX 77368 (CAS Number 76820-40-1), BMS 181168 (CAS Number 123259-91-6), BY 1949 (CAS Number 90158-59-1), AWD 5239 (CAS Number 109002-93-9), YM 796 (171252-79-2), aloracetam, CI 933 (CAS Number 91829-95-7), ST 793 (CAS Number 99306-37-3), cebaracetam, zifrosilone, talsaclidine, alvameline, JTP 2942 (148152-77-6), OPC 14117 (CAS Number 103233-65-4), elziverine, AP 521 (i.e., N-(1,3-Benzodioxol-5-ylmethyl)-1,2,3,4-tetrahydro[1]benzothieno[2,3-c]pyridine-3(R)-carboxamide hydrochloride), S 8510 (CAS Number 151466-23-8), JTP 4819 (CAS Number 162203-65-8), icopezil, SC 110, FK 960 (CAS Number 133920-70-4), DMP 543 (CAS Number 160588-45-4), ganstigmine, CI 1017 (i.e., (R)-(−)-(Z)-1-Azabicyclo[2.2.1]heptan-3-one, O-(3-(3'-methoxyphenyl)-2-propynyl)-oxime maleate), T 82 (i.e., 2-[2-(1-Benzylpiperidin-4-yl)ethyl]-2,3-dihydro-9-methoxy-1H-pyrrolo[3,4-b]quinolin-1-one hemifumarate), NGD 971, vaccine of Aspartyl-alanyl-glutamyl-phenylalanyl-arginyl-histidyl-aspartyl-seryl-glycyl-tyrosyl-glutamyl-valyl-histidyl-histidyl-glutaminyl-lysyl-leucyl-valyl-phenylalanyl-phenylalanyl-alanyl-glutamyl-aspartyl-valyl-glycyl-seryl-asparaginyl-lysyl-glycyl-alanyl-isoleucyl-isoleucyl-glycyl-leucyl-methionyl-valyl-glycyl-glycyl-valyl-valyl-isoleucyl-alanine, PBT 1 (CAS Number 130-26-7), TCH 346, FK 962 (i.e., N-(1-acetylpiperidin-4-yl)-4-fluorobenzamide), voxergolide, KW 6055 (CAS Number 63233-46-5), thiopilocarpine, ZK 93426 (CAS Number 89592-45-0), SDZ NVI 085 (CAS Number 104195-17-7), CI 1002 (CAS Number 149028-28-4), Z 321 (CAS Number 130849-58-0), mirisetron, CHF 2060 (i.e., N-Heptylcarbamic acid 2,4a,9-trimethyl-2,3,4,4a,9,9a-hexahydro-1,2-oxazino[6,5-b]indol-6-yl ester-L-tartrate), gedocarnil, terbequinil, HOE 065 (CAS Number 123060-44-6), SL 650102, GR 253035, ALE 26015, SB 271046 (i.e., 5-Chloro-N-(4-methoxy-3-piperazin-1-yl-phenyl)-3-methyl-2-benzothiophenesulfonamide), iAbeta5, SCH 211803 (i.e., Piperidine, 1-[1-(3-methyl-2-aminophenyl)carbonylpiperidin-4yl]-4-[(3-chlorophenyl)sulphonylphenyl-4]methyl-), EVT 301, alpha-Linolenic acid/linoleic acid, Kamikihi-To, siagoside, FG 7142 (CAS Number 78538-74-6), RU 47067 (CAS Number 111711-92-3), RU 35963 (CAS Number 139886-03-6), FG 7080 (CAS Number 100332-18-1), E 2030 (CAS Number 142007-70-3), transforming growth factor beta-1, A 72055 (i.e., 2',1-Dimethylspiro[piperidine-4,5'oxazolidine]-3-carboxaldehyde), NS 626, dimiracetam, GT 3001, GT 2501, GT 2342, GT 2016 (CAS Number 152241-24-2), ORG 20091 (CAS Number 141545-50-8), BCE 001 (CAS Number 95678-81-2), CGP 35348 (CAS Number 123690-79-9), WAY 100635 (CAS Number 146714-97-8), E 4804 (CAS Number 162559-34-4), LIGA 20 (CAS Number 126586-85-4), NG 121 (i.e., 2-[4,8-Dimethyl-3(E),7(E)-nonadienyl]-3,5-dihydroxy-2-methyl-3,4,7,9-tetrahydro-2H-furo[3,4-h]-1-benzopyran-7-one), MF 247 (i.e., N-[10-(Diethylamino) decyl]carbamic acid (3aS,8aR)-1,3a,8-trimethyl-1,2,3,3a,8,8a-hexahydropyrrolo[2,3-b]indol-5-yl ester), JTP 3399 (i.e., N-Benzyl-2(S)-[2(S)-(phenoxyacetyl)pyrrolidin-1-ylcarbonyl]pyrrolidine-1-carboxamide), KF 17329, thioperamide, F 3796 (i.e., 1-[2-(1-Benzylpiperidin-4-yl)ethyl]-3-[3,4-(methylene-dioxy)benzoyl]thiourea), GT 4001, GT 4002, FPL 14995 (CAS Number 123319-03-9), RU 34332 (CAS Number 137157-58-5), SR 96777A (CAS Number 115767-94-7), SIB T1980, NS 649 (CAS Number 146828-02-6), PD 142505 (CAS Number 149929-08-8), GYKI 52466 (CAS Number 102771-26-6), RO 246173 (CAS Number 159723-57-6), SCH 50911 (CAS Number 160415-07-6), Z 4105 (CAS Number 119737-52-9), RS 67333 (CAS Number 168986-60-5), NS 1546, ZM 241385 (CAS Number 139180-30-6), RO 249975 (i.e., [1S,3S(2'S),5R]-3-(1-Benzyl-5-oxopyrrolidin-2-ylmethyl)-5-(1H-imidazol-5-ylmethyl)cyclohexane-1-acetamide), AF 185 (i.e., 8-Methyl-3-(2-propynyl)-1,3,8-triazaspiro[4,5]decane-2,4-dione), CEP 427, CX 423, CX 438, CX 480, CDP-ethanolamine, GT 4003, GT 4011, GT 5011, MS 430 (CAS Number 122113-44-4), MBF 379 (i.e., [3,3-Bis(hydroxymethyl)-8-hydroxy-3,4-dihydro-2H-1,4-benzoxazin-5-yl][3,5-dihydroxy-4-(2-oxo-2-phenylethoxy)phenyl]methanone), NGD 187 (CAS Number 163565-48-8), DUP 856, MR 3066, MF 8615 (i.e., 5-Amino-6-chloro-4-hydroxy-3,4-dihydro-1H-thiopyrano-[3,4-b]quinoline), himbacine, ABS 300, RJR 2403 (CAS Number 538-79-4), MF 268 (CAS Number 174721-00-7), RO 465934 (i.e., N,N-Dimethylcarbamic acid 3-(2-cyclohexylethyl)-2,3,3a,4,5,9b-hexahydro-1H-benz[e]indol-6-yl ester), NS 393, RGH 2716 (CAS Number 134069-68-4), WIN 678702 (12,12-Bis(3-furyl)-6,11-dihydro-6,11-ethanobenzo[b]quinolizinium chloride), RS 66252 (i.e., 1-Butyl-2-[(2-(2H-tetrazol-5-yl)-biphenyl-4-yl)methyl]-1H-indole-3-carboxylic acid), AIT 034 (CAS Number 138117-48-3), NG 012 (CAS Number 131774-53-3), PD 142012 (CAS Number 5778-84-7), GT 4054, GT 4077, GT 4035, P 26 (CAS Number 152191-74-7), RGH 5279 (i.e., (−)-(13aR,13bS)-13a-Ethyl-2,3,5,6,13a,13b-hexahydro-1H-indolo[3,2,1-de]pyrido[3,2,1-ij][1,5]naphthyridine-12-carboxylic acid 2-acetoxyethyl ester), AIT 083, CeNeS, estradiol (i.e., 1,3,5(10)-Estratriene-3,17beta-diol), WAY 132983 ((3R,4R)-3-(3-hexylsulfanylpyrazin-2-yloxy)-1-azabicyclo[2.2.1]heptane hydrochloride), ABS 205, ABS 401, SX 3507 (i.e., 3-(3-Propyl-1,2,4-oxadiazol-5-yl)quinoxaline-2(1H)-one), ARR 17779 (i.e., (−)-Spiro[1-azabicyclo[2.2.2]octane-3,5-oxazolidine]-2-one), XE 991 (i.e., 10,10-bis(4-Pyridylmethyl)anthracen-10(9H)-one), phenethylnorcymserine, RO 657199, RJR 1781 (i.e., R(+)-2-(3-pyridyl)-1-azabicyclo[2.2.2.]octane), RJR 1782 (i.e., S(−)-2-(3-pyridyl)-1-azabicyclo[2.2.2.]octane), gilatide, tolserine, TC 2559 (i.e., (E)-N-Methyl-4-[3-(5-ethoxypyridin)yl]-3-buten-1-amine), ER 127528 (i.e., 1-(3-Fluorobenzyl)-4-[(2-fluoro-5,6-dimethoxy-1-indanone-2-yl)methyl] piperidine hydrochloride), thiatolserine, targacept, axonyx, cymserine, thiacymserine, monoclonal antibody 266, ApanCH, DP 103, SPI 339 (i.e., 4-[3-(4-Oxo-4,5,6,7-tetrahydroindol-1-yl)propionylamino]benzoic acid ethyl ester), S 37245 (i.e., 4-(1,4-Benzodioxan-5-yl)-1-[3(S)-hydroxy-5-nitro-indan-2-yl]-piperazine), LLG 88, AZD 2858, trometamol, AN 240, NG 002 (i.e., 5-Hydroxy-5-(2-hydroxy-1-methylethyl)-4-methoxyfuran-2(5H)-one), UCB 29427 (i.e., 2-Cyclopropyl-4-(cyclopropylamino)-6-(morpholino)-1,3,5-triazine), TRH-SR, RO 401641 (CAS Number 122199-02-4), MPV 1743AIII (CAS Number 150586-64-4), IDRA 21 (CAS Number 22503-72-6), CEP 431, ACPD (CAS Number 67684-64-4), CT 3577 (i.e., 3,7-Dimethyl-1-[11-(3,4,5-trimethoxybenzylamino)-11-oxoundecyl]xanthine), CT 2583, NXD 9062, Desferrinordanoxamine, DP b99, PBT 1, T 817MA, Alfatradiol (CAS No. 57-91-0), AL 108, SL 650102, RS 67333 (CAS No. 168986-60-5), RS 17017, SGS 518, SYN 114, SB 271046, RO 657199, PRX 07034, Suritozole (CAS No. 110623-33-19), Terbequinil (CAS No. 113079-82-6), FG 7142 (CAS No. 78538-74-6). RU 34332 (CAS No. 137157-58-5), SX 3507, RO 153505 (CAS No. 78771-13-8), RU 33965 (CAS No. 122321-05-5), S 8510 (CAS No. 151466-23-8), Sabeluzole (CAS No. 104383-17-7), Cerebrocrast (CAS No. 118790-71-9), NS 626, NS 649 (CAS No. 146828-02-6), U 92032 (CAS No. 142223-92-5), MEM 1003, U 92798, RGH 2716 (CAS No. 134069-68-4), Safinamide (CAS No. 133865-89-1), AZD 0328, MEM 63908, ABT 418 (CAS No. 147402-53-7), ARR 17779, RJR 2403 (CAS No. 538-79-4), TC 2559, A 82695 (CAS No. 147388-86-1), A 84543, A 98284, DBO 83, RJR 2557, SIB 1765F (CAS No. 179120-52-6), GTS 21 (CAS No. 156223-05-1), MEM 3454, SIB 1553A, EVP 6124, SSR 180711, ABT 089 (CAS No. 161417-03-4), ABT 107, ABT 560, TC 5619, TAK 070, N-[(1S,2R)-3-(3,5-Difluorophenyl)-1-hydroxy-1-[(5S,6R)-5-methyl-6-(neopentyloxy)morpholin-3-yl]propan-2- yl]acetamide hydroCl, 6-Fluoro-5-(2-fluoro-5-methylphenyl)-3,4-dihydropyridine, 2-Amino-6-[2-(3-methoxybiphenyl-3-yl)ethyl]-3,6-dimethyl-5,6-dihydropyrimidin-4(3H)-one, AZD 1080, ARA 014418, XD 4241, Z 321 (CAS No. 130849-58-0), ONO 1603 (CAS No. 114668-76-7), JTP 3399, Eurystatin A (CAS No. 137563-63-4), Eurystatin B (CAS No. 137563-64-5), P 128 (CAS No. 157716-52-4), Y 29794 (CAS No. 129184-48-1), ZTTA 1, JTP 4819 (CAS No. 162203-65-8), Monoclonal antibody 266, duloxetine, escitalopram oxalate, fluoxetine, fluvoxamine maleate, paroxetine, sertraline, dapoxetine, desvenlafaxine, sibutramine, nefazodone, milnacipran, desipramine, duloxetine, and bicifadine.

DETAILED DESCRIPTION OF THE INVENTION

The present invention will now be described in detail with reference to examples; however, the examples are provided only for illustration purposes. The prophylactic or therapeutic agent for a disease caused by Aβ according to the present invention is not limited to the following specific examples in any cases. A person skilled in the art can fully implement the present invention by making various modifications to not only the following reference examples and examples but also the claims of the present specification, and such modifications are within the scope of the claims of the present specification.

When the compound in the Examples include stereoisomers, and the absolute configuration has not been determined, there are the cases that the name of the compounds with optical rotating power and its chemical structural formula are not described correspondingly in the following Examples.

The following abbreviations are used in the following examples.

DMF: N,N-Dimethylformamide
THF: Tetrahydrofuran
EDC: 1-Ethyl-3-(3-dimethylaminopropyl)carbodiimide hydrochloride
HOBT: 1-Hydroxybenzotriazole
IPEA: Diisopropylethylamine
IPA: 2-Propanol
DMAP: 4-(Dimethylamino)pyridine
TEA: Triethylamine
CDI: Carbonyldiimidazole
TBAF: Tetrabutylammonium fluoride
DBU: 1,8-Diazabicyclo[5.4.0]undec-7-ene
t: Tertiary
BOPCl: Bis(2-oxo-3-oxazolidinyl)phosphonic chloride
DIBAL-H: Diisobutylaluminum hydride
DAST: Diethylaminosulfur trifluoride
BINAP: 2,2'-Bis(diphenylphosphino)-1,1'-binaphthyl Chromatography was performed using BW-300 manufactured by Fuji Silysia Chemical Ltd. as a carrier unless otherwise specified.

LC-MS: High performance liquid chromatography for preparative isolation of a target compound using mass spectroscopy. As an elution solvent, a 10% to 99% linear gradient system of water containing 0.1% trifluoroacetic acid and acetonitrile containing 0.1% trifluoroacetic acid was used.

Reference Examples 1 and 2

Synthesis of (+)-2-{(E)-2-[5-methoxy-6-(4-methyl-1H-imidazol-1-yl)pyridin-3-yl]vinyl}-8-(3,4,5-trifluorophenyl)-5,6,7,8-tetrahydro[1,2,4]triazolo[1,5-a]pyridine and (−)-2-{(E)-2-[5-methoxy-6-(4-methyl-1H-imidazol-1-yl)pyridin-3-yl]vinyl}-8-(3,4,5-trifluorophenyl)-5,6,7,8-tetrahydro[1,2,4]triazolo[1,5-a]pyridine

[Formula 49]

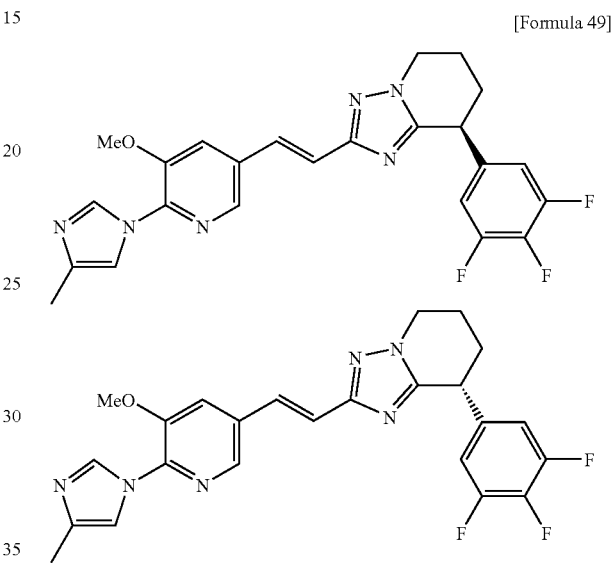

Synthesis of 5-chloro-2-(3,4,5-trifluorophenyl)pentanoic acid N'-{(E)-3-[5-methoxy-6-(4-methyl-1H-imidazol-1-yl)pyridin-3-yl]acryloyl}hydrazide IPEA (0.14 mL) and BOPCl (100 mg) were added to a solution of 5-chloro-2-(3,4,5-trifluorophenyl)pentanoic acid hydrazide hydrochloride (83 mg) and (E)-3-[5-methoxy-6-(4-methyl-1H-imidazol-1-yl)pyridin-3-yl]acrylic acid (CAS No. 870837-77-7, 68 mg) in methylene chloride (5 mL), and the reaction solution was stirred at room temperature for 18 hours. Ethyl acetate and saturated sodium bicarbonate water were added to the reaction solution, and the organic layer was separated. The resulting organic layer was dried over anhydrous magnesium sulfate and concentrated under reduced pressure to obtain 112 mg of the title compound. The property value of the compound is as follows.

ESI-MS; m/z 522 [M⁺+H].

Synthesis of 5-{(E)-2-{5-[4-chloro-1-(3,4,5-trifluorophenyl)butyl]-[1,3,4]oxadiazol-2-yl}vinyl}-3-methoxy-2-(4-methyl-1H-imidazol-1-yl)pyridine A solution of 5-chloro-2-(3,4,5-trifluorophenyl)pentanoic acid N'-{(E)-3-[5-methoxy-6-(4-methyl-1H-imidazol-1-yl)pyridin-3-yl]acryloyl}hydrazide (112 mg) in phosphorus oxychloride (2 mL) was stirred at 120° C. for 3.5 hours. The reaction solution was left to cool to room temperature and then concentrated under reduced pressure to obtain 108 mg of the title compound. The property value of the compound is as follows.

ESI-MS; m/z 504 [M⁺+H].

Synthesis of (+)-2-{(E)-2-[5-methoxy-6-(4-methyl-1H-imidazol-1-yl)pyridin-3-yl]vinyl}-8-(3,4,5-trifluorophenyl)-5,6,7,8-tetrahydro[1,2,4]triazolo[1,5-a]pyridine and (−)-2-{(E)-2-[5-methoxy-6-(4-methyl-1H-imidazol-1-yl)pyridin-3-yl]vinyl}-8-(3,4,5-trifluorophenyl)-5,6,7,8-tetrahydro[1,2,4]triazolo[1,5-a]pyridine A solution of 5-{(E)-2-{5-[4-chloro-1-(3,4,5-trifluorophenyl)butyl]-[1,3,4]oxadiazol-2-yl}vinyl}-3-methoxy-2-(4-methyl-1H-imidazol-1-yl)pyridine (495 mg) in acetic acid (2 mL) was stirred at 150° C. for 25 hours. The reaction solution was left to cool to room temperature. Then, ethyl acetate and saturated sodium bicarbonate water were added to the reaction solution, and the organic layer was separated. The resulting organic layer was dried over anhydrous magnesium sulfate and then concentrated under reduced pressure. The residue was purified by silica gel column chromatography (carrier: Chromatorex NH; elution solvent: heptane:ethyl acetate=1:1→ethyl acetate) to obtain a racemate of the title compound. The resulting racemate was separated by CHIRALPAK™ IA manufactured by Daicel Chemical Industries, Ltd. (2 cm×25 cm; mobile phase: ethanol) to obtain the title optically active compound with a retention time of 20 minutes and positive optical rotation (11 mg, >99% ee) and the title optically active compound with a retention time of 25 minutes and negative optical rotation (12 mg, >99% ee).

The property values of (+)-2-{(E)-2-[5-methoxy-6-(4-methyl-1H-imidazol-1-yl)pyridin-3-yl]vinyl}-8-(3,4,5-trifluorophenyl)-5,6,7,8-tetrahydro[1,2,4]triazolo[1,5-a]pyridine are as follows.

$^1$H-NMR (CDCl$_3$) δ (ppm): 1.97-2.06 (m, 1H), 2.07-2.25 (m, 2H), 2.29 (s, 3H), 2.34-2.42 (m, 1H), 3.97 (s, 3H), 4.23-4.30 (m, 3H), 6.81 (dd, J=8.0, 6.4 Hz, 2H), 7.08 (d, J=16.0 Hz, 1H), 7.46 (d, J=2.0 Hz, 1H), 7.49 (d, J=16.0 Hz, 1H), 7.52 (brs, 1H), 8.14 (d, J=2.0 Hz, 1H), 8.34 (brs, 1H).

The property values of (−)-2-{(E)-2-[5-methoxy-6-(4-methyl-1H-imidazol-1-yl)pyridin-3-yl]vinyl}-8-(3,4,5-trifluorophenyl)-5,6,7,8-tetrahydro[1,2,4]triazolo[1,5-a]pyridine are as follows.

$^1$H-NMR (CDCl$_3$) δ (ppm): 1.97-2.06 (m, 1H), 2.07-2.25 (m, 2H), 2.29 (s, 3H), 2.34-2.42 (m, 1H), 3.97 (s, 3H), 4.23-4.30 (m, 3H), 6.81 (dd, J=8.0, 6.4 Hz, 2H), 7.08 (d, J=16.0 Hz, 1H), 7.46 (d, J=2.0 Hz, 1H), 7.49 (d, J=16.0 Hz, 1H), 7.52 (brs, 1H), 8.14 (d, J=2.0 Hz, 1H), 8.34 (brs, 1H).

Reference Examples 3 and 4

Synthesis of (−)-2-{(E)-2-[5-methoxy-6-(4-methyl-1H-imidazol-1-yl)pyridin-3-yl]vinyl}-8-(3,4,5-trifluorophenyl)-5,6,7,8-tetrahydro[1,2,4]triazolo[1,5-a]pyridin-8-ol and (+)-2-{(E)-2-[5-methoxy-6-(4-methyl-1H-imidazol-1-yl)pyridin-3-yl]vinyl}-8-(3,4,5-trifluorophenyl)-5,6,7,8-tetrahydro[1,2,4]triazolo[1,5-a]pyridin-8-ol

[Formula 50]

Sodium hydride (containing 40% of mineral oil, 4 mg) was added to a solution of 2-{(E)-2-[5-methoxy-6-(4-methyl-1H-imidazol-1-yl)pyridin-3-yl]vinyl}-8-(3,4,5-trifluorophenyl)-5,6,7,8-tetrahydro[1,2,4]triazolo[1,5-a]pyridine synthesized by the method in Reference Examples 1 and 2 (21 mg) in DMF (2 mL), and the reaction solution was stirred at room temperature for 30 minutes while bubbling with oxygen gas. Ethyl acetate and saturated aqueous ammonium chloride were added to the reaction solution, and the organic layer was separated. The resulting organic layer was dried over anhydrous magnesium sulfate and then concentrated under reduced pressure. The resulting racemic crude product of the title compound was separated by CHIRALPAK™ AD-H manufactured by Daicel Chemical Industries, Ltd. (2 cm×25 cm; mobile phase: hexane:ethanol=1:1) to obtain the title optically active compound with a retention time of 7 minutes and negative optical rotation (3.7 mg, >99% ee) and the title optically active compound with a retention time of 10 minutes and positive optical rotation (3.2 mg, >99% ee).

The property values of (−)-2-{(E)-2-[5-methoxy-6-(4-methyl-1H-imidazol-1-yl)pyridin-3-yl]vinyl}-8-(3,4,5-trifluorophenyl)-5,6,7,8-tetrahydro[1,2,4]triazolo[1,5-a]pyridin-8-ol are as follows.

ESI-MS; m/z 483 [M$^+$+H]. $^1$H-NMR (CDCl$_3$) δ (ppm): 2.01-2.16 (m, 2H), 2.28 (s, 3H), 2.30-2.39 (m, 1H), 2.40-2.53 (m, 1H), 3.91 (s, 3H), 4.19-4.28 (m, 1H), 4.29-4.36 (m, 1H), 7.00-7.05 (m, 3H), 7.33 (d, J=1.6 Hz, 1H), 7.41 (d, J=16.8 Hz, 1H), 7.46 (brs, 1H), 8.02 (d, J=1.6 Hz, 1H), 8.28 (brs, 1H).

The property values of (+)-2-{(E)-2-[5-methoxy-6-(4-methyl-1H-imidazol-1-yl)pyridin-3-yl]vinyl}-8-(3,4,5-trifluorophenyl)-5,6,7,8-tetrahydro[1,2,4]triazolo[1,5-a]pyridin-8-ol are as follows.

ESI-MS; m/z 483 [M++H]. ¹H-NMR (CDCl₃) δ (ppm): 2.01-2.16 (m, 2H), 2.28 (s, 3H), 2.30-2.39 (m, 1H), 2.40-2.53 (m, 1H), 3.91 (s, 3H), 4.19-4.28 (m, 1H), 4.29-4.36 (m, 1H), 7.00-7.05 (m, 3H), 7.33 (d, J=1.6 Hz, 1H), 7.41 (d, J=16.8 Hz, 1H), 7.46 (brs, 1H), 8.02 (d, J=1.6 Hz, 1H), 8.28 (brs, 1H).

Examples 1 and 2

Synthesis of (+)-8-(3-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine and (−)-8-(3-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine

[Formula 51]

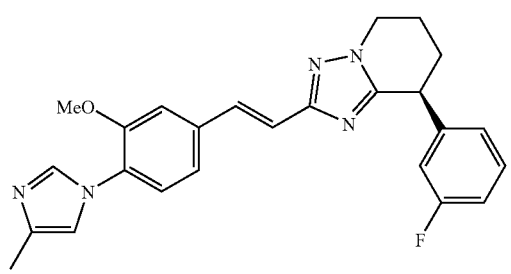

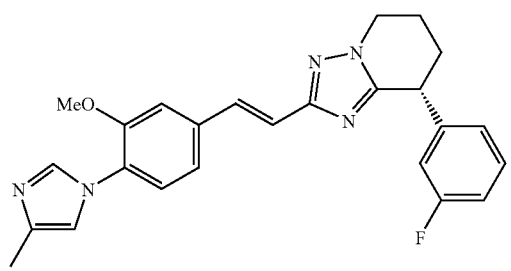

Synthesis of (E)-3-[3-methoxy-4-(4-methyl-1H-imidazol-1-yl)phenyl]acrylonitrile

A lithium hydroxide monohydrate powder (2.23 g) was added to a suspension of 3-methoxy-4-(4-methyl-1H-imidazol-1-yl)benzaldehyde (CAS No. 870837-18-6, 10 g) and diethyl cyanomethylphosphonate (8.2 g) in THF (50 ml) under ice-cooling, and the reaction solution was stirred at the same temperature for one hour. Ethyl acetate (200 mL) and water were added to the reaction solution, and the organic layer was separated. The organic layer was washed with brine, dried over anhydrous magnesium sulfate and then filtered through a silica gel pad (carrier: Chromatorex™ NH). The filtrate was concentrated under reduced pressure. The resulting residue was crystallized from ethyl acetate and hexane, and the crystals were collected by filtration. The resulting crystals were dried under reduced pressure to obtain 7.49 g of the title compound. The property values of the compound are as follows.

¹H-NMR (CDCl₃) δ (ppm): 2.30 (s, 3H), 3.91 (s, 3H), 5.90 (d, J=16.8 Hz, 1H), 6.93 (d, J=0.8 Hz, 1H), 7.06 (d, J=1.6 Hz, 1H), 7.13 (dd, J=8.0, 1.6 Hz, 1H), 7.29 (d, J=8.0 Hz, 1H), 7.39 (d, J=16.8 Hz, 1H), 7.74 (d, J=0.8 Hz, 1H).

Synthesis of ethyl (E)-3-[3-methoxy-4-(4-methyl-1H-imidazol-1-yl)phenyl]acrylimidate dihydrochloride A suspension of (E)-3-[3-methoxy-4-(4-methyl-1H-imidazol-1-yl)phenyl]acrylonitrile (7.45 g) in ethanol (75 mL) was bubbled with hydrogen chloride gas under ice-cooling for 10 minutes and at room temperature for 15 minutes, and then the reaction solution was stirred at room temperature overnight. The reaction solution was concentrated under reduced pressure. Then, ethanol and diethyl ether were added to the residue, and the precipitated powder was collected by filtration. The resulting powder was crystallized from ethanol and diethyl ether to obtain 9.22 g of the title compound. The property values of the compound are as follows.

ESI-MS; m/z 286 [M++H-2HCl]. ¹H-NMR (DMSO-D₆) δ (ppm): 1.46 (t, J=6.8 Hz, 3H), 2.35 (s, 3H), 3.93 (s, 3H), 4.54 (q, J=6.8 Hz, 2H), 7.18 (d, J=16.0 Hz, 1H), 7.50 (dd, J=8.0, 1.2 Hz, 1H), 7.68-7.77 (m, 3H), 8.01 (d, J=16.0 Hz, 1H), 9.35 (s, 1H).

Synthesis of 5-chloro-2-(3-fluorophenyl)pentanoic acid

A solution of 3-fluorophenylacetic acid (500 mg) in THF (15 mL) was stirred at −78° C. for 5 minutes. A 2.66 M solution of n-butyl lithium in hexane (2.44 mL) was added, and the reaction solution was stirred at −78° C. for three hours. Thereafter, the reaction solution was stirred at 0° C. for one hour, 1-bromo-3-chloropropane was added, and the reaction solution was stirred at room temperature for 17 hours. Thereafter, ethyl acetate and 1 N aqueous hydrochloric acid were added to the reaction solution, and the organic layer was separated. The resulting organic layer was dried over anhydrous magnesium sulfate and concentrated under reduced pressure to obtain 734 mg of the title compound. The property values of the compound are as follows.

¹H-NMR (CDCl₃) δ (ppm): 1.64-1.85 (m, 2H), 1.90-2.02 (m, 1H), 2.14-2.32 (m, 1H), 3.46-3.61 (m, 3H), 6.93-7.11 (m, 3H), 7.23-7.37 (m, 1H).

Synthesis of tert-butyl N'-[5-chloro-2-(3-fluorophenyl)pentanoyl]hydrazinecarboxylate IPEA (1.9 mL), HOBt (859 mg) and EDC (1.22 g) were added to a solution of 5-chloro-2-(3-fluorophenyl)pentanoic acid (734 mg) and tert-butyl carbazate (504 mg) in DMF (10 mL), and the reaction solution was stirred at room temperature for seven hours. Ethyl acetate and water were added to the reaction solution, and the organic layer was separated. The resulting organic layer was dried over anhydrous magnesium sulfate and then concentrated under reduced pressure. The residue was purified by silica gel column chromatography (elution solvent: heptane-ethyl acetate system) to obtain 711 mg of the title compound. The property values of the compound are as follows.

¹H-NMR (CDCl₃) δ (ppm): 1.43 (s, 9H), 1.56-2.06 (m, 3H), 2.12-2.32 (m, 1H), 3.36-3.58 (m, 3H), 6.55 (brs, 1H), 6.90-7.16 (m, 3H), 7.20-7.34 (m, 1H), 7.67 (brs, 1H).

Synthesis of (+)-8-(3-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine and (−)-8-(3-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine A solution of 4 N hydrochloric acid in ethyl acetate (12.1 mL) was added to tert-butyl N'-[5-chloro-2-(3-fluorophenyl)pentanoyl]hydrazinecarboxylate (711 mg), and the reaction solution was stirred at room temperature for two hours. The reaction solution was concentrated under reduced pressure to obtain a crude product of 5-chloro-2-(3-fluorophenyl)pentanoic acid hydrazide hydrochloride. A solution of ethyl (E)-3-[3-methoxy-4-(4-methyl-1H-imidazol-1-yl)phenyl]acrylimidate dihydrochloride (576 mg) and triethylamine (1.24 mL) in ethanol (10 mL) was added to a solution of the resulting crude product of 5-chloro-2-(3-fluorophenyl)pentanoic acid hydrazide hydrochloride and triethylamine (1 mL) in ethanol (10 mL), and the reaction solution was stirred at 80° C. in a nitrogen atmosphere for 23 hours. The reaction solution was cooled to room temperature and then the solvent was evaporated under reduced pressure. Ethyl acetate and saturated sodium bicarbonate water were added to the resulting residue, and the organic layer was separated. The resulting organic layer was dried over anhydrous magnesium sulfate and concentrated under reduced pressure. The residue was purified by silica gel column chromatography (carrier: Chromatorex NH; elution solvent: heptane:ethyl acetate=1:1→ethyl acetate→ethyl acetate:methanol=9:1) and further purified by silica gel column chromatography (elution solvent: ethyl acetate→ethyl acetate:methanol=9:1) to obtain 306 mg of a racemate of the title compound. The resulting racemate (152 mg) was separated by CHIRALPAK™ IA manufactured by Daicel Chemical Industries, Ltd. (2 cm×25 cm; mobile phase: hexane:ethanol=1:1) to obtain a (+)-isomer of the title optically active compound with a retention time of 14 minutes (60 mg; >99% ee) and a (−)-isomer of the title optically active compound with a retention time of 15.5 minutes (61 mg; 92% ee).

The property values of (+)-8-(3-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine are as follows.

ESI-MS; m/z 430 [M$^+$+H]. $^1$H-NMR (CDCl$_3$) δ (ppm): 2.01-2.46 (m, 7H), 3.85 (s, 3H), 4.21-4.38 (m, 3H), 6.81-7.02 (m, 4H), 7.06 (d, J=16.0 Hz, 1H), 7.10-7.24 (m, 3H), 7.26-7.34 (m, 1H), 7.51 (d, J=16.0 Hz, 1H), 7.69 (brs, 1H).

The property values of (−)-8-(3-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine are as follows.

ESI-MS; m/z 430 [M$^+$+H]. $^1$H-NMR (CDCl$_3$) δ (ppm): 2.01-2.46 (m, 7H), 3.85 (s, 3H), 4.21-4.38 (m, 3H), 6.81-7.02 (m, 4H), 7.06 (d, J=16.0 Hz, 1H), 7.10-7.24 (m, 3H), 7.26-7.34 (m, 1H), 7.51 (d, J=16.0 Hz, 1H), 7.69 (brs, 1H).

Examples 3 and 4

Synthesis of (−)-1-{4-{2-{(E)-2-[3-methoxy-4-(4-methyl-1H-imidazol-1-yl)phenyl]vinyl}-5,6,7,8-tetrahydro[1,2,4]triazolo[1,5-a]pyridin-8-yl}phenyl}pentan-1-one and (+)-1-{4-{2-{(E)-2-[3-methoxy-4-(4-methyl-1H-imidazol-1-yl)phenyl]vinyl}-5,6,7,8-tetrahydro[1,2,4]triazolo[1,5-a]pyridin-8-yl}phenyl}pentan-1-one

[Formula 52]

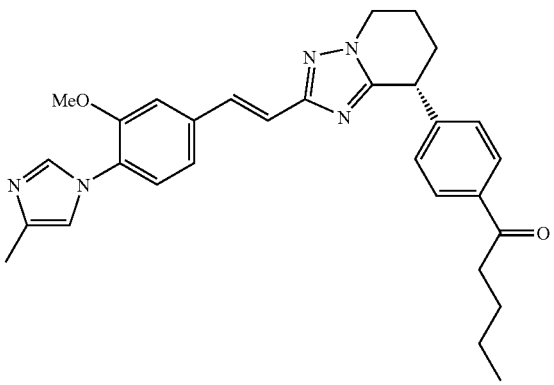

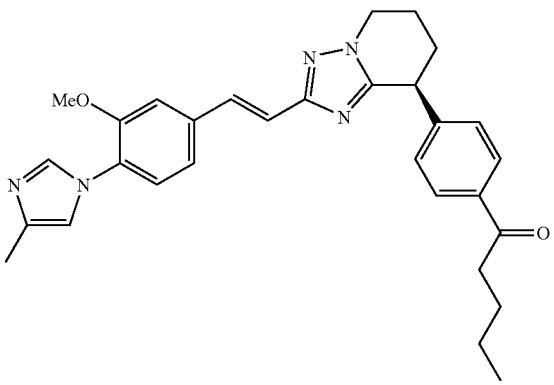

119 mg of a racemate of the title compound was obtained from 4-cyanophenylacetic acid (1 g) by the same method as in Examples 1 and 2. The racemate (60 mg) was separated by CHIRALPAK™ IB manufactured by Daicel Chemical Industries, Ltd. (2 cm×25 cm; mobile phase: ethanol) to obtain a (−)-isomer of the title optically active compound with a retention time of 18.5 minutes (22.3 mg; 98% ee) and a (+)-isomer of the title optically active compound with a retention time of 33 minutes (23 mg; 98% ee).

The property values of (−)-1-{4-{2-{(E)-2-[3-methoxy-4-(4-methyl-1H-imidazol-1-yl)phenyl]vinyl}-5,6,7,8-tetrahydro[1,2,4]triazolo[1,5-a]pyridin-8-yl}phenyl}pentan-1-one are as follows.

ESI-MS; m/z 496 [M$^+$+H]. $^1$H-NMR (CDCl$_3$) δ (ppm): 0.95 (t, J=7.2 Hz, 3H), 1.34-1.46 (m, 2H), 1.66-1.76 (m, 2H), 2.00-2.48 (m, 7H), 2.94 (t, J=7.6 Hz, 2H), 3.85 (s, 3H), 4.24-4.35 (m, 2H), 4.36-4.43 (m, 1H), 6.91 (brs, 1H), 7.06 (d, J=16.4 Hz, 1H), 7.10-7.17 (m, 2H), 7.18-7.30 (m, 3H), 7.50 (d, J=16.4 Hz, 1H), 7.73 (brs, 1H), 7.87-7.97 (m, 2H).

The property values of (+)-1-{4-{2-{(E)-2-[3-methoxy-4-(4-methyl-1H-imidazol-1-yl)phenyl]vinyl}-5,6,7,8-tetrahydro[1,2,4]triazolo[1,5-a]pyridin-8-yl}phenyl}pentan-1-one are as follows.

ESI-MS; m/z 496 [M$^+$+H]. $^1$H-NMR (CDCl$_3$) δ (ppm): 0.95 (t, J=7.2 Hz, 3H), 1.34-1.46 (m, 2H), 1.66-1.76 (m, 2H), 2.00-2.48 (m, 7H), 2.94 (t, J=7.6 Hz, 2H), 3.85 (s, 3H), 4.24-4.35 (m, 2H), 4.36-4.43 (m, 1H), 6.91 (brs, 1H), 7.06 (d, J=16.4 Hz, 1H), 7.10-7.17 (m, 2H), 7.18-7.30 (m, 3H), 7.50 (d, J=16.4 Hz, 1H), 7.73 (brs, 1H), 7.87-7.97 (m, 2H).

Examples 5 and 6

Synthesis of (−)-8-(4-isopropylphenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine and (+)-8-(4-isopropylphenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine

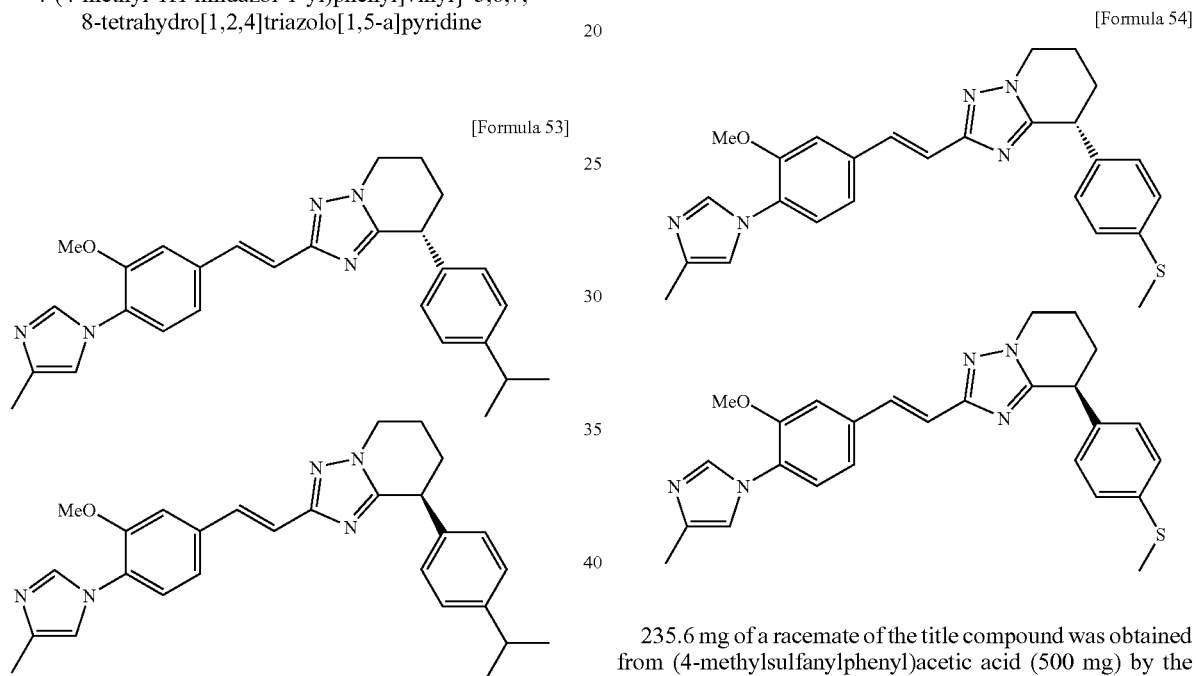

[Formula 53]

[Formula 54]

242.4 mg of a racemate of the title compound was obtained from 4-isopropylphenylacetic acid (1 g) by the same method as in Examples 1 and 2. The racemate (100 mg) was separated by CHIRALCEL™ OJ-H manufactured by Daicel Chemical Industries, Ltd. (2 cm×25 cm; mobile phase: ethanol) to obtain a (−)-isomer of the title optically active compound with a retention time of 8.5 minutes (40.7 mg; >99% ee) and a (+)-isomer of the title optically active compound with a retention time of 15 minutes (39.1 mg; 96% ee).

The property values of (−)-8-(4-isopropylphenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine are as follows.

ESI-MS; m/z 454 [M$^+$+H]. $^1$H-NMR (CDCl$_3$) δ (ppm): 1.23 (d, J=6.8 Hz, 6H), 1.80-2.40 (m, 7H), 2.82-2.95 (m, 1H), 3.85 (s, 3H), 4.20-4.35 (m, 3H), 6.90 (brs, 1H), 6.98-7.24 (m, 8H), 7.51 (d, J=16.4 Hz, 1H), 7.67-7.72 (m, 1H).

The property values of (+)-8-(4-isopropylphenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine are as follows.

ESI-MS; m/z 454 [M$^+$+H]. $^1$H-NMR (CDCl$_3$) δ (ppm): 1.23 (d, J=6.8 Hz, 6H), 1.80-2.40 (m, 7H), 2.82-2.95 (m, 1H), 3.85 (s, 3H), 4.20-4.35 (m, 3H), 6.90 (brs, 1H), 6.98-7.24 (m, 8H), 7.51 (d, J=16.4 Hz, 1H), 7.67-7.72 (m, 1H).

Examples 7 and 8

Synthesis of (−)-2-{(E)-2-[3-methoxy-4-(4-methyl-1H-imidazol-1-yl)phenyl]vinyl}-8-(4-methylsulfanylphenyl)-5,6,7,8-tetrahydro-[1,2,4]triazolo[1,5-a]pyridine and (+)-2-{(E)-2-[3-methoxy-4-(4-methyl-1H-imidazol-1-yl)phenyl]vinyl}-8-(4-methylsulfanylphenyl)-5,6,7,8-tetrahydro-[1,2,4]triazolo[1,5-a]pyridine 235.6 mg of a racemate of the title compound was obtained from (4-methylsulfanylphenyl)acetic acid (500 mg) by the same method as in Examples 1 and 2. The racemate (100 mg) was separated by CHIRALPAK™ IB manufactured by Daicel Chemical Industries, Ltd. (2 cm×25 cm; mobile phase: hexane:ethanol=1:1) to obtain a (−)-isomer of the title optically active compound with a retention time of 21 minutes (49.2 mg; >99% ee) and a (+)-isomer of the title optically active compound with a retention time of 29.5 minutes (49.6 mg; >99% ee).

The property values of (−)-2-{(E)-2-[3-methoxy-4-(4-methyl-1H-imidazol-1-yl)phenyl]vinyl}-8-(4-methylsulfanylphenyl)-5,6,7,8-tetrahydro-[1,2,4]triazolo[1,5-a]pyridine are as follows.

ESI-MS; m/z 458 [M$^+$+H]. $^1$H-NMR (CDCl$_3$) δ (ppm): 1.98-2.40 (m, 7H), 2.47 (s, 3H), 3.85 (s, 3H), 4.21-4.34 (m, 3H), 6.87-6.93 (m, 1H), 7.01-7.28 (m, 8H), 7.50 (d, J=16.0 Hz, 1H), 7.69 (d, J=1.2 Hz, 1H).

The property values of (+)-2-{(E)-2-[3-methoxy-4-(4-methyl-1H-imidazol-1-yl)phenyl]vinyl}-8-(4-methylsulfanylphenyl)-5,6,7,8-tetrahydro-[1,2,4]triazolo[1,5-a]pyridine are as follows.

ESI-MS; m/z 458 [M$^+$+H]. $^1$H-NMR (CDCl$_3$) δ (ppm): 1.98-2.40 (m, 7H), 2.47 (s, 3H), 3.85 (s, 3H), 4.21-4.34 (m, 3H), 6.87-6.93 (m, 1H), 7.01-7.28 (m, 8H), 7.50 (d, J=16.0 Hz, 1H), 7.69 (d, J=1.2 Hz, 1H).

Example 9

Synthesis of 8-(4-methanesulfonylphenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine

[Formula 55]

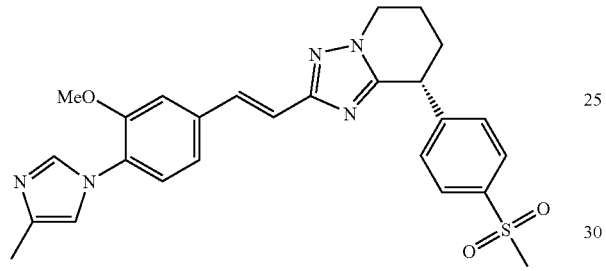

mCPBA (6.83 mg) was added to a solution of (−)-(2-{(E)-2-[3-methoxy-4-(4-methyl-1H-imidazol-1-yl)phenyl]vinyl}-8-(4-methylsulfanylphenyl)-5,6,7,8-tetrahydro-[1,2,4]triazolo[1,5-a]pyridine obtained in Example 7 (4.5 mg) in chloroform (1 mL), and the reaction solution was stirred at room temperature for one hour. Brine and ethyl acetate were added to the reaction solution and the organic layer was separated. The resulting organic layer was dried over anhydrous magnesium sulfate and then concentrated under reduced pressure. The resulting residue was purified by silica gel column chromatography (carrier: Chromatorex NH; elution solvent: ethyl acetate→ethyl acetate:methanol=9:1) to obtain 0.44 mg of the title compound.

The property values of 8-(4-methanesulfonylphenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine are as follows.

ESI-MS; m/z 490 [M$^+$+H]. $^1$H-NMR (CDCl$_3$) δ (ppm): 1.96-2.48 (m, 7H), 3.05 (s, 3H), 3.85 (s, 3H), 4.31 (t, J=5.6 Hz, 2H), 4.42 (t, J=7.2 Hz, 1H), 6.91 (brs, 1H), 7.05 (d, J=16.4 Hz, 1H), 7.10-7.30 (m, 3H), 7.38 (d, J=8.4 Hz, 2H), 7.49 (d, J=16.4 Hz, 1H) 7.69 (d, J=0.8 Hz, 1H), 7.92 (d, J=8.4 Hz, 2H).

Examples 10 and 11

Synthesis of (−)-2-{(E)-2-[3-methoxy-4-(4-methyl-1H-imidazol-1-yl)phenyl]vinyl}-8-thiophen-2-yl-5,6,7,8-tetrahydro[1,2,4]triazolo[1,5-a]pyridine and (+)-2-{(E)-2-[3-methoxy-4-(4-methyl-1H-imidazol-1-yl)phenyl]vinyl}-8-thiophen-2-yl-5,6,7,8-tetrahydro[1,2,4]triazolo[1,5-a]pyridine

[Formula 56]

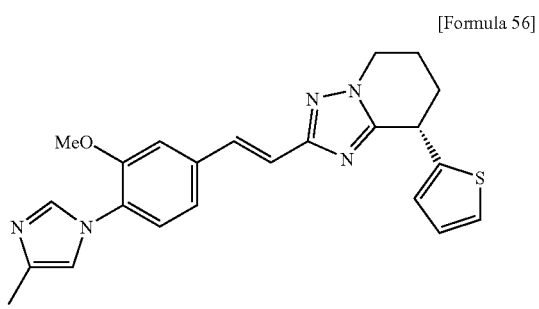

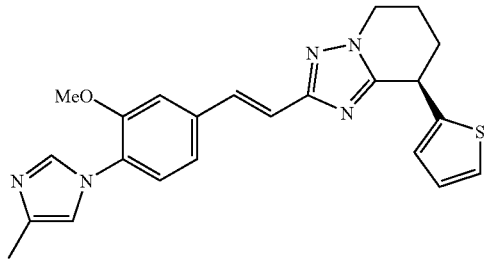

258.6 mg of a racemate of the title compound was obtained from thiophen-2-ylacetic acid (500 mg) by the same method as in Examples 1 and 2. The racemate (106 mg) was separated by CHIRALCEL™ OJ-H manufactured by Daicel Chemical Industries, Ltd. (2 cm×25 cm; mobile phase: ethanol) to obtain a (−)-isomer of the title optically active compound with a retention time of 11 minutes (51.5 mg; >99% ee) and a (+)-isomer of the title optically active compound with a retention time of 19 minutes (52.1 mg; 98% ee).

The property values of (−)-2-{(E)-2-[3-methoxy-4-(4-methyl-1H-imidazol-1-yl)phenyl]vinyl}-8-thiophen-2-yl-5,6,7,8-tetrahydro[1,2,4]triazolo[1,5-a]pyridine are as follows.

ESI-MS; m/z 418 [M$^+$+H]. $^1$H-NMR (CDCl$_3$) δ (ppm): 2.03-2.48 (m, 7H), 3.86 (s, 3H), 4.16-4.32 (m, 2H), 4.63 (t, J=6.0 Hz, 1H), 6.88-6.98 (m, 3H), 7.07 (d, J=16.8 Hz, 1H), 7.12-7.24 (m, 4H), 7.54 (d, J=16.8 Hz, 1H), 7.69 (d, J=1.2 Hz, 1H).

The property values of (+)-2-{(E)-2-[3-methoxy-4-(4-methyl-1H-imidazol-1-yl)phenyl]vinyl}-8-thiophen-2-yl-5,6,7,8-tetrahydro[1,2,4]triazolo[1,5-a]pyridine are as follows.

ESI-MS; m/z 418 [M$^+$+H]. $^1$H-NMR (CDCl$_3$) δ (ppm): 2.03-2.48 (m, 7H), 3.86 (s, 3H), 4.16-4.32 (m, 2H), 4.63 (t, J=6.0 Hz, 1H), 6.88-6.98 (m, 3H), 7.07 (d, J=16.8 Hz, 1H), 7.12-7.24 (m, 4H), 7.54 (d, J=16.8 Hz, 1H), 7.69 (d, J=1.2 Hz, 1H).

Example 12

Synthesis of 2-{(E)-2-[3-methoxy-4-(4-methyl-1H-imidazol-1-yl)phenyl]vinyl}-8-[1-phenylmethy-(E)-lidene]-5,6,7,8-tetrahydro[1,2,4]triazolo[1,5-a]pyridine

[Formula 57]

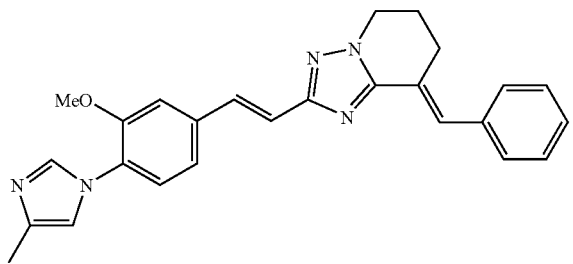

Synthesis of tert-butyl 5-chloro-2-[1-phenylmethy-(E)-lidene]pentanoate

Ethanol (30 mL), benzaldehyde (3 mL) and lithium hydroxide monohydrate (3.71 g) were added to a solution of a solution of tert-butyl 5-chloro-2-(diethoxyphosphoryl)pentanoate (CAS No. 870843-25-7) (10.7 g) in THF (90 mL), and the reaction solution was stirred at room temperature for 19.5 hours. Thereafter, ethyl acetate and saturated sodium bicarbonate water were added to the reaction solution, and the organic layer was separated. The resulting organic layer was dried over anhydrous magnesium sulfate and then concentrated under reduced pressure. The resulting residue was purified by silica gel column chromatography (elution solvent: heptane-ethyl acetate system) to obtain 6.57 g of the title compound. The property values of the compound are as follows.

$^1$H-NMR (CDCl$_3$) δ (ppm): 1.55 (S, 9H), 1.96-2.14 (m, 2H), 2.59-2.68 (m, 2H), 3.56 (t, J=6.8 Hz, 2H), 7.23-7.41 (m, 5H), 7.62 (brs, 1H).

Synthesis of 5-chloro-2-[1-phenylmethy-(E)-lidene]pentanoic acid

Anisole (1.16 mL) was added to tert-butyl 5-chloro-2-[1-phenylmethy-(E)-lidene]pentanoate (1 g). Trifluoroacetic acid (5 mL) was further added under ice-cooling, and the reaction solution was stirred in a nitrogen atmosphere under ice-cooling for four hours. Thereafter, the reaction solution was concentrated under reduced pressure and the resulting residue was dissolved in ethyl acetate at 80° C. The solution was left to stand at room temperature and the precipitated crystals were collected by filtration. The crystals collected by filtration was washed with ethyl acetate:heptane=1:1 to obtain 188.6 mg of the title compound. The property values of the compound are as follows.

$^1$H-NMR (CDCl$_3$) δ (ppm): 2.02-2.22 (m, 2H), 2.67-2.77 (m, 2H), 3.60 (t, J=6.4 Hz, 2H), 7.32-7.47 (m, 5H), 7.86 (brs, 1H).

Synthesis of 2-{(E)-2-[3-methoxy-4-(4-methyl-1H-imidazol-1-yl)phenyl]vinyl}-8-[1-phenylmethy-(E)-lidene]-5,6,7,8-tetrahydro[1,2,4]triazolo[1,5-a]pyridine IPEA (4 mL), HOBt (1.81 g) and EDC (2.56 g) were added to a solution of 5-chloro-2-[1-phenylmethy-(E)-lidene]pentanoic acid (1.5 g) and tert-butyl carbazate (1.06 g) in DMF (20 mL), and the reaction solution was stirred at room temperature for 2.5 hours. Ethyl acetate and water were added to the reaction solution and the organic layer was separated. The resulting organic layer was dried over anhydrous magnesium sulfate and then concentrated under reduced pressure. The residue was purified by silica gel column chromatography (elution solvent: heptane-ethyl acetate system) to obtain an (E)/(Z) mixture of tert-butyl N'-{5-chloro-2-[1-phenylmethylidene]pentanoyl}hydrazinecarboxylate (1.97 g). A solution of 4 N hydrochloric acid in ethyl acetate (12.1 mL) was added to the resulting (E)/(Z) mixture of tert-butyl N'-{5-chloro-2-[1-phenylmethylidene]pentanoyl}hydrazinecarboxylate (0.726 g), and the reaction solution was stirred at room temperature for seven hours. The reaction solution was concentrated under reduced pressure. A solution of ethyl (E)-3-[3-methoxy-4-(4-methyl-1H-imidazol-1-yl)phenyl]acrylimidate dihydrochloride (0.576 g) and triethylamine (1.24 mL) in ethanol (10 mL) was added to a solution of the resulting residue and triethylamine (1 mL) in ethanol (10 mL). The reaction solution was stirred at 80° C. in a nitrogen atmosphere for 16 hours. The reaction solution was cooled to room temperature and then the solvent was evaporated under reduced pressure. Ethyl acetate and saturated sodium bicarbonate water were added to the resulting residue, and the organic layer was separated. The resulting organic layer was dried over anhydrous magnesium sulfate and then concentrated under reduced pressure. The residue was purified by silica gel column chromatography (carrier: Chromatorex NH; elution solvent: heptane:ethyl acetate=1:1→ethyl acetate→ethyl acetate:methanol=9:1) and further purified by silica gel column chromatography (elution solvent: ethyl acetate→ethyl acetate:methanol=9:1). Then, the purified product was separated by CHIRALPAK™ IA manufactured by Daicel Chemical Industries, Ltd. (2 cm×25 cm; mobile phase: ethanol) to obtain the title compound with a retention time of 33 minutes (12.3 mg).

The property values of 2-{(E)-2-[3-methoxy-4-(4-methyl-1H-imidazol-1-yl)phenyl]vinyl}-8-[1-phenylmethy-(E)-lidene]-5,6,7,8-tetrahydro[1,2,4]triazolo[1,5-a]pyridine are as follows.

ESI-MS; m/z 424 [M$^+$+H]. $^1$H-NMR (CDCl$_3$) δ (ppm): 2.11-2.21 (m, 2H), 2.30 (s, 3H), 2.93-3.01 (m, 2H), 3.89 (s, 3H), 4.29 (t, J=6.0 Hz, 2H), 6.92 (brs, 1H), 7.10 (d, J=16.0 Hz, 1H), 7.16-7.46 (m, 8H), 7.62 (d, J=16.0 Hz, 1H), 7.70 (d, J=1.2 Hz, 1H), 7.79 (brs, 1H).

Examples 13 and 14

Synthesis of (−)-2-{(E)-2-[3-methoxy-4-(4-methyl-1H-imidazol-1-yl)phenyl]vinyl}-8-thiophen-3-yl-5,6,7,8-tetrahydro[1,2,4]triazolo[1,5-a]pyridine and (+)-2-{(E)-2-[3-methoxy-4-(4-methyl-1H-imidazol-1-yl)phenyl]vinyl}-8-thiophen-3-yl-5,6,7,8-tetrahydro[1,2,4]triazolo[1,5-a]pyridine

[Formula 58]

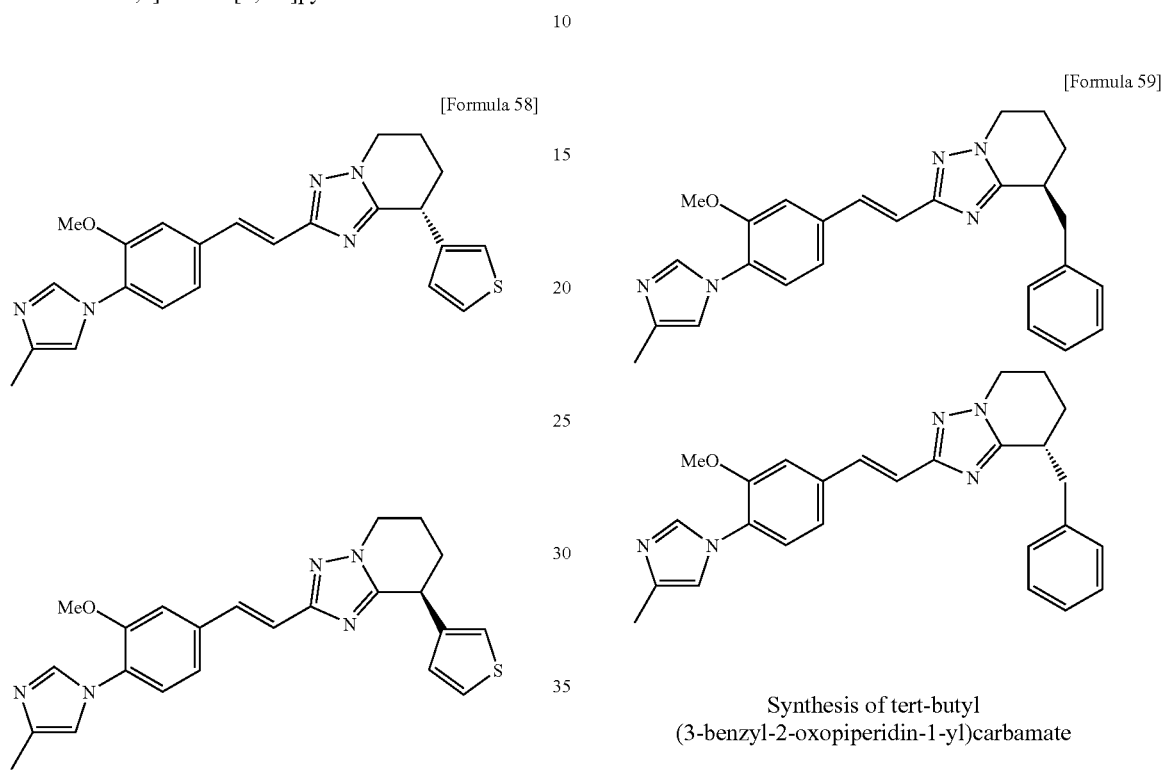

244.7 mg of a racemate of the title compound was obtained from thiophen-3-ylacetic acid (500 mg) by the same method as in Examples 1 and 2. The racemate (103 mg) was separated by CHIRALCEL™ OJ-H manufactured by Daicel Chemical Industries, Ltd. (2 cm×25 cm; mobile phase: ethanol) to obtain a (−)-isomer of the title optically active compound with a retention time of 11 minutes (47.1 mg; >99% ee) and a (+)-isomer of the title optically active compound with a retention time of 19.5 minutes (45.9 mg).

The property values of (−)-2-{(E)-2-[3-methoxy-4-(4-methyl-1H-imidazol-1-yl)phenyl]vinyl}-8-thiophen-3-yl-5,6,7,8-tetrahydro[1,2,4]triazolo[1,5-a]pyridine are as follows.

ESI-MS; m/z 418 [M$^+$+H]. $^1$H-NMR (CDCl$_3$) δ (ppm): 2.00-2.42 (m, 7H), 3.86 (s, 3H), 4.16-4.32 (m, 2H), 4.45 (t, J=5.2 Hz, 1H), 6.91 (brs, 1H), 6.98-7.24 (m, 6H), 7.31 (dd, J=3.2, 5.2 Hz, 1H), 7.54 (d, J=16.0 Hz, 1H), 7.69 (d, J=1.2 Hz, 1H).

The property values of (+)-2-{(E)-2-[3-methoxy-4-(4-methyl-1H-imidazol-1-yl)phenyl]vinyl}-8-thiophen-3-yl-5,6,7,8-tetrahydro[1,2,4]triazolo[1,5-a]pyridine are as follows.

ESI-MS; m/z 418 [M$^+$+H]. $^1$H-NMR (CDCl$_3$) δ (ppm): 2.00-2.42 (m, 7H), 3.86 (s, 3H), 4.16-4.32 (m, 2H), 4.45 (t, J=5.2 Hz, 1H), 6.91 (brs, 1H), 6.98-7.24 (m, 6H), 7.31 (dd, J=3.2, 5.2 Hz, 1H), 7.54 (d, J=16.0 Hz, 1H), 7.69 (d, J=1.2 Hz, 1H).

Examples 15 and 16

Synthesis of (+)-8-benzyl-2-{(E)-2-[3-methoxy-4-(4-methyl-1H-imidazol-1-yl)phenyl]vinyl}-5,6,7,8-tetrahydro[1,2,4]triazolo[1,5-a]pyridine and (−)-8-benzyl-2-{(E)-2-[3-methoxy-4-(4-methyl-1H-imidazol-1-yl)phenyl]vinyl}-5,6,7,8-tetrahydro[1,2,4]triazolo[1,5-a]pyridine

[Formula 59]

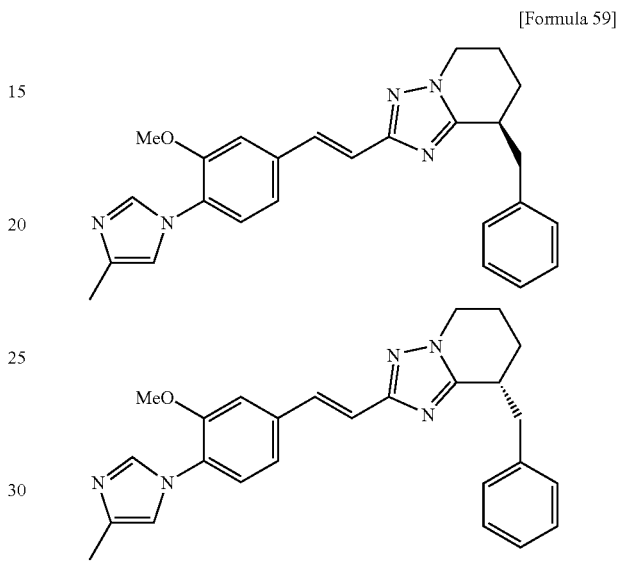

Synthesis of tert-butyl (3-benzyl-2-oxopiperidin-1-yl)carbamate

10% palladium-carbon powder (50.36% aqueous, 1.92 g) was added to a solution of the (E)/(Z) mixture of tert-butyl N'-[5-chloro-2-(1-phenylmethylidene)pentanoyl]hydrazinecarboxylate obtained in the process of Example 12 in ethanol (20 mL), and the reaction solution was stirred in a hydrogen atmosphere at room temperature for 10 days. Thereafter, the reaction solution was filtered through celite and the solvent was evaporated under reduced pressure. DBU (0.598 mL) was added to a solution of the resulting residue in THF (50 mL) and the mixture was heated under reflux for 44 hours. Thereafter, the solvent was evaporated under reduced pressure. The resulting residue was purified by silica gel column chromatography (elution solvent: heptane-ethyl acetate system) to obtain 727 mg of the title compound. The property values of the compound are as follows.

$^1$H-NMR (CDCl$_3$) δ (ppm): 1.36-1.60 (m, 10H), 1.70-1.98 (m, 3H), 2.60-2.78 (m, 2H), 3.36-3.48 (m, 1H), 3.50-3.66 (m, 2H), 6.69 (brs, 1H), 7.11-7.32 (m, 5H).

Synthesis of (+)-8-benzyl-2-{(E)-2-[3-methoxy-4-(4-methyl-1H-imidazol-1-yl)phenyl]vinyl}-5,6,7,8-tetrahydro[1,2,4]triazolo[1,5-a]pyridine and (−)-8-benzyl-2-{(E)-2-[3-methoxy-4-(4-methyl-1H-imidazol-1-yl)phenyl]vinyl}-5,6,7,8-tetrahydro[1,2,4]triazolo[1,5-a]pyridine A solution of 4 N hydrochloric acid in ethyl acetate (13 mL) was added to tert-butyl (3-benzyl-2-oxopiperidin-1-yl)

carbamate (727 mg), and the reaction solution was stirred at room temperature for three hours. The reaction solution was concentrated under reduced pressure. IPEA (2.45 mL), HOBT (646 mg) and EDC (916 mg) were added to a solution of the resulting residue and (E)-3-[3-methoxy-4-(4-methyl-1H-imidazol-1-yl)phenyl]acrylic acid (CAS No. 970839-41-1, 617 mg) in DMF (15 mL), and the reaction solution was stirred at room temperature for 25 hours. Ethyl acetate and water were added to the reaction solution and the organic layer was separated. The resulting organic layer was dried over anhydrous magnesium sulfate and then concentrated under reduced pressure. A solution of the resulting residue in phosphorus oxychloride (20 mL) was heated under reflux for 1.5 hours. The reaction solution was left to cool to room temperature and then concentrated under reduced pressure. Acetic acid (12 mL) and ammonium acetate (7.34 g) were added to the resulting residue, and the reaction solution was stirred at 150° C. for 2.5 hours. The reaction solution was left to cool to room temperature and then concentrated under reduced pressure. Ethyl acetate and saturated sodium bicarbonate water were added to the resulting residue, and the organic layer was separated. The resulting organic layer was dried over anhydrous magnesium sulfate and then concentrated under reduced pressure. The residue was purified by silica gel column chromatography (carrier: Chromatorex NH; elution solvent: heptane:ethyl acetate=1:1→ethyl acetate→ethyl acetate:methanol=9:1) and further purified by silica gel column chromatography (elution solvent: ethyl acetate→ethyl acetate:methanol=9:1) to obtain 10.3 mg of a racemate of the title compound. The resulting racemate (10.3 mg) was separated by CHIRALCEL™ OD-H manufactured by Daicel Chemical Industries, Ltd. (2 cm×25 cm; mobile phase: hexane:ethanol=1:1) to obtain a (+)-isomer of the title optically active compound with a retention time of 8 minutes (2.83 mg, >99% ee) and a (−)-isomer of the title optically active compound with a retention time of 13.5 minutes (3.27 mg, >99% ee).

The property values of (+)-8-benzyl-2-{(E)-2-[3-methoxy-4-(4-methyl-1H-imidazol-1-yl)phenyl]vinyl}-5,6,7,8-tetrahydro[1,2,4]triazolo[1,5-a]pyridine are as follows.

ESI-MS; m/z 426 [M$^+$+H]. $^1$H-NMR (CDCl$_3$) δ (ppm): 1.50-1.76 (m, 1H), 1.86-2.02 (m, 2H), 2.06-2.18 (m, 1H), 2.30 (s, 3H), 2.76 (dd, J=10.4, 13.2 Hz, 1H), 3.16-3.28 (m, 1H), 3.65 (dd, J=3.6, 13.2 Hz, 1H), 3.89 (s, 3H), 4.03-4.13 (m, 1H), 4.14-4.24 (m, 1H), 6.92 (brs, 1H), 7.09 (d, J=16.4 Hz, 1H), 7.16-7.35 (m, 8H), 7.58 (d, J=16.4 Hz, 1H), 7.71 (d, J=1.2 Hz, 1H).

The property values of (−)-8-benzyl-2-{(E)-2-[3-methoxy-4-(4-methyl-1H-imidazol-1-yl)phenyl]vinyl}-5,6,7,8-tetrahydro[1,2,4]triazolo[1,5-a]pyridine are as follows.

ESI-MS; m/z 426 [M$^+$+H]. $^1$H-NMR (CDCl$_3$) δ (ppm): 1.50-1.76 (m, 1H), 1.86-2.02 (m, 2H), 2.06-2.18 (m, 1H), 2.30 (s, 3H), 2.76 (dd, J=10.4, 13.2 Hz, 1H), 3.16-3.28 (m, 1H), 3.65 (dd, J=3.6, 13.2 Hz, 1H), 3.89 (s, 3H), 4.03-4.13 (m, 1H), 4.14-4.24 (m, 1H), 6.92 (brs, 1H), 7.09 (d, J=16.4 Hz, 1H), 7.16-7.35 (m, 8H), 7.58 (d, J=16.4 Hz, 1H), 7.71 (d, J=1.2 Hz, 1H).

Examples 17 and 18

Synthesis of (−)-8-(6-chloropyridin-3-yl)-2-{(E)-2-[3-methoxy-4-(4-methyl-1H-imidazol-1-yl)phenyl]vinyl}-5,6,7,8-tetrahydro[1,2,4]triazolo[1,5-a]pyridine and (+)-8-(6-chloropyridin-3-yl)-2-{(E)-2-[3-methoxy-4-(4-methyl-1H-imidazol-1-yl)phenyl]vinyl}-5,6,7,8-tetrahydro[1,2,4]triazolo[1,5-a]pyridine

[Formula 60]

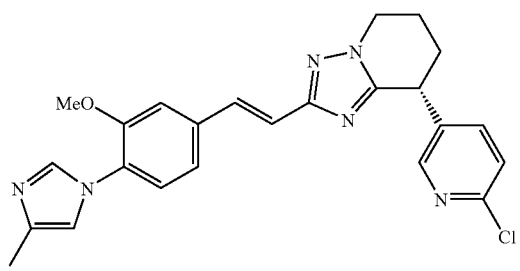

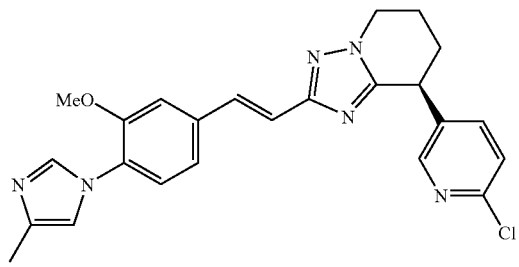

230 mg of a racemate of the title compound was obtained from (2-chloropyridyl)-5-acetic acid (500 mg) by the same method as in Examples 1 and 2. The racemate (104 mg) was separated by CHIRALPAK™ IB manufactured by Daicel Chemical Industries, Ltd. (2 cm×25 cm; mobile phase: hexane:ethanol=1:1) to obtain a (−)-isomer of the title optically active compound with a retention time of 30 minutes (39 mg; >99% ee) and a (+)-isomer of the title optically active compound with a retention time of 54 minutes (38.7 mg; >99% ee).

The property values of (−)-8-(6-chloropyridin-3-yl)-2-{(E)-2-[3-methoxy-4-(4-methyl-1H-imidazol-1-yl)phenyl]vinyl}-5,6,7,8-tetrahydro[1,2,4]triazolo[1,5-a]pyridine are as follows.

ESI-MS; m/z 447 [M$^+$+H]. $^1$H-NMR (CDCl$_3$) δ (ppm): 1.94-2.34 (m, 6H), 2.36-2.46 (m, 1H), 3.86 (s, 3H), 4.23-4.37 (m, 3H), 6.91 (brs, 1H), 7.03 (d, J=16.4 Hz, 1H), 7.10-7.24 (m, 3H), 7.31 (d, J=8.4 Hz, 1H), 7.42-7.54 (m, 2H), 7.70 (d, J=1.2 Hz, 1H), 8.30 (d, J=2.8 Hz, 1H).

The property values of (+)-8-(6-chloropyridin-3-yl)-2-{(E)-2-[3-methoxy-4-(4-methyl-1H-imidazol-1-yl)phenyl]vinyl}-5,6,7,8-tetrahydro[1,2,4]triazolo[1,5-a]pyridine are as follows.

ESI-MS; m/z 447 [M$^+$+H]. $^1$H-NMR (CDCl$_3$) δ (ppm): 1.94-2.34 (m, 6H), 2.36-2.46 (m, 1H), 3.86 (s, 3H), 4.23-4.37 (m, 3H), 6.91 (brs, 1H), 7.03 (d, J=16.4 Hz, 1H), 7.10-7.24

(m, 3H), 7.31 (d, J=8.4 Hz, 1H), 7.42-7.54 (m, 2H), 7.70 (d, J=1.2 Hz, 1H), 8.30 (d, J=2.8 Hz, 1H).

Example 19

Synthesis of 1-{4-{2-{(E)-2-[3-methoxy-4-(4-methyl-1H-imidazol-1-yl)phenyl]vinyl}-5,6,7,8-tetrahydro[1,2,4]triazolo[1,5-a]pyridin-8-yl}phenyl}pentan-1-ol

[Formula 61]

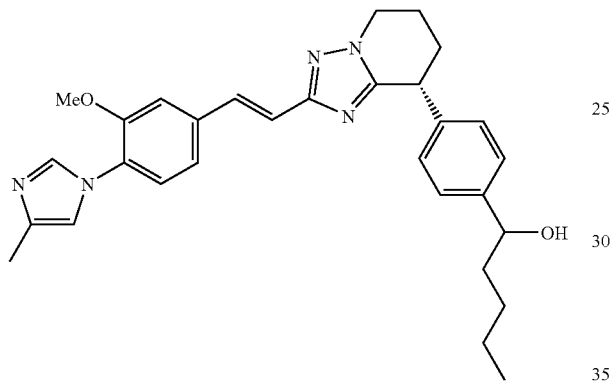

Sodium tetrahydroborate (0.166 mg) was added to a solution of (−)-1-{4-{2-{(E)-2-[3-methoxy-4-(4-methyl-1H-imidazol-1-yl)phenyl]vinyl}-5,6,7,8-tetrahydro[1,2,4]triazolo[1,5-a]pyridin-8-yl}phenyl}pentan-1-one obtained in Example 3 (2 mg) in methanol (0.5 mL), and the reaction solution was stirred in a nitrogen atmosphere at room temperature for one hour. Brine and ethyl acetate were added to the reaction solution and the organic layer was separated. The resulting organic layer was dried over anhydrous magnesium sulfate and then concentrated under reduced pressure. The resulting residue was purified by silica gel column chromatography (carrier: Chromatorex NH; elution solvent: ethyl acetate→ethyl acetate:methanol=9:1) to obtain 1.19 mg of the title compound.

The property values of 1-{4-{2-{(E)-2-[3-methoxy-4-(4-methyl-1H-imidazol-1-yl)phenyl]vinyl}-5,6,7,8-tetrahydro[1,2,4]triazolo[1,5-a]pyridin-8-yl}phenyl}pentan-1-ol are as follows.

ESI-MS; m/z 498 [M$^+$+H]. $^1$H-NMR (CDCl$_3$) δ (ppm): 0.89 (t, J=6.8 Hz, 3H), 1.10-2.40 (m, 13H), 3.85 (s, 3H), 4.16-4.38 (m, 3H), 4.60-4.70 (m, 1H), 6.90 (brs, 1H), 7.01-7.35 (m, 8H), 7.51 (d, J=16.0 Hz, 1H), 7.68 (d, J=1.2 Hz, 1H).

Examples 20 and 21

Synthesis of (−)-8-(4-bromophenyl)-2-{(E)-2-[3-methoxy-4-(4-methyl-1H-imidazol-1-yl)phenyl]vinyl}-5,6,7,8-tetrahydro-[1,2,4]triazolo[1,5-a]pyridine and (+)-8-(4-bromophenyl)-2-{(E)-2-[3-methoxy-4-(4-methyl-1H-imidazol-1-yl)phenyl]vinyl}-5,6,7,8-tetrahydro-[1,2,4]triazolo[1,5-a]pyridine

[Formula 62]

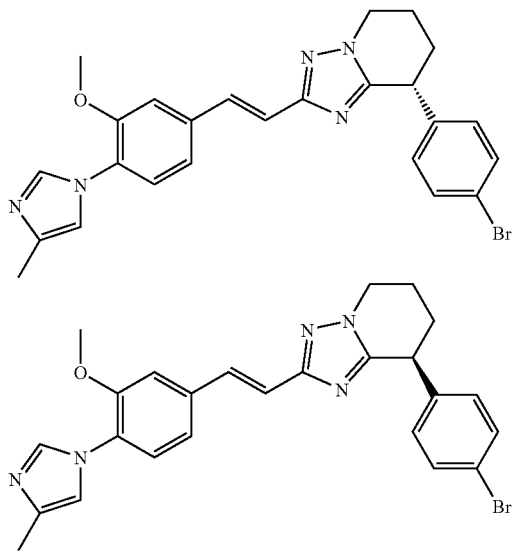

Synthesis of 1-amino-3-(2-bromophenyl)piperidin-2-one

A solution of ethyl 4-bromophenylacetate (2.0 g) in DMF (5 mL) was added to a suspension of sodium hydride (containing 40% of mineral oil, 362 mg) in DMF (20 mL) under ice-cooling. The reaction solution was stirred for 10 minutes, further stirred at room temperature for 30 minutes and then ice-cooled again. A solution of 1-chloro-3-iodopropane (1.85 g) in DMF (5 mL) was added to the reaction mixture, and the reaction solution was stirred at room temperature overnight. Water and ethyl acetate were added to the reaction mixture and the organic layer was separated. The resulting organic layer was washed with saturated aqueous sodium chloride, dried over anhydrous magnesium sulfate and then concentrated under reduced pressure. Hydrazine monohydrate (8 mL) was added to a solution of the resulting residue in ethanol (20 mL), and the reaction solution was stirred at room temperature for one day. The reaction mixture was concentrated under reduced pressure. Saturated sodium bicarbonate water and ethyl acetate and were added to the residue, and the organic layer was separated. The resulting organic layer was washed with saturated aqueous sodium chloride, dried over anhydrous magnesium sulfate and then concentrated under reduced pressure. The residue was purified by silica gel column chromatography (carrier: Chromatorex NH; elution solvent: heptane-ethyl acetate system) to obtain 898 mg of the title compound. The property values of the compound are as follows.

¹H-NMR (CDCl₃) δ (ppm): 1.80-2.00 (m, 3H), 2.08-2.15 (m, 1H), 2.14-3.67 (m, 3H), 4.62 (s, 2H), 7.06 (d, J=8.4 Hz, 2H), 7.42 (d, J=8.4 Hz, 2H).

Synthesis of (E)-N-[3-(4-bromophenyl)-2-oxopiperidin-1-yl]-3-[3-methoxy-4-(4-methyl-1H-imidazol-1-yl)phenyl]acrylamide BOPCl (1.18 g) was added to a suspension of (E)-3-[3-methoxy-4-(4-methyl-1H-imidazol-1-yl)phenyl]acrylic acid (800 mg), 1-amino-3-(4-bromophenyl)piperidin-2-one (898 mg) and TEA (0.9 mL) in DMF (20 mL), and the reaction solution was stirred at room temperature overnight. Water and ethyl acetate were added to the reaction mixture and the organic layer was separated. The resulting organic layer was washed with saturated aqueous sodium chloride, dried over anhydrous magnesium sulfate and then concentrated under reduced pressure. The resulting residue was purified by silica gel column chromatography (carrier: Chromatorex NH; elution solvent: ethyl acetate-methanol system) to obtain 1.484 g of the title compound. The property values of the compound are as follows.

¹H-NMR (CDCl₃) δ (ppm): 1.90-2.08 (m, 3H), 2.20-2.26 (m, 1H), 2.30 (s, 3H), 3.60-3.66 (m, 1H), 3.74-3.83 (m, 2H), 3.78 (s, 3H), 6.44 (d, J=15.6 Hz, 1H), 6.84-6.91 (m, 3H), 7.11 (d, J=8 Hz, 1H), 7.21 (d, J=8.4 Hz, 2H), 7.40-7.46 (m, 3H), 7.72 (d, J=1.6 Hz, 1H), 10.22 (s, 1H).

Synthesis of (−)-8-(4-bromophenyl)-2-{(E)-2-[3-methoxy-4-(4-methyl-1H-imidazol-1-yl)phenyl]vinyl}-5,6,7,8-tetrahydro-[1,2,4]triazolo[1,5-a]pyridine and (+)-8-(4-bromophenyl)-2-{(E)-2-[3-methoxy-4-(4-methyl-1H-imidazol-1-yl)phenyl]vinyl}-5,6,7,8-tetrahydro-[1,2,4]triazolo[1,5-a]pyridine A solution of (E)-N-[3-(4-bromophenyl)-2-oxopiperidin-1-yl]-3-[3-methoxy-4-(4-methyl-1H-imidazol-1-yl)phenyl]acrylamide (1.434 g) in phosphorus oxychloride (6 mL) was heated under reflux for one hour. The reaction mixture was left to cool to room temperature and then concentrated under reduced pressure. Acetic acid (7 mL) and ammonium acetate (4.8 g) were added to the residue, and the reaction solution was stirred at 150° C. for one hour. The reaction mixture was left to cool to room temperature and then concentrated under reduced pressure. Saturated sodium bicarbonate water and ethyl acetate and were added to the residue, and the organic layer was separated. The resulting organic layer was washed with saturated aqueous sodium chloride, dried over anhydrous magnesium sulfate and then concentrated under reduced pressure. The resulting residue was purified by silica gel column chromatography (carrier: Chromatorex NH; elution solvent: heptane-ethyl acetate system) to obtain 770 mg of a racemate of the title compound. The resulting racemate (73 mg) was separated by CHIRALPAK™ IB manufactured by Daicel Chemical Industries, Ltd. (2 cm×25 cm, mobile phase: ethanol, flow rate: 10 mL/min) to obtain the title optically active compound with a retention time of 17 minutes and negative optical rotation (21 mg) and the title optically active compound with a retention time of 20 minutes and positive optical rotation (23 mg).

The property values of the title optically active compound with a retention time of 17 minutes are as follows.

¹H-NMR (CDCl₃) δ (ppm): 1.98-2.26 (m, 3H), 2.30 (s, 3H), 2.32-2.39 (m, 1H), 3.86 (s, 3H), 4.27-4.32 (m, 3H), 6.92 (s, 1H), 7.03-7.09 (m, 3H), 7.14-7.16 (m, 2H), 7.22 (d, J=7.6 Hz, 1H), 7.47 (d, J=8.4 Hz, 2H), 7.51 (d, J=16 Hz, 1H), 7.72 (s, 1H).

The property values of the title optically active compound with a retention time of 20 minutes are as follows.

¹H-NMR (CDCl₃) δ (ppm): 1.98-2.26 (m, 3H), 2.30 (s, 3H), 2.32-2.39 (m, 1H), 3.86 (s, 3H), 4.27-4.32 (m, 3H), 6.92 (s, 1H), 7.03-7.09 (m, 3H), 7.14-7.16 (m, 2H), 7.22 (d, J=7.6 Hz, 1H), 7.47 (d, J=8.4 Hz, 2H), 7.51 (d, J=16 Hz, 1H), 7.72 (s, 1H).

Examples 22 and 23

Synthesis of (−)-2-{(E)-2-[3-methoxy-4-(4-methyl-1H-imidazol-1-yl)phenyl]vinyl}-8-(2-methoxymethylphenyl)-5,6,7,8-tetrahydro-[1,2,4]triazolo[1,5-a]pyridine and (+)-2-{(E)-2-[3-methoxy-4-(4-methyl-1H-imidazol-1-yl)phenyl]vinyl}-8-(2-methoxymethylphenyl)-5,6,7,8-tetrahydro-[1,2,4]triazolo[1,5-a]pyridine

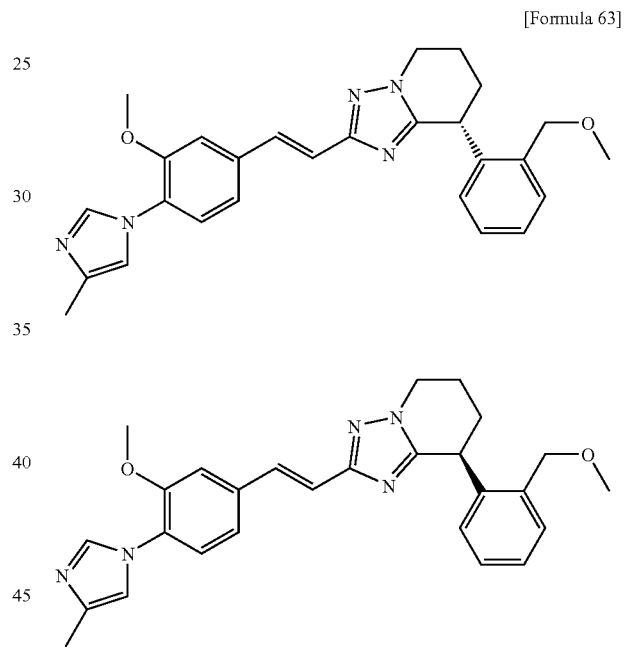

[Formula 63]

Synthesis of 8-(2-bromophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine 663 mg of the title compound was obtained from (E)-N-[3-(2-bromophenyl)-2-oxopiperidin-1-yl]-3-[3-methoxy-4-(4-methyl-1H-imidazol-1-yl)phenyl]acrylamide (1.130 g) using ethyl 2-bromophenylacetate as a starting material by the same method as in Examples 20 and 21. The property values of the compound are as follows.

¹H-NMR (CDCl₃) δ (ppm): 2.03-2.20 (m, 3H), 2.30 (s, 3H), 2.35-2.42 (m, 1H), 3.86 (s, 3H), 4.25-4.35 (m, 2H), 4.76 (t, J=6.4 Hz, 1H), 6.86 (brd, J=7.6 Hz, 1H), 6.92 (s, 1H), 7.08 (d, J=16.4, 0.8 Hz, 1H), 7.13-7.17 (m, 3H), 7.21 (d, J=7.6 Hz, 1H), 7.26-7.27 (m, 2H), 7.51 (dd, J=7.6, 0.8 Hz, 1H), 7.69 (d, J=0.8 Hz, 1H).

Synthesis of (−)-2-{(E)-2-[3-methoxy-4-(4-methyl-1H-imidazol-1-yl)phenyl]vinyl}-8-(2-methoxymethylphenyl)-5,6,7,8-tetrahydro-[1,2,4]triazolo[1,5-a]pyridine and (+)-2-{(E)-2-[3-methoxy-4-(4-methyl-1H-imidazol-1-yl)phenyl]vinyl}-8-(2-methoxymethylphenyl)-5,6,7,8-tetrahydro-[1,2,4]triazolo[1,5-a]pyridine Potassium methoxymethyl trifluoroborate (CAS No. 910251-11-5, 372 mg), palladium acetate (7 mg), BINAP (19 mg) and cesium carbonate (1.2 g) were added to a mixed solution of 8-(2-bromophenyl)-2-{(E)-2-[3-methoxy-4-(4-methyl-1H-imidazol-1-yl)phenyl]vinyl}-5,6,7,8-tetrahydro [1,2,4]triazolo[1,5-a]pyridine (150 mg) in dioxane (7 mL) and water (0.7 mL). The reaction solution was stirred in a nitrogen atmosphere at 100° C. overnight. The reaction mixture was left to cool to room temperature. Then, water and ethyl acetate were added to the reaction mixture and the organic layer was separated. The resulting organic layer was washed with saturated aqueous sodium chloride, dried over anhydrous magnesium sulfate and then concentrated under reduced pressure. The resulting residue was purified by silica gel column chromatography (carrier: Chromatorex NH; elution solvent: heptane-ethyl acetate system) and further separated by CHIRALPAK™ AD-H manufactured by Daicel Chemical Industries, Ltd. (2 cm×25 cm, mobile phase: ethanol, flow rate: 10 mL/min) to obtain the title optically active compound with a retention time of 16 minutes and negative optical rotation (6.2 mg) and the title optically active compound with a retention time of 18 minutes and positive optical rotation (8 mg).

The property values of the title optically active compound with a retention time of 16 minutes are as follows.

$^1$H-NMR (CDCl$_3$) δ (ppm): 1.98-2.15 (m, 2H), 2.20-2.29 (m, 1H), 2.30 (s, 3H), 2.36-2.43 (m, 1H), 3.41 (s, 3H), 3.85 (s, 3H), 4.31 (t, J=5.6 Hz, 2H), 4.46 (dd, J=11.6 Hz, 1.6 Hz, 1H), 4.61 (t, J=6.4 Hz, 1H), 4.71 (dd, J=11.6 Hz, 1.6 Hz, 1H), 6.85-6.88 (m, 2H), 6.91 (t, J=1.2 Hz, 1H), 7.06 (dd, J=16 Hz, 1.6 Hz, 1H), 7.11-7.15 (m, 2H), 7.21 (dd, J=8 Hz, 1.6 Hz, 1H), 7.24-7.29 (m, 1H), 7.37-7.40 (m, 1H), 7.48 (dd, J=16 Hz, 1.6 Hz, 1H), 7.69 (t, J=1.6 Hz, 1H).

The property values of the title optically active compound with a retention time of 18 minutes are as follows.

$^1$H-NMR (CDCl$_3$) δ (ppm): 1.98-2.15 (m, 2H), 2.20-2.29 (m, 1H), 2.30 (s, 3H), 2.36-2.43 (m, 1H), 3.41 (s, 3H), 3.85 (s, 3H), 4.31 (t, J=5.6 Hz, 2H), 4.46 (dd, J=11.6 Hz, 1.6 Hz, 1H), 4.61 (t, J=6.4 Hz, 1H), 4.71 (dd, J=11.6 Hz, 1.6 Hz, 1H), 6.85-6.88 (m, 2H), 6.91 (t, J=1.2 Hz, 1H), 7.06 (dd, J=16 Hz, 1.6 Hz, 1H), 7.11-7.15 (m, 2H), 7.21 (dd, J=8 Hz, 1.6 Hz, 1H), 7.24-7.29 (m, 1H), 7.37-7.40 (m, 1H), 7.48 (dd, J=16 Hz, 1.6 Hz, 1H), 7.69 (t, J=1.6 Hz, 1H).

Examples 24 and 25

Synthesis of (−) and (+)-8-(4-fluoro-2-methoxymethylphenyl)-2-{(E)-2-[3-methoxy-4-(4-methyl-1H-imidazol-1-yl)phenyl]vinyl}-5,6,7,8-tetrahydro-[1,2,4]triazolo[1,5-a]pyridine

[Formula 64]

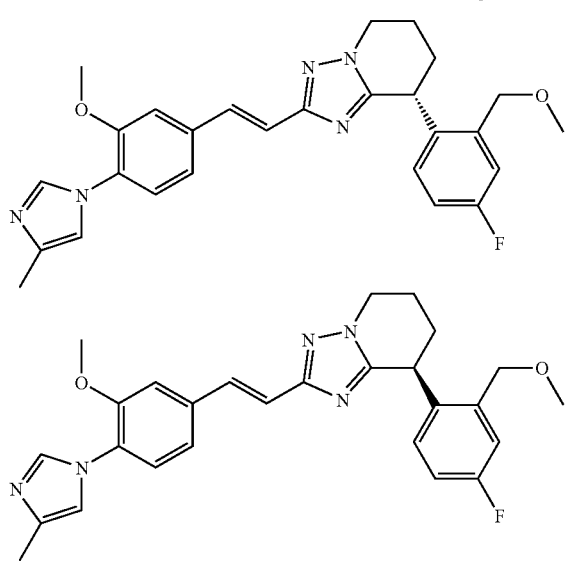

Synthesis of 8-(2-bromo-4-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine 559 mg of the title compound was obtained from (E)-N-[3-(2-bromo-4-fluorophenyl)-2-oxopiperidin-1-yl]-3-[3-methoxy-4-(4-methyl-1H-imidazol-1-yl)phenyl]acrylamide (953 mg) using methyl 2-bromo-4-fluorophenylacetate as a starting material by the same method as in Examples 20 and 21. The property values of the compound are as follows.

$^1$H-NMR (CDCl$_3$) δ (ppm): 1.98-2.20 (m, 3H), 2.30 (s, 3H), 2.35-2.42 (m, 1H), 3.86 (s, 3H), 4.28-4.31 (m, 2H), 4.71 (t, J=6.4 Hz, 1H), 6.87 (dd, J=8.4 Hz, 5.6 Hz, 1H), 6.92 (t, J=1.2 Hz, 1H), 6.96-7.01 (m, 1H), 7.07 (d, J=16.4 Hz, 1H), 7.14-7.16 (m, 2H), 7.22 (d, J=8.0 Hz, 1H), 7.36 (dd, J=8.0, 2.8 Hz, 1H), 7.51 (d, J=16.4 Hz, 1H), 7.70 (d, J=1.2 Hz, 1H).

Synthesis of (−) and (+)-8-(4-fluoro-2-methoxymethylphenyl)-2-{(E)-2-[3-methoxy-4-(4-methyl-1H-imidazol-1-yl)phenyl]vinyl}-5,6,7,8-tetrahydro-[1,2,4]triazolo[1,5-a]pyridine The title optically active compound with a retention time of 15 minutes in CHIRALPAK™ IB manufactured by Daicel Chemical Industries, Ltd. (2 cm×25 cm, mobile phase: hexane:ethanol=1:1, flow rate: 20 mL/min) and positive optical rotation (1.1 mg) and the title optically active compound with a retention time of 25 minutes in the CHIRALPAK™ IB and negative optical rotation (0.4 mg) were obtained from 8-(2- bromo-4-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine (40 mg) by the same method as in Examples 22 and 23.

The property values of the title optically active compound with a retention time of 15 minutes are as follows.

$^1$H-NMR (CDCl$_3$) δ (ppm): 1.93-2.02 (m, 1H), 2.04-2.14 (m, 1H), 2.18-2.28 (m, 1H), 2.29 (s, 3H), 2.32-2.40 (m, 1H), 3.42 (s, 3H), 3.84 (s, 3H), 4.30 (t, J=6 Hz, 2H), 4.44 (d, J=12 Hz, 1H), 4.50 (t, J=6 Hz, 1H), 4.65 (d, J=12 Hz, 1H), 6.84 (dd, J=8.4 Hz, 5.2 Hz, 1H), 6.90 (s, 1H), 6.92-6.97 (m, 1H), 7.04 (d, J=16 Hz, 1H), 7.11-7.14 (m, 3H), 7.20 (d, J=8.0 Hz, 1H), 7.47 (d, J=16 Hz, 1H), 7.69 (d, J=1.2 Hz, 1H).

The property values of the title optically active compound with a retention time of 25 minutes are as follows.

$^1$H-NMR (CDCl$_3$) δ (ppm): 1.93-2.02 (m, 1H), 2.04-2.14 (m, 1H), 2.18-2.28 (m, 1H), 2.29 (s, 3H), 2.32-2.40 (m, 1H), 3.42 (s, 3H), 3.84 (s, 3H), 4.30 (t, J=6 Hz, 2H), 4.44 (d, J=12 Hz, 1H), 4.50 (t, J=6 Hz, 1H), 4.65 (d, J=12 Hz, 1H), 6.84 (dd, J=8.4 Hz, 5.2 Hz, 1H), 6.90 (s, 1H), 6.92-6.97 (m, 1H), 7.04 (d, J=16 Hz, 1H), 7.11-7.14 (m, 3H), 7.20 (d, J=8.0 Hz, 1H), 7.47 (d, J=16 Hz, 1H), 7.69 (d, J=1.2 Hz, 1H).

Examples 26 and 27

Synthesis of (−)-2-{2-{(E)-2-[3-methoxy-4-(4-methyl-1H-imidazol-1-yl)phenyl]vinyl}-5,6,7,8-tetrahydro-[1,2,4]triazolo[1,5-a]pyridin-8-yl}benzonitrile and (+)-2-{2-{(E)-2-[3-methoxy-4-(4-methyl-1H-imidazol-1-yl)phenyl]vinyl}-5,6,7,8-tetrahydro-[1,2,4]triazolo[1,5-a]pyridin-8-yl}benzonitrile

[Formula 65]

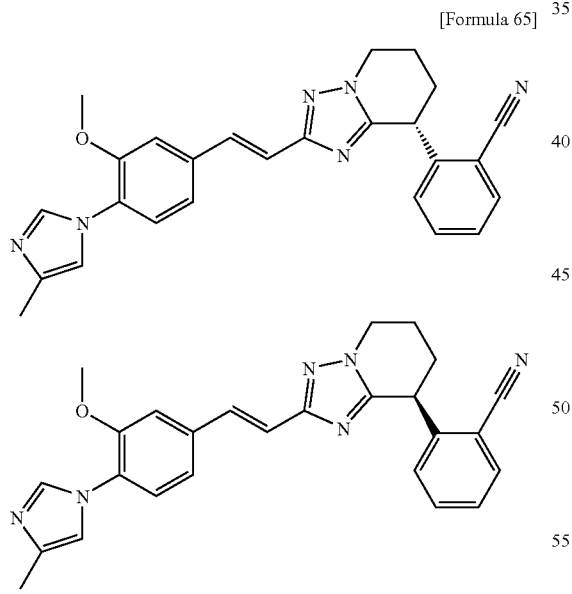

A suspension of 8-(2-bromophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine (45 mg), zinc cyanide (22 mg) and tetrakistriphenylphosphine palladium (11 mg) in DMF (2 mL) was subjected to microwave reaction in a nitrogen atmosphere at 160° C. for two hours. The reaction mixture was left to cool to room temperature. Then, aqueous ammonia and ethyl acetate were added to the reaction mixture and the organic layer was separated. The resulting organic layer was washed with saturated aqueous sodium chloride, dried over anhydrous magnesium sulfate and then concentrated under reduced pressure. The resulting residue was purified by silica gel column chromatography (carrier: Chromatorex NH; elution solvent: heptane-ethyl acetate system) to obtain 34 mg of a racemate of the title compound. The resulting racemate (28 mg) was separated by CHIRALPAK™ IB manufactured by Daicel Chemical Industries, Ltd. (2 cm×25 cm, mobile phase: ethanol, flow rate: 10 mL/min) to obtain the title optically active compound with a retention time of 17 minutes and negative optical rotation (11.9 mg) and the title optically active compound with a retention time of 19 minutes and positive optical rotation (13 mg).

The property values of the title optically active compound with a retention time of 17 minutes are as follows.

$^1$H-NMR (CDCl$_3$) δ (ppm): 2.05-2.27 (m, 3H), 2.31 (s, 3H), 2.47-2.53 (m, 1H), 3.86 (s, 3H), 4.30-4.37 (m, 2H), 4.66 (dd, J=8.8 Hz, 6 Hz, 1H), 6.92 (s, 1H), 7.06 (d, J=16 Hz, 1H), 7.13-7.17 (m, 3H), 7.22 (d, J=8 Hz, 1H), 7.26-7.31 (m, 2H), 7.42 (dd, J=8 Hz, 2.8 Hz, 1H), 7.48 (d, J=16 Hz, 1H), 7.73 (s, 1H).

The property values of the title optically active compound with a retention time of 19 minutes are as follows.

$^1$H-NMR (CDCl$_3$) δ (ppm): 2.05-2.27 (m, 3H), 2.31 (s, 3H), 2.47-2.53 (m, 1H), 3.86 (s, 3H), 4.30-4.37 (m, 2H), 4.66 (dd, J=8.8 Hz, 6 Hz, 1H), 6.92 (s, 1H), 7.06 (d, J=16 Hz, 1H), 7.13-7.17 (m, 3H), 7.22 (d, J=8 Hz, 1H), 7.26-7.31 (m, 2H), 7.42 (dd, J=8 Hz, 2.8 Hz, 1H), 7.48 (d, J=16 Hz, 1H), 7.73 (s, 1H).

Examples 28 and 29

Synthesis of 5-fluoro-2-{(−)-2-{(E)-2-[3-methoxy-4-(4-methyl-1H-imidazol-1-yl)phenyl]vinyl}-5,6,7,8-tetrahydro-[1,2,4]triazolo[1,5-a]pyridin-8-yl}benzonitrile and 5-fluoro-2-{(+)-2-{(E)-2-[3-methoxy-4-(4-methyl-1H-imidazol-1-yl)phenyl]vinyl}-5,6,7,8-tetrahydro-[1,2,4]triazolo[1,5-a]pyridin-8-yl}benzonitrile

[Formula 66]

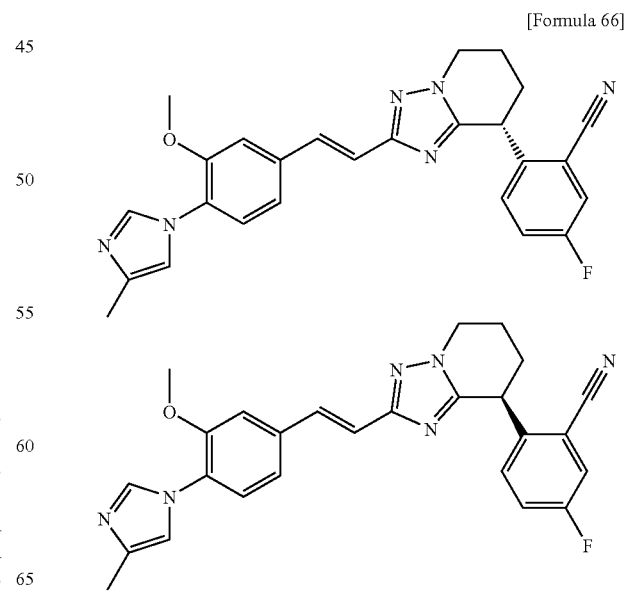

The title optically active compound with a retention time of 17 minutes in CHIRALPAK™ IB manufactured by Daicel Chemical Industries, Ltd. (2 cm×25 cm, mobile phase: hexane:ethanol=9:1, flow rate: 20 mL/min) and negative optical rotation (9.5 mg) and the title optically active compound with a retention time of 23 minutes in the CHIRALPAK™ IB and positive optical rotation (9.4 mg) were obtained from 8-(2-bromo-4-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine (40 mg) by the same method as in Examples 26 and 27.

The property values of the title optically active compound with a retention time of 17 minutes are as follows.

$^1$H-NMR (CDCl$_3$) δ (ppm): 2.00-2.09 (m, 1H), 2.16-2.27 (m, 2H), 2.30 (s, 3H), 2.46-2.53 (m, 1H), 3.86 (s, 3H), 4.27-4.39 (m, 2H), 4.66 (dd, J=8.8 Hz, 6 Hz, 1H), 6.92 (s, 1H), 7.06 (d, J=16 Hz, 1H), 7.13-7.16 (m, 3H), 7.22 (d, J=7.6 Hz, 1H), 7.30 (dd, J=8 Hz, 2.8 Hz, 1H), 7.42 (dd, J=8 Hz, 2.8 Hz, 1H), 7.48 (d, J=16 Hz, 1H), 7.73 (s, 1H).

The property values of the title optically active compound with a retention time of 23 minutes are as follows.

$^1$H-NMR (CDCl$_3$) δ (ppm): 2.00-2.09 (m, 1H), 2.16-2.27 (m, 2H), 2.30 (s, 3H), 2.46-2.53 (m, 1H), 3.86 (s, 3H), 4.27-4.39 (m, 2H), 4.66 (dd, J=8.8 Hz, 6 Hz, 1H), 6.92 (s, 1H), 7.06 (d, J=16 Hz, 1H), 7.13-7.16 (m, 3H), 7.22 (d, J=7.6 Hz, 1H), 7.30 (dd, J=8 Hz, 2.8 Hz, 1H), 7.42 (dd, J=8 Hz, 2.8 Hz, 1H), 7.48 (d, J=16 Hz, 1H), 7.73 (s, 1H).

Examples 30 and 31

Synthesis of (−)-8-(4-fluoro-2-pyridin-3-yl-phenyl)-2-{(E)-2-[3-methoxy-4-(4-methyl-1H-imidazol-1-yl)-phenyl]-vinyl}-5,6,7,8-tetrahydro-[1,2,4]triazolo[1,5-a]pyridine and (+)-8-(4-fluoro-2-pyridin-3-yl-phenyl)-2-{(E)-2-[3-methoxy-4-(4-methyl-1H-imidazol-1-yl)-phenyl]-vinyl}-5,6,7,8-tetrahydro-[1,2,4]triazolo[1,5-a]pyridine

[Formula 67]

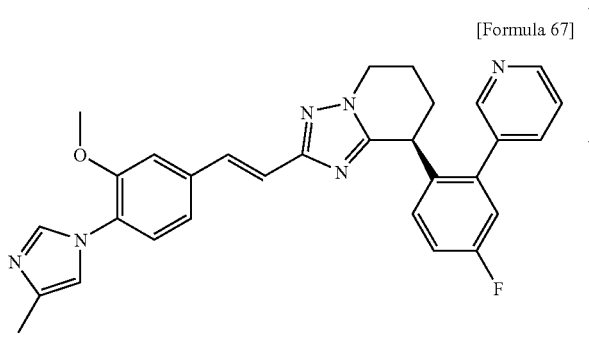

Pyridine-3-borane acid (18.1 mg), tetrakis(triphenylphosphine)palladium (5.7 mg) and a 2 M sodium carbonate solution (197 μl) in toluene (1.2 ml)/ethanol (0.3 ml) were added to 8-(2-bromo-4-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine (50 mg) as a starting material, and the reaction solution was stirred at 100° C. for two hours. Thereafter, tetrakis(triphenylphosphine)palladium (17.0 mg) was added and the reaction solution was stirred for 16 hours. The reaction solution was diluted with ethyl acetate and the organic layer was washed with brine. The resulting organic layer was dried over anhydrous magnesium sulfate and then concentrated under reduced pressure. The residue was purified by silica gel column chromatography (elution solvent: heptane-ethyl acetate system) to obtain 15.4 mg of a racemate of the title compound. The resulting racemate (15.4 mg) was separated by CHIRALPAK™ IB manufactured by Daicel Chemical Industries, Ltd. (2 cm×cm, mobile phase: hexane:ethanol=3:7, flow rate: 20 mL/min) to obtain the title optically active compound with a retention time of 31 minutes and negative optical rotation (5.0 mg) and the title optically active compound with a retention time of 41 minutes and positive optical rotation (4.7 mg).

The property values of the title optically active compound with a retention time of 31 minutes are as follows.

$^1$H-NMR (CDCl$_3$) δ (ppm): 1.80-2.20 (m, 4H), 2.30 (s, 3H), 3.86 (s, 3H), 4.05-4.30 (m, 3H), 6.90 (s, 1H), 7.00-7.05 (m, 1H), 7.05 (d, J=16.0 Hz, 1H), 7.10-7.20 (m, 2H), 7.25-7.45 (m, 3H), 7.50 (d, J=16.0 Hz, 1H), 7.70 (d, J=8.4 Hz, 1H), 7.71 (s, 1H), 7.80 (d, J=8.4 Hz, 1H), 8.70 (d, J=4.8 Hz, 1H), 8.80 (brd-s, 1H).

The property values of the title optically active compound with a retention time of 41 minutes are as follows.

$^1$H-NMR (CDCl$_3$) δ (ppm): 1.80-2.20 (m, 4H), 2.30 (s, 3H), 3.86 (s, 3H), 4.05-4.30 (m, 3H), 6.90 (s, 1H), 7.00-7.05 (m, 1H), 7.05 (d, J=16.0 Hz, 1H), 7.10-7.20 (m, 2H), 7.25-7.45 (m, 3H), 7.50 (d, J=16.0 Hz, 1H), 7.70 (d, J=8.4 Hz, 1H), 7.71 (s, 1H), 7.80 (d, J=8.4 Hz, 1H), 8.70 (d, J=4.8 Hz, 1H), 8.80 (brd-s, 1H).

Examples 32 and 33

Synthesis of 2-((−)-2-{(E)-2-[3-methoxy-4-(4-methyl-1H-imidazol-1-yl)phenyl]vinyl}-5,6,7,8-tetrahydro-[1,2,4]triazolo[1,5-a]pyridin-8-yl)phenylamine and 2-((+)-2-{(E)-2-[3-methoxy-4-(4-methyl-1H-imidazol-1-yl)phenyl]vinyl}-5,6,7,8-tetrahydro-[1,2,4]triazolo[1,5-a]pyridin-8-yl)phenylamine

[Formula 68]

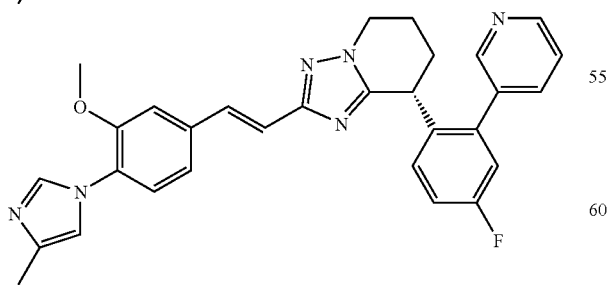

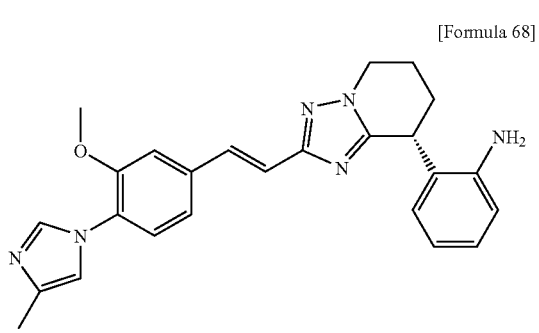

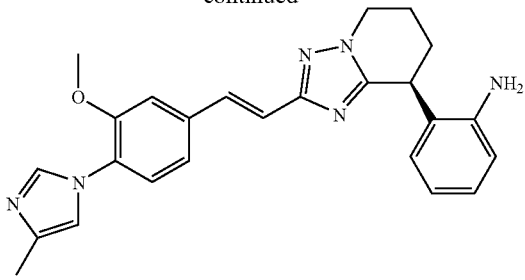

Synthesis of 2-{(E)-2-[3-methoxy-4-(4-methyl-1H-imidazol-1-yl)phenyl]vinyl}-8-(2-nitrophenyl)-5,6,7,8-tetrahydro[1,2,4]triazolo[1,5-a]pyridine The title compound (920 mg) was obtained from (E)-3-[3-methoxy-4-(4-methyl-1H-imidazol-1-yl)phenyl]-N-[3-(2-nitrophenyl)-2-oxopiperidin-1-yl]acrylamide (1.279 g) using methyl 2-nitrophenylacetate as a starting material by the same method as in Examples 20 and 21. The property values of the compound are as follows.

$^1$H-NMR (CDCl$_3$) δ (ppm): 2.13-2.32 (m, 3H), 2.29 (s, 3H), 2.55-2.61 (m, 1H), 3.85 (s, 3H), 4.31-4.35 (m, 2H), 4.92-4.95 (m, 1H), 6.91-6.92 (m, 1H), 7.04 (d, J=16.4 Hz, 1H), 7.12-7.14 (m, 3H), 7.21 (d, J=7.6 Hz, 1H), 7.43-7.49 (m, 2H), 7.56-7.60 (m, 1H), 7.69 (d, J=1.6 Hz, 1H), 8.03 (dd, J=8.0, 1.6 Hz, 1H).

Synthesis of 2-((−)-2-{(E)-2-[3-methoxy-4-(4-methyl-1H-imidazol-1-yl)phenyl]vinyl}-5,6,7,8-tetrahydro-[1,2,4]triazolo[1,5-a]pyridin-8-yl)phenylamine and 2-((+)-2-{(E)-2-[3-methoxy-4-(4-methyl-1H-imidazol-1-yl)phenyl]vinyl}-5,6,7,8-tetrahydro-[1,2,4]triazolo[1,5-a]pyridin-8-yl)phenylamine A mixed solution of 2-{(E)-2-[3-methoxy-4-(4-methyl-1H-imidazol-1-yl)phenyl]vinyl}-8-(2-nitrophenyl)-5,6,7,8-tetrahydro[1,2,4]triazolo[1,5-a]pyridine (178 mg) and sodium dithionite (340 mg) in ethanol (10 mL) and water (2 mL) was stirred at room temperature for one hour. Water and ethyl acetate were added to the reaction mixture and the organic layer was separated. The resulting organic layer was washed with saturated aqueous sodium chloride, dried over anhydrous magnesium sulfate and then concentrated under reduced pressure. The resulting residue was purified by silica gel column chromatography (carrier: Chromatorex NH; elution solvent: heptane-ethyl acetate system) to obtain 70 mg of a racemate of the title compound. The resulting racemate (30 mg) was separated by CHIRALPAK™ ADH manufactured by Daicel Chemical Industries, Ltd. (2 cm×25 cm, mobile phase: ethanol, flow rate: 10 mL/min) to obtain the title optically active compound with a retention time of 17 minutes and negative optical rotation (12.7 mg) and the title optically active compound with a retention time of 28 minutes and positive optical rotation (13.2 mg).

The property values of the title optically active compound with a retention time of 17 minutes are as follows.

$^1$H-NMR (CDCl$_3$) δ (ppm): 2.10-2.18 (m, 1H), 2.24-2.34 (m, 3H), 2.30 (s, 3H), 3.87 (s, 3H), 4.03 (brs, 2H), 4.26-2.30 (m, 2H), 4.36 (t, J=5.6 Hz, 1H), 6.77-6.81 (m, 2H), 6.88 (dd, J=7.6 Hz, 1.2 Hz, 1H), 6.92 (t, J=1.6 Hz, 1H), 7.05 (d, J=16 Hz, 1H), 7.10-7.15 (m, 3H), 7.22 (d, J=7.6 Hz, 1H), 7.50 (d, J=16 Hz, 1H), 7.70 (d, J=1.2 Hz, 1H).

The property values of the title optically active compound with a retention time of 28 minutes are as follows.

$^1$H-NMR (CDCl$_3$) δ (ppm): 2.10-2.18 (m, 1H), 2.24-2.34 (m, 3H), 2.30 (s, 3H), 3.87 (s, 3H), 4.03 (brs, 2H), 4.26-2.30 (m, 2H), 4.36 (t, J=5.6 Hz, 1H), 6.77-6.81 (m, 2H), 6.88 (dd, J=7.6 Hz, 1.2 Hz, 1H), 6.92 (t, J=1.6 Hz, 1H), 7.05 (d, J=16 Hz, 1H), 7.10-7.15 (m, 3H), 7.22 (d, J=7.6 Hz, 1H), 7.50 (d, J=16 Hz, 1H), 7.70 (d, J=1.2 Hz, 1H).

Examples 34 and 35

Synthesis of N-[2-((−)-2-{(E)-2-[3-methoxy-4-(4-methyl-1H-imidazol-1-yl)phenyl]vinyl}-5,6,7,8-tetrahydro-[1,2,4]triazolo[1,5-a]pyridin-8-ylphenyl]acetamide and N-[2-((+)-2-{(E)-2-[3-methoxy-4-(4-methyl-1H-imidazol-1-yl)phenyl]vinyl}-5,6,7,8-tetrahydro-[1,2,4]triazolo[1,5-a]pyridin-8-ylphenyl]acetamide

[Formula 69]

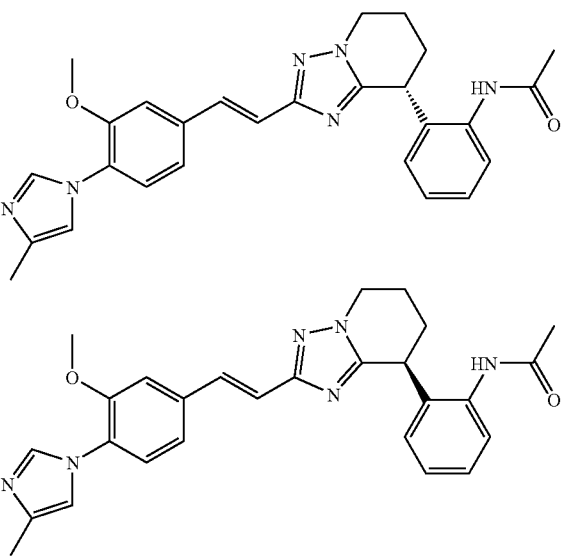

Acetic anhydride (0.045 mL) was added to a solution of 2-((−)-2-{(E)-2-[3-methoxy-4-(4-methyl-1H-imidazol-1-yl)phenyl]vinyl}-5,6,7,8-tetrahydro-[1,2,4]triazolo[1,5-a]pyridin-8-yl)phenylamine (41 mg) in pyridine (2 mL), and the reaction solution was stirred at 50° C. overnight. The reaction mixture was left to cool to room temperature and then concentrated under reduced pressure. The resulting residue was purified by CHIRALPAK™ IB manufactured by Daicel Chemical Industries, Ltd. (2 cm×25 cm, mobile phase: ethanol, flow rate: 10 mL/min) to obtain the title optically active compound with a retention time of 11 minutes and negative optical rotation (14.9 mg) and the title optically active compound with a retention time of 14 minutes and positive optical rotation (15.1 mg).

The property values of the title optically active compound with a retention time of 11 minutes are as follows.

$^1$H-NMR (CDCl$_3$) δ (ppm): 2.20-2.28 (m, 1H), 2.23 (s, 3H), 2.30 (s, 3H), 2.32-2.48 (m, 3H), 3.89 (s, 3H), 4.24-4.32 (m, 2H), 4.37 (t, J=6 Hz, 1H), 6.93 (t, J=1.2 Hz, 1H), 7.01 (d, J=16 Hz, 1H), 7.14-7.16 (m, 2H), 7.19-7.25 (m, 2H), 7.29-7.39 (m, 2H), 7.45 (d, J=16 Hz, 1H), 7.72-7.75 (m, 2H), 9.87 (s, 1H).

The property values of the title optically active compound with a retention time of 14 minutes are as follows.

¹H-NMR (CDCl₃) δ (ppm): 2.20-2.28 (m, 1H), 2.23 (s, 3H), 2.30 (s, 3H), 2.32-2.48 (m, 3H), 3.89 (s, 3H), 4.24-4.32 (m, 2H), 4.37 (t, J=6 Hz, 1H), 6.93 (t, J=1.2 Hz, 1H), 7.01 (d, J=16 Hz, 1H), 7.14-7.16 (m, 2H), 7.19-7.25 (m, 2H), 7.29-7.39 (m, 2H), 7.45 (d, J=16 Hz, 1H), 7.72-7.75 (m, 2H), 9.87 (s, 1H).

Examples 36 and 37

Synthesis of (−)-8-(3,4-dimethoxyphenyl)-2-{(E)-2-[3-methoxy-4-(4-methyl-1H-imidazol-1-yl)phenyl]vinyl}-5,6,7,8-tetrahydro-[1,2,4]triazolo[1,5-a]pyridine and (+)-8-(3,4-dimethoxyphenyl)-2-{(E)-2-[3-methoxy-4-(4-methyl-1H-imidazol-1-yl)phenyl]vinyl}-5,6,7,8-tetrahydro-[1,2,4]triazolo[1,5-a]pyridine

[Formula 70]

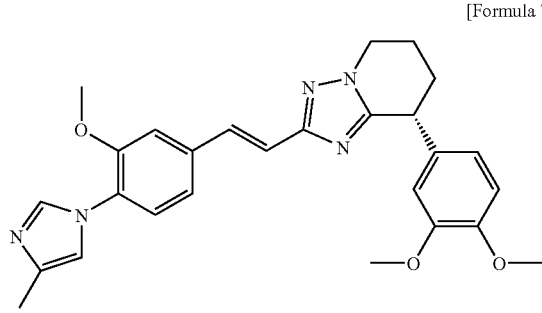

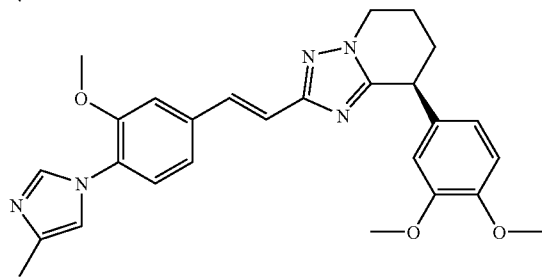

559 mg of the title compound was obtained from (E)-N-[3-(3,4-dimethoxyphenyl)-2-oxopiperidin-1-yl]-3-[3-methoxy-4-(4-methyl-1H-imidazol-1-yl)phenyl]acrylamide (401 mg) using ethyl 3,4-dimethoxyphenylacetate as a starting material by the same method as in Examples 20 and 21. The resulting racemate (77 mg) was separated by CHIRALPAK™ IA manufactured by Daicel Chemical Industries, Ltd. (2 cm×25 cm, mobile phase: ethanol, flow rate: 10 mL/min) to obtain the title optically active compound with a retention time of 24 minutes and negative optical rotation (17.8 mg) and the title optically active compound with a retention time of 31 minutes and positive optical rotation (19.0 mg).

The property values of the title optically active compound with a retention time of 24 minutes are as follows.

¹H-NMR (CDCl₃) δ (ppm): 2.20-2.14 (m, 2H), 2.18-2.27 (m, 1H), 2.30 (s, 3H), 2.31-2.38 (m, 1H), 3.86 (s, 6H), 3.87 (s, 3H), 4.23-4.36 (m, 3H), 6.64 (dd, J=8.4 Hz, 1.6 Hz, 1H), 6.71 (d, J=1.6 Hz, 1H), 6.83 (d, J=8.4 Hz, 1H), 6.91 (q, J=1.2 Hz, 1H), 7.08 (dd, J=16.4 Hz, 0.8 Hz, 1H), 7.13-7.16 (m, 2H), 7.22 (d, J=8.4 Hz, 1H), 7.53 (d, J=16.4 Hz, 1H), 7.70 (s, 1H).

The property values of the title optically active compound with a retention time of 31 minutes are as follows.

¹H-NMR (CDCl₃) δ (ppm): 2.20-2.14 (m, 2H), 2.18-2.27 (m, 1H), 2.30 (s, 3H), 2.31-2.38 (m, 1H), 3.86 (s, 6H), 3.87 (s, 3H), 4.23-4.36 (m, 3H), 6.64 (dd, J=8.4 Hz, 1.6 Hz, 1H), 6.71 (d, J=1.6 Hz, 1H), 6.83 (d, J=8.4 Hz, 1H), 6.91 (q, J=1.2 Hz, 1H), 7.08 (dd, J=16.4 Hz, 0.8 Hz, 1H), 7.13-7.16 (m, 2H), 7.22 (d, J=8.4 Hz, 1H), 7.53 (d, J=16.4 Hz, 1H), 7.70 (s, 1H).

Examples 38 and 39

Synthesis of (−)-2-{(E)-2-[3-methoxy-4-(4-methyl-1H-imidazol-1-yl)phenyl]vinyl}-8-(pyridin-2-yl)-5,6,7,8-tetrahydro[1,2,4]triazolo[1,5-a]pyridine and (+)-2-{(E)-2-[3-methoxy-4-(4-methyl-1H-imidazol-1-yl)phenyl]vinyl}-8-(pyridin-2-yl)-5,6,7,8-tetrahydro[1,2,4]triazolo[1,5-a]pyridine

[Formula 71]

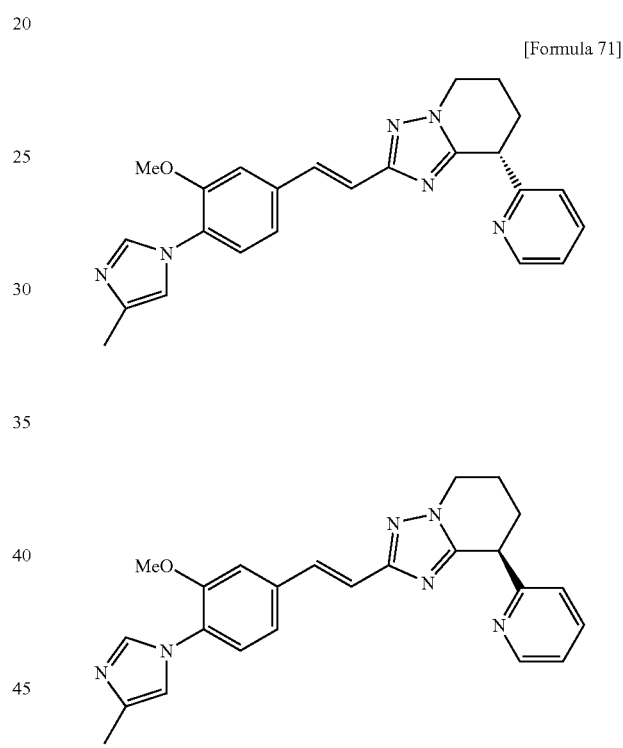

208.5 mg of a racemate of the title compound was obtained from methyl 2-pyridylacetate (6.76 g) by the same method as in Examples 20 and 21. The racemate (100 mg) was separated by CHIRALCEL™ OD-H manufactured by Daicel Chemical Industries, Ltd. (2 cm×25 cm; mobile phase: ethanol) to obtain a (−)-isomer of the title optically active compound with a retention time of 17 minutes (43.6 mg; 79% ee) and a (+)-isomer of the title optically active compound with a retention time of 24 minutes (47.7 mg; 87% ee).

The property values of (−)-2-{(E)-2-[3-methoxy-4-(4-methyl-1H-imidazol-1-yl)phenyl]vinyl}-8-(pyridin-2-yl)-5,6,7,8-tetrahydro[1,2,4]triazolo[1,5-a]pyridine are as follows.

ESI-MS; m/z 413 [M⁺+H]. ¹H-NMR (CDCl₃) δ (ppm): 2.04-2.17 (m, 1H), 2.19-2.46 (m, 6H), 3.85 (s, 3H), 4.20-4.37 (m, 2H), 4.48 (t, J=6.4 Hz, 1H), 6.90 (t, J=1.2 Hz, 1H), 7.06 (d, J=16.4 Hz, 1H), 7.10-7.24 (m, 5H), 7.49 (d, J=16.4 Hz, 1H), 7.62-7.72 (m, 2H), 8.57 (dd, J=2.4, 5.6 Hz, 1H).

The property values of (+)-2-{(E)-2-[3-methoxy-4-(4-methyl-1H-imidazol-1-yl)phenyl]vinyl}-8-(pyridin-2-yl)-5,6,7,8-tetrahydro[1,2,4]triazolo[1,5-a]pyridine are as follows.

ESI-MS; m/z 413 [M⁺+H]. ¹H-NMR (CDCl₃) δ (ppm): 2.04-2.17 (m, 1H), 2.19-2.46 (m, 6H), 3.85 (s, 3H), 4.20-4.37 (m, 2H), 4.48 (t, J=6.4 Hz, 1H), 6.90 (t, J=1.2 Hz, 1H), 7.06 (d, J=16.4 Hz, 1H), 7.10-7.24 (m, 5H), 7.49 (d, J=16.4 Hz, 1H), 7.62-7.72 (m, 2H), 8.57 (dd, J=2.4, 5.6 Hz, 1H).

Examples 40 and 41

Synthesis of (−)-8-(5-chlorothiophen-2-yl)-2-{(E)-2-[3-methoxy-4-(4-methyl-1H-imidazol-1-yl)phenyl]vinyl}-5,6,7,8-tetrahydro[1,2,4]triazolo[1,5-a]pyridine and (+)-8-(5-chlorothiophen-2-yl)-2-{(E)-2-[3-methoxy-4-(4-methyl-1H-imidazol-1-yl)phenyl]vinyl}-5,6,7,8-tetrahydro[1,2,4]triazolo[1,5-a]pyridine

[Formula 72]

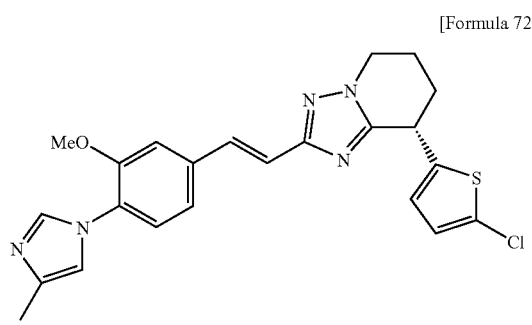

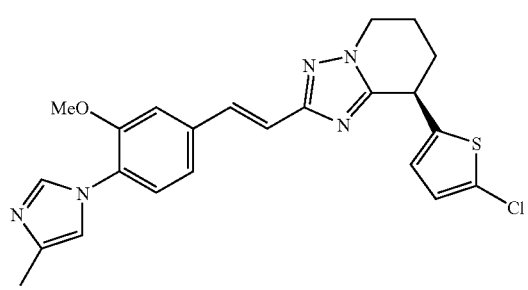

Synthesis of ethyl (5-chlorothiophen-2-yl)acetate

Methyl methylsulfinylmethyl sulfide (5.53 g) and potassium hydroxide (2 g) were added to a solution of 5-chloro-2-thiophenecarboxyaldehyde (6.21 g) in methanol (70 mL), and the reaction solution was stirred with heating under reflux for 21 hours. After leaving to cool to room temperature, the solvent was evaporated under reduced pressure. Methylene chloride was added to the residue, the insoluble matter was removed by filtration, and the solvent was evaporated under reduced pressure. Then, the residue was purified by silica gel column chromatography (elution solvent: heptane-ethyl acetate system) to obtain 5.61 g of a (E)/(Z) mixture of 2-chloro-5-(2-methanesulfinyl-2-methylsulfanylvinyl)thiophene. A saturated solution of hydrogen chloride in ethanol (10 mL) was added to a solution of the resulting (E)/(Z) mixture of 2-chloro-5-(2-methanesulfinyl-2-methylsulfanylvinyl)thiophene (5.61 g) in ethanol (80 mL), and the reaction solution was stirred with heating under reflux for 23 hours. After leaving to cool to room temperature, the solvent was evaporated under reduced pressure. The residue was purified by silica gel column chromatography (elution solvent: heptane-ethyl acetate system) to obtain 3.31 g of the title compound. The property values of the compound are as follows.

ESI-MS; m/z 205 [M⁺+H]. ¹H-NMR (CDCl₃) δ (ppm): 1.28 (t, J=7.2 Hz, 3H), 3.72 (d, J=0.8 Hz, 2H), 4.18 (q, J=7.2 Hz, 2H), 6.67-6.71 (m, 1H), 6.75 (d, J=3.6 Hz, 1H).

Synthesis of (−)-8-(5-chlorothiophen-2-yl)-2-{(E)-2-[3-methoxy-4-(4-methyl-1H-imidazol-1-yl)phenyl]vinyl}-5,6,7,8-tetrahydro[1,2,4]triazolo[1,5-a]pyridine and (+)-8-(5-chlorothiophen-2-yl)-2-{(E)-2-[3-methoxy-4-(4-methyl-1H-imidazol-1-yl)phenyl]vinyl}-5,6,7,8-tetrahydro[1,2,4]triazolo[1,5-a]pyridine 5.2 mg of a racemate of the title compound was obtained from ethyl (5-chlorothiophen-2-yl)acetate (3.31 g) by the same method as in Examples 20 and 21. The racemate (5.2 mg) was separated by CHIRALPAK™ IA manufactured by Daicel Chemical Industries, Ltd. (2 cm×25 cm; mobile phase: hexane:ethanol=1:1) to obtain a (−)-isomer of the title optically active compound with a retention time of 11.5 minutes (1.08 mg; >99% ee) and a (+)-isomer of the title optically active compound with a retention time of 24 minutes (0.74 mg; >99% ee).

The property values of (−)-8-(5-chlorothiophen-2-yl)-2-{(E)-2-[3-methoxy-4-(4-methyl-1H-imidazol-1-yl)phenyl]vinyl}-5,6,7,8-tetrahydro[1,2,4]triazolo[1,5-a]pyridine are as follows.

ESI-MS; m/z 452 [M⁺+H]. ¹H-NMR (CDCl₃) δ (ppm): 2.03-2.22 (m, 2H), 2.23-2.36 (m, 4H), 2.37-2.47 (m, 1H), 3.86 (s, 3H), 4.29 (t, J=5.6 Hz, 2H), 4.74 (t, J=7.6 Hz, 1H), 6.92 (brs, 1H), 6.94 (d, J=5.6 Hz, 1H), 7.07 (d, J=16.4 Hz, 1H), 7.12-7.24 (m, 4H), 7.53 (d, J=16.4 Hz, 1H), 7.71 (brs, 1H).

The property values of (+)-8-(5-chlorothiophen-2-yl)-2-{(E)-2-[3-methoxy-4-(4-methyl-1H-imidazol-1-yl)phenyl]vinyl}-5,6,7,8-tetrahydro[1,2,4]triazolo[1,5-a]pyridine are as follows.

ESI-MS; m/z 452 [M⁺+H]. ¹H-NMR (CDCl₃) δ (ppm): 2.03-2.22 (m, 2H), 2.23-2.36 (m, 4H), 2.37-2.47 (m, 1H), 3.86 (s, 3H), 4.29 (t, J=5.6 Hz, 2H), 4.74 (t, J=7.6 Hz, 1H), 6.92 (brs, 1H), 6.94 (d, J=5.6 Hz, 1H), 7.07 (d, J=16.4 Hz, 1H), 7.12-7.24 (m, 4H), 7.53 (d, J=16.4 Hz, 1H), 7.71 (brs, 1H).

The following compounds were obtained by the same method as in Examples 20 and 21 (Table 1).

TABLE 1

[Structure: core compound with MeO, 4-methylimidazole, styryl linker to triazolopyridine bearing E1 and E2 substituents]

| Example | E₁ | E2 | DATA: MS m/z | Note |
|---|---|---|---|---|
| 42 | *-(quinolin-2-yl) | H | M⁺ + H: 463 (ESI) | Optically active compound (separation conditions OD-H: retention time 36 min, optical rotation (−)) |
| 43 | *-(quinolin-2-yl) (opposite stereo) | H | M⁺ + H: 463 (ESI) | Optically active compound (separation conditions OD-H: retention time 46 min, optical rotation (+)) |
| 44 | *-(4-CF₃-phenyl) | H | M⁺ + H: 480 (ESI) | Optically active compound (separation conditions AD-H: retention time 33 min, optical rotation (+)) |
| 45 | *-(4-CF₃-phenyl) (opposite stereo) | H | M⁺ + H: 480 (ESI) | Optically active compound (separation conditions AD-H: retention time 47 min, optical rotation (−)) |
| 46 | *-(1,3-dimethyl-1H-pyrazol-5-yl) | H | M⁺ + H: 430 (ESI) | Optically active compound (separation conditions 80% ethanol-hexane:IB: retention time 15 min, optical rotation (+)) |
| 47 | *-(1,3-dimethyl-1H-pyrazol-5-yl) | H | M⁺ + H: 430 (ESI) | Optically active compound (separation conditions 80% ethanol-hexane:IB: retention time 27 min, optical rotation (−)) |
| 48 | *-(3,5-difluorophenyl) | H | M⁺ + H: 448 (ESI) | |
| 49 | *-(2,4-difluorophenyl) | H | M⁺ + H: 448 (ESI) | |
| 50 | *-(3-chloro-4-fluorophenyl) | H | M⁺ + H: 464 (ESI) | |

TABLE 1-continued

| Example | E₁ | E2 | DATA: MS m/z | Note |
|---|---|---|---|---|
| 51 | (2,4,5-trifluorophenyl, attached at *) | H | M⁺ + H: 466 (ESI) | |
| 52 | (2,3,6-trifluorophenyl, attached at *) | H | M⁺ + H: 466 (ESI) | |

Examples 53 and 54

Synthesis of (+)-2-{(E)-2-[3-methoxy-4-(4-methyl-1H-imidazol-1-yl)phenyl]vinyl}-8-(pyridin-2-yl)-5,6,7,8-tetrahydro[1,2,4]triazolo[1,5-a]pyridin-8-ol and (−)-2-{(E)-2-[3-methoxy-4-(4-methyl-1H-imidazol-1-yl)phenyl]vinyl}-8-(pyridin-2-yl)-5,6,7,8-tetrahydro[1,2,4]triazolo[1,5-a]pyridin-8-ol

[Formula 73]

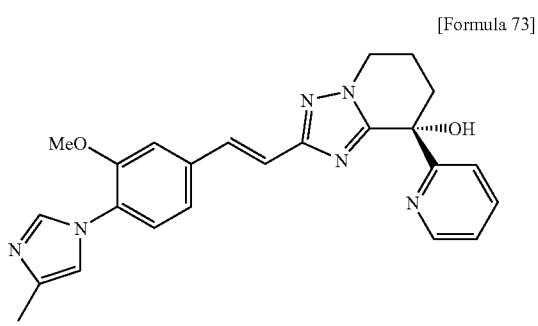

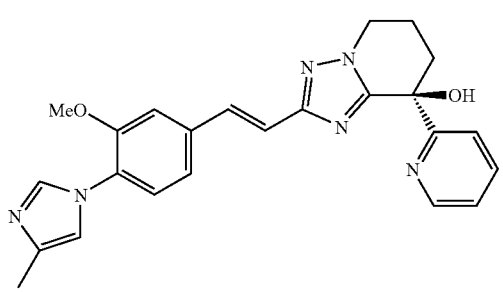

Sodium hydride (containing 40% of mineral oil, 21 mg) was added to a solution of 2-{(E)-2-[3-methoxy-4-(4-methyl-1H-imidazol-1-yl)phenyl]vinyl}-8-(pyridin-2-yl)-5,6,7,8-tetrahydro[1,2,4]triazolo[1,5-a]pyridine synthesized by the method in Example 38 and 39 (108 mg) in DMF (1.2 mL), and the reaction solution was stirred at room temperature for three hours under oxygen bubbling. Sodium thiosulfate pentahydride was added to the reaction solution, and the reaction solution was stirred at room temperature for several minutes. Ethyl acetate and a saturated ammonium chloride solution were added to the reaction solution and the organic layer was separated. The resulting organic layer was dried over anhydrous magnesium sulfate and concentrated under reduced pressure to obtain the racemic title compound.

The racemate of the title compound was separated by CHIRALPAK™ IA manufactured by Daicel Chemical Industries, Ltd. (2 cm×25 cm; mobile phase: ethanol) to obtain a (+)-isomer of the title optically active compound with a retention time of 11 minutes (49.3 mg, >99% ee) and a (−)-isomer of the title optically active compound with a retention time of 13 minutes (44.6 mg, 94% ee).

The property values of (+)-2-{(E)-2-[3-methoxy-4-(4-methyl-1H-imidazol-1-yl)phenyl]vinyl}-8-(pyridin-2-yl)-5,6,7,8-tetrahydro[1,2,4]triazolo[1,5-a]pyridin-8-ol are as follows.

ESI-MS; m/z 429 [M⁺+H]. ¹H-NMR (CDCl₃) δ (ppm): 2.11-2.37 (m, 6H), 2.50-2.64 (m, 1H), 3.81 (s, 3H), 4.22-4.32 (m, 1H), 4.35-4.44 (m, 1H), 6.88 (brs, 1H), 6.96-7.10 (m, 3H), 7.16 (d, J=8.0 Hz, 1H), 7.24-7.38 (m, 2H), 7.43 (d, J=16.4 Hz, 1H), 7.66 (d, J=1.2 Hz, 1H), 7.74 (dt, J=1.2, 8.0 Hz, 1H), 8.54-8.62 (m, 1H).

The property values of (−)-2-{(E)-2-[3-methoxy-4-(4-methyl-1H-imidazol-1-yl)phenyl]vinyl}-8-(pyridin-2-yl)-5,6,7,8-tetrahydro[1,2,4]triazolo[1,5-a]pyridin-8-ol are as follows.

ESI-MS; m/z 429 [M⁺+H]. ¹H-NMR (CDCl₃) δ (ppm): 2.11-2.37 (m, 6H), 2.50-2.64 (m, 1H), 3.81 (s, 3H), 4.22-4.32 (m, 1H), 4.35-4.44 (m, 1H), 6.88 (brs, 1H), 6.96-7.10 (m, 3H), 7.16 (d, J=8.0 Hz, 1H), 7.24-7.38 (m, 2H), 7.43 (d, J=16.4 Hz, 1H), 7.66 (d, J=1.2 Hz, 1H), 7.74 (dt, J=1.2, 8.0 Hz, 1H), 8.54-8.62 (m, 1H).

Examples 55 and 56

Synthesis of (−)-8-(4-isopropylphenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridin-8-ol and (+)-8-(4-isopropylphenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridin-8-ol ESI-MS; m/z 470 [M$^+$+H]. $^1$H-NMR (CDCl$_3$) δ (ppm): 1.23 (d, J=6.8 Hz, 6H), 1.92-2.05 (m, 1H), 2.21-2.40 (m, 6H), 2.84-2.96 (m, 1H), 3.82 (s, 3H), 4.25 (t, J=5.6 Hz, 2H), 6.89 (brs, 1H), 7.02-7.13 (m, 3H), 7.14-7.24 (m, 5H), 7.49 (d, J=16.4 Hz, 1H), 7.69 (d, J=1.2 Hz, 1H).

Examples 57 and 58

Synthesis of (−)-2-{(E)-2-[3-methoxy-4-(4-methyl-1H-imidazol-1-yl)phenyl]vinyl}-8-phenyl-5,6,7,8-tetrahydro-[1,2,4]triazolo[1,5-a]pyridin-8-ol and (+)-2-{(E)-2-[3-methoxy-4-(4-methyl-1H-imidazol-1-yl)phenyl]vinyl}-8-phenyl-5,6,7,8-tetrahydro-[1,2,4]triazolo[1,5-a]pyridin-8-ol

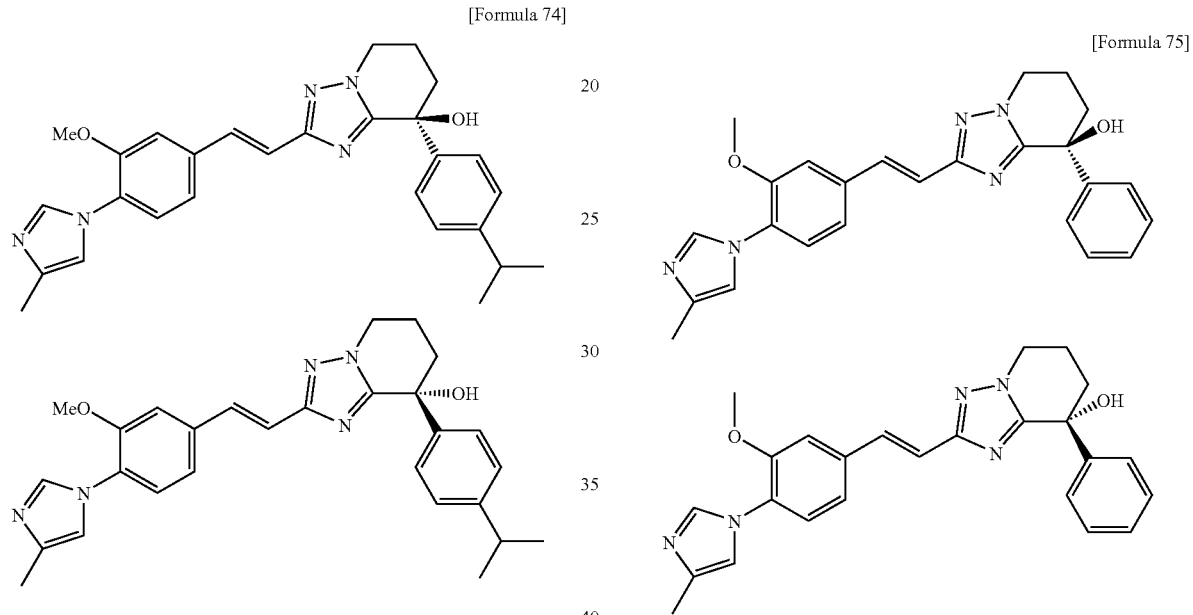

[Formula 74]

[Formula 75]

A racemate of title compound (67.1 mg) was obtained from 8-(4-isopropylphenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine synthesized in Examples 5 and 6 (117.4 mg) by the same method as in Examples 53 and 54. The racemate of the title compound was separated by CHIRALPAK™ AD-H manufactured by Daicel Chemical Industries, Ltd. (2 cm×25 cm; mobile phase: hexane:ethanol=1:1) to obtain a (−)-isomer of the title optically active compound with a retention time of 13.5 minutes (20.7 mg; >99% ee) and a (+)-isomer of the title optically active compound with a retention time of 16.5 minutes (20.1 mg; 98% ee).

The property values of (−)-8-(4-isopropylphenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridin-8-ol are as follows.

ESI-MS; m/z 470 [M$^+$+H]. $^1$H-NMR (CDCl$_3$) δ (ppm): 1.23 (d, J=6.8 Hz, 6H), 1.92-2.05 (m, 1H), 2.21-2.40 (m, 6H), 2.84-2.96 (m, 1H), 3.82 (s, 3H), 4.25 (t, J=5.6 Hz, 2H), 6.89 (brs, 1H), 7.02-7.13 (m, 3H), 7.14-7.24 (m, 5H), 7.49 (d, J=16.4 Hz, 1H), 7.69 (d, J=1.2 Hz, 1H).

The property values of (+)-8-(4-isopropylphenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridin-8-ol are as follows.

Synthesis of 2-{(E)-2-[3-methoxy-4-(4-methyl-1H-imidazol-1-yl)phenyl]vinyl}-8-phenyl-5,6,7,8-tetrahydro[1,2,4]triazolo[1,5-a]pyridine 59 mg of the title compound was obtained from ethyl (E)-3-[3-methoxy-4-(4-methyl-1H-imidazol-1-yl)phenyl] acrylimidate dihydrochloride (650 mg) and 5-chloro-2-phenylpentanoic acid hydrazide (436 mg) by the same method as in Example 1. The property values of the compound are as follows.

$^1$H-NMR (CDCl$_3$) δ (ppm): 2.06-2.12 (m, 2H), 2.16-2.24 (m, 1H), 2.29 (s, 3H), 2.33-2.40 (m, 1H), 3.85 (s, 3H), 4.21-4.37 (m, 3H), 6.91 (s, 1H), 7.07 (d, J=16.4 Hz, 1H), 7.13-7.15 (m, 3H), 7.21 (d, J=7.6 Hz, 1H), 7.26-7.29 (m, 2H), 7.32-7.36 (m, 2H), 7.52 (d, J=16.4 Hz, 1H), 7.69 (s, 1H).

Synthesis of (−)-2-{(E)-2-[3-methoxy-4-(4-methyl-1H-imidazol-1-yl)phenyl]vinyl}-8-phenyl-5,6,7,8-tetrahydro-[1,2,4]triazolo[1,5-a]pyridin-8-ol and (+)-2-{(E)-2-[3-methoxy-4-(4-methyl-1H-imidazol-1-yl)phenyl]vinyl}-8-phenyl-5,6,7,8-tetrahydro-[1,2,4]triazolo[1,5-a]pyridin-8-ol The title optically active compound with a retention time of 14 minutes in CHIRALPAK™ ADH manufactured by Daicel Chemical Industries, Ltd. (2 cm×25 cm, mobile phase: ethanol, flow rate: 10 mL/min) and negative optical rotation (9.5 mg) and the title optically active compound with a retention time of 16 minutes in the CHIRALPAK™ ADH and positive optical rotation (9.4 mg) were obtained from 2-{(E)-2-[3-methoxy-4-(4-methyl-1H-imidazol-1-yl)phenyl]vinyl}-8-phenyl-5,6,7,8-tetrahydro[1,2,4]triazolo[1,5-a]pyridine (59 mg) by the same method as in Examples 53 and 54.

The property values of the title optically active compound with a retention time of 14 minutes are as follows.

$^1$H-NMR (CDCl$_3$) δ (ppm): 1.95-2.03 (m, 1H), 2.21-2.27 (m, 1H), 2.28 (s, 3H), 2.31-2.38 (m, 2H), 3.81 (s, 3H), 4.25 (t, J=6 Hz, 2H), 6.88 (s, 1H), 7.00-7.07 (m, 3H), 7.16 (d, J=8 Hz, 1H), 7.29-7.35 (m, 5H), 7.46 (d, J=16.4 Hz, 1H), 7.71 (d, J=1.2 Hz, 1H).

The property values of the title optically active compound with a retention time of 16 minutes are as follows.

$^1$H-NMR (CDCl$_3$) δ (ppm): 1.95-2.03 (m, 1H), 2.21-2.27 (m, 1H), 2.28 (s, 3H), 2.31-2.38 (m, 2H), 3.81 (s, 3H), 4.25 (t, J=6 Hz, 2H), 6.88 (s, 1H), 7.00-7.07 (m, 3H), 7.16 (d, J=8 Hz, 1H), 7.29-7.35 (m, 5H), 7.46 (d, J=16.4 Hz, 1H), 7.71 (d, J=1.2 Hz, 1H).

Examples 59 and 60

Synthesis of (−)-8-(2-fluorophenyl)-2-{(E)-2-[3-methoxy-4-(4-methyl-1H-imidazol-1-yl)phenyl]vinyl}-5,6,7,8-tetrahydro-[1,2,4]triazolo[1,5-a]pyridin-8-ol and (+)-8-(2-fluorophenyl)-2-{(E)-2-[3-methoxy-4-(4-methyl-1H-imidazol-1-yl)phenyl]vinyl}-5,6,7,8-tetrahydro-[1,2,4]triazolo[1,5-a]pyridin-8-ol

[Formula 76]

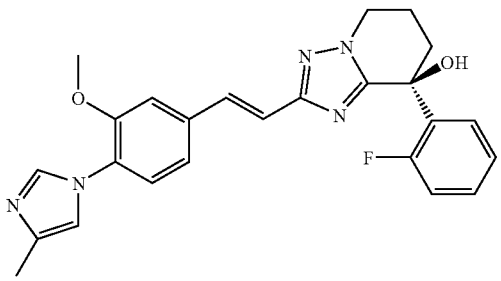

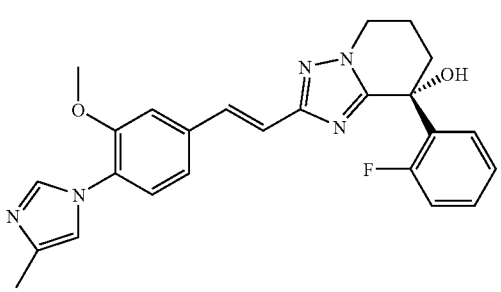

Synthesis of 8-(2-fluorophenyl)-2-{(E)-2-[3-methoxy-4-(4-methyl-1H-imidazol-1-yl)phenyl]vinyl}-5,6,7,8-tetrahydro-[1,2,4]triazolo[1,5-a]pyridine 468 mg of the title compound was obtained from (E)-N-[3-(2-fluorophenyl)-2-oxopiperidin-1-yl]-3-[3-methoxy-4-(4-methyl-1H-imidazol-1-yl)phenyl]acrylamide (761 mg) using methyl 2-fluorophenylacetate as a starting material by the same method as in Examples 20 and 21. The property values of the compound are as follows.

$^1$H-NMR (CDCl$_3$) δ (ppm): 2.03-2.24 (m, 3H), 2.29 (s, 3H), 2.33-2.39 (m, 1H), 3.85 (s, 3H), 4.27-4.30 (m, 2H), 4.58-4.61 (m, 1H), 6.91-6.92 (m, 1H), 6.93-6.98 (m, 1H), 7.05-7.15 (m, 5H), 7.21 (d, J=7.6 Hz, 1H), 7.24-7.30 (m, 1H), 7.51 (d, J=16.4 Hz, 1H), 7.69 (d, J=1.2 Hz, 1H).

Synthesis of (−)-2-{(E)-2-[3-methoxy-4-(4-methyl-1H-imidazol-1-yl)phenyl]vinyl}-8-phenyl-5,6,7,8-tetrahydro-[1,2,4]triazolo[1,5-a]pyridin-8-ol and (+)-2-{(E)-2-[3-methoxy-4-(4-methyl-1H-imidazol-1-yl)phenyl]vinyl}-8-phenyl-5,6,7,8-tetrahydro-[1,2,4]triazolo[1,5-a]pyridin-8-ol The title optically active compound with a retention time of 12 minutes in CHIRALPAK™ IA manufactured by Daicel Chemical Industries, Ltd. (2 cm×25 cm, mobile phase: ethanol, flow rate: 10 mL/min) and positive optical rotation (20.6 mg) and the title optically active compound with a retention time of 14 minutes in the CHIRALPAK™ IA and negative optical rotation (17.2 mg) were obtained from 8-(2-fluorophenyl)-2-{(E)-2-[3-methoxy-4-(4-methyl-1H-imidazol-1-yl)phenyl]vinyl}-5,6,7,8-tetrahydro-[1,2,4]triazolo[1,5-a]pyridine (50 mg) by the same method as in Examples 53 and 54.

The property values of the title optically active compound with a retention time of 12 minutes are as follows.

$^1$H-NMR (CDCl$_3$) δ (ppm): 2.04-2.11 (m, 1H), 2.22-2.36 (m, 2H), 2.30 (s, 3H), 3.76 (s, 3H), 4.13-4.20 (m, 1H), 4.29-4.35 (m, 1H), 6.85-6.99 (m, 4H), 7.09 (d, J=8 Hz, 2H), 7.20-7.25 (m, 1H), 7.27-7.33 (m, 2H), 7.34 (d, J=18.8 Hz, 1H), 7.65 (d, J=0.8 Hz, 1H), 7.83-7.88 (m, 1H).

The property values of the title optically active compound with a retention time of 14 minutes are as follows.

$^1$H-NMR (CDCl$_3$) δ (ppm): 2.04-2.11 (m, 1H), 2.22-2.36 (m, 2H), 2.30 (s, 3H), 3.76 (s, 3H), 4.13-4.20 (m, 1H), 4.29-4.35 (m, 1H), 6.85-6.99 (m, 4H), 7.09 (d, J=8 Hz, 2H), 7.20-7.25 (m, 1H), 7.27-7.33 (m, 2H), 7.34 (d, J=18.8 Hz, 1H), 7.65 (d, J=0.8 Hz, 1H), 7.83-7.88 (m, 1H).

The following compounds were obtained by the same method as in Examples 53 and 54 (Table 2).

TABLE 2

![Structure]

| Example | E₁ | E2 | DATA: MS m/z | Note |
|---|---|---|---|---|
| 61 | *-C₆H₄-CF₃ (para) | OH | M⁺ + H: 496 (ESI) | Optically active compound (separation conditions IA: retention time 21 min, optical rotation (−)) |
| 62 | *-C₆H₄-CF₃ (para) | OH | M⁺ + H: 496 (ESI) | Optically active compound (separation conditions IA: retention time 29 min, optical rotation (+)) |
| 63 | *-quinolin-2-yl | OH | M⁺ + H: 479 (ESI) | Optically active compound (separation conditions AD-H: retention time 15 min, optical rotation (−)) |
| 64 | *-quinolin-2-yl | OH | M⁺ + H: 479 (ESI) | Optically active compound (separation conditions AD-H: retention time 21 min, optical rotation (+)) |

Examples 65 and 66

Synthesis of (+)-8-(3-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine-8-carbonitrile and (−)-8-(3-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine-8-carbonitrile

[Formula 77]

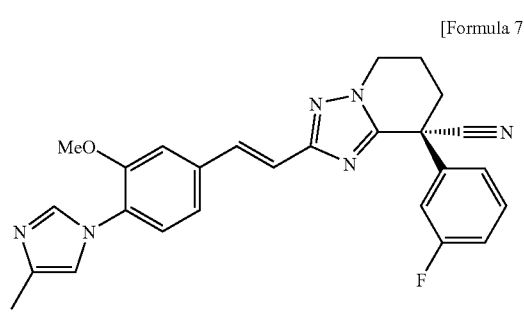

Synthesis of (8-(3-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridin-8-yl)methanol

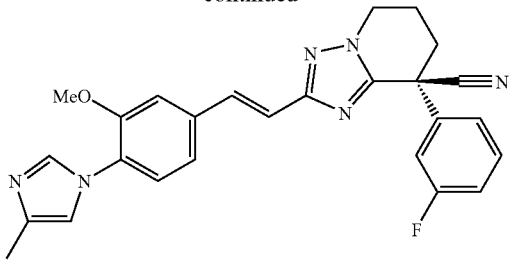

Paraformaldehyde (186 mg) and sodium hydride (containing 40% of mineral oil, 28.7 mg) were added to a solution of 8-(3-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine synthesized by the method in Examples 1 and 2 (154 mg) in DMF (3 mL), and the reaction solution was stirred at room temperature for 30 minutes. Thereafter, ethyl acetate and saturated sodium bicarbonate water were added to the reaction solution, and the organic layer was separated. The resulting organic layer was dried over anhydrous magnesium sulfate and concentrated under reduced pressure to obtain 204 mg of the title compound. The property value of the compound is as follows.

ESI-MS; m/z 460 [M⁺+H].

Synthesis of 8-(3-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine-8-carbaldehyde Dess-Martin periodinane (304 mg) was added to a solution of (8-(3-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridin-8-yl)methanol (165 mg) in methylene chloride (10 mL), and the reaction solution was stirred in a nitrogen atmosphere at room temperature for four hours. Ethyl acetate and saturated sodium bicarbonate water were added to the reaction solution, and the organic layer was separated. The resulting organic layer was dried over anhydrous magnesium sulfate and concentrated under reduced pressure to obtain 227 mg of the title compound. The property value of the compound is as follows.
ESI-MS; m/z 458 [M$^+$+H].

Synthesis of 8-(3-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine-8-carbaldehyde oxime Sodium acetate (58.7 mg) and hydroxylammonium chloride (49.8 mg) were added to a solution of 8-(3-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine-8-carbaldehyde (164 mg) in ethanol (10 mL), and the reaction solution was stirred at room temperature for five hours. Ethyl acetate and saturated sodium bicarbonate water were added to the reaction solution and the organic layer was separated. The resulting organic layer was dried over anhydrous magnesium sulfate and then concentrated under reduced pressure to obtain 169 mg of the title compound. The property value of the compound is as follows.
ESI-MS; m/z 473 [M$^+$+H].

Synthesis of (+)-8-(3-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine-8-carbonitrile and (−)-8-(3-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine-8-carbonitrile 1,1-Carbonylbis-1H-imidazole (290 mg) was added to a solution of 8-(3-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine-8-carbaldehyde oxime (169 mg) in THF (15 mL), and the mixture was heated under reflux for 2.5 hours. The reaction solution was cooled to room temperature. Then, ethyl acetate and brine were added to the reaction solution and the organic layer was separated. The resulting organic layer was dried over anhydrous magnesium sulfate and concentrated under reduced pressure. The residue was purified by silica gel column chromatography (carrier: Chromatorex NH; elution solvent: heptane:ethyl acetate=1:1→ethyl acetate→ethyl acetate:methanol=9:1) to obtain 84.6 mg of a racemate of the title compound. The resulting racemate (84.6 mg) was separated by CHIRALPAK™ IA manufactured by Daicel Chemical Industries, Ltd. (2 cm×25 cm; mobile phase: hexane:ethanol=1:1) to obtain a (+)-isomer of the title optically active compound with a retention time of 14 minutes (26.5 mg; >99% ee) and a (−)-isomer of the title optically active compound with a retention time of 17 minutes (25.1 mg; 98% ee).

The property values of (+)-8-(3-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine-8-carbonitrile are as follows.
ESI-MS; m/z 455 [M$^+$+H]. $^1$H-NMR (CDCl$_3$) δ (ppm): 2.12-2.25 (m, 1H), 2.26-2.51 (m, 5H), 2.67-2.77 (m, 1H), 3.87 (s, 3H), 4.26-4.42 (m, 2H), 6.92 (t, J=1.2 Hz, 1H), 6.99-7.27 (m, 7H), 7.37-7.44 (m, 1H), 7.58 (d, J=16.0 Hz, 1H), 7.71 (d, J=1.6 Hz, 1H).

The property values of (−)-8-(3-fluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine-8-carbonitrile are as follows.
ESI-MS; m/z 455 [M$^+$+H]. $^1$H-NMR (CDCl$_3$) δ (ppm): 2.12-2.25 (m, 1H), 2.26-2.51 (m, 5H), 2.67-2.77 (m, 1H), 3.87 (s, 3H), 4.26-4.42 (m, 2H), 6.92 (t, J=1.2 Hz, 1H), 6.99-7.27 (m, 7H), 7.37-7.44 (m, 1H), 7.58 (d, J=16.0 Hz, 1H), 7.71 (d, J=1.6 Hz, 1H).

Examples 67 and 68

Synthesis of (−)-2-{(E)-2-[3-methoxy-4-(4-methyl-1H-imidazol-1-yl)phenyl]vinyl}-8-(4-methylsulfanylphenyl)-5,6,7,8-tetrahydro[1,2,4]triazolo[1,5-a]pyridine-8-carbonitrile and (+)-2-{(E)-2-[3-methoxy-4-(4-methyl-1H-imidazol-1-yl)phenyl]vinyl}-8-(4-methylsulfanylphenyl)-5,6,7,8-tetrahydro[1,2,4]triazolo[1,5-a]pyridine-8-carbonitrile

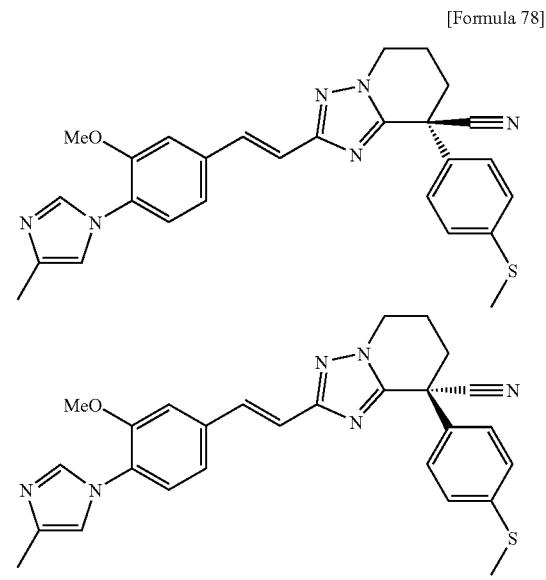

[Formula 78]

62 mg of a racemate of the title compound was obtained by the same method as in Examples 65 and 66 from 2-{(E)-2-[3-methoxy-4-(4-methyl-1H-imidazol-1-yl)phenyl]vinyl}-8-(4-methylsulfanylphenyl)-5,6,7,8-tetrahydro[1,2,4]triazolo[1,5-a]pyridine obtained by the method in Examples 28 and 29 (135.6 mg). The racemate (62 mg) was separated by CHIRALPAK™ AD-H manufactured by Daicel Chemical Industries, Ltd. (2 cm×25 cm; mobile phase: ethanol) to obtain a (−)-isomer of the title optically active compound with a retention time of 23 minutes (13.9 mg; >99% ee) and a (+)-isomer of the title optically active compound with a retention time of 32.5 minutes (15.3 mg; >99% ee).

The property values of (−)-2-{(E)-2-[3-methoxy-4-(4-methyl-1H-imidazol-1-yl)phenyl]vinyl}-8-(4-methylsulfanylphenyl)-5,6,7,8-tetrahydro-[1,2,4]triazolo[1,5-a]pyridine-8-carbonitrile are as follows.

ESI-MS; m/z 483 [M$^+$+H]. $^1$H-NMR (CDCl$_3$) δ (ppm): 2.12-2.24 (m, 1H), 2.28-2.54 (m, 8H), 2.64-2.74 (m, 1H), 3.86 (s, 3H), 4.26-4.40 (m, 2H), 6.91 (t, J=1.2 Hz, 1H), 7.06 (d, J=16.0 Hz, 1H), 7.13-7.30 (m, 7H), 7.57 (d, J=16.0 Hz, 1H), 7.70 (d, J=1.2 Hz, 1H).

The property values of (+)-2-{(E)-2-[3-methoxy-4-(4-methyl-1H-imidazol-1-yl)phenyl]vinyl}-8-(4-methylsulfanylphenyl)-5,6,7,8-tetrahydro-[1,2,4]triazolo[1,5-a]pyridine-8-carbonitrile are as follows.

ESI-MS; m/z 483 [M$^+$+H]. $^1$H-NMR (CDCl$_3$) δ (ppm): 2.12-2.24 (m, 1H), 2.28-2.54 (m, 8H), 2.64-2.74 (m, 1H), 3.86 (s, 3H), 4.26-4.40 (m, 2H), 6.91 (t, J=1.2 Hz, 1H), 7.06 (d, J=16.0 Hz, 1H), 7.13-7.30 (m, 7H), 7.57 (d, J=16.0 Hz, 1H), 7.70 (d, J=1.2 Hz, 1H).

Examples 69 and 70

Synthesis of (−)-{2-{(E)-2-[3-methoxy-4-(4-methyl-1H-imidazol-1-yl)phenyl]vinyl}-8-(3,4,5-trifluorophenyl)-5,6,7,8-tetrahydro[1,2,4]triazolo[1,5-a]pyridin-8-yl}methanol and (+)-{2-{(E)-2-[3-methoxy-4-(4-methyl-1H-imidazol-1-yl)phenyl]vinyl}-8-(3,4,5-trifluorophenyl)-5,6,7,8-tetrahydro[1,2,4]triazolo[1,5-a]pyridin-8-yl}methanol

[Formula 79]

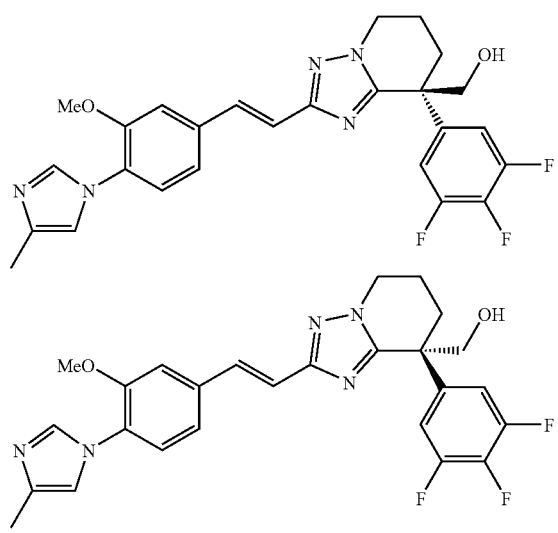

Synthesis of tert-butyl N'-[5-chloro-2-(3,4,5-trifluorophenyl)pentanoyl]hydrazinecarboxylate and tert-butyl N'-[5-(benzotriazol-1-yloxy)-2-(3,4,5-trifluorophenyl)pentanoyl]hydrazinecarboxylate IPEA (1.7 mL), HOBT (851 mg) and EDC (1.2 g) were added to a solution of 5-chloro-2-(3,4,5-trifluorophenyl)pentanoic acid (840 mg) synthesized according to the method described in Tetrahedron Letters, 2003, vol. 44, p. 365 and tert-butyl carbazate (500 mg) in DMF (5 mL), and the reaction solution was stirred at room temperature for 23 hours. Ethyl acetate and saturated sodium bicarbonate water were added to the reaction solution, and the organic layer was separated. The resulting organic layer was dried over anhydrous magnesium sulfate and then concentrated under reduced pressure. The residue was purified by silica gel column chromatography (elution solvent: heptane→heptane:ethyl acetate=1:1) to obtain 718 mg of tert-butyl N'-[5-chloro-2-(3,4,5-trifluorophenyl)pentanoyl]hydrazinecarboxylate and 420 mg of tert-butyl N'-[5-(benzotriazol-1-yloxy)-2-(3,4,5-trifluorophenyl)pentanoyl]hydrazinecarboxylate.

The property values of tert-butyl N'-[5-chloro-2-(3,4,5-trifluorophenyl)pentanoyl]hydrazinecarboxylate are as follows.

ESI-MS; m/z 403 [M$^+$+Na]. $^1$H-NMR (CDCl$_3$) δ (ppm): 1.45 (s, 9H), 1.64-2.00 (m, 3H), 2.15-2.26 (m, 1H), 3.30 (t, J=7.2 Hz, 1H), 3.47-3.60 (m, 2H), 6.99 (dd, J=8.4, 6.4 Hz, 2H).

The property value of tert-butyl N'-[5-(benzotriazol-1-yloxy)-2-(3,4,5-trifluorophenyl)pentanoyl]hydrazinecarboxylate is as follows.

ESI-MS; m/z 480 [M$^+$+H].

Synthesis of tert-butyl[2-oxo-3-(3,4,5-trifluorophenyl)piperidin-1-yl]carbamate

Sodium iodide (131 mg) and sodium hydride (containing 40% of mineral oil, 70 mg) were added to a solution of tert-butyl N'-[5-(benzotriazol-1-yloxy)-2-(3,4,5-trifluorophenyl)pentanoyl]hydrazinecarboxylate (420 mg) in DMF (3 mL), and the reaction solution was stirred at 100° C. for 19 hours. The reaction solution was left to cool to room temperature. Ethyl acetate and saturated sodium bicarbonate water were added to the reaction solution, and the organic layer was separated. The resulting organic layer was dried over anhydrous magnesium sulfate and then concentrated under reduced pressure. The residue was purified by silica gel column chromatography (elution solvent: heptane→ethyl acetate) to obtain 134 mg of the title compound. The property values of the compound are as follows.

$^1$H-NMR (CD$_3$OD) δ (ppm): 1.50 (s, 9H), 1.90-2.05 (m, 3H), 2.15-2.23 (m, 1H), 3.61-3.80 (m, 3H), 6.70 (brs, 1H), 6.90 (t, J=8.0, 6.8 Hz, 2H).

Synthesis of 1-amino-3-(3,4,5-trifluorophenyl)piperidin-2-one hydrochloride

A solution of 4 N hydrochloric acid in ethyl acetate (1 mL) was added to a solution of tert-butyl [2-oxo-3-(3,4,5-trifluorophenyl)piperidin-1-yl]carbamate (134 mg) in chloroform (1 mL), and the reaction solution was stirred at room temperature for three hours. The reaction solution was concentrated under reduced pressure to obtain 109 mg of the title compound. The property value of the compound is as follows.

ESI-MS; m/z 245 [M$^+$+H].

Synthesis of (E)-3-[3-methoxy-4-(4-methyl-1H-imidazol-1-yl)phenyl]-N-[2-oxo-3-(3,4,5-trifluorophenyl)piperidin-1-yl]acrylamide IPEA (0.41 mL), HOBT (105 mg) and EDC (149 mg) were added to a solution of 1-amino-3-(3,4,5-trifluorophenyl)piperidin-2-one hydrochloride (109 mg) and (E)-3-[3-methoxy-4-(4-methyl-1H-imidazol-1-yl)phenyl]acrylic acid (100 mg) in DMF (2 mL), and the reaction solution was stirred at room temperature for three hours. Ethyl acetate and saturated sodium bicarbonate water were added to the reaction solution, and the organic layer was separated. The resulting organic layer was dried over anhydrous magnesium sulfate and then concentrated under reduced pressure. The residue was purified by silica gel column chromatography (elution solvent: ethyl acetate→ethyl acetate:methanol=5:1) to obtain 95 mg of the title compound. The property values of the compound are as follows.

ESI-MS; m/z 485 [M$^+$+H]. $^1$H-NMR (CD$_3$OD) δ (ppm): 1.94-2.10 (m, 3H), 2.22-2.30 (m, 1H), 2.31 (s, 3H), 3.64-3.72 (m, 1H), 3.78-3.82 (m, 2H), 3.84 (s, 3H), 6.41 (d, J=16.0 Hz, 1H), 6.88 (brd, J=8.0 Hz, 1H), 6.90 (brs, 1H), 6.93 (s, 1H), 7.00 (dd, J=6.8, 3.6 Hz, 2H), 7.14 (d, J=8.0 Hz, 1H), 7.44 (d, J=16.0 Hz, 1H), 7.74 (d, J=1.2 Hz, 1H), 9.87 (brs, 1H).

Synthesis of 2-{(E)-2-[3-methoxy-4-(4-methyl-1H-imidazol-1-yl)phenyl]vinyl}-8-(3,4,5-trifluorophenyl)-5,6,7,8-tetrahydro[1,2,4]triazolo[1,5-a]pyridine A solution of (E)-3-[3-methoxy-4-(4-methyl-1H-imidazol-1-yl)phenyl]-N-[2-oxo-3-(3,4,5-trifluorophenyl)piperidin-1-yl]acrylamide (95 mg) in phosphorus oxychloride (2 mL) was stirred at 120° C. for one hour. The reaction solution was left to cool to room temperature and then concentrated under reduced pressure. Ammonium acetate (302 mg) was added to a solution of the residue in acetic acid (1 mL), and the reaction solution was stirred at 150° C. for three hours. The reaction solution was left to cool to room temperature. Then, ethyl acetate and saturated sodium bicarbonate water were added to the reaction solution, and the organic layer was separated. The resulting organic layer was dried over anhydrous magnesium sulfate and then concentrated under reduced pressure. The residue was purified by silica gel column chromatography (carrier: Chromatorex NH; elution solvent: heptane:ethyl acetate=1:1→ethyl acetate) to obtain 50 mg of a racemate of the title compound. The property values of the compound are as follows.

ESI-MS; m/z 466 [M$^+$+H]. $^1$H-NMR (CDCl$_3$) δ (ppm): 1.97-2.25 (m, 3H), 2.30 (s, 3H), 2.32-2.42 (m, 1H), 3.86 (s, 3H), 4.24-4.30 (m, 3H), 6.82 (dd, J=8.0, 6.0 Hz, 2H), 6.91 (brs, 1H), 7.05 (d, J=16.8 Hz, 1H), 7.14 (dd, J=8.4, 1.6 Hz, 1H), 7.16 (s, 1H), 7.21 (d, J=8.4 Hz, 1H), 7.50 (d, J=16.8 Hz, 1H), 7.69 (d, J=1.2 Hz, 1H).

Synthesis of (−)-{2-{(E)-2-[3-methoxy-4-(4-methyl-1H-imidazol-1-yl)phenyl]vinyl}-8-(3,4,5-trifluorophenyl)-5,6,7,8-tetrahydro[1,2,4]triazolo[1,5-a]pyridin-8-yl}methanol and (+)-{2-{(E)-2-[3-methoxy-4-(4-methyl-1H-imidazol-1-yl)phenyl]vinyl}-8-(3,4,5-trifluorophenyl)-5,6,7,8-tetrahydro[1,2,4]triazolo[1,5-a]pyridin-8-yl}methanol Sodium hydride (40% oil suspension, 31 mg) was added to a solution of 2-{(E)-2-[3-methoxy-4-(4-methyl-1H-imidazol-1-yl)phenyl]vinyl}-8-(3,4,5-trifluorophenyl)-5,6,7,8-tetrahydro[1,2,4]triazolo[1,5-a]pyridine (180 mg) and paraformaldehyde (200 mg) in DMF (3 mL), and the reaction solution was stirred at room temperature for 30 minutes. Ethyl acetate and saturated sodium bicarbonate water were added to the reaction solution, and the organic layer was separated. The resulting organic layer was dried over anhydrous magnesium sulfate and then concentrated under reduced pressure to obtain 194 mg of a racemic crude product. The resulting racemate (40 mg) was separated by CHIRALPAK™ IB manufactured by Daicel Chemical Industries, Ltd. (2 cm×25 cm, mobile phase: hexane:ethanol=7:3) to obtain the title optically active compound with a retention time of 9 minutes and negative optical rotation (10 mg) and the title optically active compound with a retention time of 11 minutes and positive optical rotation (10 mg).

The property values of the title optically active compound with a retention time of 9 minutes are as follows.
$^1$H-NMR (CDCl$_3$) δ (ppm): 1.84-1.97 (m, 1H), 2.05-2.16 (m, 2H), 2.21-2.29 (m, 1H), 2.30 (s, 3H), 3.89 (s, 3H), 3.89 (d, J=11.6 Hz, 1H), 4.08 (d, J=11.6 Hz, 1H), 4.10 (td, J=13.2, 6.0 Hz, 1H), 4.30 (dd, J=13.2, 6.0 Hz, 1H), 6.80 (dd, J=8.8, 6.4 Hz, 2H), 6.92 (brs, 1H), 7.07 (d, J=16.4 Hz, 1H), 7.16 (brs, 1H), 7.18 (dd, J=8.0, 1.6 Hz, 1H), 7.24 (d, J=8.0 Hz, 1H), 7.57 (d, J=16.4 Hz, 1H), 7.72 (brs, 1H).

The property values of the title optically active compound with a retention time of 11 minutes are as follows.
$^1$H-NMR (CDCl$_3$) δ (ppm): 1.84-1.97 (m, 1H), 2.05-2.16 (m, 2H), 2.21-2.29 (m, 1H), 2.30 (s, 3H), 3.89 (s, 3H), 3.89 (d, J=11.6 Hz, 1H), 4.08 (d, J=11.6 Hz, 1H), 4.10 (td, J=13.2, 6.0 Hz, 1H), 4.30 (dd, J=13.2, 6.0 Hz, 1H), 6.80 (dd, J=8.8, 6.4 Hz, 2H), 6.92 (brs, 1H), 7.07 (d, J=16.4 Hz, 1H), 7.16 (brs, 1H), 7.18 (dd, J=8.0, 1.6 Hz, 1H), 7.24 (d, J=8.0 Hz, 1H), 7.57 (d, J=16.4 Hz, 1H), 7.72 (brs, 1H).

Examples 71 and 72

Synthesis of (+)-2-{(E)-2-[3-methoxy-4-(4-methyl-1H-imidazol-1-yl)phenyl]vinyl}-8-(3,4,5-trifluorophenyl)-5,6,7,8-tetrahydro[1,2,4]triazolo[1,5-a]pyridine-8-carbonitrile and (−)-2-{(E)-2-[3-methoxy-4-(4-methyl-1H-imidazol-1-yl)phenyl]vinyl}-8-(3,4,5-trifluorophenyl)-5,6,7,8-tetrahydro[1,2,4]triazolo[1,5-a]pyridine-8-carbonitrile

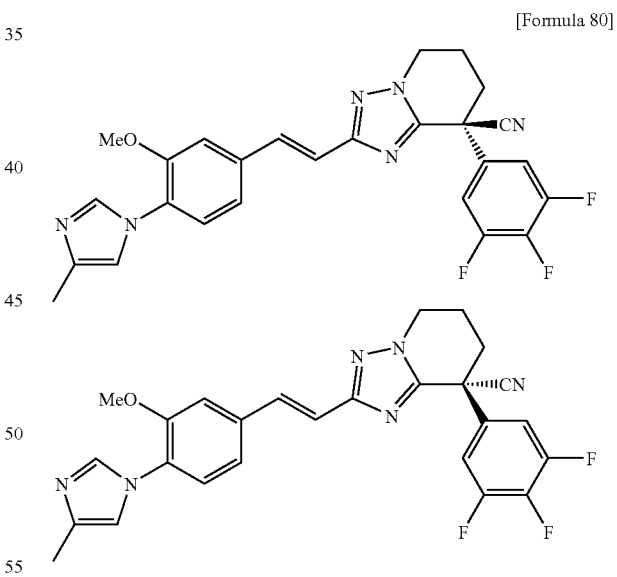

[Formula 80]

Dess-Martin periodinane (190 mg) was added to a solution of the crude product of {2-{(E)-2-[3-methoxy-4-(4-methyl-1H-imidazol-1-yl)phenyl]vinyl}-8-(3,4,5-trifluorophenyl)-5,6,7,8-tetrahydro[1,2,4]triazolo[1,5-a]pyridin-8-yl}methanol obtained in Examples 69 and 70 (111 mg) in methylene chloride (8 mL), and the reaction solution was stirred at room temperature for 10 hours. Ethyl acetate and saturated sodium bicarbonate water were added to the reaction solution, and the organic layer was separated. The resulting organic layer was dried over anhydrous magnesium sulfate and then concentrated under reduced pressure. Sodium acetate (35 mg) and hydroxyamine hydrochloride (30 mg) were added to a solution of the residue in ethanol (7 mL), and the reaction solution was stirred at room temperature for four hours. Ethyl acetate and saturated sodium bicarbonate water were added to the reaction solution, and the organic layer was separated. The resulting organic layer was dried over anhydrous magnesium sulfate and then concentrated under reduced pressure. CDI (180 mg) was added to a solution of the residue in THF (13 mL), and the reaction solution was heated under reflux for one hour. The reaction solution was left to cool to room temperature. Then, ethyl acetate and brine were added to the reaction solution, and the organic layer was separated. The resulting organic layer was dried over anhydrous magnesium sulfate and then concentrated under reduced pressure. The resulting racemic crude product was separated by CHIRALPAK™ IA manufactured by Daicel Chemical Industries, Ltd. (2 cm×25 cm, mobile phase: hexane:ethanol=1:1) to obtain the title optically active compound with a retention time of 11 minutes and negative optical rotation (38 mg) and the title optically active compound with a retention time of 15 minutes and positive optical rotation (40 mg).

The property values of the title optically active compound with a retention time of 11 minutes are as follows.

$^1$H-NMR (CDCl$_3$) δ (ppm): 2.20-2.29 (m, 1H), 2.30 (s, 3H), 2.35-2.50 (m, 2H), 2.68-2.75 (m, 1H), 3.87 (s, 3H), 4.26-4.34 (m, 1H), 4.36-4.44 (m, 1H), 6.92 (brs, 1H), 7.04 (d, J=16.8 Hz, 1H), 7.05 (dd, J=7.6, 6.4 Hz, 2H), 7.16 (brs, 1H), 7.17 (brd, J=7.2 Hz, 1H), 7.24 (d, J=7.2 Hz, 1H), 7.56 (d, J=16.8 Hz, 1H), 7.70 (brs, 1H).

The property values of the title optically active compound with a retention time of 15 minutes corresponded to the property values of the title optically active compound with a retention time of 11 minutes.

Examples 73 and 74

Synthesis of (+)-8-(4-chlorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine-8-carbonitrile and (−)-8-(4-chlorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine-8-carbonitrile

[Formula 81]

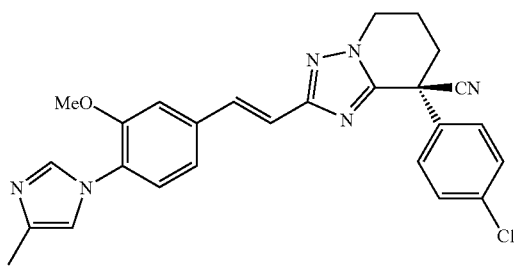

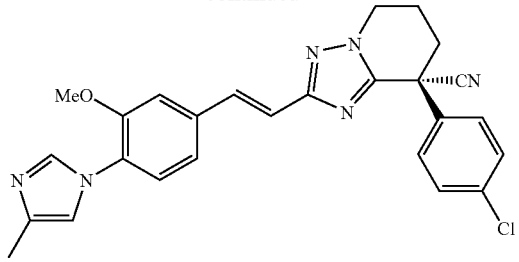

A racemate of the title compound obtained from 8-(4-chlorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine (197 mg) by the same method as in Examples 65 and 66 was separated by CHIRALPAK™ IA manufactured by Daicel Chemical Industries, Ltd. (2 cm×25 cm, mobile phase: ethanol) to obtain the title optically active compound with a retention time of 16 minutes and positive optical rotation (40 mg) and the title optically active compound with a retention time of 18 minutes and negative optical rotation (47 mg).

The property values of the title optically active compound with a retention time of 16 minutes are as follows.

$^1$H-NMR (CDCl$_3$) δ (ppm): 2.13-2.25 (m, 1H), 2.30 (s, 3H), 2.32-2.47 (m, 2H), 2.66-2.75 (m, 1H), 3.87 (s, 3H), 4.28-4.42 (m, 2H), 6.93 (brs, 1H), 7.06 (d, J=16.0 Hz, 1H), 7.17 (d, J=1.6 Hz, 1H), 7.18 (dd, J=8.4, 1.6 Hz, 1H), 7.24 (d, J=8.4 Hz, 1H), 7.28 (d, J=8.8 Hz, 2H), 7.41 (d, J=8.8 Hz, 2H), 7.57 (d, J=16.0 Hz, 1H), 7.71 (d, J=1.2 Hz, 1H).

The property values of the title optically active compound with a retention time of 18 minutes are as follows.

$^1$H-NMR (CDCl$_3$) δ (ppm): 2.13-2.25 (m, 1H), 2.30 (s, 3H), 2.32-2.47 (m, 2H), 2.66-2.75 (m, 1H), 3.87 (s, 3H), 4.28-4.42 (m, 2H), 6.93 (brs, 1H), 7.06 (d, J=16.0 Hz, 1H), 7.17 (d, J=1.6 Hz, 1H), 7.18 (dd, J=8.4, 1.6 Hz, 1H), 7.24 (d, J=8.4 Hz, 1H), 7.28 (d, J=8.8 Hz, 2H), 7.41 (d, J=8.8 Hz, 2H), 7.57 (d, J=16.0 Hz, 1H), 7.71 (d, J=1.2 Hz, 1H).

Examples 75 and 76

Synthesis of (+)-8-(3,4-difluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine-8-carbonitrile and (−)-8-(3,4-difluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine-8-carbonitrile

[Formula 82]

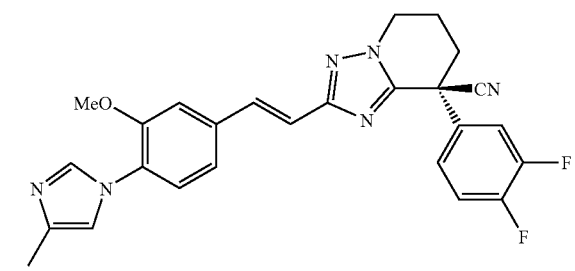

-continued

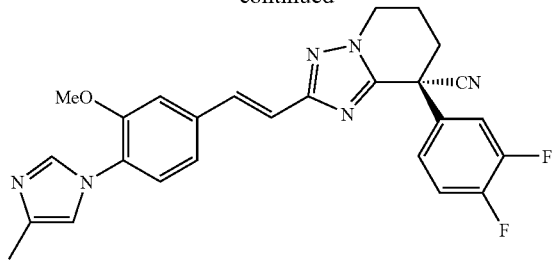

A racemate of the title compound obtained from 8-(3,4-dichlorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine (132 mg) by the same method as in Examples 65 and 66 was separated by CHIRALPAK™ IA manufactured by Daicel Chemical Industries, Ltd. (2 cm×25 cm, mobile phase: ethanol) to obtain the title optically active compound with a retention time of 13 minutes and positive optical rotation (24 mg) and the title optically active compound with a retention time of 16 minutes and negative optical rotation (24 mg).

The property values of the title optically active compound with a retention time of 13 minutes are as follows.

$^1$H-NMR (CDCl$_3$) δ (ppm): 2.16-2.27 (m, 1H), 2.30 (s, 3H), 2.36-2.47 (m, 2H), 2.68-2.75 (m, 1H), 3.87 (s, 3H), 4.27-4.43 (m, 2H), 6.92 (brs, 1H), 7.05 (d, J=16.4 Hz, 1H), 7.10-7.14 (m, 1H), 7.15-7.27 (m, 5H), 7.57 (d, J=16.4 Hz, 1H), 7.70 (brs, 1H).

The property values of the title optically active compound with a retention time of 16 minutes are as follows.

$^1$H-NMR (CDCl$_3$) δ (ppm): 2.16-2.27 (m, 1H), 2.30 (s, 3H), 2.36-2.47 (m, 2H), 2.68-2.75 (m, 1H), 3.87 (s, 3H), 4.27-4.43 (m, 2H), 6.92 (brs, 1H), 7.05 (d, J=16.4 Hz, 1H), 7.10-7.14 (m, 1H), 7.15-7.27 (m, 5H), 7.57 (d, J=16.4 Hz, 1H), 7.70 (brs, 1H).

Examples 77, 78, 79 and 80

Synthesis of (−)-8-(3,5-difluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine-8-carbonitrile, (+)-8-(3,5-difluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine-8-carbonitrile, (−)-8-(3,5-difluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridin-8-ol and (+)-8-(3,5-difluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridin-8-ol

[Formula 83]

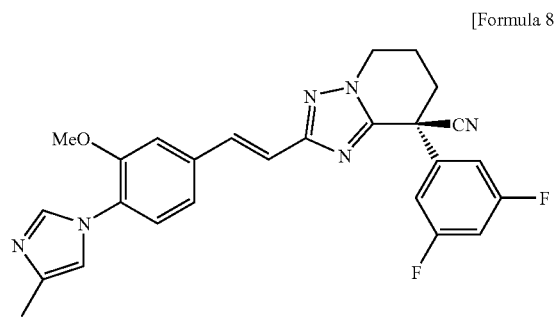

-continued

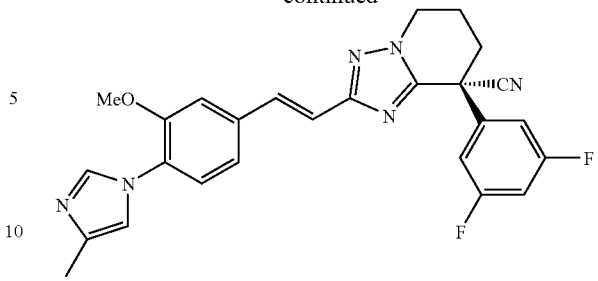

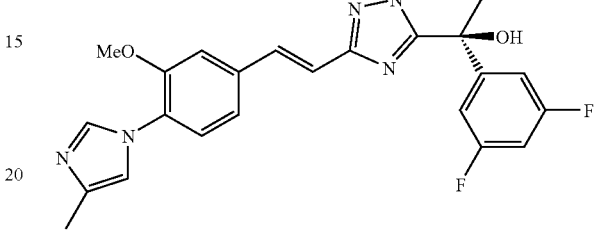

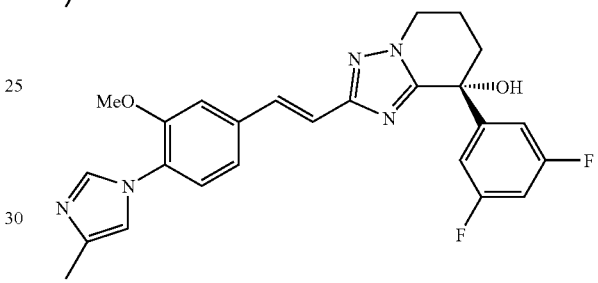

8-(3,5-Difluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine-8-carbonitrile (80 mg) was obtained from 8-(3,5-difluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine (160 mg) by the same method as in Examples 65 and 66. At the same time, 8-(3,5-difluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridin-8-ol generated in the reaction step in the middle (80 mg) was isolated.

The resulting 8-(3,5-difluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine-8-carbonitrile (80 mg) was optically resolved by CHIRALPAK™ ADH manufactured by Daicel Chemical Industries, Ltd. (2 cm×25 cm, mobile phase: 80% ethanol-hexane, flow rate: 10 mL/min) to obtain the title optically active compound with a retention time of 15 minutes and positive optical rotation ((+)-8-(3,5-difluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine-8-carbonitrile, 29.6 mg) and the title optically active compound with a retention time of 18 minutes and negative optical rotation ((−)-8-(3,5-difluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridine-8-carbonitrile, 35.1 mg).

The property values of the title optically active compound with a retention time of 18 minutes and negative optical rotation are as follows.

$^1$H-NMR (CDCl$_3$) δ (ppm): 2.16-2.32 (m, 1H), 2.30 (s, 3H), 2.34-2.50 (m, 2H), 2.66-2.78 (m, 1H), 3.88 (s, 3H), 4.26-4.44 (m, 2H), 6.84-6.96 (m, 4H), 7.06 (d, J=16 Hz, 1H), 7.16-7.22 (m, 2H), 7.24 (d, J=8.4 Hz, 1H), 7.59 (d, J=16 Hz, 1H), 7.71 (d, J=0.80 Hz, 1H).

ESI-MS; m/z 473 [M$^+$+H].

The property values of the title optically active compound with a retention time of 15 minutes and positive optical rotation corresponded to the values of the (−)-isomer.

8-(3,5-Difluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridin-8-ol obtained in the same manner (80 mg) was optically resolved by CHIRALPAK™ ADH manufactured by Daicel Chemical Industries, Ltd. (2 cm×25 cm, mobile phase: 50% ethanol-hexane, flow rate: 10 mL/min) to obtain the title optically active compound with a retention time of 20 minutes and positive optical rotation ((+)-8-(3,5-difluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridin-8-ol, 11.3 mg) and the title optically active compound with a retention time of 22 minutes and negative optical rotation ((−)-8-(3,5-difluorophenyl)-2-{(E)-2-[3-methoxy-4-(4-methyl-1H-imidazol-1-yl)phenyl]vinyl}-5,6,7,8-tetrahydro[1,2,4]triazolo[1,5-a]pyridin-8-ol, 11.6 mg). The property values of the title optically active compound with a retention time of 22 minutes and negative optical rotation are as follows.

$^1$H-NMR (CDCl$_3$) δ (ppm): 1.98-2.20 (m, 2H), 2.28 (s, 3H), 2.26-2.40 (m, 1H), 2.40-2.56 (m, 1H), 3.77 (s, 3H), 4.18-4.36 (m, 2H), 6.70-6.78 (m, 1H), 6.80-6.90 (m, 2H), 6.90-7.05 (m, 4H), 7.11 (d, J=8.0 Hz, 1H), 7.40 (d, J=16 Hz, 1H), 7.73 (s, 1H).

ESI-MS; m/z 464 [M$^+$+H].

The property values of the title optically active compound with a retention time of 20 minutes and positive optical rotation corresponded to the values of the (−)-isomer.

The following compounds were obtained by the same method as in Examples 65 and 66 (Table 3).

TABLE 3

| Example | E$_1$ | E2 | DATA: MS m/z | Note |
|---|---|---|---|---|
| 81 | *-C$_6$H$_4$-CF$_3$ (para) | CN | M$^+$ + H: 505 (ESI) | Optically active compound (separation conditions IA: retention time 27 min, optical rotation (−)) |
| 82 | *-C$_6$H$_4$-CF$_3$ (para, opposite stereo) | CN | M$^+$ + H: 505 (ESI) | Optically active compound (separation conditions IA: retention time 28 min, optical rotation (+)) |
| 83 | *-C$_6$H$_4$-F (ortho) | CN | M$^+$ + H: 455 (ESI) | Optically active compound (separation conditions AD-H:ethanol: retention time 15 min, optical rotation (+)) |
| 84 | *-C$_6$H$_4$-F (ortho, opposite stereo) | CN | M$^+$ + H: 455 (ESI) | Optically active compound (separation conditions AD-H:ethanol: retention time 18 min, optical rotation (−)) |
| 85 | *-C$_6$H$_3$-2,4-F$_2$ | CN | M$^+$ + H: 473 (ESI) | Optically active compound (separation conditions IA:80% ethanol-hexane: retention time 15 min, optical rotation (+)) |

TABLE 3-continued

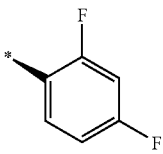

| Example | E₁ | E2 | DATA: MS m/z | Note |
|---|---|---|---|---|
| 86 | 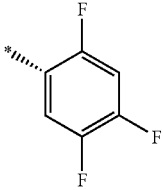 | CN | M⁺ + H: 473 (ESI) | Optically active compound (separation conditions IA:80% ethanol-hexane: retention time 20 min, optical rotation (−)) |
| 87 | 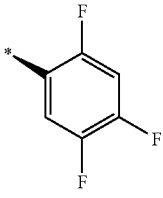 | CN | M⁺ + H: 491 (ESI) | Optically active compound (separation conditions IA:70% ethanol-hexane: retention time 28 min, optical rotation (+)) |
| 88 | 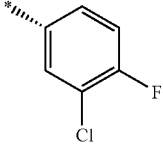 | CN | M⁺ + H: 491 (ESI) | Optically active compound (separation conditions IA:70% ethanol-hexane: retention time 33 min, optical rotation (−)) |
| 89 | 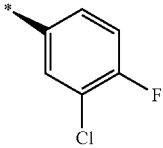 | CN | M⁺ + H: 489 (ESI) | Optically active compound (separation conditions AD-H:ethanol: retention time 17 min, optical rotation (−)) |
| 90 |  | CN | M⁺ + H: 489 (ESI) | Optically active compound (separation conditions AD-H:ethanol: retention time 37 min, optical rotation (+)) |

Examples 91 and 92

Synthesis of (−)-2-{(Z)-1-fluoro-2-[3-methoxy-4-(4-methyl-1H-imidazol-1-yl)phenyl]vinyl}-8-(2,4,6-trifluorophenyl)-5,6,7,8-tetrahydro[1,2,4]triazolo[1,5-a]pyridine and (+)-2-{(Z)-1-fluoro-2-[3-methoxy-4-(4-methyl-1H-imidazol-1-yl)phenyl]vinyl}-8-(2,4,6-trifluorophenyl)-5,6,7,8-tetrahydro[1,2,4]triazolo[1,5-a]pyridine

[Formula 84]

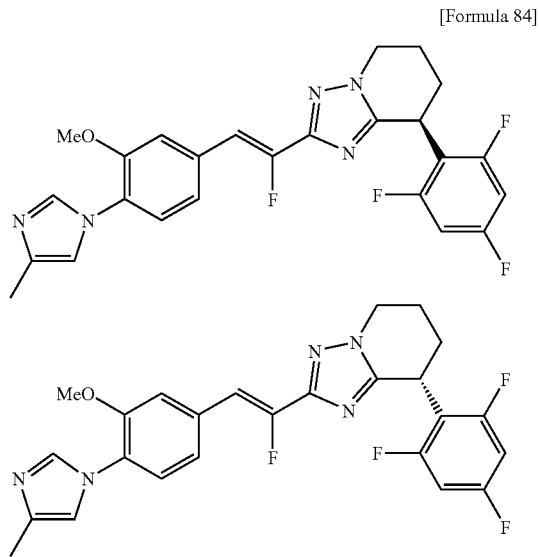

Synthesis of (Z)-2-fluoro-3-[3-methoxy-4-(4-methyl-1H-imidazol-1-yl)phenyl]-N-[2-oxo-3-(2,4,6-trifluorophenyl)piperidin-1-yl]acrylamide BOPCl (221 mg) was added to a suspension of (Z)-2-fluoro-3-[3-methoxy-4-(4-methyl-1H-imidazol-1-yl)phenyl]acrylic acid (CAS No. 870838-71-4, 240 mg), 1-amino-3-(2,4,6-trifluorophenyl)piperidin-2-one (106 g) and IPEA (0.45 mL) in DMF (5 mL), and the reaction solution was stirred at room temperature for 16 hours. Saturated sodium bicarbonate water and ethyl acetate were added to the reaction mixture and the organic layer was separated. The resulting organic layer was dried over anhydrous magnesium sulfate and then concentrated under reduced pressure. The resulting residue was purified by silica gel column chromatography (carrier: Chromatorex NH; elution solvent: ethyl acetate) to obtain 110 mg of the title compound. The property value of the compound is as follows.
ESI-MS; m/z 503 [M⁺+H].

Synthesis of (−)-2-{(Z)-1-fluoro-2-[3-methoxy-4-(4-methyl-1H-imidazol-1-yl)phenyl]vinyl}-8-(2,4,6-trifluorophenyl)-5,6,7,8-tetrahydro[1,2,4]triazolo[1,5-a]pyridine and (+)-2-{(Z)-1-fluoro-2-[3-methoxy-4-(4-methyl-1H-imidazol-1-yl)phenyl]vinyl}-8-(2,4,6-trifluorophenyl)-5,6,7,8-tetrahydro[1,2,4]triazolo[1,5-a]pyridine A solution of (Z)-2-fluoro-3-[3-methoxy-4-(4-methyl-1H-imidazol-1-yl)phenyl]-N-[2-oxo-3-(2,4,6-trifluorophenyl)piperidin-1-yl]acrylamide (110 mg) in phosphorus oxychloride (2 mL) was heated under reflux for three hours. The reaction mixture was left to cool to room temperature and then concentrated under reduced pressure. Acetic acid (3 mL) and ammonium acetate (506 mg) were added to the residue, and the reaction solution was stirred at 150° C. for two hours. The reaction mixture was left to cool to room temperature and then concentrated under reduced pressure. Saturated aqueous sodium bicarbonate and ethyl acetate were added to the residue, and the organic layer was separated. The resulting organic layer was washed with saturated aqueous sodium chloride, dried over anhydrous magnesium sulfate and then concentrated under reduced pressure. The resulting residue was purified by silica gel column chromatography (carrier: Chromatorex NH; elution solvent: heptane:ethyl acetate=1:1→ethyl acetate→ethyl acetate:methanol=9:1) to obtain 42 mg of a racemate of the title compound. The resulting racemate (22 mg) was separated by CHIRALPAK™ AD-H manufactured by Daicel Chemical Industries, Ltd. (2 cm×25 cm, mobile phase: hexane:ethanol=1:1) to obtain the title optically active compound with a retention time of 10 minutes and negative optical rotation (3.8 mg) and the title optically active compound with a retention time of 13 minutes and positive optical rotation (4.4 mg).

The property values of the title optically active compound with a retention time of 10 minutes are as follows.
¹H-NMR (CDCl₃) δ (ppm): 2.03-2.24 (m, 3H), 2.29 (s, 3H), 2.30-2.39 (m, 1H), 3.85 (s, 3H), 4.21-4.30 (m, 1H), 4.37-4.45 (m, 1H), 4.52-4.59 (m, 1H), 6.65 (d, J=38.8 Hz, 1H), 6.70 (t, J=8.8 Hz, 2H), 6.92 (brs, 1H), 7.21 (d, J=8.0 Hz, 1H), 7.24 (dd, J=8.0, 1.6 Hz, 1H), 7.33 (brs, 1H), 7.72 (d, J=1.2 Hz, 1H).

The property values of the title optically active compound with a retention time of 13 minutes are as follows.
¹H-NMR (CDCl₃) δ (ppm): 2.03-2.24 (m, 3H), 2.29 (s, 3H), 2.30-2.39 (m, 1H), 3.85 (s, 3H), 4.21-4.30 (m, 1H), 4.37-4.45 (m, 1H), 4.52-4.59 (m, 1H), 6.65 (d, J=38.8 Hz, 1H), 6.70 (t, J=8.8 Hz, 2H), 6.92 (brs, 1H), 7.21 (d, J=8.0 Hz, 1H), 7.24 (dd, J=8.0, 1.6 Hz, 1H), 7.33 (brs, 1H), 7.72 (d, J=1.2 Hz, 1H).

Examples 93 and 94

Synthesis of (+)-2-{(Z)-1-fluoro-2-[3-methoxy-4-(4-methyl-1H-imidazol-1-yl)phenyl]vinyl}-8-(3,4,5-trifluorophenyl)-5,6,7,8-tetrahydro[1,2,4]triazolo[1,5-a]pyridin-8-ol and (−)-2-{(Z)-1-fluoro-2-[3-methoxy-4-(4-methyl-1H-imidazol-1-yl)phenyl]vinyl}-8-(3,4,5-trifluorophenyl)-5,6,7,8-tetrahydro[1,2,4]triazolo[1,5-a]pyridin-8-ol

[Formula 85]

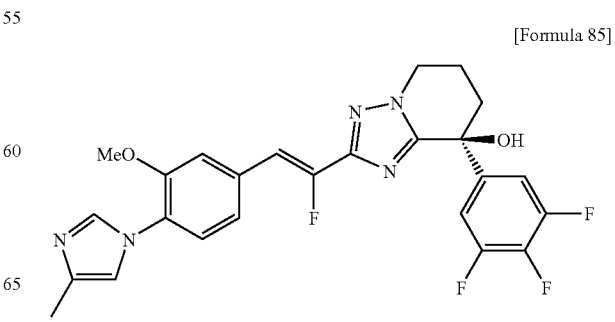

-continued

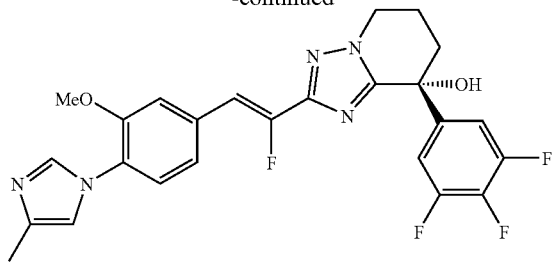

Synthesis of 5-chloro-2-(3,4,5-trifluorophenyl)pentanoic acid hydrazide hydrochloride A solution of 4 N hydrochloric acid in ethyl acetate (2 mL) was added to a solution of tert-butyl N'-[5-chloro-2-(3,4,5-trifluorophenyl)pentanoyl]hydrazinecarboxylate (300 mg) in ethyl acetate (2 mL), and the reaction solution was stirred at room temperature for one hour. The reaction solution was concentrated under reduced pressure to obtain 250 mg of the title compound. The property value of the compound is as follows.

ESI-MS; m/z 281 [M$^+$+H].

Synthesis of 5-chloro-2-(3,4,5-trifluorophenyl)pentanoic acid N'-{(Z)-2-fluoro-3-[3-methoxy-4-(4-methyl-1H-imidazol-1-yl)phenyl]acryloyl}hydrazide IPEA (0.14 mL) and BOPCl (100 mg) were added to a solution of 5-chloro-2-(3,4,5-trifluorophenyl)pentanoic acid hydrazide hydrochloride (83 mg) and (Z)-2-fluoro-3-[3-methoxy-4-(4-methyl-1H-imidazol-1-yl)phenyl]acrylic acid (CAS No. 870838-71-4, 72 mg) in methylene chloride (5 mL), and the reaction solution was stirred at room temperature for 13 hours. Ethyl acetate and saturated sodium bicarbonate water were added to the reaction solution, and the organic layer was separated. The resulting organic layer was dried over anhydrous magnesium sulfate and then concentrated under reduced pressure. The residue was purified by silica gel column chromatography (elution solvent: heptane: ethyl acetate=1:1→ethyl acetate→ethyl acetate:methanol=9:1) to obtain 84 mg of the title compound. The property value of the compound is as follows.

ESI-MS; m/z 539 [M$^+$+H].

Synthesis of 2-[4-chloro-1-(3,4,5-trifluorophenyl)butyl]-5-{(Z)-1-fluoro-2-[3-methoxy-4-(4-methyl-1H-imidazol-1-yl)phenyl]vinyl}-[1,3,4]oxadiazole A solution of 5-chloro-2-(3,4,5-trifluorophenyl)pentanoic acid N'-{(Z)-2-fluoro-3-[3-methoxy-4-(4-methyl-1H-imidazol-1-yl)phenyl]acryloyl}hydrazide (84 mg) in phosphorus oxychloride (1 mL) was stirred at 120° C. for 7.5 hours. The reaction solution was left to cool to room temperature and then concentrated under reduced pressure to obtain 81 mg of the title compound. The property value of the compound is as follows.

ESI-MS; m/z 521 [M$^+$+H].

Synthesis of 2-{(Z)-1-fluoro-2-[3-methoxy-4-(4-methyl-1H-imidazol-1-yl)phenyl]vinyl}-8-(3,4,5-trifluorophenyl)-5,6,7,8-tetrahydro[1,2,4]triazolo[1,5-a]pyridine A solution of 2-[4-chloro-1-(3,4,5-trifluorophenyl)butyl]-5-{(Z)-1-fluoro-2-[3-methoxy-4-(4-methyl-1H-imidazol-1-yl)phenyl]vinyl}-[1,3,4]oxadiazole (81 mg) and ammonium acetate (358 mg) in acetic acid (2 mL) was stirred at 150° C. for three hours. The reaction solution was left to cool to room temperature. Then, ethyl acetate and saturated sodium bicarbonate water were added to the reaction solution, and the organic layer was separated. The resulting organic layer was dried over anhydrous magnesium sulfate and then concentrated under reduced pressure. The residue was purified by silica gel column chromatography (carrier: Chromatorex NH; elution solvent: heptane:ethyl acetate=1:1→ethyl acetate) to obtain 98 mg of the title compound. The property values of the compound are as follows.

$^1$H-NMR (CDCl$_3$) δ (ppm): 1.99-2.08 (m, 1H), 2.09-2.28 (m, 2H), 2.31 (s, 3H), 2.35-2.44 (m, 1H), 3.87 (s, 3H), 4.28 (t, J=7.2 Hz, 1H), 4.34 (t, J=5.2 Hz, 2H), 6.74 (d, J=38.4 Hz, 1H), 6.82 (dd, J=8.0, 6.4 Hz, 2H), 6.94 (brs, 1H), 7.25 (d, J=8.4 Hz, 1H), 7.28 (dd, J=8.4, 1.6 Hz, 1H), 7.36 (brs, 1H), 7.73 (d, J=0.8 Hz, 1H).

Synthesis of (+)-2-{(Z)-1-fluoro-2-[3-methoxy-4-(4-methyl-1H-imidazol-1-yl)phenyl]vinyl}-8-(3,4,5-trifluorophenyl)-5,6,7,8-tetrahydro[1,2,4]triazolo[1,5-a]pyridin-8-ol and (−)-2-{(Z)-1-fluoro-2-[3-methoxy-4-(4-methyl-1H-imidazol-1-yl)phenyl]vinyl}-8-(3,4,5-trifluorophenyl)-5,6,7,8-tetrahydro[1,2,4]triazolo[1,5-a]pyridin-8-ol Sodium hydride (containing 40% of mineral oil, 16.2 mg) was added to a solution of 2-{(Z)-1-fluoro-2-[3-methoxy-4-(4-methyl-1H-imidazol-1-yl)phenyl]vinyl}-8-(3,4,5-trifluorophenyl)-5,6,7,8-tetrahydro[1,2,4]triazolo[1,5-a]pyridine (98 mg) in DMF (2 mL), and the reaction solution was stirred at room temperature for 40 minutes. Ethyl acetate and a saturated sodium thiosulfate solution were added to the reaction solution, and the organic layer was separated. The resulting organic layer was washed with saturated sodium bicarbonate water, dried over anhydrous magnesium sulfate and then concentrated under reduced pressure. The residue was separated by CHIRALCEL™ OD-H manufactured by Daicel Chemical Industries, Ltd. (2 cm×25 cm; mobile phase: ethanol) to obtain the title optically active compound with a retention time of 9 minutes and positive optical rotation (22 mg) and the title optically active compound with a retention time of 11 minutes and negative optical rotation (23 mg).

The property values of (+)-2-{(Z)-1-fluoro-2-[3-methoxy-4-(4-methyl-1H-imidazol-1-yl)phenyl]vinyl}-8-(3,4,5-trifluorophenyl)-5,6,7,8-tetrahydro[1,2,4]triazolo[1,5-a]pyridin-8-ol are as follows.

$^1$H-NMR (CDCl$_3$) δ (ppm): 2.03-2.16 (m, 2H), 2.28 (s, 3H), 2.31-2.39 (m, 1H), 2.46-2.58 (m, 1H), 3.77 (s, 3H), 4.23-4.31 (m, 1H), 4.36-4.43 (m, 1H), 6.60 (d, J=37.6 Hz, 1H), 6.89 (brs, 1H), 6.98 (dd, J=8.4, 1.6 Hz, 1H), 7.06 (dd, J=8.4, 6.4 Hz, 2H), 7.13 (d, J=8.4 Hz, 1H), 7.16 (brs, 1H), 7.72 (d, J=1.2 Hz, 1H).

The property values of (−)-2-{(Z)-1-fluoro-2-[3-methoxy-4-(4-methyl-1H-imidazol-1-yl)phenyl]vinyl}-8-(3,4,5-trifluorophenyl)-5,6,7,8-tetrahydro[1,2,4]triazolo[1,5-a]pyridin-8-ol are as follows.

$^1$H-NMR (CDCl$_3$) δ (ppm): 2.03-2.16 (m, 2H), 2.28 (s, 3H), 2.31-2.39 (m, 1H), 2.46-2.58 (m, 1H), 3.77 (s, 3H), 4.23-4.31 (m, 1H), 4.36-4.43 (m, 1H), 6.60 (d, J=37.6 Hz, 1H), 6.89 (brs, 1H), 6.98 (dd, J=8.4, 1.6 Hz, 1H), 7.06 (dd, J=8.4, 6.4 Hz, 2H), 7.13 (d, J=8.4 Hz, 1H), 7.16 (brs, 1H), 7.72 (d, J=1.2 Hz, 1H).

Examples 95 and 96

Synthesis of (+)-2-{(E)-2-[2-fluoro-5-methoxy-4-(4-methyl-1H-imidazol-1-yl)phenyl]vinyl}-8-(3,4,5-trifluorophenyl)-5,6,7,8-tetrahydro[1,2,4]triazolo[1,5-a]pyridin-8-ol and (−)-2-{(E)-2-[2-fluoro-5-methoxy-4-(4-methyl-1H-imidazol-1-yl)phenyl]vinyl}-8-(3,4,5-trifluorophenyl)-5,6,7,8-tetrahydro[1,2,4]triazolo[1,5-a]pyridin-8-ol

[Formula 86]

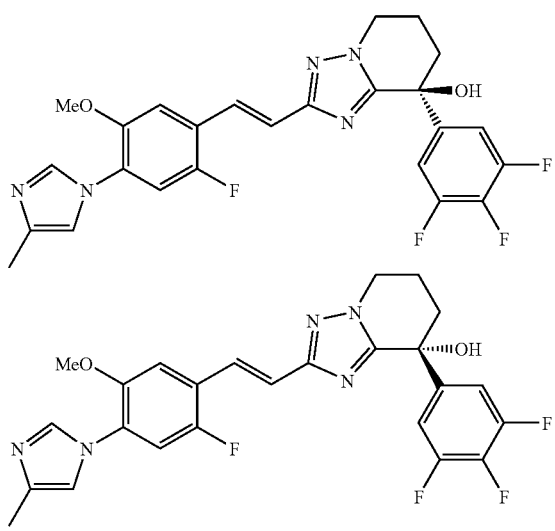

Synthesis of (E)-3-[2-fluoro-5-methoxy-4-(4-methyl-1H-imidazol-1-yl)phenyl]acrylic acid Lithium hydroxide monohydrate (240 mg) was added to a mixed solution of 2-fluoro-5-methoxy-4-(4-methyl-1H-imidazol-1-yl)benzaldehyde (CAS No. 870851-52-8, 1.03 g) and triethyl phosphonoacetate (1.09 g) in THF (4 mL)-ethanol (1 mL), and the reaction solution was stirred at room temperature for five hours. A 2 N sodium hydroxide solution (4 mL) was added to the reaction solution, and the reaction solution was stirred for 17 hours. 2 N aqueous hydrochloric acid (4 mL) was added to the reaction solution, and the reaction solution was stirred at room temperature for 30 minutes. The precipitated solid was collected by filtration and washed with water and ether. The resulting solid was air-dried to obtain 1.03 g of the title compound. The property value of the compound is as follows.
ESI-MS; m/z 277 [M$^+$+H].

Synthesis of 5-chloro-2-(3,4,5-trifluorophenyl)pentanoic acid N'-{(E)-3-[2-fluoro-5-methoxy-4-(4-methyl-1H-imidazol-1-yl)phenyl]acryloyl}hydrazide IPEA (0.31 mL) and BOPCl (119 mg) were added to a solution of 5-chloro-2-(3,4,5-trifluorophenyl)pentanoic acid hydrazide hydrochloride (114 mg) and (E)-3-[2-fluoro-5-methoxy-4-(4-methyl-1H-imidazol-1-yl)phenyl]acrylic acid (99 mg) in methylene chloride (5 mL), and the reaction solution was stirred at room temperature for one hour. Ethyl acetate and a saturated ammonium chloride solution were added to the reaction solution, and the organic layer was separated. The resulting organic layer was dried over anhydrous magnesium sulfate and concentrated under reduced pressure to obtain 200 mg of the title compound. The property value of the compound is as follows.
ESI-MS; m/z 539 [M$^+$+H].

Synthesis of 2-[4-chloro-1-(3,4,5-trifluorophenyl) butyl]-5-{(E)-2-[2-fluoro-5-methoxy-4-(4-methyl-1H-imidazol-1-yl)phenyl]vinyl}-[1,3,4]oxadiazole A solution of 5-chloro-2-(3,4,5-trifluorophenyl)pentanoic acid N'-{(E)-3-[2-fluoro-5-methoxy-4-(4-methyl-1H-imidazol-1-yl)phenyl]acryloyl}hydrazide (200 mg) in phosphorus oxychloride (2 mL) was stirred at 120° C. for 5.5 hours. The reaction solution was left to cool to room temperature and then concentrated under reduced pressure. Ethyl acetate and saturated sodium bicarbonate water were added to the residue, and the organic layer was separated. The resulting organic layer was dried over anhydrous magnesium sulfate and concentrated under reduced pressure to obtain 180 mg of the title compound. The property value of the compound is as follows.
ESI-MS; m/z 521 [M$^+$+H].

Synthesis of (+)-2-{(E)-2-[2-fluoro-5-methoxy-4-(4-methyl-1H-imidazol-1-yl)phenyl]vinyl}-8-(3,4,5-trifluorophenyl)-5,6,7,8-tetrahydro[1,2,4]triazolo[1,5-a]pyridin-8-ol and (−)-2-{(E)-2-[2-fluoro-5-methoxy-4-(4-methyl-1H-imidazol-1-yl)phenyl]vinyl}-8-(3,4,5-trifluorophenyl)-5,6,7,8-tetrahydro[1,2,4]triazolo[1,5-a]pyridin-8-ol A solution of 2-[4-chloro-1-(3,4,5-trifluorophenyl)butyl]-5-{(E)-2-[2-fluoro-5-methoxy-4-(4-methyl-1H-imidazol-1-yl)phenyl]vinyl}-[1,3,4]oxadiazole (180 mg) and ammonium acetate (533 mg) in acetic acid (2 mL) was stirred at 150° C. for 24 hours. The reaction solution was left to cool to room temperature. Then, ethyl acetate and saturated sodium bicarbonate water were added to the reaction solution, and the organic layer was separated. The resulting organic layer was dried over anhydrous magnesium sulfate and then concentrated under reduced pressure. The residue was purified by silica gel column chromatography (elution solvent: heptane:ethyl acetate=1:1→ethyl acetate→ethyl acetate:methanol=4:1) to obtain a racemate of the title compound. Sodium hydride (40% oil suspension, 22.2 mg) was added to a solution of the resulting racemate (134 mg) in DMF (2 mL), and the reaction solution was stirred at room temperature for one hour. Ethyl acetate and a saturated sodium thiosulfate solution were added to the reaction solution, and the organic layer was separated. The resulting organic layer was washed with saturated sodium bicarbonate water, dried over anhydrous magnesium sulfate and then concentrated under reduced pressure. The residue was separated by CHIRALPAK™ IA manufactured by Daicel Chemical Industries, Ltd. (2 cm×25 cm; mobile phase: hexane:ethanol=1:1) to obtain the title optically active compound with a retention time of 7 minutes (26 mg) and the title optically active compound with a retention time of 8 minutes (24 mg).

The property values of the title optically active compound with a retention time of 7 minutes are as follows.
ESI-MS; m/z 500 [M$^+$+H]. $^1$H-NMR (CDCl$_3$) δ (ppm): 2.01-2.14 (m, 2H), 2.26 (s, 3H), 2.28-2.36 (m, 1H), 2.45-2.57 (m, 1H), 3.74 (s, 3H), 4.17-4.25 (m, 1H), 4.28-4.37 (m, 1H), 6.83 (brs, 1H), 6.88 (d, J=10.4 Hz, 1H), 6.89 (d, J=6.4 Hz, 1H), 7.05 (d, J=16.4 Hz, 1H), 7.06 (dd, J=8.8, 6.4 Hz, 2H), 7.42 (d, J=16.4 Hz, 1H), 7.67 (d, J=1.6 Hz, 1H).

The property values of the title optically active compound with a retention time of 8 minutes are as follows.

ESI-MS; m/z 500 [M$^+$+H]. $^1$H-NMR (CDCl$_3$) δ (ppm): 2.01-2.14 (m, 2H), 2.26 (s, 3H), 2.28-2.36 (m, 1H), 2.45-2.57 (m, 1H), 3.74 (s, 3H), 4.17-4.25 (m, 1H), 4.28-4.37 (m, 1H), 6.83 (brs, 1H), 6.88 (d, J=10.4 Hz, 1H), 6.89 (d, J=6.4 Hz, 1H), 7.05 (d, J=16.4 Hz, 1H), 7.06 (dd, J=8.8, 6.4 Hz, 2H), 7.42 (d, J=16.4 Hz, 1H), 7.67 (d, J=1.6 Hz, 1H).

Examples 97, 98, 99 and 100

Synthesis of (6R,8R)-8-(4-fluorophenyl)-2-{(E)-2-[3-methoxy-4-(4-methyl-1H-imidazol-1-yl)phenyl]vinyl}-6-methyl-5,6,7,8-tetrahydro-[1,2,4]triazolo[1,5-a]pyridine, (6R,8S)-8-(4-fluorophenyl)-2-{(E)-2-[3-methoxy-4-(4-methyl-1H-imidazol-1-yl)phenyl]vinyl}-6-methyl-5,6,7,8-tetrahydro-[1,2,4]triazolo[1,5-a]pyridine, (6S,8R)-8-(4-fluorophenyl)-2-{(E)-2-[3-methoxy-4-(4-methyl-1H-imidazol-1-yl)phenyl]vinyl}-6-methyl-5,6,7,8-tetrahydro-[1,2,4]triazolo[1,5-a]pyridine and (6S,8S)-8-(4-fluorophenyl)-2-{(E)-2-[3-methoxy-4-(4-methyl-1H-imidazol-1-yl)phenyl]vinyl}-6-methyl-5,6,7,8-tetrahydro-[1,2,4]triazolo[1,5-a]pyridine

[Formula 87]

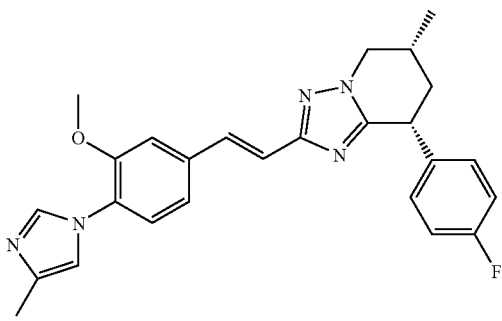

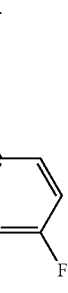

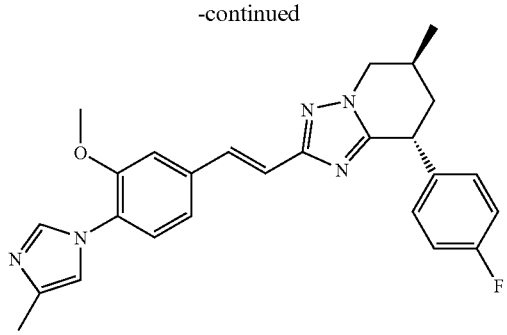

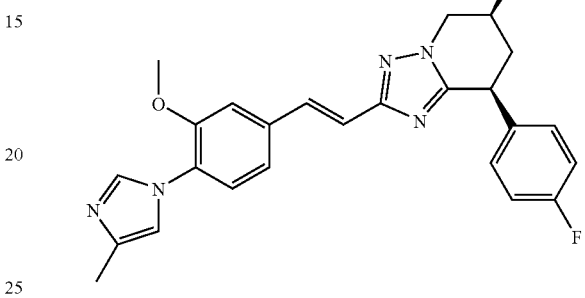

388 mg of a diastereomer mixture of the title compound was obtained from (E)-N-[3-(4-fluorophenyl)-5-methyl-2-oxopiperidin-1-yl]-3-[3-methoxy-4-(4-methyl-1H-imidazol-1-yl)phenyl]acrylamide (662 mg) using methyl 4-fluorophenylacetate and 1-bromo-3-chloro-2-methylpropane as starting materials by the same method as in Examples 20 and 21. The resulting diastereomer mixture (388 mg) was separated by CHIRALPAK™ OD-H manufactured by Daicel Chemical Industries, Ltd. (2 cm×25 cm, mobile phase: ethanol, flow rate: 10 mL/min) to obtain the title optically active compound with a retention time of 10 minutes and negative optical rotation (67 mg), the title optically active compound with a retention time of 13 minutes and positive optical rotation (69 mg), the title optically active compound with a retention time of 15 minutes and negative optical rotation (93 mg) and the title optically active compound with a retention time of 30 minutes and positive optical rotation (92 mg).

The property values of the title optically active compound with a retention time of 10 minutes are as follows.

$^1$H-NMR (CDCl$_3$) δ (ppm): 1.12 (d, J=6.8 Hz, 3H), 2.08-2.11 (m, 2H), 2.30 (s, 3H), 2.31-2.37 (m, 1H), 3.76 (dd, J=12.8 Hz, 9.6 Hz, 1H), 3.87 (s, 3H), 4.37 (dd, J=12.8 Hz, 5.2 Hz, 1H), 4.49 (t, J=4.4 Hz, 1H), 6.92 (t, J=0.8 Hz, 1H), 7.00-7.03 (m, 4H), 7.08 (d, J=16.4 Hz, 1H), 7.14-7.17 (m, 2H), 7.23 (d, J=8.0 Hz, 1H), 7.54 (d, J=16.4 Hz, 1H), 7.70 (d, J=1.6 Hz, 1H).

The property values of the title optically active compound with a retention time of 13 minutes are as follows.

$^1$H-NMR (CDCl$_3$) δ (ppm): 1.12 (d, J=6.8 Hz, 3H), 2.08-2.11 (m, 2H), 2.30 (s, 3H), 2.31-2.37 (m, 1H), 3.76 (dd, J=12.8 Hz, 9.6 Hz, 1H), 3.87 (s, 3H), 4.37 (dd, J=12.8 Hz, 5.2 Hz, 1H), 4.49 (t, J=4.4 Hz, 1H), 6.92 (t, J=0.8 Hz, 1H), 7.00-7.03 (m, 4H), 7.08 (d, J=16.4 Hz, 1H), 7.14-7.17 (m, 2H), 7.23 (d, J=8.0 Hz, 1H), 7.54 (d, J=16.4 Hz, 1H), 7.70 (d, J=1.6 Hz, 1H).

The property values of the title optically active compound with a retention time of 15 minutes are as follows.

$^1$H-NMR (CDCl$_3$) δ (ppm): 1.20 (d, J=6.4 Hz, 3H), 1.66-1.76 (m, 1H), 2.29 (s, 3H), 2.30-2.42 (m, 2H), 3.76-3.83 (m, 1H), 3.85 (s, 3H), 4.19 (dd, J=11.6 Hz, 5.6 Hz, 1H), 4.36 (dd, J=11.6 Hz, 5.6 Hz, 1H), 6.91 (t, J=1.2 Hz, 1H), 7.02-7.07 (m, 3H), 7.11-7.14 (m, 2H), 7.19-7.23 (m, 3H), 7.48 (d, J=16.0 Hz, 1H), 7.69 (d, J=1.6 Hz, 1H).

The property values of the title optically active compound with a retention time of 30 minutes are as follows.

$^1$H-NMR (CDCl$_3$) δ (ppm): 1.20 (d, J=6.4 Hz, 3H), 1.66-1.76 (m, 1H), 2.29 (s, 3H), 2.30-2.42 (m, 2H), 3.76-3.83 (m, 1H), 3.85 (s, 3H), 4.19 (dd, J=11.6 Hz, 5.6 Hz, 1H), 4.36 (dd, J=11.6 Hz, 5.6 Hz, 1H), 6.91 (t, J=1.2 Hz, 1H), 7.02-7.07 (m, 3H), 7.11-7.14 (m, 2H), 7.19-7.23 (m, 3H), 7.48 (d, J=16.0 Hz, 1H), 7.69 (d, J=1.6 Hz, 1H).

Examples 101 and 102

Synthesis of (7S,8S)-8-(4-fluorophenyl)-2-{(E)-2-[3-methoxy-4-(4-methyl-1H-imidazol-1-yl)phenyl]vinyl}-7-methyl-5,6,7,8-tetrahydro-[1,2,4]triazolo[1,5-a]pyridine and (7R,8R)-8-(4-fluorophenyl)-2-{(E)-2-[3-methoxy-4-(4-methyl-1H-imidazol-1-yl)phenyl]vinyl}-7-methyl-5,6,7,8-tetrahydro-[1,2,4]triazolo[1,5-a]pyridine

[Formula 88]

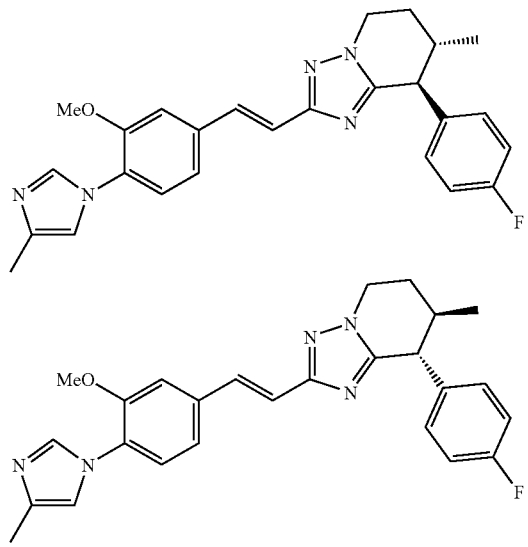

Synthesis of 3-(tert-butyldiphenylsilanyloxy)-1-methylpropyl toluene-4-sulfonate Triethylamine (4.64 mL), p-toluenesulfonyl chloride (4.66 g) and DMAP (271 mg) were added to a solution of 4-(tert-butyldiphenylsilanyloxy)butan-2-ol (7.3 g; CAS #114079-44-6) in 1,2-dichloroethane (80 mL) at 0° C., and the reaction solution was stirred at 60° C. for three hours. The reaction solution was left to cool to room temperature and then concentrated under reduced pressure. Ethyl acetate and brine were added to the residue, and the organic layer was separated. The resulting organic layer was dried over anhydrous sodium sulfate and then concentrated under reduced pressure. The residue was purified by silica gel column chromatography (elution solvent: heptane-ethyl acetate system) to obtain 6.4 g of the title compound. The property value of the compound is as follows.

ESI-MS; m/z 505 [M$^+$+Na].

Synthesis of 5-(tert-butyldiphenylsilanyloxy-2-(4-fluorophenyl)-3-methylpentanoic acid n-Butyl lithium (4.89 mL; 2.66 M solution in hexane) was added dropwise to a solution of 4-fluorophenylacetic acid (1 g) in THF (30 mL) at −78° C., and the reaction solution was stirred for 20 minutes. The reaction solution was heated to 0° C. and stirred for 30 minutes. Then, a solution of 3-(tert-butyldiphenylsilanyloxy)-1-methylpropyl toluene-4-sulfonate (3.2 g) in THF (10 mL) was added dropwise to the reaction solution. The reaction solution was heated to room temperature and stirred at the same temperature for 12 hours. Then, 1 N hydrochloric acid and ethyl acetate were added to the reaction solution, and the organic layer was separated. The resulting organic layer was washed with brine, dried over anhydrous magnesium sulfate and then concentrated under reduced pressure. The residue was purified by silica gel column chromatography (elution solvent: heptane-ethyl acetate system) to obtain 986 mg of the title compound. The property values of the compound are as follows.

$^1$H-NMR (CDCl$_3$) δ (ppm): 0.64 (d, J=6.8 Hz, 3H), 1.04 (s, 9H), 1.31-1.43 (m, 1H), 1.79-1.86 (m, 1H), 2.29-2.45 (m, 1H), 3.31 (d, J=10.0 Hz, 1H), 3.67-3.78 (m, 2H), 6.98 (t, J=8.8 Hz, 2H), 7.21-7.28 (m, 3H), 7.32-7.42 (m, 5H), 7.65 (d, J=7.6 Hz, 4H).

Synthesis of tert-butyl N'-[5-(tert-butyldiphenylsilanyloxy)-2-(4-fluorophenyl)-3-methylpentanoyl]hydrazinecarboxylate BOPCl (860 mg) and IPEA (0.552 mL) were added to a solution of 5-(tert-butyldiphenylsilanyloxy-2-(4-fluorophenyl)-3-methylpentanoic acid (980 mg) and tert-butyl carbazate (558 mg) in methylene chloride (15 mL) at 0° C. The reaction solution was stirred at room temperature for 15 hours. Then, ethyl acetate and a saturated ammonium chloride solution were added to the reaction solution, and the organic layer was separated. The resulting organic layer was washed with brine, dried over anhydrous magnesium sulfate and then concentrated under reduced pressure. The residue was purified by silica gel column chromatography (elution solvent: heptane-ethyl acetate system) to obtain 1.04 g of the title compound. The property value of the compound is as follows.

ESI-MS; m/z 601 [M$^+$+Na].

Synthesis of tert-butyl N'-[2-(4-fluorophenyl)-5-hydroxy-3-methylpentanoyl]hydrazinecarboxylate TBAF (2.7 mL; 1 M solution in THF) was added to a solution of tert-butyl N'-[5-(tert-butyldiphenylsilanyloxy)-2-(4-fluorophenyl)-3-methylpentanoyl]hydrazinecarboxylate (1.04 g) in THF (20 mL). The reaction solution was stirred at room temperature for 1 hours. Then, ethyl acetate and a saturated ammonium chloride solution were added to the reaction solution, and the organic layer was separated. The resulting organic layer was washed with brine, dried over anhydrous magnesium sulfate and then concentrated under reduced pressure. The residue was purified by silica gel column chromatography (elution solvent: heptane-ethyl acetate system) to obtain 525 mg of the title compound. The property value of the compound is as follows.

ESI-MS; m/z 363 [M$^+$+Na].

Synthesis of 5-(N'-tert-butoxycarbonylhydrazino)-4-(4-fluorophenyl)-3-methyl-5-oxo-1-pentyl toluene-4-sulfonate p-Toluenesulfonyl chloride (321 mg) was added to a solution of tert-butyl N'-[2-(4-fluorophenyl)-5-hydroxy-3-methylpentanoyl]hydrazinecarboxylate (520 mg) in pyridine (6 mL). The reaction solution was stirred at room temperature for 12 hours and then concentrated under reduced pressure. Ethyl acetate and brine were added to the residue, and the organic layer was separated. The resulting organic layer was dried over anhydrous magnesium sulfate and concentrated under reduced pressure. The residue was purified by silica gel column chromatography (elution solvent: heptane-ethyl acetate system) to obtain 335 mg of the title compound. The property value of the compound is as follows.

ESI-MS; m/z 517 [M$^+$+Na].

Synthesis of tert-butyl N'-[5-chloro-2-(4-fluorophenyl)-5-hydroxy-3-methylpentanoyl]hydrazinecarboxylate Lithium chloride (283 mg) was added to a solution of 5-(N'-tert-butoxycarbonylhydrazino)-4-(4-fluorophenyl)-3-methyl-5-oxo-1-pentyl toluene-4-sulfonate (330 mg) in DMF (5 mL). The reaction solution was stirred at 80° C. for three hours and then left to cool to room temperature. Water and ethyl acetate were added to the reaction solution, and the organic layer was separated. The resulting organic layer was washed with brine, and then dried over anhydrous magnesium sulfate and concentrated under reduced pressure. The residue was purified by silica gel column chromatography (elution solvent: heptane-ethyl acetate system) to obtain 170 mg of the title compound. The property value of the compound is as follows.

ESI-MS; m/z 381 [M$^+$+Na].

Synthesis of (7S,8S)-8-(4-fluorophenyl)-2-{(E)-2-[3-methoxy-4-(4-methyl-1H-imidazol-1-yl)phenyl]vinyl}-7-methyl-5,6,7,8-tetrahydro-[1,2,4]triazolo[1,5-a]pyridine and (7R,8R)-8-(4-fluorophenyl)-2-{(E)-2-[3-methoxy-4-(4-methyl-1H-imidazol-1-yl)phenyl]vinyl}-7-methyl-5,6,7,8-tetrahydro-[1,2,4]triazolo[1,5-a]pyridine A solution of 4 N hydrochloric acid in ethyl acetate (3 mL) was added to tert-butyl N'-[5-chloro-2-(4-fluorophenyl)-5-hydroxy-3-methylpentanoyl]hydrazinecarboxylate (170 mg). The reaction solution was stirred at room temperature for two hours and then concentrated under reduced pressure. Subsequently, triethylamine (0.292 mL) was added to a solution of the residue in ethanol (3 mL). A mixed solution of ethyl (E)-3-[3-methoxy-4-(4-methyl-1H-imidazol-1-yl)phenyl]acrylimidate dihydrochloride (150 mg) and triethylamine (0.292 mL) in ethanol (3 mL) was added dropwise to the solution, and the reaction solution was stirred at 80° C. for 12 hours. The reaction solution was left to cool to room temperature and then concentrated under reduced pressure. Saturated sodium bicarbonate water and ethyl acetate were added to the resulting residue, and the organic layer was separated. The resulting organic layer was washed with brine, dried over anhydrous magnesium sulfate and then concentrated under reduced pressure. The residue was purified by silica gel column chromatography (elution solvent: ethyl acetate-methanol system) to obtain a racemate of the title compound. The resulting racemate was separated by CHIRALPAK™ IB manufactured by Daicel Chemical Industries, Ltd. (2 cm×25 cm; mobile phase: hexane:ethanol=1:1) to obtain the title optically active compound with a retention time of 25 minutes (20.7 mg, >99% ee) and the title optically active compound with a retention time of 36 minutes (22.4 mg, >99% ee).

The property values of the title compound with a retention time of 25 minutes are as follows.

ESI-MS; m/z 444 [M$^+$+H]. $^1$H-NMR (CDCl$_3$) δ (ppm): 1.06 (d, J=6.4 Hz, 3H), 1.88-2.00 (m, 1H), 2.11-2.25 (m, 2H), 2.29 (s, 3H), 3.72 (d, J=9.2 Hz, 1H), 3.84 (s, 3H), 4.26-4.37 (m, 2H), 6.90 (s, 1H), 7.00-7.12 (m, 7H), 7.19 (d, J=8.0 Hz, 1H), 7.45 (d, J=16.4 Hz, 1H), 7.69 (s, 1H).

The property values of the title compound with a retention time of 36 minutes are as follows.

ESI-MS; m/z 444 [M$^+$+H]. $^1$H-NMR (CDCl$_3$) δ (ppm): 1.06 (d, J=6.4 Hz, 3H), 1.88-2.00 (m, 1H), 2.11-2.25 (m, 2H), 2.29 (s, 3H), 3.72 (d, J=9.2 Hz, 1H), 3.84 (s, 3H), 4.26-4.37 (m, 2H), 6.90 (s, 1H), 7.00-7.12 (m, 7H), 7.19 (d, J=8.0 Hz, 1H), 7.45 (d, J=16.4 Hz, 1H), 7.69 (s, 1H).

Examples 103 and 104

Synthesis of (7S,8S)-2-{(E)-2-[3-methoxy-4-(4-methyl-1H-imidazol-1-yl)phenyl]vinyl}-8-(3,4,5-trifluorophenyl)-5,6,7,8-tetrahydro-[1,2,4]triazolo[1,5-a]pyridin-7-ol and (7R,8R)-2-{(E)-2-[3-methoxy-4-(4-methyl-1H-imidazol-1-yl)phenyl]vinyl}-8-(3,4,5-trifluorophenyl)-5,6,7,8-tetrahydro-[1,2,4]triazolo[1,5-a]pyridin-7-ol

[Formula 89]

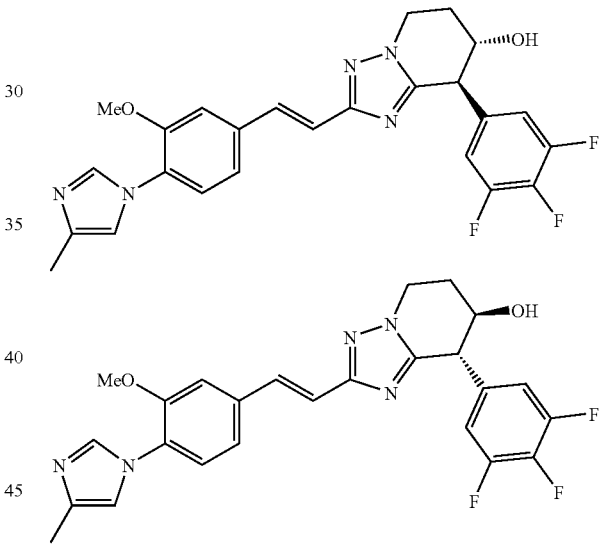

Synthesis of benzyl (3,4,5-trifluorophenyl)acetate

Triethylamine (0.808 mL) and benzyl chloroformate (0.752 mL) were sequentially added dropwise to a solution of 3,4,5-trifluorophenylacetic acid (1 g) in methylene chloride (15 mL) at 0° C., and the reaction solution was stirred at 0° C. for five minutes. DMAP (64.4 mg) was added to the reaction solution which was then stirred at 0° C. for 30 minutes. Ethyl acetate and saturated sodium bicarbonate water were added to the reaction solution, and the organic layer was separated. The resulting organic layer was washed with brine, dried over anhydrous magnesium sulfate and then concentrated under reduced pressure. The residue was purified by silica gel column chromatography (elution solvent: heptane-ethyl acetate system) to obtain 1.43 g of the title compound. The property values of the compound are as follows.

$^1$H-NMR (CDCl$_3$) δ (ppm): 3.59 (s, 2H), 5.14 (s, 2H), 6.90 (dd, J=8.0, 6.4 Hz, 2H), 7.29-7.38 (m, 5H), 3.83 (s, 3H), 3.89

(s, 3H), 6.44 (s, 1H), 6.95 (brs, 1H), 7.04 (d, J=1.6 Hz, 1H), 7.07 (dd, J=8.0, 1.6 Hz, 1H), 7.20 (t, J=8.8 Hz, 2H), 7.28 (d, J=8.0 Hz, 1H), 7.78 (d, J=1.2 Hz, 1H), 7.83 (s, 1H), 8.09 (dd, J=8.8, 5.2 Hz, 2H).

Synthesis of benzyl (2S*,3R*)-5-(tert-butyldiphenylsilanyloxy)-3-hydroxy-2-(3,4,5-trifluorophenyl)pentanoate and benzyl (2S*,3S*)-5-(tert-butyldiphenylsilanyloxy)-3-hydroxy-2-(3,4,5-trifluorophenyl)pentanoate n-Butyl lithium (1.82 mL; 2.66 M solution in hexane) was added dropwise to a solution of diisopropylamine (0.735 mL) in THF (6 mL) at 0° C. The reaction solution was stirred at 0° C. for 20 minutes and then cooled to −78° C. Benzyl (3,4,5-trifluorophenyl)acetate (1.13 g) in THF (18 mL) was added dropwise to the reaction solution, and the reaction solution was stirred at −78° C. for 15 minutes. Thereafter, 3-(tert-butyldiphenylsiloxy)propanol (CAS No. 112897-03-7, 1.26 g) in THF (6 mL) was added dropwise to the reaction solution, and the reaction solution was stirred at −78° C. for 30 minutes. A saturated ammonium chloride solution was added to the reaction solution, and the reaction solution was returned to room temperature. Ethyl acetate was added and the organic layer was separated. The resulting organic layer was washed with brine, dried over anhydrous magnesium sulfate and then concentrated under reduced pressure. The residue was purified by silica gel column chromatography (elution solvent: heptane-ethyl acetate system) to obtain 840 mg of benzyl (2S*,3R*)-5-(tert-butyldiphenylsilanyloxy)-3-hydroxy-2-(3,4,5-trifluorophenyl)pentanoate and 765 mg of benzyl (2S*,3S*)-5-(tert-butyldiphenylsilanyloxy)-3-hydroxy-2-(3,4,5-trifluorophenyl)pentanoate.

The property values of benzyl (2S*,3R*)-5-(tert-butyldiphenylsilanyloxy)-3-hydroxy-2-(3,4,5-trifluorophenyl)pentanoate are as follows.

ESI-MS; m/z 615 [M++Na]. $^1$H-NMR (CDCl$_3$) δ (ppm): 1.03 (s, 9H), 1.57-1.62 (m, 2H), 3.49 (d, J=2.4 Hz, 1H), 3.57 (d, J=6.8 Hz, 1H), 3.77-3.85 (m, 2H), 4.46 (m, 1H), 5.07 (d, J=12.4 Hz, 1H), 5.14 (d, J=12.4 Hz, 1H), 7.02 (dd, J=8.8, 6.4 Hz, 2H), 7.20-7.45 (m, 11H), 7.62 (d, J=8.0 Hz, 4H).

The property values of benzyl (2S*,3S*)-5-(tert-butyldiphenylsilanyloxy)-3-hydroxy-2-(3,4,5-trifluorophenyl)pentanoate are as follows.

ESI-MS; m/z 615 [M++Na]. $^1$H-NMR (CDCl$_3$) δ (ppm): 1.03 (s, 9H), 1.45-1.51 (m, 2H), 3.54 (d, J=4.0 Hz, 1H), 3.57 (d, J=9.2 Hz, 1H), 3.73-3.81 (m, 2H), 4.38 (m, 1H), 5.13 (d, J=12.4 Hz, 1H), 5.19 (d, J=12.4 Hz, 1H), 6.91 (dd, J=8.8, 6.4 Hz, 2H), 7.24-7.44 (m, 11H), 7.57-7.62 (m, 4H).

Synthesis of benzyl (2S*,3R*)-5-(tert-butyldiphenylsilanyloxy)-3-methoxymethoxy-2-(3,4,5-trifluorophenyl)pentanoate IPEA (0.742 mL) and chloromethyl methyl ether (0.324 mL) were added to a solution of benzyl (2S,3R)-5-(tert-butyldiphenylsilanyloxy)-3-hydroxy-2-(3,4,5-trifluorophenyl)pentanoate (840 mg) in 1,2-dichloroethane (20 mL) at 0° C. The reaction solution was stirred at 60° C. for 4 hours and then left to cool to room temperature and concentrated under reduced pressure. Ethyl acetate and a saturated ammonium chloride solution were added to the residue, and the organic layer was separated. The resulting organic layer was washed with brine, dried over anhydrous magnesium sulfate and then concentrated under reduced pressure. The residue was purified by silica gel column chromatography (elution solvent: heptane-ethyl acetate system) to obtain 875 mg of the title compound. The property values of the compound are as follows.

$^1$H-NMR (CDCl$_3$) δ (ppm): 1.03 (s, 9H), 1.55-1.64 (m, 1H), 1.70-1.82 (m, 1H), 3.11 (s, 3H), 3.60-3.73 (m, 2H), 3.74 (d, J=6.0 Hz, 1H), 4.38-4.41 (m, 1H), 4.39 (d, J=6.4 Hz, 1H), 4.51 (d, J=6.4 Hz, 1H), 5.12 (s, 2H), 6.95 (dd, J=8.8, 6.8 Hz, 2H), 7.25-7.43 (m, 11H), 7.61 (d, J=8.0 Hz, 4H).

Synthesis of tert-butyl N'-[(2S*,3R*)-5-(tert-butyldiphenylsilanyloxy)-3-methoxymethoxy-2-(3,4,5-trifluorophenyl)pentanoyl]hydrazinecarboxylate Palladium-carbon (258 mg; 10 wt %) was added to a solution of benzyl (2S*,3R*)-5-(tert-butyldiphenylsilanyloxy)-3-methoxymethoxy-2-(3,4,5-trifluorophenyl)pentanoate (770 mg) in methanol (10 mL). The reaction solution was stirred in a hydrogen atmosphere for two hours and then filtered through celite, and the filtrate was concentrated under reduced pressure. Subsequently, BOPCl (493 mg) and IPEA (0.316 mL) were added to a solution of the residue of tert-butyl carbazate (320 mg) in methylene chloride (20 mL) at 0° C. The reaction solution was stirred at room temperature for 15 hours. Then, ethyl acetate and a saturated ammonium chloride solution were added to the reaction solution, and the organic layer was separated. The resulting organic layer was washed with brine, dried over anhydrous magnesium sulfate and then concentrated under reduced pressure. The residue was purified by silica gel column chromatography (elution solvent: heptane-ethyl acetate system) to obtain 603 mg of the title compound. The property value of the compound is as follows.

ESI-MS; m/z 683 [M++Na].

Synthesis of tert-butyl N'-[(2S*,3R*)-5-hydroxy-3-methoxymethoxy-2-(3,4,5-trifluorophenyl)pentanoyl]hydrazinecarboxylate TBAF (1.36 mL; 1 M solution in THF) was added to a solution of tert-butyl N'-[(2S*,3R*)-5-(tert-butyldiphenylsilanyloxy)-3-methoxymethoxy-2-(3,4,5-trifluorophenyl)pentanoyl]hydrazinecarboxylate (600 mg) in THF (10 mL). The reaction solution was stirred at room temperature for one hour. Then, ethyl acetate and a saturated ammonium chloride solution were added to the reaction solution, and the organic layer was separated. The resulting organic layer was washed with brine, dried over anhydrous magnesium sulfate and then concentrated under reduced pressure. The residue was purified by silica gel column chromatography (elution solvent: heptane-ethyl acetate system) to obtain 383 mg of the title compound. The property value of the compound is as follows.

ESI-MS; m/z 445 [M++Na].

Synthesis of tert-butyl N'-[(2S*,3R*)-5-chloro-3-methoxymethoxy-2-(3,4,5-trifluorophenyl)pentanoyl]hydrazinecarboxylate Triethylamine (0.209 mL) and methanesulfonyl chloride (58 uL) were added to a solution of tert-butyl N'-[(2S*,3R*)-5-hydroxy-3-methoxymethoxy-2-(3,4,5-trifluorophenyl)pentanoyl]hydrazinecarboxylate (264 mg) in methylene chloride (10 mL) at 0° C. The reaction solution was stirred at 0° C. for 30 minutes. Then, ethyl acetate and saturated sodium bicarbonate water were added to the reaction solution, and the organic layer was separated. The resulting organic layer was washed with brine, dried over anhydrous magnesium sulfate and then concentrated under reduced pressure. Subsequently, lithium chloride (265 mg) was added to a solution of the residue in DMF (5 mL), and the reaction solution was stirred at 80° C. for three hours. The reaction solution was left to cool to room temperature. Then, water and ethyl acetate were added to the reaction solution, and the organic layer was separated. The resulting organic layer was washed with brine, dried over anhydrous magnesium sulfate and then concentrated under reduced pressure. The residue was purified by silica gel column chromatography (elution solvent: heptane-ethyl acetate system) to obtain 87.5 mg of the title compound. The property value of the compound is as follows.

ESI-MS; m/z 463 [M⁺+Na].

Synthesis of (7S,8S)-2-{(E)-2-[3-methoxy-4-(4-methyl-1H-imidazol-1-yl)phenyl]vinyl}-8-(3,4,5-trifluorophenyl)-5,6,7,8-tetrahydro-[1,2,4]triazolo[1,5-a]pyridin-7-ol and (7R,8R)-2-{(E)-2-[3-methoxy-4-(4-methyl-1H-imidazol-1-yl)phenyl]vinyl}-8-(3,4,5-trifluorophenyl)-5,6,7,8-tetrahydro-[1,2,4]triazolo[1,5-a]pyridin-7-ol A solution of 4 N hydrochloric acid in ethyl acetate (2 mL) was added to tert-butyl N'-[(2S*,3R*)-5-chloro-3-methoxymethoxy-2-(3,4,5-trifluorophenyl)pentanoyl]hydrazinecarboxylate (100 mg). The reaction solution was stirred at room temperature for two hours and then concentrated under reduced pressure. Subsequently, triethylamine (0.156 mL) was added to a solution of the residue in ethanol (2.5 mL). A mixed solution of ethyl (E)-3-[3-methoxy-4-(4-methyl-1H-imidazol-1-yl)phenyl]acrylimidate dihydrochloride (80 mg) and triethylamine (0.156 mL) in ethanol (2.5 mL) was added dropwise to the solution, and the reaction solution was stirred at 80° C. for 12 hours. The reaction solution was left to cool to room temperature and then concentrated under reduced pressure. Saturated sodium bicarbonate water and ethyl acetate were added to the resulting residue, and the organic layer was separated. The resulting organic layer was washed with brine, dried over anhydrous magnesium sulfate and then concentrated under reduced pressure. The residue was purified by silica gel column chromatography (elution solvent: heptane-ethyl acetate system) to obtain a racemate of the title compound. The resulting racemate was separated by CHIRALCEL™ OD-H manufactured by Daicel Chemical Industries, Ltd. (2 cm×25 cm; mobile phase: hexane:ethanol=8:2) to obtain the title optically active compound with a retention time of 11 minutes (8.2 mg, >99% ee) and the title optically active compound with a retention time of 17 minutes (7.4 mg, >99% ee).

The property values of the title compound with a retention time of 11 minutes are as follows.

ESI-MS; m/z 482 [M⁺+H]. ¹H-NMR (CDCl₃) δ (ppm): 2.20-2.35 (m, 2H), 2.27 (s, 3H), 3.84 (s, 3H), 4.26-4.34 (m, 3H), 4.39-4.45 (m, 1H), 6.77 (dd, J=8.0, 6.8 Hz, 2H), 6.90 (d, J=1.2 Hz, 1H), 7.01 (d, J=16.4 Hz, 1H), 7.07 (d, J=8.4 Hz, 1H), 7.08 (s, 1H), 7.20 (d, J=8.4 Hz, 1H), 7.45 (d, J=16.4 Hz, 1H), 7.56 (d, J=1.2 Hz, 1H).

The property values of the title compound with a retention time of 17 minutes corresponded to the property values of the title compound with a retention time of 11 minutes.

ESI-MS; m/z 482 [M⁺+H]. ¹H-NMR (CDCl₃) δ (ppm): 2.20-2.35 (m, 2H), 2.27 (s, 3H), 3.84 (s, 3H), 4.26-4.34 (m, 3H), 4.39-4.45 (m, 1H), 6.77 (dd, J=8.0, 6.8 Hz, 2H), 6.86 (d, J=7.2 Hz, 1H), 6.90 (d, J=2.0 Hz, 1H), 7.01 (d, J=16.4 Hz, 1H), 7.07 (d, J=8.4 Hz, 1H), 7.08 (d, J=2.0 Hz, 1H), 7.20 (d, J=8.4 Hz, 1H), 7.45 (d, J=16.4 Hz, 1H), 7.56 (d, J=1.2 Hz, 1H).

Examples 105 and 106

Synthesis of (7R,8S)-2-{(E)-2-[3-methoxy-4-(4-methyl-1H-imidazol-1-yl)phenyl]vinyl}-8-(3,4,5-trifluorophenyl)-5,6,7,8-tetrahydro-[1,2,4]triazolo[1,5-a]pyridin-7-ol and (7S,8R)-2-{(E)-2-[3-methoxy-4-(4-methyl-1H-imidazol-1-yl)phenyl]vinyl}-8-(3,4,5-trifluorophenyl)-5,6,7,8-tetrahydro-[1,2,4]triazolo[1,5-a]pyridin-7-ol

[Formula 90]

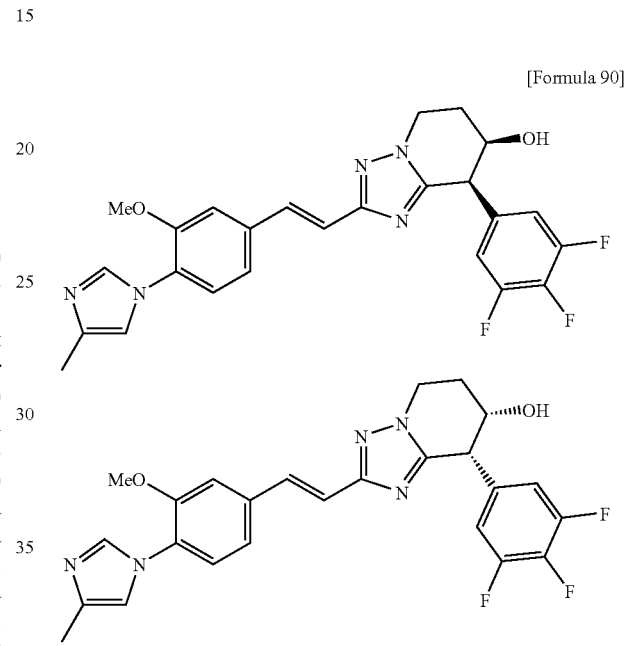

(1) Synthesis of (7R,8S)-2-{(E)-2-[3-methoxy-4-(4-methyl-1H-imidazol-1-yl)phenyl]vinyl}-8-(3,4,5-trifluorophenyl)-5,6,7,8-tetrahydro-trifluorophenyl)-[1,2,4]triazolo[1,5-a]pyridin-7-ol and (7S,8R)-2-{(E)-2-[3-methoxy-4-(4-methyl-1H-imidazol-1-yl)phenyl]vinyl}-8-(3,4,5-trifluorophenyl)-5,6,7,8-tetrahydro-[1,2,4]triazolo[1,5-a]pyridin-7-ol A racemate of the title compound (55.1 mg) was obtained from benzyl (2S*,3S*)-5-(tert-butyldiphenylsilanyloxy)-3-hydroxy-2-(3,4,5-trifluorophenyl)pentanoate (1.01 g) by the same method as in Examples 103 and 104. The resulting racemate was separated by CHIRALPAK™ AD-H manufactured by Daicel Chemical Industries, Ltd. (2 cm×25 cm; mobile phase: ethanol) to obtain the title optically active compound with a retention time of 6 minutes (11.0 mg, >99% ee) and the title optically active compound with a retention time of 11 minutes (8.6 mg, >99% ee).

The property values of the title compound with a retention time of 6 minutes are as follows.

ESI-MS; m/z 482 [M⁺+H]. ¹H-NMR (CDCl₃) δ (ppm): 2.20-2.40 (m, 2H), 2.28 (s, 3H), 3.85 (s, 3H), 4.20-4.34 (m, 3H), 4.40-4.47 (m, 1H), 6.79 (dd, J=8.0, 6.0 Hz, 2H), 6.90 (s, 1H), 7.01 (d, J=16.0 Hz, 1H), 7.10 (d, J=8.8 Hz, 1H), 7.11 (s, 1H), 7.20 (d, J=8.8 Hz, 1H), 7.46 (d, J=16.0 Hz, 1H), 7.59 (s, 1H).

The property values of the title compound with a retention time of 11 minutes corresponded to the property values of the title compound with a retention time of 6 minutes.

ESI-MS; m/z 482 [M⁺+H]. ¹H-NMR (CDCl₃) δ (ppm): 2.20-2.40 (m, 2H), 2.28 (s, 3H), 3.85 (s, 3H), 4.20-4.34 (m, 3H), 4.40-4.47 (m, 1H), 6.79 (dd, J=8.0, 6.0 Hz, 2H), 6.90 (s, 1H), 7.01 (d, J=16.0 Hz, 1H), 7.10 (d, J=8.8 Hz, 1H), 7.11 (s, 1H), 7.20 (d, J=8.8 Hz, 1H), 7.46 (d, J=16.0 Hz, 1H), 7.59 (s, 1H).

Examples 107, 108, 109 and 110

Synthesis of (6R,8S)-2-{(E)-2-[3-methoxy-4-(4-methyl-1H-imidazol-1-yl)phenyl]vinyl}-8-(3,4,5-trifluorophenyl)-5,6,7,8-tetrahydro-[1,2,4]triazolo[1,5-a]pyridin-6-ol, (6S,8R)-2-{(E)-2-[3-methoxy-4-(4-methyl-1H-imidazol-1-yl)phenyl]vinyl}-8-(3,4,5-trifluorophenyl)-5,6,7,8-tetrahydro-[1,2,4]triazolo[1,5-a]pyridin-6-ol, (6S,8S)-2-{(E)-2-[3-methoxy-4-(4-methyl-1H-imidazol-1-yl)phenyl]vinyl}-8-(3,4,5-trifluorophenyl)-5,6,7,8-tetrahydro-[1,2,4]triazolo[1,5-a]pyridin-6-ol and (6R,8R)-2-{(E)-2-[3-methoxy-4-(4-methyl-1H-imidazol-1-yl)phenyl]vinyl}-8-(3,4,5-trifluorophenyl)-5,6,7,8-tetrahydro-[1,2,4]triazolo[1,5-a]pyridin-6-ol

[Formula 91]

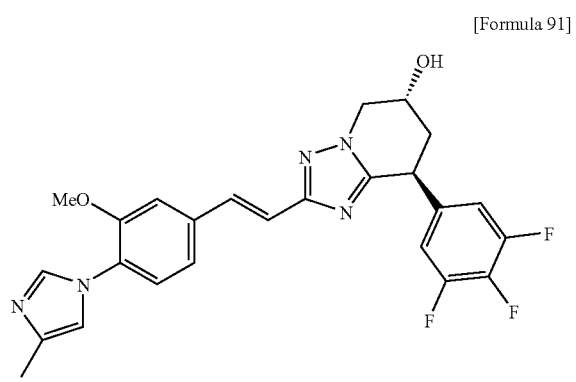

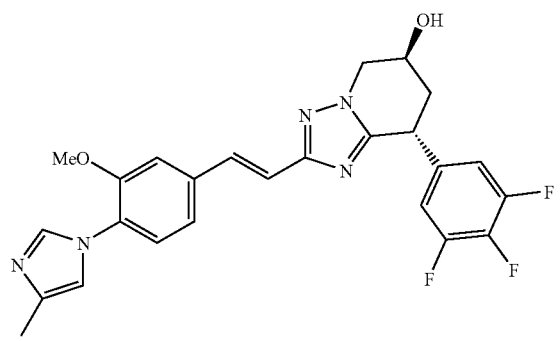

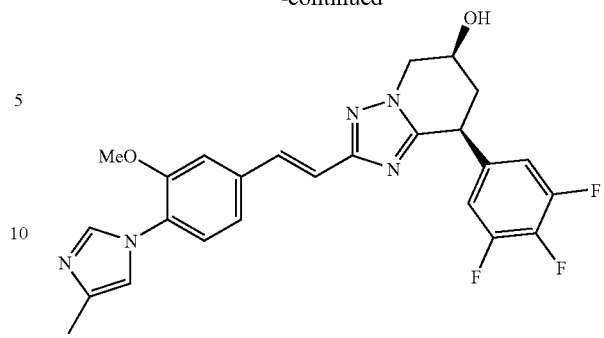

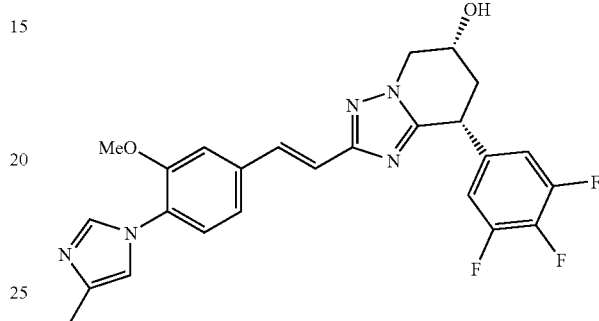

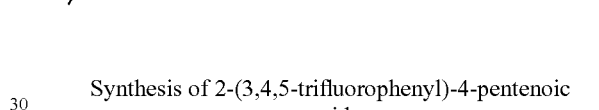

Synthesis of 2-(3,4,5-trifluorophenyl)-4-pentenoic acid n-Butyl lithium (7.89 mL; 2.66 M solution in hexane) was added to a solution of 3,4,5-trifluorophenylacetic acid (2 g) in THF (50 mL) at −78° C. The reaction solution was stirred at −78° C. for 20 minutes. Then, the reaction solution was heated to 0° C. and further stirred for 30 minutes. Allyl bromide (0.999 mL) was added dropwise to the reaction solution, and the reaction solution was stirred at room temperature for three hours. A 1 N sodium hydroxide solution and diethyl ether were added to the reaction solution, and the aqueous layer was separated. 5 N hydrochloric acid and ethyl acetate were added to the resulting aqueous layer, and the organic layer was separated. The resulting organic layer was washed with brine, dried over anhydrous magnesium sulfate and then concentrated under reduced pressure. The residue was purified by silica gel column chromatography (elution solvent: heptane-ethyl acetate system) to obtain 1.45 g of the title compound. The property values of the compound are as follows.

¹H-NMR (CDCl₃) δ (ppm): 2.44-2.52 (m, 1H), 2.72-2.81 (m, 1H), 3.58 (t, J=7.6 Hz, 1H), 5.03-5.10 (m, 2H), 5.60-5.71 (m, 1H), 6.90 (dd, J=8.4, 6.4 Hz, 2H).

Synthesis of tert-butyl N'-[2-(3,4,5-trifluorophenyl)penten-4-oyl]hydrazinecarboxylate BOPCl (2.57 g) and IPEA (1.65 mL) were added to a solution of 2-(3,4,5-trifluorophenyl)-4-pentenoic acid (1.45 g) and tert-butyl carbazate (1.94 g) in methylene chloride (30 mL) at 0° C. The reaction solution was stirred at room temperature for 15 hours. Then, ethyl acetate and a saturated ammonium chloride solution were added to the reaction solution, and the organic layer was separated. The resulting organic layer was washed with brine, dried over anhydrous magnesium sulfate and then concentrated under reduced pressure. The residue was purified by silica gel column chromatography (elution solvent: heptane-ethyl acetate system) to obtain 1.77 g of the title compound. The property value of the compound is as follows.

ESI-MS; m/z 345 [M$^+$+H].

Synthesis of tert-butyl N'-[4,5-dihydroxy-2-(3,4,5-trifluorophenyl)pentanoyl]hydrazinecarboxylate Osmium tetroxide (2.61 mL; 2.5 wt %) was added to a solution of tert-butyl N'-[2-(3,4,5-trifluorophenyl)penten-4-oyl]hydrazinecarboxylate (1.77 g) and N-methylmorpholine N-oxide (1.81 g) in acetone (40 mL) and water (40 mL). The reaction solution was stirred at room temperature for 4 hours. Then, ethyl acetate and a saturated sodium thiosulfate solution were added to the reaction solution, and the organic layer was separated. The resulting organic layer was washed with 1 N hydrochloric acid and brine, dried over anhydrous sodium sulfate and then concentrated under reduced pressure. The residue was purified by silica gel column chromatography (elution solvent: ethyl acetate-methanol system) to obtain 1.09 g of the title compound. The property value of the compound is as follows.

ESI-MS; m/z 401 [M$^+$+Na].

Synthesis of 5-(N'-tert-butoxycarbonylhydrazino)-2-hydroxy-5-oxo-4-(3,4,5-trifluorophenyl)pentyl toluene-4-sulfonate p-Toluenesulfonyl chloride (605 mg) was added to a solution of tert-butyl N'-[4,5-dihydroxy-2-(3,4,5-trifluorophenyl)pentanoyl]hydrazinecarboxylate (1.09 g) in pyridine (11 mL) at room temperature. The reaction solution was stirred at room temperature for 12 hours and then concentrated under reduced pressure. Ethyl acetate was added to the residue, and the organic layer was washed with brine, dried over anhydrous sodium sulfate and then concentrated under reduced pressure. The residue was purified by silica gel column chromatography (elution solvent: heptane-ethyl acetate system) to obtain 1.03 g of the title compound. The property value of the compound is as follows.

ESI-MS; m/z 555 [M$^+$+H].

Synthesis of tert-butyl N'-[5-chloro-4-hydroxy-2-(3,4,5-trifluorophenyl)pentanoyl]hydrazinecarboxylate Lithium chloride (818 mg) was added to a solution of 5-(N'-tert-butoxycarbonylhydrazino)-2-hydroxy-5-oxo-4-(3,4,5-trifluorophenyl)pentyl toluene-4-sulfonate (1.03 g) in DMF (8 mL). The reaction solution was stirred at 80° C. for three hours and then left to cool to room temperature. Water and ethyl acetate were added to the reaction solution, and the organic layer was separated. The resulting organic layer was washed with brine, dried over anhydrous magnesium sulfate and then concentrated under reduced pressure. The residue was purified by silica gel column chromatography (elution solvent: heptane-ethyl acetate system) to obtain 734 mg of the title compound. The property value of the compound is as follows.

ESI-MS; m/z 419 [M$^+$+Na].

Synthesis of tert-butyl N'-[4-(tert-butyldiphenylsilanyloxy)-5-chloro-2-(3,4,5-trifluorophenyl)pentanoyl]hydrazinecarboxylate tert-Butyldiphenylchlorosilane (0.889 mL), imidazole (233 mg) and DMAP (41.9 mg) were added to a solution of tert-butyl N'-[5-chloro-4-hydroxy-2-(3,4,5-trifluorophenyl)pentanoyl]hydrazinecarboxylate (680 mg) in DMF (5 mL). The reaction solution was stirred at 60° C. for two hours and then left to cool to room temperature. A saturated ammonium chloride solution and ethyl acetate were added to the reaction solution, and the organic layer was separated. The resulting organic layer was washed with brine, dried over anhydrous magnesium sulfate and then concentrated under reduced pressure. The residue was purified by silica gel column chromatography (elution solvent: heptane-ethyl acetate system) to obtain 831 mg of the title compound. The property value of the compound is as follows.

ESI-MS; m/z 657 [M$^+$+Na].

Synthesis of 6-(tert-butyldiphenylsilanyloxy)-2-{(E)-2-[3-methoxy-4-(4-methyl-1H-imidazol-1-yl)phenyl]vinyl}-8-(3,4,5-trifluorophenyl)-5,6,7,8-tetrahydro-[1,2,4]triazolo[1,5-a]pyridine TFA (5 mL) was added dropwise to a solution of tert-butyl N'-[4-(tert-butyldiphenylsilanyloxy)-5-chloro-2-(3,4,5-trifluorophenyl)pentanoyl]hydrazinecarboxylate (830 mg) in methylene chloride (10 mL) at 0° C. The reaction solution was stirred at room temperature for two hours. Then, saturated sodium bicarbonate water and chloroform were added, and the organic layer was separated. The aqueous layer was extracted with chloroform twice. The resulting organic layers were combined, washed with brine, dried over anhydrous magnesium sulfate and then concentrated under reduced pressure. Subsequently, triethylamine (1.28 mL) was added to a solution of the residue in ethanol (10 mL). A mixed solution of ethyl (E)-3-[3-methoxy-4-(4-methyl-1H-imidazol-1-yl)phenyl]acrylimidate dihydrochloride (400 mg) in ethanol (10 mL) and triethylamine (1.28 mL) was added dropwise to the solution, and the reaction solution was stirred at 80° C. for 12 hours. The reaction solution was left to cool to room temperature and then concentrated under reduced pressure. Saturated sodium bicarbonate water and ethyl acetate were added to the resulting residue, and the organic layer was separated. The resulting organic layer was washed with brine, dried over anhydrous magnesium sulfate and then concentrated under reduced pressure. The residue was purified by silica gel column chromatography (elution solvent: heptane-ethyl acetate system) to obtain 510 mg of the title compound. The property value of the compound is as follows.

ESI-MS; m/z 720 [M$^+$+H].

Synthesis of (6R,8S)-2-{(E)-2-[3-methoxy-4-(4-methyl-1H-imidazol-1-yl)phenyl]vinyl}-8-(3,4,5-trifluorophenyl)-5,6,7,8-tetrahydro-[1,2,4]triazolo[1,5-a]pyridin-6-ol, (6S,8R)-2-{(E)-2-[3-methoxy-4-(4-methyl-1H-imidazol-1-yl)phenyl]vinyl}-8-(3,4,5-trifluorophenyl)-5,6,7,8-tetrahydro-[1,2,4]triazolo[1,5-a]pyridin-6-ol, (6S,8S)-2-{(E)-2-[3-methoxy-4-(4-methyl-1H-imidazol-1-yl)phenyl]vinyl}-8-(3,4,5-trifluorophenyl)-5,6,7,8-tetrahydro-[1,2,4]triazolo[1,5-a]pyridin-6-ol and (6R,8R)-2-{(E)-2-[3-methoxy-4-(4-methyl-1H-imidazol-1-yl)phenyl]vinyl}-8-(3,4,5-trifluorophenyl)-5,6,7,8-tetrahydro-[1,2,4]triazolo[1,5-a]pyridin-6-ol TBAF (1.06 mL; 1 M solution in THF) was added to a solution of 6-(tert-butyldiphenylsilanyloxy)-2-{(E)-2-[3-methoxy-4-(4-methyl-1H-imidazol-1-yl)phenyl]vinyl}-8-(3,4,5-trifluorophenyl)-5,6,7,8-tetrahydro-[1,2,4]triazolo[1,5-a]pyridine (510 mg) in THF (10 mL), and the reaction solution was stirred at room temperature for one hour. Saturated sodium bicarbonate water and ethyl acetate were added to the reaction solution, and the organic layer was separated. The resulting organic layer was washed with brine, dried over anhydrous magnesium sulfate and then concentrated under reduced pressure. The residue was purified by silica gel column chromatography (elution solvent: ethyl acetate-methanol system) to obtain a diastereomer mixture of the title compound. The resulting mixture was separated by CHIRALPAK™ IA manufactured by Daicel Chemical Industries, Ltd. (2 cm×25 cm; mobile phase: ethanol) to obtain (6R,8S)-2-{(E)-2-[3-methoxy-4-(4-methyl-1H-imidazol-1-yl)phenyl]vinyl}-8-(3,4,5-trifluorophenyl)-5,6,7,8-tetrahydro-[1,2,4]triazolo[1,5-a]pyridin-6-ol and (6S,8R)-2-{(E)-2-[3-methoxy-4-(4-methyl-1H-imidazol-1-yl)phenyl]vinyl}-8-(3,4,5-trifluorophenyl)-5,6,7,8-tetrahydro-[1,2,4]triazolo[1,5-a]pyridin-6-ol as an optically active compound with a retention time of 5.8 minutes (40.6 mg) and an optically active compound with a retention time of 7.1 minutes (39.0 mg), respectively.

The property values of the compound with a retention time of 5.8 minutes are as follows.

ESI-MS; m/z 482 [M$^+$+H]. $^1$H-NMR (CD$_3$OD) δ (ppm): 1.90-2.20 (m, 1H), 2.24 (s, 3H), 2.40-2.49 (m, 1H), 3.91 (s, 3H), 4.25 (d, J=13.2 Hz, 1H), 4.41-4.53 (m, 3H), 7.06 (d, J=1.6 Hz, 1H), 7.08 (d, J=16.0 Hz, 1H), 7.14 (dd, J=8.8, 6.0 Hz, 1H), 7.23 (dd, J=8.0, 1.6 Hz, 1H), 7.33 (d, J=8.0 Hz, 1H), 7.35 (d, J=1.6 Hz, 1H), 7.48 (d, J=16.0 Hz, 1H), 7.79 (s, 1H).

The property values of the compound with a retention time of 7.1 minutes are as follows.

ESI-MS; m/z 482 [M$^+$+H]. $^1$H-NMR (CD$_3$OD) δ (ppm): 1.90-2.20 (m, 1H), 2.24 (s, 3H), 2.40-2.49 (m, 1H), 3.91 (s, 3H), 4.25 (d, J=13.2 Hz, 1H), 4.41-4.53 (m, 3H), 7.06 (d, J=1.6 Hz, 1H), 7.08 (d, J=16.0 Hz, 1H), 7.14 (dd, J=8.8, 6.0 Hz, 1H), 7.23 (dd, J=8.0, 1.6 Hz, 1H), 7.33 (d, J=8.0 Hz, 1H), 7.35 (d, J=1.6 Hz, 1H), 7.48 (d, J=16.0 Hz, 1H), 7.79 (s, 1H).

The remaining diastereomers were separated by CHIRALPAK™ AD-H manufactured by Daicel Chemical Industries, Ltd. (2 cm×25 cm; mobile phase: ethanol) to obtain (6S,8S)-2-{(E)-2-[3-methoxy-4-(4-methyl-1H-imidazol-1-yl)phenyl]vinyl}-8-(3,4,5-trifluorophenyl)-5,6,7,8-tetrahydro-[1,2,4]triazolo[1,5-a]pyridin-6-ol and (6R,8R)-2-{(E)-2-[3-methoxy-4-(4-methyl-1H-imidazol-1-yl)phenyl]vinyl}-8-(3,4,5-trifluorophenyl)-5,6,7,8-tetrahydro-[1,2,4]triazolo[1,5-a]pyridin-6-ol as an optically active compound with a retention time of 6.2 minutes (10.2 mg) and an optically active compound with a retention time of 8.2 minutes (7.4 mg), respectively.

The property values of the compound with a retention time of 6.2 minutes are as follows.

ESI-MS; m/z 482 [M$^+$+H]. $^1$H-NMR (CD$_3$OD) δ (ppm): 2.06-2.15 (m, 1H), 2.23 (s, 3H), 2.49-2.55 (m, 1H), 3.90 (s, 3H), 4.06 (dd, J=12.0, 8.0 Hz, 1H), 4.35-4.48 (m, 3H), 7.03-7.12 (m, 2H), 7.15 (dd, J=8.8, 6.4 Hz, 2H), 7.22 (dd, J=8.0, 1.6 Hz, 1H), 7.32 (d, J=8.0 Hz, 1H), 7.33 (d, J=1.6 Hz, 1H), 7.46 (d, J=16.4 Hz, 1H), 7.79 (s, 1H).

The property values of the compound with a retention time of 8.2 minutes are as follows.

ESI-MS; m/z 482 [M$^+$+H]. $^1$H-NMR (CD$_3$OD) δ (ppm): 2.06-2.15 (m, 1H), 2.23 (s, 3H), 2.49-2.55 (m, 1H), 3.90 (s, 3H), 4.06 (dd, J=12.0, 8.0 Hz, 1H), 4.35-4.48 (m, 3H), 7.03-7.12 (m, 2H), 7.15 (dd, J=8.8, 6.4 Hz, 2H), 7.22 (dd, J=8.0, 1.6 Hz, 1H), 7.32 (d, J=8.0 Hz, 1H), 7.33 (d, J=1.6 Hz, 1H), 7.46 (d, J=16.4 Hz, 1H), 7.79 (s, 1H).

Examples 111 and 112

Synthesis of (−) and (+)-8-cyclopropyl-2-{(E)-2-[3-methoxy-4-(4-methyl-1H-imidazol-1-yl)phenyl]vinyl}-5,6,7,8-tetrahydro[1,2,4]triazolo[1,5-a]pyridine

[Formula 92]

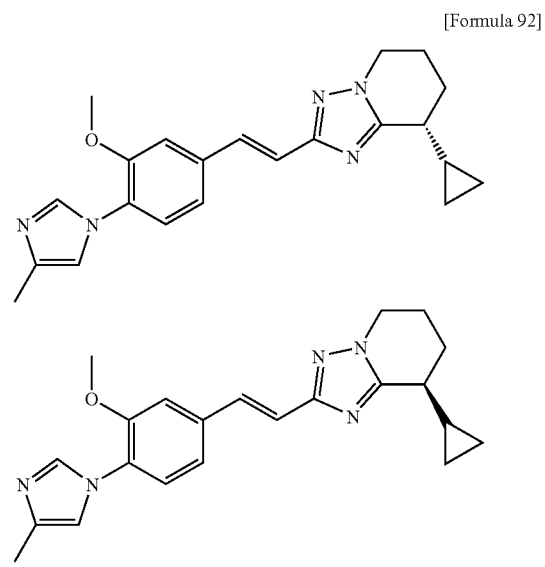

Synthesis of tert-butyl N'-(5-chloro-2-cyclopropyl-pentanoyl)-hydrazinecarboxylate n-Butyl lithium (2.64 M solution in hexane, 3.8 ml) was added dropwise to a solution of diisopropylamine (1.5 ml) in THF (15 ml) at −30° C., and the reaction solution was stirred at the same temperature for 15 minutes. The reaction solution was cooled to −78° C. Then, a solution of cyclopropylacetic acid (CAS No. 5239-82-7, 500 mg) in THF (3 ml) was added dropwise and the reaction solution was further stirred at room temperature for three hours. The reaction solution was cooled to 0° C., and then 1-bromo-3-chloropropane (CAS No. 109-70-6, 0.55 ml) was added dropwise. The reaction solution was stirred at the same temperature for 10 minutes and at room temperature for further one hour. Ice water and diethyl ether were added to the reaction solution, and the aqueous layer was separated. Then, 5 N hydrochloric acid (3 ml) and ethyl acetate were added to the aqueous layer, and the organic layer was separated. The resulting ethyl acetate layer was washed with brine, dried over anhydrous magnesium sulfate and then concentrated under reduced pressure to obtain crude 5-chloro-2-cyclopropyl-valeric acid (550 mg).

IPEA (1.6 ml) and BOPCl (1.2 g) were added to a solution of the crude 5-chloro-2-cyclopropyl-valeric acid (550 mg) and tert-butyl carbazate (CAS No. 870-46-2, 555 mg) in methylene chloride (5 ml), and the reaction solution was stirred at room temperature for three hours. Ethyl acetate and water were added to the reaction solution, and the organic layer was separated. The organic layer was sequentially washed with 1 N hydrochloric acid, water, a saturated sodium bicarbonate solution and brine, dried over anhydrous magnesium sulfate and then concentrated under reduced pressure.

The resulting residue was purified by silica gel column chromatography (elution solvent: heptane-ethyl acetate system) to obtain 210 mg of the title compound. The property value of the compound is as follows.

ESI-MS; m/z 313 [M$^+$+Na]. $^1$H-NMR (CDCl$_3$) δ (ppm): 0.20-0.31 (m, 2H), 0.57-0.70 (m, 2H), 0.90-1.00 (m, 1H), 1.43-1.55 (m, 1H), 1.48 (s, 9H), 1.81-1.97 (m, 4H), 3.49-3.60 (m, 2H), 6.48 (brs, 1H), 7.38 (brs, 1H).

Synthesis of 5-chloro-2-cyclopropyl-valeric acid hydrazide

Trifluoroacetic acid (0.5 ml) was added to a solution of tert-butyl N'-(5-chloro-2-cyclopropyl-pentanoyl)-hydrazinecarboxylate (208 mg) in methylene chloride (1 ml) under ice-cooling, and then the reaction solution was stirred at room temperature for two hours. A saturated sodium bicarbonate solution and ethyl acetate were added to the reaction solution, and the organic layer was separated. The organic layer was sequentially washed with a saturated sodium bicarbonate solution and brine. The combined aqueous layers were reextracted with ethyl acetate (twice). The combined organic layers were dried over anhydrous magnesium sulfate and then concentrated under reduced pressure to obtain 127 mg of the title compound. The property values of the compound are as follows.

ESI-MS; m/z 191 [M$^+$+H]. $^1$H-NMR (CDCl$_3$) δ (ppm): 0.16-0.24 (m, 2H), 0.52-0.68 (m, 2H), 0.86-0.95 (m, 1H), 1.31-1.37 (m, 1H), 1.78-2.00 (m, 4H), 3.48-3.60 (m, 2H), 3.96 (brs, 2H), 6.88 (brs, 1H).

Synthesis of (−) and (+)-8-cyclopropyl-2-{(E)-2-[3-methoxy-4-(4-methyl-1H-imidazol-1-yl)phenyl]vinyl}-5,6,7,8-tetrahydro[1,2,4]triazolo[1,5-a]pyridine A solution of 5-chloro-2-cyclopropyl-valeric acid hydrazide (125 mg) in ethanol (1.5 mL) was added to a solution of ethyl (E)-3-[3-methoxy-4-(4-methyl-1H-imidazol-1-yl)phenyl]acrylimidate dihydrochloride (259 mg) and TEA (0.46 ml) in ethanol (3 ml), and the reaction solution was stirred at 70° C. for 22 hours. The reaction solution was left to cool to room temperature. Then, ethyl acetate and water were added to the reaction solution, and the organic layer was separated. The organic layer was washed with brine, dried over anhydrous magnesium sulfate and then concentrated under reduced pressure. The resulting residue was purified by silica gel column chromatography (carrier: Chromatorex™ NH; elution solvent: heptane-ethyl acetate system) and again purified by silica gel column chromatography (elution solvent: ethyl acetate-methanol system) to obtain 43 mg of racemic 8-cyclopropyl-2-{(E)-2-[3-methoxy-4-(4-methyl-1H-imidazol-1-yl)phenyl]vinyl}-5,6,7,8-tetrahydro[1,2,4]triazolo[1,5-a]pyridine. Then, the racemate was separated by CHIRALPAK™ IB manufactured by Daicel Chemical Industries, Ltd. (2 cm×25 cm; mobile phase: 20% ethanol-hexane) to obtain the title optically active compound with a retention time of 28 minutes and negative optical rotation (16.4 mg; 100% ee) and the title optically active compound with a retention time of 49 minutes and positive optical rotation (16.3 mg; 99% ee).

The property values of the title optically active compound with a retention time of 28 minutes are as follows.

ESI-MS; m/z 376 [M$^+$+H]. $^1$H-NMR (CDCl$_3$) δ (ppm): 0.31-0.39 (m, 1H), 0.52-0.65 (m, 2H), 0.73-0.81 (m, 1H), 0.99-1.09 (m, 1H), 1.83-1.93 (m, 1H), 1.97-2.17 (m, 2H), 2.21-2.32 (m, 1H), 2.30 (s, 3H), 2.33-2.40 (m, 1H), 3.88 (s, 3H), 4.16 (t, J=6.0 Hz, 2H), 6.91 (d, J=0.8 Hz, 1H), 7.08 (d, J=16.4 Hz, 1H), 7.16 (dd, J=8.0, 1.6 Hz, 1H), 7.19 (d, J=1.6 Hz, 1H), 7.22 (d, J=8.0 Hz, 1H), 7.54 (d, J=16.4 Hz, 1H), 7.69 (d, J=0.8 Hz, 1H).

The property values of the title optically active compound with a retention time of 49 minutes are as follows.

ESI-MS; m/z 376 [M$^+$+H]. $^1$H-NMR (CDCl$_3$) δ (ppm): 0.31-0.39 (m, 1H), 0.52-0.65 (m, 2H), 0.73-0.81 (m, 1H), 0.99-1.09 (m, 1H), 1.83-1.93 (m, 1H), 1.97-2.17 (m, 2H), 2.21-2.32 (m, 1H), 2.30 (s, 3H), 2.33-2.40 (m, 1H), 3.88 (s, 3H), 4.16 (t, J=6.0 Hz, 2H), 6.91 (d, J=0.8 Hz, 1H), 7.08 (d, J=16.4 Hz, 1H), 7.16 (dd, J=8.0, 1.6 Hz, 1H), 7.19 (d, J=1.6 Hz, 1H), 7.22 (d, J=8.0 Hz, 1H), 7.54 (d, J=16.4 Hz, 1H), 7.69 (d, J=0.8 Hz, 1H).

Examples 113 and 114

Synthesis of (+) and (−)-8-cyclohexyl-2-{(E)-2-[3-methoxy-4-(4-methyl-1H-imidazol-1-yl)phenyl]vinyl}-5,6,7,8-tetrahydro[1,2,4]triazolo[1,5-a]pyridine

[Formula 93]

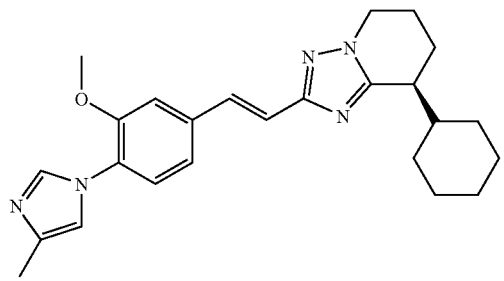

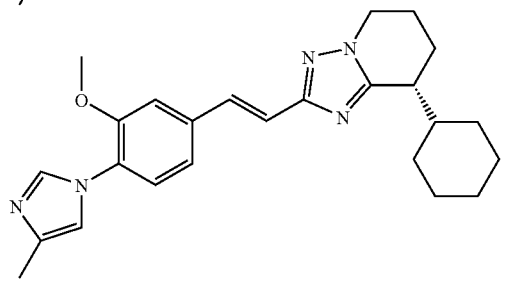

Synthesis of methyl 5-chloro-2-cyclohexyl-valerate n-Butyl lithium (2.64 M solution in hexane, 3.8 ml) was added dropwise to a solution of diisopropylamine (1.55 ml) in THF (15 ml) under ice-cooling, and the reaction solution was stirred at the same temperature for 10 minutes. The reaction solution was cooled to −78° C. Then, a solution of methyl cyclohexylacetate (CAS No. 14352-61-5, 500 mg) in THF (3 ml) was added dropwise and the reaction solution was stirred at the same temperature for 30 minutes. Then, 1-chloro-3-iodopropane (CAS No. 6940-76-7, 1.1 ml) was added dropwise to the reaction solution. The reaction solution was stirred at the same temperature for 20 minutes and then gradually heated to room temperature. Water and ethyl acetate were added to the reaction solution, and the organic layer was separated. The organic layer was sequentially washed with 1 N hydrochloric acid, water, a saturated sodium bicarbonate solution and brine, dried over anhydrous magnesium sulfate and then concentrated under reduced pressure. The resulting residue was purified by silica gel column chromatography (elution solvent: hexane-diethyl ether system) to obtain 1.00 g of the title compound. The property value of the compound is as follows.

ESI-MS; m/z 233 [M+ +H].

Synthesis of tert-butyl N'-(5-chloro-2-cyclohexyl-pentanoyl)-hydrazinecarboxylate A 5 N sodium hydroxide solution (2.5 ml) was added to a solution of methyl 5-chloro-2-cyclohexyl-valerate (1.00 g) in THF (3 ml)-methanol (6 ml). The reaction solution was stirred at room temperature for six hours and at 60° C. for further two hours. After allowing the reaction solution to cool, water and diethyl ether were added to the reaction solution, and the aqueous layer was separated. 5 N hydrochloric acid (2.6 ml) and ethyl acetate were added to the aqueous layer, and the organic layer was separated. The ethyl acetate extraction layer was washed with brine, dried over anhydrous magnesium sulfate and then concentrated under reduced pressure. The resulting residue was purified by silica gel column chromatography (heptane-ethyl acetate system) to obtain 5-chloro-2-cyclohexyl-valeric acid (287 mg).

IPEA (0.68 ml) and BOPCl (496 mg) were added to a solution of 5-chloro-2-cyclohexyl-valeric acid (285 mg) and tert-butyl carbazate (215 mg) in methylene chloride (2.5 ml), and the reaction solution was stirred at room temperature for 5.5 hours. Ethyl acetate and water were added to the reaction solution, and the organic layer was separated. The organic layer was sequentially washed with 1 N hydrochloric acid, water, a saturated sodium bicarbonate solution and brine, dried over anhydrous magnesium sulfate and then concentrated under reduced pressure. The resulting residue was purified by silica gel column chromatography (elution solvent: heptane-ethyl acetate system) to obtain 156 mg of the title compound. The property values of the compound are as follows.

ESI-MS; m/z 355 [M+ +Na]. $^1$H-NMR (CDCl$_3$) δ (ppm): 0.90-1.32 (m, 6H), 1.47 (s, 9H), 1.50-1.94 (m, 1H), 3.46-3.61 (m, 2H), 6.46 (brs, 1H), 7.14 (brs, 1H).

Synthesis of 5-chloro-2-cyclohexyl-valeric acid hydrazide hydrochloride tert-Butyl N'-(5-chloro-2-cyclohexyl-pentanoyl)-hydrazinecarboxylate (155 mg) was dissolved in a solution of 4 N hydrogen chloride in dioxane (2 ml), and the reaction solution was stirred at room temperature for one hour. The reaction solution was concentrated under reduced pressure to obtain 144 mg of the title compound. The property value of the compound is as follows.

ESI-MS; m/z 233 [M+ +H—HCl].

Synthesis of (+) and (−)-8-cyclohexyl-2-{(E)-2-[3-methoxy-4-(4-methyl-1H-imidazol-1-yl)phenyl]vinyl}-5,6,7,8-tetrahydro[1,2,4]triazolo[1,5-a]pyridine A solution of 5-chloro-2-cyclohexyl-valeric acid hydrazide hydrochloride (144 mg) and TEA (0.32 ml) in ethanol (1 ml) was added to a solution of ethyl (E)-3-[3-methoxy-4-(4-methyl-1H-imidazol-1-yl)phenyl]acrylimidate dihydrochloride obtained in Example 1 (167 mg) and TEA (0.32 ml) in ethanol (1.6 ml), and the reaction solution was stirred at 70° C. for two days. The reaction solution was left to cool to room temperature. Then, ethyl acetate and water were added to the reaction solution, and the organic layer was separated. The organic layer was washed with brine, dried over anhydrous magnesium sulfate and then concentrated under reduced pressure. The resulting residue was purified by silica gel column chromatography (carrier: Chromatorex™ NH; elution solvent: heptane-ethyl acetate system) and again purified by silica gel column chromatography (elution solvent: ethyl acetate-methanol system) to obtain 27 mg of racemic 8-cyclohexyl-2-{(E)-2-[3-methoxy-4-(4-methyl-1H-imidazol-1-yl)phenyl]vinyl}-5,6,7,8-tetrahydro[1,2,4]triazolo[1,5-a]pyridine. Then, the racemate was separated by CHIRALPAK™ IB manufactured by Daicel Chemical Industries, Ltd. (2 cm×25 cm; mobile phase: 20% ethanol-hexane) to obtain the title optically active compound with a retention time of 16 minutes and positive optical rotation (11.0 mg; 100% ee) and the title optically active compound with a retention time of 39 minutes and negative optical rotation (10.2 mg; 100% ee).

The property values of the title optically active compound with a retention time of 16 minutes are as follows.

ESI-MS; m/z 418 [M+ +H]. $^1$H-NMR (CDCl$_3$) δ (ppm): 1.07-1.54 (m, 7H), 1.66-1.85 (m, 4H), 1.90-2.06 (m, 2H), 2.13-2.25 (m, 2H), 2.30 (s, 3H), 2.84-2.92 (m, 1H), 3.88 (s, 3H), 4.01-4.11 (m, 1H), 4.16-4.24 (m, 1H), 6.91 (s, 1H), 7.06 (d, J=16.4 Hz, 1H), 7.17 (dd, J=8.0, 1.6 Hz, 1H), 7.19 (d, J=1.6 Hz, 1H), 7.22 (d, J=8.0 Hz, 1H), 7.52 (d, J=16.4 Hz, 1H), 7.69 (s, 1H).

The property values of the title optically active compound with a retention time of 39 minutes are as follows.

ESI-MS; m/z 418 [M+ +H]. $^1$H-NMR (CDCl$_3$) δ (ppm): 1.07-1.54 (m, 7H), 1.66-1.85 (m, 4H), 1.90-2.06 (m, 2H), 2.13-2.25 (m, 2H), 2.30 (s, 3H), 2.84-2.92 (m, 1H), 3.88 (s, 3H), 4.01-4.11 (m, 1H), 4.16-4.24 (m, 1H), 6.91 (s, 1H), 7.06 (d, J=16.4 Hz, 1H), 7.17 (dd, J=8.0, 1.6 Hz, 1H), 7.19 (d, J=1.6 Hz, 1H), 7.22 (d, J=8.0 Hz, 1H), 7.52 (d, J=16.4 Hz, 1H), 7.69 (s, 1H).

Example 115

Synthesis of 2-{(E)-2-[3-methoxy-4-(4-methyl-1H-imidazol-1-yl)phenyl]vinyl}-5,6,7,8-tetrahydro[1,2,4]triazolo[1,5-a]pyridine

[Formula 94]

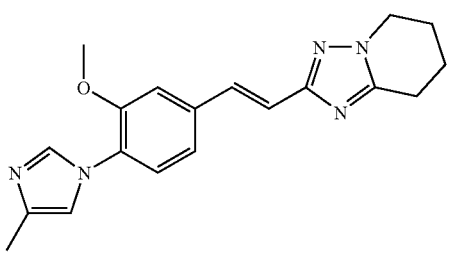

Synthesis of tert-butyl (2-oxopiperidin-1-yl)carbamate

A 4 N sodium hydroxide solution (4 ml) and 5-bromo-valeryl chloride (CAS No. 4509-90-4, 1.06 ml) were added to a solution of tert-butyl carbazate (CAS No. 870-46-2, 1 g) in methylene chloride (10 ml) under ice-cooling. The reaction solution was stirred at the same temperature for 40 minutes, and then the organic layer was separated. The organic layer was sequentially washed with water and brine, dried over anhydrous magnesium sulfate and then concentrated under reduced pressure. The resulting residue was purified by silica gel column chromatography (carrier: Chromatorex™ NH; elution solvent: ethyl acetate) to obtain 2.03 g of a carbazide compound.

Potassium tert-butoxide (850 mg) was added to a solution of the carbazide compound (2.03 g) in THF (30 ml) under ice-cooling. The reaction solution was stirred at the same temperature for 30 minutes and at room temperature for further 1.5 hours. Ethyl acetate and water were added to the reaction solution, and the organic layer was separated. The organic layer was sequentially washed with water and brine, dried over anhydrous magnesium sulfate and then concentrated under reduced pressure. The resulting residue was purified by silica gel column chromatography (elution solvent: heptane-ethyl acetate system) to obtain 907 mg of the title compound. The property values of the compound are as follows.

ESI-MS; m/z 237 [M+Na]. $^1$H-NMR (CDCl$_3$) δ (ppm): 1.48 (s, 9H), 1.78-1.96 (m, 4H), 2.47 (t, J=6.4 Hz, 2H), 3.58 (t, J=6.0 Hz, 2H), 6.66 (brs, 1H).

Synthesis of 1-aminopiperidin-2-one hydrochloride tert-Butyl (2-oxopiperidin-1-yl)carbamate (129 mg) was dissolved in a solution of 4 N hydrogen chloride in dioxane (2 ml), and the reaction solution was stirred at room temperature for one hour. The reaction solution was concentrated under reduced pressure to obtain 92 mg of the title compound. The property values of the compound are as follows.

$^1$H-NMR (DMSO-D$_6$) δ (ppm): 1.69-1.77 (m, 2H), 1.82-1.90 (m, 2H), 2.41 (t, J=6.4 Hz, 2H), 3.54 (t, J=6.0 Hz, 2H).

Synthesis of (E)-3-[3-methoxy-4-(4-methyl-1H-imidazol-1-yl)phenyl]-N-(2-oxopiperidin-1-yl)acrylamide IPEA (0.26 ml), HOBT (121 mg) and EDC (172 mg) were sequentially added to a suspension of 1-aminopiperidin-2-one hydrochloride (92 mg) and (E)-3-[3-methoxy-4-(4-methyl-1H-imidazol-1-yl)phenyl]acrylic acid (CAS No. 870839-41-1, 150 mg) in DMF (4 ml), and the reaction solution was stirred at room temperature overnight. Ethyl acetate and water were added to the reaction solution, and the organic layer was separated. The organic layer was sequentially washed with a saturated sodium bicarbonate solution and brine. The combined aqueous layers were reextracted with ethyl acetate (twice). The combined organic layers were dried over anhydrous magnesium sulfate and concentrated under reduced pressure. The resulting residue was triturated with ethyl acetate to obtain 97 mg of the title compound. The property values of the compound are as follows.

ESI-MS; m/z 355 [M$^+$+H]. $^1$H-NMR (CDCl$_3$) δ (ppm): 1.87-2.04 (m, 4H), 2.30 (s, 3H), 2.56 (t, J=6.4 Hz, 2H), 3.70 (t, J=6.0 Hz, 2H), 3.86 (s, 3H), 6.47 (d, J=16.0 Hz, 1H), 6.92 (s, 1H), 7.00 (s, 1H), 7.04 (d, J=8.0 Hz, 1H), 7.20 (d, J=8.0 Hz, 1H), 7.52 (d, J=16.0 Hz, 1H), 7.72 (s, 1H), 9.03 (brs, 1H).

Synthesis of 2-{(E)-2-[3-methoxy-4-(4-methyl-1H-imidazol-1-yl)phenyl]vinyl}-5,6,7,8-tetrahydro[1,2,4]triazolo[1,5-a]pyridine A suspension of (E)-3-[3-methoxy-4-(4-methyl-1H-imidazol-1-yl)phenyl]-N-(2-oxopiperidin-1-yl)acrylamide (96 mg) in phosphorus oxychloride (1 ml) was stirred at 150° C. for 1.5 hours. Phosphorus oxychloride was evaporated from the reaction solution under reduced pressure. Glacial acetic acid (3 ml) and ammonium acetate (630 mg) were added to the resulting residue, and the reaction solution was stirred at 130° C. for three hours. The reaction solution was left to cool to room temperature and then concentrated under reduced pressure. Ethyl acetate, water and a saturated sodium bicarbonate solution were added to the resulting residue, and then the organic layer was separated. The resulting organic layer was washed with brine, dried over anhydrous magnesium sulfate and then concentrated under reduced pressure. The resulting residue was purified by silica gel column chromatography (carrier: Chromatorex™ NH; elution solvent: heptane-ethyl acetate system) to obtain 20 mg of the title compound. The property values of the compound are as follows.

ESI-MS; m/z 336 [M$^+$+H]. $^1$H-NMR (CDCl$_3$) δ (ppm): 1.97-2.16 (m, 4H), 2.30 (s, 3H), 2.95 (t, J=6.4 Hz, 2H), 3.88 (s, 3H), 4.17 (t, J=6.0 Hz, 2H), 6.91 (s, 1H), 7.06 (d, J=16.0 Hz, 1H), 7.14-7.20 (m, 2H), 7.23 (d, J=8.0 Hz, 1H), 7.52 (d, J=16.0 Hz, 1H), 7.69 (s, 1H).

Examples 116 and 117

Synthesis of (–) and (+)-2-{(E)-2-[3-methoxy-4-(4-methyl-1H-imidazol-1-yl)phenyl]vinyl}-8-(tetrahydropyran-4-yl)-5,6,7,8-tetrahydro[1,2,4]triazolo[1,5-a]pyridine

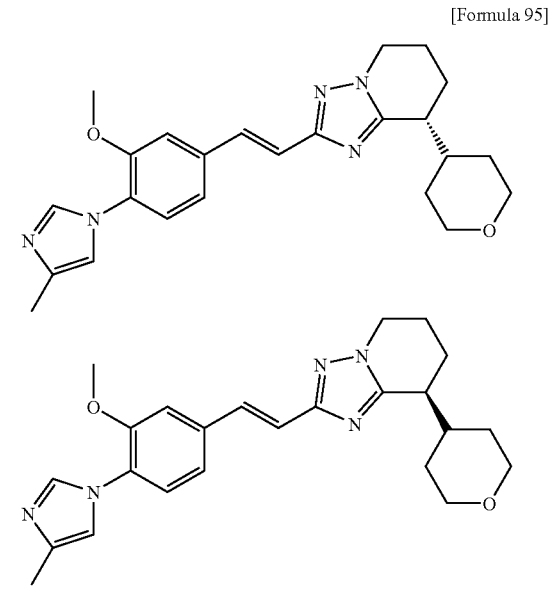

[Formula 95]

Synthesis of ethyl 5-chloro-2-(tetrahydropyran-4-yl)-valerate 672 mg of the title compound was obtained from ethyl (tetrahydropyran-4-yl)acetate (CAS No. 103260-44-2, 650 mg) and 1-chloro-3-iodopropane (0.61 ml) according to the method in Example 113. The property value of the compound is as follows.

ESI-MS; m/z 249 [M$^+$+H].

Synthesis of tert-butyl N'-[5-chloro-2-(tetrahydropyran-4-yl)-pentanoyl]-hydrazinecarboxylate A 5 N sodium hydroxide solution (1.6 ml) was added to a solution of ethyl 5-chloro-2-(tetrahydropyran-4-yl)-valerate (672 mg) in THF (2.5 ml)-ethanol (7.5 ml), and the reaction solution was stirred at room temperature for four days. Water and diethyl ether were added to the reaction solution, and the aqueous layer was separated. The aqueous layer was washed with diethyl ether again. Then, 5 N hydrochloric acid (1.6 ml) and ethyl acetate were added to the aqueous layer, and the organic layer was separated. The ethyl acetate extraction layer was washed with brine, dried over anhydrous magnesium sulfate and then concentrated under reduced pressure to obtain crude 5-chloro-2-(tetrahydropyran-4-yl)valeric acid (442 mg).

IPEA (1.03 ml) and BOPCl (756 mg) were added to a solution of the crude 5-chloro-2-(tetrahydropyran-4-yl)valeric acid (442 mg) and tert-butyl carbazate (357 mg) in methylene chloride (7 ml), and the reaction solution was stirred at room temperature overnight. Ethyl acetate and water were added to the reaction solution, and the organic layer was separated. The organic layer was sequentially washed with 1 N hydrochloric acid, water, a saturated sodium bicarbonate solution and brine, dried over anhydrous magnesium sulfate and then concentrated under reduced pressure. The resulting residue was triturated with ethyl acetate to obtain 250 mg of the title compound. The property values of the compound are as follows.

ESI-MS; m/z 357 [M$^+$+Na]. $^1$H-NMR (CDCl$_3$) δ (ppm): 1.28-1.44 (m, 2H), 1.44-1.54 (m, 1H), 1.45 (s, 9H), 1.60-1.83 (m, 7H), 3.30-3.41 (m, 2H), 3.46-3.60 (m, 2H), 3.91-4.03 (m, 2H), 6.43 (brs, 1H), 7.17 (brs, 1H).

Synthesis of
5-chloro-2-(tetrahydropyran-4-yl)-valeric acid
hydrazide hydrochloride tert-Butyl N'-[5-chloro-2-(tetrahydropyran-4-yl)-pentanoyl]-hydrazinecarboxylate (250 mg) was dissolved in a solution of 4 N hydrogen chloride in dioxane (2 ml), and the reaction solution was stirred at room temperature for 2.5 hours. The reaction solution was concentrated under reduced pressure to obtain 215 mg of the title compound. The property value of the compound is as follows.

ESI-MS; m/z 235 [M$^+$+H—HCl].

Synthesis of (−) and (+)-2-{(E)-2-[3-methoxy-4-(4-methyl-1H-imidazol-1-yl)phenyl]vinyl}-8-(tetrahydropyran-4-yl)-5,6,7,8-tetrahydro[1,2,4]triazolo[1,5-a]pyridine 70 mg of racemic 2-{(E)-2-[3-methoxy-4-(4-methyl-1H-imidazol-1-yl)phenyl]vinyl}-8-(tetrahydropyran-4-yl)-5,6,7,8-tetrahydro[1,2,4]triazolo[1,5-a]pyridine was obtained according to the method in Example 113 from ethyl (E)-3-[3-methoxy-4-(4-methyl-1H-imidazol-1-yl)phenyl]acrylimidate dihydrochloride obtained in Example 1 (300 mg) and 5-chloro-2-(tetrahydropyran-4-yl)-valeric acid hydrazide hydrochloride (215 mg). Then, the racemate was separated by CHIRALPAK™ AD-H manufactured by Daicel Chemical Industries, Ltd. (2 cm×25 cm; mobile phase: ethanol) to obtain the title optically active compound with a retention time of 29 minutes and negative optical rotation (22.7 mg; 100% ee) and the title optically active compound with a retention time of 41 minutes and positive optical rotation (21.3 mg; 99% ee).

The property values of the title optically active compound with a retention time of 29 minutes are as follows.

ESI-MS; m/z 420 [M$^+$+H]. $^1$H-NMR (CDCl$_3$) δ (ppm): 1.40-1.1.48 (m, 1H), 1.52-1.83 (m, 4H), 1.95-2.10 (m, 2H), 2.18-2.28 (m, 1H), 2.30 (d, J=0.8 Hz, 3H), 2.33-2.46 (m, 1H), 2.87-2.95 (m, 1H), 3.42-3.53 (m, 2H), 3.88 (s, 3H), 3.97-4.12 (m, 3H), 4.17-4.26 (m, 1H), 6.92 (dd, J=1.2, 0.8 Hz, 1H), 7.06 (d, J=16.4 Hz, 1H), 7.15-7.20 (m, 2H), 7.23 (d, J=8.4 Hz, 1H), 7.53 (d, J=16.4 Hz, 1H), 7.70 (d, J=1.2 Hz, 1H).

The property values of the title optically active compound with a retention time of 41 minutes are as follows.

ESI-MS; m/z 420 [M$^+$+H]. $^1$H-NMR (CDCl$_3$) δ (ppm): 1.40-1.1.48 (m, 1H), 1.52-1.83 (m, 4H), 1.95-2.10 (m, 2H), 2.18-2.28 (m, 1H), 2.30 (s, 3H), 2.33-2.46 (m, 1H), 2.87-2.95 (m, 1H), 3.42-3.53 (m, 2H), 3.88 (s, 3H), 3.97-4.12 (m, 3H), 4.17-4.26 (m, 1H), 6.92 (d, J=1.2 Hz, 1H), 7.06 (d, J=16.4 Hz, 1H), 7.15-7.20 (m, 2H), 7.23 (d, J=8.4 Hz, 1H), 7.53 (d, J=16.4 Hz, 1H), 7.70 (d, J=1.2 Hz, 1H).

Examples 118 and 119

Synthesis of (+) and (−)-2-{(E)-2-[3-methoxy-4-(4-methyl-1H-imidazol-1-yl)phenyl]vinyl}-8-(piperidin-4-yl)-5,6,7,8-tetrahydro[1,2,4]triazolo[1,5-a]pyridine

[Formula 96]

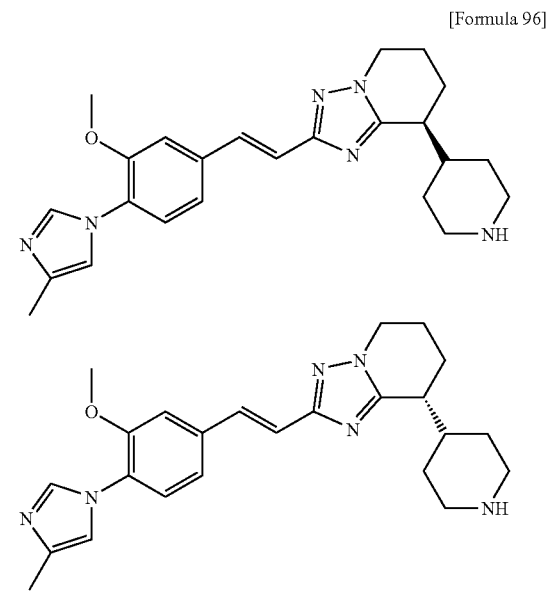

Synthesis of tert-butyl 4-(4-chloro-1-ethoxycarbonyl-butan-1-yl)piperidine-1-carboxylate 1.76 g of the title compound was obtained from tert-butyl 4-ethoxycarbonylmethyl-piperidine-1-carboxylate (CAS No. 142851-03-4, 1.95 g) and 1-chloro-3-iodopropane (1.16 ml) according to the method in Example 113. The property value of the compound is as follows.

ESI-MS; m/z 370 [M$^+$+Na].

Synthesis of tert-butyl 4-[1-(N'-benzyloxycarbonyl-hydrazinocarbonyl)-4-chlorobutan-1-yl]piperidine-1-carboxylate A 5 N sodium hydroxide solution (3 ml) was added to a solution of tert-butyl 4-(4-chloro-1-ethoxycarbonyl-butan-1-yl)piperidine-1-carboxylate (1.76 g) in THF (5 ml)-ethanol (15 ml), and the reaction solution was stirred at room temperature for four days. Water and diethyl ether were added to the reaction solution, and the aqueous layer was separated.

The aqueous layer was washed with diethyl ether again. Then, 5 N hydrochloric acid (3 ml) and ethyl acetate were added to the aqueous layer, and the organic layer was separated. The ethyl acetate extraction layer was washed with brine, dried over anhydrous magnesium sulfate and then concentrated under reduced pressure to obtain crude tert-butyl 4-(1-carboxy-4-chlorobutan-1-yl)piperidine-1-carboxylate (1.25 g).

IPEA (2.0 ml) and BOPCl (1.55 g) were added to a solution of the crude tert-butyl 4-(1-carboxy-4-chlorobutan-1-yl)piperidine-1-carboxylate (1.25 g) and benzyl carbazate (CAS No. 5331-43-1, 883 mg) in methylene chloride (15 ml), and the reaction solution was stirred at room temperature overnight. Ethyl acetate and water were added to the reaction solution, and the organic layer was separated. The organic layer was sequentially washed with 1 N hydrochloric acid, water, a saturated sodium bicarbonate solution and brine, dried over anhydrous magnesium sulfate and then concentrated under reduced pressure. The resulting residue was purified by silica gel column chromatography (elution solvent: heptane-ethyl acetate system) to obtain 928 mg of the title compound. The property value of the compound is as follows.
ESI-MS; m/z 490 [M$^+$+Na].

Synthesis of tert-butyl 4-[4-chloro-1-hydrazinocarbonyl-butan-1-yl]piperidine-1-carboxylate 10% palladium-carbon (50% wet, 200 mg) was added to a solution of tert-butyl 4-[1-(N'-benzyloxycarbonyl-hydrazinocarbonyl)-4-chlorobutan-1-yl]piperidine-1-carboxylate (928 mg) in methanol (15 ml), and the reaction solution was hydrogenated at normal pressure at room temperature for 4.5 hours. The catalyst is removed by filtration and the filtrate is concentrated under reduced pressure to obtain 663 mg of the title compound. The property value of the compound is as follows.
ESI-MS; m/z 356[M$^+$+Na].

Synthesis of tert-butyl 4-(2-{(E)-2-[3-methoxy-4-(4-methyl-1H-imidazol-1-yl)phenyl]vinyl}-5,6,7,8-tetrahydro[1,2,4]triazolo[1,5-a]pyridin-8-yl)piperidine-1-carboxylate A solution of tert-butyl 4-[4-chloro-1-hydrazinocarbonyl-butan-1-yl]piperidine-1-carboxylate (663 mg) in 1-propanol (4 mL) was added to a solution of ethyl (E)-3-[3-methoxy-4-(4-methyl-1H-imidazol-1-yl)phenyl]acrylimidate dihydrochloride obtained in Example 1 (792 mg) and TEA (1.7 mL) in 1-propanol (16 mL), and the reaction solution was stirred at 90° C. overnight. The reaction solution was left to cool to room temperature and then concentrated under reduced pressure. Ethyl acetate, water and a saturated sodium bicarbonate solution were added to the concentration residue, and the organic layer was separated. The organic layer was washed with brine, dried over anhydrous magnesium sulfate and then concentrated under reduced pressure. The resulting residue was purified by silica gel column chromatography (carrier: Chromatorex™ NH; elution solvent: heptane-ethyl acetate system) to obtain 361 mg of the title compound. The property value of the compound is as follows.
ESI-MS; m/z 519[M$^+$+H].

Synthesis of 2-{(E)-2-[3-methoxy-4-(4-methyl-1H-imidazol-1-yl)phenyl]vinyl}-8-(piperidin-4-yl)-5,6,7,8-tetrahydro[1,2,4]triazolo[1,5-a]pyridine Trifluoroacetic acid (1 ml) was added to a solution of tert-butyl 4-(2-{(E)-2-[3-methoxy-4-(4-methyl-1H-imidazol-1-yl)phenyl]vinyl}-5,6,7,8-tetrahydro[1,2,4]triazolo[1,5-a]pyridin-8-yl)piperidine-1-carboxylate (361 mg) in methylene chloride (3 ml), and the mixture was stirred at room temperature for two hours. A saturated sodium bicarbonate solution and ethyl acetate were added to the reaction solution, and the organic layer was separated. The organic layer was sequentially washed with a saturated sodium bicarbonate solution and brine. Since most of the target compound was present in the aqueous layers, the combined aqueous layers were extracted with methylene chloride three times. The methylene chloride extraction layer was dried over anhydrous magnesium sulfate and then concentrated under reduced pressure. The resulting residue was purified by silica gel column chromatography (carrier: Chromatorex™ NH; elution solvent: chloroform-methanol system) to obtain 166 mg of the title compound. The property values of the compound are as follows.

ESI-MS; m/z 419 [M$^+$+H]. $^1$H-NMR (CDCl$_3$) δ (ppm): 1.34-1.56 (m, 3H), 1.72-1.83 (m, 2H), 1.93-2.09 (m, 2H), 2.16-2.36 (m, 2H), 2.30 (d, J=1.2 Hz, 3H), 2.63-2.75 (m, 2H), 2.87-2.93 (m, 1H), 3.06-3.20 (m, 2H), 3.88 (s, 3H), 4.02-4.12 (m, 1H), 4.17-4.25 (m, 1H), 6.92 (t, J=1.2 Hz, 1H), 7.06 (d, J=16.0 Hz, 1H), 7.15-7.20 (m, 2H), 7.22 (d, J=8.0 Hz, 1H), 7.53 (d, J=16.0 Hz, 1H), 7.69 (d, J=1.2 Hz, 1H).

Synthesis of (+) and (−)-2-{(E)-2-[3-methoxy-4-(4-methyl-1H-imidazol-1-yl)phenyl]vinyl}-8-(piperidin-4-yl)-5,6,7,8-tetrahydro[1,2,4]triazolo[1,5-a]pyridine Racemic 2-{(E)-2-[3-methoxy-4-(4-methyl-1H-imidazol-1-yl)phenyl]vinyl}-8-(piperidin-4-yl)-5,6,7,8-tetrahydro[1,2,4]triazolo[1,5-a]pyridine (5 mg) was separated by CHIRALPAK™ OD-H manufactured by Daicel Chemical Industries, Ltd. (2 cm×25 cm; mobile phase: 50% ethanol-hexane) to obtain the title optically active compound with a retention time of 29 minutes and positive optical rotation (1.58 mg, 100% ee) and the title optically active compound with a retention time of 55 minutes and negative optical rotation (1.40 mg, 99% ee).

The property values of the title optically active compound with a retention time of 29 minutes are as follows.

ESI-MS; m/z 419 [M$^+$+H]. $^1$H-NMR (CDCl$_3$) δ (ppm): 1.34-1.56 (m, 3H), 1.72-1.83 (m, 2H), 1.93-2.09 (m, 2H), 2.16-2.36 (m, 2H), 2.30 (d, J=1.2 Hz, 3H), 2.63-2.75 (m, 2H), 2.87-2.93 (m, 1H), 3.06-3.20 (m, 2H), 3.88 (s, 3H), 4.02-4.12 (m, 1H), 4.17-4.25 (m, 1H), 6.92 (t, J=1.2 Hz, 1H), 7.06 (d, J=16.0 Hz, 1H), 7.15-7.20 (m, 2H), 7.22 (d, J=8.0 Hz, 1H), 7.53 (d, J=16.0 Hz, 1H), 7.69 (d, J=1.2 Hz, 1H).

The property values of the title optically active compound with a retention time of 55 minutes are as follows.

ESI-MS; m/z 419 [M$^+$+H]. $^1$H-NMR (CDCl$_3$) δ (ppm): 1.34-1.56 (m, 3H), 1.72-1.83 (m, 2H), 1.93-2.09 (m, 2H), 2.16-2.36 (m, 2H), 2.30 (d, J=1.2 Hz, 3H), 2.63-2.75 (m, 2H), 2.87-2.93 (m, 1H), 3.06-3.20 (m, 2H), 3.88 (s, 3H), 4.02-4.12 (m, 1H), 4.17-4.25 (m, 1H), 6.92 (t, J=1.2 Hz, 1H), 7.06 (d,

Examples 120 and 121

Synthesis of (+) and (−)-1-[4-(2-{(E)-2-[3-methoxy-4-(4-methyl-1H-imidazol-1-yl)phenyl]vinyl}-5,6,7,8-tetrahydro[1,2,4]triazolo[1,5-a]pyridin-8-yl)piperidin-1-yl]ethanone

[Formula 97]

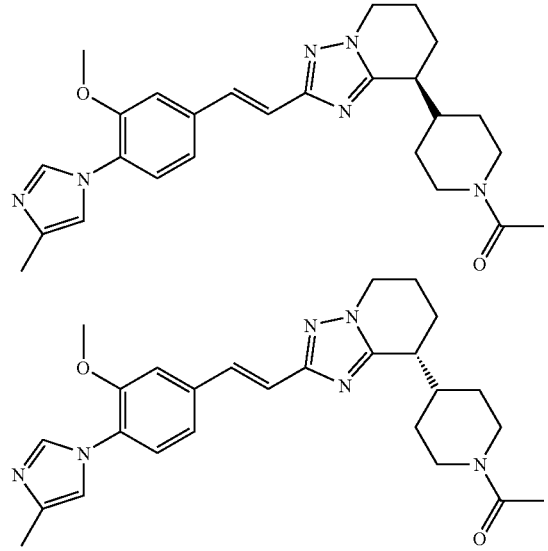

A 1 N sodium hydroxide solution (0.5 ml) and acetyl chloride (14 ul) were added to a solution of racemic 2-{(E)-2-[3-methoxy-4-(4-methyl-1H-imidazol-1-yl)phenyl]vinyl}-8-(piperidin-4-yl)-5,6,7,8-tetrahydro[1,2,4]triazolo[1,5-a]pyridine obtained in Examples 118 and 119 (25 mg) in methylene chloride (0.5 ml), and the reaction solution was stirred at room temperature for 40 minutes. Chloroform was added to the reaction solution, and the organic layer was separated. The aqueous layer was reextracted with chloroform twice. The combined organic layers were dried over anhydrous magnesium sulfate and concentrated under reduced pressure to obtain 25 mg of racemic 1-[4-(2-{(E)-2-[3-methoxy-4-(4-methyl-1H-imidazol-1-yl)phenyl]vinyl}-5,6,7,8-tetrahydro[1,2,4]triazolo[1,5-a]pyridin-8-yl)piperidin-1-yl]ethanone. Then, the racemate was separated by CHIRALPAK™ IA manufactured by Daicel Chemical Industries, Ltd. (2 cm×25 cm; mobile phase: ethanol) to obtain the title optically active compound with a retention time of 27 minutes and positive optical rotation (7.4 mg; 100% ee) and the title optically active compound with a retention time of 34 minutes and negative optical rotation (6.7 mg; 97% ee)

The property values of the title optically active compound with a retention time of 27 minutes are as follows.

ESI-MS; m/z 461 [M$^+$+H]. $^1$H-NMR (CDCl$_3$) δ (ppm): 1.30-1.85 (m, 3H), 1.88-2.65 (m, 7H), 2.09 and 2.11 (each s, 3H), 2.30 (s, 3H), 2.88-3.01 (m, 1H), 3.05-3.16 (m, 1H), 3.80-3.95 (m, 1H), 3.88 (s, 3H), 4.01-4.13 (m, 1H), 4.18-4.28 (m, 1H), 4.66-4.80 (m, 1H), 6.92 (s, 1H), 7.06 (d, J=16.0 Hz, 1H), 7.15-7.20 (m, 2H), 7.23 (d, J=8.0 Hz, 1H), 7.52 (d, J=16.0 Hz, 1H), 7.70 (d, J=1.2 Hz, 1H).

The property values of the title optically active compound with a retention time of 34 minutes are as follows.

ESI-MS; m/z 461 [M$^+$+H]. $^1$H-NMR (CDCl$_3$) δ (ppm): 1.30-1.85 (m, 3H), 1.88-2.65 (m, 7H), 2.09 and 2.11 (each s, 3H), 2.30 (s, 3H), 2.88-3.01 (m, 1H), 3.05-3.16 (m, 1H), 3.80-3.95 (m, 1H), 3.88 (s, 3H), 4.01-4.13 (m, 1H), 4.18-4.28 (m, 1H), 4.66-4.80 (m, 1H), 6.92 (s, 1H), 7.06 (d, J=16.0 Hz, 1H), 7.15-7.20 (m, 2H), 7.23 (d, J=8.0 Hz, 1H), 7.52 (d, J=16.0 Hz, 1H), 7.70 (d, J=1.2 Hz, 1H).

Examples 122 and 123

Synthesis of (+) and (−)-8-(1-isopropylpiperidin-4-yl)-2-{(E)-2-[3-methoxy-4-(4-methyl-1H-imidazol-1-yl)phenyl]vinyl}-5,6,7,8-tetrahydro[1,2,4]triazolo[1,5-a]pyridine

[Formula 98]

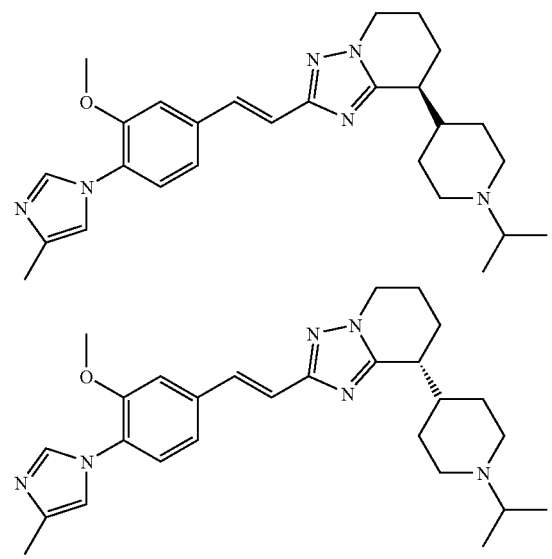

Acetone (16 μl) and glacial acetic acid (17 μl) were added to a solution of racemic 2-{(E)-2-[3-methoxy-4-(4-methyl-1H-imidazol-1-yl)phenyl]vinyl}-8-(piperidin-4-yl)-5,6,7,8-tetrahydro[1,2,4]triazolo[1,5-a]pyridine obtained in Examples 118 and 119 (30 mg) in THF (3 ml), and the reaction solution was stirred at room temperature for 30 minutes. Sodium triacetoxyhydroborate (46 mg) was added to the reaction solution, and the reaction solution was stirred at room temperature for 1.5 hours. Acetone (80 μl) and sodium triacetoxyhydroborate (184 mg) were added to the reaction solution, and the reaction solution was stirred at room temperature overnight. A saturated sodium bicarbonate solution and ethyl acetate were added to the reaction solution, and the organic layer was separated. The organic layer was sequentially washed with water and brine and dried over anhydrous magnesium sulfate.

On the other hand, cesium carbonate (47 μl) was added to a solution of racemic 2-{(E)-2-[3-methoxy-4-(4-methyl-1H-imidazol-1-yl)phenyl]vinyl}-8-(piperidin-4-yl)-5,6,7,8-tetrahydro[1,2,4]triazolo[1,5-a]pyridine (20 mg) and 2-iodopropane (15 μl) in DMF (1 ml), and the reaction solution was stirred at room temperature overnight. The reaction solution was concentrated under reduced pressure. Water and ethyl acetate were added to the residue, and the organic layer was separated. The organic layer was washed with brine and dried over anhydrous magnesium sulfate.

At this time, the organic layer was combined with the after-treatment solution in the above experiment, and the layers were concentrated under reduced pressure. The resulting residue was purified by silica gel column chromatography (carrier: Chromatorex™ NH; elution solvent: ethyl acetate) and again purified by silica gel column chromatography (elution solvent: ethyl acetate-methanol system) to obtain 21 mg of racemic 8-(1-isopropylpiperidin-4-yl)-2-{(E)-2-[3-methoxy-4-(4-methyl-1H-imidazol-1-yl)phenyl]vinyl}-5,6,7,8-tetrahydro[1,2,4]triazolo[1,5-a]pyridine. Then, the racemate was separated by CHIRALCEL™ OD-H manufactured by Daicel Chemical Industries, Ltd. (2 cm×25 cm; mobile phase: 40% ethanol-hexane) to obtain the title optically active compound with a retention time of 9 minutes and positive optical rotation (4.61 mg; 100% ee) and the title optically active compound with a retention time of 15 minutes and negative optical rotation (4.83 mg; 99% ee).

The property values of the title optically active compound with a retention time of 9 minutes are as follows.

ESI-MS; m/z 461 [M$^+$+H]. $^1$H-NMR (CDCl$_3$) δ (ppm): 1.06 (s, 3H), 1.07 (s, 3H), 1.40-1.56 (m, 3H), 1.70-1.88 (m, 2H), 1.91-2.09 (m, 2H), 2.13-2.35 (m, 4H), 2.30 (s, 3H), 2.68-2.80 (m, 1H), 2.88-3.04 (m, 3H), 3.88 (s, 3H), 4.02-4.12 (m, 1H), 4.17-4.25 (m, 1H), 6.92 (s, 1H), 7.06 (d, J=16.0 Hz, 1H), 7.17 (dd, J=8.0, 1.6 Hz, 1H), 7.19 (d, J=1.6 Hz, 1H), 7.23 (d, J=8.0 Hz, 1H), 7.53 (d, J=16.0 Hz, 1H), 7.70 (d, J=1.2 Hz, 1H).

The property values of the title optically active compound with a retention time of 15 minutes are as follows.

ESI-MS; m/z 461 [M$^+$+H]. $^1$H-NMR (CDCl$_3$) δ (ppm): 1.06 (s, 3H), 1.07 (s, 3H), 1.40-1.56 (m, 3H), 1.70-1.88 (m, 2H), 1.91-2.09 (m, 2H), 2.13-2.35 (m, 4H), 2.30 (s, 3H), 2.68-2.80 (m, 1H), 2.88-3.04 (m, 3H), 3.88 (s, 3H), 4.02-4.12 (m, 1H), 4.17-4.25 (m, 1H), 6.92 (s, 1H), 7.06 (d, J=16.0 Hz, 1H), 7.17 (dd, J=8.0, 1.6 Hz, 1H), 7.19 (d, J=1.6 Hz, 1H), 7.23 (d, J=8.0 Hz, 1H), 7.53 (d, J=16.0 Hz, 1H), 7.70 (d, J=1.2 Hz, 1H).

Examples 124 and 125

Synthesis of (+) and (−)-8-(1-benzylpiperidin-4-yl)-2-{(E)-2-[3-methoxy-4-(4-methyl-1H-imidazol-1-yl)phenyl]vinyl}-5,6,7,8-tetrahydro[1,2,4]triazolo[1,5-a]pyridine

[Formula 99]

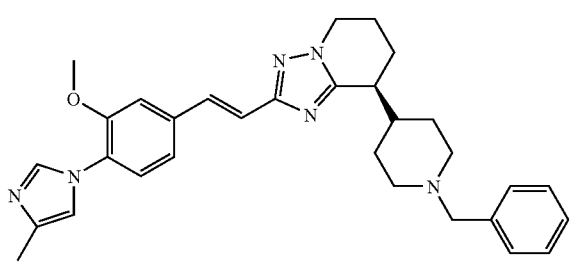

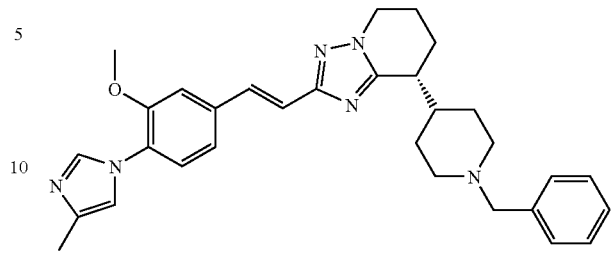

Benzaldehyde (15 μl) and glacial acetic acid (16 μl) were added to a solution of racemic 2-{(E)-2-[3-methoxy-4-(4-methyl-1H-imidazol-1-yl)phenyl]vinyl}-8-(piperidin-4-yl)-5,6,7,8-tetrahydro[1,2,4]triazolo[1,5-a]pyridine obtained in Examples 118 and 119 (30 mg) in THF (2 ml), and the reaction solution was stirred at room temperature for 30 minutes. Sodium triacetoxyhydroborate (46 mg) was added to the reaction solution, and the reaction solution was stirred at room temperature for four hours. A saturated sodium bicarbonate solution and ethyl acetate were added to the reaction solution, and the organic layer was separated. The organic layer was washed with brine, dried over anhydrous magnesium sulfate and concentrated under reduced pressure. The resulting residue was purified by silica gel column chromatography (carrier: Chromatorex™ NH; elution solvent: ethyl acetate) to obtain 27 mg of racemic 8-(1-benzylpiperidin-4-yl)-2-{(E)-2-[3-methoxy-4-(4-methyl-1H-imidazol-1-yl)phenyl]vinyl}-5,6,7,8-tetrahydro[1,2,4]triazolo[1,5-a]pyridine. Then, the racemate was separated by CHIRALPAK™ IB manufactured by Daicel Chemical Industries, Ltd. (2 cm×25 cm; mobile phase: 50% ethanol-hexane) to obtain the title optically active compound with a retention time of 14 minutes and positive optical rotation (9.4 mg; >99% ee) and the title optically active compound with a retention time of 20 minutes and negative optical rotation (8.9 mg; 99% ee).

The property values of the title optically active compound with a retention time of 14 minutes are as follows.

ESI-MS; m/z 509 [M$^+$+H]. $^1$H-NMR (CDCl$_3$) δ (ppm): 1.40-1.70 (m, 3H), 1.72-1.82 (m, 2H), 1.90-2.10 (m, 4H), 2.12-2.25 (m, 2H), 2.30 (d, J=1.2 Hz, 3H), 2.87-3.01 (m, 3H), 3.51 (d, J=13.2 Hz, 1H), 3.53 (d, J=13.2 Hz, 1H), 3.88 (s, 3H), 4.02-4.11 (m, 1H), 4.16-4.25 (m, 1H), 6.91 (t, J=1.2 Hz, 1H), 7.05 (d, J=16.0 Hz, 1H), 7.16 (dd, J=8.0, 1.6 Hz, 1H), 7.18 (d, J=1.6 Hz, 1H), 7.22 (d, J=8.0 Hz, 1H), 7.23-7.35 (m, 5H), 7.51 (d, J=16.0 Hz, 1H), 7.69 (d, J=1.2 Hz, 1H).

The property values of the title optically active compound with a retention time of 20 minutes are as follows.

ESI-MS; m/z 509 [M$^+$+H]. $^1$H-NMR (CDCl$_3$) δ (ppm): 1.40-1.70 (m, 3H), 1.72-1.82 (m, 2H), 1.90-2.10 (m, 4H), 2.12-2.25 (m, 2H), 2.30 (d, J=1.2 Hz, 3H), 2.87-3.01 (m, 3H), 3.51 (d, J=13.2 Hz, 1H), 3.53 (d, J=13.2 Hz, 1H), 3.88 (s, 3H), 4.02-4.11 (m, 1H), 4.16-4.25 (m, 1H), 6.91 (t, J=1.2 Hz, 1H), 7.05 (d, J=16.0 Hz, 1H), 7.16 (dd, J=8.0, 1.6 Hz, 1H), 7.18 (d, J=1.6 Hz, 1H), 7.22 (d, J=8.0 Hz, 1H), 7.23-7.35 (m, 5H), 7.51 (d, J=16.0 Hz, 1H), 7.69 (d, J=1.2 Hz, 1H).

Examples 126 and 127

Synthesis of (+) and (−)-1-[4-(2-{(E)-2-[3-methoxy-4-(4-methyl-1H-imidazol-1-yl)phenyl]vinyl}-5,6,7,8-tetrahydro[1,2,4]triazolo[1,5-a]pyridin-8-yl)piperidin-1-yl]phenylmethanone

[Formula 100]

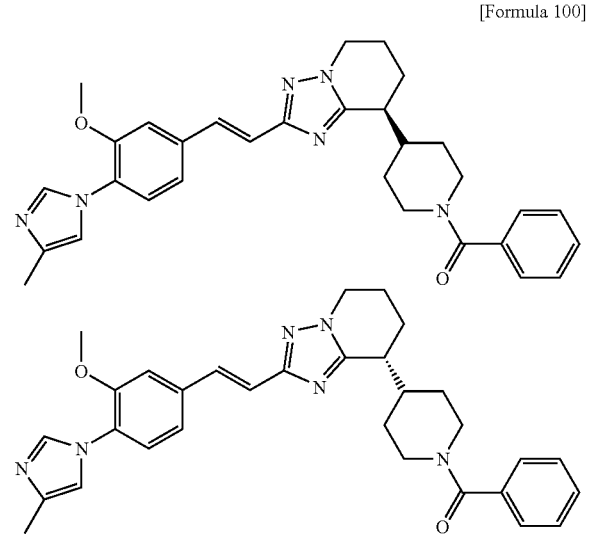

A 1 N sodium hydroxide solution (0.5 ml) and benzoyl chloride (11 ul) were added to a solution of racemic 2-{(E)-2-[3-methoxy-4-(4-methyl-1H-imidazol-1-yl)phenyl]vinyl}-8-(piperidin-4-yl)-5,6,7,8-tetrahydro[1,2,4]triazolo[1,5-a]pyridine obtained in Examples 118 and 119 (20 mg) in methylene chloride (1 ml), and the reaction solution was stirred under ice-cooling for four hours. Methylene chloride was added to the reaction solution, and the organic layer was separated. The aqueous layer was reextracted with methylene chloride. The combined organic layers were dried over anhydrous magnesium sulfate and concentrated under reduced pressure to obtain 19 mg of racemic 1-[4-(2-{(E)-2-[3-methoxy-4-(4-methyl-1H-imidazol-1-yl)phenyl]vinyl}-5,6,7,8-tetrahydro[1,2,4]triazolo[1,5-a]pyridin-8-yl)piperidin-1-yl]phenylmethanone. Then, the racemate was separated by CHIRALPAK™ IB manufactured by Daicel Chemical Industries, Ltd. (2 cm×25 cm; mobile phase: 50% ethanol-hexane) to obtain the title optically active compound with a retention time of 16 minutes and positive optical rotation (6.9 mg; 100% ee) and the title optically active compound with a retention time of 22 minutes and negative optical rotation (6.8 mg; >99% ee).

The property values of the title optically active compound with a retention time of 16 minutes are as follows.

ESI-MS; m/z 523 [M$^+$+H]. $^1$H-NMR (CDCl$_3$) δ (ppm): 1.30-2.14 (m, 6H), 2.17-2.28 (m, 2H), 2.30 (s, 3H), 2.33-2.58 (m, 1H), 2.70-3.15 (m, 3H), 3.73-3.95 (m, 1H), 3.88 (s, 3H), 4.00-4.16 (m, 1H), 4.18-4.28 (m, 1H), 4.70-4.95 (m, 1H), 6.92 (s, 1H), 7.05 (d, J=16.4 Hz, 1H), 7.14-7.20 (m, 2H), 7.22 (d, J=8.0 Hz, 1H), 7.40 (s, 5H), 7.52 (d, J=16.4 Hz, 1H), 7.70 (d, J=1.2 Hz, 1H).

The property values of the title optically active compound with a retention time of 22 minutes are as follows.

ESI-MS; m/z 523 [M$^+$+H]. $^1$H-NMR (CDCl$_3$) δ (ppm): 1.30-2.14 (m, 6H), 2.17-2.28 (m, 2H), 2.30 (s, 3H), 2.33-2.58 (m, 1H), 2.70-3.15 (m, 3H), 3.73-3.95 (m, 1H), 3.88 (s, 3H), 4.00-4.16 (m, 1H), 4.18-4.28 (m, 1H), 4.70-4.95 (m, 1H), 6.92 (s, 1H), 7.05 (d, J=16.4 Hz, 1H), 7.14-7.20 (m, 2H), 7.22 (d, J=8.0 Hz, 1H), 7.40 (s, 5H), 7.52 (d, J=16.4 Hz, 1H), 7.70 (d, J=1.2 Hz, 1H).

Examples 128 and 129

Synthesis of (+) and (−)-8-(1-benzenesulfonylpiperidin-4-yl)-2-{(E)-2-[3-methoxy-4-(4-methyl-1H-imidazol-1-yl)phenyl]vinyl}-5,6,7,8-tetrahydro[1,2,4]triazolo[1,5-a]pyridine

[Formula 101]

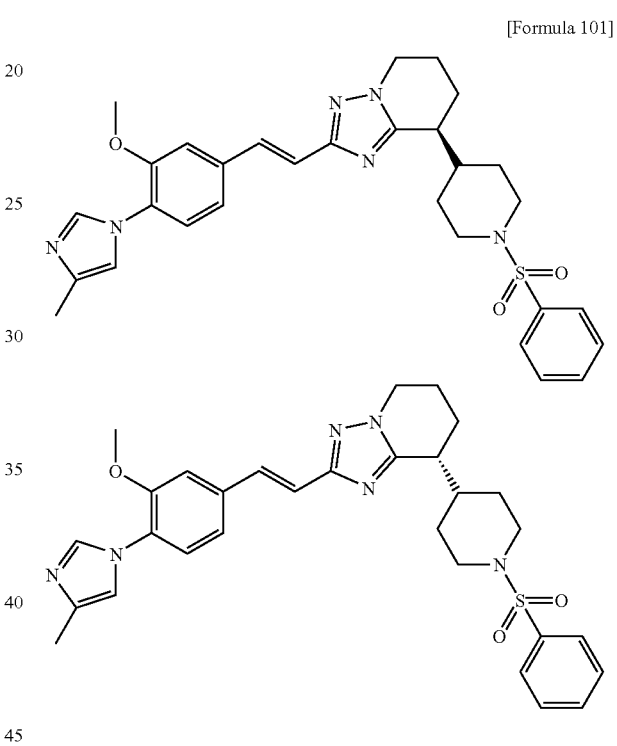

TEA (20 μl) and benzenesulfonyl chloride (8 μl) were added to a solution of racemic 2-{(E)-2-[3-methoxy-4-(4-methyl-1H-imidazol-1-yl)phenyl]vinyl}-8-(piperidin-4-yl)-5,6,7,8-tetrahydro[1,2,4]triazolo[1,5-a]pyridine obtained in Examples 118 and 119 (20 mg) in methylene chloride (1 ml), and the reaction solution was stirred at room temperature for 40 minutes. Water and ethyl acetate were added to the reaction solution, and the organic layer was separated. The organic layer was sequentially washed with a saturated sodium bicarbonate solution and brine, dried over anhydrous magnesium sulfate and concentrated under reduced pressure to obtain 24 mg of racemic 8-(1-benzenesulfonylpiperidin-4-yl)-2-{(E)-2-[3-methoxy-4-(4-methyl-1H-imidazol-1-yl)phenyl]vinyl}-5,6,7,8-tetrahydro[1,2,4]triazolo[1,5-a]pyridine. Then, the racemate was separated by CHIRALCEL™ OD-H manufactured by Daicel Chemical Industries, Ltd. (2 cm×25 cm; mobile phase: ethanol) to obtain the title optically active compound with a retention time of 24 minutes and positive optical rotation (7.3 mg; 100% ee) and the title optically active compound with a retention time of 29 minutes and negative optical rotation (7.4 mg; >98% ee).

The property values of the title optically active compound with a retention time of 24 minutes are as follows.

ESI-MS; m/z 559 [M++H]. ¹H-NMR (CDCl₃) δ (ppm): 1.50-1.76 (m, 3H), 1.82-2.37 (m, 8H), 2.30 (d, J=1.2 Hz, 3H), 2.87-2.95 (m, 1H), 3.80-3.96 (m, 2H), 3.87 (s, 3H), 4.00-4.10 (m, 1H), 4.17-4.27 (m, 1H), 6.91 (t, J=1.2 Hz, 1H), 7.01 (d, J=16.0 Hz, 1H), 7.13 (dd, J=8.0, 1.2 Hz, 1H), 7.16 (d, J=1.2 Hz, 1H), 7.21 (d, J=8.0 Hz, 1H), 7.46 (d, J=16.0 Hz, 1H), 7.53 (td, J=7.2, 1.2 Hz, 2H), 7.61 (tt, J=7.2, 1.2 Hz, 1H), 7.69 (d, J=1.2 Hz, 1H), 7.76 (dt, J=8.0, 1.2 Hz, 2H).

The property values of the title optically active compound with a retention time of 29 minutes are as follows.

ESI-MS; m/z 559 [M++H]. ¹H-NMR (CDCl₃) δ (ppm): 1.50-1.76 (m, 3H), 1.82-2.37 (m, 8H), 2.30 (d, J=1.2 Hz, 3H), 2.87-2.95 (m, 1H), 3.80-3.96 (m, 2H), 3.87 (s, 3H), 4.00-4.10 (m, 1H), 4.17-4.27 (m, 1H), 6.91 (t, J=1.2 Hz, 1H), 7.01 (d, J=16.0 Hz, 1H), 7.13 (dd, J=8.0, 1.2 Hz, 1H), 7.16 (d, J=1.2 Hz, 1H), 7.21 (d, J=8.0 Hz, 1H), 7.46 (d, J=16.0 Hz, 1H), 7.53 (td, J=7.2, 1.2 Hz, 2H), 7.61 (tt, J=7.2, 1.2 Hz, 1H), 7.69 (d, J=1.2 Hz, 1H), 7.76 (dt, J=8.0, 1.2 Hz, 2H).

Examples 130, 131, 132 and 133

Synthesis of (−), (+), (+) and (−)-8-(1-benzylpyrrolidin-2-yl)-2-{(E)-2-[3-methoxy-4-(4-methyl-1H-imidazol-1-yl)phenyl]vinyl}-5,6,7,8-tetrahydro[1,2,4]triazolo[1,5-a]pyridine

[Formula 102]

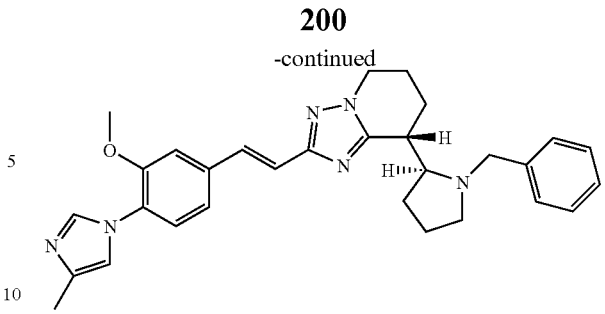

-continued

Synthesis of tert-butyl 2-methoxycarbonylmethyl-pyrrolidine-1-carboxylate

Trimethylsilyldiazomethane (2 M solution in hexane, 1.5 ml) was added dropwise to a mixed solution of tert-butyl 2-carboxymethylpyrrolidine-1-carboxylate (CAS No. 194154-91-1, 500 mg) in methanol (1 ml)-toluene (1 ml) under ice-cooling, and the reaction solution was stirred at the same temperature for three hours. The reaction solution was concentrated. The resulting residue was purified by silica gel column chromatography (elution solvent: heptane-ethyl acetate system) to obtain 506 mg of the title compound. The property values of the compound are as follows.

¹H-NMR (CDCl₃) δ (ppm): 1.46 (s, 9H), 1.67-1.90 (m, 3H), 1.98-2.12 (m, 1H), 2.30 (dd, J=15.2, 10.0 Hz, 1H), 2.75-3.02 (m, 1H), 3.26-3.45 (m, 2H), 3.67 (s, 3H), 4.04-4.25 (m, 1H)

Synthesis of tert-butyl 2-(4-chloro-1-methoxycarbonyl-butan-1-yl)pyrrolidine-1-carboxylate 335 mg of the title compound was obtained from tert-butyl 2-methoxycarbonylmethyl-pyrrolidine-1-carboxylate (506 mg) and 1-chloro-3-iodopropane (335 µl) according to the method in Example 113. The property value of the compound is as follows.

ESI-MS; m/z 342 [M++Na].

Synthesis of tert-butyl 2-[1-(N'-benzyloxycarbonyl-hydrazinocarbonyl)-4-chlorobutan-1-yl]pyrrolidine-1-carboxylate 142 mg of the title compound was obtained from tert-butyl 2-(4-chloro-1-methoxycarbonyl-butan-1-yl)pyrrolidine-1-carboxylate (335 mg) according to the method in Example 118. The property value of the compound is as follows.

ESI-MS; m/z 476 [M++Na].

Synthesis of tert-butyl 2-[4-chloro-1-hydrazinocarbonyl-butan-1-yl]pyrrolidine-1-carboxylate 107 mg of the title compound was obtained from tert-butyl 2-[1-(N'-benzyloxycarbonyl-hydrazinocarbonyl)-4-chlorobutan-1-yl]pyrrolidine-1-carboxylate (142 mg) according to the method in Example 118. The property value of the compound is as follows.

ESI-MS; m/z 342 [M++Na].

Synthesis of tert-butyl 2-(2-{(E)-2-[3-methoxy-4-(4-methyl-1H-imidazol-1-yl)phenyl]vinyl}-5,6,7,8-tetrahydro[1,2,4]triazolo[1,5-a]pyridin-8-yl)pyrrolidine-1-carboxylate 56 mg of the title compound was obtained from ethyl (E)-3-[3-methoxy-4-(4-methyl-1H-imidazol-1-yl)phenyl]

acrylimidate dihydrochloride (125 mg) and tert-butyl 2-[4-chloro-1-hydrazinocarbonyl-butan-1-yl]pyrrolidine-1-carboxylate (107 mg) according to the method in Example 118. The property value of the compound is as follows.

ESI-MS; m/z 505 [M$^+$+H].

Synthesis of 2-{(E)-2-[3-methoxy-4-(4-methyl-1H-imidazol-1-yl)phenyl]vinyl}-8-(pyrrolidin-2-yl)-5,6,7,8-tetrahydro[1,2,4]triazolo[1,5-a]pyridine 24 mg of the title compound was obtained from tert-butyl 2-(2-{(E)-2-[3-methoxy-4-(4-methyl-1H-imidazol-1-yl)phenyl]vinyl}-5,6,7,8-tetrahydro[1,2,4]triazolo[1,5-a]pyridin-8-yl)pyrrolidine-1-carboxylate (56 mg) according to the method in Example 118. The property value of the compound is as follows.

ESI-MS; m/z 405 [M$^+$+H].

Synthesis of (−), (+), (+) and (−)-8-(1-benzylpyrrolidin-2-yl)-2-{(E)-2-[3-methoxy-4-(4-methyl-1H-imidazol-1-yl)phenyl]vinyl}-5,6,7,8-tetrahydro[1,2,4]triazolo[1,5-a]pyridine 8 mg of a diastereomer mixture, 8-(1-benzylpyrrolidin-2-yl)-2-{(E)-2-[3-methoxy-4-(4-methyl-1H-imidazol-1-yl)phenyl]vinyl}-5,6,7,8-tetrahydro[1,2,4]triazolo[1,5-a]pyridine, was obtained from 2-{(E)-2-[3-methoxy-4-(4-methyl-1H-imidazol-1-yl)phenyl]vinyl}-8-(pyrrolidin-2-yl)-5,6,7,8-tetrahydro[1,2,4]triazolo[1,5-a]pyridine (10 mg) according to the method in Example 124. The diastereomer mixture was separated by CHIRALPAK™ AD-H manufactured by Daicel Chemical Industries, Ltd. (2 cm×25 cm; mobile phase: 100% ethanol) to obtain the title optically active compound with a retention time of 26 minutes and negative optical rotation (1.43 mg; >96% ee). Then, the diastereomer mixture with a retention time of 19.5 to 23 minutes in the AD-H column was separated again by CHIRALPAK™ IB manufactured by Daicel Chemical Industries, Ltd. (2 cm×25 cm; mobile phase: 50% ethanol-hexane) to obtain the title optically active compound with a retention time of 7.5 minutes and positive optical rotation (0.90 mg; >99% ee), the title optically active compound with a retention time of 8 minutes and positive optical rotation (1.75 mg; >99% ee) and the title optically active compound with a retention time of 14 minutes and negative optical rotation (8.9 mg; 99% ee).

The property values of the title optically active compound with a retention time of 26 minutes in the AD-H column are as follows.

ESI-MS; m/z 495 [M$^+$+H]. $^1$H-NMR (CDCl$_3$) δ (ppm): 1.70-1.79 (m, 2H), 1.84-2.35 (m, 7H), 2.30 (s, 3H), 2.91-2.98 (m, 1H), 3.02-3.09 (m, 1H), 3.23 (d, J=13.2 Hz, 1H), 3.52 (d, J=13.2 Hz, 1H), 3.57-3.64 (m, 1H), 3.87 (s, 3H), 3.99-4.08 (m, 1H), 4.14-4.23 (m, 1H), 6.91 (s, 1H), 7.04 (d, J=16.0 Hz, 1H), 7.12-7.26 (m, 8H) 7.52 (d, J=16.0 Hz, 1H), 7.69 (d, J=0.8 Hz, 1H).

The property values of the title optically active compound with a retention time of 7.5 minutes in the IB column are as follows.

ESI-MS; m/z 495 [M$^+$+H]. $^1$H-NMR (CDCl$_3$) δ (ppm): 1.25-1.40 (m, 1H), 1.55-2.02 (m, 5H), 2.16-2.37 (m, 3H), 2.30 (s, 3H), 2.95-3.03 (m, 1H), 3.22-3.30 (m, 1H), 3.37 (d, J=13.2 Hz, 1H), 3.50-3.60 (m, 1H), 3.88 (s, 3H), 4.00-4.11 (m, 2H), 4.24-4.31 (m, 1H), 6.92 (s, 1H), 7.06 (d, J=16.4 Hz, 1H), 7.16 (dd, J=8.0, 1.6 Hz, 1H), 7.19 (d, J=1.6 Hz, 1H), 7.23 (d, J=8.0 Hz, 1H), 7.25-7.40 (m, 5H), 7.52 (d, J=16.4 Hz, 1H), 7.70 (d, J=1.6 Hz, 1H).

The property values of the title optically active compound with a retention time of 8 minutes in the IB column are as follows.

ESI-MS; m/z 495 [M$^+$+H]. $^1$H-NMR (CDCl$_3$) δ (ppm): 1.70-1.79 (m, 2H), 1.84-2.35 (m, 7H), 2.30 (s, 3H), 2.91-2.98 (m, 1H), 3.02-3.09 (m, 1H), 3.23 (d, J=13.2 Hz, 1H), 3.52 (d, J=13.2 Hz, 1H), 3.57-3.64 (m, 1H), 3.87 (s, 3H), 3.99-4.08 (m, 1H), 4.14-4.23 (m, 1H), 6.91 (s, 1H), 7.04 (d, J=16.0 Hz, 1H), 7.12-7.26 (m, 8H) 7.52 (d, J=16.0 Hz, 1H), 7.69 (d, J=0.8 Hz, 1H).

The property values of the title optically active compound with a retention time of 14 minutes in the IB column are as follows.

ESI-MS; m/z 495 [M$^+$+H]. $^1$H-NMR (CDCl$_3$) δ (ppm): 1.25-1.40 (m, 1H), 1.55-2.02 (m, 5H), 2.16-2.37 (m, 3H), 2.30 (s, 3H), 2.95-3.03 (m, 1H), 3.22-3.30 (m, 1H), 3.37 (d, J=13.2 Hz, 1H), 3.50-3.60 (m, 1H), 3.88 (s, 3H), 4.00-4.11 (m, 2H), 4.24-4.31 (m, 1H), 6.92 (s, 1H), 7.06 (d, J=16.4 Hz, 1H), 7.16 (dd, J=8.0, 1.6 Hz, 1H), 7.19 (d, J=1.6 Hz, 1H), 7.23 (d, J=8.0 Hz, 1H), 7.25-7.40 (m, 5H), 7.52 (d, J=16.4 Hz, 1H), 7.70 (d, J=1.6 Hz, 1H).

Examples 134 and 135

Synthesis of erythro- and threo-2-{(E)-2-[3-methoxy-4-(4-methyl-1H-imidazol-1-yl)phenyl]vinyl}-8-(1-phenylpyrrolidin-2-yl)-5,6,7,8-tetrahydro[1,2,4]triazolo[1,5-a]pyridine

[Formula 103]

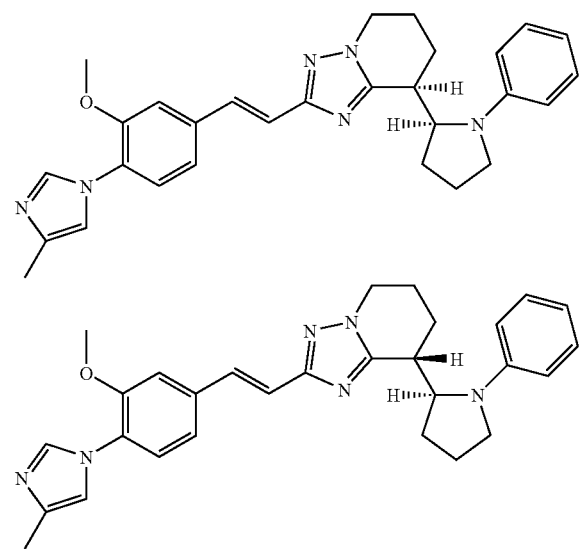

Bromobenzene (12 ul) was added to a solution of 2-{(E)-2-[3-methoxy-4-(4-methyl-1H-imidazol-1-yl)phenyl]vinyl}-8-(pyrrolidin-2-yl)-5,6,7,8-tetrahydro[1,2,4]triazolo[1,5-a]pyridine obtained in Examples 130, 131, 132 and 133 (15 mg), tris(dibenzylideneacetone)dipalladium (0) (7 mg), bis(diphenylphosphino)-1,1-binaphthalene (10 mg) and sodium tert-butoxide (13 mg) in toluene (3 ml)-dioxane (1 ml). The reaction solution was stirred at an external temperature of 100° C. overnight. Tris(dibenzylideneacetone)dipalladium (0) (7 mg), bis(diphenylphosphino)-1,1-binaphthalene (10 mg), sodium tert-butoxide (13 mg) and bromobenzene (12 ul) were added to the reaction solution, and the reaction solution was heated for further nine hours. After leaving the reaction solution to cool, ethyl acetate and water were added to the reaction solution and the organic layer was separated. The resulting organic layer was washed with brine, dried over anhydrous magnesium sulfate and then evaporated under reduced pressure. The resulting residue was purified by silica gel column chromatography (carrier: Chromatorex™ NH; elution solvent: heptane-ethyl acetate system) to obtain 10.3 mg of a diastereomer mixture of the title compound.

The mixture was separated by LC-MS. A saturated sodium bicarbonate solution and ethyl acetate were added to each of the resulting diastereomers, and the organic layer was separated. The resulting organic layer was washed with brine, dried over anhydrous magnesium sulfate and then concentrated under reduced pressure to obtain 0.35 mg of the title compound with a short retention time in LC-MS and 0.25 mg of the title compound with a long retention time in LC-MS.

The property value of the title diastereomer with a short retention time in LC-MS is as follows.

ESI-MS; m/z 481 [M$^+$+H].

The property value of the title diastereomer with a long retention time in LC-MS is as follows.

ESI-MS; m/z 481 [M$^+$+H].

Examples 136, 137, 138 and 139

Synthesis of (+), (+), (−) and (−)-8-(6,6-dimethyltetrahydropyran-2-yl)-2-{(E)-2-[3-methoxy-4-(4-methyl-1H-imidazol-1-yl)phenyl]vinyl}-5,6,7,8-tetrahydro[1,2,4]triazolo[1,5-a]pyridine

[Formula 104]

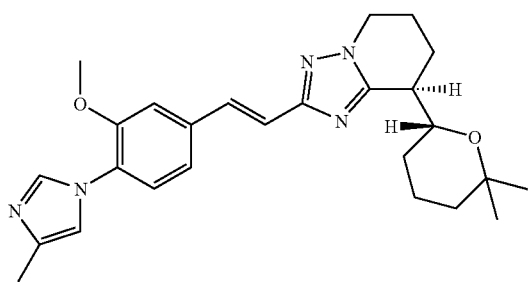

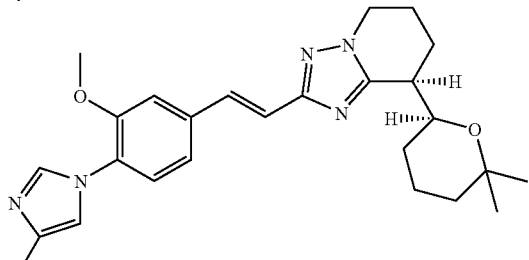

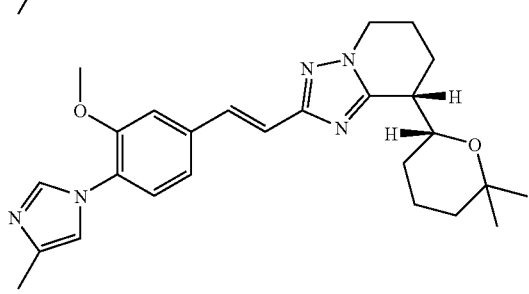

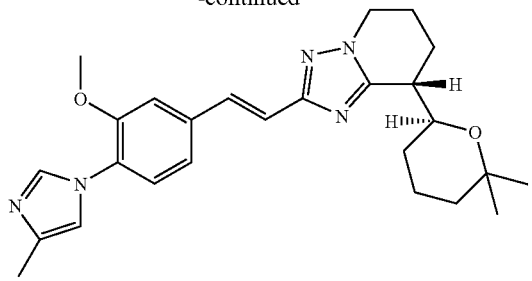

Synthesis of methyl 2-(6,6-dimethyltetrahydropyran-2-yl)acetate

Cerium chloride heptahydrate (812 mg) and sodium iodide (327 mg) were added to a solution of methyl 3-hydroxy-7-methyl-6-octenoate obtained by the method described in Heterocycles, 34, 1107-1117 (1992) (4.06 g) in acetonitrile (10 ml), and the reaction solution was heated under reflux for 10 hours. The reaction solution was left to cool and then concentrated under reduced pressure. Diethyl ether and 12 ml of 1 N hydrochloric acid were added to the resulting residue, and the organic layer was separated. Diethyl ether was added to the aqueous layer, and the organic layer was separated. The combined organic layers were sequentially washed with water, a saturated sodium bicarbonate solution (pH=9), a 5% sodium thiosulfate solution, water and brine, dried over anhydrous magnesium sulfate and then concentrated under reduced pressure. The resulting residue was purified by silica gel column chromatography (elution solvent: heptane-ethyl acetate system) to obtain 2.65 g of the title compound. The property values of the compound are as follows.

$^1$H-NMR (CDCl$_3$) δ (ppm): 1.08-1.48 (m, 3H), 1.18 (s, 3H), 1.20 (s, 3H), 1.57-1.73 (m, 3H), 2.34 (dd, J=14.8, 6.0 Hz, 1H), 2.48 (dd, J=14.8, 7.2 Hz, 1H), 3.67 (s, 3H), 3.94-4.02 (m, 1H).

Synthesis of tert-butyl N'-[5-chloro-2-(6,6-dimethyltetrahydropyran-2-yl)pentanoyl]hydrazinecarboxylate n-Butyl lithium (2.64 M solution in hexane, 1.1 ml) was added dropwise to a solution of diisopropylamine (0.45 ml) in THF (6 ml), and the reaction solution was stirred at −30° C. for 15 minutes. The reaction solution was cooled to −78° C. Hexamethylphosphoramide (0.75 ml) and a solution of methyl 2-(6,6-dimethyltetrahydropyran-2-yl)acetate (500 mg) in THF (3 ml) were sequentially added dropwise to the reaction solution, and the reaction solution was stirred at the same temperature for 20 minutes. 1-Chloro-3-iodopropane (0.43 ml) was added dropwise to the resulting reaction solution. The reaction solution was gradually heated, and then a saturated ammonium chloride solution was added to the reaction solution. Ethyl acetate and water were added to the reaction solution, and the organic layer was separated. The resulting organic layer was sequentially washed with 1 N hydrochloric acid, water, a saturated sodium bicarbonate solution and brine, dried over anhydrous magnesium sulfate and then concentrated under reduced pressure. The resulting residue was purified by silica gel column chromatography (elution solvent: heptane-ethyl acetate system) to obtain 278 mg of methyl 5-chloro-2-(6,6-dimethyltetrahydropyran-2-yl) valerate.

39 mg of the title compound was obtained from 278 mg of methyl 5-chloro-2-(6,6-dimethyltetrahydropyran-2-yl)valerate according to the method in Example 113. The property values of the compound are as follows.

ESI-MS; m/z 385 [M$^+$+H]. $^1$H-NMR (CDCl$_3$) δ (ppm): 1.15-1.33 (m, 1H), 1.21 (s, 3H), 1.23 (s, 3H), 1.36-1.57 (m, 3H), 1.47 (s, 9H), 1.58-1.98 (m, 6H), 2.26-2.33 (m, 1H), 3.48-3.62 (m, 2H), 3.63-3.76 (m, 1H), 6.39 (brs, 1H), 8.17 and 8.40 (each brs, 1H).

Synthesis of 5-chloro-2-(6,6-dimethyltetrahydropyran-2-yl)-valeric acid hydrazide hydrochloride 36 mg of the title compound was obtained from 39 mg of tert-butyl N'-[5-chloro-2-(6,6-dimethyltetrahydropyran-2-yl)pentanoyl]hydrazinecarboxylate according to the method in Example 113. The property value of the compound is as follows.

ESI-MS; m/z 263 [M$^+$−HCl+H].

Synthesis of (+), (+), (−) and (−)-8-(6,6-dimethyltetrahydropyran-2-yl)-2-{(E)-2-[3-methoxy-4-(4-methyl-1H-imidazol-1-yl)phenyl]vinyl}-5,6,7,8-tetrahydro[1,2,4]triazolo[1,5-a]pyridine 5.2 mg of a diastereomer mixture, 8-(6,6-dimethyltetrahydropyran-2-yl)-2-{(E)-2-[3-methoxy-4-(4-methyl-1H-imidazol-1-yl)phenyl]vinyl}-5,6,7,8-tetrahydro[1,2,4]triazolo[1,5-a]pyridine, was obtained according to the method in Example 113 from ethyl (E)-3-[3-methoxy-4-(4-methyl-1H-imidazol-1-yl)phenyl]acrylimidate dihydrochloride obtained in Example 1 (47 mg) and 5-chloro-2-(6,6-dimethyltetrahydropyran-2-yl)-valeric acid hydrazide hydrochloride (36 mg). The diastereomer mixture was separated by CHIRALPAK™ IA manufactured by Daicel Chemical Industries, Ltd. (2 cm×25 cm, mobile phase: 30% ethanol-hexane) to obtain the title optically active compound with a retention time of 13 minutes and positive optical rotation (0.75 mg), the title optically active compound with a retention time of 14 minutes and positive optical rotation (0.21 mg), the title optically active compound with a retention time of 16 minutes and negative optical rotation (0.13 mg) and the title optically active compound with a retention time of 24 minutes and negative optical rotation (0.54 mg).

The property values of the title optically active compound with a retention time of 13 minutes are as follows.

ESI-MS; m/z 448 [M$^+$+H]. $^1$H-NMR (CDCl$_3$) δ (ppm): 1.12 (s, 3H), 1.14 (s, 3H), 1.30-1.50 (m, 3H), 1.60-1.76 (m, 2H), 1.73-2.00 (m, 3H), 2.12-2.35 (m, 2H), 2.30 (d, J=0.8 Hz, 3H), 2.93 (dd, J=11.6, 6.0 Hz, 1H), 3.88 (s, 3H), 4.04-4.20 (m, 3H), 6.91 (brs, 1H), 7.07 (d, J=16.0 Hz, 1H), 7.16 (dd, J=8.0, 1.6 Hz, 1H), 7.19 (d, J=1.6 Hz, 1H), 7.22 (d, J=8.0 Hz, 1H), 7.51 (d, J=16.0 Hz, 1H), 7.69 (d, J=1.2 Hz, 1H).

The property values of the title optically active compound with a retention time of 14 minutes are as follows.

ESI-MS; m/z 448 [M$^+$+H]. $^1$H-NMR (CDCl$_3$) δ (ppm): 1.15-1.80 (m, 6H), 1.19 (s, 3H), 1.28 (s, 3H), 1.81-2.05 (m, 2H), 2.10-2.40 (m, 2H), 2.30 (s, 3H), 3.12-3.20 (m, 1H), 3.88 (s, 3H), 4.02-4.40 (m, 3H), 6.92 (brs, 1H), 7.07 (d, J=16.0 Hz, 1H), 7.17 (dd, J=8.0, 1.6 Hz, 1H), 7.21 (d, J=1.6 Hz, 1H), 7.22 (d, J=8.0 Hz, 1H), 7.52 (d, J=16.0 Hz, 1H), 7.70 (s, 1H).

The property values of the title optically active compound with a retention time of 16 minutes are as follows.

ESI-MS; m/z 448 [M$^+$+H]. $^1$H-NMR (CDCl$_3$) δ (ppm): 1.15-1.80 (m, 6H), 1.19 (s, 3H), 1.28 (s, 3H), 1.81-2.05 (m, 2H), 2.10-2.40 (m, 2H), 2.30 (s, 3H), 3.12-3.20 (m, 1H), 3.88 (s, 3H), 4.02-4.40 (m, 3H), 6.92 (brs, 1H), 7.07 (d, J=16.0 Hz, 1H), 7.17 (dd, J=8.0, 1.6 Hz, 1H), 7.21 (d, J=1.6 Hz, 1H), 7.22 (d, J=8.0 Hz, 1H), 7.52 (d, J=16.0 Hz, 1H), 7.70 (s, 1H).

The property values of the title optically active compound with a retention time of 24 minutes are as follows.

ESI-MS; m/z 448 [M$^+$+H]. $^1$H-NMR (CDCl$_3$) δ (ppm): 1.12 (s, 3H), 1.14 (s, 3H), 1.30-1.50 (m, 3H), 1.60-1.76 (m, 2H), 1.73-2.00 (m, 3H), 2.12-2.35 (m, 2H), 2.30 (d, J=0.8 Hz, 3H), 2.93 (dd, J=11.6, 6.0 Hz, 1H), 3.88 (s, 3H), 4.04-4.20 (m, 3H), 6.91 (brs, 1H), 7.07 (d, J=16.0 Hz, 1H), 7.16 (dd, J=8.0, 1.6 Hz, 1H), 7.19 (d, J=1.6 Hz, 1H), 7.22 (d, J=8.0 Hz, 1H), 7.51 (d, J=16.0 Hz, 1H), 7.69 (d, J=1.2 Hz, 1H).

Examples 140 and 141

Synthesis of (+)-2-{(E)-2-[3-methoxy-4-(4-methyl-1H-imidazol-1-yl)phenyl]vinyl}-7-phenyl-6,7-dihydro-5H-pyrrolo[1,2-b][1,2,4]triazole and (−)-2-{(E)-2-[3-methoxy-4-(4-methyl-1H-imidazol-1-yl)phenyl]vinyl}-7-phenyl-6,7-dihydro-5H-pyrrolo[1,2-b][1,2,4]triazole

[Formula 105]

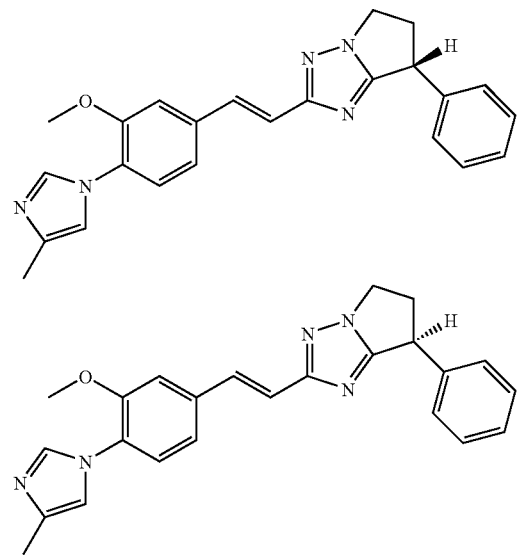

Synthesis of 4-chloro-2-phenylbutyric acid

A 2.64 M solution of butyl lithium in hexane (28 mL) was added to a solution of phenylacetic acid (5.07 g) in THF (150 mL) in a nitrogen atmosphere at −78° C., and the reaction solution was stirred at −78° C. for 20 minutes. The reaction solution was further stirred at 0° C. for one hour. Then, 1-bromo-2-chloroethane (3.1 mL) was added at 0° C., and the reaction solution was stirred at room temperature for 14 hours. Ethyl acetate and 1 N hydrochloric acid were added to the reaction solution, and the organic layer was separated. The resulting organic layer was washed with a saturated sodium chloride solution. The resulting organic layer was dried over magnesium sulfate and then concentrated under reduced pressure. The residue was purified by silica gel column chromatography (elution solvent: heptane-ethyl acetate system) to obtain 5.54 g of the title compound. The property values of the compound are as follows.

$^1$H-NMR (CDCl$_3$) δ (ppm): 2.19-2.28 (m, 1H), 2.47-2.57 (m, 1H), 3.32-3.40 (m, 1H), 3.52-3.58 (m, 1H), 3.92 (dd, J=8.0, 7.2 Hz, 1H), 7.26-7.37 (m, 5H).

Synthesis of (+)-2-{(E)-2-[3-methoxy-4-(4-methyl-1H-imidazol-1-yl)phenyl]vinyl}-7-phenyl-6,7-dihydro-5H-pyrrolo[1,2-b][1,2,4]triazole and (−)-2-{(E)-2-[3-methoxy-4-(4-methyl-1H-imidazol-1-yl)phenyl]vinyl}-7-phenyl-6,7-dihydro-5H-pyrrolo[1,2-b][1,2,4]triazole Oxalyl chloride (1.56 mL) and DMF (1 drop) were added to a solution of 4-chloro-2-phenylbutyric acid (2.28 g) in methylene chloride (40 mL) at 0° C., and the reaction solution was stirred at room temperature for one hour. The reaction solution was concentrated under reduced pressure to obtain 4-chloro-2-phenylbutyric acid chloride. A solution of 4-chloro-2-phenylbutyric acid chloride in THF (10 mL) was added to a solution of tert-butyl carbazate (1.5 g) and triethylamine (7.8 mL) in THF (40 mL) at 0° C., and the reaction solution was stirred at room temperature for one hour. The reaction solution was added to a saturated sodium bicarbonate solution, followed by extraction with ethyl acetate. The resulting extract was dried over magnesium sulfate and then concentrated under reduced pressure. The residue was purified by silica gel column chromatography (elution solvent: heptane-ethyl acetate system) to obtain tert-butyl N'-(4-chloro-2-phenylbutyryl)hydrazinecarboxylate (3.17 g). A solution of 4 N hydrogen chloride in ethyl acetate (50 mL) was added to tert-butyl N'-(4-chloro-2-phenylbutyryl)hydrazinecarboxylate (3.17 g). The reaction solution was stirred at room temperature for one hour and then concentrated under reduced pressure to obtain 4-chloro-2-phenylbutyric acid hydrazide hydrochloride (2.52 g). A solution of 4-chloro-2-phenylbutyric acid hydrazide hydrochloride (2.52 g) and triethylamine (5.7 mL) in ethanol (40 mL) was added to a solution of ethyl (E)-3-[3-methoxy-4-(4-methyl-1H-imidazol-1-yl)phenyl]acrylimidate dihydrochloride (3.00 g) and triethylamine (6.0 mL) in ethanol (50 mL) at room temperature, and the reaction solution was stirred at 80° C. for 24 hours. The reaction solution was left to cool to room temperature and then concentrated under reduced pressure. A saturated sodium bicarbonate solution was added to the resulting residue, followed by extraction with chloroform. The resulting extract was dried over magnesium sulfate and then concentrated under reduced pressure. The residue was purified by silica gel column chromatography (carrier: Chromatorex NH; elution solvent: heptane-ethyl acetate system) to obtain 231 mg of the racemic title compound. The property values of the compound are as follows.

ESI-MS; m/z 398 [M$^+$+H]. $^1$H-NMR (CDCl$_3$) δ (ppm): 2.29 (d, J=0.4 Hz, 3H), 2.67-2.76 (m, 1H), 3.20-3.30 (m, 1H), 3.87 (s, 3H), 4.17-4.25 (m, 1H), 4.30-4.38 (m, 1H), 4.45 (dd, J=8.8, 6.0 Hz, 1H), 6.89-6.92 (m, 1H), 7.08 (d, J=16.0 Hz, 1H), 7.14-7.38 (m, 8H), 7.56 (d, J=16.0 Hz, 1H), 7.69 (d, J=1.2 Hz, 1H).

The racemic title compound (16 mg) was separated by CHIRALPAK™ IB manufactured by Daicel Chemical Industries, Ltd. (2 cm×25 cm; mobile phase: hexane:ethanol=7:3) to obtain the title optically active compound with a retention time of 32 minutes and positive optical rotation (4 mg) and the title optically active compound with a retention time of 39 minutes and negative optical rotation (6 mg).

The following compounds were obtained by the same method as in Examples 140 and 141 (Table 4).

TABLE 4

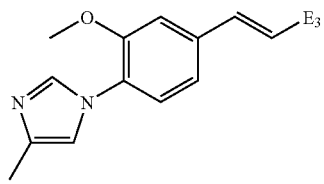

| Example | E$_3$ | DATA: MS m/z | Note |
|---|---|---|---|
| 142 | | M$^+$ + H: 432 (ESI) | Optically active compound (separation conditions IA:ethanol: retention time 22 min, optical rotation (+)) |
| 143 | | M$^+$ + H: 432 (ESI) | Optically active compound (separation conditions IA:ethanol: retention time 27 min, optical rotation (−)) |
| 144 | | M$^+$ + H: 416 (ESI) | Optically active compound (separation conditions IA:ethanol: retention time 25 min, optical rotation (+)) |

TABLE 4-continued

| Example | E₃ | DATA: MS m/z | Note |
|---|---|---|---|
| 145 | (structure) | M⁺ + H: 416 (ESI) | Optically active compound (separation conditions IA:ethanol: retention time 28 min, optical rotation (−)) |

The following compounds were obtained by the same method as in Examples 53 and 54 (Table 5).

TABLE 5

| Example | E₃ | DATA: MS m/z | Note |
|---|---|---|---|
| 146 | (structure) | M⁺ + H: 414 (ESI) | Optically active compound (separation conditions OJ-H, hexane:ethanol = 4:1, retention time 20 min, optical rotation (−)) |
| 147 | (structure) | M⁺ + H: 414 (ESI) | Optically active compound (separation conditions OJ-H, hexane:ethanol = 4:1, retention time 34 min, optical rotation (+)) |
| 148 | (structure) | M⁺ + H: 432 (ESI) | Optically active compound (separation conditions IA, hexane:ethanol = 4:1, retention time 31 min, optical rotation (−)) |
| 149 | (structure) | M⁺ + H: 432 (ESI) | Optically active compound (separation conditions IA, hexane:ethanol = 4:1, retention time 47 min, optical rotation (+)) |

TABLE 5-continued

[Structure: 4-methylimidazole attached to phenyl with OMe and vinyl-E₃ substituents]

| Example | E₃ | DATA: MS m/z | Note |
|---|---|---|---|
| 150 | [pyrrolotriazole with OH and 4-Cl-phenyl] | M⁺ + H: 448 (ESI) | Optically active compound (separation conditions IA, hexane:ethanol = 4:1, retention time 35 min, optical rotation (−)) |
| 151 | [pyrrolotriazole with OH and 4-Cl-phenyl, opposite stereo] | M⁺ + H: 448 (ESI) | Optically active compound (separation conditions IA, hexane:ethanol = 4:1, retention time 39 min, optical rotation (+)) |

The following compounds were obtained by the same method as in Examples 65 and 66 (Table 6).

TABLE 6

[Structure: 4-methylimidazole attached to phenyl with OMe and vinyl-E₃ substituents]

| Example | E₃ | DATA: MS m/z | Note |
|---|---|---|---|
| 152 | [pyrrolotriazole with CN and phenyl] | M⁺ + H: 423 (ESI) | Optically active compound (separation conditions IA, hexane:ethanol = 1:1, retention time 15 min, optical rotation (+)) |
| 153 | [pyrrolotriazole with CN and phenyl, opposite stereo] | M⁺ + H: 423 (ESI) | Optically active compound (separation conditions IA, hexane:ethanol = 1:1, retention time 18 min, optical rotation (−)) |
| 154 | [pyrrolotriazole with CN and 4-F-phenyl] | M⁺ + H: 441 (ESI) | Optically active compound (separation conditions IB, hexane:ethanol = 4:1, retention time 28 min, optical rotation (−)) |

TABLE 6-continued

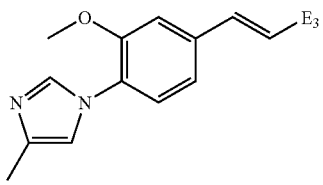

| Example | E₃ | DATA: MS m/z | Note |
|---|---|---|---|
| 155 | 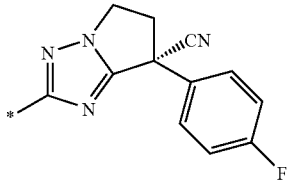 | M⁺ + H: 441 (ESI) | Optically active compound (separation conditions IB, hexane:ethanol = 4:1, retention time 34 min, optical rotation (+)) |
| 156 | 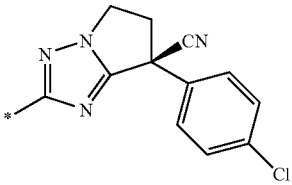 | M⁺ + H: 457 (ESI) | Optically active compound (separation conditions IB, hexane:ethanol = 4:1, retention time 23 min, optical rotation (−)) |
| 157 | 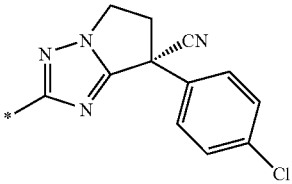 | M⁺ + H: 457 (ESI) | Optically active compound (separation conditions IB, hexane:ethanol = 4:1, retention time 32 min, optical rotation (+)) |
| 158 | 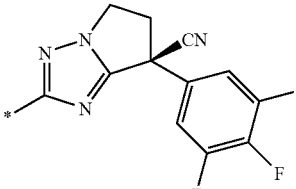 | M⁺ + H: 477 (ESI) | Optically active compound (separation conditions IB, hexane:ethanol = 1:1, retention time 10 min, optical rotation (−)) |
| 159 | 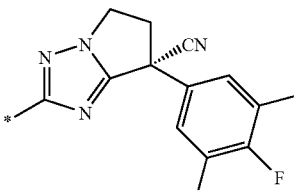 | M⁺ + H: 477 (ESI) | Optically active compound (separation conditions IB, hexane:ethanol = 1:1, retention time 13 min, optical rotation (+)) |

Examples 160 and 161

Synthesis of (−)-7-fluoro-2-{(E)-2-[3-methoxy-4-(4-methyl-1H-imidazol-1-yl)phenyl]vinyl}-7-phenyl-6,7-dihydro-5H-pyrrolo[1,2-b][1,2,4]triazole and (+)-7-fluoro-2-{(E)-2-[3-methoxy-4-(4-methyl-1H-imidazol-1-yl)phenyl]vinyl}-7-phenyl-6,7-dihydro-5H-pyrrolo[1,2-b][1,2,4]triazole

[Formula 106]

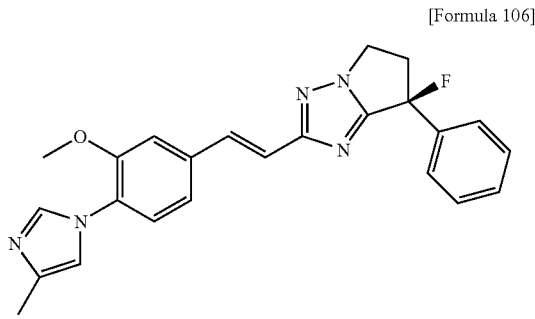

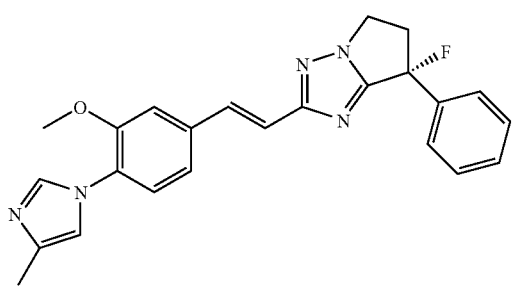

DAST (0.11 mL) was added to a solution of racemic 2-{(E)-2-[3-methoxy-4-(4-methyl-1H-imidazol-1-yl)phenyl]vinyl}-7-phenyl-6,7-dihydro-5H-pyrrolo[1,2-b][1,2,4]triazol-7-ol synthesized in Examples 146 and 147 (115 mg) in methylene chloride (5 mL) in a nitrogen atmosphere at 0° C., and the reaction solution was stirred at 0° C. for one hour. A saturated sodium bicarbonate solution was added to the reaction solution, followed by extraction with ethyl acetate. The resulting extract was dried over magnesium sulfate and then concentrated under reduced pressure. The residue was purified by silica gel column chromatography (carrier: Chromatorex NH; elution solvent: heptane-ethyl acetate system) to obtain 33 mg of the racemic title compound. The property values of the compound are as follows.

ESI-MS; m/z 416 [M++H]. $^1$H-NMR (CDCl$_3$) δ (ppm): 2.30 (s, 3H), 3.10-3.26 (m, 1H), 3.28-3.42 (m, 1H), 3.88 (s, 3H), 4.30-4.40 (m, 1H), 4.44-4.53 (m, 1H), 6.92 (brs, 1H), 7.11 (d, J=16.0 Hz, 1H), 7.15-7.26 (m, 3H), 7.39-7.48 (m, 3H), 7.54-7.59 (m, 2H), 7.64 (d, J=16.0 Hz, 1H), 7.70 (brs, 1H).

The racemic title compound (33 mg) was separated by CHIRALPAK™ IB manufactured by Daicel Chemical Industries, Ltd. (2 cm×25 cm; mobile phase: hexane:ethanol=8:2) to obtain the title optically active compound with a retention time of 32 minutes and negative optical rotation (10 mg) and the title optically active compound with a retention time of 36 minutes and positive optical rotation (10 mg).

Example 162

Synthesis of (4-fluorophenyl)-{5-{(E)-2-[3-methoxy-4-(4-methyl-1H-imidazol-1-yl)phenyl]vinyl}-4H-[1,2,4]triazol-3-yl}amine

[Formula 107]

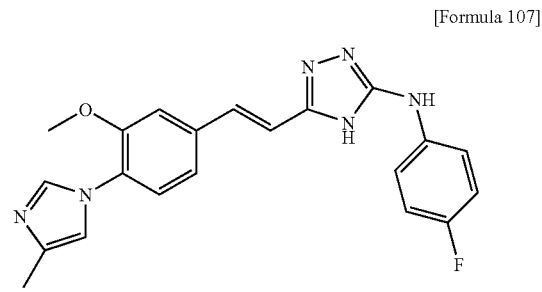

Synthesis of tert-butyl N'-{(E)-3-[3-methoxy-4-(4-methyl-1H-imidazol-1-yl)phenyl]acryloyl}hydrazinecarboxylate HOBT (420 mg) and EDC (590 mg) were sequentially added to a solution of (E)-3-[3-methoxy-4-(4-methyl-1H-imidazol-1-yl)phenyl]acrylic acid (530 mg), tert-butyl carbazate (271 mg) and IPEA (0.71 mL) in DMF (10 mL), and the reaction solution was stirred at room temperature for 15 hours. Ethyl acetate and saturated sodium bicarbonate water were added to the reaction solution, and the organic layer was separated. The resulting organic layer was dried over anhydrous magnesium sulfate and then concentrated under reduced pressure. The resulting solid was recrystallized from a mixed solution of ethyl acetate and ethanol to obtain 668 mg of the title compound. The property values of the compound are as follows.

$^1$H-NMR (CDCl$_3$) δ (ppm): 1.51 (s, 9H), 2.30 (s, 3H), 3.88 (s, 3H), 6.45 (d, J=15.6 Hz, 1H), 6.76 (brs, 1H), 6.93 (s, 1H), 7.09 (brs, 1H), 7.11 (brd, J=8.0 Hz, 1H), 7.25 (d, J=8.0 Hz, 1H), 7.65 (d, J=15.6 Hz, 1H), 7.73 (s, 1H), 8.80 (brs, 1H).

Synthesis of (E)-3-[3-methoxy-4-(4-methyl-1H-imidazol-1-yl)phenyl]acrylic acid hydrazide dihydrochloride A solution of 4 N hydrochloric acid in ethyl acetate (3 mL) was added to a solution of tert-butyl N'-{(E)-3-[3-methoxy-4-(4-methyl-1H-imidazol-1-yl)phenyl]acryloyl}hydrazinecarboxylate (668 mg) in ethyl acetate (5 mL) and methanol (1 mL), and the reaction solution was stirred at room temperature for two hours. The solid precipitated in the reaction solution was collected by filtration and washed with diethyl ether to obtain 658 mg of the title compound. The property value of the compound is as follows.

ESI-MS; m/z 273 [M++H].

Synthesis of (4-fluorophenyl)-{5-{(E)-2-[3-methoxy-4-(4-methyl-1H-imidazol-1-yl)phenyl]vinyl}-[1,3,4]oxadiazol-2-yl}amine TEA (1.25 mL) was added to a solution of (E)-3-[3-methoxy-4-(4-methyl-1H-imidazol-1-yl)phenyl]acrylic acid hydrazide dihydrochloride (771 mg) in DMF (15 mL) at room temperature, and the reaction solution was stirred at room temperature for 10 minutes. 4-Fluorophenyl isocyanate (0.26 mL) was added to the reaction solution at room temperature, and the reaction solution was stirred at room temperature for one hour. The reaction solution was added to cold water. The generated solid was separated by filtration, washed with water and diethyl ether and then dried at 60° C. for three hours. Phosphorus oxychloride (15 mL) was added to the resulting solid at room temperature, and the reaction solution was heated under reflux for three hours. The reaction solution was left to cool to room temperature and then concentrated under reduced pressure. A saturated sodium bicarbonate solution was added to the residue. The generated solid was separated by filtration, washed with diethyl ether and then dried at 60° C. for one hour to obtain 820 mg of the title compound. The property value of the compound is as follows.

ESI-MS; m/z 392 [M$^+$+H].

Synthesis of (4-fluorophenyl)-{5-{(E)-2-[3-methoxy-4-(4-methyl-1H-imidazol-1-yl)phenyl]vinyl}-4H-[1,2,4]triazol-3-yl}amine Acetic acid (10 mL) and ammonium acetate (6.8 g) were added to (4-fluorophenyl)-{5-{(E)-2-[3-methoxy-4-(4-methyl-1H-imidazol-1-yl)phenyl]vinyl}-[1,3,4]oxadiazol-2-yl}amine (692 mg), and the reaction solution was stirred at 150° C. for 12 hours. The reaction solution was left to cool to room temperature and then concentrated under reduced pressure. A saturated sodium bicarbonate solution was added to the resulting residue, followed by extraction with chloroform. The insoluble matter generated during separation was added to the resulting extract, and THF and ethanol were further added to provide a mixed solution. The mixed solution was concentrated under reduced pressure and solidified with ethyl acetate and diethyl ether to obtain 372 mg of the title compound. The property values of the compound are as follows.

ESI-MS; m/z 391 [M$^+$+H]. $^1$H-NMR (DMSO-d$_6$) δ (ppm): 2.16 (s, 3H), 3.91 (s, 3H), 7.04-7.19 (m, 4H), 7.27-7.30 (m, 1H), 7.36-7.48 (m, 2H), 7.51 (s, 1H), 7.57-7.64 (m, 2H), 7.80 (s, 1H).

Example 163

Synthesis of 8-(4-fluorophenyl)-3-{(E)-2-[3-methoxy-4-(4-methyl-1H-imidazol-1-yl)phenyl]vinyl}-5,6-dihydro-8H-[1,2,4]triazolo[4,3-a]pyrimidin-7-one

[Formula 108]

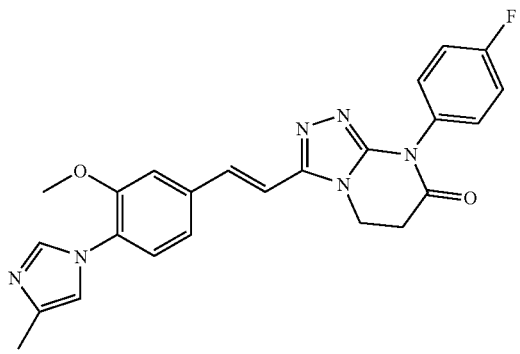

Synthesis of N-(4-fluorophenyl)-N-{5-{(E)-2-[3-methoxy-4-(4-methyl-1H-imidazol-1-yl)phenyl]vinyl}-[1,3,4]oxadiazol-2-yl}acrylamide TEA (0.07 mL) was added to a suspension of (4-fluorophenyl)-{5-{(E)-2-[3-methoxy-4-(4-methyl-1H-imidazol-1-yl)phenyl]vinyl}-[1,3,4]oxadiazol-2-yl}amine synthesized in Example 162 (100 mg) in methylene chloride (3 mL) and THF (2 mL) at room temperature. Acrylic acid chloride (0.03 mL) was added to the reaction solution at 0° C., and the reaction solution was stirred at room temperature for two hours. TEA (0.08 mL) and acrylic acid chloride (0.04 mL) were added to the reaction solution at room temperature, and the reaction solution was stirred at room temperature for two hours. Further, DMF (0.5 mL), acetonitrile (0.5 mL), DMAP (2 mg), TEA (0.08 mL) and acrylic acid chloride (0.04 mL) were added and the reaction solution was stirred at room temperature for 12 hours. The reaction solution was concentrated under reduced pressure. Ethyl acetate and a saturated sodium bicarbonate solution were added to the residue, and the organic layer was separated. The resulting organic layer was dried over magnesium sulfate and then concentrated under reduced pressure. The residue was purified by silica gel column chromatography (elution solvent: heptane-ethyl acetate system, then ethyl acetate-methanol system) to obtain 22 mg of the title compound. The property value of the compound is as follows.

ESI-MS; m/z 446 [M$^+$+H].

Synthesis of 8-(4-fluorophenyl)-3-{(E)-2-[3-methoxy-4-(4-methyl-1H-imidazol-1-yl)phenyl]vinyl}-5,6-dihydro-8H-[1,2,4]triazolo[4,3-a]pyrimidin-7-one Acetic acid (1 mL) and ammonium acetate (0.11 g) were added to N-(4-fluorophenyl)-N-{5-{(E)-2-[3-methoxy-4-(4-methyl-1H-imidazol-1-yl)phenyl]vinyl}-[1,3,4]oxadiazol-2-yl}acrylamide (22 mg), and the reaction solution was stirred at 150° C. for six hours. The reaction solution was left to cool to room temperature and then concentrated under reduced pressure. A saturated sodium bicarbonate solution was added to the resulting residue, followed by extraction with chloroform. The resulting extract was dried over magnesium sulfate and then concentrated under reduced pressure. The residue was purified by silica gel column chromatography (carrier: Chromatorex NH; elution solvent: heptane-ethyl acetate system, then ethyl acetate-methanol system) to obtain 1 mg of the title compound. The property values of the compound are as follows.

ESI-MS; m/z 445 [M$^+$+H]. $^1$H-NMR (CDCl$_3$) δ (ppm): 2.30 (s, 3H), 3.16 (t, J=6.8 Hz, 2H), 3.91 (s, 3H), 4.39 (t, J=6.8

Hz, 2H), 6.85 (d, J=16.0 Hz, 1H), 6.94 (s, 1H), 7.12-7.29 (m, 5H), 7.33-7.40 (m, 2H), 7.59 (d, J=16.0 Hz, 1H), 7.73 (d, J=1.2 Hz, 1H).

Example 164

Synthesis of 4-(4-fluorophenyl)-2-{(E)-2-[3-methoxy-4-(4-methyl-1H-imidazol-1-yl)phenyl]vinyl}-6,7-dihydro-4H-[1,2,4]triazolo[1,5-a]pyrimidin-5-one

[Formula 109]

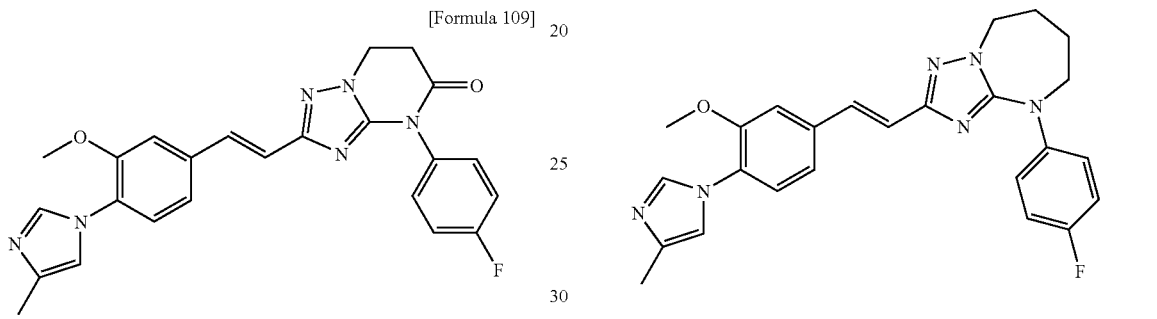

DMF (3 mL) and TEA (0.06 mL) were added to (4-fluorophenyl)-{5-{(E)-2-[3-methoxy-4-(4-methyl-1H-imidazol-1-yl)phenyl]vinyl}-4H-[1,2,4]triazol-3-yl}amine synthesized in Example 162 (44 mg), and the reaction solution was stirred at room temperature for 10 minutes. Acrylic acid chloride (0.01 mL) was added to the reaction solution at room temperature, and the reaction solution was stirred at room temperature for one hour and at 60° C. for two hours. TEA (0.03 mL) and acrylic acid chloride (0.01 mL) were added to the reaction solution at 60° C., and the reaction solution was stirred at 60° C. for four hours. The reaction solution was left to cool to room temperature and then diluted with ethyl acetate and washed with a saturated sodium bicarbonate solution and a saturated sodium chloride solution. The resulting organic layer was dried over magnesium sulfate and then concentrated under reduced pressure. The residue was purified by silica gel column chromatography (carrier: Chromatorex NH; elution solvent: heptane-ethyl acetate system, then ethyl acetate-methanol system) and further purified by silica gel column chromatography (elution solvent: heptane-ethyl acetate system, then ethyl acetate-methanol system) to obtain 6 mg of the title compound. The property values of the compound are as follows.

ESI-MS; m/z 445 [M$^+$+H]. $^1$H-NMR (CDCl$_3$) δ (ppm): 2.29 (d, J=0.8 Hz, 3H), 3.23 (t, J=7.2 Hz, 2H), 3.86 (s, 3H), 4.47 (t, J=7.2 Hz, 2H), 6.90-6.92 (m, 1H), 6.94 (d, J=16.0 Hz, 1H), 7.11-7.15 (m, 2H), 7.19-7.27 (m, 3H), 7.33-7.38 (m, 2H), 7.46 (d, J=16.0 Hz, 1H), 7.70 (d, J=1.2 Hz, 1H).

Example 165

Synthesis of 8-(4-fluorophenyl)-2-{(E)-2-[3-methoxy-4-(4-methyl-1H-imidazol-1-yl)phenyl]vinyl}-5,6,7,8-tetrahydro-4H-1,3,3a,8-tetraazaazulene

[Formula 110]

60% sodium hydride (10 mg) was added to a solution of (4-fluorophenyl)-{5-{(E)-2-[3-methoxy-4-(4-methyl-1H-imidazol-1-yl)phenyl]vinyl}-4H-[1,2,4]triazol-3-yl}amine synthesized in Example 162 (47.5 mg) in DMF (3 mL) at room temperature, and the reaction solution was stirred at room temperature for 10 minutes. 1,4-Dibromobutane (0.02 mL) was added to the reaction solution at room temperature, and the reaction solution was stirred at room temperature for two hours. 60% sodium hydride (5 mg) was added to the reaction solution at room temperature, and the reaction solution was stirred at room temperature for two hours. A saturated ammonium chloride solution was added to the reaction solution at 0° C., followed by extraction with ethyl acetate. The resulting extract was washed with a saturated sodium bicarbonate solution and a saturated sodium chloride solution. The resulting organic layer was dried over magnesium sulfate and then concentrated under reduced pressure. The residue was purified by silica gel column chromatography (carrier: Chromatorex NH; elution solvent: heptane-ethyl acetate system, then ethyl acetate-methanol system), silica gel column chromatography (elution solvent: heptane-ethyl acetate system, then ethyl acetate-methanol system) and CHIRALPAK™ IA manufactured by Daicel Chemical Industries, Ltd. (2 cm×25 cm; mobile phase: ethanol) to obtain 14 mg of the title compound. The property values of the compound are as follows.

ESI-MS; m/z 445 [M$^+$+H]. $^1$H-NMR (CDCl$_3$) δ (ppm): 1.94-2.06 (m, 4H), 2.29 (s, 3H), 3.69-3.76 (m, 2H), 3.85 (s, 3H), 4.23-4.30 (m, 2H), 6.89-6.95 (m, 2H), 7.00-7.06 (m, 2H), 7.10-7.22 (m, 5H), 7.40 (d, J=16.0 Hz, 1H), 7.68 (d, J=0.8 Hz, 1H).

Examples 166 and 167

Synthesis of (−)-2-{(E)-2-[3-methoxy-4-(4-methyl-1H-imidazol-1-yl)phenyl]vinyl}-7-phenyl-5,6,7,8-tetrahydro-[1,2,4]triazolo[1,5-a]pyridine and (+)-2-{(E)-2-[3-methoxy-4-(4-methyl-1H-imidazol-1-yl)phenyl]vinyl}-7-phenyl-5,6,7,8-tetrahydro-[1,2,4]triazolo[1,5-a]pyridine

[Formula 111]

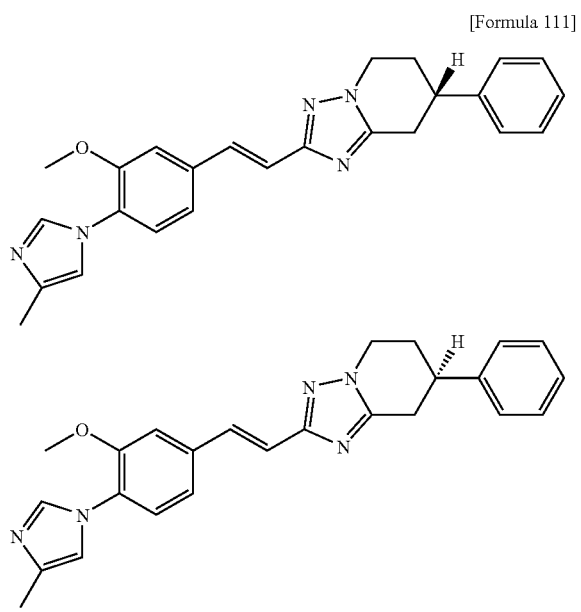

Synthesis of 5-hydroxy-3-phenylpentanoic acid hydrazide

Hydrazine monohydrate (1.6 mL) was added to a solution of 4-phenyl-tetrahydropyran-2-one (573 mg; CAS No. 61949-75-5) in ethanol (3 mL) at room temperature, and the reaction solution was heated under reflux for three hours. The reaction solution was left to cool to room temperature and then concentrated under reduced pressure. A saturated sodium bicarbonate solution was added to the resulting residue, followed by extraction with chloroform. The resulting extract was dried over magnesium sulfate and then concentrated under reduced pressure. The residue was purified by silica gel column chromatography (elution solvent: ethyl acetate-methanol system) to obtain 492 mg of the title compound. The property value of the compound is as follows.
ESI-MS; m/z 209 [M$^+$+H].

Synthesis of and 2-(4-chloro-2-phenylbutyl)-5-{(E)-2-[3-methoxy-4-(4-methyl-1H-imidazol-1-yl)phenyl]vinyl}-[1,3,4]oxadiazole IPEA (2.0 mL), (E)-3-[3-methoxy-4-(4-methyl-1H-imidazol-1-yl)phenyl]acrylic acid (600 mg) and BOPCl (0.71 g) were added to a solution of 5-hydroxy-3-phenylpentanoic acid hydrazide (492 mg) in methylene chloride (20 mL) at room temperature, and the reaction solution was stirred at room temperature for seven hours. Water was added to the reaction solution, followed by extraction with chloroform. The resulting extract was washed with a saturated sodium bicarbonate solution. The resulting organic layer was dried over magnesium sulfate and then concentrated under reduced pressure. Phosphorus oxychloride (10 mL) was added to the resulting residue at room temperature, and the reaction solution was heated under reflux for 1.5 hours. The reaction solution was left to cool to room temperature and then concentrated under reduced pressure. A saturated sodium bicarbonate solution was added to the residue, followed by extraction with ethyl acetate. The resulting extract was dried over magnesium sulfate and then concentrated under reduced pressure. The residue was purified by silica gel column chromatography (carrier: Chromatorex NH; elution solvent: heptane-ethyl acetate system) to obtain 445 mg of the title compound. The property value of the compound is as follows.
ESI-MS; m/z 449 [M$^+$+H].

Synthesis of (−)-2-{(E)-2-[3-methoxy-4-(4-methyl-1H-imidazol-1-yl)phenyl]vinyl}-7-phenyl-5,6,7,8-tetrahydro-[1,2,4]triazolo[1,5-a]pyridine and (+)-2-{(E)-2-[3-methoxy-4-(4-methyl-1H-imidazol-1-yl)phenyl]vinyl}-7-phenyl-5,6,7,8-tetrahydro-[1,2,4]triazolo[1,5-a]pyridine Acetic acid (5 mL) and ammonium acetate (1.2 g) were added to 2-(4-chloro-2-phenylbutyl)-5-{(E)-2-[3-methoxy-4-(4-methyl-1H-imidazol-1-yl)phenyl]vinyl}-[1,3,4]oxadiazole (224 mg), and the reaction solution was stirred at 150° C. for 17 hours. The reaction solution was left to cool to room temperature and then concentrated under reduced pressure. A saturated sodium bicarbonate solution was added to the resulting residue, followed by extraction with ethyl acetate. The resulting extract was dried over magnesium sulfate and then concentrated under reduced pressure. The residue was purified by silica gel column chromatography (carrier: Chromatorex NH; elution solvent: heptane-ethyl acetate system) to obtain 115 mg of the racemic title compound. The property values of the compound are as follows.

ESI-MS; m/z 412 [M$^+$+H]. $^1$H-NMR (CDCl$_3$) δ (ppm): 2.27-2.44 (m, 2H), 2.30 (d, J=0.8 Hz, 3H), 3.00-3.11 (m, 1H), 3.25-3.37 (m, 2H), 3.88 (s, 3H), 4.17-4.26 (m, 1H), 4.27-4.35 (m, 1H), 6.91-6.94 (m, 1H), 7.08 (d, J=16.4 Hz, 1H), 7.15-7.32 (m, 6H), 7.35-7.40 (m, 2H), 7.55 (d, J=16.4 Hz, 1H), 7.70 (d, J=1.6 Hz, 1H).

The racemic title compound (26 mg) was separated by CHIRALPAK™ IA manufactured by Daicel Chemical Industries, Ltd. (2 cm×25 cm; mobile phase: hexane:IPA=1: 4) to obtain the title optically active compound with a retention time of 25 minutes and negative optical rotation (10 mg) and the title optically active compound with a retention time of 29 minutes and positive optical rotation (6.6 mg).

Examples 168 and 169

Synthesis of (+)-2-{(E)-2-[6-methoxy-5-(4-methyl-1H-imidazol-1-yl)pyridin-2-yl]vinyl}-8-(3,4,5-trifluorophenyl)-5,6,7,8-tetrahydro-[1,2,4]triazolo[1,5-a]pyridine and (−)-2-{(E)-2-[6-methoxy-5-(4-methyl-1H-imidazol-1-yl)pyridin-2-yl]vinyl}-8-(3,4,5-trifluorophenyl)-5,6,7,8-tetrahydro-[1,2,4]triazolo[1,5-a]pyridine

[Formula 112]

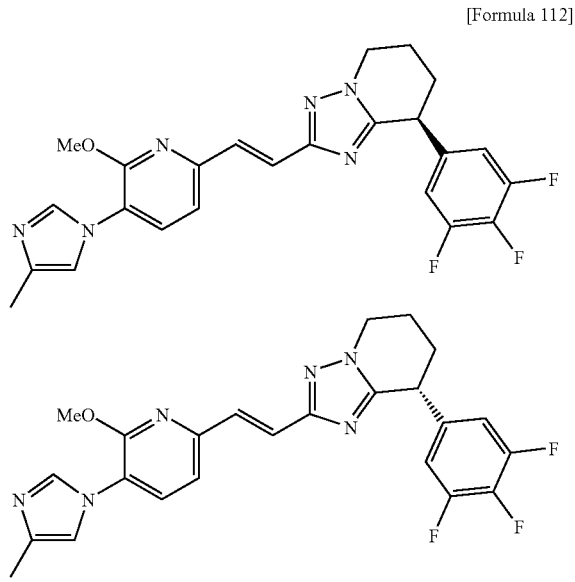

Synthesis of 6-chloro-2-methoxy-3-nitropyridine

Sodium methoxide (2.8 g) was added to a solution of 2,6-dichloro-3-nitropyridine (10 g) in THF (100 mL) at 0° C., and the reaction solution was stirred at room temperature for 13 hours. A saturated ammonium chloride solution and ethyl acetate were added to the reaction solution, and the organic layer was separated. The resulting organic layer was washed with brine, dried over anhydrous magnesium sulfate and then concentrated under reduced pressure. The residue was purified by silica gel column chromatography (elution solvent: heptane-ethyl acetate system) to obtain 6.49 g of the title compound. The property value of the compound is as follows.

ESI-MS; m/z 189 [M$^+$+H].

Synthesis of ethyl (E)-3-(6-methoxy-5-nitropyridin-2-yl)acrylate

Palladium acetate (386 mg), 2-(di-tert-butylphosphino)biphenyl (1.03 g), triethylamine (9.59 mL) and ethyl acrylate (18.6 mL) were added to a solution of 6-chloro-2-methoxy-3-nitropyridine (6.49 g) in DMF (100 mL). The reaction solution was stirred in a nitrogen atmosphere at 120° C. for two hours and then left to cool to room temperature. The reaction solution was concentrated under reduced pressure. Water and ethyl acetate were added to the resulting residue, and the organic layer was separated. The resulting organic layer was washed with water and brine, dried over anhydrous sodium sulfate and then concentrated under reduced pressure. The residue was purified by silica gel column chromatography (elution solvent: heptane-ethyl acetate system) and crystallized from heptane to obtain 2.1 g of the title compound. The property values of the compound are as follows.

$^1$H-NMR (CDCl$_3$) δ (ppm): 1.37 (t, J=7.6 Hz, 3H), 4.15 (s, 3H), 4.30 (q, J=7.6 Hz, 2H), 7.00 (d, J=16.0 Hz, 1H), 7.09 (d, J=8.4 Hz, 1H), 7.56 (d, J=16.0 Hz, 1H), 8.28 (d, J=8.4 Hz, 1H).

Synthesis of ethyl (E)-3-(5-amino-6-methoxypyridin-2-yl)acrylate

Iron (3.72 g) and ammonium chloride (7.13 g) were added to a solution of ethyl (E)-3-(6-methoxy-5-nitropyridin-2-yl)acrylate (2.1 g) in ethanol (100 mL) and water (20 mL). The reaction solution was stirred at 100° C. for one hour and then left to cool to room temperature. The reaction solution was filtered through celite. Ethyl acetate was added and the organic layer was separated. The resulting organic layer was washed with saturated sodium bicarbonate water and brine, dried over anhydrous magnesium sulfate and then concentrated under reduced pressure. The residue was purified by silica gel column chromatography (elution solvent: heptane-ethyl acetate system) to obtain 1.85 g of the title compound. The property values of the compound are as follows.

$^1$H-NMR (CDCl$_3$) δ (ppm): 1.33 (t, J=7.2 Hz, 3H), 4.01 (s, 3H), 4.07 (brs, 2H), 4.25 (q, J=7.2 Hz, 2H), 6.71 (d, J=15.6 Hz, 1H), 6.78 (d, J=7.6 Hz, 1H), 6.84 (d, J=7.6 Hz, 1H), 7.51 (d, J=15.6 Hz, 1H).

Synthesis of ethyl (E)-3-[6-methoxy-5-(4-methyl-1H-imidazol-1-yl)pyridin-2-yl]acrylate A mixed solution prepared from acetic anhydride (6.29 mL) and formic acid (9.42 mL) was added dropwise to a solution of ethyl (E)-3-(5-amino-6-methoxypyridin-2-yl)acrylate (1.85 g) in THF (30 mL) at 0° C. The reaction solution was stirred at room temperature for one hour and then added dropwise to ice water. Ethyl acetate was added and the organic layer was separated. The resulting organic layer was washed with saturated sodium bicarbonate water and brine, dried over anhydrous magnesium sulfate and then concentrated under reduced pressure. Subsequently, cesium carbonate (4.87 g), potassium iodide (124 mg) and chloroacetone (1.23 mL) were added to a solution of the residue in DMF (20 mL), and the reaction solution was stirred at room temperature for 12 hours. Ice water and ethyl acetate were added to the reaction solution, and the organic layer was separated. The resulting organic layer was washed with water and brine, dried over anhydrous magnesium sulfate and then concentrated under reduced pressure. The residue was purified by silica gel column chromatography (elution solvent: heptane-ethyl acetate system) to obtain a crude product. Subsequently, ammonium acetate (2.88 g) was added to a solution of the resulting compound in acetic acid (4.28 mL), and the reaction solution was stirred at 130° C. for one hour. The reaction solution was left to cool to room temperature. Ice water and ethyl acetate were added and the organic layer was separated. The resulting organic layer was washed with saturated sodium bicarbonate water and brine, dried over anhydrous magnesium sulfate and then concentrated under reduced pressure. The residue was purified by silica gel column chromatography (elution solvent: heptane-ethyl acetate system) to obtain 1.50 g of the title compound. The property values of the compound are as follows.

$^1$H-NMR (CDCl$_3$) δ (ppm): 1.36 (t, J=7.2 Hz, 3H), 2.30 (d, J=0.8 Hz, 3H), 4.07 (s, 3H), 4.29 (q, J=7.2 Hz, 2H), 6.95 (d, J=15.6 Hz, 1H), 6.80 (d, J=8.0 Hz, 1H), 7.54 (d, J=8.0 Hz, 1H), 7.58 (d, J=15.6 Hz, 1H), 7.83 (d, J=0.8 Hz, 1H).

Synthesis of (E)-3-[6-methoxy-5-(4-methyl-1H-imidazol-1-yl)pyridin-2-yl]acrylic acid A 5 N sodium hydroxide solution (4 mL) was added to a solution of ethyl (E)-3-[6-methoxy-5-(4-methyl-1H-imidazol-1-yl)pyridin-2-yl]acrylate (1.5 g) in methanol (10 mL) and THF (6 mL). The reaction solution was stirred at room temperature for two hours, and then 5 N hydrochloric acid (5 mL) was added to the reaction solution. The generated precipitate was filtered and washed with THF to obtain 755 mg of the title compound. The property values of the compound are as follows.

ESI-MS; m/z 260 [M$^+$+H]. $^1$H-NMR (DMSO-d$_6$) δ (ppm): 2.16 (s, 3H), 3.99 (s, 3H), 6.81 (d, J=16.0 Hz, 1H), 7.27 (s, 1H), 7.42 (d, J=8.0 Hz, 1H), 7.57 (d, J=16.0 Hz, 1H), 7.89 (d, J=8.0 Hz, 1H), 7.94 (s, 1H).

Synthesis of 1-amino-3-(3,4,5-trifluorophenyl)piperidin-2-one 6.6 g of the title compound was obtained from 3,4,5-trifluorophenylacetic acid (11 g) according to the method in Examples 20 and 21. The property value of the compound is as follows.

ESI-MS; m/z 245 [M$^+$+H].

Synthesis of (E)-3-[6-methoxy-5-(4-methyl-1H-imidazol-1-yl)pyridin-2-yl]-N-[2-oxo-3-(3,4,5-trifluorophenyl)piperidin-1-yl]acrylamide EDC (667 mg), HOBT (470 mg) and IPEA (1.01 mL) were added to a suspension of (E)-3-[6-methoxy-5-(4-methyl-1H-imidazol-1-yl)pyridin-2-yl]acrylic acid (300 mg) and 1-amino-3-(3,4,5-trifluorophenyl)piperidin-2-one (368 mg) in DMF (10 mL). The reaction solution was stirred at room temperature for 15 hours. Then, water and ethyl acetate were added to the reaction solution, and the organic layer was separated. The resulting organic layer was washed with brine, dried over anhydrous magnesium sulfate and then concentrated under reduced pressure. The residue was purified by silica gel column chromatography (elution solvent: ethyl acetate-methanol system) to obtain 508 mg of the title compound. The property value of the compound is as follows.

ESI-MS; m/z 486 [M$^+$+H].

Synthesis of (+)-2-{(E)-2-[6-methoxy-5-(4-methyl-1H-imidazol-1-yl)pyridin-2-yl]vinyl}-8-(3,4,5-trifluorophenyl)-5,6,7,8-tetrahydro-[1,2,4]triazolo[1,5-a]pyridine and (−)-2-{(E)-2-[6-methoxy-5-(4-methyl-1H-imidazol-1-yl)pyridin-2-yl]vinyl}-8-(3,4,5-trifluorophenyl)-5,6,7,8-tetrahydro-[1,2,4]triazolo[1,5-a]pyridine Phosphorus oxychloride (5 mL) was added to (E)-3-[6-methoxy-5-(4-methyl-1H-imidazol-1-yl)pyridin-2-yl]-N-[2-oxo-3-(3,4,5-trifluorophenyl)piperidin-1-yl]acrylamide (508 mg). The reaction solution was stirred at 120° C. for one hour and then concentrated under reduced pressure. Subsequently, ammonium acetate (2.43 g) was added to a solution of the residue in acetic acid (5 mL), and the reaction solution was stirred at 150° C. for two hours. The reaction solution was left to cool to room temperature and then concentrated under reduced pressure. Saturated sodium bicarbonate water and ethyl acetate were added to the resulting residue, and the organic layer was separated. The resulting organic layer was washed with brine, dried over anhydrous magnesium sulfate and then concentrated under reduced pressure. The residue was purified by silica gel column chromatography (elution solvent: heptane-ethyl acetate system) to obtain a racemate of the title compound. The resulting racemate was separated by CHIRALCEL™ OD-H manufactured by Daicel Chemical Industries, Ltd. (2 cm×25 cm; mobile phase: ethanol) to obtain the title optically active compound with a retention time of 6 minutes and positive optical rotation (108.8 mg, >99% ee) and the title optically active compound with a retention time of 8 minutes and negative optical rotation (104.8 mg, >99% ee).

The property values of the title compound with a retention time of 6 minutes are as follows.

ESI-MS; m/z 467 [M$^+$+H]. $^1$H-NMR (CDCl$_3$) δ (ppm): 1.99-2.06 (m, 1H), 2.11-2.22 (m, 2H), 2.29 (d, J=1.2 Hz, 3H), 2.34-2.40 (m, 1H), 4.05 (s, 3H), 4.25-4.31 (m, 3H), 4.39-4.45 (m, 1H), 6.81 (dd, J=8.0, 6.4 Hz, 2H), 6.94 (d, J=8.0 Hz, 1H), 6.95 (d, J=1.2 Hz, 1H), 7.45 (d, J=15.2 Hz, 1H), 7.47 (d, J=8.0 Hz, 1H), 7.64 (d, J=15.2 Hz, 1H), 7.76 (d, J=1.2 Hz, 1H).

The property values of the title compound with a retention time of 8 minutes are as follows.

ESI-MS; m/z 467 [M$^+$+H]. $^1$H-NMR (CDCl$_3$) δ (ppm): 1.99-2.06 (m, 1H), 2.11-2.22 (m, 2H), 2.29 (d, J=1.2 Hz, 3H), 2.34-2.40 (m, 1H), 4.05 (s, 3H), 4.25-4.31 (m, 3H), 4.39-4.45 (m, 1H), 6.81 (dd, J=8.0, 6.4 Hz, 2H), 6.94 (d, J=8.0 Hz, 1H), 6.95 (d, J=1.2 Hz, 1H), 7.45 (d, J=15.2 Hz, 1H), 7.47 (d, J=8.0 Hz, 1H), 7.64 (d, J=15.2 Hz, 1H), 7.76 (d, J=1.2 Hz, 1H).

Examples 170 and 171

Synthesis of (+) and (−)-8-(3,4-difluorophenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine

[Formula 113]

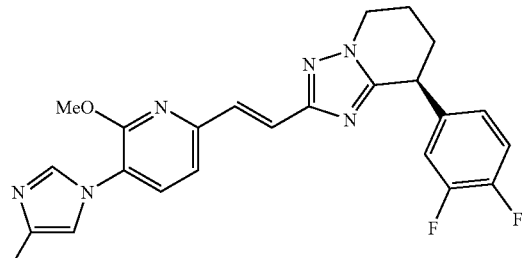

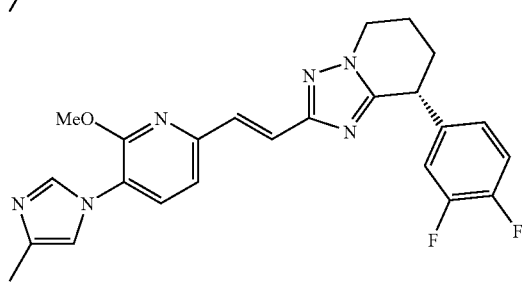

242 mg of the racemic title compound was obtained from (E)-3-[6-methoxy-5-(4-methyl-1H-imidazol-1-yl)pyridin-2- yl]acrylic acid (600 mg) and 1-amino-3-(3,4-difluorophenyl)piperidin-2-one (471 mg) in the same manner as in Examples 168 and 169. The property values of the compound are as follows.

ESI-MS; m/z 449 [M$^+$+H].

$^1$H-NMR (CDCl$_3$) δ (ppm): 2.00-2.25 (m, 3H), 2.29 (s, 3H), 2.31-2.41 (m, 1H), 4.05 (s, 3H), 4.27-4.32 (m, 3H), 6.87-6.91 (m, 1H), 6.93-6.95 (m, 2H), 6.97-7.00 (m, 1H), 7.09-7.16 (m, 1H), 7.45 (d, J=15.6 Hz, 1H), 7.46 (d, J=7.2 Hz, 1H), 7.64 (d, J=15.6 Hz, 1H), 7.76 (d, J=1.6 Hz, 1H).

The racemic title compound was separated by CHIRALPAK™ IB manufactured by Daicel Chemical Industries, Ltd. (2 cm×25 cm; mobile phase: ethanol) to obtain the title optically active compound with a retention time of 13.5 minutes and positive optical rotation (100 mg) and the title optically active compound with a retention time of 20.0 minutes and negative optical rotation (94 mg).

Examples 172 and 173

Synthesis of (+)-8-(4-fluorophenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine and (−)-8-(4-fluorophenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine

[Formula 114]

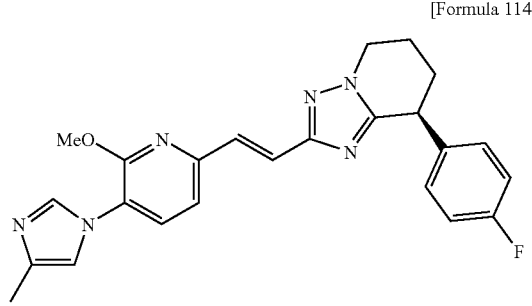

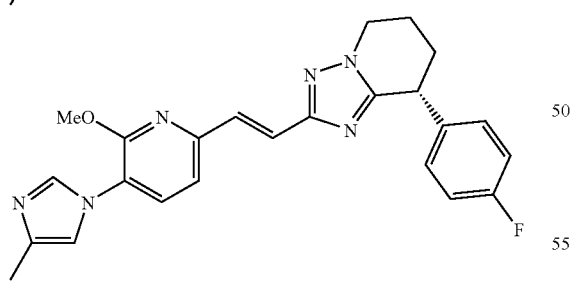

Synthesis of 1-amino-3-(4-fluorophenyl)piperidin-2-one 3.6 g of the title compound was obtained from 4-fluorophenylacetic acid (6 g) according to the method in Examples 20 and 21. The property value of the compound is as follows.

ESI-MS; m/z 209 [M$^+$+H].

Synthesis of (+)-8-(4-fluorophenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine and (−)-8-(4-fluorophenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine A racemate of the title compound was obtained from (E)-3-[6-methoxy-5-(4-methyl-1H-imidazol-1-yl)pyridin-2-yl]acrylic acid (150 mg) and 1-amino-3-(4-fluorophenyl)piperidin-2-one (181 mg) according to the method in Examples 168 and 169. The resulting racemate was separated by CHIRALPAK™ IB manufactured by Daicel Chemical Industries, Ltd. (2 cm×25 cm; mobile phase: hexane:ethanol=1:1) to obtain the title optically active compound with a retention time of 18 minutes and positive optical rotation (6.2 mg, >99% ee) and the title optically active compound with a retention time of 42 minutes and negative optical rotation (5.5 mg, >99% ee).

The property values of the title compound with a retention time of 18 minutes are as follows.

ESI-MS; m/z 431 [M$^+$+H]. $^1$H-NMR (CDCl$_3$) δ (ppm): 2.01-2.10 (m, 2H), 2.16-2.22 (m, 1H), 2.29 (s, 3H), 2.33-2.38 (m, 1H), 4.04 (s, 3H), 4.27-4.35 (m, 3H), 6.93 (d, J=8.0 Hz, 1H), 6.94 (s, 1H), 6.99-7.05 (m, 2H), 7.08-7.12 (m, 2H), 7.45 (d, J=15.6 Hz, 1H), 7.46 (d, J=8.0 Hz, 1H), 7.64 (d, J=15.6 Hz, 1H), 7.76 (s, 1H).

The property values of the title compound with a retention time of 42 minutes are as follows.

ESI-MS; m/z 431 [M$^+$+H]. $^1$H-NMR (CDCl$_3$) δ (ppm): 2.01-2.10 (m, 2H), 2.16-2.22 (m, 1H), 2.29 (s, 3H), 2.33-2.38 (m, 1H), 4.04 (s, 3H), 4.27-4.35 (m, 3H), 6.93 (d, J=8.0 Hz, 1H), 6.94 (s, 1H), 6.99-7.05 (m, 2H), 7.08-7.12 (m, 2H), 7.45 (d, J=15.6 Hz, 1H), 7.46 (d, J=8.0 Hz, 1H), 7.64 (d, J=15.6 Hz, 1H), 7.76 (s, 1H).

Examples 174 and 175

Synthesis of (−)-8-(3-chloro-4-fluorophenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine and (+)-8-(3-chloro-4-fluorophenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine

[Formula 115]

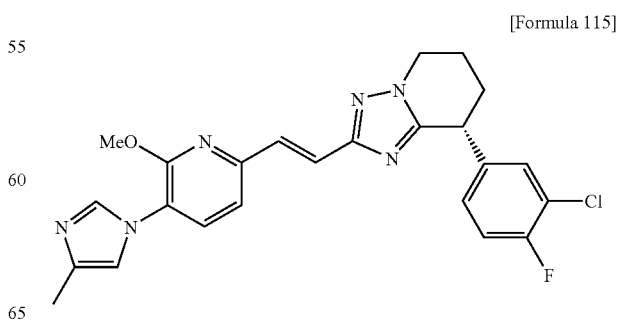

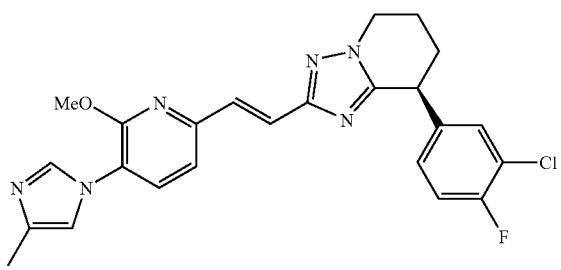

Synthesis of 1-amino-3-(3-chloro-4-fluorophenyl)piperidin-2-one

The title compound (2.8 g) was obtained from 3-chloro-4-fluorophenylacetic acid (5.0 g) according to the method in Examples 20 and 21. The property value of the compound is as follows.

ESI-MS; m/z 243 [M$^+$+H].

Synthesis of (−)-8-(3-chloro-4-fluorophenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine and (+)-8-(3-chloro-4-fluorophenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine A racemate of the title compound (30 mg) was obtained from 1-amino-3-(3-chloro-4-fluorophenyl)piperidin-2-one (100 mg) and (E)-3-[6-methoxy-5-(4-methyl-1H-imidazol-1-yl)pyridin-2-yl]acrylic acid (200 mg) according to the method in Examples 168 and 169. The racemate was optically resolved by CHIRALPAK™ AD-H manufactured by Daicel Chemical Industries, Ltd. (2 cm×25 cm, mobile phase: 80% ethanol-hexane, flow rate: 10 mL/min) to isolate the title optically active compound with a retention time of 19 minutes and positive optical rotation (13.6 mg) and the title optically active compound with a retention time of 23 minutes and negative optical rotation (13.6 mg). The property values of the title optically active compound with a retention time of 23 minutes are as follows.

$^1$H-NMR (CDCl$_3$) δ (ppm): 1.96-2.26 (m, 3H), 2.26-2.44 (m, 1H), 2.29 (s, 3H), 4.05 (s, 3H), 4.30 (t, J=6.0 Hz, 3H), 6.95 (d, J=8.0 Hz, 1H), 6.96 (s, 1H), 7.00-7.06 (m, 1H), 7.12 (t, J=8.0 Hz, 1H), 7.20 (dd, J=2.4, 6.8 Hz, 1H), 7.46 (d, J=16 Hz, 1H), 7.47 (d, J=8.0 Hz, 1H), 7.65 (d, J=16 Hz, 1H), 7.77 (d, J=1.6 Hz, 1H).

ESI-MS; m/z 465 [M$^+$+H].

The property values of the title optically active compound with a retention time of 19 minutes and positive optical rotation corresponded to the values of the (−)-isomer.

Examples 176 and 177

Synthesis of (−)-8-(4-chloro-3-fluorophenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine and (+)-8-(4-chloro-3-fluorophenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine

[Formula 116]

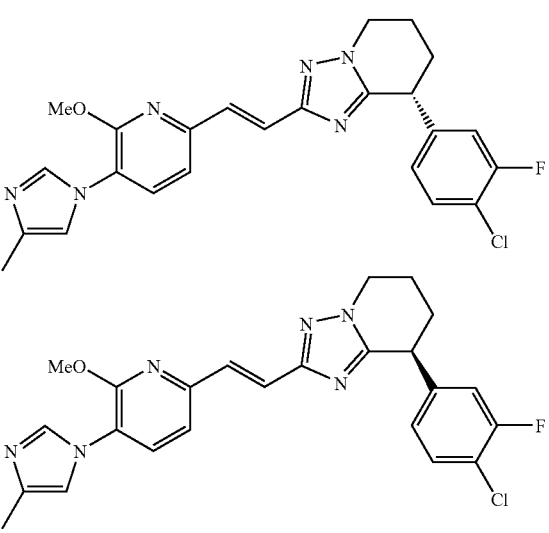

Synthesis of 1-amino-3-(4-chloro-3-fluorophenyl)piperidin-2-one

The title compound (940 mg) was obtained from 4-chloro-3-fluorobenzaldehyde (5.0 g) according to the method in Examples 20 and 21. The property value of the compound is as follows.

ESI-MS; m/z 243 [M$^+$+H].

Synthesis of (−)-8-(4-chloro-3-fluorophenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine and (+)-8-(4-chloro-3-fluorophenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine A racemate of the title compound (300 mg) was obtained from 1-amino-3-(4-chloro-3-fluorophenyl)piperidin-2-one (200 mg) and (E)-3-[6-methoxy-5-(4-methyl-1H-imidazol-1-yl)pyridin-2-yl]acrylic acid (477 mg) according to the method in Examples 168 and 169. The racemate was optically resolved by CHIRALPAK™ IB manufactured by Daicel Chemical Industries, Ltd. (2 cm×25 cm, mobile phase: ethanol, flow rate: 10 mL/min) to isolate the title optically active compound with a retention time of 15 minutes and positive optical rotation (91 mg) and the title optically active compound with a retention time of 23 minutes and negative optical rotation (82 mg). The property values of the title optically active compound with a retention time of 23 minutes are as follows.

¹H-NMR (CDCl₃) δ (ppm): 1.96-2.32 (m, 3H), 2.29 (s, 3H), 2.32-2.44 (m, 1H), 4.05 (s, 3H), 4.24-4.36 (m, 3H), 6.88-7.00 (m, 4H), 7.37 (t, J=7.2 Hz, 1H), 7.46 (d, J=15.6 Hz, 1H), 7.47 (d, J=7.2 Hz, 1H), 7.65 (d, J=15.6 Hz, 1H), 7.70 (s, 1H).

ESI-MS; m/z 465 [M⁺+H].

The property values of the title optically active compound with a retention time of 15 minutes and positive optical rotation corresponded to the values of the (−)-isomer.

Examples 178 and 179

Synthesis of (−)-8-(2,4,5-trifluorophenyl)-2-{(E)-2-[6-methoxy-5-(4-methyl-1H-imidazol-1-yl)pyridin-2-yl]vinyl}-5,6,7,8-tetrahydro[1,2,4]triazolo[1,5-a]pyridine and (+)-8-(2,4,5-trifluorophenyl)-2-{(E)-2-[6-methoxy-5-(4-methyl-1H-imidazol-1-yl)pyridin-2-yl]vinyl}-5,6,7,8-tetrahydro[1,2,4]triazolo[1,5-a]pyridine

[Formula 117]

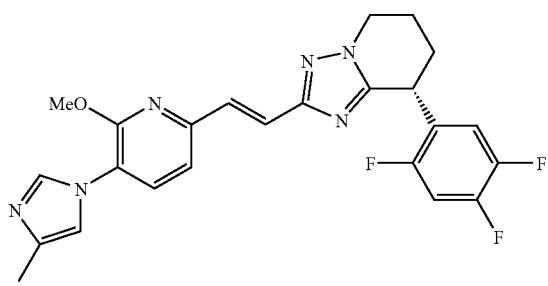

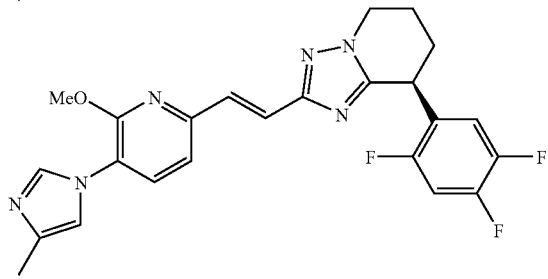

Synthesis of 1-amino-3-(2,4,5-trifluorophenyl)piperidin-2-one

The title compound (2.4 g) was obtained from 2,4,5-trifluorophenylacetic acid (5.0 g) according to the method in Examples 20 and 21. The property value of the compound is as follows.

ESI-MS; m/z 245 [M⁺+H].

Synthesis of (−)-8-(2,4,5-trifluorophenyl)-2-{(E)-2-[6-methoxy-5-(4-methyl-1H-imidazol-1-yl)pyridin-2-yl]vinyl}-5,6,7,8-tetrahydro[1,2,4]triazolo[1,5-a]pyridine and (+)-8-(2,4,5-trifluorophenyl)-2-{(E)-2-[6-methoxy-5-(4-methyl-1H-imidazol-1-yl)pyridin-2-yl]vinyl}-5,6,7,8-tetrahydro[1,2,4]triazolo[1,5-a]pyridine A racemate of the title compound (19 mg) was obtained from 1-amino-3-(2,4,5-trifluorophenyl)piperidin-2-one (200 mg) and (E)-3-[6-methoxy-5-(4-methyl-1H-imidazol-1-yl)pyridin-2-yl]acrylic acid (439 mg) according to the method in Examples 168 and 169. The racemate was optically resolved by CHIRALPAK™ AD-H manufactured by Daicel Chemical Industries, Ltd. (2 cm×25 cm, mobile phase: 80% ethanol-hexane, flow rate: 10 mL/min) to isolate the title optically active compound with a retention time of 17 minutes and positive optical rotation (6.6 mg) and the title optically active compound with a retention time of 26 minutes and negative optical rotation (6.6 mg). The property values of the title optically active compound with a retention time of 26 minutes are as follows.

¹H-NMR (CDCl₃) δ (ppm): 1.96-2.32 (m, 3H), 2.94 (s, 3H), 2.32-2.46 (m, 1H), 4.05 (s, 3H), 4.26-4.38 (m, 2H), 4.50-4.56 (m, 1H), 6.78-6.88 (m, 1H), 6.92-7.02 (m, 3H), 7.45 (d, J=16 Hz, 1H), 7.48 (d, J=7.6 Hz, 1H), 7.65 (d, J=16 Hz, 1H), 7.78 (d, J=1.2 Hz, 1H).

ESI-MS; m/z 467 [M⁺+H].

The property values of the title optically active compound with a retention time of 17 minutes and positive optical rotation corresponded to the values of the (−)-isomer.

Examples 180 and 181

Synthesis of (−)-8-(2,3,6-trifluorophenyl)-2-{(E)-2-[6-methoxy-5-(4-methyl-1H-imidazol-1-yl)pyridin-2-yl]vinyl}-5,6,7,8-tetrahydro[1,2,4]triazolo[1,5-a]pyridine and (+)-8-(2,3,6-trifluorophenyl)-2-{(E)-2-[6-methoxy-5-(4-methyl-1H-imidazol-1-yl)pyridin-2-yl]vinyl}-5,6,7,8-tetrahydro[1,2,4]triazolo[1,5-a]pyridine

[Formula 118]

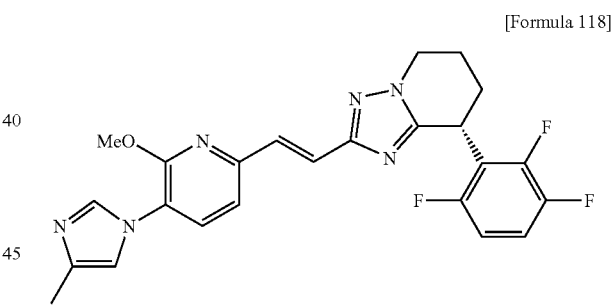

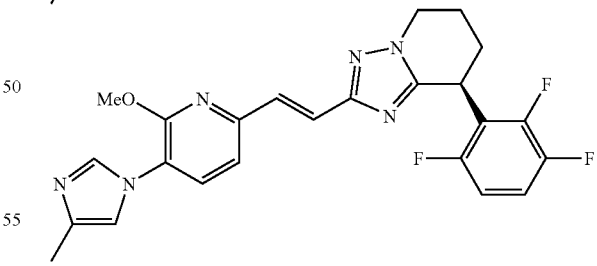

Synthesis of 1-amino-3-(2,3,6-trifluorophenyl)piperidin-2-one

The title compound (820 mg) was obtained from 2,3,6-trifluorophenylacetic acid (2.0 g) according to the method in Examples 20 and 21. The property value of the compound is as follows.

ESI-MS; m/z 245 [M⁺+H].

233

Synthesis of (−)-8-(2,3,6-trifluorophenyl)-2-{(E)-2-[6-methoxy-5-(4-methyl-1H-imidazol-1-yl)pyridin-2-yl]vinyl}-5,6,7,8-tetrahydro[1,2,4]triazolo[1,5-a]pyridine and (+)-8-(2,3,6-trifluorophenyl)-2-{(E)-2-[6-methoxy-5-(4-methyl-1H-imidazol-1-yl)pyridin-2-yl]vinyl}-5,6,7,8-tetrahydro[1,2,4]triazolo[1,5-a]pyridine A racemate of the title compound (120 mg) was obtained from 1-amino-3-(2,3,6-trifluorophenyl)piperidin-2-one (200 mg) and (E)-3-[6-methoxy-5-(4-methyl-1H-imidazol-1-yl)pyridin-2-yl]acrylic acid (439 mg) according to the method in Examples 168 and 169. The racemate was optically resolved by CHIRALPAK™ IB manufactured by Daicel Chemical Industries, Ltd. (2 cm×25 cm, mobile phase: ethanol, flow rate: 10 mL/min) to isolate the title optically active compound with a retention time of 11 minutes and positive optical rotation (54 mg) and the title optically active compound with a retention time of 16 minutes and negative optical rotation (55 mg). The property values of the title optically active compound with a retention time of 16 minutes are as follows.

$^1$H-NMR (CDCl$_3$) δ (ppm): 2.00-2.44 (m, 4H), 2.29 (s, 3H), 4.04 (s, 3H), 4.20-4.32 (m, 1H), 4.32-4.44 (m, 1H), 4.60-4.70 (m, 1H), 6.80-6.90 (m, 1H), 6.93 (d, J=7.6 Hz, 1H), 6.95 (s, 1H), 7.04-7.16 (m, 1H), 7.41 (d, J=15.6 Hz, 1H), 7.46 (d, J=7.6 Hz, 1H), 7.62 (d, J=15.6 Hz, 1H), 7.76 (s, 1H).

ESI-MS; m/z 467 [M$^+$+H].

The property values of the title optically active compound with a retention time of 11 minutes and positive optical rotation corresponded to the values of the (−)-isomer.

Examples 182 and 183

Synthesis of (−)-8-(2,5-difluorophenyl)-2-{(E)-2-[6-methoxy-5-(4-methyl-1H-imidazol-1-yl)pyridin-2-yl]vinyl}-5,6,7,8-tetrahydro[1,2,4]triazolo[1,5-a]pyridine and (+)-8-(2,5-difluorophenyl)-2-{(E)-2-[6-methoxy-5-(4-methyl-1H-imidazol-1-yl)pyridin-2-yl]vinyl}-5,6,7,8-tetrahydro[1,2,4]triazolo[1,5-a]pyridine

[Formula 119]

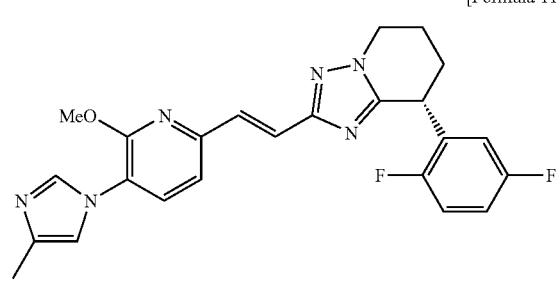

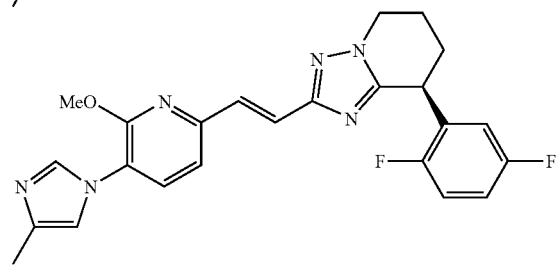

234

Synthesis of 1-amino-3-(2,5-difluorophenyl)piperidin-2-one

The title compound (790 mg) was obtained from 2,5-difluorophenylacetic acid (930 mg) according to the method in Examples 20 and 21. The property value of the compound is as follows.

ESI-MS; m/z 227 [M$^+$+H].

Synthesis of (−)-8-(2,5-difluorophenyl)-2-{(E)-2-[6-methoxy-5-(4-methyl-1H-imidazol-1-yl)pyridin-2-yl]vinyl}-5,6,7,8-tetrahydro[1,2,4]triazolo[1,5-a]pyridine and (+)-8-(2,5-difluorophenyl)-2-{(E)-2-[6-methoxy-5-(4-methyl-1H-imidazol-1-yl)pyridin-2-yl]vinyl}-5,6,7,8-tetrahydro[1,2,4]triazolo[1,5-a]pyridine A racemate of the title compound (170 mg) was obtained from 1-amino-3-(2,5-difluorophenyl)piperidin-2-one (200 mg) and (E)-3-[6-methoxy-5-(4-methyl-1H-imidazol-1-yl)pyridin-2-yl]acrylic acid (477 mg) according to the method in Examples 168 and 169. The racemate was optically resolved by CHIRALPAK™ IB manufactured by Daicel Chemical Industries, Ltd. (2 cm×25 cm, mobile phase: ethanol, flow rate: 10 mL/min) to obtain the title optically active compound with a retention time of 11 minutes and positive optical rotation (48 mg) and the title optically active compound with a retention time of 22 minutes and negative optical rotation (51 mg). The property values of the title optically active compound with a retention time of 22 minutes are as follows.

$^1$H-NMR (CDCl$_3$) δ (ppm): 1.98-2.32 (m, 3H), 2.29 (s, 3H), 2.32-2.46 (m, 1H), 4.05 (s, 3H), 4.31 (t, J=5.6 Hz, 2H), 4.57 (t, J=5.6 Hz, 1H), 6.64-6.73 (m, 1H), 6.90-7.00 (m, 3H), 7.00-7.10 (m, 1H), 7.46 (d, J=16 Hz, 1H), 7.47 (d, J=7.6 Hz, 1H), 7.66 (d, J=16 Hz, 1H), 7.77 (s, 1H).

ESI-MS; m/z 449 [M$^+$+H].

The property values of the title optically active compound with a retention time of 11 minutes and positive optical rotation corresponded to the values of the (−)-isomer.

Examples 184 and 185

Synthesis of (+) and (−)-8-(2-bromo-4-fluorophenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine

[Formula 120]

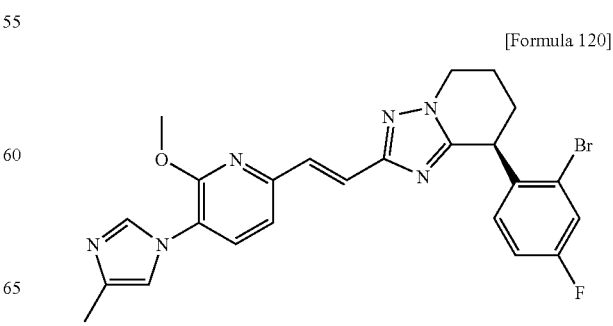

235
-continued

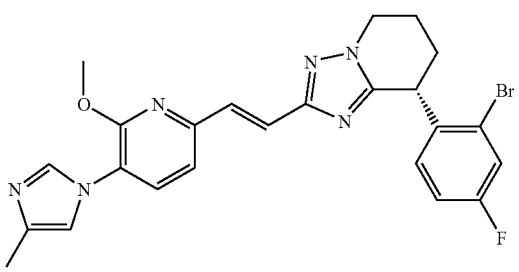

Synthesis of 1-amino-3-(2-bromo-4-fluorophenyl) piperidin-2-one The title compound (2.6 g) was obtained using 2-bromo-4-fluorophenylacetic acid (3 g) as a starting material according to the method in Examples 20 and 21. The property value of the compound is as follows.

ESI-MS; m/z 289 [M$^+$+H].

Synthesis of (+) and (−)-8-(2-bromo-4-fluorophenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine A racemate of the title compound (149 mg) was obtained using 1-amino-3-(2-bromo-4-fluorophenyl)piperidin-2-one (300 mg) as a starting material according to the method in Examples 168 and 169. The resulting racemate (149 mg) was separated by CHIRALPAK™ OD-H manufactured by Daicel Chemical Industries, Ltd. (2 cm×25 cm, mobile phase: ethanol, flow rate: 10 mL/min) to obtain the title optically active compound with a retention time of 23 minutes and positive optical rotation (44 mg) and the title optically active compound with a retention time of 31 minutes and negative optical rotation (45 mg).

The property values of the title optically active compound with a retention time of 23 minutes are as follows.

$^1$H-NMR (CDCl$_3$) δ (ppm): 1.98-2.20 (m, 3H), 2.29 (s, 3H), 2.35-2.45 (m, 1H), 4.05 (s, 3H), 4.29-4.32 (m, 2H), 4.72 (dd, J=6.8, 6.8 Hz, 1H), 6.84-7.00 (m, 4H), 7.36 (dd, J=8.0, 2.8 Hz, 1H), 7.46 (d, J=16.0 Hz, 1H), 7.47 (d, J=4.8 Hz, 1H), 7.65 (d, J=16.0 Hz, 1H), 7.70 (d, J=1.2 Hz, 1H).

The property values of the title optically active compound with a retention time of 31 minutes are as follows.

$^1$H-NMR (CDCl$_3$) δ (ppm): 1.98-2.20 (m, 3H), 2.29 (s, 3H), 2.35-2.45 (m, 1H), 4.05 (s, 3H), 4.29-4.32 (m, 2H), 4.72 (dd, J=6.8, 6.8 Hz, 1H), 6.84-7.00 (m, 4H), 7.36 (dd, J=8.0, 2.8 Hz, 1H), 7.46 (d, J=16.0 Hz, 1H), 7.47 (d, J=4.8 Hz, 1H), 7.65 (d, J=16.0 Hz, 1H), 7.70 (d, J=1.2 Hz, 1H).

236
Examples 186 and 187

Synthesis of (+)-8-(2-chloro-4-fluorophenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine and (−)-8-(2-chloro-4-fluorophenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine

[Formula 121]

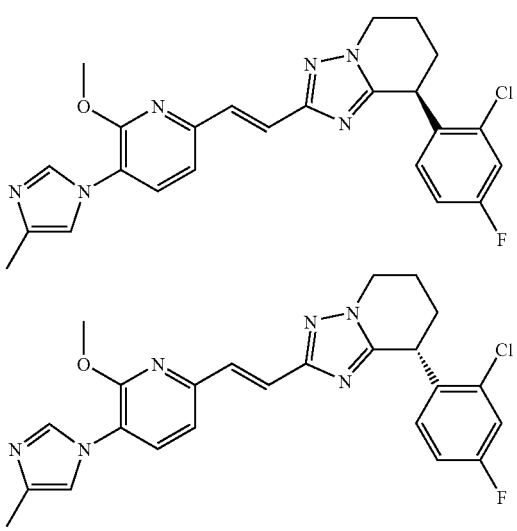

Synthesis of 1-amino-3-(2-chloro-4-fluorophenyl)piperidin-2-one 2.9 g of the title compound was obtained using methyl 2-chloro-4-fluorophenylacetate (3 g) as a starting material according to the method in Examples 20 and 21. The property value of the compound is as follows.

ESI-MS; m/z 243 [M$^+$+H].

Synthesis of (+)-8-(2-chloro-4-fluorophenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine and (−)-8-(2-chloro-4-fluorophenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine A racemate of the title compound (174 mg) was obtained using 1-amino-3-(2-chloro-4-fluorophenyl)piperidin-2-one (300 mg) as a starting material according to the method in Examples 168 and 169. The resulting racemate (174 mg) was separated by CHIRALPAK™ OD-H manufactured by Daicel Chemical Industries, Ltd. (2 cm×25 cm, mobile phase: ethanol, flow rate: 10 mL/min) to obtain the title optically active compound with a retention time of 22 minutes and positive optical rotation (68 mg) and the title optically active compound with a retention time of 30 minutes and negative optical rotation (69 mg).

The property values of the title optically active compound with a retention time of 22 minutes are as follows.

$^1$H-NMR (CDCl$_3$) δ (ppm): 1.99-2.41 (m, 7H), 4.05 (s, 3H), 4.27-4.34 (m, 2H), 4.72 (dd, J=6.0, 6.0 Hz, 1H), 6.85-6.95 (m, 4H), 7.18 (dd, J=8.6, 2.8 Hz, 1H), 7.43-7.48 (m, 2H), 7.66 (d, J=16 Hz, 1H), 7.70 (s, 1H).

The property values of the title optically active compound with a retention time of 30 minutes are as follows.

$^1$H-NMR (CDCl$_3$) δ (ppm): 1.99-2.41 (m, 7H), 4.05 (s, 3H), 4.27-4.34 (m, 2H), 4.72 (dd, J=6.0, 6.0 Hz, 1H), 6.85-6.95 (m, 4H), 7.18 (dd, J=8.6, 2.8 Hz, 1H), 7.43-7.48 (m, 2H), 7.66 (d, J=16 Hz, 1H), 7.70 (s, 1H).

Examples 188 and 189

Synthesis of (−)-8-(3-fluorophenyl)-2-{(E)-2-[6-methoxy-5-(4-methyl-1H-imidazol-1-yl)pyridin-2-yl]vinyl}-5,6,7,8-tetrahydro[1,2,4]triazolo[1,5-a]pyridine and (+)-8-(3-fluorophenyl)-2-{(E)-2-[6-methoxy-5-(4-methyl-1H-imidazol-1-yl)pyridin-2-yl]vinyl}-5,6,7,8-tetrahydro[1,2,4]triazolo[1,5-a]pyridine

[Formula 122]

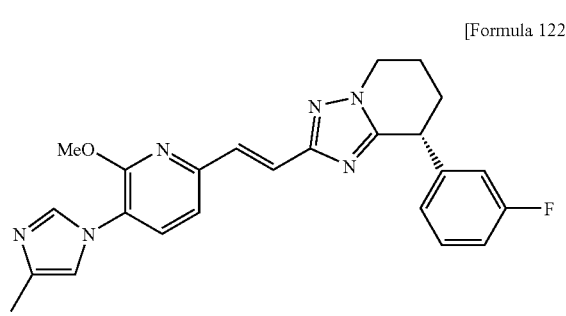

Synthesis of 1-amino-3-(3-fluorophenyl)piperidin-2-one

The title compound (3.0 g) was obtained from 3-fluorophenylacetic acid (5.0 g) according to the method in Examples 20 and 21. The property value of the compound is as follows.

ESI-MS; m/z 209 [M$^+$+H].

Synthesis of (−)-8-(3-fluorophenyl)-2-{(E)-2-[6-methoxy-5-(4-methyl-1H-imidazol-1-yl)pyridin-2-yl]vinyl}-5,6,7,8-tetrahydro[1,2,4]triazolo[1,5-a]pyridine and (+)-8-(3-fluorophenyl)-2-{(E)-2-[6-methoxy-5-(4-methyl-1H-imidazol-1-yl)pyridin-2-yl]vinyl}-5,6,7,8-tetrahydro[1,2,4]triazolo[1,5-a]pyridine A racemate of the title compound (110 mg) was obtained from 1-amino-3-(3-fluorophenyl)piperidin-2-one (200 mg) and (E)-3-[6-methoxy-5-(4-methyl-1H-imidazol-1-yl)pyridin-2-yl]acrylic acid (439 mg) according to the method in Examples 168 and 169. The racemate was optically resolved by CHIRALPAK™ IB manufactured by Daicel Chemical Industries, Ltd. (2 cm×25 cm, mobile phase: ethanol, flow rate: 10 mL/min) to obtain the title optically active compound with a retention time of 13 minutes and positive optical rotation (29 mg) and the title optically active compound with a retention time of 22 minutes and negative optical rotation (29 mg). The property values of the title optically active compound with a retention time of 22 minutes are as follows.

$^1$H-NMR (CDCl$_3$) δ (ppm): 2.00-2.30 (m, 3H), 2.29 (s, 3H), 2.30-2.46 (m, 1H), 4.05 (s, 3H), 4.20-4.40 (m, 3H), 6.85 (d, J=10.4 Hz, 1H), 6.90-7.02 (m, 4H), 7.24-7.36 (m, 1H), 7.47 (d, J=7.6 Hz, 1H), 7.47 (d, J=15.6 Hz, 1H), 7.66 (d, J=15.6 Hz, 1H), 7.77 (s, 1H).

ESI-MS; m/z 431 [M$^+$+H].

The property values of the title optically active compound with a retention time of 13 minutes and positive optical rotation corresponded to the values of the (−)-isomer.

Examples 190 and 191

Synthesis of (−)-8-(3-chlorophenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine and (+)-8-(3-chlorophenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine

[Formula 123]

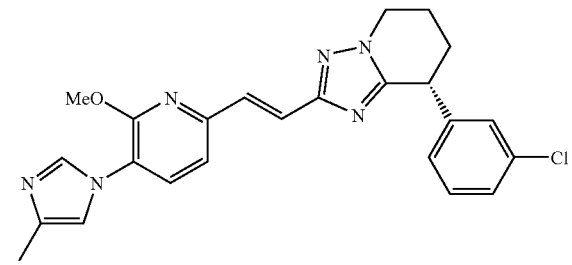

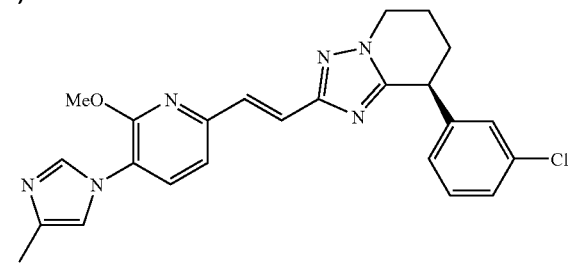

Synthesis of 1-amino-3-(3-chlorophenyl)piperidin-2-one

The title compound (3.5 g) was obtained from 3-chlorophenylacetic acid (5.0 g) according to the method in Examples 20 and 21. The property value of the compound is as follows.

ESI-MS; m/z 225 [M$^+$+H].

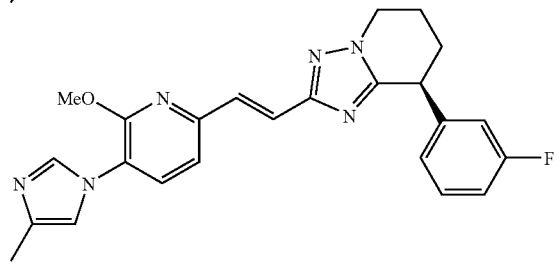

Synthesis of (−)-8-(3-chlorophenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine and (+)-8-(3-chlorophenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine A racemate of the title compound (160 mg) was obtained from 1-amino-3-(3-chlorophenyl)piperidin-2-one (200 mg) and (E)-3-[6-methoxy-5-(4-methyl-1H-imidazol-1-yl)pyridin-2-yl]acrylic acid (477 mg) according to the method in Examples 168 and 169. The racemate was optically resolved by CHIRALPAK™ IB manufactured by Daicel Chemical Industries, Ltd. (2 cm×25 cm, mobile phase: ethanol, flow rate: 10 mL/min) to isolate the title optically active compound with a retention time of 14 minutes and positive optical rotation (68 mg) and the title optically active compound with a retention time of 24 minutes and negative optical rotation (67 mg). The property values of the title optically active compound with a retention time of 24 minutes are as follows.

$^1$H-NMR (CDCl$_3$) δ (ppm): 2.00-2.23 (m, 3H), 2.29 (s, 3H), 2.30-2.46 (m, 1H), 4.05 (s, 3H), 4.20-4.38 (m, 3H), 6.92-6.98 (m, 2H), 7.00-7.06 (m, 1H), 7.14 (s, 1H), 7.22-7.32 (m, 2H), 7.47 (d, J=7.6 Hz, 1H), 7.47 (d, J=15.6 Hz, 1H), 7.66 (d, J=15.6 Hz, 1H), 7.77 (d, J=1.2 Hz, 1H).

ESI-MS; m/z 447 [M$^+$+H].

The property values of the title optically active compound with a retention time of 14 minutes and positive optical rotation corresponded to the values of the (−)-isomer.

Examples 192 and 193

Synthesis of (+)-8-(2-chlorophenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-pyridine and (−)-8-(2-chlorophenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine

[Formula 124]

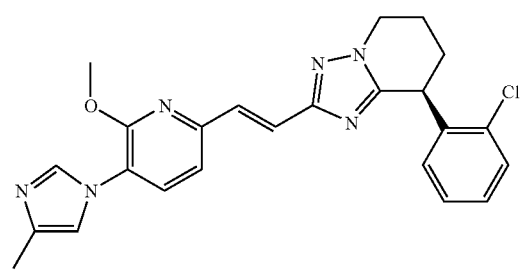

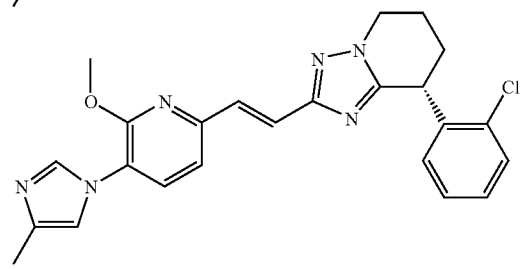

Synthesis of 1-amino-3-(2-chlorophenyl)piperidin-2-one

The title compound (831 mg) was obtained using 2-chlorophenylacetic acid (1 g) as a starting material according to the method in Examples 20 and 21. The property value of the compound is as follows.

ESI-MS; m/z 225 [M$^+$+H].

Synthesis of (+)-8-(2-chlorophenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine and (−)-8-(2-chlorophenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine A racemate of the title compound (192 mg) was obtained from 1-amino-3-(2-chlorophenyl)piperidin-2-one (250 mg) according to the method in Examples 168 and 169. The resulting racemate (192 mg) was separated by CHIRALPAK™ OJ-H manufactured by Daicel Chemical Industries, Ltd. (2 cm×25 cm, mobile phase: hexane:ethanol=8:2, flow rate: 11 mL/min) to obtain the title optically active compound with a retention time of 34 minutes and positive optical rotation (37 mg) and the title optically active compound with a retention time of 40 minutes and negative optical rotation (31 mg).

The property values of the title optically active compound with a retention time of 34 minutes are as follows.

$^1$H-NMR (CDCl$_3$) δ (ppm): 2.00-2.41 (m, 7H), 4.04 (s, 3H), 4.25-4.34 (m, 2H), 4.76-4.79 (m, 1H), 6.85-6.95 (m, 3H), 7.18-7.26 (m, 2H), 7.40-7.48 (m, 3H), 7.66 (d, J=16 Hz, 1H), 7.76 (s, 1H).

The property values of the title optically active compound with a retention time of 40 minutes are as follows.

$^1$H-NMR (CDCl$_3$) δ (ppm): 2.00-2.41 (m, 7H), 4.04 (s, 3H), 4.25-4.34 (m, 2H), 4.76-4.79 (m, 1H), 6.85-6.95 (m, 3H), 7.18-7.26 (m, 2H), 7.40-7.48 (m, 3H), 7.66 (d, J=16 Hz, 1H), 7.76 (s, 1H).

Examples 194 and 195

Synthesis of (+)-2-{(E)-2-[6-methoxy-5-(4-methyl-1H-imidazol-1-yl)pyridin-2-yl]vinyl}-8-(2-trifluoromethylphenyl)-5,6,7,8-tetrahydro-[1,2,4]triazolo[1,5-a]pyridine and (−)-2-{(E)-2-[6-methoxy-5-(4-methyl-1H-imidazol-1-yl)pyridin-2-yl]vinyl}-8-(2-trifluoromethylphenyl)-5,6,7,8-tetrahydro-[1,2,4]triazolo[1,5-a]pyridine

[Formula 125]

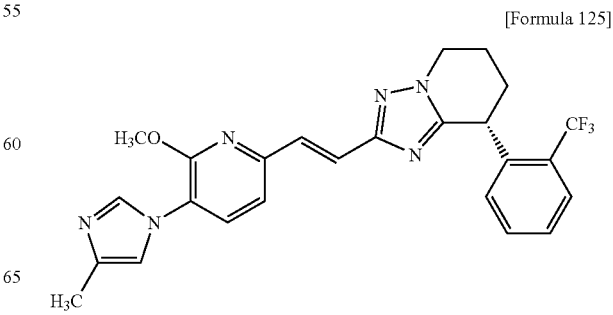

-continued

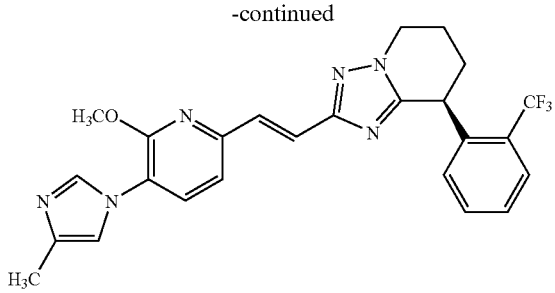

Synthesis of
1-amino-3-(2-trifluoromethylphenyl)piperidin-2-one

Thionyl chloride (2.72 mL) was added to a solution of 2-trifluoromethylphenylacetic acid (1.9 g) in methanol (38 mL), and the reaction solution was stirred at room temperature for three hours. The reaction solution was concentrated under reduced pressure. The resulting residue was diluted with DMF. Sodium hydride (containing 40% of mineral oil, 410 mg) was added under ice-cooling, and the reaction solution was stirred for 10 minutes. The reaction solution was further stirred at room temperature for 30 minutes and then ice-cooled again. 1-Chloro-3-iodopropane (1.02 mL) was added to the reaction mixture, and the reaction solution was stirred at room temperature overnight. Water and ethyl acetate were added to the reaction mixture and the organic layer was separated. The resulting organic layer was washed with saturated aqueous sodium chloride, dried over anhydrous magnesium sulfate and then concentrated under reduced pressure. The resulting residue was diluted with ethanol (26.6 mL). Hydrazine monohydrate (7.6 mL) was added, and the reaction solution was stirred at room temperature for two hours and then at 60° C. for further three hours. The reaction mixture was concentrated under reduced pressure. Saturated aqueous sodium bicarbonate and ethyl acetate and were added to the residue, and the organic layer was separated. The resulting organic layer was washed with saturated aqueous sodium chloride, dried over anhydrous magnesium sulfate and then concentrated under reduced pressure. The residue was purified by silica gel column chromatography (carrier: Chromatorex NH; elution solvent: heptane-ethyl acetate system) to obtain 1.68 g of the title compound. The property values of the compound are as follows.

ESI-MS; m/z 259 [M$^+$+H]. $^1$H-NMR (CDCl$_3$) δ (ppm): 1.82-2.10 (m, 3H), 2.18-2.26 (m, 1H), 3.58-3.76 (m, 2H), 4.07 (dd, J=10.0, 5.6 Hz, 1H), 4.60 (s, 2H), 7.24 (d, J=7.6 Hz, 1H), 7.35 (t, J=7.6 Hz, 1H), 7.51 (t, J=7.6 Hz, 1H), 7.66 (d, J=7.6 Hz, 1H).

Synthesis of (E)-3-[6-methoxy-5-(4-methyl-1H-imidazol-1-yl)pyridin-2-yl]-N-[2-oxo-3-(2-trifluoromethylphenyl)piperidin-1-yl]acrylamide EDC (834 mg), HOBT (588 mg) and IPEA (2.03 mL) were added to a suspension of (E)-3-[6-methoxy-5-(4-methyl-1H-imidazol-1-yl)pyridin-2-yl]acrylic acid trifluoroacetate (1.42 g) and 1-amino-3-(2-trifluoromethylphenyl)piperidin-2-one (750 mg) in DMF (30 mL). The reaction mixture was stirred at room temperature for 14 hours. Then, saturated aqueous sodium bicarbonate and ethyl acetate were added to the reaction solution, and the organic layer was separated. The resulting organic layer was dried over anhydrous magnesium sulfate and then concentrated under reduced pressure. The residue was purified by silica gel column chromatography (carrier: Chromatorex NH; elution solvent: ethyl acetate-methanol system) to obtain 1.23 g of the title compound. The property value of the compound is as follows.

ESI-MS; m/z 500 [M$^+$+H].

Synthesis of (+)-2-{(E)-2-[6-methoxy-5-(4-methyl-1H-imidazol-1-yl)pyridin-2-yl]vinyl}-8-(2-trifluoromethylphenyl)-5,6,7,8-tetrahydro-[1,2,4]triazolo[1,5-a]pyridine and (−)-2-{(E)-2-[6-methoxy-5-(4-methyl-1H-imidazol-1-yl)pyridin-2-yl]vinyl}-8-(2-trifluoromethylphenyl)-5,6,7,8-tetrahydro-[1,2,4]triazolo[1,5-a]pyridine Phosphorus oxychloride (24.2 mL) was added to (E)-3-[6-methoxy-5-(4-methyl-1H-imidazol-1-yl)pyridin-2-yl]-N-[2-oxo-3-(2-trifluoromethylphenyl)piperidin-1-yl]acrylamide (1.2 g). The reaction solution was stirred at 100° C. for one hour and then concentrated under reduced pressure. Subsequently, the residue was diluted with acetic acid (24.2 mL). Then, ammonium acetate (1.9 g) was added and the reaction solution was stirred at 150° C. for two hours. The reaction solution was left to cool to room temperature and then concentrated under reduced pressure. Saturated aqueous sodium bicarbonate and ethyl acetate were added to the resulting residue, and the organic layer was separated. The resulting organic layer was dried over anhydrous magnesium sulfate and then concentrated under reduced pressure. The residue was purified by silica gel column chromatography (carrier: Chromatorex NH; elution solvent: heptane-ethyl acetate system) to obtain a racemate of the title compound (750 mg). The resulting racemate (410 mg) was separated by CHIRALPAK™ IA manufactured by Daicel Chemical Industries, Ltd. (2 cm×25 cm, mobile phase; hexane:ethanol=8:2, flow rate: 10 mL/min) to obtain the title optically active compound with a retention time of 28 minutes and positive optical rotation (174 mg), and the title optically active compound with a retention time of 33 minutes and negative optical rotation (170 mg).

The property values of the title optically active compound with a retention time of 28 minutes are as follows.

$^1$H-NMR (CDCl$_3$) δ (ppm): 1.90-2.01 (m, 1H), 2.10-2.35 (m, 2H), 2.29 (d, J=1.2 Hz, 3H), 2.42-2.51 (m, 1H), 4.03 (s, 3H), 4.28-4.41 (m, 2H), 4.70 (dd, J=8.4, 6.0 Hz, 1H), 6.92 (d, J=8.0 Hz, 1H), 6.95 (t, J=1.2 Hz, 1H), 7.01 (d, J=7.6 Hz, 1H), 7.39 (t, J=7.6 Hz, 1H), 7.44 (d, J=16.0 Hz, 1H), 7.45 (d, J=8.0 Hz, 1H), 7.49 (t, J=7.6 Hz, 1H), 7.63 (d, J=16.0 Hz, 1H), 7.72 (d, J=7.6 Hz, 1H), 7.76 (d, J=1.2 Hz, 1H).

The property values of the title optically active compound with a retention time of 33 minutes are as follows.

$^1$H-NMR (CDCl$_3$) δ (ppm): 1.90-2.01 (m, 1H), 2.10-2.35 (m, 2H), 2.29 (d, J=1.2 Hz, 3H), 2.42-2.51 (m, 1H), 4.03 (s, 3H), 4.28-4.41 (m, 2H), 4.70 (dd, J=8.4, 6.0 Hz, 1H), 6.92 (d, J=8.0 Hz, 1H), 6.95 (t, J=1.2 Hz, 1H), 7.01 (d, J=7.6 Hz, 1H), 7.39 (t, J=7.6 Hz, 1H), 7.44 (d, J=16.0 Hz, 1H), 7.45 (d, J=8.0 Hz, 1H), 7.49 (t, J=7.6 Hz, 1H), 7.63 (d, J=16.0 Hz, 1H), 7.72 (d, J=7.6 Hz, 1H), 7.76 (d, J=1.2 Hz, 1H).

Examples 196 and 197

Synthesis of (+)-2-{(E)-2-[6-methoxy-5-(4-methyl-1H-imidazol-1-yl)-pyridin-2-yl]-vinyl}-8-(4-trifluoromethyl-phenyl)-5,6,7,8-tetrahydro-[1,2,4]triazolo[1,5-a]pyridine and (−)-2-{(E)-2-[6-methoxy-5-(4-methyl-1H-imidazol-1-yl)-pyridin-2-yl]-vinyl}-8-(4-trifluoromethyl-phenyl)-5,6,7,8-tetrahydro-[1,2,4]triazolo[1,5-a]pyridine

[Formula 126]

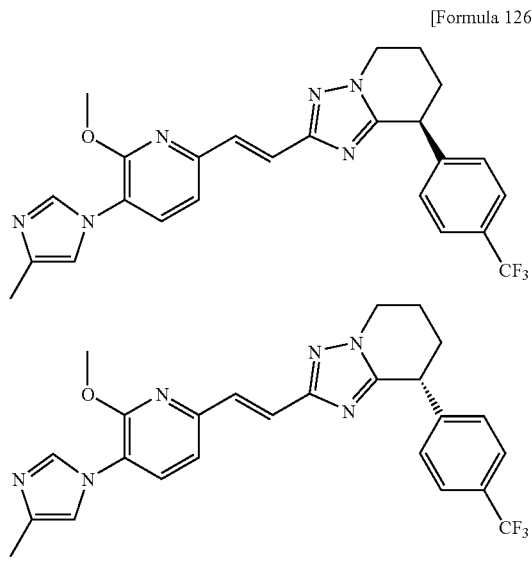

Synthesis of 1-amino-6-(4-trifluoromethyl-phenyl)-piperidin-2-one 1.0 g of the title compound was obtained using 4-(trifluoromethyl)phenylacetic acid as a starting material according to the method in Examples 20 and 21. The property value of the compound is as follows.
ESI-MS; m/z 259 [M$^+$+H].

Synthesis of (+)-2-{(E)-2-[6-methoxy-5-(4-methyl-1H-imidazol-1-yl)-pyridin-2-yl]-vinyl}-8-(4-trifluoromethyl-phenyl)-5,6,7,8-tetrahydro-[1,2,4]triazolo[1,5-a]pyridine and (−)-2-{(E)-2-[6-methoxy-5-(4-methyl-1H-imidazol-1-yl)-pyridin-2-yl]-vinyl}-8-(4-trifluoromethyl-phenyl)-5,6,7,8-tetrahydro-[1,2,4]triazolo[1,5-a]pyridine A racemate of the title compound (13.2 mg) was obtained using 1-amino-6-(4-trifluoromethyl-phenyl)-piperidin-2-one (203 mg) as a starting material according to the method in Examples 168 and 169. Here, the compounds of Examples 200 and 201 described below (149 mg) were generated at the same time. The resulting racemate (13.2 mg) was separated by CHIRALPAK™ IB manufactured by Daicel Chemical Industries, Ltd. (2 cm×25 cm, mobile phase: ethanol, flow rate: 12 mL/min) to obtain the title optically active compound with a retention time of 10 minutes and positive optical rotation (2.8 mg) and the title optically active compound with a retention time of 15 minutes and negative optical rotation (3.0 mg).

The property values of the title optically active compound with a retention time of 10 minutes are as follows.
$^1$H-NMR (CDCl$_3$) δ (ppm): 2.00-2.26 (m, 3H), 2.30 (s, 3H), 2.36-2.48 (m, 1H), 4.05 (s, 3H), 4.28-4.36 (m, 2H), 4.41 (t, J=7.3 Hz, 1H), 6.94 (d, J=8.1 Hz, 1H), 6.95-6.97 (m, 1H), 7.26-7.30 (m, 2H), 7.45 (d, J=8.1 Hz, 1H), 7.46 (d, J=16.1 Hz, 1H), 7.59-7.63 (m, 2H), 7.65 (d, J=16.1 Hz, 1H), 7.77 (d, J=1.5 Hz, 1H).

The property values of the title optically active compound with a retention time of 15 minutes are as follows.
$^1$H-NMR (CDCl$_3$) δ (ppm): 2.00-2.26 (m, 3H), 2.30 (s, 3H), 2.36-2.48 (m, 1H), 4.05 (s, 3H), 4.28-4.36 (m, 2H), 4.41 (t, J=7.3 Hz, 1H), 6.94 (d, J=8.1 Hz, 1H), 6.95-6.97 (m, 1H), 7.26-7.30 (m, 2H), 7.45 (d, J=8.1 Hz, 1H), 7.46 (d, J=16.1 Hz, 1H), 7.59-7.63 (m, 2H), 7.65 (d, J=16.1 Hz, 1H), 7.77 (d, J=1.5 Hz, 1H).

Examples 198 and 199

Synthesis of (−)-2-{(E)-2-[6-methoxy-5-(4-methyl-1H-imidazol-1-yl)pyridin-2-yl]vinyl}-8-(naphthalen-1-yl)-5,6,7,8-tetrahydro-[1,2,4]triazolo[1,5-a]pyridine and (+)-2-{(E)-2-[6-methoxy-5-(4-methyl-1H-imidazol-1-yl)pyridin-2-yl]vinyl}-8-(naphthalen-1-yl)-5,6,7,8-tetrahydro-[1,2,4]triazolo[1,5-a]pyridine

[Formula 127]

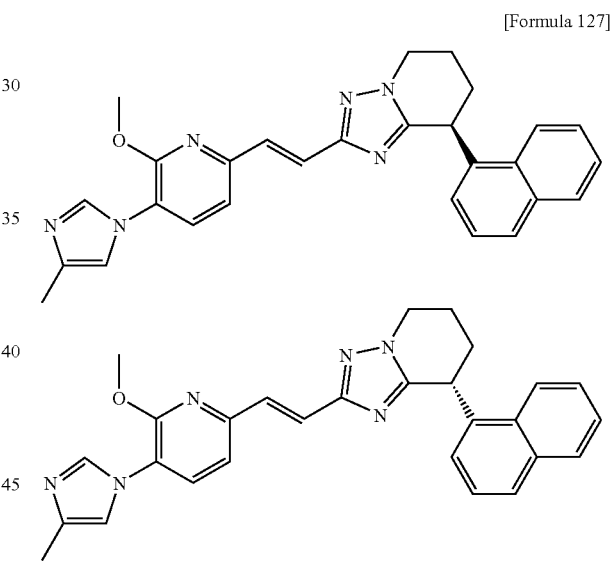

Synthesis of 1-amino-3-(naphthalen-1-yl)piperidin-2-one 858 mg of the title compound was obtained using 1-naphthylacetic acid as a starting material according to the method in Examples 20 and 21. The property value of the compound is as follows.
ESI-MS; m/z 241 [M$^+$+H].

Synthesis of (−)-2-{(E)-2-[6-methoxy-5-(4-methyl-1H-imidazol-1-yl)pyridin-2-yl]vinyl}-8-(naphthalen-1-yl)-5,6,7,8-tetrahydro-[1,2,4]triazolo[1,5-a]pyridine and (+)-2-{(E)-2-[6-methoxy-5-(4-methyl-1H-imidazol-1-yl)pyridin-2-yl]vinyl}-8-(naphthalen-1-yl)-5,6,7,8-tetrahydro-[1,2,4]triazolo[1,5-a]pyridine A racemate of the title compound (173 mg) was obtained from 1-amino-3-(naphthalen-1-yl)piperidin-2-one (254 mg)

as a starting material according to the method in Examples 168 and 169. The resulting racemate (173 mg) was separated by CHIRALPAK™ IB manufactured by Daicel Chemical Industries, Ltd. (2 cm×25 cm, mobile phase: ethanol, flow rate: 12 mL/min) to obtain the title optically active compound with a retention time of 11 minutes and negative optical rotation (74 mg) and the title optically active compound with a retention time of 30 minutes and positive optical rotation (52 mg).

The property values of the title optically active compound with a retention time of 11 minutes are as follows.

$^1$H-NMR (CDCl$_3$) δ (ppm): 2.02-2.32 (m, 3H), 2.29 (s, 3H), 2.40-2.50 (m, 1H), 4.05 (s, 3H), 4.29 (ddd, J=13.2, 8.8, 5.9 Hz, 1H), 4.43 (ddd, J=13.2, 5.1, 5.1 Hz, 1H), 5.22 (t, J=5.5 Hz, 1H), 6.86 (d, J=7.3 Hz, 1H), 6.92 (d, J=7.7 Hz, 1H), 6.94-6.97 (m, 1H), 7.35-7.40 (m, 1H), 7.45 (d, J=7.7 Hz, 1H), 7.48 (d, J=15.7 Hz, 1H), 7.50-7.60 (m, 2H), 7.69 (d, J=15.7 Hz, 1H), 7.77 (d, J=1.1 Hz, 1H), 7.78 (d, J=8.4 Hz, 1H), 7.89-7.92 (m, 1H), 8.01 (d, J=8.4 Hz, 1H).

The property values of the title optically active compound with a retention time of 30 minutes are as follows.

$^1$H-NMR (CDCl$_3$) δ (ppm): 2.02-2.32 (m, 3H), 2.29 (s, 3H), 2.40-2.50 (m, 1H), 4.05 (s, 3H), 4.29 (ddd, J=13.2, 8.8, 5.9 Hz, 1H), 4.43 (ddd, J=13.2, 5.1, 5.1 Hz, 1H), 5.22 (t, J=5.5 Hz, 1H), 6.86 (d, J=7.3 Hz, 1H), 6.92 (d, J=7.7 Hz, 1H), 6.94-6.97 (m, 1H), 7.35-7.40 (m, 1H), 7.45 (d, J=7.7 Hz, 1H), 7.48 (d, J=15.7 Hz, 1H), 7.50-7.60 (m, 2H), 7.69 (d, J=15.7 Hz, 1H), 7.77 (d, J=1.1 Hz, 1H), 7.78 (d, J=8.4 Hz, 1H), 7.89-7.92 (m, 1H), 8.01 (d, J=8.4 Hz, 1H).

Examples 200 and 201

Synthesis of (+)-3-(4-methyl-1H-imidazol-1-yl)-6-{(E)-2-[8-(4-trifluoromethyl-phenyl)-5,6,7,8-tetrahydro-[1,2,4]triazolo[1,5-a]pyridin-2-yl]vinyl}-pyridin-2-ol and (−)-3-(4-methyl-1H-imidazol-1-yl)-6-{(E)-2-[8-(4-trifluoromethyl-phenyl)-5,6,7,8-tetrahydro-[1,2,4]triazolo[1,5-a]pyridin-2-yl]vinyl}-pyridin-2-ol

[Formula 128]

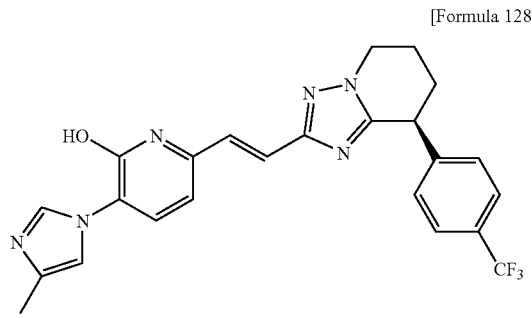

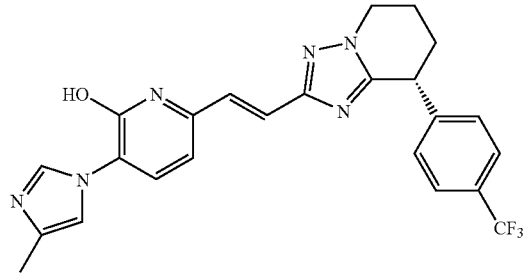

A racemate of the title compound (149 mg) was obtained from 1-amino-6-(4-trifluoromethyl-phenyl)-piperidin-2-one (203 mg) according to the method in Examples 168 and 169. The resulting racemate (149 mg) was separated by CHIRALPAK™ IA manufactured by Daicel Chemical Industries, Ltd. (2 cm×25 cm, mobile phase: ethanol, flow rate: 12 mL/min) to obtain the title optically active compound with a retention time of 19 minutes and positive optical rotation (39 mg) and the title optically active compound with a retention time of 39 minutes and negative optical rotation (41 mg).

The property values of the title optically active compound with a retention time of 19 minutes are as follows.

$^1$H-NMR (CDCl$_3$) δ (ppm): 2.00-2.26 (m, 3H), 2.28 (s, 3H), 2.37-2.44 (m, 1H), 4.30-4.37 (m, 2H), 4.40 (t, J=7.0 Hz, 1H), 6.35 (d, J=7.7 Hz, 1H), 7.18 (d, J=16.5 Hz, 1H), 7.20 (3.6 Hz, 1H), 7.24-7.28 (m, 2H), 7.39 (d, J=16.5 Hz, 1H), 7.40 (d, J=7.3 Hz, 1H), 7.62-7.56 (m, 2H), 8.18 (brd-s, 1H).

The property values of the title optically active compound with a retention time of 39 minutes are as follows.

$^1$H-NMR (CDCl$_3$) δ (ppm): 2.00-2.26 (m, 3H), 2.28 (s, 3H), 2.37-2.44 (m, 1H), 4.30-4.37 (m, 2H), 4.40 (t, J=7.0 Hz, 1H), 6.35 (d, J=7.7 Hz, 1H), 7.18 (d, J=16.5 Hz, 1H), 7.20 (3.6 Hz, 1H), 7.24-7.28 (m, 2H), 7.39 (d, J=16.5 Hz, 1H), 7.40 (d, J=7.3 Hz, 1H), 7.62-7.56 (m, 2H), 8.18 (brd-s, 1H).

Examples 202 and 203

Synthesis of (+)-3-(4-methyl-1H-imidazol-1-yl)-6-{(E)-2-[8-(4-fluorophenyl)-5,6,7,8-tetrahydro-[1,2,4]triazolo[1,5-a]pyridin-2-yl]vinyl}-pyridin-2-ol and (−)-3-(4-methyl-1H-imidazol-1-yl)-6-{(E)-2-[8-(4-fluorophenyl)-5,6,7,8-tetrahydro-[1,2,4]triazolo[1,5-a]pyridin-2-yl]vinyl}-pyridin-2-ol

[Formula 129]

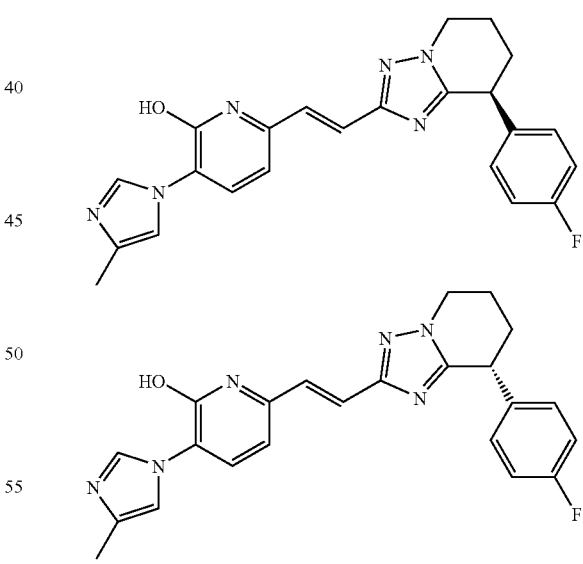

A racemate of the title compound (30 mg) was obtained from 1-amino-6-(4-fluorophenyl)-piperidin-2-one (500 mg) according to the method in Examples 168 and 169. The resulting racemate (30 mg) was separated by CHIRALPAK™ IA manufactured by Daicel Chemical Industries, Ltd. (2 cm×25 cm, mobile phase: ethanol, flow rate: 10 mL/min) to obtain the title optically active compound with a retention time of 41 minutes and positive optical rotation (8.2 mg) and the title optically active compound with a retention time of 51 minutes and negative optical rotation (8.2 mg).

The property values of the title optically active compound with a retention time of 51 minutes are as follows.
$^1$H-NMR (CDCl$_3$) δ (ppm): 2.00-2.44 (m, 4H), 2.28 (s, 3H), 4.26-4.38 (m, 3H), 6.35 (d, J=7.6 Hz, 1H), 6.98-7.07 (m, 2H), 7.07-7.14 (m, 2H), 7.16-7.22 (m, 2H), 7.24-7.38 (m, 1H), 7.39 (d, J=7.6 Hz, 1H), 8.14 (d, J=1.6 Hz, 1H).

The property values of the title optically active compound with a retention time of 41 minutes corresponded to those of the title optically active compound with a retention time of 51 minutes.

Examples 204 and 205

Synthesis of (+)-2-{(E)-2-[6-ethoxy-5-(4-methyl-1H-imidazol-1-yl)-pyridin-2-yl]-vinyl}-8-(4-trifluoromethyl-phenyl)-5,6,7,8-tetrahydro-[1,2,4]triazolo[1,5-a]pyridine and (−)-2-{(E)-2-[6-ethoxy-5-(4-methyl-1H-imidazol-1-yl)-pyridin-2-yl]-vinyl}-8-(4-trifluoromethyl-phenyl)-5,6,7,8-tetrahydro-[1,2,4]triazolo[1,5-a]pyridine

[Formula 130]

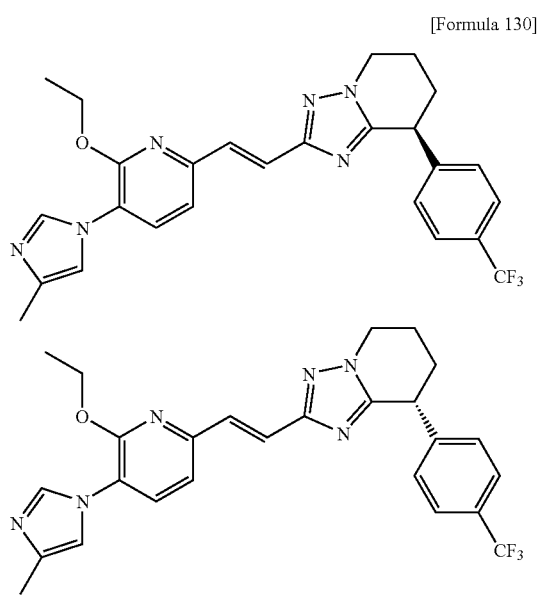

Cesium carbonate (22.6 mg) and methyl iodide (6.5 μl) were added to racemic 3-(4-methyl-1H-imidazol-1-yl)-6-{(E)-2-[8-(4-trifluoromethyl-phenyl)-5,6,7,8-tetrahydro-[1,2,4]triazolo[1,5-a]pyridin-2-yl]vinyl}-pyridin-2-ol (26.9 mg) as a starting material in DMF (0.6 ml), and the reaction solution was stirred at room temperature for four hours. Water and ethyl acetate were added to the reaction solution, and the organic layer was separated. The organic layer was washed with brine. The resulting organic layer was dried over anhydrous magnesium sulfate and then concentrated under reduced pressure. The residue was purified by silica gel column chromatography (elution solvent: heptane-ethyl acetate system) to obtain 13.6 mg of a racemate of the title compound. The resulting racemate (13.6 mg) was separated by CHIRALPAK™ IB manufactured by Daicel Chemical Industries, Ltd. (2 cm×25 cm, mobile phase: ethanol, flow rate: 12 mL/min) to obtain the title optically active compound with a retention time of 11 minutes and positive optical rotation (35 mg) and the title optically active compound with a retention time of 16 minutes and negative optical rotation (41 mg).

The property values of the title optically active compound with a retention time of 11 minutes are as follows.
$^1$H-NMR (CDCl$_3$) δ (ppm): 1.41 (t, J=7.3 Hz, 3H), 2.00-2.26 (m, 3H), 2.29 (s, 3H), 2.36-2.45 (m, 1H), 4.29-4.34 (m, 2H), 4.42 (t, J=7.0 Hz, 1H), 4.57 (q, J=7.3 Hz, 2H), 6.91 (d, J=7.7 Hz, 1H), 6.95-6.98 (m, 1H), 7.25-7.31 (m, 2H), 7.45 (d, J=15.7 Hz, 1H), 7.46 (d, J=7.7 Hz, 1H), 7.58-7.63 (m, 2H), 7.62 (d, J=15.7 Hz, 1H), 7.83 (d, J=1.1 Hz, 1H).

The property values of the title optically active compound with a retention time of 16 minutes are as follows.
$^1$H-NMR (CDCl$_3$) δ (ppm): 1.41 (t, J=7.3 Hz, 3H), 2.00-2.26 (m, 3H), 2.29 (s, 3H), 2.36-2.45 (m, 1H), 4.29-4.34 (m, 2H), 4.42 (t, J=7.0 Hz, 1H), 4.57 (q, J=7.3 Hz, 2H), 6.91 (d, J=7.7 Hz, 1H), 6.95-6.98 (m, 1H), 7.25-7.31 (m, 2H), 7.45 (d, J=15.7 Hz, 1H), 7.46 (d, J=7.7 Hz, 1H), 7.58-7.63 (m, 2H), 7.62 (d, J=15.7 Hz, 1H), 7.83 (d, J=1.1 Hz, 1H).

Examples 206 and 207

Synthesis of (+)-2-{(E)-2-[6-methoxy-5-(4-methyl-1H-imidazol-1-yl)pyridin-2-yl]vinyl}-8-phenyl-5,6,7,8-tetrahydro-[1,2,4]triazolo[1,5-a]pyridine and (−)-2-{(E)-2-[6-methoxy-5-(4-methyl-1H-imidazol-1-yl)pyridin-2-yl]vinyl}-8-phenyl-5,6,7,8-tetrahydro-[1,2,4]triazolo[1,5-a]pyridine

[Formula 131]

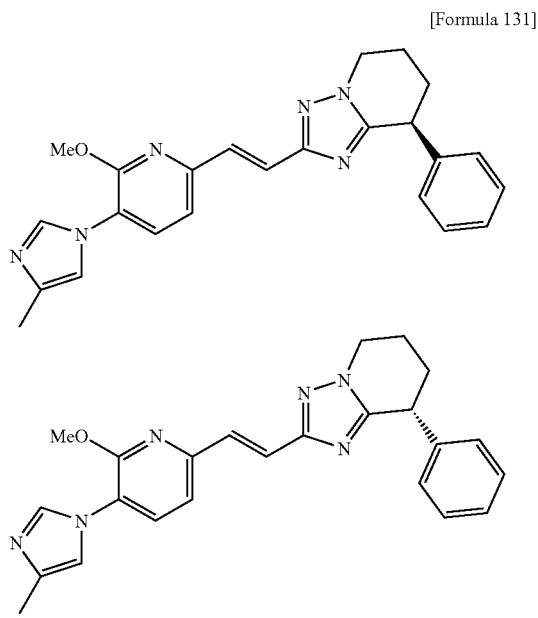

A racemate of the title compound was obtained from (E)-3-[6-methoxy-5-(4-methyl-1H-imidazol-1-yl)pyridin-2-yl]acrylic acid (150 mg) and 1-amino-3-phenylpiperidin-2-one (120 mg) according to the method in Examples 168 and 169. The resulting racemate was separated by CHIRALPAK™ IB manufactured by Daicel Chemical Industries, Ltd. (2 cm×25 cm; mobile phase: hexane:ethanol=1:1) to obtain the title optically active compound with a retention time of 18 minutes and positive optical rotation (45.1 mg, >99% ee) and the title optically active compound with a retention time of 42 minutes and negative optical rotation (46.5 mg, >99% ee).

The property values of the title compound with a retention time of 18 minutes are as follows.

ESI-MS; m/z 413 [M$^+$+H]. $^1$H-NMR (CDCl$_3$) δ (ppm): 2.02-2.10 (m, 2H), 2.16-2.21 (m, 1H), 2.29 (d, J=1.2 Hz, 3H), 2.33-2.38 (m, 1H), 4.04 (s, 3H), 4.26-4.38 (m, 3H), 6.92 (d, J=8.0 Hz, 1H), 6.94 (s, 1H), 7.11-7.13 (m, 2H), 7.26-7.35 (m, 3H), 7.45 (d, J=8.0 Hz, 1H), 7.46 (d, J=16.0 Hz, 1H), 7.65 (d, J=16.0 Hz, 1H), 7.75 (d, J=1.2 Hz, 1H).

The property values of the title compound with a retention time of 42 minutes are as follows.

ESI-MS; m/z 413 [M$^+$+H]. $^1$H-NMR (CDCl$_3$) δ (ppm): 2.02-2.10 (m, 2H), 2.16-2.21 (m, 1H), 2.29 (d, J=1.2 Hz, 3H), 2.33-2.38 (m, 1H), 4.04 (s, 3H), 4.26-4.38 (m, 3H), 6.92 (d, J=8.0 Hz, 1H), 6.94 (s, 1H), 7.11-7.13 (m, 2H), 7.26-7.35 (m, 3H), 7.45 (d, J=8.0 Hz, 1H), 7.46 (d, J=16.0 Hz, 1H), 7.65 (d, J=16.0 Hz, 1H), 7.75 (d, J=1.2 Hz, 1H).

Examples 208 and 209

Synthesis of (+)-8-(4-chlorophenyl)-2-{(E)-2-[6-methoxy-5-(4-methyl-1H-imidazol-1-yl)pyridin-2-yl]vinyl}-8-phenyl-5,6,7,8-tetrahydro-[1,2,4]triazolo[1,5-a]pyridine and (−)-8-(4-chlorophenyl)-2-{(E)-2-[6-methoxy-5-(4-methyl-1H-imidazol-1-yl)pyridin-2-yl]vinyl}-8-phenyl-5,6,7,8-tetrahydro-[1,2,4]triazolo[1,5-a]pyridine

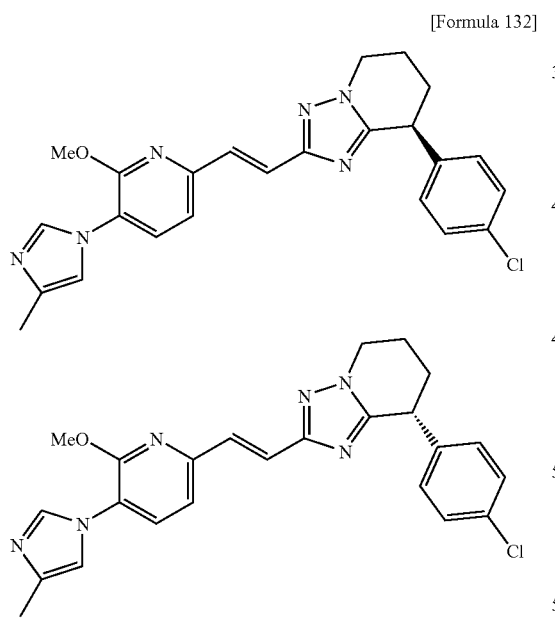

[Formula 132]

Synthesis of 1-amino-3-(4-chlorophenyl)piperidin-2-one 1.69 g of the title compound was obtained from methyl 4-chlorophenylacetate (5 g) according to the method in Examples 20 and 21. The property value of the compound is as follows.

ESI-MS; m/z 225 [M$^+$+H].

Synthesis of (+)-8-(4-chlorophenyl)-2-{(E)-2-[6-methoxy-5-(4-methyl-1H-imidazol-1-yl)pyridin-2-yl]vinyl}-8-phenyl-5,6,7,8-tetrahydro-[1,2,4]triazolo[1,5-a]pyridine and (−)-8-(4-chlorophenyl)-2-{(E)-2-[6-methoxy-5-(4-methyl-1H-imidazol-1-yl)pyridin-2-yl]vinyl}-8-phenyl-5,6,7,8-tetrahydro-[1,2,4]triazolo[1,5-a]pyridine A racemate of the title compound was obtained from (E)-3-[6-methoxy-5-(4-methyl-1H-imidazol-1-yl)pyridin-2-yl]acrylic acid (150 mg) and 1-amino-3-(4-chlorophenyl)piperidin-2-one (143 mg) according to the method in Examples 168 and 169. The resulting racemate was separated by CHIRALPAK™ IA manufactured by Daicel Chemical Industries, Ltd. (2 cm×25 cm; mobile phase: hexane:ethanol=8:2) to obtain the title optically active compound with a retention time of 20 minutes and positive optical rotation (45.3 mg, >99% ee) and the title optically active compound with a retention time of 24 minutes and negative optical rotation (45.9 mg, >99% ee).

The property values of the title compound with a retention time of 20 minutes are as follows.

ESI-MS; m/z 447 [M$^+$+H]. $^1$H-NMR (CDCl$_3$) δ (ppm): 2.01-2.12 (m, 2H), 2.16-2.19 (m, 1H), 2.29 (d, J=1.2 Hz, 3H), 2.31-2.41 (m, 1H), 4.04 (s, 3H), 4.27-4.34 (m, 3H), 6.93 (d, J=8.0 Hz, 1H), 6.94 (d, J=1.2 Hz, 1H), 7.05-7.09 (m, 2H), 7.28-7.32 (m, 2H), 7.44 (d, J=8.0 Hz, 1H), 7.45 (d, J=15.6 Hz, 1H), 7.64 (d, J=15.6 Hz, 1H), 7.76 (d, J=1.2 Hz, 1H).

The property values of the title compound with a retention time of 24 minutes are as follows.

ESI-MS; m/z 447 [M$^+$+H]. $^1$H-NMR (CDCl$_3$) δ (ppm): 2.01-2.12 (m, 2H), 2.16-2.19 (m, 1H), 2.29 (d, J=1.2 Hz, 3H), 2.31-2.41 (m, 1H), 4.04 (s, 3H), 4.27-4.34 (m, 3H), 6.93 (d, J=8.0 Hz, 1H), 6.94 (d, J=1.2 Hz, 1H), 7.05-7.09 (m, 2H), 7.28-7.32 (m, 2H), 7.44 (d, J=8.0 Hz, 1H), 7.45 (d, J=15.6 Hz, 1H), 7.64 (d, J=15.6 Hz, 1H), 7.76 (d, J=1.2 Hz, 1H).

Examples 210 and 211

Synthesis of (+)-2-{(E)-2-[5-methoxy-6-(4-methyl-1H-imidazol-1-yl)pyridin-3-yl]vinyl}-8-phenyl-5,6,7,8-tetrahydro-[1,2,4]triazolo[1,5-a]pyridine and (−)-2-{(E)-2-[5-methoxy-6-(4-methyl-1H-imidazol-1-yl)pyridin-3-yl]vinyl}-8-phenyl-5,6,7,8-tetrahydro-[1,2,4]triazolo[1,5-a]pyridine

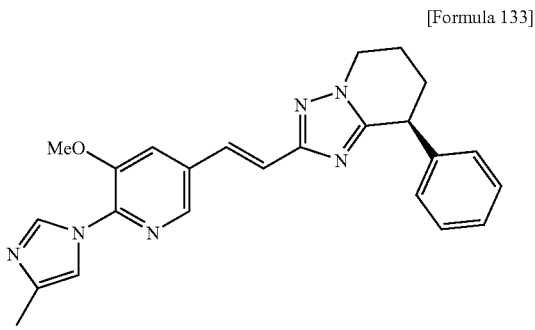

[Formula 133]

-continued

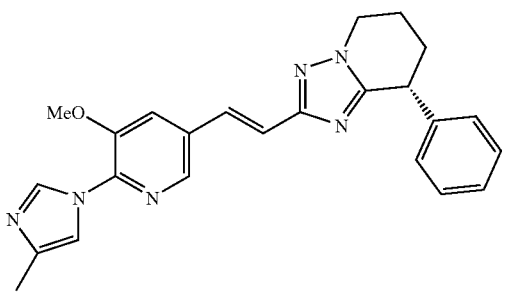

Synthesis of 1-amino-3-phenylpiperidin-2-one 2.83 g of the title compound was obtained from methyl phenylacetate (5 g) according to the method in Examples 20 and 21. The property value of the compound is as follows.
ESI-MS; m/z 191 [M$^+$+H].

Synthesis of (+)-2-{(E)-2-[5-methoxy-6-(4-methyl-1H-imidazol-1-yl)pyridin-3-yl]vinyl}-8-phenyl-5,6,7,8-tetrahydro-[1,2,4]triazolo[1,5-a]pyridine and (−)-2-{(E)-2-[5-methoxy-6-(4-methyl-1H-imidazol-1-yl)pyridin-3-yl]vinyl}-8-phenyl-5,6,7,8-tetrahydro-[1,2,4]triazolo[1,5-a]pyridine A racemate of the title compound was obtained from (E)-3-[5-methoxy-6-(4-methyl-1H-imidazol-1-yl)pyridin-3-yl]acrylic acid (CAS No. 870837-77-7, 300 mg) and 1-amino-3-phenylpiperidin-2-one (110 mg) according to the method in Examples 168 and 169. The resulting racemate was separated by CHIRALPAK™ AD-H manufactured by Daicel Chemical Industries, Ltd. (2 cm×25 cm; mobile phase: ethanol) to obtain the title optically active compound with a retention time of 5 minutes and negative optical rotation (33.8 mg, >99% ee) and the title optically active compound with a retention time of 8 minutes and positive optical rotation (34.5 mg, >99% ee).

The property values of the title compound with a retention time of 5 minutes are as follows.

ESI-MS; m/z 413 [M$^+$+H]. $^1$H-NMR (CDCl$_3$) δ (ppm): 2.02-2.11 (m, 2H), 2.16-2.24 (m, 1H), 2.29 (d, J=1.2 Hz, 3H), 2.34-2.40 (m, 1H), 3.97 (s, 3H), 4.25-4.37 (m, 3H), 7.10 (d, J=16.4 Hz, 1H), 7.12 (s, 1H), 7.13 (d, J=8.0 Hz, 1H), 7.26-7.37 (m, 3H), 7.46 (d, J=1.2 Hz, 1H), 7.51 (d, J=8.0 Hz, 1H), 7.52 (d, J=16.4 Hz, 1H), 8.14 (d, J=2.0 Hz, 1H), 8.34 (d, J=1.2 Hz, 1H).

The property values of the title compound with a retention time of 8 minutes are as follows.

ESI-MS; m/z 413 [M$^+$+H]. $^1$H-NMR (CDCl$_3$) δ (ppm): 2.02-2.11 (m, 2H), 2.16-2.24 (m, 1H), 2.29 (d, J=1.2 Hz, 3H), 2.34-2.40 (m, 1H), 3.97 (s, 3H), 4.25-4.37 (m, 3H), 7.10 (d, J=16.4 Hz, 1H), 7.12 (s, 1H), 7.13 (d, J=8.0 Hz, 1H), 7.26-7.37 (m, 3H), 7.46 (d, J=1.2 Hz, 1H), 7.51 (d, J=8.0 Hz, 1H), 7.52 (d, J=16.4 Hz, 1H), 8.14 (d, J=2.0 Hz, 1H), 8.34 (d, J=1.2 Hz, 1H).

Examples 212 and 213

Synthesis of (+)-8-(4-fluorophenyl)-2-{(E)-2-[5-methoxy-6-(4-methyl-1H-imidazol-1-yl)pyridin-3-yl]vinyl}-5,6,7,8-tetrahydro-[1,2,4]triazolo[1,5-a]pyridine and (−)-8-(4-fluorophenyl)-2-{(E)-2-[5-methoxy-6-(4-methyl-1H-imidazol-1-yl)pyridin-3-yl]vinyl}-5,6,7,8-tetrahydro-[1,2,4]triazolo[1,5-a]pyridine

[Formula 134]

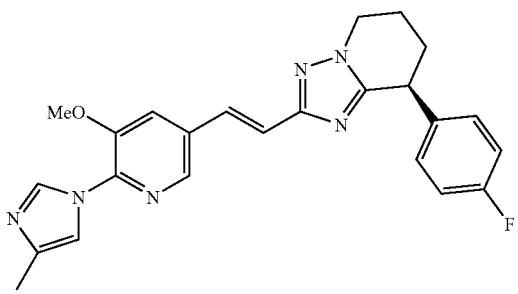

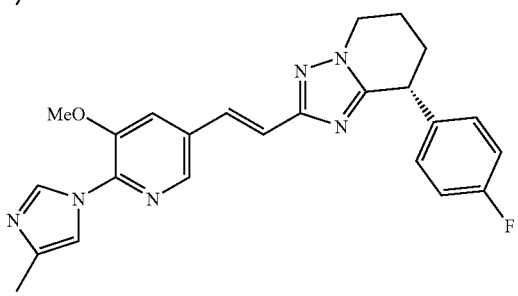

A racemate of the title compound was obtained from (E)-3-[5-methoxy-6-(4-methyl-1H-imidazol-1-yl)pyridin-3-yl]acrylic acid (300 mg) and 1-amino-3-(4-fluorophenyl)piperidin-2-one (133 mg) according to the method in Examples 168 and 169. The resulting racemate was separated by CHIRALPAK™ AD-H manufactured by Daicel Chemical Industries, Ltd. (2 cm×25 cm; mobile phase: ethanol) to obtain the title optically active compound with a retention time of 5.6 minutes and negative optical rotation (48.1 mg, >99% ee) and the title optically active compound with a retention time of 8 minutes and positive optical rotation (46.2 mg, >99% ee).

The property values of the title compound with a retention time of 5.6 minutes are as follows.

ESI-MS; m/z 431 [M$^+$+H]. $^1$H-NMR (CDCl$_3$) δ (ppm): 2.01-2.10 (m, 2H), 2.16-2.22 (m, 1H), 2.29 (s, 3H), 2.33-2.38 (m, 1H), 4.04 (s, 3H), 4.27-4.35 (m, 3H), 6.93 (d, J=8.0 Hz, 1H), 6.94 (s, 1H), 6.99-7.05 (m, 2H), 7.08-7.12 (m, 2H), 7.45 (d, J=15.6 Hz, 1H), 7.46 (d, J=8.0 Hz, 1H), 7.64 (d, J=15.6 Hz, 1H), 7.76 (s, 1H).

The property values of the title compound with a retention time of 8 minutes are as follows.

ESI-MS; m/z 431 [M$^+$+H]. $^1$H-NMR (CDCl$_3$) δ (ppm): 2.01-2.10 (m, 2H), 2.16-2.22 (m, 1H), 2.29 (s, 3H), 2.33-2.38 (m, 1H), 4.04 (s, 3H), 4.27-4.35 (m, 3H), 6.93 (d, J=8.0 Hz, 1H), 6.94 (s, 1H), 6.99-7.05 (m, 2H), 7.08-7.12 (m, 2H), 7.45 (d, J=15.6 Hz, 1H), 7.46 (d, J=8.0 Hz, 1H), 7.64 (d, J=15.6 Hz, 1H), 7.76 (s, 1H).

Examples 214 and 215

Synthesis of (+)-8-(4-chlorophenyl)-2-{(E)-2-[5-methoxy-6-(4-methyl-1H-imidazol-1-yl)pyridin-3-yl]vinyl}-8-phenyl-5,6,7,8-tetrahydro-[1,2,4]triazolo[1,5-a]pyridine and (−)-8-(4-chlorophenyl)-2-{(E)-2-[5-methoxy-6-(4-methyl-1H-imidazol-1-yl)pyridin-3-yl]vinyl}-8-phenyl-5,6,7,8-tetrahydro-[1,2,4]triazolo[1,5-a]pyridine (m, 3H), 7.29-7.32 (m, 2H), 7.46 (d, J=7.6 Hz, 1H), 7.48 (d, J=7.6 Hz, 1H), 7.49 (d, J=16.0 Hz, 1H), 8.13 (d, J=1.2 Hz, 1H), 8.33 (d, J=1.2 Hz, 1H).

Examples 216 and 217

Synthesis of (+)-2-{(E)-2-[5-methoxy-6-(4-methyl-1H-imidazol-1-yl)-pyridin-3-yl]-vinyl}-8-(4-trifluoromethyl-phenyl)-5,6,7,8-tetrahydro-[1,2,4]triazolo[1,5-a]pyridine and (−)-2-{(E)-2-[5-methoxy-6-(4-methyl-1H-imidazol-1-yl)-pyridin-3-yl]-vinyl}-8-(4-trifluoromethyl-phenyl)-5,6,7,8-tetrahydro-[1,2,4]triazolo[1,5-a]pyridine

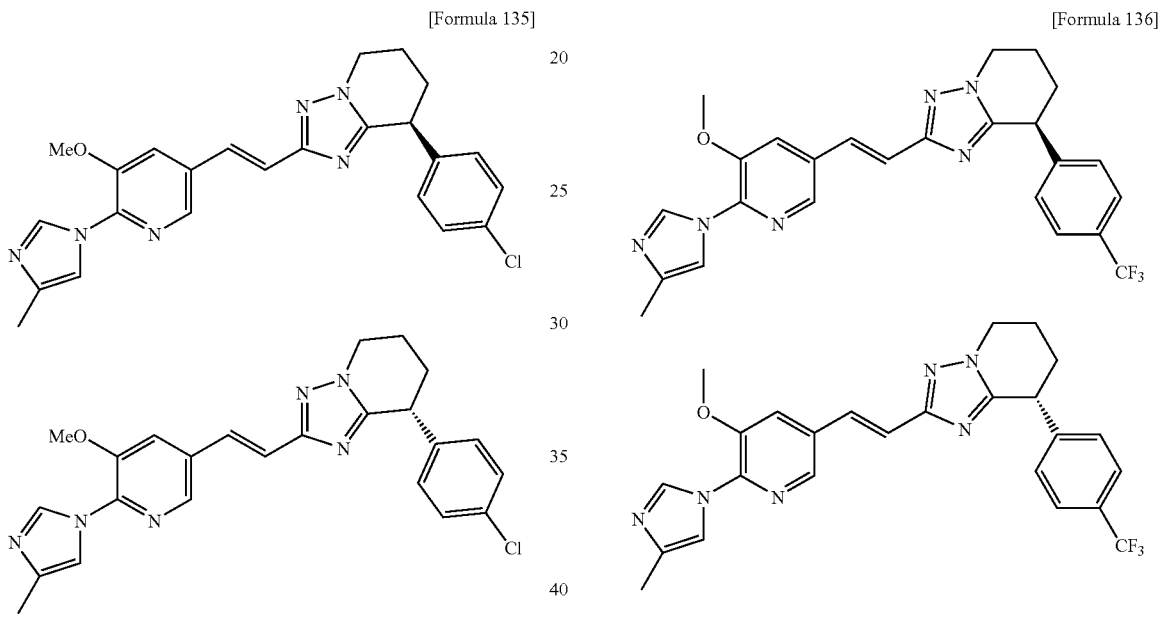

[Formula 135]

[Formula 136]

A racemate of the title compound was obtained from (E)-3-[5-methoxy-6-(4-methyl-1H-imidazol-1-yl)pyridin-3-yl] acrylic acid (300 mg) and 1-amino-3-(4-fluorophenyl)piperidin-2-one (143 mg) according to the method in Examples 168 and 169. The resulting racemate was separated by CHIRALPAK™ IA manufactured by Daicel Chemical Industries, Ltd. (2 cm×25 cm; mobile phase: hexane:ethanol=65:35) to obtain the title optically active compound with a retention time of 26 minutes and positive optical rotation (26.2 mg, >99% ee) and the title optically active compound with a retention time of 31 minutes and negative optical rotation (20.7 mg, >99% ee).

The property values of the title compound with a retention time of 26 minutes are as follows. ESI-MS; m/z 447 [M⁺+H]. ¹H-NMR (CDCl₃) δ (ppm): 2.02-2.13 (m, 2H), 2.17-2.22 (m, 1H), 2.29 (d, J=1.2 Hz, 3H), 2.33-2.38 (m, 1H), 3.96 (s, 3H), 4.26-4.32 (m, 3H), 7.05-7.10 (m, 3H), 7.29-7.32 (m, 2H), 7.46 (d, J=7.6 Hz, 1H), 7.48 (d, J=7.6 Hz, 1H), 7.49 (d, J=16.0 Hz, 1H), 8.13 (d, J=1.2 Hz, 1H), 8.33 (d, J=1.2 Hz, 1H).

The property values of the title compound with a retention time of 31 minutes are as follows.

ESI-MS; m/z 447 [M⁺+H]. ¹H-NMR (CDCl₃) δ (ppm): 2.02-2.13 (m, 2H), 2.17-2.22 (m, 1H), 2.29 (d, J=1.2 Hz, 3H), 2.33-2.38 (m, 1H), 3.96 (s, 3H), 4.26-4.32 (m, 3H), 7.05-7.10

A racemate of the title compound (28.5 mg) was obtained using 1-amino-6-(4-trifluoromethylphenyl)-piperidin-2-one (203 mg) as a starting material according to the method in Examples 168 and 169. The resulting racemate (28.5 mg) was separated by CHIRALPAK™ IA manufactured by Daicel Chemical Industries, Ltd. (2 cm×25 cm, mobile phase: ethanol, flow rate: 12 mL/min) to obtain the title optically active compound with a retention time of 13 minutes and positive optical rotation (12 mg) and the title optically active compound with a retention time of 16 minutes and negative optical rotation (15 mg).

The property values of the title optically active compound with positive optical rotation are as follows.

¹H-NMR (CDCl₃) δ (ppm): 2.00-2.26 (m, 3H), 2.29 (s, 3H), 2.36-2.46 (m, 1H), 3.96 (s, 3H), 4.27-4.34 (m, 2H), 4.38 (t, J=6.9 Hz, 1H), 7.04 (d, J=16.4 Hz, 1H), 7.25-7.30 (m, 2H), 7.45 (d, J=1.8 Hz, 1H), 7.48 (d, J=16.4 Hz, 1H), 7.51 (d, J=1.1 Hz, 1H), 7.58-7.63 (m, 2H), 8.13 (d, J=1.8 Hz, 1H), 8.33 (d, J=1.8 Hz, 1H).

The property values of the title optically active compound with negative optical rotation are as follows.

¹H-NMR (CDCl₃) δ (ppm): 2.00-2.26 (m, 3H), 2.29 (s, 3H), 2.36-2.46 (m, 1H), 3.96 (s, 3H), 4.27-4.34 (m, 2H), 4.38 (t, J=6.9 Hz, 1H), 7.04 (d, J=16.4 Hz, 1H), 7.25-7.30 (m, 2H), 7.45 (d, J=1.8 Hz, 1H), 7.48 (d, J=16.4 Hz, 1H), 7.51 (d, J=1.1 Hz, 1H), 7.58-7.63 (m, 2H), 8.13 (d, J=1.8 Hz, 1H), 8.33 (d, J=1.8 Hz, 1H).

Examples 218 and 219

Synthesis of (+)-8-(3,4-difluorophenyl)-2-{(E)-2-[5-methoxy-6-(4-methyl-1H-imidazol-1-yl)pyridin-3-yl]vinyl}-5,6,7,8-tetrahydro-[1,2,4]triazolo[1,5-a]pyridine and (−)-8-(3,4-difluorophenyl)-2-{(E)-2-[5-methoxy-6-(4-methyl-1H-imidazol-1-yl)pyridin-3-yl]vinyl}-5,6,7,8-tetrahydro-[1,2,4]triazolo[1,5-a]pyridine

[Formula 137]

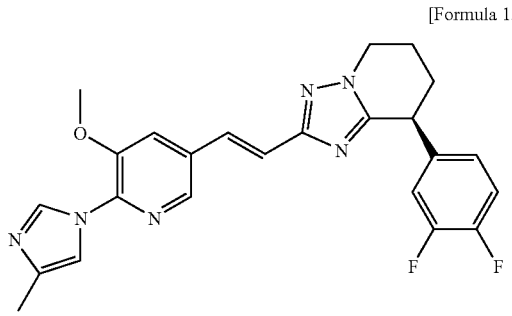

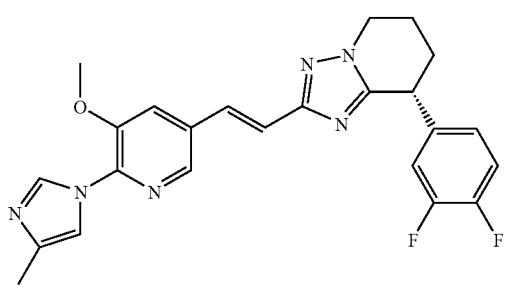

601 mg of the racemic title compound was obtained from (E)-3-[5-methoxy-6-(4-methyl-1H-imidazol-1-yl)pyridin-3-yl]acrylic acid (1.25 g) and 1-amino-3-(3,4-difluorophenyl)piperidin-2-one (547 mg) according to the method in Examples 168 and 169. The property values of the compound are as follows.

ESI-MS; m/z 449 [M$^+$+H].

$^1$H-NMR (CDCl$_3$) δ (ppm): 2.01-2.25 (m, 3H), 2.29 (s, 3H), 2.31-2.40 (m, 1H), 3.96 (s, 3H), 4.26-4.31 (m, 3H), 6.87-6.91 (m, 1H), 6.95-7.00 (m, 1H), 7.08 (d, J=16.4 Hz, 1H), 7.10-7.17 (m, 1H), 7.26-7.51 (m, 3H), 8.13 (d, J=1.6 Hz, 1H), 8.33 (d, J=1.2 Hz, 1H).

The racemic title compound (60 mg) was separated by CHIRALPAK™ AD-H manufactured by Daicel Chemical Industries, Ltd. (2 cm×25 cm; mobile phase: ethanol) to obtain the title optically active compound with a retention time of 21.7 minutes and negative optical rotation (13.6 mg) and the title optically active compound with a retention time of 28.8 minutes and positive optical rotation (14.8 mg).

Examples 220 and 221

Synthesis of (R)-2-{(E)-2-[6-methoxy-5-(4-methyl-1H-imidazol-1-yl)pyridin-2-yl]vinyl}-8-(3,4,5-trifluorophenyl)-5,6,7,8-tetrahydro-[1,2,4]triazolo[1,5-a]pyridine and (S)-2-{(E)-2-[6-methoxy-5-(4-methyl-1H-imidazol-1-yl)pyridin-2-yl]vinyl}-8-(3,4,5-trifluorophenyl)-5,6,7,8-tetrahydro-[1,2,4]triazolo[1,5-a]pyridine

[Formula 138]

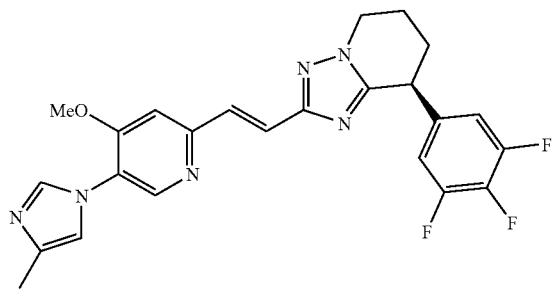

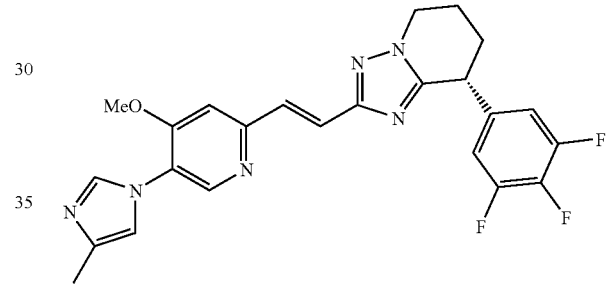

Synthesis of 4-methoxy-5-(4-methyl-1H-imidazol-1-yl)pyridine-2-carboxylic acid diisopropylamide 4-Methyl-1H-imidazole (680 mg), copper iodide (78.8 mg), trans-1,2-bis(methylamino)cyclohexane (0.265 mL) and potassium carbonate (2.52 g) were added to a solution of 5-iodo-4-methoxypyridine-2-carboxylic acid diisopropylamide synthesized according to the method in Organic Letters, 2002, vol. 4, p. 2385 (3 g) in DMF (10 mL). The reaction solution was stirred in a sealed tube at 110° C. for 20 hours. The reaction solution was left to cool to room temperature, and ethyl acetate was added. The insoluble matter was removed by filtration through celite. The resulting organic layer was washed with brine, dried over anhydrous magnesium sulfate and then concentrated under reduced pressure. The residue was purified by silica gel column chromatography (elution solvent: heptane-ethyl acetate system) to obtain 881 mg of the title compound. The property value of the compound is as follows.

ESI-MS; m/z 317 [M$^+$+H].

Synthesis of ethyl (E)-3-[4-methoxy-5-(4-methyl-1H-imidazol-1-yl)pyridin-2-yl]acrylate DIBAL-H (1.39 mL; 1.02 M solution in hexane) was added dropwise to a solution of 4-methoxy-5-(4-methyl-1H-imidazol-1-yl)pyridine-2-carboxylic acid diisopropylamide (150 mg) in THF (5 mL) at −78° C. The reaction solution was stirred at −78° C. for 15 minutes, and then heated to room temperature and stirred for 45 minutes. A saturated ammonium chloride solution and ethyl acetate were added to the reaction solution. A saturated Rochelle salt solution was further added and the reaction solution was vigorously stirred for one hour. The resulting organic layer was washed with saturated sodium bicarbonate water and brine, dried over anhydrous magnesium sulfate and then concentrated under reduced pressure. Subsequently, ethyl diethylphosphonoacetate (0.142 mL) and lithium hydroxide (18.2 mg) were added to a solution of the resulting residue in THF (3 mL), and the reaction solution was stirred at room temperature for 12 hours. Water and ethyl acetate were added to the reaction solution, and the organic layer was separated. The resulting organic layer was washed with brine, dried over anhydrous magnesium sulfate and then concentrated under reduced pressure. The residue was purified by silica gel column chromatography (elution solvent: heptane-ethyl acetate system) to obtain 53 mg of the title compound. The property value of the compound is as follows.

ESI-MS; m/z 288 [M⁺+H].

Synthesis of (R)-2-{(E)-2-[6-methoxy-5-(4-methyl-1H-imidazol-1-yl)pyridin-2-yl]vinyl}-8-(3,4,5-trifluorophenyl)-5,6,7,8-tetrahydro-[1,2,4]triazolo[1,5-a]pyridine and (S)-2-{(E)-2-[6-methoxy-5-(4-methyl-1H-imidazol-1-yl)pyridin-2-yl]vinyl}-8-(3,4,5-trifluorophenyl)-5,6,7,8-tetrahydro-[1,2,4]triazolo[1,5-a]pyridine A 5 N sodium hydroxide solution (0.5 mL) was added to a mixed solution of ethyl (E)-3-[4-methoxy-5-(4-methyl-1H-imidazol-1-yl)pyridin-2-yl]acrylate (90 mg) in THF (2 mL) and methanol (1 mL). The reaction solution was stirred at room temperature for two hours. Then, 5 N hydrochloric acid (0.5 mL) was added, and the reaction solution was concentrated under reduced pressure. Subsequently, 1-amino-3-(3,4,5-trifluorophenyl)piperidin-2-one (115 mg), EDC (180 mg), HOBT (127 mg) and IPEA (0.327 mL) were added to a solution of the resulting residue in DMF (3 mL). The reaction solution was stirred at room temperature for 15 hours. Then, water and ethyl acetate were added to the reaction solution, and the organic layer was separated. The resulting organic layer was washed with brine, dried over anhydrous magnesium sulfate and then concentrated under reduced pressure. The residue was purified by silica gel column chromatography (elution solvent: ethyl acetate-methanol system) to obtain a crude coupled compound. Subsequently, phosphorous oxychloride (3 mL) was added to the compound. The reaction solution was stirred at 120° C. for one hour and then concentrated under reduced pressure. Subsequently, ammonium acetate (727 mg) was added to a solution of the residue in acetic acid (2 mL), and the reaction solution was stirred at 150° C. for two hours. The reaction solution was left to cool to room temperature and then concentrated under reduced pressure. Saturated sodium bicarbonate water and ethyl acetate were added to the resulting residue, and the organic layer was separated. The resulting organic layer was washed with brine, dried over anhydrous magnesium sulfate and then concentrated under reduced pressure. The residue was purified by silica gel column chromatography (elution solvent: heptane-ethyl acetate system) to obtain a racemate of the title compound. The resulting racemate was separated by CHIRALPAK™ IA manufactured by Daicel Chemical Industries, Ltd. (2 cm×25 cm; mobile phase: ethanol) to obtain the title optically active compound with a retention time of 7 minutes (5.7 mg, >99% ee) and the title optically active compound with a retention time of 9 minutes (5.6 mg, >99% ee).

The property values of the title compound with a retention time of 7 minutes are as follows.

ESI-MS; m/z 467 [M⁺+H]. ¹H-NMR (CDCl₃) δ (ppm): 1.97-2.22 (m, 1H), 2.11-2.22 (m, 2H), 2.30 (d, J=1.2 Hz, 3H), 2.34-2.40 (m, 1H), 3.91 (s, 3H), 4.24-4.30 (m, 3H), 6.82 (dd, J=8.0, 6.0 Hz, 2H), 6.90 (s, 1H), 6.99 (s, 1H), 7.52 (d, J=16.0 Hz, 1H), 7.58 (d, J=16.0 Hz, 1H), 7.67 (d, J=1.2 Hz, 1H), 8.41 (s, 1H).

The property values of the title compound with a retention time of 9 minutes are as follows.

ESI-MS; m/z 467 [M⁺+H]. ¹H-NMR (CDCl₃) δ (ppm): 1.97-2.22 (m, 1H), 2.11-2.22 (m, 2H), 2.30 (d, J=1.2 Hz, 3H), 2.34-2.40 (m, 1H), 3.91 (s, 3H), 4.24-4.30 (m, 3H), 6.82 (dd, J=8.0, 6.0 Hz, 2H), 6.90 (s, 1H), 6.99 (s, 1H), 7.52 (d, J=16.0 Hz, 1H), 7.58 (d, J=16.0 Hz, 1H), 7.67 (d, J=1.2 Hz, 1H), 8.41 (s, 1H).

Examples 222 and 223

Synthesis of (+) and (−)-8-(3,4-difluorophenyl)-2-{(E)-2-[6-methoxy-5-(4-methyl-1H-imidazol-1-yl)pyridin-2-yl]-1-methylvinyl}-5,6,7,8-tetrahydro-[1,2,4]triazolo[1,5-a]pyridine

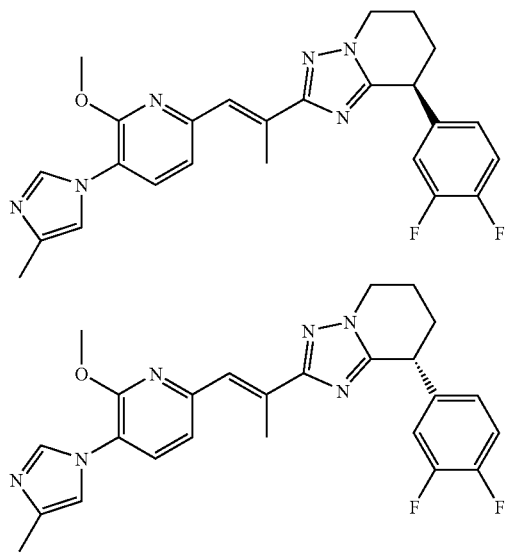

[Formula 139]

Synthesis of N-(6-chloro-2-methoxypyridin-3-yl)formamide

Iron (11.9 g) and ammonium chloride (22.7 g) were added to a solution of 6-chloro-2-methoxy-3-nitropyridine (10.0 g, CAS: 40851-91-0) in ethanol (130 mL) and water (52 mL). The reaction solution was stirred at 80 to 90° C. for one hour and 20 minutes and then left to cool to room temperature. The reaction solution was filtered through celite and washed with ethanol. Then, the filtrate was concentrated under reduced pressure. The residue was diluted with ethyl acetate and water, and the organic layer was separated. The resulting organic layer was washed with brine, dried over anhydrous magnesium sulfate and then concentrated under reduced pressure. The residue was diluted with THF (26 mL). The THF solution was added dropwise to a mixed solution of formic acid (20.1 mL) and acetic anhydride (20.1 mL) at room temperature. Then, the reaction solution was stirred for one hour. Ice water (120 mL) was added to the reaction solution, and the precipitated crystals were collected by filtration. The crystals were washed with water and then air-dried to obtain 5.85 g of the title compound. The property value of the compound is as follows.

ESI-MS; m/z 187 [M$^+$+H].

Synthesis of N-(6-chloro-2-methoxypyridin-3-yl)-N-(2-oxopropyl)formamide

Cesium carbonate (20.5 g), potassium iodide (521 mg) and chloroacetone (5.0 mL) were added to a solution of N-(6-chloro-2-methoxypyridin-3-yl)formamide (5.85 g) in DMF (34.3 mL), and the reaction solution was stirred at 100° C. for one hour. Ice water and chloroform were added to the reaction solution, and the organic layer was separated. The organic layer was dried over anhydrous magnesium sulfate and then concentrated under reduced pressure. The residue was purified by silica gel column chromatography (elution solvent: heptane-ethyl acetate system) to obtain 4.71 g of the title compound. The property value of the compound is as follows.

ESI-MS; m/z 243 [M$^+$+H].

Synthesis of 6-chloro-2-methoxy-3-(4-methyl-1H-imidazol-1-yl)pyridine

A mixture of N-(6-chloro-2-methoxypyridin-3-yl)-N-(2-oxopropyl)formamide (4.71 g), acetic acid (11.1 mL) and ammonium acetate (7.48 g) was stirred at 130° C. for one hour. The reaction solution was left to cool to room temperature. Ice water, ethyl acetate and aqueous ammonia were added and the organic layer was separated. The organic layer was dried over anhydrous magnesium sulfate and then concentrated under reduced pressure. The residue was purified by silica gel column chromatography (elution solvent: heptane-ethyl acetate system) to obtain 2.42 g of the title compound. The property values of the compound are as follows.

ESI-MS; m/z 224 [M$^+$+H].
$^1$H-NMR (CDCl$_3$) δ (ppm): 2.29 (s, 3H), 4.02 (s, 3H), 6.91 (brs, 1H), 6.99 (d, J=7.6 Hz, 1H), 7.48 (d, J=7.6 Hz, 1H), 7.71 (brs, 1H).

Synthesis of (E)-3-[6-methoxy-5-(4-methyl-1H-imidazol-1-yl)pyridin-2-yl]-2-methylacrylic acid A mixture of 6-chloro-2-methoxy-3-(4-methyl-1H-imidazol-1-yl)pyridine (400 mg), an allylpalladium chloride dimer (32.8 mg), tri-o-tolylphosphine (54.4 mg), sodium acetate (441 mg), dimethylacetamide (0.640 mL), tert-butyl methacrylate (0.724 mL) and toluene (2 mL) was stirred in a nitrogen atmosphere at 120° C. for 3.5 hours. The reaction solution was left to cool to room temperature. Then, a silica gel was added and the reaction solution was concentrated under reduced pressure. The residue was purified by silica gel column chromatography (elution solvent: heptane-ethyl acetate system) to obtain 313 mg of tert-butyl (E)-3-[6-methoxy-5-(4-methyl-1H-imidazol-1-yl)pyridin-2-yl]-2-methylacrylate. The ester was diluted with trifluoroacetic acid (2.48 mL) and methylene chloride (2.48 mL), and the reaction solution was stirred at room temperature for 3.5 hours. The reaction solution was concentrated under reduced pressure to obtain 260 mg of the title compound. The property value of the compound is as follows.

ESI-MS; m/z 274 [M$^+$+H].

Synthesis of (+) and (−)-8-(3,4-difluorophenyl)-2-{(E)-2-[6-methoxy-5-(4-methyl-1H-imidazol-1-yl)pyridin-2-yl]-1-methylvinyl}-5,6,7,8-tetrahydro-[1,2,4]triazolo[1,5-a]pyridine 74.6 mg of the racemic title compound was obtained from (E)-3-[6-methoxy-5-(4-methyl-1H-imidazol-1-yl)pyridin-2-yl]-2-methylacrylic acid (260 mg) and 1-amino-3-(3,4-difluorophenyl)piperidin-2-one (172 mg) according to the method in Examples 168 and 169. The racemic title compound was separated by CHIRALPAK™ IA manufactured by Daicel Chemical Industries, Ltd. (2 cm×25 cm; mobile phase: ethanol:hexane=1:1) to obtain the title optically active compound with a retention time of 7.4 minutes and positive optical rotation (11.9 mg) and the title optically active compound with a retention time of 9.8 minutes and negative optical rotation (12.2 mg).

The property values of the title optically active compound with negative optical rotation are as follows.

ESI-MS; m/z 463 [M$^+$+H].
$^1$H-NMR (CDCl$_3$) δ (ppm): 2.00-2.21 (m, 3H), 2.30 (s, 3H), 2.30-2.37 (m, 1H), 2.75 (s, 3H), 4.06 (s, 3H), 4.23-4.36 (m, 3H), 6.86-6.90 (m, 1H), 6.94-7.02 (m, 3H), 7.10-7.17 (m, 1H), 7.47-7.49 (m, 2H), 7.79 (d, J=1.2 Hz, 1H).

The property values of the title optically active compound with positive optical rotation corresponded to the property values of the title optically active compound with negative optical rotation.

Example 224

Synthesis of 8-(3,4-difluorophenyl)-2-{(E)-2-[6-methoxy-5-(4-methyl-1H-imidazol-1-yl)pyridin-2-yl]vinyl}-5,6,7,8-tetrahydro[1,2,4]triazolo[1,5-a]pyridin-8-ol

[Formula 140]

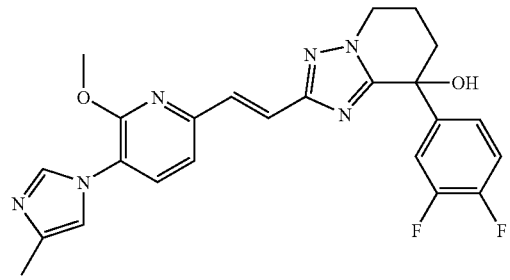

10.1 mg of the racemic title compound was obtained according to the method in Example 53 from (+)-8-(3,4-difluorophenyl)-2-{(E)-2-[6-methoxy-5-(4-methyl-1H-imidazol-1-yl)pyridin-2-yl]vinyl}-5,6,7,8-tetrahydro[1,2,4]triazolo[1,5-a]pyridine obtained in Example 170 (20 mg). The property values of the compound are as follows.

ESI-MS; m/z 465 [M$^+$+H]. $^1$H-NMR (CDCl$_3$) δ (ppm): 1.98-2.08 (m, 1H), 2.16 (ddd, J=13.6, 10.0, 3.2 Hz, 1H), 2.29 (s, 3H), 2.35 (ddd, J=13.6, 8.0, 2.4 Hz, 1H), 2.36-2.50 (m, 1H), 4.00 (s, 3H), 4.23-4.40 (m, 2H), 5.23 (brs, 1H), 6.78 (d, J=5.2 Hz, 1H), 6.94 (s, 1H), 7.01-7.07 (m, 1H), 7.13 (q, J=8.4

Hz, 1H) 7.25-7.32 (m, 1H), 7.39 (d, J=15.6 Hz, 1H), 7.41 (d, J=5.2 Hz, 1H), 7.62 (d, J=15.6 Hz, 1H), 7.80 (d, J=1.2 Hz, 1H).

Example 225

Synthesis of 8-(3,4-difluorophenyl)-2-{(E)-2-[5-methoxy-6-(4-methyl-1H-imidazol-1-yl)pyridin-3-yl]vinyl}-5,6,7,8-tetrahydro[1,2,4]triazolo[1,5-a]pyridin-8-ol

[Formula 141]

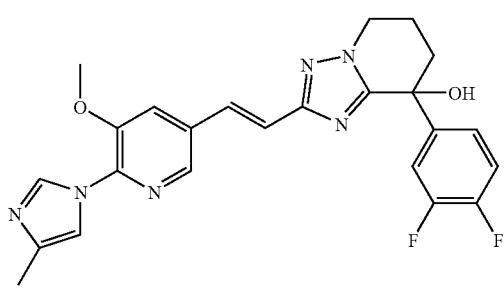

7.2 mg of the title compound was obtained according to the method in Example 53 from (+)-8-(3,4-difluorophenyl)-2-{(E)-2-[5-methoxy-6-(4-methyl-1H-imidazol-1-yl)pyridin-3-yl]vinyl}-5,6,7,8-tetrahydro[1,2,4]triazolo[1,5-a]pyridine obtained in Example 219 (10.2 mg). The property values of the compound are as follows.

ESI-MS; m/z 465 [M$^+$+H]. $^1$H-NMR (CDCl$_3$) δ (ppm): 1.97-2.08 (m, 1H), 2.16 (ddd, J=13.6, 10.4, 3.2 Hz, 1H), 2.28 (s, 3H), 2.35 (ddd, J=13.6, 8.4, 3.2 Hz, 1H), 2.34-2.48 (m, 1H), 3.92 (s, 3H), 4.21-4.37 (m, 2H), 4.80 (brs, 1H), 6.98-7.04 (m, 1H), 7.06 (d, J=16.0 Hz, 1H), 7.12 (q, J=8.4 Hz, 1H) 7.20-7.28 (m, 1H), 7.36 (d, J=1.6 Hz, 1H), 7.43 (d, J=16.0 Hz, 1H), 7.48 (s, 1H), 8.06 (d, J=1.6 Hz, 1H), 8.30 (s, 1H).

Examples 226 and 227

Synthesis of (−) and (+)-8-(3,4-difluorophenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine-8-carbonitrile

[Formula 142]

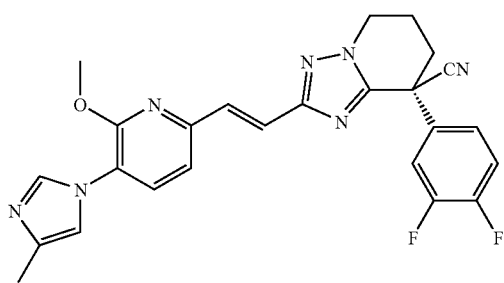

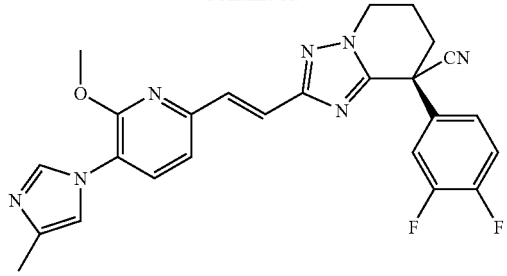

70.6 mg of the racemic title compound was obtained from 8-(3,4-difluorophenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine (100 mg) in the same manner as in Example 65. The property values of the compound are as follows.

ESI-MS; m/z 474 [M$^+$+H].
$^1$H-NMR (CDCl$_3$) δ (ppm): 2.15-2.26 (m, 1H), 2.30 (s, 3H), 2.35-2.48 (m, 2H), 2.68-2.76 (m, 1H), 4.07 (s, 3H), 4.29-4.45 (m, 2H), 6.97 (d, J=1.2 Hz, 1H), 6.98 (d, J=7.6 Hz, 1H), 7.10-7.28 (m, 3H), 7.50 (d, J=7.6 Hz, 1H), 7.52 (d, J=15.6 Hz, 1H), 7.64 (d, J=15.6 Hz, 1H), 7.79 (d, J=1.2 Hz, 1H).

The racemic title compound was separated by CHIRAL-PAK™ IB manufactured by Daicel Chemical Industries, Ltd. (2 cm×25 cm; mobile phase: hexane:ethanol=7:3) to obtain the title optically active compound with a retention time of 12.8 minutes and negative optical rotation (18.5 mg) and the title optically active compound with a retention time of 16.8 minutes and positive optical rotation (19.8 mg).

Examples 228 and 229

Synthesis of (+) and (−)-2-{(E)-2-[5-methoxy-6-(4-methyl-1H-imidazol-1-yl)pyridin-3-yl]vinyl}-8-(3,4,5-trifluorophenyl)-5,6,7,8-tetrahydro-[1,2,4]triazolo[1,5-a]pyridine-8-carbonitrile

[Formula 143]

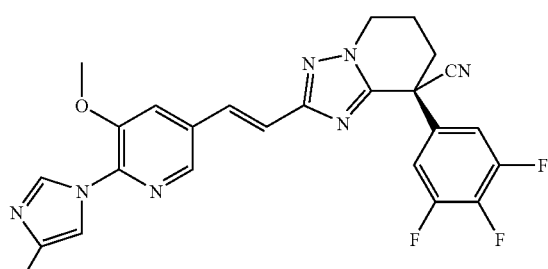

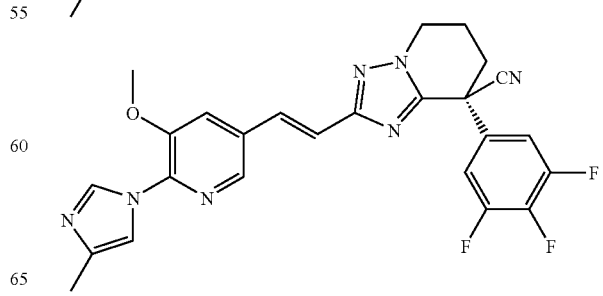

308 mg of the racemic title compound was obtained from 2-{(E)-2-[5-methoxy-6-(4-methyl-1H-imidazol-1-yl)pyridin-3-yl]vinyl}-8-(3,4,5-trifluorophenyl)-5,6,7,8-tetrahydro[1,2,4]triazolo[1,5-a]pyridine (255 mg) in the same manner as in Example 65. The property values of the compound are as follows.

ESI-MS; m/z 492 [M⁺+H].

¹H-NMR (CDCl₃) δ (ppm): 2.22-2.29 (m, 1H), 2.29 (s, 3H), 2.36-2.50 (m, 2H), 2.69-2.75 (m, 1H), 3.98 (s, 3H), 4.27-4.42 (m, 2H), 7.02-7.06 (m, 2H), 7.07 (d, J=16.4 Hz, 1H), 7.46 (d, J=2.0 Hz, 1H), 7.53 (s, 1H), 7.56 (d, J=16.4 Hz, 1H), 8.17 (d, J=2.0 Hz, 1H), 8.36 (s, 1H).

The racemic title compound (48 mg) was separated by CHIRALPAK™ IA manufactured by Daicel Chemical Industries, Ltd. (2 cm×25 cm; mobile phase: ethanol) to obtain the title optically active compound with a retention time of 12.9 minutes and positive optical rotation (8.35 mg) and the title optically active compound with a retention time of 14.6 minutes and negative optical rotation (9.62 mg).

Examples 230 and 231

Synthesis of (−) and (+)-8-(3,4-difluorophenyl)-2-{(E)-2-[5-methoxy-6-(4-methyl-1H-imidazol-1-yl)pyridin-3-yl]vinyl}-5,6,7,8-tetrahydro-[1,2,4]triazolo[1,5-a]pyridine-8-carbonitrile

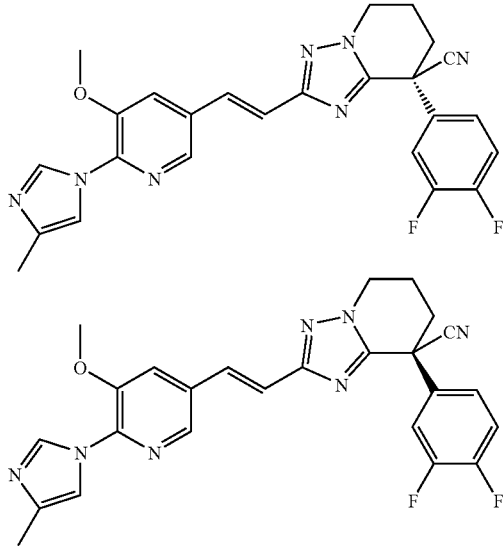

[Formula 144]

174 mg of the racemic title compound was obtained as a crude product from 8-(3,4-difluorophenyl)-2-{(E)-2-[5-methoxy-6-(4-methyl-1H-imidazol-1-yl)pyridin-3-yl]vinyl}-5,6,7,8-tetrahydro-[1,2,4]triazolo[1,5-a]pyridine (100 mg) in the same manner as in Example 65. The crude product was separated by CHIRALPAK™ AD-H manufactured by Daicel Chemical Industries, Ltd. (2 cm×25 cm; mobile phase: ethanol) to obtain the title optically active compound with a retention time of 14.3 minutes and negative optical rotation (22.4 m) and the title optically active compound with a retention time of 18.2 minutes and positive optical rotation (9.26 mg).

The property values of the title optically active compound with negative optical rotation are as follows.

ESI-MS; m/z 474 [M⁺+H].

¹H-NMR (CDCl₃) δ (ppm): 2.18-2.28 (m, 1H), 2.30 (d, J=1.2 Hz, 3H), 2.36-2.48 (m, 2H), 2.69-2.74 (m, 1H), 3.99 (s, 3H), 4.28-4.44 (m, 2H), 7.08-7.25 (m, 4H), 7.48 (d, J=2.0 Hz, 1H), 7.55-7.59 (m, 2H), 8.18 (d, J=2.0 Hz, 1H), 8.39 (d, J=1.2 Hz, 1H).

The property values of the title optically active compound with positive optical rotation corresponded to those of the title optically active compound with negative optical rotation.

Example 232

Synthesis of 4-(4-chlorophenyl)-2-{(E)-2-[6-methoxy-5-(4-methyl-1H-imidazol-1-yl)pyridin-2-yl]vinyl}-4,5,6,7-tetrahydro-[1,2,4]triazolo[1,5-a]pyrimidine

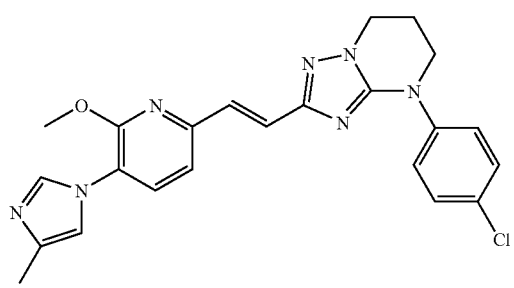

[Formula 145]

Synthesis of 3-(4-chlorophenylamino)propan-1-ol

4-Chloroaniline (4.39 g) and lithium tetrafluoroborate (3.32 g) were added to a solution of oxetane (1.00 g) in acetonitrile (20 mL) at room temperature, and the reaction solution was stirred at room temperature for 52 hours. A saturated sodium bicarbonate solution was added to the reaction solution, followed by extraction with chloroform. The resulting extract was dried over magnesium sulfate and then concentrated under reduced pressure. The residue was purified by silica gel column chromatography (elution solvent: heptane-ethyl acetate system) to obtain 2.17 g of the title compound. The property values of the compound are as follows.

¹H-NMR (CDCl₃) δ (ppm): 1.88 (tt, J=6.4, 6.0 Hz, 2H), 3.25 (t, J=6.4 Hz, 2H), 3.81 (brt, J=6.0 Hz, 2H), 3.90 (brs, 1H), 6.52-6.56 (m, 2H), 7.08-7.13 (m, 2H).

Synthesis of 1-amino-3-(4-chlorophenyl)tetrahydropyrimidin-2-one

Thionyl chloride (4.4 mL) was added to a solution of 3-(4-chlorophenylamino)propan-1-ol (2.17 g) in toluene (30 mL) at room temperature, and the reaction solution was stirred at 60° C. for five hours. The reaction solution was left to cool to room temperature and then concentrated under reduced pressure. Ice and a saturated sodium bicarbonate solution were added, followed by extraction with ethyl acetate (200 mL). Heptane (100 mL) was added to the resulting extract to prepare a mixed solution. The solution was purified by silica gel column chromatography (elution solvent: heptane:ethyl acetate=2:1) to obtain (4-chlorophenyl)-(3-chloropropyl)amine. (4-Chlorophenyl)-(3-chloropropyl)amine was dissolved in THF (45 mL). Triethylamine (4.9 mL) and phenyl chlorocarbonate (1.8 mL) were added at 0° C., and the reaction solution was stirred at room temperature for 15 hours. Water was added to the reaction solution, followed by extraction with ethyl acetate. The resulting extract was dried over magnesium sulfate and then concentrated under reduced pressure. The residue was purified by silica gel column chromatography (elution solvent: heptane-ethyl acetate system) to obtain phenyl (4-chlorophenyl)-(3-chloropropyl)carbamate (3.70 g). Phenyl (4-chlorophenyl)-(3-chloropropyl)carbamate (3.70 g) was dissolved in ethanol (60 mL). Hydrazine monohydrate (5.65 mL) was added at room temperature, and the reaction solution was heated under reflux for 17 hours. The reaction solution was left to cool to room temperature and then concentrated under reduced pressure. A saturated sodium bicarbonate solution was added, followed by extraction with chloroform. The resulting extract was dried over magnesium sulfate and then concentrated under reduced pressure. The residue was purified by silica gel column chromatography (elution solvent: heptane-ethyl acetate system, then ethyl acetate-methanol system) to obtain 2.19 g of the title compound. The property values of the compound are as follows.

ESI-MS; m/z 226 [M$^+$+H]. $^1$H-NMR (CDCl$_3$) δ (ppm): 2.15 (tt, J=6.4, 5.6 Hz, 2H), 3.62 (t, J=6.4 Hz, 2H), 3.65 (t, J=5.6 Hz, 2H), 4.31 (brs, 2H), 7.17-7.22 (m, 2H), 7.26-7.31 (m, 2H).

Synthesis of (E)-N-[3-(4-chlorophenyl)-2-oxo-tetrahydropyrimidin-1-yl]-3-[6-methoxy-5-(4-methyl-1H-imidazol-1-yl)pyridin-2-yl]acrylamide IPEA (0.65 mL), 1-amino-3-(4-chlorophenyl)tetrahydropyrimidin-2-one (139 mg), EDC (177 mg) and HOBT (125 mg) were added to a solution of (E)-3-[6-methoxy-5-(4-methyl-1H-imidazol-1-yl)pyridin-2-yl]acrylic acid (300 mg) in DMF (6 mL) at room temperature. The reaction solution was stirred at room temperature for 24 hours. The reaction solution was diluted with ethyl acetate and washed with a saturated sodium bicarbonate solution and a saturated sodium chloride solution. The resulting organic layer was dried over magnesium sulfate and then concentrated under reduced pressure. The residue was purified by silica gel column chromatography (carrier: Chromatorex NH; elution solvent: heptane-ethyl acetate system, then ethyl acetate-methanol system) to obtain 287 mg of the title compound. The property value of the compound is as follows.

ESI-MS; m/z 467 [M$^+$+H].

Synthesis of 4-(4-chlorophenyl)-2-{(E)-2-[6-methoxy-5-(4-methyl-1H-imidazol-1-yl)pyridin-2-yl]vinyl}-4,5,6,7-tetrahydro-[1,2,4]triazolo[1,5-a]pyrimidine Phosphorus oxychloride (5 mL) was added to (E)-N-[3-(4-chlorophenyl)-2-oxo-tetrahydropyrimidin-1-yl]-3-[6-methoxy-5-(4-methyl-1H-imidazol-1-yl)pyridin-2-yl]acrylamide (287 mg), and the reaction mixture was heated under reflux for one hour. The reaction solution was left to cool to room temperature and then concentrated under reduced pressure. Acetic acid (5 mL) and ammonium acetate (2.4 g) were added to the resulting residue, and the reaction solution was stirred at 150° C. for two hours. The reaction solution was left to cool to room temperature and then concentrated under reduced pressure. A saturated sodium bicarbonate solution was added to the resulting residue, followed by extraction with chloroform. The resulting extract was dried over magnesium sulfate and then concentrated under reduced pressure. The residue was purified by silica gel column chromatography (carrier: Chromatorex NH; elution solvent: heptane-ethyl acetate system) and further solidified with a mixed solvent of ethyl acetate, diethyl ether and heptane to obtain 117 mg of the title compound. The property values of the compound are as follows.

ESI-MS; m/z 448 [M$^+$+H]. $^1$H-NMR (CDCl$_3$) δ (ppm): 2.29 (d, J=1.2 Hz, 3H), 2.35-2.42 (m, 2H), 3.84 (brt, J=5.6 Hz, 2H), 4.05 (s, 3H), 4.23 (t, J=6.0 Hz, 2H), 6.93-6.97 (m, 2H), 7.33-7.41 (m, 3H), 7.46 (d, J=7.6 Hz, 1H), 7.49-7.55 (m, 3H), 7.76 (d, J=1.2 Hz, 1H).

Example 233

Synthesis of 2-{(E)-2-[6-methoxy-5-(4-methyl-1H-imidazol-1-yl)pyridin-2-yl]vinyl}-4-phenyl-4,5,6,7-tetrahydro-[1,2,4]triazolo[1,5-a]pyrimidine

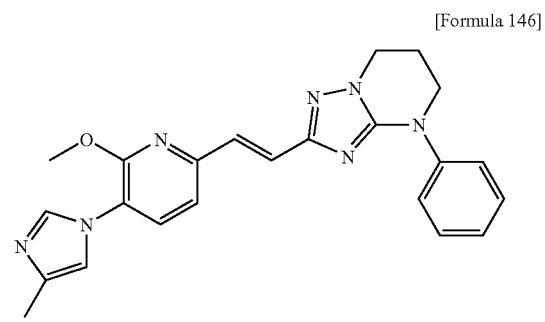

[Formula 146]

120 mg of the title compound was obtained from (E)-3-[6-methoxy-5-(4-methyl-1H-imidazol-1-yl)pyridin-2-yl]-N-(2-oxo-3-phenyl-tetrahydropyrimidin-1-yl)acrylamide (259 mg) by the same method as in Example 232. The property values of the compound are as follows.

ESI-MS; m/z 414 [M$^+$+H]. $^1$H-NMR (CDCl$_3$) δ (ppm): 2.29 (s, 3H), 2.34-2.41 (m, 2H), 3.88 (brt, J=5.6 Hz, 2H), 4.05 (s, 3H), 4.24 (t, J=6.0 Hz, 2H), 6.93-6.96 (m, 2H), 7.12-7.27 (m, 1H), 7.36-7.43 (m, 3H), 7.45 (d, J=7.6 Hz, 1H), 7.51-7.57 (m, 3H), 7.75 (brs, 1H).

Example 234

Synthesis of 2-{(E)-2-[6-methoxy-5-(4-methyl-1H-imidazol-1-yl)pyridin-2-yl]vinyl}-4-(3,4,5-trifluorophenyl)-4,5,6,7-tetrahydro-[1,2,4]triazolo[1,5-a]pyrimidine

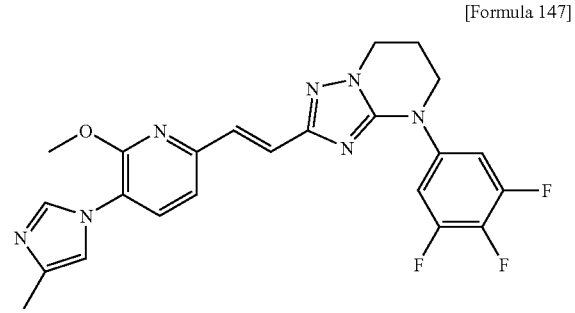

[Formula 147]

175 mg of the title compound was obtained from (E)-3-[6-methoxy-5-(4-methyl-1H-imidazol-1-yl)pyridin-2-yl]-N-[2-oxo-3-(3,4,5-trifluorophenyl)-tetrahydropyrimidin-1-yl] acrylamide (298 mg) by the same method as in Example 232. The property values of the compound are as follows.

ESI-MS; m/z 468 [M$^+$+H]. $^1$H-NMR (CDCl$_3$) δ (ppm): 2.30 (s, 3H), 2.35-2.44 (m, 2H), 3.81 (t, J=5.6 Hz, 2H), 4.06 (s, 3H), 4.24 (t, J=6.0 Hz, 2H), 6.95-7.01 (m, 2H), 7.31-7.37 (m, 2H), 7.41 (d, J=16.0 Hz, 1H), 7.48 (d, J=7.6 Hz, 1H), 7.53 (d, J=16.0 Hz, 1H), 7.77 (s, 1H).

Examples 235 and 236

Synthesis of (R)-4-(4-fluorophenyl)-2-{(E)-2-[6-methoxy-5-(4-methyl-1H-imidazol-1-yl)pyridin-2-yl]vinyl}-5-methyl-4,5,6,7-tetrahydro-[1,2,4]triazolo [1,5-a]pyrimidine and (S)-4-(4-fluorophenyl)-2-{(E)-2-[6-methoxy-5-(4-methyl-1H-imidazol-1-yl) pyridin-2-yl]vinyl}-5-methyl-4,5,6,7-tetrahydro-[1,2,4]triazolo[1,5-a]pyrimidine

[Formula 148]

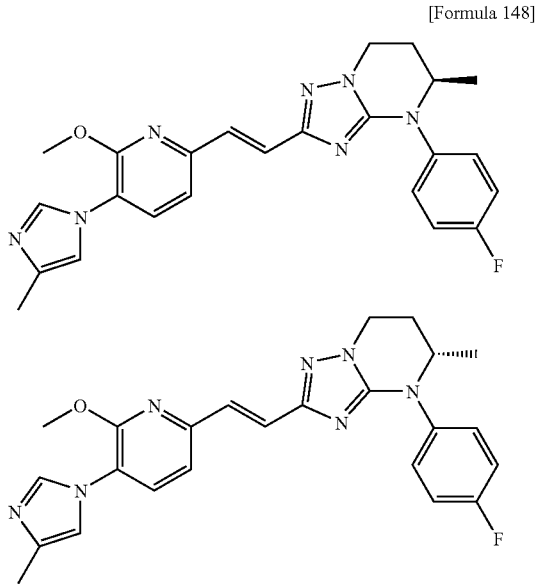

178 mg of the racemic title compound was obtained from (E)-N-[3-(4-fluorophenyl)-4-methyl-2-oxo-tetrahydropyrimidin-1-yl]-3-[6-methoxy-5-(4-methyl-1H-imidazol-1-yl) pyridin-2-yl]acrylamide (378 mg) by the same method as in Example 232. The racemic title compound (178 mg) was separated by CHIRALPAK™ IB manufactured by Daicel Chemical Industries, Ltd. (2 cm×25 cm; mobile phase: hexane:ethanol=1:1) to obtain the title optically active compound with a retention time of 31 minutes (75 mg) and the title optically active compound with a retention time of 39 minutes (75 mg).

The property values of the title optically active compound with a retention time of 31 minutes are as follows (Example 235).

ESI-MS; m/z 446 [M$^+$+H]. $^1$H-NMR (CDCl$_3$) δ (ppm): 1.29 (d, J=6.4 Hz, 3H), 2.10-2.18 (m, 1H), 2.29 (d, J=0.8 Hz, 3H), 2.37-2.48 (m, 1H), 4.03 (s, 3H), 4.08-4.17 (m, 1H), 4.19-4.32 (m, 2H), 6.91 (d, J=7.6 Hz, 1H), 6.94 (brs, 1H), 7.07-7.13 (m, 2H), 7.33 (d, J=15.6 Hz, 1H), 7.39-7.44 (m, 2H), 7.44 (d, J=7.6 Hz, 1H), 7.51 (d, J=15.6 Hz, 1H), 7.75 (d, J=0.8 Hz, 1H).

The property values of the title optically active compound with a retention time of 39 minutes are as follows (Example 236).

ESI-MS; m/z 446 [M$^+$+H]. $^1$H-NMR (CDCl$_3$) δ (ppm): 1.29 (d, J=6.4 Hz, 3H), 2.10-2.18 (m, 1H), 2.29 (d, J=0.8 Hz, 3H), 2.37-2.48 (m, 1H), 4.03 (s, 3H), 4.08-4.17 (m, 1H), 4.19-4.32 (m, 2H), 6.91 (d, J=7.6 Hz, 1H), 6.94 (brs, 1H), 7.07-7.13 (m, 2H), 7.33 (d, J=15.6 Hz, 1H), 7.39-7.44 (m, 2H), 7.44 (d, J=7.6 Hz, 1H), 7.51 (d, J=15.6 Hz, 1H), 7.75 (d, J=0.8 Hz, 1H).

Example 237

Synthesis of 2-{(E)-2-[5-methoxy-6-(4-methyl-1H-imidazol-1-yl)pyridin-3-yl]vinyl}-4-phenyl-4,5,6,7-tetrahydro-[1,2,4]triazolo[1,5-a]pyrimidine

[Formula 149]

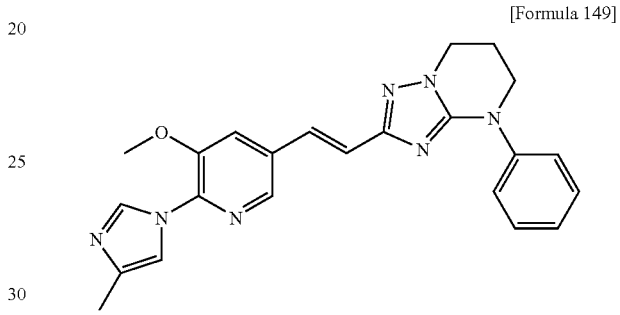

Synthesis of (E)-3-[5-methoxy-6-(4-methyl-1H-imidazol-1-yl)pyridin-3-yl]-N-(2-oxo-3-phenyl-tetrahydropyrimidin-1-yl)acrylamide 1-Amino-3-phenyl-tetrahydropyrimidin-2-one synthesized by the same method as in Example 232 at room temperature (111 mg; ESI-MS; m/z 192 [M$^+$+H]), IPEA (0.41 mL), EDC (166 mg) and HOBT (117 mg) were added to a solution of (E)-3-[5-methoxy-6-(4-methyl-1H-imidazol-1-yl)pyridin-3-yl]acrylic acid (300 mg) in DMF (6 mL). The reaction solution was stirred at room temperature for 24 hours. The reaction solution was diluted with ethyl acetate and washed with a saturated sodium bicarbonate solution and a saturated sodium chloride solution. The resulting organic layer was dried over magnesium sulfate and then concentrated under reduced pressure. The residue was purified by silica gel column chromatography (carrier: Chromatorex NH; elution solvent: heptane-ethyl acetate system, then ethyl acetate-methanol system) to obtain 250 mg of the title compound. The property value of the compound is as follows.

ESI-MS; m/z 433 [M$^+$+H].

Synthesis of 2-{(E)-2-[5-methoxy-6-(4-methyl-1H-imidazol-1-yl)pyridin-3-yl]vinyl}-4-phenyl-4,5,6,7-tetrahydro-[1,2,4]triazolo[1,5-a]pyrimidine Phosphorus oxychloride (4 mL) was added to (E)-3-[5-methoxy-6-(4-methyl-1H-imidazol-1-yl)pyridin-3-yl]-N-(2-oxo-3-phenyl-tetrahydropyrimidin-1-yl)acrylamide (250 mg), and the reaction solution was heated under reflux for one hour. The reaction solution was left to cool to room temperature and then concentrated under reduced pressure. Acetic acid (3 mL) and ammonium acetate (2.3 g) were added to the resulting residue, and the reaction solution was stirred at 150° C. for two hours. The reaction solution was left to cool to room temperature and then concentrated under reduced pressure. A saturated sodium bicarbonate solution was added to the resulting residue, followed by extraction with chloroform. The resulting extract was dried over magnesium sulfate and then concentrated under reduced pressure. The residue was purified by silica gel column chromatography (carrier: Chromatorex NH; elution solvent: heptane-ethyl acetate system) and further solidified with a mixed solvent of ethyl acetate, diethyl ether and heptane to obtain 123 mg of the title compound. The property values of the compound are as follows.

ESI-MS; m/z 414 [M$^+$+H]. $^1$H-NMR (CDCl$_3$) δ (ppm): 2.30 (d, J=1.2 Hz, 3H), 2.35-2.42 (m, 2H), 3.88 (t, J=6.0 Hz, 2H), 3.97 (s, 3H), 4.24 (t, J=6.0 Hz, 2H), 6.99 (d, J=16.0 Hz, 1H), 7.14-7.19 (m, 1H), 7.39-7.58 (m, 7H), 8.15 (d, J=1.6 Hz, 1H), 8.34 (d, J=1.2 Hz, 1H).

Example 238

Synthesis of 4-(4-chlorophenyl)-2-{(E)-2-[5-methoxy-6-(4-methyl-1H-imidazol-1-yl)pyridin-3-yl]vinyl}-4,5,6,7-tetrahydro-[1,2,4]triazolo[1,5-a]pyrimidine

[Formula 150]

199 mg of the racemic title compound was obtained from (E)-N-[3-(4-chlorophenyl)-2-oxo-tetrahydropyrimidin-1-yl]-3-[5-methoxy-6-(4-methyl-1H-imidazol-1-yl)pyridin-3-yl]acrylamide (270 mg) by the same method as in Example 237. The property values of the compound are as follows.

ESI-MS; m/z 448 [M$^+$+H]. $^1$H-NMR (CDCl$_3$) δ (ppm): 2.30 (d, J=1.2 Hz, 3H), 2.35-2.42 (m, 2H), 3.85 (brt, J=5.6 Hz, 2H), 3.98 (s, 3H), 4.23 (t, J=6.4 Hz, 2H), 6.98 (d, J=16.4 Hz, 1H), 7.35-7.39 (m, 2H), 7.44 (d, J=16.4 Hz, 1H), 7.47 (d, J=2.0 Hz, 1H), 7.49-7.54 (m, 3H), 8.16 (d, J=2.0 Hz, 1H), 8.34 (d, J=1.2 Hz, 1H).

Example 239

Synthesis of 2-{(E)-2-[5-methoxy-6-(4-methyl-1H-imidazol-1-yl)pyridin-3-yl]vinyl}-4-(3,4,5-trifluorophenyl)-4,5,6,7-tetrahydro-[1,2,4]triazolo[1,5-a]pyrimidine

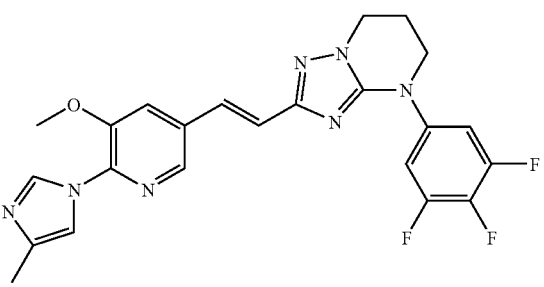

[Formula 151]

180 mg of the title compound was obtained from (E)-3-[5-methoxy-6-(4-methyl-1H-imidazol-1-yl)pyridin-3-yl]-N-[2-oxo-3-(3,4,5-trifluorophenyl)-tetrahydropyrimidin-1-yl]acrylamide (280 mg) by the same method as in Example 237. The property values of the compound are as follows.

ESI-MS; m/z 468 [M$^+$+H]. $^1$H-NMR (CDCl$_3$) δ (ppm): 2.30 (d, J=1.2 Hz, 3H), 2.37-2.43 (m, 2H), 3.82 (brt, J=5.6 Hz, 2H), 4.00 (s, 3H), 4.24 (t, J=6.0 Hz, 2H), 6.99 (d, J=16.4 Hz, 1H), 7.31-7.37 (m, 2H), 7.44-7.55 (m, 3H), 8.20 (d, J=1.6 Hz, 1H), 8.35 (d, J=1.2 Hz, 1H).

Examples 240 and 241

Synthesis of (R)-4-(4-fluorophenyl)-2-{(E)-2-[5-methoxy-6-(4-methyl-1H-imidazol-1-yl)pyridin-3-yl]vinyl}-5-methyl-4,5,6,7-tetrahydro-[1,2,4]triazolo[1,5-a]pyrimidine and (S)-4-(4-fluorophenyl)-2-{(E)-2-[5-methoxy-6-(4-methyl-1H-imidazol-1-yl)pyridin-3-yl]vinyl}-5-methyl-4,5,6,7-tetrahydro-[1,2,4]triazolo[1,5-a]pyrimidine

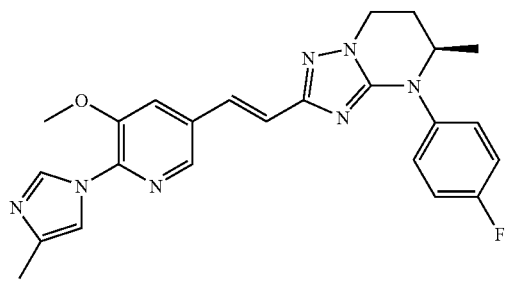

[Formula 152]

-continued

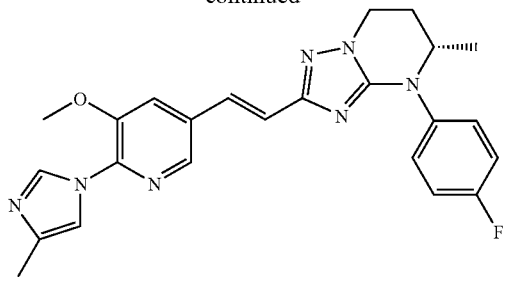

245 mg of the racemic title compound was obtained from (E)-N-[3-(4-fluorophenyl)-4-methyl-2-oxo-tetrahydropyrimidin-1-yl]-3-[5-methoxy-6-(4-methyl-1H-imidazol-1-yl)pyridin-3-yl]acrylamide (445 mg) by the same method as in Example 237. The racemic title compound (180 mg) was separated by CHIRALPAK™ AD-H manufactured by Daicel Chemical Industries, Ltd. (2 cm×25 cm; mobile phase: hexane:ethanol=1:1) to obtain the title optically active compound with a retention time of 22 minutes (80 mg) and the title optically active compound with a retention time of 28 minutes (70 mg).

The property values of the title optically active compound with a retention time of 22 minutes are as follows (Example 240).

ESI-MS; m/z 446 [M$^+$+H]. $^1$H-NMR (CDCl$_3$) δ (ppm): 1.29 (d, J=6.8 Hz, 3H), 2.11-2.19 (m, 1H), 2.29 (d, J=1.2 Hz, 3H), 2.38-2.48 (m, 1H), 3.96 (s, 3H), 4.08-4.17 (m, 1H), 4.20-4.31 (m, 2H), 6.96 (d, J=16.4 Hz, 1H), 7.08-7.15 (m, 2H), 7.35-7.46 (m, 4H), 7.51 (brs, 1H), 8.13 (d, J=2.0 Hz, 1H), 8.33 (d, J=1.2 Hz, 1H).

The property values of the title optically active compound with a retention time of 28 minutes are as follows (Example 241).

ESI-MS; m/z 446 [M$^+$+H]. $^1$H-NMR (CDCl$_3$) δ (ppm): 1.29 (d, J=6.8 Hz, 3H), 2.11-2.19 (m, 1H), 2.29 (d, J=1.2 Hz, 3H), 2.38-2.48 (m, 1H), 3.96 (s, 3H), 4.08-4.17 (m, 1H), 4.20-4.31 (m, 2H), 6.96 (d, J=16.4 Hz, 1H), 7.08-7.15 (m, 2H), 7.35-7.46 (m, 4H), 7.51 (brs, 1H), 8.13 (d, J=2.0 Hz, 1H), 8.33 (d, J=1.2 Hz, 1H).

The following compounds were obtained using (E)-3-[3-methoxy-4-(4-methyl-1H-imidazol-1-yl)phenyl]acrylic acid by the same method as in Example 232 (Table 7).

TABLE 7

| Example | E$_3$ | DATA: MS m/z | Note |
|---|---|---|---|
| 242 | | M$^+$ + H: 413 (ESI) | |
| 243 | | M$^+$ + H: 447 (ESI) | |
| 244 | | M$^+$ + H: 467 (ESI) | |

TABLE 7-continued

| Example | E₃ | DATA: MS m/z | Note |
|---|---|---|---|
| 245 | | M⁺ + H: 427 (ESI) | Optically active compound (separation conditions IA, hexane:ethanol = 1:1, retention time 18 min) |
| 246 | | M⁺ + H: 427 (ESI) | Optically active compound (separation conditions IA, hexane:ethanol = 1:1, retention time 23 min) |
| 247 | | M⁺ + H: 463 (ESI) | Optically active compound (separation conditions IB, hexane:ethanol = 1:1, retention time 30 min) |
| 248 | | M⁺ + H: 463 (ESI) | Optically active compound (separation conditions IB, hexane:ethanol = 1:1, retention time 36 min) |
| 249 | | M⁺ + H: 445 (ESI) | Optically active compound (separation conditions IA, IPA, retention time 20 min) |
| 250 | | M⁺ + H: 445 (ESI) | Optically active compound (separation conditions IA, IPA, retention time 25 min) |

TABLE 7-continued

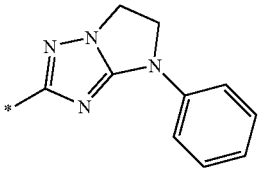

| Example | E₃ | DATA: MS m/z | Note |
|---|---|---|---|
| 251 | 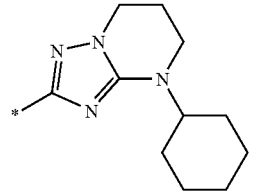 | M⁺ + H: 399 (ESI) | |
| 252 | 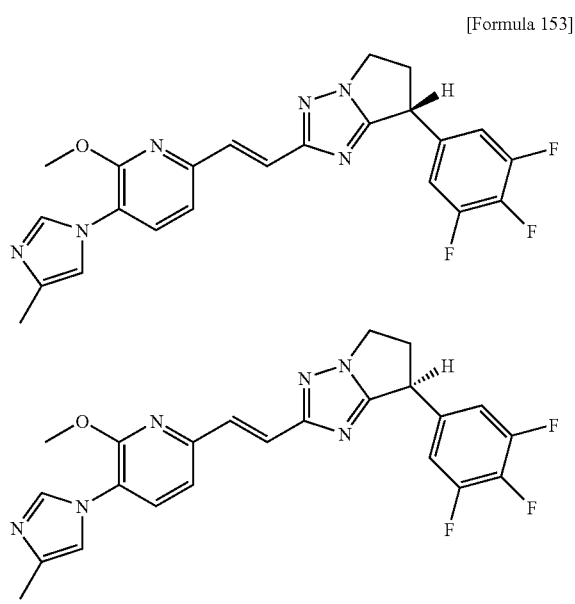 | M⁺ + H: 419 (ESI) | |

Example 253 and 254

Synthesis of (+) and (−)-2-{(E)-2-[6-methoxy-5-(4-methyl-1H-imidazol-1-yl)pyridin-2-yl]vinyl}-7-(3,4,5-trifluorophenyl)-6,7-dihydro-5H-pyrrolo[1,2-b][1,2,4]triazole

[Formula 153]

Synthesis of 4-chloro-2-(3,4,5-trifluorophenyl)butyric acid

A 2.66 M solution of butyl lithium in hexane (20 mL) was added to a solution of 3,4,5-trifluorophenylacetic acid (5.00 g) in THF (150 mL) in a nitrogen atmosphere at −78° C., and the reaction solution was stirred at −78° C. for 20 minutes. The reaction solution was further stirred at 0° C. for one hour. Then, 1-bromo-2-chloroethane (2.2 mL) was added at 0° C., and the reaction solution was stirred at room temperature for 14 hours. Ethyl acetate and 1 N hydrochloric acid were added to the reaction solution, and the organic layer was separated. The resulting organic layer was washed with a saturated sodium chloride solution. The resulting organic layer was dried over magnesium sulfate and then concentrated under reduced pressure. The residue was purified by silica gel column chromatography (elution solvent: heptane-ethyl acetate system) to obtain 4.54 g of the title compound. The property values of the compound are as follows.

¹H-NMR (CDCl₃) δ (ppm): 2.13-2.22 (m, 1H), 2.45-2.54 (m, 1H), 3.36 (ddd, J=11.6, 8.4, 4.8 Hz, 1H), 3.58 (ddd, J=11.6, 6.4, 5.2 Hz, 1H), 3.89 (dd, J=7.6, 7.6 Hz, 1H), 6.94-7.02 (m, 2H).

Synthesis of tert-butyl N'-[4-chloro-2-(3,4,5-trifluorophenyl)butyryl]hydrazinecarboxylate oxalyl chloride (0.63 mL) and DMF (1 drop) were added to a solution of 4-chloro-2-(3,4,5-trifluorophenyl)butyric acid (1.17 g) in methylene chloride (30 mL) at 0° C., and the reaction solution was stirred at room temperature for one hour. The reaction solution was concentrated under reduced pressure to obtain 4-chloro-2-(3,4,5-trifluorophenyl)butyric acid chloride. A solution of 4-chloro-2-(3,4,5-trifluorophenyl)butyric acid chloride in THF (5 mL) was added to a solution of tert-butyl carboxylate (600 mg) and triethylamine (3.1 mL) in THF (20 mL) at 0° C., and the reaction solution was stirred at room temperature for one hour. The reaction solution was added to a saturated sodium bicarbonate solution, followed by extraction with ethyl acetate. The resulting extract was dried over magnesium sulfate and then concentrated under reduced pressure. The residue was purified by silica gel column chromatography (elution solvent: heptane-ethyl acetate system) to obtain 1.35 g of the title compound. The property value of the compound is as follows.

ESI-MS; m/z 389 [M++Na]

Synthesis of (E)-3-[6-methoxy-5-(4-methyl-1H-imidazol-1-yl)pyridin-2-yl]acrylamide Isopropyl chloroformate (3.99 mL) was added dropwise to a solution of (E)-3-[6-methoxy-5-(4-methyl-1H-imidazol-1-yl)pyridin-2-yl]acrylic acid (5.2 g) and N,N-diisopropylethylamine (7.44 mL) in DMF (52 mL) under ice-cooling, and the reaction solution was stirred for 20 minutes. Aqueous ammonic (5.2 mL) was added to the reaction solution, and the reaction solution was stirred at room temperature for 30 minutes. Similarly, ethyl chloroformate (3.76 mL) was added dropwise to a solution of (E)-3-[6-methoxy-5-(4-methyl-1H-imidazol-1-yl)pyridin-2-yl]acrylic acid (4.8 g) and N,N-diisopropylethylamine (6.87 mL) in DMF (48 mL) under ice-cooling, and the reaction solution was stirred for 10 minutes. Then, aqueous ammonia (5.2 mL) was added to the reaction solution, and the reaction solution was stirred at room temperature for 30 minutes. The reaction solutions were mixed and diluted with water and chloroform, and then the organic layer was separated. The aqueous layer was extracted with chloroform five times. The organic layers were combined, dried over anhydrous magnesium sulfate and then concentrated under reduced pressure. The residue was purified by silica gel column chromatography (chloroform-2-propanol system) to obtain 3.54 g of the title compound. The property value of the compound is as follows.

ESI-MS; m/z 259 [M++H].

Synthesis of (E)-3-[6-methoxy-5-(4-methyl-1H-imidazol-1-yl)pyridin-2-yl]acrylonitrile A mixture of (E)-3-[6-methoxy-5-(4-methyl-1H-imidazol-1-yl)pyridin-2-yl]acrylamide (3.54 g) and phosphorus oxychloride (12 ml) was stirred at 90° C. for one hour. The reaction solution was concentrated under reduced pressure and then diluted with ice water, chloroform and aqueous ammonia, and the organic layer was separated. The organic layer was dried over anhydrous magnesium sulfate and then concentrated under reduced pressure. The residue was diluted with ether and the precipitated crystals were collected by filtration. The crystals were washed with ether and then air-dried to obtain 2.27 g of the title compound. The property value of the compound is as follows.

ESI-MS; m/z 241 [M++H].

(E)-3-[6-Methoxy-5-(4-methyl-1H-imidazol-1-yl)pyridin-2-yl]acrylonitrile is also synthesized by the following synthesis method.

Synthesis of N-(6-bromo-2-methoxypyridin-3-yl)formaldehyde

Acetic anhydride (203 ml) was added dropwise to formic acid (204 ml) under ice-cooling, and the reaction solution was stirred at the same temperature for 25 minutes. 6-Bromo-2-methoxypyridine-3-amine powder (CAS No. 89466-18-2, 146 g) was put into the reaction mixture over 10 minutes, and then the reaction solution was stirred at the same temperature for 30 minutes. The water bath was removed. tert-Butyl methyl ether (300 ml) and n-heptane (500 ml) were sequentially added dropwise to the reaction solution, and then the reaction solution was stirred for 30 minutes. The precipitated powder was collected by filtration. The resulting powder was crushed with a mortar, washed with tert-butyl methyl ether and then dried under reduced pressure to obtain 137.4 g of the title compound.

Then, the combined filtrate and washing solution were concentrated under reduced pressure. The residue was triturated with tert-butyl methyl ether and dried under reduced pressure to obtain 21.9 g of the title compound.

The property values of the compound are as follows.

$^1$H-NMR (CDCl$_3$) δ (ppm): 4.03 (s, 3H), 7.08 (d, J=8.0 Hz, 1H), 7.61 (brs, 1H), 8.47-8.51 (m, 2H).

Synthesis of N-(6-bromo-2-methoxypyridin-3-yl)-N-(2-oxopropyl)formamide

Chloroacetone (82 ml) was added dropwise to a suspension of N-(6-bromo-2-methoxypyridin-3-yl)formamide (159.3 g), cesium carbonate (359 g) and potassium iodide (11.4 g) in N,N-dimethylformamide (800 ml) over seven minutes. Then, the reaction solution was stirred at room temperature for one hour and 20 minutes.

The reaction solution was concentrated under reduced pressure. Ethyl acetate and water were added to the resulting residue, and the organic layer was separated. The resulting organic layer was washed with brine, dried over anhydrous magnesium sulfate and then concentrated under reduced pressure to obtain 215.2 g of the title compound. The property values of the compound are as follows.

$^1$H-NMR (CDCl$_3$) δ (ppm): 2.17 (s, 3H), 4.00 (s, 3H), 4.47 (s, 2H), 7.13 (d, J=7.6 Hz, 1H), 7.48 (d, J=7.6 Hz, 1H), 8.22 (s, 1H).

Synthesis of 6-bromo-2-methoxy-3-(4-methyl-1H-imidazol-1-yl)pyridine

A suspension of ammonium acetate (267 g) and N-(6-bromo-2-methoxypyridin-3-yl)-N-(2-oxopropyl)formamide (199 g) in glacial acetic acid (400 ml) was stirred at 130° C. for one hour and 10 minutes. The reaction solution was returned to room temperature. Ethyl acetate and ice water were added to the reaction solution, and the reaction solution was ice-cooled. Then, concentrated aqueous ammonia (500 ml) was added dropwise and then the organic layer was separated. The resulting organic layer was sequentially washed with water and brine and dried over anhydrous magnesium sulfate. Then, the organic layer was purified by short silica gel column chromatography (carrier: Wakogel C-200; elution solvent: ethyl acetate). The eluted fraction was concentrated. The resulting residue was triturated with ethyl acetate and tert-butyl methyl ether and dried under reduced pressure to obtain 107.7 g of the title compound.

Then, the trituration mother liquor was concentrated. The resulting residue was purified by silica gel column chromatography (carrier: Wakogel C-200; elution solvent: toluene-ethyl acetate system). The target fraction was concentrated. The resulting residue was triturated with tert-butyl methyl ether and dried under reduced pressure to obtain 12.9 g of the title compound.

The property values of the compound are as follows.

$^1$H-NMR (CDCl$_3$) δ (ppm): 2.29 (d, J=0.8 Hz, 3H), 4.03 (s, 3H), 6.92 (dd, J=1.2, 0.8 Hz, 1H), 7.16 (d, J=8.0 Hz, 1H), 7.40 (d, J=8.0 Hz, 1H), 7.73 (d, J=1.2 Hz, 1H).

ESI-MS; m/z 268 [M++H].

Synthesis of (E)-3-[6-methoxy-5-(4-methyl-1H-imidazol-1-yl)pyridin-2-yl]acrylamide Triethylamine (52 ml) was added to a suspension of 6-bromo-2-methoxy-3-(4-methyl-1H-imidazol-1-yl)pyridine (49.8 g), tris(dibenzylideneacetone)dipalladium (0) (5.11 g), tri-o-tolylphosphine (3.41 g) and acrylamide (14.5 g) in N,N-dimethyl formamide (260 ml). The reaction solution was stirred at 100° C. for 50 minutes. The reaction solution was returned to room temperature and then filtered through celite. The filter cake was sequentially washed with N,N-dimethylformamide, methanol, a 50% N,N-dimethylformamide solution and N,N-dimethylformamide. The resulting filtrate was filtered through celite again, and the filtrate was concentrated under reduced pressure. Toluene was added to the residue, and the reaction solution was concentrated again. Toluene and a saturated sodium bicarbonate solution were added to the resulting residue, and the insoluble matter was collected by filtration. The resulting powder was dried under reduced pressure to obtain 42.96 g of the title compound. The property values of the compound are as follows.

$^1$H-NMR (CDCl$_3$) δ (ppm): 2.30 (d, J=0.8 Hz, 3H), 4.07 (s, 3H), 5.57 (brs, 1H), 5.68 (brs, 1H), 6.98 (brs, 1H), 7.00 (d, J=15.2 Hz, 1H), 7.06 (d, J=7.6 Hz, 1H), 7.54 (d, J=7.6 Hz, 1H), 7.56 (d, J=15.2 Hz, 1H), 7.82 (d, J=1.2 Hz, 1H).

ESI-MS; m/z 259 [M$^+$+H].

Synthesis of (E)-3-[6-methoxy-5-(4-methyl-1H-imidazol-1-yl)pyridin-2-yl]acrylonitrile Methyl dichlorophosphate (33 ml) was added dropwise to a suspension of (E)-3-[6-methoxy-5-(4-methyl-1H-imidazol-1-yl)pyridin-2-yl]acrylamide (42.96 g) and 1,8-diazabicyclo[5,4,0]-7-undecene (112 ml) in methylene chloride (400 ml) under ice-cooling over 20 minutes. The reaction solution was stirred at the same temperature for 10 minutes and at room temperature for further 35 minutes. Then, a saturated sodium bicarbonate solution (200 ml) was added to the reaction solution, and the reaction solution was stirred at room temperature for 10 minutes. Water was added to the reaction solution. Then, the reaction solution was filtered and the organic layer in the filtrate was separated. The aqueous layer was reextracted with methylene chloride (twice). The combined organic layers were dried over anhydrous magnesium sulfate and purified by short silica gel column chromatography (carrier: Chromatorex NH; elution solvent: methylene chloride). The eluted fraction was concentrated. The resulting residue was triturated with ethyl acetate and tert-butyl methyl ether and dried under reduced pressure overnight to obtain 34.28 g of the title compound.

Then, the trituration mother liquor was concentrated. The resulting residue was triturated with acetone and dried under reduced pressure to obtain 0.56 g of the title compound.

The property values of the compound are as follows.

$^1$H-NMR (CDCl$_3$) δ (ppm): 2.30 (s, 3H), 4.07 (s, 3H), 6.54 (d, J=16.0 Hz, 1H), 7.00 (brs, 1H), 7.02 (d, J=7.6 Hz, 1H), 7.32 (d, J=16.0 Hz, 1H), 7.57 (d, J=7.6 Hz, 1H), 7.84 (d, J=1.2 Hz, 1H).

ESI-MS; m/z 241 [M$^+$+H].

Synthesis of ethyl (E)-3-[6-methoxy-5-(4-methyl-1H-imidazol-1-yl)pyridin-2-yl]acrylimidate dihydrochloride A suspension of (E)-3-[6-methoxy-5-(4-methyl-1H-imidazol-1-yl)pyridin-2-yl]acrylonitrile (2.27 g) in ethanol (45 mL) was bubbled with hydrogen chloride gas under ice-cooling for 20 minutes, and the reaction solution was stirred at room temperature for 4.5 hours. The reaction solution was concentrated under reduced pressure. Then, ethyl acetate was added to the residue, and the precipitated powder was collected by filtration. The resulting powder was washed with ethyl acetate containing 50% of ethanol and then dried under reduced pressure to obtain 1.83 g of the title compound. The property values of the compound are as follows.

ESI-MS; m/z 287 [M$^+$+H-2HCl].

$^1$H-NMR (DMSO-D$_6$) δ (ppm): 1.47 (t, J=6.8 Hz, 3H), 2.35 (s, 3H), 4.06 (s, 3H), 4.53 (q, J=6.8 Hz, 2H), 7.45 (d, J=15.6 Hz, 1H), 7.64 (d, J=8.4 Hz, 1H), 7.80 (brs, 1H), 7.92 (d, J=15.6 Hz, 1H), 8.18 (d, J=8.4 Hz, 1H), 9.33 (brs, 1H).

Synthesis of (+) and (−)-2-{(E)-2-[6-methoxy-5-(4-methyl-1H-imidazol-1-yl)pyridin-2-yl]vinyl}-7-(3,4,5-trifluorophenyl)-6,7-dihydro-5H-pyrrolo[1,2-b][1,2,4]triazole A solution of 4 N hydrogen chloride in ethyl acetate (120 mL) was added to tert-butyl N'-[4-chloro-2-(3,4,5-trifluorophenyl)butyryl]hydrazinecarboxylate (6.6 g). The reaction solution was stirred at room temperature for one hour and then concentrated under reduced pressure to obtain 4-chloro-2-(3,4,5-trifluorophenyl)butyric acid hydrazide hydrochloride (6.03 g). A solution of 4-chloro-2-(3,4,5-trifluorophenyl)butyric acid hydrazide hydrochloride (565 mg) and triethylamine (1.0 mL) in ethanol (10 mL) was added to a solution of ethyl (E)-3-[6-methoxy-5-(4-methyl-1H-imidazol-1-yl)pyridin-2-yl]acrylimidate dihydrochloride (500 mg) and triethylamine (0.95 mL) in ethanol (10 mL) at room temperature. The reaction solution was stirred at 80° C. for 25 hours. The reaction solution was left to cool to room temperature and then concentrated under reduced pressure. A saturated sodium bicarbonate solution was added to the resulting residue, followed by extraction with chloroform. The resulting extract was dried over magnesium sulfate and then concentrated under reduced pressure. The residue was purified by silica gel column chromatography (carrier: Chromatorex NH; elution solvent: heptane-ethyl acetate system) to obtain 150 mg of the racemic title compound. The racemic title compound (150 mg) was separated by CHIRALPAK™ IB manufactured by Daicel Chemical Industries, Ltd. (2 cm×25 cm; mobile phase: hexane:ethanol=1:1) to obtain the title optically active compound with a retention time of 13 minutes and positive optical rotation (54 mg) and the title optically active compound with a retention time of 34 minutes and negative optical rotation (51 mg).

The property values of the title optically active compound with a retention time of 34 minutes are as follows.

ESI-MS; m/z 453 [M$^+$+H]. $^1$H-NMR (CDCl$_3$) δ (ppm): 2.30 (d, J=1.2 Hz, 3H), 2.62-2.72 (m, 1H), 3.22-3.32 (m, 1H), 4.08 (s, 3H), 4.19-4.27 (m, 1H), 4.31-4.45 (m, 2H), 6.93-7.02 (m, 4H), 7.50 (d, J=8.0 Hz, 1H), 7.53 (d, J=15.6 Hz, 1H), 7.66 (d, J=15.6 Hz, 1H), 7.79 (d, J=1.2 Hz, 1H).

The property values of the title optically active compound with a retention time of 13 minutes corresponded to the property values of the title optically active compound with a retention time of 34 minutes.

Examples 255 and 256

Synthesis of (+) and (−)-2-{(E)-2-[5-methoxy-6-(4-methyl-1H-imidazol-1-yl)pyridin-3-yl]vinyl}-7-(3,4,5-trifluorophenyl)-6,7-dihydro-5H-pyrrolo[1,2-b][1,2,4]triazole

[Formula 154]

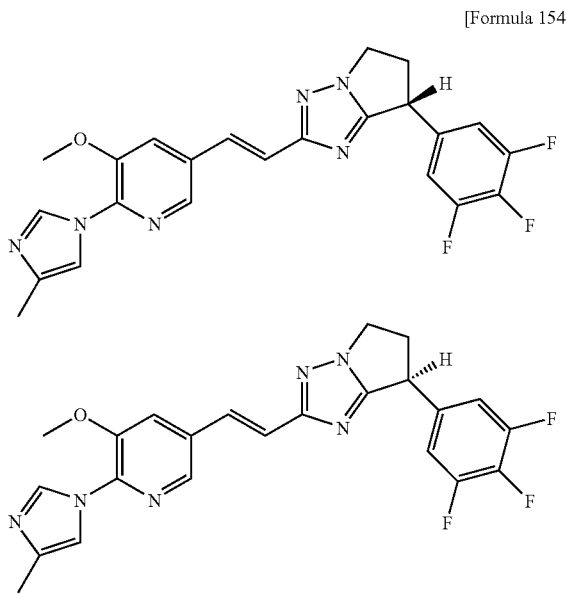

Synthesis of N-(5-bromo-3-methoxypyridin-2-yl)formamide

Iron (67.3 g) and ammonium chloride (129 g) were added to a solution of 5-bromo-3-methoxy-2-nitropyridine (56.0 g, CAS: 152684-26-9) in ethanol (500 mL) and water (200 mL). The reaction solution was stirred at 80 to 90° C. for one hour and then left to cool to room temperature. The reaction solution was filtered through celite and washed with ethanol. Then, the filtrate was concentrated under reduced pressure. The residue was diluted with ethyl acetate and water, and the organic layer was separated. The resulting organic layer was washed with brine, dried over anhydrous magnesium sulfate and then concentrated under reduced pressure. The residue was diluted with THF (84 mL). The THF solution was added dropwise to a mixed solution of formic acid (78.1 mL) and acetic anhydride (78.3 mL) at room temperature. Then, the reaction solution was stirred for one hour. Ice water (500 mL) was added to the reaction solution, and the precipitated crystals were collected by filtration. The crystals were washed with water and then air-dried. The crystals were recrystallized from toluene to obtain 34.1 g of the title compound. The property value of the compound is as follows.
ESI-MS; m/z 231 [M$^+$+H].

Synthesis of N-(5-bromo-3-methoxypyridin-2-yl)-N-(2-oxopropyl)formamide

Cesium carbonate (96 g), potassium iodide (2.45 g) and chloroacetone (23.5 mL) were added to a solution of N-(5-chloro-3-methoxypyridin-2-yl)formamide (34.1 g) in DMF (200 mL), and the reaction solution was stirred at 80° C. for 45 minutes. Ice water and ethyl acetate were added to the reaction solution, and the organic layer was separated. The organic layer was washed with brine and then dried over anhydrous magnesium sulfate and concentrated under reduced pressure to obtain 52.8 g of the crude title compound. The property value of the compound is as follows.
ESI-MS; m/z 287 [M$^+$+H].

Synthesis of 5-bromo-3-methoxy-2-(4-methyl-1H-imidazol-1-yl)pyridine

A mixture of the crude N-(5-bromo-3-methoxypyridin-2-yl)-N-(2-oxopropyl)formamide obtained above (26.4 g), acetic acid (52.8 mL) and ammonium acetate (35.5 g) was stirred at 130° C. for one hour. The reaction solution was left to cool to room temperature and concentrated under reduced pressure. The residue diluted with ice water, ethyl acetate and aqueous ammonia, and the organic layer was separated. The organic layer was washed with brine and then dried over anhydrous magnesium sulfate and concentrated under reduced pressure. The residue was purified by silica gel column chromatography (elution solvent: heptane-ethyl acetate system) to obtain 5.69 g of the title compound. The property values of the compound are as follows.
ESI-MS; m/z 268 [M$^+$+H].
$^1$H-NMR (CDCl$_3$) δ (ppm): 2.29 (s, 3H), 3.97 (s, 3H), 7.48 (brs, 1H), 7.49 (d, J=2.0 Hz, 1H), 8.12 (d, J=2.0 Hz, 1H), 8.30 (brs, 1H).

Synthesis of (E)-3-[5-methoxy-6-(4-methyl-1H-imidazol-1-yl)pyridin-3-yl]acrylonitrile A mixture of 5-bromo-3-methoxy-2-(4-methyl-1H-imidazol-1-yl)pyridine (3.8 g), tris(dibenzylideneacetone)dipalladium (650 mg), tri-o-tolylphosphine (433 mg), N,N-diisopropylethylamine (4.86 mL), DMF (14.1 mL) and acrylonitrile (2.82 mL) was stirred in a nitrogen atmosphere at 110° C. for five hours. The reaction solution was left to cool to room temperature and then concentrated under reduced pressure. The residue was diluted with ethyl acetate and then filtered through celite, and the filtrate was washed with water. The organic layer was concentrated under reduced pressure, and the precipitated crystals were hot dissolved in ethyl acetate. After leaving to cool to room temperature, the precipitated crystals were collected by filtration and air-dried to obtain 1.79 g of the title compound. The filtrate was concentrated under reduced pressure. Then, the residue was purified by silica gel column chromatography (heptane-ethyl acetate system) and then recrystallized from ethyl acetate to obtain 0.312 g of the title compound. The property value of the compound is as follows.
ESI-MS; m/z 241 [M$^+$+H].

Synthesis of ethyl (E)-3-[5-methoxy-6-(4-methyl-1H-imidazol-1-yl)pyridin-3-yl]acrylimidate dihydrochloride A suspension of (E)-3-[5-methoxy-6-(4-methyl-1H-imidazol-1-yl)pyridin-3-yl]acrylonitrile (2.1 g) in ethanol (40 mL) was bubbled with hydrogen chloride gas under ice-cooling for one hour, and the reaction solution was stirred at room temperature overnight. The reaction solution was concentrated under reduced pressure. Then, ethyl acetate was added to the residue, and the precipitated powder was collected by filtration. The resulting powder was washed with ethyl acetate containing 50% of ethanol and then dried under reduced pressure to obtain 1.82 g of the title compound. The property values of the compound are as follows.
ESI-MS; m/z 287 [M$^+$+H−2HCl].

$^1$H-NMR (DMSO-D$_6$) δ (ppm): 1.47 (t, J=6.8 Hz, 3H), 2.36 (s, 3H), 4.06 (s, 3H), 4.55 (q, J=6.8 Hz, 2H), 7.26 (d, J=16.4 Hz, 1H), 8.04 (brs, 1H), 8.05 (d, J=16.4 Hz, 1H), 8.21 (d, J=1.6 Hz, 1H), 8.50 (d, J=1.6 Hz, 1H), 9.61 (brs, 1H).

Synthesis of (+) and (−)-2-{(E)-2-[5-methoxy-6-(4-methyl-1H-imidazol-1-yl)pyridin-3-yl]vinyl}-7-(3,4,5-trifluorophenyl)-6,7-dihydro-5H-pyrrolo[1,2-b][1,2,4]triazole A solution of 4-chloro-2-(3,4,5-trifluorophenyl)butyric acid hydrazide hydrochloride synthesized in Examples 253 and 254 (565 mg) and triethylamine (1.0 mL) in ethanol (10 mL) was added to a solution of ethyl (E)-3-[5-methoxy-6-(4-methyl-1H-imidazol-1-yl)pyridin-3-yl]acrylimidate dihydrochloride (500 mg) and triethylamine (0.95 mL) in ethanol (10 mL) at room temperature. The reaction solution was stirred at 80° C. for 25 hours. The reaction solution was left to cool to room temperature and then concentrated under reduced pressure. A saturated sodium bicarbonate solution was added to the resulting residue, followed by extraction with chloroform. The resulting extract was dried over magnesium sulfate and then concentrated under reduced pressure. The residue was purified by silica gel column chromatography (carrier: Chromatorex NH; elution solvent: heptane-ethyl acetate system) to obtain 154 mg of the racemic title compound. The racemic title compound (154 mg) was purified by CHIRALPAK™ IA manufactured by Daicel Chemical Industries, Ltd. (2 cm×25 cm; mobile phase: hexane:ethanol=1:1) and then separated by CHIRALPAK™ IB manufactured by Daicel Chemical Industries, Ltd. (2 cm×25 cm; mobile phase: hexane:ethanol=7:3) to obtain the title optically active compound with a retention time of 17 minutes and positive optical rotation (40 mg) and the title optically active compound with a retention time of 23 minutes and negative optical rotation (37 mg).

The property values of the title optically active compound with a retention time of 23 minutes are as follows.

ESI-MS; m/z 453 [M$^+$+H]. $^1$H-NMR (CDCl$_3$) δ (ppm): 2.30 (d, J=1.2 Hz, 3H), 2.62-2.72 (m, 1H), 3.22-3.32 (m, 1H), 4.00 (s, 3H), 4.19-4.26 (m, 1H), 4.31-4.45 (m, 2H), 6.93-7.02 (m, 2H), 7.11 (d, J=16.4 Hz, 1H), 7.49 (d, J=2.0 Hz, 1H), 7.53-7.55 (m, 1H), 7.58 (d, J=16.4 Hz, 1H), 8.18 (d, J=2.0 Hz, 1H), 8.36 (d, J=1.2 Hz, 1H).

The property values of the title optically active compound with a retention time of 17 minutes corresponded to the property values of the title optically active compound with a retention time of 23 minutes.

Examples 257 and 258

Synthesis of (+) and (−)-8-(4-fluorophenyl)-2-{(E)-2-[5-methoxy-6-(4-methyl-1H-imidazol-1-yl)pyridin-3-yl]vinyl}-hexahydro-[1,2,4]triazolo[5,1-c][1,4]oxazine

[Formula 155]

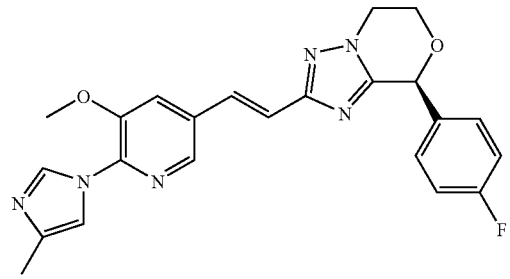

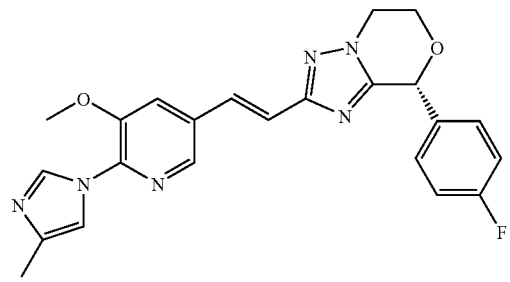

Synthesis of 1-[bis-(2-chloroethoxy)methyl]-4-fluorobenzene

A solution containing 4-fluorobenzaldehyde (5 g), 2-chloroethanol (13.5 mL) and p-toluenesulfonic acid (767 mg) in ethanol (100 mL) was heated under reflux for 15 hours while dehydrating with a Dean-Stalk trap for 15 hours. The reaction solution was concentrated. Ethyl acetate and saturated sodium bicarbonate water were added to the residue, and the organic layer was separated. The organic layer was washed with brine and dried over anhydrous magnesium sulfate. The solvent was evaporated under reduced pressure. The residue was purified by silica gel column chromatography (carrier: Chromatorex NH, elution solvent: heptane/ethyl acetate) to obtain the title compound (5.43 g). The property values of the compound are as follows.

$^1$H-NMR (CDCl$_3$) δ (ppm): 3.67 (t, J=5.6 Hz, 4H), 3.74-3.83 (m, 4H), 7.06 (dd, J=8.8, 8.8 Hz, 2H), 7.45 (dd, J=8.8, 5.6 Hz, 2H).

Synthesis of (2-chloroethoxy)-(4-fluorophenyl)acetonitrile

A solution containing 1-[bis-(2-chloroethoxy)methyl]-4-fluorobenzene (5.43 g), trimethylsilyl cyanide (4.06 mL) and tetracyanoethylene (520 mg) in acetonitrile (100 mL) was heated under reflux for four hours. The reaction solution was returned to room temperature and the solvent was evaporated under reduced pressure. Ethyl acetate and brine were added to the residue, and the organic layer was separated. The organic layer was dried over anhydrous magnesium sulfate. The solvent was evaporated under reduced pressure. The residue was purified by silica gel column chromatography (carrier: Chromatorex, elution solvent: heptane/ethyl acetate) to obtain the title compound (4.3 g). The property values of the compound are as follows.

$^1$H-NMR (CDCl$_3$) δ (ppm): 3.70 (t, J=5.2 Hz, 2H), 3.82-3.87 (m, 1H), 3.96-4.01 (m, 1H), 5.36 (s, 1H), 7.13 (dd, J=8.4, 8.4 Hz, 2H), 7.48-7.52 (m, 2H).

Synthesis of (2-chloroethoxy)-(4-fluorophenyl)acetic acid

A mixture of (2-chloroethoxy)-(4-fluorophenyl)acetonitrile (3 g) and 5 N hydrochloric acid was heated under reflux for 15 hours. After returning to room temperature, the reaction solution was made basic with 5 N sodium hydroxide and washed with ether. The aqueous layer was made acidic with 5 N hydrochloric acid. Ethyl acetate was added, and the organic layer was separated. The organic layer was dried over anhydrous magnesium sulfate, and the solvent was evaporated under reduced pressure to obtain the title compound (2.8 g). The property values of the compound are as follows.

$^1$H-NMR (CDCl$_3$) δ (ppm): 3.68 (t, J=6.0 Hz, 2H), 3.73-3.79 (m, 1H), 3.80-3.86 (m, 1H), 4.97 (s, 1H), 7.09 (dd, J=8.4, 8.4 Hz, 2H), 7.45 (dd, J=8.8, 5.2 Hz, 2H).

Synthesis of tert-butyl N'-[2-(2-chloroethoxy)-2-(4-fluorophenyl)acetyl]-hydrazinecarboxylate Bis(2-oxo-3-oxazolidinyl)phosphinic acid chloride (4.38 g) was added to a solution of (2-chloroethoxy)-(4-fluorophenyl)acetic acid (2 g), tert-butyl carbazate (2.27 g) and triethylamine (3.58 mL) in tetrahydrofuran (20 mL), and the reaction solution was stirred at room temperature for 16 hours. Saturated aqueous ammonium chloride and ethyl acetate were added to the reaction solution, and the organic layer was separated. The organic layer was washed with brine and dried over anhydrous magnesium sulfate. The solvent was evaporated under reduced pressure. The residue was purified by silica gel column chromatography (carrier: Chromatorex, elution solvent: heptane/ethyl acetate) to obtain the title compound (2.8 g). The property values of the compound are as follows.

$^1$H-NMR (CDCl$_3$) δ (ppm): 1.46 (s, 9H), 3.68 (t, J=6.0 Hz, 2H), 3.74-3.81 (m, 2H), 4.90 (s, 1H), 7.03 (brs, 1H), 7.03-7.09 (m, 2H), 7.41-7.45 (m, 2H), 8.40 (brs, 1H).

Synthesis of (+) and (−)-8-(4-fluorophenyl)-2-{(E)-2-[5-methoxy-6-(4-methyl-1H-imidazol-1-yl)pyridin-3-yl]vinyl}-5,6-dihydro-8H-[1,2,4]triazolo[5,1-c][1,4]oxazine A solution of 4 N hydrochloric acid in ethyl acetate (5 mL) was added to a solution of tert-butyl N'-[2-(2-chloroethoxy)-2-(4-fluorophenyl)acetyl]-hydrazinecarboxylate (363 mg) in ethyl acetate (5 mL). The reaction solution was stirred at room temperature for 1.5 hours, and then the solvent was evaporated under reduced pressure. Ethanol (5 mL) and triethylamine (0.58 mL) were added to the residue. A solution of ethyl (E)-3-[5-methoxy-6-(4-methyl-1H-imidazol-1-yl)pyridin-3-yl]acrylimidate hydrochloride (300 mg) and triethylamine (0.58 mL) in ethanol (5 mL) was added dropwise to the mixture. The reaction solution was heated under reflux for 14 hours. The reaction solution was returned to room temperature and the solvent was evaporated under reduced pressure. Ethyl acetate and sodium bicarbonate water were added. The organic layer was separated and washed with brine. The organic layer was dried over anhydrous magnesium sulfate, and the solvent was evaporated under reduced pressure. The residue was purified by silica gel column chromatography (carrier: Chromatorex NH, elution solvent: heptane/ethyl acetate→ethyl acetate) to obtain a racemate of the title compound (180 mg). The resulting racemate (180 mg) was optically resolved by CHIRALPAK™ IB manufactured by Daicel Chemical Industries, Ltd. (2 cm×25 cm, elution solvent: 50% solution of hexane in ethanol) to obtain the title optically active compound with positive optical rotation and a retention time of 33 minutes (60 mg) and the title optically active compound with negative optical rotation and a retention time of 42 minutes (53 mg).

The property values of the title optically active compound with a retention time of 33 minutes are as follows.

ESI-MS; m/z 433 [M$^+$+H].

$^1$H-NMR (CDCl$_3$) δ (ppm): 2.29 (s, 3H), 3.98 (s, 3H), 4.14-4.19 (m, 1H), 4.31-4.42 (m, 3H), 5.92 (s, 1H), 7.08-7.13 (m, 3H), 7.43-7.48 (m, 3H), 7.52-7.56 (m, 2H), 8.16 (s, 1H), 8.36 (s, 1H).

The property values of the title optically active compound with a retention time of 42 minutes are as follows.

ESI-MS; m/z 433 [M$^+$+H].

$^1$H-NMR (CDCl$_3$) δ (ppm): 2.29 (s, 3H), 3.98 (s, 3H), 4.14-4.19 (m, 1H), 4.31-4.42 (m, 3H), 5.92 (s, 1H), 7.08-7.13 (m, 3H), 7.43-7.48 (m, 3H), 7.52-7.56 (m, 2H), 8.16 (s, 1H), 8.36 (s, 1H).

Examples 259 and 260

Synthesis of (+) and (−)-8-(4-chlorophenyl)-2-{(E)-2-[5-methoxy-6-(4-methyl-1H-imidazol-1-yl)pyridin-1-yl]vinyl}-hexahydro-[1,2,4]triazolo[5,1-c][1,4]oxazine

[Formula 156]

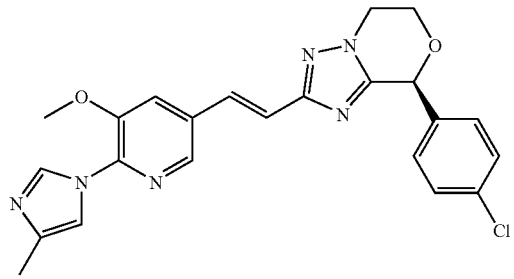

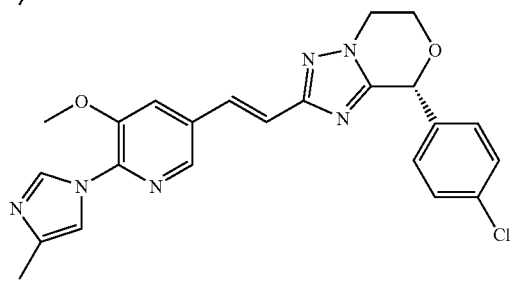

Synthesis of tert-butyl N'-[2-(2-chloroethoxy)-2-(4-chlorophenyl)acetyl]-hydrazinecarboxylate The title compound (2.24 g) was obtained from 4-chlorobenzaldehyde (5 g) by the same method as in Examples 257 and 258. The property values of the compound are as follows.
ESI-MS; m/z 385 [M$^+$+Na].
$^1$H-NMR (CDCl$_3$) δ (ppm): 1.45 (s, 9H), 3.68 (d, J=5.6 Hz, 2H), 3.75-3.82 (m, 2H), 4.90 (s, 1H), 6.36 (brs, 1H), 7.33-7.41 (m, 4H), 8.39 (s, 1H).

Synthesis of 4-chlorobenzoic acid hydrazide hydrochloride

4 N hydrochloric acid-ethyl acetate (10 mL) was added to a solution of tert-butyl N'-[2-(2-chloroethoxy)-2-(4-chlorophenyl)acetyl]-hydrazinecarboxylate (2.24 g) in ethyl acetate (10 mL), and the reaction solution was stirred at room temperature for six hours. The solvent was evaporated under reduced pressure to obtain the title compound (1.8 g).
$^1$H-NMR (CDCl$_3$) δ (ppm): 3.50-3.67 (m, 4H), 4.91 (s, 1H), 7.25-7.32 (m, 4H).

Synthesis of (+) and (−)-8-(4-chlorophenyl)-2-{(E)-2-[5-methoxy-6-(4-methyl-1H-imidazol-1-yl)pyridin-1-yl]vinyl}-hexahydro-[1,2,4]triazolo[5,1-c][1,4]oxazine A solution of 4-chlorobenzoic acid hydrazide hydrochloride (250 mg) and triethylamine (0.58 mL) in ethanol (5 mL) was added dropwise to a solution of ethyl (E)-3-[5-methoxy-6-(4-methyl-1H-imidazol-1-yl)pyridin-3-yl]acrylimidate hydrochloride (250 mg) and triethylamine (0.58 mL) in ethanol (5 mL). The reaction solution was heated under reflux for 14 hours. The reaction solution was returned to room temperature and the solvent was evaporated under reduced pressure. Ethyl acetate and sodium bicarbonate water were added. The organic layer was separated and washed with brine. The organic layer was dried over anhydrous magnesium sulfate, and the solvent was evaporated under reduced pressure. The residue was purified by silica gel column chromatography (carrier: Chromatorex NH, elution solvent: heptane/ethyl acetate→ethyl acetate) to obtain a racemate of the title compound (145 mg). The resulting racemate (145 mg) was optically resolved by CHIRALPAK™ IA manufactured by Daicel Chemical Industries, Ltd. (2 cm×25 cm, elution solvent: 50% solution of hexane in ethanol, flow rate: 10 mL/min) to obtain the title optically active compound with positive optical rotation and a retention time of 14.7 minutes (analysis conditions: CHIRALPAK™ IA manufactured by Daicel Chemical Industries, Ltd. (0.46 cm×25 cm, elution solvent: 50% solution of hexane in ethanol, flow rate: 1 mL/min) (40 mg) and the title optically active compound with negative optical rotation and a retention time of 16.4 minutes (analysis conditions: CHIRALPAK™ IA manufactured by Daicel Chemical Industries, Ltd. (0.46 cm×25 cm, elution solvent: 50% solution of hexane in ethanol, flow rate: 1 mL/min) (54 mg).

The property values of the title optically active compound with a retention time of 14.7 minutes are as follows.
ESI-MS; m/z 449 [M$^+$+H].
$^1$H-NMR (CDCl$_3$) δ (ppm): 2.29 (d, J=1.2 Hz, 3H), 3.98 (s, 3H), 4.14-4.31 (m, 1H), 4.29-4.40 (m, 3H), 5.90 (s, 1H), 7.08 (d, J=16.0 Hz, 1H), 7.37-7.43 (m, 4H), 7.46 (d, J=2.0 Hz, 1H), 7.52 (s, 1H), 7.52 (d, J=16.0 Hz, 1H), 8.15 (d, J=1.6 Hz, 1H), 8.34 (d, J=1.2 Hz, 1H).

The property values of the title optically active compound with a retention time of 16.4 minutes are as follows.
ESI-MS; m/z 449 [M$^+$+H].
$^1$H-NMR (CDCl$_3$) δ (ppm): 2.29 (d, J=1.2 Hz, 3H), 3.98 (s, 3H), 4.14-4.31 (m, 1H), 4.29-4.40 (m, 3H), 5.90 (s, 1H), 7.08 (d, J=16.0 Hz, 1H), 7.37-7.43 (m, 4H), 7.46 (d, J=2.0 Hz, 1H), 7.52 (s, 1H), 7.52 (d, J=16.0 Hz, 1H), 8.15 (d, J=2.0 Hz, 1H), 8.34 (d, J=1.2 Hz, 1H).

Examples 261 and 262

Synthesis of (+) and (−)-8-(4-chlorophenyl)-2-{(E)-2-[6-methoxy-5-(4-methyl-1H-imidazol-1-yl)pyridin-2-yl]vinyl}-5,6-dihydro-8H-[1,2,4]triazolo[5,1-c][1,4]oxazine

[Formula 157]

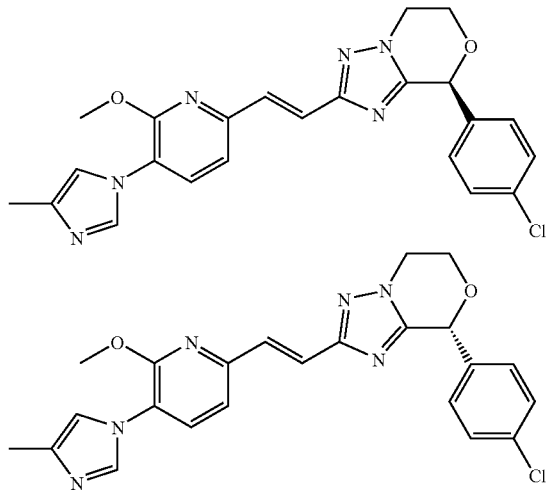

Synthesis of (+) and (−)-8-(4-chlorophenyl)-2-{(E)-2-[6-methoxy-5-(4-methyl-1H-imidazol-1-yl)pyridin-2-yl]vinyl}-5,6-dihydro-8H-[1,2,4]triazolo[5,1-c][1,4]oxazine A solution of 4-chlorobenzoic acid hydrazide hydrochloride (250 mg) and triethylamine (0.58 mL) in ethanol (5 mL) was added dropwise to a solution of ethyl (E)-3-[6-methoxy-5-(4-methyl-1H-imidazol-1-yl)pyridin-2-yl]acrylimidate hydrochloride (300 mg) and triethylamine (0.58 mL) in ethanol (5 mL). The reaction solution was heated under reflux for 14 hours. The reaction solution was returned to room temperature and the solvent was evaporated under reduced pressure. Ethyl acetate and sodium bicarbonate water were added. The organic layer was separated and washed with brine. The organic layer was dried over anhydrous magnesium sulfate, and the solvent was evaporated under reduced pressure. The residue was purified by silica gel column chromatography (carrier: Chromatorex NH, elution solvent: heptane/ethyl acetate→ethyl acetate) to obtain a racemate of the title compound (170 mg). The resulting racemate (170 mg) was optically resolved by CHIRALPAK™ IB manufactured by Daicel Chemical Industries, Ltd. (2 cm×25 cm, elution solvent: ethanol, flow rate: 10 mL/min) to obtain the title optically active compound with positive optical rotation and a retention time of 16 minutes (68 mg) and the title optically active compound with negative optical rotation and a retention time of 25 minutes (63 mg).

The property values of the title optically active compound with a retention time of 16 minutes are as follows.
ESI-MS; m/z 449 [M$^+$+H].

¹H-NMR (CDCl₃) δ (ppm): 2.29 (d, J=1.2 Hz, 3H), 4.06 (s, 3H), 4.11-4.20 (m, 1H), 4.28-4.42 (m, 3H), 5.92 (s, 1H), 6.96 (s, 1H), 6.96 (d, J=7.6 Hz, 1H), 7.38-7.44 (m, 4H), 7.47 (d, J=7.6 Hz, 1H), 7.50 (d, J=16.0 Hz, 1H), 7.65 (d, J=16.0 Hz, 1H), 7.78 (d, J=1.2 Hz, 1H).

The property values of the title optically active compound with a retention time of 25 minutes are as follows.

ESI-MS; m/z 449 [M$^+$+H].

¹H-NMR (CDCl₃) δ (ppm): 2.29 (d, J=1.2 Hz, 3H), 4.06 (s, 3H), 4.11-4.20 (m, 1H), 4.28-4.42 (m, 3H), 5.92 (s, 1H), 6.96 (s, 1H), 6.96 (d, J=7.6 Hz, 1H), 7.38-7.44 (m, 4H), 7.47 (d, J=7.6 Hz, 1H), 7.50 (d, J=16.0 Hz, 1H), 7.65 (d, J=16.0 Hz, 1H), 7.78 (d, J=1.2 Hz, 1H).

The following compounds were obtained using ethyl (E)-3-[3-methoxy-4-(4-methyl-1H-imidazol-1-yl)phenyl]acrylimidate dihydrochloride by the same method as in Examples 257 and 258 (Table 8).

TABLE 8

| Example | E₃ | DATA: MS m/z | Note |
|---|---|---|---|
| 263 | (4-fluorophenyl triazole-morpholine) | M$^+$ + H: 432 (ESI) | Optically active compound (separation conditions IB: retention time 22 min, optical rotation (+)) |
| 264 | (4-fluorophenyl triazole-morpholine) | M$^+$ + H: 432 (ESI) | Optically active compound (separation conditions IB: retention time 27 min, optical rotation (−)) |
| 265 | (4-chlorophenyl triazole-morpholine) | M$^+$ + H: 448 (ESI) | Optically active compound (separation conditions IA: retention time 31 min, optical rotation (+)) |
| 266 | (4-chlorophenyl triazole-morpholine) | M$^+$ + H: 448 (ESI) | Optically active compound (separation conditions IA: retention time 35 min, optical rotation (−)) |

TABLE 8-continued

[Structure: 2-methoxy-4-(E-vinyl-E₃)-1-(4-methylimidazol-1-yl)benzene]

| Example | E₃ | DATA: MS m/z | Note |
|---|---|---|---|
| 267 | [5,6-dihydro-[1,2,4]triazolo[3,4-c][1,4]oxazine with 4-(trifluoromethyl)phenyl substituent, wedge bond] | M⁺ + H: 482 (ESI) | Optically active compound (separation conditions IA: retention time 19 min, optical rotation (+)) |
| 268 | [5,6-dihydro-[1,2,4]triazolo[3,4-c][1,4]oxazine with 4-(trifluoromethyl)phenyl substituent, dashed bond] | M⁺ + H: 482 (ESI) | Optically active compound (separation conditions IA: retention time 25 min, optical rotation (−)) |
| 269 | [5,6-dihydro-[1,2,4]triazolo[3,4-c][1,4]oxazine with 4-(dimethylamino)phenyl substituent, wedge bond] | M⁺ + H: 457 (ESI) | Optically active compound (separation conditions OJ-H: retention time 11 min, optical rotation (−)) |
| 270 | [5,6-dihydro-[1,2,4]triazolo[3,4-c][1,4]oxazine with 4-(dimethylamino)phenyl substituent, dashed bond] | M⁺ + H: 457 (ESI) | Optically active compound (separation conditions OJ-H: retention time 27 min, optical rotation (+)) |
| 271 | [5,6-dihydro-[1,2,4]triazolo[3,4-c][1,4]oxazine with phenyl substituent, wedge bond] | M⁺ + H: 414 (ESI) | Optically active compound (separation conditions AD-H: retention time 10 min, optical rotation (−)) |

TABLE 8-continued

| Example | E₃ | DATA: MS m/z | Note |
|---|---|---|---|
| 272 | (structure) | M⁺ + H: 414 (ESI) | Optically active compound (separation conditions AD-H: retention time 12 min, optical rotation (+)) |
| 273 | (structure) | M⁺ + H: 446 (ESI) | Optically active compound (separation conditions AD-H:ethanol: retention time 30 min, optical rotation (−)) |
| 274 | (structure) | M⁺ + H: 446 (ESI) | Optically active compound (separation conditions AD-H:ethanol: retention time 36 min, optical rotation (+)) |

Examples 275 and 276

Synthesis of (+) and (−)-8-(4-fluorophenyl)-2-{(E)-2-[6-methoxy-5-(4-methyl-1H-imidazol-1-yl)pyridin-2-yl]vinyl}-5,6-dihydro-8H-[1,2,4]triazolo[5,1-c][1,4]oxazine

[Formula 158]

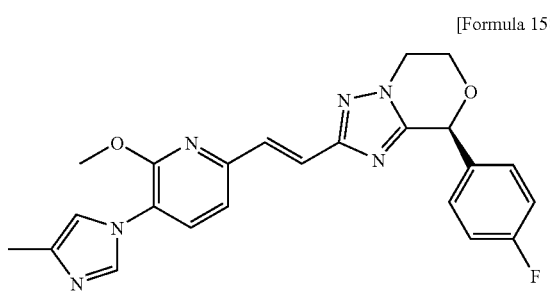

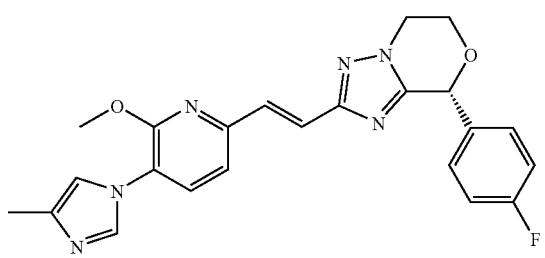

Synthesis of (+) and (−)-8-(4-fluorophenyl)-2-{(E)-2-[6-methoxy-5-(4-methyl-1H-imidazol-1-yl)pyridin-2-yl]vinyl}-5,6-dihydro-8H-[1,2,4]triazolo[5,1-c][1,4]oxazine A solution of 4 N hydrochloric acid in ethyl acetate (5 mL) was added to a solution of tert-butyl N'-[2-(2-chloroethoxy)-2-(4-fluorophenyl)acetyl]-hydrazinecarboxylate (363 mg) in ethyl acetate (5 mL). The reaction solution was stirred at room temperature for 1.5 hours, and then the solvent was evaporated under reduced pressure. Ethanol (5 mL) and triethylamine (0.58 mL) were added to the residue. A solution of ethyl (E)-3-[6-methoxy-5-(4-methyl-1H-imidazol-1-yl)pyridin-2-yl]acrylimidate hydrochloride (300 mg) and triethylamine (0.58 mL) in ethanol (5 mL) was added dropwise to the mixture. Then, the reaction solution was heated under reflux for 14 hours. The reaction solution was returned to room temperature and the solvent was evaporated under reduced pressure. Ethyl acetate and sodium bicarbonate water were added. The organic layer was separated and washed with brine. The organic layer was dried over anhydrous magnesium sulfate, and the solvent was evaporated under reduced pressure. The residue was purified by silica gel column chromatography (carrier: Chromatorex NH, elution solvent: heptane/ethyl acetate→ethyl acetate) to obtain a racemate of the title compound (130 mg). The resulting racemate (130 mg) was optically resolved by CHIRALPAK™ IB manufactured by Daicel Chemical Industries, Ltd. (2 cm×25 cm, elution solvent: ethanol) to obtain the title optically active compound with positive optical rotation and a retention time of 17 minutes (28 mg) and the title optically active compound with negative optical rotation and a retention time of 26 minutes (35 mg).

The property values of the title optically active compound with a retention time of 17 minutes are as follows.

ESI-MS; m/z 433 [M⁺+H].

¹H-NMR (CDCl₃) δ (ppm): 2.30 (s, 3H), 4.06 (s, 3H), 4.13-4.20 (m, 1H), 4.29-4.41 (m, 3H), 5.93 (s, 1H), 6.96 (d, J=8.0 Hz, 1H), 6.97 (s, 1H), 7.11 (dd, J=8.8, 8.4 Hz, 2H), 7.45 (dd, J=8.8, 5.2 Hz, 2H), 7.48 (d, J=15.6 Hz, 1H), 7.48 (d, J=8.0 Hz, 1H), 7.66 (d, J=15.6 Hz, 1H), 7.78 (s, 1H).

The property values of the title optically active compound with a retention time of 26 minutes are as follows.

ESI-MS; m/z 433 [M⁺+H].

¹H-NMR (CDCl₃) δ (ppm): 2.30 (s, 3H), 4.06 (s, 3H), 4.13-4.20 (m, 1H), 4.29-4.41 (m, 3H), 5.93 (s, 1H), 6.96 (d, J=8.0 Hz, 1H), 6.97 (s, 1H), 7.11 (dd, J=8.8, 8.4 Hz, 2H), 7.45 (dd, J=8.8, 5.2 Hz, 2H), 7.48 (d, J=15.6 Hz, 1H), 7.48 (d, J=8.0 Hz, 1H), 7.66 (d, J=15.6 Hz, 1H), 7.78 (s, 1H).

Examples 277 and 278

Synthesis of (+)-2-{(E)-2-[6-methoxy-5-(4-methyl-1H-imidazol-1-yl)pyridin-2-yl]vinyl}-8-(2,4,6-trifluorophenyl)-5,6,7,8-tetrahydro-[1,2,4]triazolo[1,5-a]pyridine and (−)-2-{(E)-2-[6-methoxy-5-(4-methyl-1H-imidazol-1-yl)pyridin-2-yl]vinyl}-8-(2,4,6-trifluorophenyl)-5,6,7,8-tetrahydro-[1,2,4]triazolo[1,5-a]pyridine

[Formula 159]

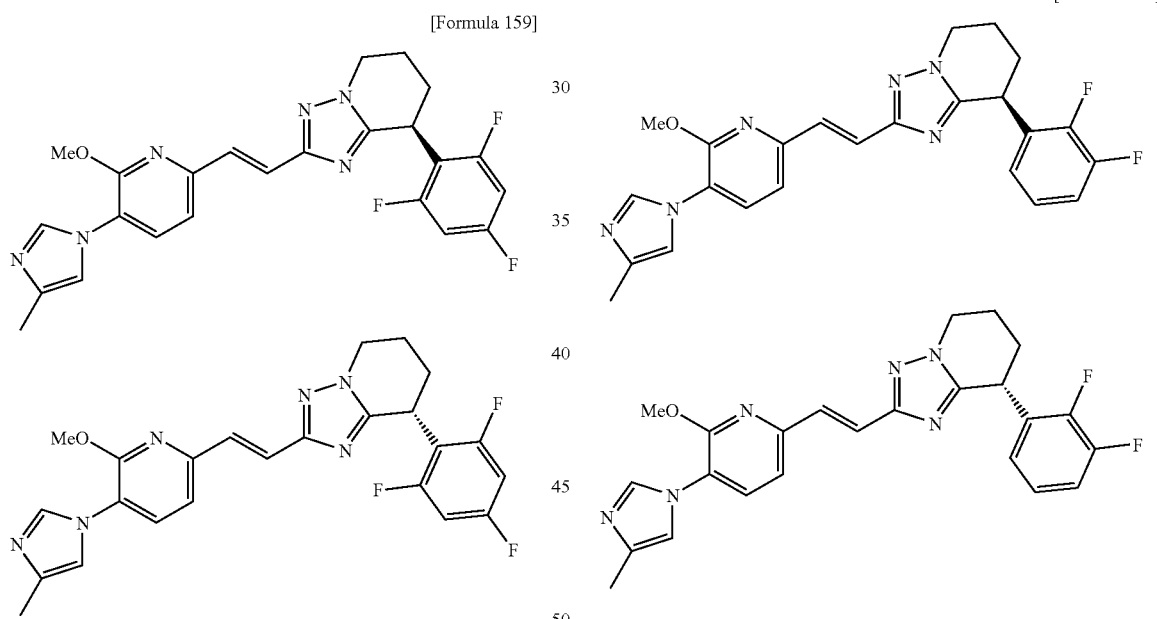

A racemate of the title compound was obtained from (E)-3-[6-methoxy-5-(4-methyl-1H-imidazol-1-yl)pyridin-2-yl]acrylic acid (300 mg) and 1-amino-3-(2,4,6-trifluorophenyl)piperidin-2-one (180 mg) according to the method in Examples 168 and 169. The resulting racemate was separated by CHIRALPAK™ IB manufactured by Daicel Chemical Industries, Ltd. (2 cm×25 cm; mobile phase: hexane:ethanol=80:20) to obtain the title optically active compound with a retention time of 8.9 minutes and positive optical rotation (79.9 mg, >99% ee) and the title optically active compound with a retention time of 19.8 minutes and negative optical rotation (73.0 mg, >99% ee).

The property values of the title compound with positive optical rotation are as follows.

ESI-MS; m/z 467 [M⁺+H]. ¹H-NMR (CDCl₃) δ (ppm): 2.07-2.19 (m, 2H), 2.29 (s, 3H), 2.29-2.36 (m, 2H), 4.03 (s, 3H), 4.23-4.28 (m, 1H), 4.35-4.39 (m, 1H), 4.54-4.59 (m, 1H), 6.66-6.72 (m, 2H), 6.93 (d, J=8.0 Hz, 1H), 6.95 (s, 1H), 7.40 (d, J=16.0 Hz, 1H), 7.46 (d, J=8.0 Hz, 1H), 7.62 (d, J=16.0 Hz, 1H), 7.76 (s, 1H).

The property values of the title compound with negative optical rotation are as follows.

ESI-MS; m/z 467 [M⁺+H]. ¹H-NMR (CDCl₃) δ (ppm): 2.07-2.19 (m, 2H), 2.29 (s, 3H), 2.29-2.36 (m, 2H), 4.03 (s, 3H), 4.23-4.28 (m, 1H), 4.35-4.39 (m, 1H), 4.54-4.59 (m, 1H), 6.66-6.72 (m, 2H), 6.93 (d, J=8.0 Hz, 1H), 6.95 (s, 1H), 7.40 (d, J=16.0 Hz, 1H), 7.46 (d, J=8.0 Hz, 1H), 7.62 (d, J=16.0 Hz, 1H), 7.76 (s, 1H).

Examples 279 and 280

Synthesis of (+)-8-(2,3-difluorophenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine and (−)-8-(2,3-difluorophenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine

[Formula 160]

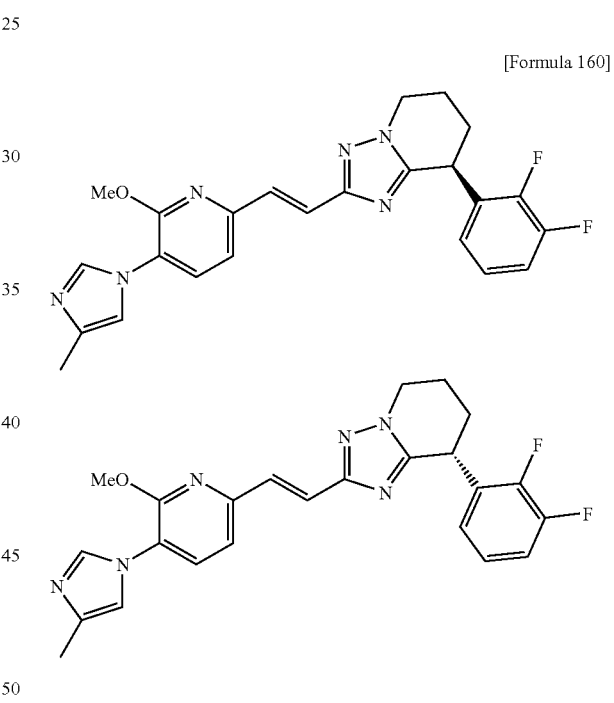

A racemate of the title compound was obtained from (E)-3-[6-methoxy-5-(4-methyl-1H-imidazol-1-yl)pyridin-2-yl]acrylic acid (300 mg) and 1-amino-3-(2,4,6-trifluorophenyl)piperidin-2-one (160 mg) according to the method in Examples 168 and 169. The resulting racemate was separated by CHIRALPAK™ IB manufactured by Daicel Chemical Industries, Ltd. (2 cm×25 cm; mobile phase: ethanol) to obtain the title optically active compound with a retention time of 3.5 minutes and positive optical rotation (53.8 mg, >99% ee) and the title optically active compound with a retention time of 4.3 minutes and negative optical rotation (54.2 mg, >99% ee).

The property values of the title compound with positive optical rotation are as follows.

ESI-MS; m/z 449 [M⁺+H]. ¹H-NMR (CDCl₃) δ (ppm): 2.04-2.24 (m, 3H), 2.29 (s, 3H), 2.37-2.43 (m, 1H), 4.05 (s, 3H), 4.31 (t, J=6.0 Hz, 2H), 4.62 (t, J=6.4 Hz, 1H), 6.73 (t, J=6.8 Hz, 1H), 6.94 (d, J=8.0 Hz, 1H), 6.96 (s, 1H), 7.01-7.14 (m, 2H), 7.45 (d, J=15.6 Hz, 1H), 7.47 (d, J=8.0 Hz, 1H), 7.65 (d, J=15.6 Hz, 1H), 7.77 (s, 1H).

The property values of the title compound with negative optical rotation are as follows.

ESI-MS; m/z 449 [M$^+$+H]. $^1$H-NMR (CDCl$_3$) δ (ppm): 2.04-2.24 (m, 3H), 2.29 (s, 3H), 2.37-2.43 (m, 1H), 4.05 (s, 3H), 4.31 (t, J=6.0 Hz, 2H), 4.62 (t, J=6.4 Hz, 1H), 6.73 (t, J=6.8 Hz, 1H), 6.94 (d, J=8.0 Hz, 1H), 6.96 (s, 1H), 7.01-7.14 (m, 2H), 7.45 (d, J=15.6 Hz, 1H), 7.47 (d, J=8.0 Hz, 1H), 7.65 (d, J=15.6 Hz, 1H), 7.77 (s, 1H).

Examples 281 and 282

Synthesis of (+)-8-(2-fluoro-3-methylphenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine and (−)-8-(2-fluoro-3-methylphenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine

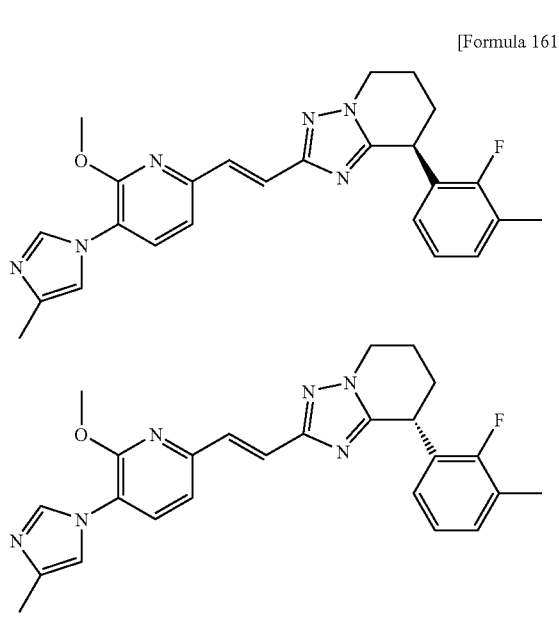

[Formula 161]

A racemate of the title compound (44.5 mg) was obtained using 1-amino-3-(2-fluoro-3-methylphenyl)piperidin-2-one (150 mg) as a starting material according to the method in Examples 168 and 169. The resulting racemate (44.5 mg) was separated by CHIRALPAK™ IB manufactured by Daicel Chemical Industries, Ltd. (2 cm×25 cm, mobile phase: ethanol, flow rate: 12 mL/min) to obtain the title optically active compound with a retention time of 13 minutes and positive optical rotation (17 mg) and the title optically active compound with a retention time of 19 minutes and negative optical rotation (15 mg).

The property values of the title optically active compound with a retention time of 13 minutes are as follows.

$^1$H-NMR (CDCl$_3$) δ (ppm): 2.12-2.24 (m, 3H), 2.28 (s, 3H), 2.29 (s, 3H), 2.32-2.40 (m, 1H), 4.04 (s, 3H), 4.23-4.36 (m, 2H), 4.59 (dd, J=6.6, 6.6 Hz, 1H), 6.72-6.78 (m, 1H), 6.93 (d, J=7.7 Hz, 1H), 6.94-6.96 (m, 1H), 6.99 (d, J=7.7 Hz, 1H), 7.09-7.14 (m, 1H), 7.46 (d, J=15.7 Hz, 1H), 7.47 (d, J=7.7 Hz, 1H), 7.65 (d, J=15.7 Hz, 1H), 7.77 (d, J=1.1 Hz, 1H).

The property values of the title optically active compound with a retention time of 19 minutes are as follows.

$^1$H-NMR (CDCl$_3$) δ (ppm): 2.12-2.24 (m, 3H), 2.28 (s, 3H), 2.29 (s, 3H), 2.32-2.40 (m, 1H), 4.04 (s, 3H), 4.23-4.36 (m, 2H), 4.59 (dd, J=6.6, 6.6 Hz, 1H), 6.72-6.78 (m, 1H), 6.93 (d, J=7.7 Hz, 1H), 6.94-6.96 (m, 1H), 6.99 (d, J=7.7 Hz, 1H), 7.09-7.14 (m, 1H), 7.46 (d, J=15.7 Hz, 1H), 7.47 (d, J=7.7 Hz, 1H), 7.65 (d, J=15.7 Hz, 1H), 7.77 (d, J=1.1 Hz, 1H).

Examples 283 and 284

Synthesis of (−)-8-(2-trifluoromethoxyphenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine and (+)-8-(2-trifluoromethoxyphenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine

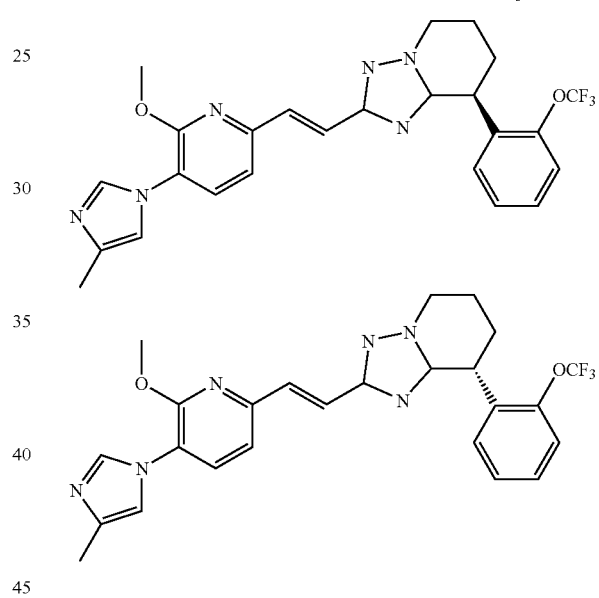

[Formula 162]

Synthesis of 1-amino-3-(2-trifluoromethoxyphenyl)piperidin-2-one 520 mg of the title compound was obtained using 2-trifluoromethoxyphenylacetic acid (1 g) as a starting material according to the method in Examples 20 and 21. The property value of the compound is as follows.

ESI-MS; m/z 275 [M$^+$+H].

Synthesis of (−)-8-(2-trifluoromethoxyphenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine and (+)-8-(2-trifluoromethoxyphenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine A racemate of the title compound (146 mg) was obtained from 1-amino-3-(2-trifluoromethoxyphenyl)piperidin-2-one (300 mg) according to the method in Examples 168 and 169. The resulting racemate (146 mg) was separated by CHIRAL- PAK™ AD-H manufactured by Daicel Chemical Industries, Ltd. (2 cm×25 cm, mobile phase: hexane:ethanol=8:2, flow rate: 11 mL/min) to obtain the title optically active compound with a retention time of 32 minutes and negative optical rotation (49.9 mg) and the title optically active compound with a retention time of 46 minutes and positive optical rotation (47.2 mg).

The property values of the title optically active compound with a retention time of 32 minutes are as follows.

$^1$H-NMR (CDCl$_3$) δ (ppm): 2.00-2.41 (m, 7H), 4.04 (s, 3H), 4.28-4.32 (m, 2H), 4.64 (m, 1H), 6.92-6.99 (m, 3H), 7.19-7.35 (m, 3H), 7.44 (d, J=15.2 Hz, 1H), 7.46 (d, J=8.2 Hz, 1H), 7.65 (d, J=16.0 Hz, 1H), 7.76 (s, 1H).

The property values of the title optically active compound with a retention time of 46 minutes are as follows.

$^1$H-NMR (CDCl$_3$) δ (ppm): 2.00-2.41 (m, 7H), 4.04 (s, 3H), 4.28-4.32 (m, 2H), 4.64 (m, 1H), 6.92-6.99 (m, 3H), 7.19-7.35 (m, 3H), 7.44 (d, J=15.2 Hz, 1H), 7.46 (d, J=8.2 Hz, 1H), 7.65 (d, J=16.0 Hz, 1H), 7.76 (s, 1H).

Examples 285 and 286

Synthesis of (+)-8-(2-trifluoromethyl-4-fluorophenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine and (−)-8-(2-trifluoromethyl-4-fluorophenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine

[Formula 163]

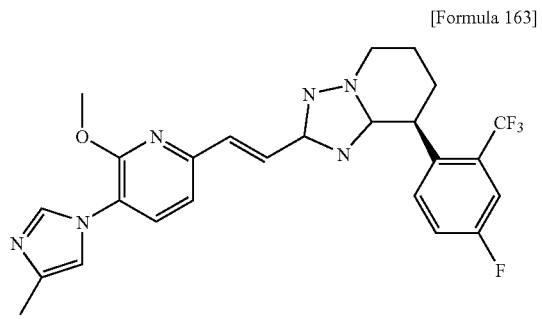

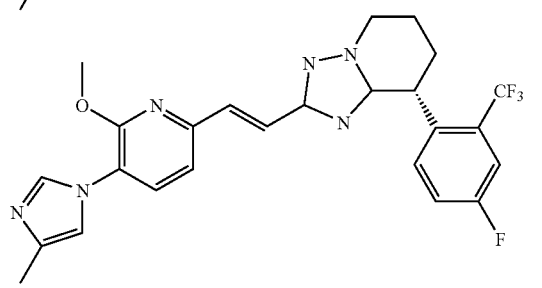

Synthesis of 1-amino-3-(2-trifluoromethyl-4-fluorophenyl)piperidin-2-one 364 mg of the title compound was obtained using 2-trifluoromethyl-4-fluorophenylacetic acid (1 g) as a starting material according to the method in Examples 194 and 195. The property value of the compound is as follows.

ESI-MS; m/z 277 [M$^+$+H].

Synthesis of (+)-8-(2-trifluoromethyl-4-fluorophenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine and (−)-8-(2-trifluoromethyl-4-fluorophenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine A racemate of the title compound (190 mg) was obtained using 1-amino-3-(2-trifluoromethyl-4-fluorophenyl)piperidin-2-one (360 mg) as a starting material according to the method in Examples 168 and 169. The resulting racemate (149 mg) was separated by CHIRALPAK™ IA manufactured by Daicel Chemical Industries, Ltd. (2 cm×25 cm, mobile phase: hexane:ethanol=8:2, flow rate: 11 mL/min) to obtain the title optically active compound with a retention time of 25 minutes and positive optical rotation (83.6 mg) and the title optically active compound with a retention time of 30 minutes and negative optical rotation (82.8 mg).

The property values of the title optically active compound with a retention time of 25 minutes are as follows.

$^1$H-NMR (CDCl$_3$) δ (ppm): 1.86-2.48 (m, 7H), 4.03 (s, 3H), 4.27-4.40 (m, 2H), 4.64 (dd, J=8.8, 6.0 Hz, 1H), 6.92-7.04 (m, 3H), 7.19 (t, J=8.0 Hz, 1H), 7.40-7.47 (m, 3H), 7.62 (d, J=15.6 Hz, 1H), 7.76 (s, 1H).

The property values of the title optically active compound with a retention time of 30 minutes are as follows.

$^1$H-NMR (CDCl$_3$) δ (ppm): 1.86-2.48 (m, 7H), 4.03 (s, 3H), 4.27-4.40 (m, 2H), 4.64 (dd, J=8.8, 6.0 Hz, 1H), 6.92-7.04 (m, 3H), 7.19 (t, J=8.0 Hz, 1H), 7.40-7.47 (m, 3H), 7.62 (d, J=15.6 Hz, 1H), 7.76 (s, 1H).

Examples 287 and 288

Synthesis of (−)-8-(2-difluoromethoxyphenyl)-2-{(E)-2-[6-methoxy-5-(4-methyl-1H-imidazol-1-yl)pyridin-2-yl]vinyl}-octahydro-[1,2,4]triazolo[1,5-a]pyridine and (+)-8-(2-difluoromethoxyphenyl)-2-{(E)-2-[6-methoxy-5-(4-methyl-1H-imidazol-1-yl)pyridin-2-yl]vinyl}-octahydro-[1,2,4]triazolo[1,5-a]pyridine

[Formula 164]

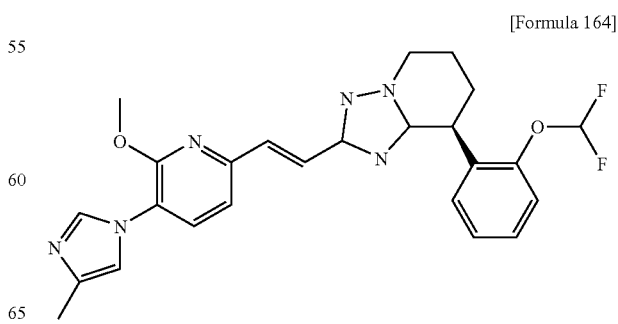

-continued

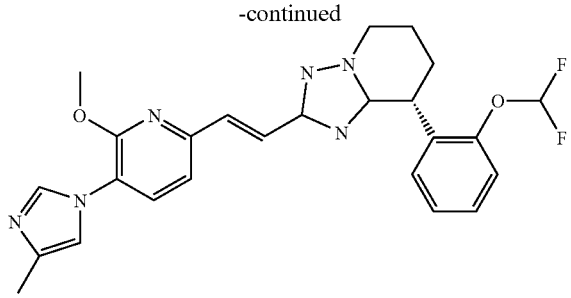

Synthesis of (2-difluoromethoxyphenyl)acetonitrile

A solution of p-toluenesulfonylmethyl isocyanide (2.4 g) in dimethoxyethane (10 mL) was added to a solution of potassium tert-butoxide (2.68 g) in dimethoxyethane (30 mL) at −35° C., and the reaction solution was stirred at the same temperature for 10 minutes. The reaction solution was cooled to −55° C. A solution of difluoromethoxybenzaldehyde (2 g) in dimethoxyethane (5 mL) was added dropwise, and the reaction solution was stirred at the same temperature for two hours. 10 mL of methanol was added to the reaction solution, and the reaction solution was heated under reflux for 15 minutes. The reaction solution was left to cool to room temperature. Then, water and dichloromethane were added and the organic layer was separated. The resulting organic layer was dried over anhydrous magnesium sulfate and then concentrated under reduced pressure. The residue was purified by silica gel column chromatography (elution solvent: heptane-ethyl acetate system) to obtain 1.45 g of the title compound. The property values of the compound are as follows.

$^1$H-NMR (CDCl$_3$) δ (ppm): 3.78 (s, 2H), 6.58 (t, J=73.2 Hz, 1H), 7.17 (d, J=8.4 Hz, 1H), 7.26 (t, J=7.0 Hz, 1H), 7.36 (t, J=8.0 Hz, 1H), 7.51 (d, J=7.6 Hz, 1H).

Synthesis of ethyl (2-difluoromethoxyphenyl)acetate (2-Difluoromethoxyphenyl)acetonitrile (1.45 g) was added dropwise to a solution of chlorotrimethylsilane (2.23 mL) in ethanol (2.0 mL), and the reaction solution was stirred at 50° C. for five hours. The reaction solution was left to cool to room temperature. Then, potassium carbonate, water and ethyl acetate were added and the organic layer was separated. The resulting organic layer was dried over anhydrous magnesium sulfate and then concentrated under reduced pressure. The residue was purified by silica gel column chromatography (elution solvent: heptane-ethyl acetate system) to obtain 620 mg of the title compound. The property values of the compound are as follows.

$^1$H-NMR (CDCl$_3$) δ (ppm): 1.26 (t, J=7.2 Hz, 3H), 3.68 (s, 2H), 4.16 (q, 7.2 Hz, 2H), 6.48 (t, J=74.4 Hz, 1H), 7.13-7.32 (m, 4H).

Synthesis of 1-amino-3-(2-difluoromethoxyphenyl)piperidin-2-one 395 mg of the title compound was obtained using ethyl 2-difluoromethoxyphenylacetate (630 mg) as a starting material according to the method in Examples 20 and 21. The property value of the compound is as follows.

ESI-MS; m/z 257 [M$^+$+H].

Synthesis of (−)-8-(2-difluoromethoxyphenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine and (+)-8-(2-difluoromethoxyphenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine A racemate of the title compound (105 mg) was obtained from 1-amino-3-(2-difluoromethoxyphenyl)piperidin-2-one (395 mg) according to the method in Examples 168 and 169. The resulting racemate (105 mg) was separated by CHIRALPAK™ AD-H manufactured by Daicel Chemical Industries, Ltd. (2 cm×25 cm, mobile phase: hexane:ethanol=8:2, flow rate: 13 mL/min) to obtain the title optically active compound with a retention time of 45 minutes and negative optical rotation (48.1 mg) and the title optically active compound with a retention time of 69 minutes and positive optical rotation (41 mg).

The property values of the title optically active compound with a retention time of 45 minutes are as follows.

$^1$H-NMR (CDCl$_3$) δ (ppm): 2.05-2.37 (m, 7H), 4.04 (s, 3H), 4.24-4.35 (m, 2H), 4.55 (m, 1H), 6.43 (t, J=74.0 Hz, 1H), 6.92 (d, J=8.0 Hz, 1H), 6.95 (s, 1H), 7.04-7.20 (m, 3H), 7.31 (t, J=7.8 Hz, 1H), 7.41 (d, J=16.0 Hz, 1H), 7.45 (d, J=8.0 Hz, 1H), 7.63 (d, J=16.0 Hz, 1H), 7.60 (s, 1H).

The property values of the title optically active compound with a retention time of 69 minutes are as follows.

$^1$H-NMR (CDCl$_3$) δ (ppm): 2.05-2.37 (m, 7H), 4.04 (s, 3H), 4.24-4.35 (m, 2H), 4.55 (m, 1H), 6.43 (t, J=74.0 Hz, 1H), 6.92 (d, J=8.0 Hz, 1H), 6.95 (s, 1H), 7.04-7.20 (m, 3H), 7.31 (t, J=7.8 Hz, 1H), 7.41 (d, J=16.0 Hz, 1H), 7.45 (d, J=8.0 Hz, 1H), 7.63 (d, J=16.0 Hz, 1H), 7.60 (s, 1H).

Examples 289 and 290

Synthesis of (+)-8-(2-bromophenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine and (−)-8-(2-bromophenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine

[Formula 165]

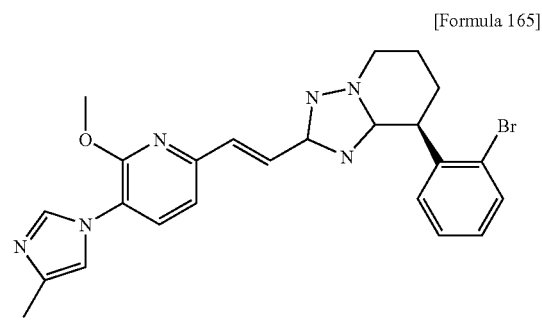

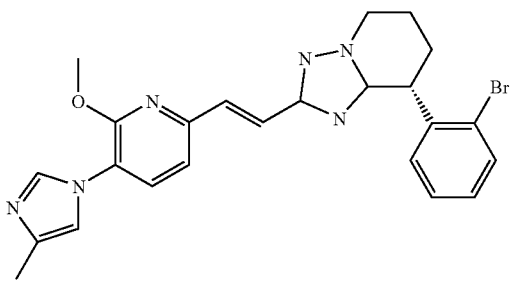

Synthesis of 1-amino-3-(2-bromophenyl)piperidin-2-one 820 mg of the title compound was obtained using 2-bromophenylacetic acid (1 g) as a starting material according to the method in Examples 20 and 21. The property value of the compound is as follows.

ESI-MS; m/z 269 [M$^+$+H].

Synthesis of (+)-8-(2-bromophenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine and (−)-8-(2-bromophenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine A racemate of the title compound (210 mg) was obtained from 1-amino-3-(2-bromophenyl)piperidin-2-one (300 mg) according to the method in Examples 168 and 169. The resulting racemate (210 mg) was separated by CHIRALPAK™ IB manufactured by Daicel Chemical Industries, Ltd. (2 cm×25 cm, mobile phase: ethanol, flow rate: 13 mL/min) to obtain the title optically active compound with a retention time of 14.5 minutes and positive optical rotation (78.6 mg) and the title optically active compound with a retention time of 19.2 minutes and negative optical rotation (68 mg).

The property values of the title optically active compound with a retention time of 14.5 minutes are as follows.

$^1$H-NMR (CDCl$_3$) δ (ppm): 2.04-2.42 (m, 7H), 4.04 (s, 3H), 4.24-4.36 (m, 2H), 4.76 (m, 1H), 6.84 (d, J=7.6 Hz, 1H), 6.93 (d, J=7.6 Hz, 1H), 6.95 (s, 1H), 7.13 (d, J=7.6 Hz, 1H), 7.23 (d, J=7.6 Hz, 1H), 7.45 (d, J=16.0 Hz, 1H), 7.46 (d, J=7.6 Hz, 1H), 7.59 (d, J=7.6 Hz, 1H), 7.65 (d, J=16.0 Hz, 1H), 7.76 (s, 1H).

The property values of the title optically active compound with a retention time of 19.2 minutes are as follows.

$^1$H-NMR (CDCl$_3$) δ (ppm): 2.04-2.42 (m, 7H), 4.04 (s, 3H), 4.24-4.36 (m, 2H), 4.76 (m, 1H), 6.84 (d, J=7.6 Hz, 1H), 6.93 (d, J=7.6 Hz, 1H), 6.95 (s, 1H), 7.13 (d, J=7.6 Hz, 1H), 7.23 (d, J=7.6 Hz, 1H), 7.45 (d, J=16.0 Hz, 1H), 7.46 (d, J=7.6 Hz, 1H), 7.59 (d, J=7.6 Hz, 1H), 7.65 (d, J=16.0 Hz, 1H), 7.76 (s, 1H).

Examples 291 and 292

Synthesis of (+)-2-{(E)-2-[6-methoxy-5-(4-methyl-1H-imidazol-1-yl)pyridin-2-yl]vinyl}-8-(4-methoxyphenyl)-5,6,7,8-tetrahydro-[1,2,4]triazolo[1,5-a]pyridine and (−)-2-{(E)-2-[6-methoxy-5-(4-methyl-1H-imidazol-1-yl)pyridin-2-yl]vinyl}-8-(4-methoxyphenyl)-5,6,7,8-tetrahydro-[1,2,4]triazolo[1,5-a]pyridine

[Formula 166]

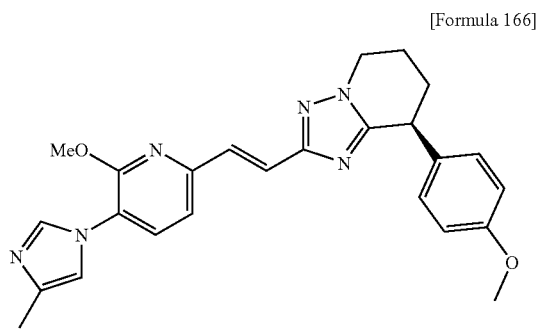

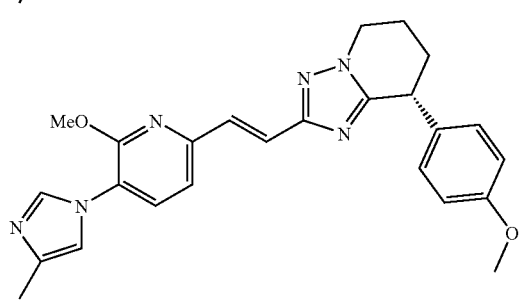

A racemate of the title compound was obtained from (E)-3-[6-methoxy-5-(4-methyl-1H-imidazol-1-yl)pyridin-2-yl]acrylic acid (300 mg) and 1-amino-3-(4-methoxyphenyl)piperidin-2-one (163 mg) according to the method in Examples 168 and 169. The resulting racemate was separated by CHIRALPAK™ IB manufactured by Daicel Chemical Industries, Ltd. (2 cm×25 cm; mobile phase: ethanol) to obtain the title optically active compound with a retention time of 4.1 minutes and positive optical rotation (76.4 mg, >99% ee) and the title optically active compound with a retention time of 4.7 minutes and negative optical rotation (78.2 mg, >99% ee).

The property values of the title compound with positive optical rotation are as follows.

ESI-MS; m/z 443 [M$^+$+H]. $^1$H-NMR (CDCl$_3$) δ (ppm): 2.01-2.09 (m, 2H), 2.16-2.22 (m, 1H), 2.29 (s, 3H), 2.29-2.37 (m, 1H), 3.80 (s, 3H), 4.05 (s, 3H), 4.24-4.33 (m, 3H), 6.87 (d, J=8.8 Hz, 2H), 6.93 (d, J=8.0 Hz, 1H), 6.96 (s, 1H), 7.06 (d, J=8.8 Hz, 2H), 7.46 (d, J=8.0 Hz, 1H), 7.47 (d, J=15.6 Hz, 1H), 7.66 (d, J=15.6 Hz, 1H), 7.77 (s, 1H).

The property values of the title compound with negative optical rotation are as follows.

ESI-MS; m/z 443 [M$^+$+H]. $^1$H-NMR (CDCl$_3$) δ (ppm): 2.01-2.09 (m, 2H), 2.16-2.22 (m, 1H), 2.29 (s, 3H), 2.29-2.37 (m, 1H), 3.80 (s, 3H), 4.05 (s, 3H), 4.24-4.33 (m, 3H), 6.87 (d, J=8.8 Hz, 2H), 6.93 (d, J=8.0 Hz, 1H), 6.96 (s, 1H), 7.06 (d, J=8.8 Hz, 2H), 7.46 (d, J=8.0 Hz, 1H), 7.47 (d, J=15.6 Hz, 1H), 7.66 (d, J=15.6 Hz, 1H), 7.77 (s, 1H).

Examples 293 and 294

Synthesis of (+)-8-(3-fluoro-2-methylphenyl)-2-{(E)-2-[5-methoxy-6-(4-methyl-1H-imidazol-1-yl)pyridin-3-yl]vinyl}-8-(4-trifluoromethylphenyl)-5,6,7,8-tetrahydro-[1,2,4]triazolo[1,5-a]pyridine and (−)-8-(3-fluoro-2-methylphenyl)-2-{(E)-2-[5-methoxy-6-(4-methyl-1H-imidazol-1-yl)pyridin-3-yl]vinyl}-8-(4-trifluoromethylphenyl)-5,6,7,8-tetrahydro-[1,2,4]triazolo[1,5-a]pyridine

[Formula 167]

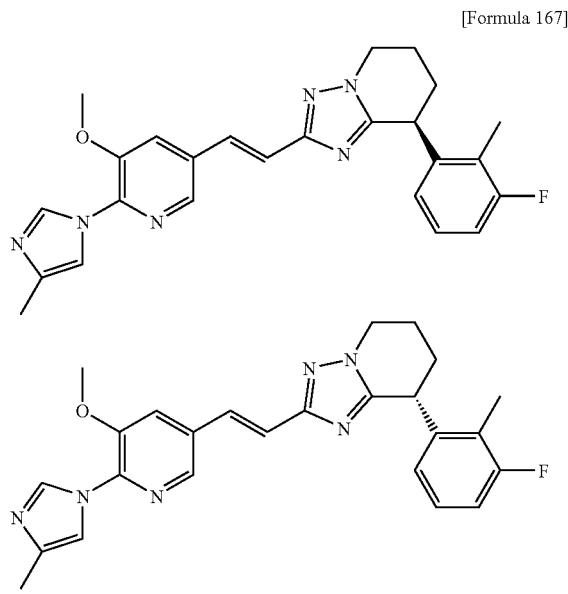

Synthesis of 1-amino-3-(3-fluoro-2-methylphenyl)piperidin-2-one 521 mg of the title compound was obtained according to the method in Examples 20 and 21 through ethyl 3-fluoro-2-methylphenylacetate as an intermediate from 3-fluoro-2-methylbenzaldehyde (1.5 g) as a starting material according to the method in Examples 40 and 41. The property value of the compound is as follows.
ESI-MS; m/z 223 [M$^+$+H].

Synthesis of (+)-8-(3-fluoro-2-methylphenyl)-2-{(E)-2-[5-methoxy-6-(4-methyl-1H-imidazol-1-yl)pyridin-3-yl]vinyl}-8-(4-trifluoromethylphenyl)-5,6,7,8-tetrahydro-[1,2,4]triazolo[1,5-a]pyridine and (−)-8-(3-fluoro-2-methylphenyl)-2-{(E)-2-[5-methoxy-6-(4-methyl-1H-imidazol-1-yl)pyridin-3-yl]vinyl}-8-(4-trifluoromethylphenyl)-5,6,7,8-tetrahydro-[1,2,4]triazolo[1,5-a]pyridine A racemate of the title compound (34.8 mg) was obtained using 1-amino-3-(3-fluoro-2-methylphenyl)piperidin-2-one (171 mg) as a starting material according to the method in Examples 168 and 169. The resulting racemate (34.8 mg) was separated by CHIRALPAK™ IB manufactured by Daicel Chemical Industries, Ltd. (2 cm×25 cm, mobile phase: etha-nol:hexane=3:7, flow rate: 20 mL/min) to obtain the title optically active compound with a retention time of 9 minutes and positive optical rotation (12 mg) and the title optically active compound with a retention time of 15 minutes and negative optical rotation (15 mg).

The property values of the title optically active compound with a retention time of 9 minutes are as follows.
$^1$H-NMR (CDCl$_3$) δ (ppm): 1.94-2.03 (m, 1H), 2.04-2.15 (m, 1H), 2.16-2.38 (m, 2H), 2.29 (s, 3H), 2.30 (s, 3H), 3.97 (s, 3H), 4.29 (ddd, J=12.5, 12.5, 5.8 Hz, 1H), 4.33 (ddd, J=12.5, 12.5, 5.5 Hz, 1H), 4.54 (t, J=6.2 Hz, 1H), 6.54 (d, J=7.7 Hz, 1H), 6.93-7.00 (m, 1H), 7.06-7.13 (m, 1H), 7.09 (d, J=16.1 Hz, 1H), 7.46 (d, J=1.8 Hz, 1H), 7.51 (d, J=16.1 Hz, 1H), 7.52 (d, J=1.1 Hz, 1H), 8.14 (d, J=1.8 Hz, 1H), 8.34 (d, J=1.1 Hz, 1H).

The property values of the title optically active compound with a retention time of 15 minutes are as follows.
$^1$H-NMR (CDCl$_3$) δ (ppm): 1.94-2.03 (m, 1H), 2.04-2.15 (m, 1H), 2.16-2.38 (m, 2H), 2.29 (s, 3H), 2.30 (s, 3H), 3.97 (s, 3H), 4.29 (ddd, J=12.5, 12.5, 5.8 Hz, 1H), 4.33 (ddd, J=12.5, 12.5, 5.5 Hz, 1H), 4.54 (t, J=6.2 Hz, 1H), 6.54 (d, J=7.7 Hz, 1H), 6.93-7.00 (m, 1H), 7.06-7.13 (m, 1H), 7.09 (d, J=16.1 Hz, 1H), 7.46 (d, J=1.8 Hz, 1H), 7.51 (d, J=16.1 Hz, 1H), 7.52 (d, J=1.1 Hz, 1H), 8.14 (d, J=1.8 Hz, 1H), 8.34 (d, J=1.1 Hz, 1H).

Examples 295 and 296

Synthesis of (+)-8-(2-fluoro-3-methylphenyl)-2-{(E)-2-[5-methoxy-6-(4-methyl-1H-imidazol-1-yl)pyridin-3-yl]vinyl}-8-(4-trifluoromethylphenyl)-5,6,7,8-tetrahydro-[1,2,4]triazolo[1,5-a]pyridine and (−)-8-(2-fluoro-3-methylphenyl)-2-{(E)-2-[5-methoxy-6-(4-methyl-1H-imidazol-1-yl)pyridin-3-yl]vinyl}-8-(4-trifluoromethylphenyl)-5,6,7,8-tetrahydro-[1,2,4]triazolo[1,5-a]pyridine

[Formula 168]

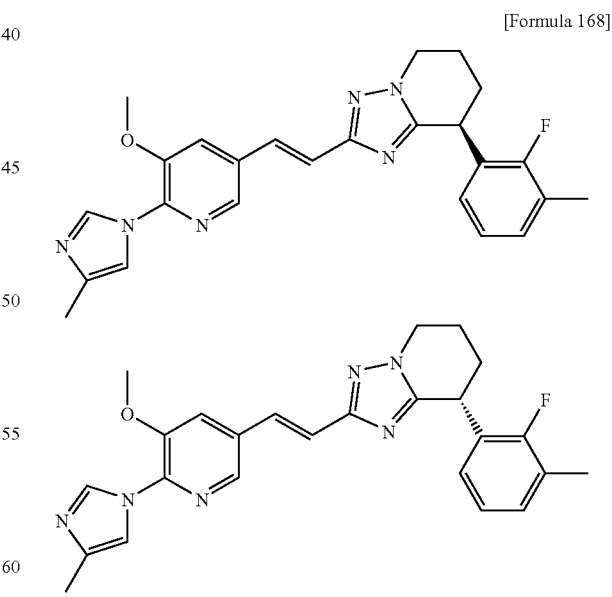

Synthesis of ethyl (2-fluoro-3-methylphenyl)acetate

A mixture of 2-fluoro-3-methylbenzyl bromide (2.0 g), sodium cyanide (2.41 g), sodium iodide (148 mg) and DMSO (10 ml) was stirred at 60° C. for two hours. Water and ethyl acetate were added to the reaction solution, and the organic layer was separated. The organic layer was washed with brine. The resulting organic layer was dried over anhydrous magnesium sulfate. The organic layer was concentrated under reduced pressure. 5 N hydrochloric acid (15 ml) was added to the residue, and the reaction solution was heated at 110° C. for 22 hours. The reaction solution was brought to room temperature. Chloroform was added and the organic layer was separated. The organic layer was concentrated under reduced pressure. Saturated hydrogen chloride-ethanol (15 ml) was added to the residue, and the reaction solution was stirred at 85° C. for four hours. The reaction solution was concentrated under reduced pressure, and then diluted with ethyl acetate and washed with saturated sodium bicarbonate water and then with brine. The resulting organic layer was dried over anhydrous magnesium sulfate and concentrated under reduced pressure to obtain the title compound (1.1 g). The property values of the compound are as follows.

$^1$H-NMR (CDCl$_3$) δ (ppm): 1.24 (t, J=6.9 Hz, 3H), 2.27 (s, 3H), 3.65 (s, 2H), 4.15 (q, J=6.9 Hz, 2H), 6.96-7.01 (m, 1H), 7.05-7.13 (m, 2H).

Synthesis of
1-amino-3-(2-fluoro-3-methylphenyl)piperidin-2-one 766 mg of the title compound was obtained using ethyl (2-fluoro-3-methylphenyl)acetate (1.1 g) as a starting material according to the method in Examples 20 and 21. The property value of the compound is as follows.

ESI-MS; m/z 223 [M$^+$+H].

Synthesis of (+)-8-(2-fluoro-3-methylphenyl)-2-{(E)-2-[5-methoxy-6-(4-methyl-1H-imidazol-1-yl)pyridin-3-yl]vinyl}-8-(4-trifluoromethylphenyl)-5,6,7,8-tetrahydro-[1,2,4]triazolo[1,5-a]pyridine and (-)-8-(2-fluoro-3-methylphenyl)-2-{(E)-2-[5-methoxy-6-(4-methyl-1H-imidazol-1-yl)pyridin-3-yl]vinyl}-8-(4-trifluoromethylphenyl)-5,6,7,8-tetrahydro-[1,2,4]triazolo[1,5-a]pyridine A racemate of the title compound (161.8 mg) was obtained using 1-amino-3-(2-fluoro-3-methylphenyl)piperidin-2-one (250 mg) as a starting material according to the method in Examples 168 and 169. The resulting racemate (34.8 mg) was separated by CHIRALPAK™ AD-H manufactured by Daicel Chemical Industries, Ltd. (2 cm×25 cm, mobile phase: ethanol, flow rate: 12 mL/min) to obtain the title optically active compound with a retention time of 18 minutes and negative optical rotation (75 mg) and the title optically active compound with a retention time of 28 minutes and positive optical rotation (70 mg).

The property values of the title optically active compound with a retention time of 18 minutes are as follows.

$^1$H-NMR (CDCl$_3$) δ (ppm): 2.10-2.40 (m, 4H), 2.28 (s, 3H), 2.29 (s, 3H), 3.96 (s, 3H), 4.23-4.26 (m, 2H), 4.57 (dd, J=7.0, 5.7 Hz, 1H), 6.73-6.77 (m, 1H), 6.98 (dd, J=7.3, 7.3 Hz, 1H), 7.10 (d, J=16.1 Hz, 1H), 7.09-7.14 (m, 1H), 7.46 (d, J=1.8 Hz, 1H), 7.51 (d, J=16.1 Hz, 1H), 7.52 (d, J=1.1 Hz, 1H), 8.14 (d, J=1.8 Hz, 1H), 8.34 (d, J=1.1 Hz, 1H).

The property values of the title optically active compound with a retention time of 15 minutes are as follows.

$^1$H-NMR (CDCl$_3$) δ (ppm): 2.10-2.40 (m, 4H), 2.28 (s, 3H), 2.29 (s, 3H), 3.96 (s, 3H), 4.23-4.26 (m, 2H), 4.57 (dd, J=7.0, 5.7 Hz, 1H), 6.73-6.77 (m, 1H), 6.98 (dd, J=7.3, 7.3 Hz, 1H), 7.10 (d, J=16.1 Hz, 1H), 7.09-7.14 (m, 1H), 7.46 (d, J=1.8 Hz, 1H), 7.51 (d, J=16.1 Hz, 1H), 7.52 (d, J=1.1 Hz, 1H), 8.14 (d, J=1.8 Hz, 1H), 8.34 (d, J=1.1 Hz, 1H).

Examples 297 and 298

Synthesis of (−)-8-(2,3-difluorophenyl)-2-{(E)-2-[5-methoxy-6-(4-methyl-1H-imidazol-1-yl)pyridin-3-yl]vinyl}-5,6,7,8-tetrahydro-[1,2,4]triazolo[1,5-a]pyridine and (+)-8-(2,3-difluorophenyl)-2-{(E)-2-[5-methoxy-6-(4-methyl-1H-imidazol-1-yl)pyridin-3-yl]vinyl}-5,6,7,8-tetrahydro-[1,2,4]triazolo[1,5-a]pyridine

[Formula 169]

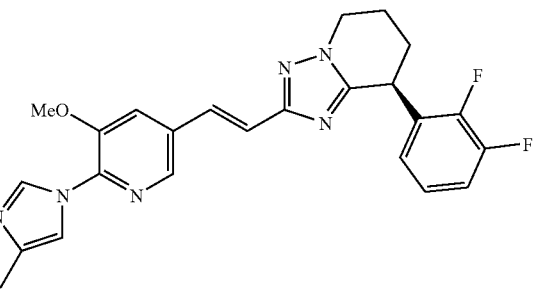

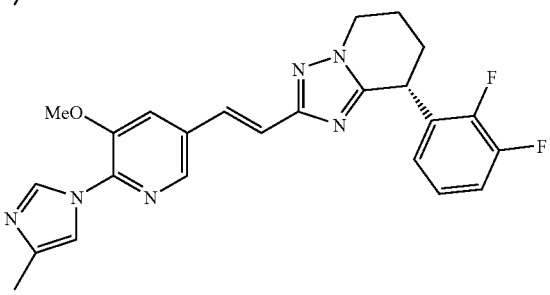

Synthesis of
1-amino-3-(2,3-difluorophenyl)piperidin-2-one 2.06 g of the title compound was obtained from methyl 2,3-difluorophenylacetate (5.63 g) according to the method in Examples 20 and 21. The property value of the compound is as follows.

ESI-MS; m/z 227 [M$^+$+H].

Synthesis of (−)-8-(2,3-difluorophenyl)-2-{(E)-2-[5-methoxy-6-(4-methyl-1H-imidazol-1-yl)pyridin-3-yl]vinyl}-5,6,7,8-tetrahydro-[1,2,4]triazolo[1,5-a]pyridine and (+)-8-(2,3-difluorophenyl)-2-{(E)-2-[5-methoxy-6-(4-methyl-1H-imidazol-1-yl)pyridin-3-yl]vinyl}-5,6,7,8-tetrahydro-[1,2,4]triazolo[1,5-a]pyridine A racemate of the title compound was obtained from (E)-3-[5-methoxy-6-(4-methyl-1H-imidazol-1-yl)pyridin-3-yl]acrylic acid (250 mg) and 1-amino-3-(2,3-difluorophenyl)piperidin-2-one (167 mg) according to the method in Examples 168 and 169. The resulting racemate was separated by CHIRALPAK™ AD-H manufactured by Daicel Chemical Industries, Ltd. (2 cm×25 cm; mobile phase: ethanol) to obtain the title optically active compound with a retention time of 7.9 minutes and negative optical rotation (27.3 mg, >99% ee) and the title optically active compound with a retention time of 12 minutes and positive optical rotation (27.1 mg, >99% ee).

The property values of the title compound with negative optical rotation are as follows.

ESI-MS; m/z 449 [M$^+$+H]. $^1$H-NMR (CDCl$_3$) δ (ppm): 2.04-2.28 (m, 3H), 2.29 (s, 3H), 2.36-2.43 (m, 1H), 3.97 (s, 3H), 4.31 (t, J=5.6 Hz, 2H), 4.60 (t, J=6.0 Hz, 1H), 6.75 (dd, J=8.0, 6.0 Hz, 1H), 7.00-7.15 (m, 3H), 7.45 (s, 1H), 7.49 (d, J=15.6 Hz, 1H), 7.52 (s, 1H), 8.15 (s, 1H), 8.34 (s, 1H).

The property values of the title compound with positive optical rotation are as follows.

ESI-MS; m/z 449 [M$^+$+H]. $^1$H-NMR (CDCl$_3$) δ (ppm): 2.04-2.28 (m, 3H), 2.29 (s, 3H), 2.36-2.43 (m, 1H), 3.97 (s, 3H), 4.31 (t, J=5.6 Hz, 2H), 4.60 (t, J=6.0 Hz, 1H), 6.75 (dd, J=8.0, 6.0 Hz, 1H), 7.00-7.15 (m, 3H), 7.45 (s, 1H), 7.49 (d, J=15.6 Hz, 1H), 7.52 (s, 1H), 8.15 (s, 1H), 8.34 (s, 1H).

Examples 299 and 300

Synthesis of (−)-2-{(E)-2-[5-methoxy-6-(4-methyl-1H-imidazol-1-yl)pyridin-3-yl]vinyl}-8-(4-methoxyphenyl)-5,6,7,8-tetrahydro-[1,2,4]triazolo[1,5-a]pyridine and (+)-2-{(E)-2-[5-methoxy-6-(4-methyl-1H-imidazol-1-yl)pyridin-3-yl]vinyl}-8-(4-methoxyphenyl)-5,6,7,8-tetrahydro-[1,2,4]triazolo[1,5-a]pyridine

[Formula 170]

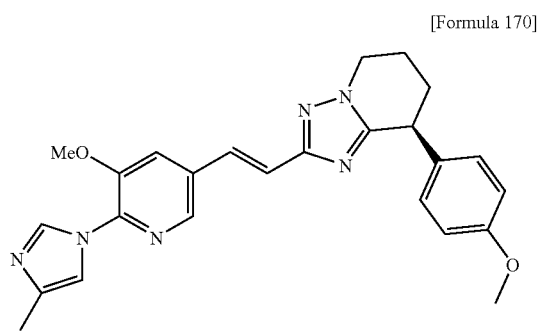

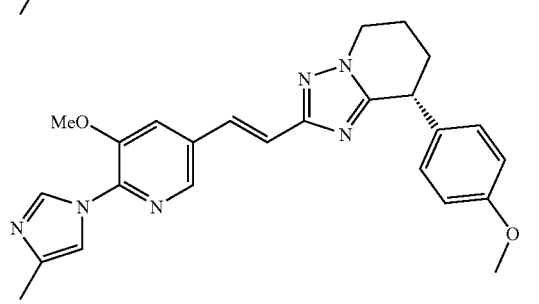

Synthesis of 1-amino-3-(4-methoxyphenyl)piperidin-2-one 0.910 g of the title compound was obtained from methyl 4-methoxyphenylacetate (5 g) according to the method in Examples 20 and 21. The property value of the compound is as follows.

ESI-MS; m/z 221 [M$^+$+H].

Synthesis of (−)-2-{(E)-2-[5-methoxy-6-(4-methyl-1H-imidazol-1-yl)pyridin-3-yl]vinyl}-8-(4-methoxyphenyl)-5,6,7,8-tetrahydro-[1,2,4]triazolo[1,5-a]pyridine and (+)-2-{(E)-2-[5-methoxy-6-(4-methyl-1H-imidazol-1-yl)pyridin-3-yl]vinyl}-8-(4-methoxyphenyl)-5,6,7,8-tetrahydro-[1,2,4]triazolo[1,5-a]pyridine A racemate of the title compound was obtained from (E)-3-[5-methoxy-6-(4-methyl-1H-imidazol-1-yl)pyridin-3-yl]acrylic acid (250 mg) and 1-amino-3-(4-methoxyphenyl)piperidin-2-one (162 mg) according to the method in Examples 168 and 169. The resulting racemate was separated by CHIRALPAK™ AD-H manufactured by Daicel Chemical Industries, Ltd. (2 cm×25 cm; mobile phase: ethanol) to obtain the title optically active compound with a retention time of 14 minutes and negative optical rotation (9.6 mg, >99% ee) and the title optically active compound with a retention time of 20 minutes and positive optical rotation (10.4 mg, >99% ee).

The property values of the title compound with negative optical rotation are as follows.

ESI-MS; m/z 443 [M$^+$+H]. $^1$H-NMR (CDCl$_3$) δ (ppm): 2.01-2.17 (m, 2H), 2.18-2.28 (m, 1H), 2.29 (d, J=1.2 Hz, 3H), 2.30-2.39 (m, 1H), 3.80 (s, 3H), 3.97 (s, 3H), 4.25-4.32 (m, 3H), 6.85-6.90 (m, 2H), 7.04-7.07 (m, 2H), 7.10 (d, J=16.0 Hz, 1H), 7.46 (d, J=2.0 Hz, 1H), 7.51 (d, J=16.0 Hz, 1H), 7.52 (s, 1H), 8.14 (d, J=2.0 Hz, 1H), 8.34 (d, J=1.2 Hz, 1H).

The property values of the title compound with positive optical rotation are as follows.

ESI-MS; m/z 443 [M$^+$+H]. $^1$H-NMR (CDCl$_3$) δ (ppm): 2.01-2.17 (m, 2H), 2.18-2.28 (m, 1H), 2.29 (d, J=1.2 Hz, 3H), 2.30-2.39 (m, 1H), 3.80 (s, 3H), 3.97 (s, 3H), 4.25-4.32 (m, 3H), 6.85-6.90 (m, 2H), 7.04-7.07 (m, 2H), 7.10 (d, J=16.0 Hz, 1H), 7.46 (d, J=2.0 Hz, 1H), 7.51 (d, J=16.0 Hz, 1H), 7.52 (s, 1H), 8.14 (d, J=2.0 Hz, 1H), 8.34 (d, J=1.2 Hz, 1H).

Examples 301 and 302

Synthesis of (−)-2-{(E)-2-[5-methoxy-6-(4-methyl-1H-imidazol-1-yl)pyridin-3-yl]vinyl}-8-(2,4,6-trifluorophenyl)-5,6,7,8-tetrahydro-[1,2,4]triazolo[1,5-a]pyridine and (+)-2-{(E)-2-[5-methoxy-6-(4-methyl-1H-imidazol-1-yl)pyridin-3-yl]vinyl}-8-(2,4,6-trifluorophenyl)-5,6,7,8-tetrahydro-[1,2,4]triazolo[1,5-a]pyridine

[Formula 171]

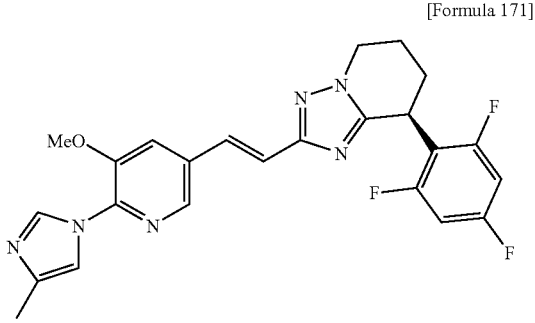

311

-continued

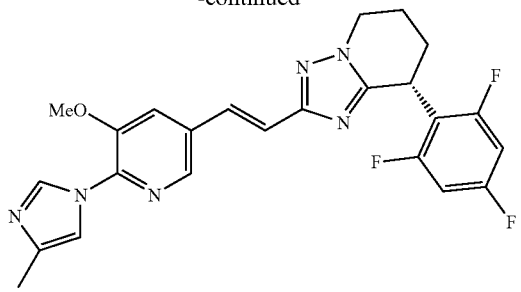

A racemate of the title compound was obtained from (E)-3-[5-methoxy-6-(4-methyl-1H-imidazol-1-yl)pyridin-3-yl]acrylic acid (250 mg) and 1-amino-3-(4-methoxyphenyl)piperidin-2-one (180 mg) according to the method in Examples 168 and 169. The resulting racemate was separated by CHIRALPAK™ AD-H manufactured by Daicel Chemical Industries, Ltd. (2 cm×25 cm; mobile phase: ethanol) to obtain the title optically active compound with a retention time of 6.4 minutes and negative optical rotation (48.6 mg, >99% ee) and the title optically active compound with a retention time of 8.1 minutes and positive optical rotation (47.7 mg, >99% ee).

The property values of the title compound with negative optical rotation are as follows.

ESI-MS; m/z 467 [M$^+$+H]. $^1$H-NMR (CDCl$_3$) δ (ppm): 2.04-2.20 (m, 3H), 2.29 (s, 3H), 2.29-2.37 (m, 1H), 3.96 (s, 3H), 4.19-4.27 (m, 1H), 4.34-4.40 (m, 1H), 4.54-4.58 (m, 1H), 6.70 (t, J=8.4 Hz, 2H), 7.06 (d, J=16.0 Hz, 1H), 7.45 (d, J=16.0 Hz, 1H), 7.46 (s, 1H), 7.52 (s, 1H), 8.13 (s, 1H), 8.34 (s, 1H).

The property values of the title compound with positive optical rotation are as follows.

ESI-MS; m/z 467 [M$^+$+H]. $^1$H-NMR (CDCl$_3$) δ (ppm): 2.04-2.20 (m, 3H), 2.29 (s, 3H), 2.29-2.37 (m, 1H), 3.96 (s, 3H), 4.19-4.27 (m, 1H), 4.34-4.40 (m, 1H), 4.54-4.58 (m, 1H), 6.70 (t, J=8.4 Hz, 2H), 7.06 (d, J=16.0 Hz, 1H), 7.45 (d, J=16.0 Hz, 1H), 7.46 (s, 1H), 7.52 (s, 1H), 8.13 (s, 1H), 8.34 (s, 1H).

Examples 303 and 304

Synthesis of (+)-8-(2-bromo-4-fluorophenyl)-2-{(E)-2-[4-methoxy-5-(4-methyl-1H-imidazol-1-yl)pyridin-2-yl]vinyl}-5,6,7,8-tetrahydro[1,2,4]triazolo[1,5-a]pyridine and (−)-8-(2-bromo-4-fluorophenyl)-2-{(E)-2-[4-methoxy-5-(4-methyl-1H-imidazol-1-yl)pyridin-2-yl]vinyl}-5,6,7,8-tetrahydro[1,2,4]triazolo[1,5-a]pyridine

[Formula 172]

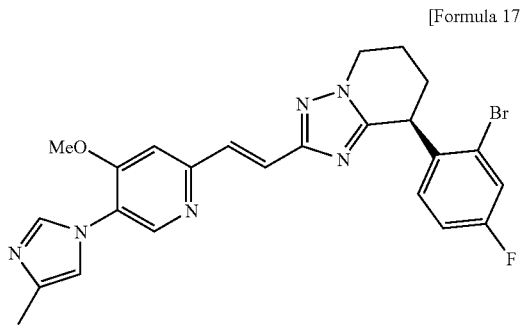

312

-continued

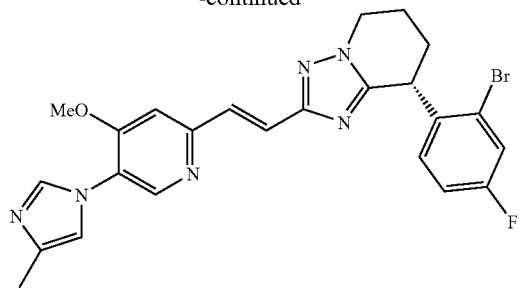

A racemate of the title compound was obtained from (E)-3-[4-methoxy-5-(4-methyl-1H-imidazol-1-yl)pyridin-2-yl]acrylic acid (63.2 mg) and 1-amino-3-(2-bromo-4-fluorophenyl)piperidin-2-one (91.1 mg) according to the method in Examples 220 and 221. The resulting racemate was separated by CHIRALPAK™ IB manufactured by Daicel Chemical Industries, Ltd. (2 cm×25 cm; mobile phase: ethanol) to obtain the title optically active compound with a retention time of 6.4 minutes and negative optical rotation (6.2 mg, >99% ee) and the title optically active compound with a retention time of 7.6 minutes and positive optical rotation (5.5 mg, >99% ee).

The property values of the title compound with negative optical rotation are as follows.

ESI-MS; m/z 509 [M$^+$+H]. $^1$H-NMR (CDCl$_3$) δ (ppm): 1.95-2.05 (m, 1H), 2.06-2.12 (m, 2H), 2.30 (d, J=0.8 Hz, 3H), 2.35-2.42 (m, 1H), 3.90 (s, 3H), 4.31 (t, J=6.0 Hz, 2H), 4.71 (t, J=6.8 Hz, 1H), 6.85-6.91 (m, 1H), 6.91 (d, J=0.8 Hz, 1H), 6.98 (dd, J=8.0, 2.4 Hz, 1H), 7.00 (d, J=1.2 Hz, 1H), 7.36 (dd, J=8.0, 2.8 Hz, 1H), 7.53 (d, J=16.0 Hz, 1H), 7.60 (d, J=16.0 Hz, 1H), 7.68 (d, J=1.2 Hz, 1H), 8.42 (s, 1H).

The property values of the title compound with positive optical rotation are as follows.

ESI-MS; m/z 509 [M$^+$+H]. $^1$H-NMR (CDCl$_3$) δ (ppm): 1.95-2.05 (m, 1H), 2.06-2.12 (m, 2H), 2.30 (d, J=0.8 Hz, 3H), 2.35-2.42 (m, 1H), 3.90 (s, 3H), 4.31 (t, J=6.0 Hz, 2H), 4.71 (t, J=6.8 Hz, 1H), 6.85-6.91 (m, 1H), 6.91 (d, J=0.8 Hz, 1H), 6.98 (dd, J=8.0, 2.4 Hz, 1H), 7.00 (d, J=1.2 Hz, 1H), 7.36 (dd, J=8.0, 2.8 Hz, 1H), 7.53 (d, J=16.0 Hz, 1H), 7.60 (d, J=16.0 Hz, 1H), 7.68 (d, J=1.2 Hz, 1H), 8.42 (s, 1H).

Example 305

Synthesis of 2-(4-bromobenzyl)-8-[1-[3-methoxy-4-(4-methyl-1H-imidazol-1-yl)phenyl]-(E)-methylidene]-5,6,7,8-tetrahydro-[1,2,4]triazolo[1,5-a]pyridine

[Formula 173]

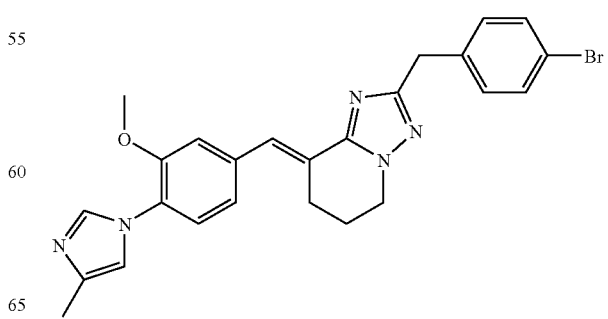

(1) Synthesis of 5-chloro-2-[1-[3-methoxy-4-(4-methyl-1H-imidazol-1-yl)phenyl]-(E)-methylidene]-pentanoic acid hydrazide 5-Chloro-2-[1-[3-methoxy-4-(4-methyl-1H-imidazol-1-yl)phenyl]-(E)-methylidene]pentanoic acid (CAS No. 870843-27-9, 10 g) was dissolved in dichloromethane (130 mL). BOPCl (4.53 g), IPEA (12.3 g) and tert-butyl carbazate (2.82 g) were added and the reaction solution was stirred at room temperature for three hours. Water and ethyl acetate were added to the reaction solution, and the organic layer was separated. The organic layer was washed with a 1 N sodium hydroxide solution and 1 N hydrochloric acid in this order. The organic layer was dried over magnesium sulfate and concentrated under reduced pressure. A solution of 4 N hydrochloric acid in ethyl acetate (100 mL) was added to the residue, and the reaction solution was stirred at room temperature for two hours. The reaction solution was concentrated under reduced pressure to obtain 3.87 g of a crude product of the title compound. The property value of the compound is as follows.

ESI-MS; m/z 349 [M$^+$+H].

(2) Synthesis of 2-(4-bromophenyl)-N-{3-[1-[3-methoxy-4-(4-methyl-1H-imidazol-1-yl)phenyl]-(E)-methylidene]-2-oxopiperidin-1-yl}acetamide EDC (109 mg), HOBT (76.9 mg) and IPEA (408 µL) were added to a mixture of 4-bromophenylacetic acid (102 mg), 5-chloro-2-[1-[3-methoxy-4-(4-methyl-1H-imidazol-1-yl)phenyl]-(E)-methylidene]-pentanoic acid hydrazide (200 mg) and DMF (4 mL), and the reaction solution was stirred at room temperature for 14 hours. The reaction solution was heated to 80° C. and stirred for two hours. The reaction solution was brought to room temperature. A saturated sodium bicarbonate solution was added, followed by separatory extraction with ethyl acetate. The organic layer was dried over magnesium sulfate and concentrated under reduced pressure. The residue was purified by silica gel chromatography (carrier: Chromatorex NH; elution solvent: heptane:ethyl acetate=1:1→ethyl acetate→ethyl acetate:methanol=8:1) to obtain the title compound (111 mg). The property value of the compound is as follows.

ESI-MS; m/z 508 [M$^+$+H].

(3) Synthesis of 2-(4-bromobenzyl)-8-[1-[3-methoxy-4-(4-methyl-1H-imidazol-1-yl)phenyl]-(E)-methylidene]-5,6,7,8-tetrahydro-[1,2,4]triazolo[1,5-a]pyridine Phosphorus oxychloride (2.4 mL) was added to 2-(4-bromophenyl)-N-{3-[1-[3-methoxy-4-(4-methyl-1H-imidazol-1-yl)phenyl]-(E)-methylidene]-2-oxopiperidin-1-yl}acetamide (111 mg), and the reaction solution was stirred at 100° C. for one hour. The reaction solution was concentrated under reduced pressure. The residue was diluted with acetic acid (1 mL) and then ammonium acetate (336 mg) was added. The reaction solution was stirred at 140° C. for one hour and 30 minutes. Ethyl acetate and a sodium bicarbonate solution were added to the reaction solution, and the organic layer was separated. The organic layer was dried over magnesium sulfate and then concentrated under reduced pressure. The residue was purified by silica gel chromatography (carrier: Chromatorex NH; elution solvent: heptane:ethyl acetate=2:1→ethyl acetate) to obtain the title compound (50 mg). The property values of the compound are as follows.

$^1$H-NMR (CDCl$_3$) δ (ppm): 2.11-2.16 (m, 2H), 2.30 (s, 3H), 2.92-2.95 (m, 2H), 3.85 (s, 3H), 4.04 (s, 2H), 4.22 (t, J=4 Hz, 2H), 6.93 (s, 1H), 7.03-7.06 (m, 2H), 7.24-7.26 (m, 3H), 7.41-7.44 (m, 2H), 7.66 (s, 1H), 7.72 (s, 1H).

Example 306

Synthesis of 2-(3-bromobenzyl)-8-[1-[3-methoxy-4-(4-methyl-1H-imidazol-1-yl)phenyl]-(E)-methylidene]-5,6,7,8-tetrahydro-[1,2,4]triazolo[1,5-a]pyridine

[Formula 174]

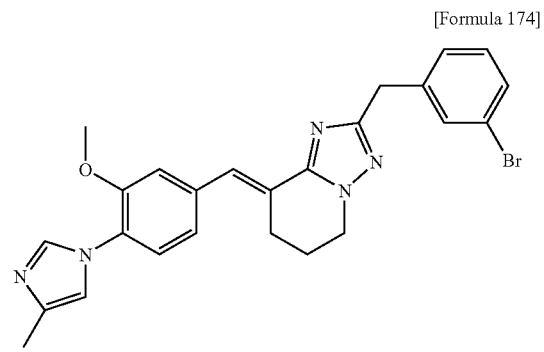

The title compound (38 mg) was obtained using 3-bromophenylacetic acid (102 mg) as a starting material according to the method in Example 305.

The property values of the title compound are as follows.
$^1$H-NMR (CDCl$_3$) δ (ppm): 2.11-2.17 (m, 2H), 2.30 (s, 3H), 2.92-2.96 (m, 2H), 3.85 (s, 3H), 4.06 (s, 2H), 4.24 (t, J=5.6 Hz, 2H), 6.93 (s, 1H), 7.03-7.07 (m, 2H), 7.16-7.36 (m, 4H), 7.51 (s, 2H), 7.67 (s, 1H), 7.72 (s, 1H).

Example 307

Synthesis of 2-(2-bromobenzyl)-8-[1-[3-methoxy-4-(4-methyl-1H-imidazol-1-yl)phenyl]-(E)-methylidene]-5,6,7,8-tetrahydro-[1,2,4]triazolo[1,5-a]pyridine

[Formula 175]

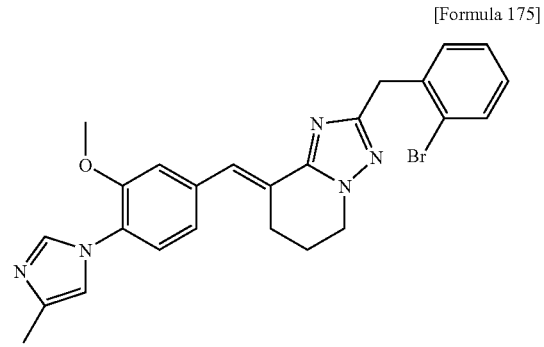

The title compound (43 mg) was obtained using 2-bromophenylacetic acid (102 mg) as a starting material according to the method in Example 305.

The property values of the title compound are as follows.
$^1$H-NMR (CDCl$_3$) δ (ppm): 2.11-2.17 (m, 2H), 2.30 (s, 3H), 2.93-2.96 (m, 2H), 3.85 (s, 3H), 4.22-4.25 (m, 4H), 6.93

(s, 1H), 7.04-7.13 (m, 3H), 7.25-7.34 (m, 3H), 7.56-7.59 (m, 1H), 7.68 (s, 1H), 7.70 (s, 1H).

Examples 308 and 309

Synthesis of 2-[(S)-1-(4-fluorophenyl)ethyl]-8-[1-[3-methoxy-4-(4-methyl-1H-imidazol-1-yl)phenyl]-(E)-methylidene]-5,6,7,8-tetrahydro-[1,2,4]triazolo[1,5-a]pyridine and 2-[(R)-1-(4-fluorophenyl)ethyl]-8-[1-[3-methoxy-4-(4-methyl-1H-imidazol-1-yl)phenyl]-(E)-methylidene]-5,6,7,8-tetrahydro-[1,2,4]triazolo[1,5-a]pyridine

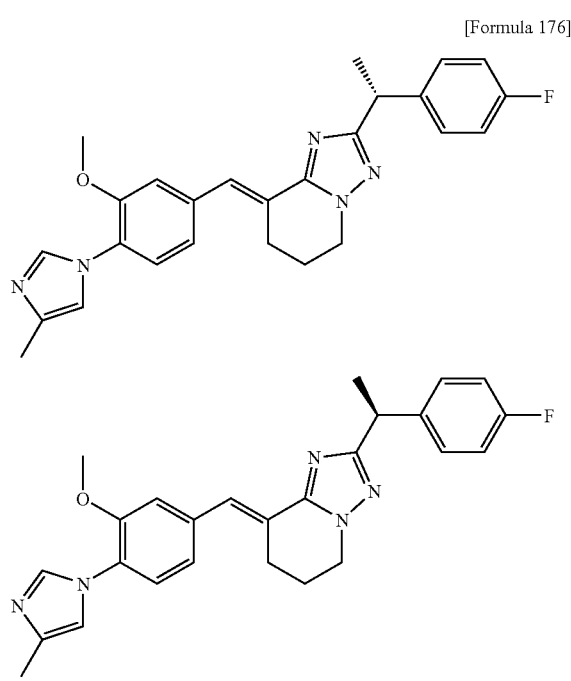

[Formula 176]

A racemate of the title compound (64 mg) was obtained using 4-fluoro-α-methyl-phenylacetic acid (109 mg) as a starting material according to the method in Example 305. The resulting racemate (64 mg) was separated by CHIRALPAK™ IB manufactured by Daicel Chemical Industries, Ltd. (2 cm×25 cm, mobile phase: hexane:ethanol=8:2, flow rate: 10 mL/min) to obtain the title optically active compound with a retention time of 26 minutes and positive optical rotation (15 mg) and the title optically active compound with a retention time of 31 minutes and negative optical rotation (16 mg).

The property values of the title optically active compound with a retention time of 26 minutes are as follows.

¹H-NMR (CDCl₃) δ (ppm): 1.70 (d, J=7.2 Hz, 3H), 2.10-2.16 (m, 2H), 2.23 (m, 3H), 2.90-2.94 (m, 2H), 3.85 (s, 3H), 4.22-4.30 (m, 3H), 6.93-7.06 (m, 5H), 7.24 (s, 1H), 7.35-7.38 (m, 2H), 7.66 (s, 1H), 7.71 (s, 1H).

The property values of the title optically active compound with a retention time of 31 minutes are as follows.

¹H-NMR (CDCl₃) δ (ppm): 1.70 (d, J=7.2 Hz, 3H), 2.10-2.16 (m, 2H), 2.23 (m, 3H), 2.90-2.94 (m, 2H), 3.85 (s, 3H), 4.22-4.30 (m, 3H), 6.93-7.06 (m, 5H), 7.24 (s, 1H), 7.35-7.38 (m, 2H), 7.66 (s, 1H), 7.71 (s, 1H).

Examples 310 and 311

Synthesis of (+) and (−)-2-{(E)-2-[3-methoxy-4-(4-methyl-1H-imidazol-1-yl)phenyl]vinyl}-8-(2-trifluoromethylphenyl)-5,6,7,8-tetrahydro-[1,2,4]triazolo[1,5-a]pyridine

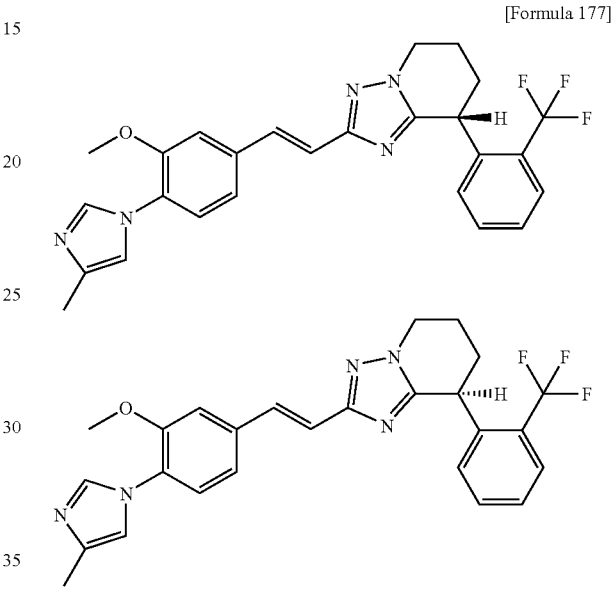

[Formula 177]

457 mg of the racemic title compound was obtained from 1-amino-3-(2-trifluoromethylphenyl)piperidin-2-one (467 mg) and (E)-3-[3-methoxy-4-(4-methyl-1H-imidazol-1-yl)phenyl]acrylic acid (500 mg) by the same method as in Examples 194 and 195. The racemic title compound (457 mg) was separated by CHIRALPAK™ IB manufactured by Daicel Chemical Industries, Ltd. (2 cm×25 cm; mobile phase: hexane:ethanol=1:1) to obtain the title optically active compound with positive optical rotation and a retention time of 12 minutes (209 mg) and the title optically active compound with negative optical rotation and a retention time of 18 minutes (206 mg).

The property values of the title optically active compound with a retention time of 12 minutes are as follows.

ESI-MS; m/z 480 [M⁺+H]. ¹H-NMR (CDCl₃) δ (ppm): 1.89-2.00 (m, 1H), 2.08-2.35 (m, 2H), 2.29 (d, J=0.8 Hz, 3H), 2.40-2.52 (m, 1H), 3.84 (s, 3H), 4.27-4.40 (m, 2H), 4.70 (dd, J=6.4, 8.8 Hz, 1H), 6.89-6.92 (m, 1H), 7.01-7.08 (m, 2H), 7.11-7.16 (m, 2H), 7.21 (d, J=8.0 Hz, 1H), 7.40 (dd, J=7.6, 7.6 Hz, 1H), 7.45-7.52 (m, 2H), 7.69 (d, J=1.2 Hz, 1H), 7.73 (d, J=8.0 Hz, 1H).

The property values of the title optically active compound with a retention time of 18 minutes are as follows.

ESI-MS; m/z 480 [M⁺+H]. ¹H-NMR (CDCl₃) δ (ppm): 1.89-2.00 (m, 1H), 2.08-2.35 (m, 2H), 2.29 (d, J=0.8 Hz, 3H), 2.40-2.52 (m, 1H), 3.84 (s, 3H), 4.27-4.40 (m, 2H), 4.70 (dd, J=6.4, 8.8 Hz, 1H), 6.89-6.92 (m, 1H), 7.01-7.08 (m, 2H), 7.11-7.16 (m, 2H), 7.21 (d, J=8.0 Hz, 1H), 7.40 (dd, J=7.6, 7.6 Hz, 1H), 7.45-7.52 (m, 2H), 7.69 (d, J=1.2 Hz, 1H), 7.73 (d, J=8.0 Hz, 1H).

Examples 312 and 313

Synthesis of (+) and (−)-2-{(E)-2-[2-fluoro-5-methoxy-4-(4-methyl-1H-imidazol-1-yl)phenyl]vinyl}-8-(2-trifluoromethylphenyl)-5,6,7,8-tetrahydro-[1,2,4]triazolo[1,5-a]pyridine

[Formula 178]

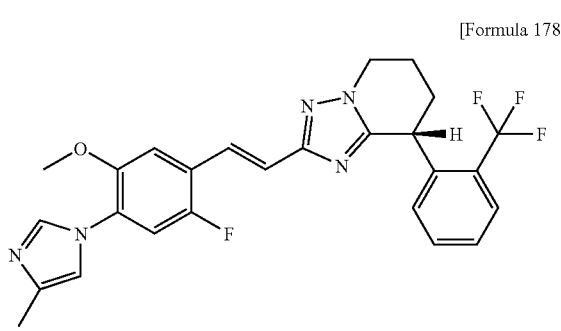

292 mg of the racemic title compound was obtained from 1-amino-3-(2-trifluoromethylphenyl)piperidin-2-one (514 mg) and (E)-3-[2-fluoro-5-methoxy-4-(4-methyl-1H-imidazol-1-yl)phenyl]acrylic acid (500 mg) by the same method as in Examples 194 and 195. The racemic title compound (18 mg) was separated by CHIRALPAK™ IB manufactured by Daicel Chemical Industries, Ltd. (2 cm×25 cm; mobile phase: hexane:ethanol=1:1) to obtain the title optically active compound with positive optical rotation and a retention time of 17 minutes (6 mg) and the title optically active compound with negative optical rotation and a retention time of 32 minutes (6 mg).

The property value of the title optically active compound with a retention time of 17 minutes is as follows.

ESI-MS; m/z 498 [M⁺+H].

The property values of the title optically active compound with a retention time of 32 minutes are as follows.

ESI-MS; m/z 498 [M⁺+H]. ¹H-NMR (CDCl₃) δ (ppm): 1.89-2.02 (m, 1H), 2.10-2.34 (m, 2H), 2.29 (s, 3H), 2.40-2.52 (m, 1H), 3.82 (s, 3H), 4.28-4.41 (m, 2H), 4.69 (dd, J=6.0, 8.0 Hz, 1H), 6.91 (s, 1H), 6.97-7.06 (m, 2H), 7.09-7.20 (m, 2H), 7.40 (dd, J=7.6, 7.6 Hz, 1H), 7.49 (dd, J=7.6, 7.6 Hz, 1H), 7.58 (d, J=16.4 Hz, 1H), 7.69-7.78 (m, 2H).

Examples 314 and 315

Synthesis of (+) and (−)-2-{(E)-2-[3-methoxy-4-(4-methyl-1H-imidazol-1-yl)phenyl]vinyl}-8-(2-trifluoromethylphenyl)-5,6,7,8-tetrahydro-[1,2,4]triazolo[1,5-a]pyridin-8-ol

[Formula 179]

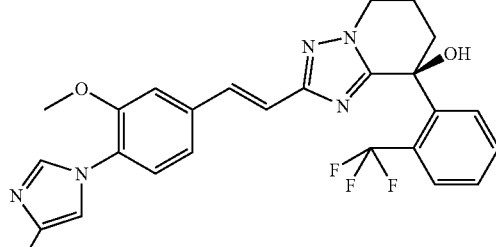

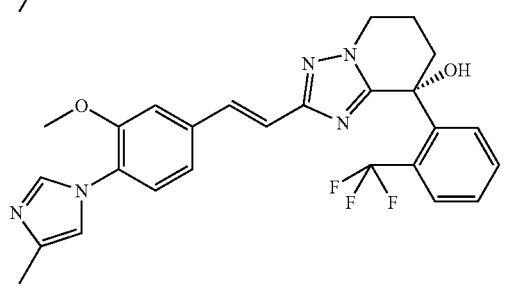

123 mg of the racemic title compound was obtained by the same method as in Examples 53 and 54 from the optically active compound synthesized by the method in Examples 310 and 311 with positive optical rotation and a retention time of 12 minutes, 2-{(E)-2-[3-methoxy-4-(4-methyl-1H-imidazol-1-yl)phenyl]vinyl}-8-(2-trifluoromethylphenyl)-5,6,7,8-tetrahydro-[1,2,4]triazolo[1,5-a]pyridine (183 mg). The racemic title compound (123 mg) was separated by CHIRALPAK™ IA manufactured by Daicel Chemical Industries, Ltd. (2 cm×25 cm; mobile phase: hexane:ethanol=1:1) to obtain the title optically active compound with positive optical rotation and a retention time of 13 minutes (47 mg) and the title optically active compound with negative optical rotation and a retention time of 21 minutes (48 mg).

The property values of the title optically active compound with a retention time of 13 minutes are as follows.

ESI-MS; m/z 496 [M⁺+H]. ¹H-NMR (CDCl₃) δ (ppm): 2.02-2.13 (m, 1H), 2.29 (d, J=0.8 Hz, 3H), 2.25-2.58 (m, 3H), 3.80 (s, 3H), 4.12-4.24 (m, 1H), 4.30-4.40 (m, 1H), 4.74 (brs, 1H), 6.85-6.90 (m, 1H), 6.95-7.07 (m, 3H), 7.15 (d, J=8.0 Hz, 1H), 7.40 (d, J=16.4 Hz, 1H), 7.46 (dd, J=7.6, 7.6 Hz, 1H), 7.58 (dd, J=7.6, 7.6 Hz, 1H), 7.66 (d, J=1.2 Hz, 1H), 7.74 (d, J=8.0 Hz, 1H), 7.79 (brs, 1H).

The property values of the title optically active compound with a retention time of 21 minutes are as follows.

ESI-MS; m/z 496 [M⁺+H]. ¹H-NMR (CDCl₃) δ (ppm): 2.02-2.13 (m, 1H), 2.29 (d, J=0.8 Hz, 3H), 2.25-2.58 (m, 3H), 3.80 (s, 3H), 4.12-4.24 (m, 1H), 4.30-4.40 (m, 1H), 4.74 (brs, 1H), 6.85-6.90 (m, 1H), 6.95-7.07 (m, 3H), 7.15 (d, J=8.0 Hz, 1H), 7.40 (d, J=16.4 Hz, 1H), 7.46 (dd, J=7.6, 7.6 Hz, 1H),

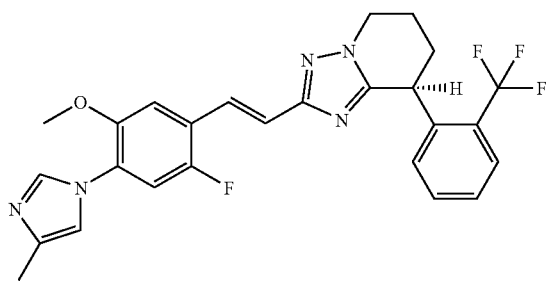

7.58 (dd, J=7.6, 7.6 Hz, 1H), 7.66 (d, J=1.2 Hz, 1H), 7.74 (d, J=8.0 Hz, 1H), 7.79 (brs, 1H).

Examples 316 and 317

Synthesis of (+) and (−)-2-{(E)-2-[3-methoxy-4-(4-methyl-1H-imidazol-1-yl)phenyl]vinyl}-7-(2-trifluoromethylphenyl)-6,7-dihydro-5H-pyrrolo[1,2-b][1,2,4]triazole

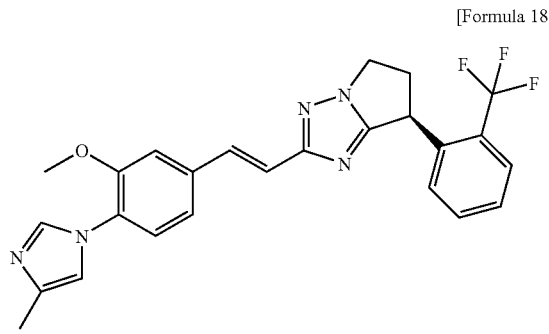

[Formula 180]

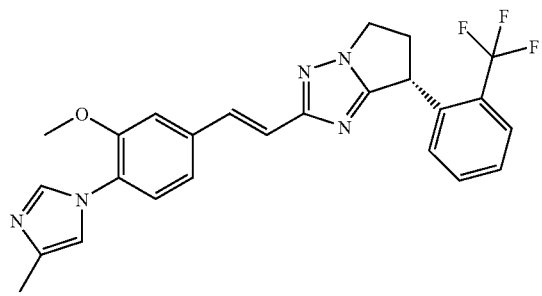

254 mg of the title compound as a racemate was obtained from ethyl (E)-3-[3-methoxy-4-(4-methyl-1H-imidazol-1-yl)phenyl]acrylimidate dihydrochloride (1.20 g) and 4-chloro-2-(2-trifluoromethylphenyl)butyric acid hydrazide hydrochloride (1.25 g) by the same method as in Examples 140 and 141. The racemic title compound (254 mg) was separated by CHIRALPAK™ IB manufactured by Daicel Chemical Industries, Ltd. (2 cm×25 cm; mobile phase: hexane:ethanol=4:1) to obtain the title optically active compound with positive optical rotation and a retention time of 28 minutes (55 mg) and the title optically active compound with negative optical rotation and a retention time of 48 minutes (40 mg).

The property value of the title optically active compound with a retention time of 28 minutes is as follows.

ESI-MS; m/z 466 [M$^+$+H].

The property value of the title optically active compound with a retention time of 48 minutes is as follows.

ESI-MS; m/z 466 [M$^+$+H].

Examples 318 and 319

Synthesis of (+) and (−)-2-{(E)-2-[6-methoxy-5-(4-methyl-1H-imidazol-1-yl)pyridin-2-yl]vinyl}-8-(o-tolyl)-5,6,7,8-tetrahydro[1,2,4]triazolo[1,5-a]pyridine

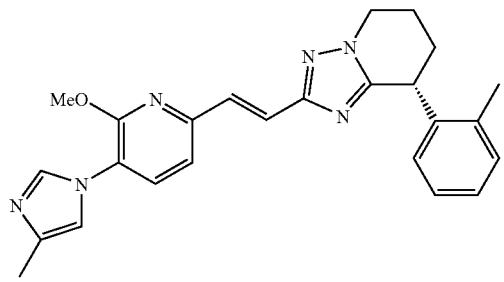

[Formula 181]

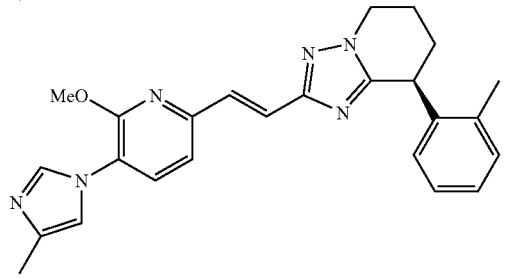

Synthesis of 1-amino-3-o-tolylpiperidin-2-one 339 mg of the title compound was obtained using o-tolylacetic acid (1 g) as a starting material according to the method in Examples 20 and 21. The property values of the compound are as follows.

ESI-MS; m/z 205 [M$^+$+H].

$^1$H-NMR (CDCl$_3$) δ (ppm): 1.70-2.20 (m, 4H), 3.33 (s, 3H), 3.40-3.98 (m, 3H), 4.63 (brs, 2H), 6.66-7.38 (m, 4H).

Synthesis of (+) and (−)-2-{(E)-2-[6-methoxy-5-(4-methyl-1H-imidazol-1-yl)pyridin-2-yl]vinyl}-8-(o-tolyl)-5,6,7,8-tetrahydro[1,2,4]triazolo[1,5-a]pyridine 175.7 mg of a racemate of the title compound was obtained using 1-amino-3-o-tolylpiperidin-2-one (339 mg) as a starting material according to the method in Examples 168 and 169. The resulting racemate (100 mg) was separated by CHIRALPAK™ IB manufactured by Daicel Chemical Industries, Ltd. (2 cm×25 cm; mobile phase: ethanol) to obtain a (+)-isomer of the title optically active compound with a retention time of 12 minutes (42.6 mg; 99% ee) and a (−)-isomer of the title optically active compound with a retention time of 25 minutes (44.7 mg; 99% ee).

The property values of the title optically active compound with a retention time of 12 minutes are as follows.

ESI-MS; m/z 427 [M$^+$+H].

$^1$H-NMR (CDCl$_3$) δ (ppm): 1.76-2.52 (m, 10H), 4.04 (s, 3H), 4.21-4.40 (m, 2H), 4.55 (t, J=6.0 Hz, 1H), 6.72 (d, J=7.6

Hz, 1H), 6.88-7.01 (m, 2H), 7.06-7.32 (m, 3H), 7.40-7.51 (m, 2H), 7.66 (d, J=15.6 Hz, 1H), 7.77 (d, J=1.2 Hz, 1H).

The property values of the title optically active compound with a retention time of 25 minutes are as follows.

ESI-MS; m/z 427 [M$^+$+H].

$^1$H-NMR (CDCl$_3$) δ (ppm): 1.76-2.52 (m, 10H), 4.04 (s, 3H), 4.21-4.40 (m, 2H), 4.55 (t, J=6.0 Hz, 1H), 6.72 (d, J=7.6 Hz, 1H), 6.88-7.01 (m, 2H), 7.06-7.32 (m, 3H), 7.40-7.51 (m, 2H), 7.66 (d, J=15.6 Hz, 1H), 7.77 (d, J=1.2 Hz, 1H).

Examples 320 and 321

Synthesis of (+) and (−)-2-{(E)-2-[6-methoxy-5-(4-methyl-1H-imidazol-1-yl)pyridin-2-yl]vinyl}-8-(3-trifluoromethylphenyl)-5,6,7,8-tetrahydro[1,2,4]triazolo[1,5-a]pyridine

[Formula 182]

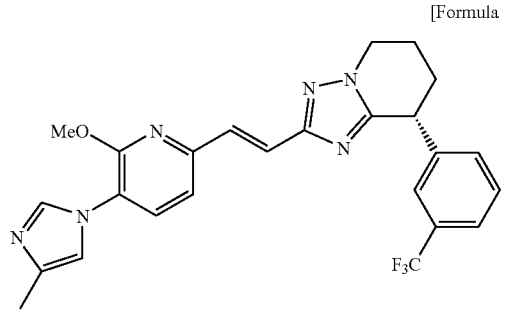

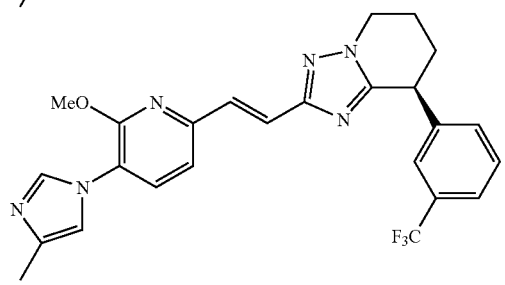

Synthesis of 1-amino-3-(3-trifluoromethylphenyl)piperidin-2-one 282.7 mg of the title compound was obtained using methyl 3-(trifluoromethyl)phenylacetate (1 g) as a starting material according to the method in Examples 20 and 21. The property value of the compound is as follows.

ESI-MS; m/z 259 [M$^+$+H].

Synthesis of (+) and (−)-2-{(E)-2-[6-methoxy-5-(4-methyl-1H-imidazol-1-yl)pyridin-2-yl]vinyl}-8-(3-trifluoromethylphenyl)-5,6,7,8-tetrahydro[1,2,4]triazolo[1,5-a]pyridine 60.7 mg of a racemate of the title compound was obtained using 1-amino-3-(3-trifluoromethylphenyl)piperidin-2-one (282.7 mg) as a starting material according to the method in Examples 168 and 169. The resulting racemate (60.7 mg) was separated by CHIRALPAK™ IB manufactured by Daicel Chemical Industries, Ltd. (2 cm×25 cm; mobile phase: hexane:ethanol=1:1) to obtain a (+)-isomer of the title optically active compound with a retention time of 16 minutes (20 mg;

>99% ee) and a (−)-isomer of the title optically active compound with a retention time of 52 minutes (19.1 mg; >99% ee).

The property values of the title optically active compound with a retention time of 16 minutes are as follows.

ESI-MS; m/z 481 [M$^+$+H].

$^1$H-NMR (CDCl$_3$) δ (ppm): 1.98-2.48 (m, 7H), 4.05 (s, 3H), 4.26-4.45 (m, 3H), 6.91-6.99 (m, 2H), 7.32 (d, J=8.0 Hz, 1H), 7.41-7.52 (m, 4H), 7.56 (d, J=8.0 Hz, 1H), 7.65 (d, J=15.6 Hz, 1H), 7.78 (brs, 1H).

The property values of the title optically active compound with a retention time of 52 minutes are as follows.

ESI-MS; m/z 481 [M$^+$+H].

$^1$H-NMR (CDCl$_3$) δ (ppm): 1.98-2.48 (m, 7H), 4.05 (s, 3H), 4.26-4.45 (m, 3H), 6.91-6.99 (m, 2H), 7.32 (d, J=8.0 Hz, 1H), 7.41-7.52 (m, 4H), 7.56 (d, J=8.0 Hz, 1H), 7.65 (d, J=15.6 Hz, 1H), 7.78 (brs, 1H).

Examples 322 and 323

Synthesis of [2-((+)-2-{(E)-2-[6-methoxy-5-(4-methyl-1H-imidazol-1-yl)pyridin-2-yl]vinyl}-5,6,7,8-tetrahydro[1,2,4]triazolo[1,5-a]pyridin-8-yl)phenyl]methanol and [2-((+)-2-{(E)-2-[6-methoxy-5-(4-methyl-1H-imidazol-1-yl)pyridin-2-yl]vinyl}-5,6,7,8-tetrahydro[1,2,4]triazolo[1,5-a]pyridin-8-yl)phenyl]methanol

[Formula 183]

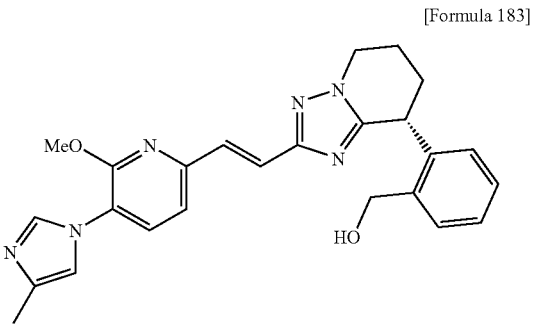

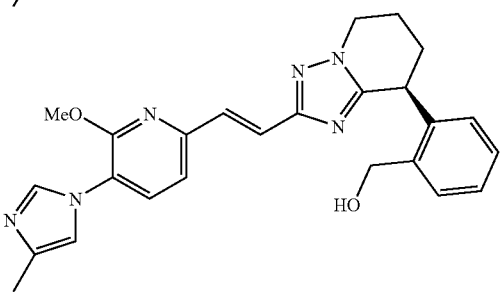

Synthesis of 5-chloro-2-(2-hydroxymethylphenyl)pentanoic acid hydrazide 1.29 g of the title compound was obtained using 3-isochromanone (25 g) as a starting material according to the method in Examples 1 and 2. The property value of the compound is as follows.

ESI-MS; m/z 257 [M$^+$+H].

Synthesis of [2-((+)-2-{(E)-2-[6-methoxy-5-(4-methyl-1H-imidazol-1-yl)pyridin-2-yl]vinyl}-5,6,7,8-tetrahydro[1,2,4]triazolo[1,5-a]pyridin-8-yl)phenyl]methanol and [2-((+)-2-{(E)-2-[6-methoxy-5-(4-methyl-1H-imidazol-1-yl)pyridin-2-yl]vinyl}-5,6,7,8-tetrahydro[1,2,4]triazolo[1,5-a]pyridin-8-yl)phenyl]methanol 4.4 mg of a racemate of the title compound was obtained using 5-chloro-2-(2-hydroxymethylphenyl)pentanoic acid hydrazide (388 mg) as a starting material according to the method in Examples 1 and 2. The resulting racemate (4.4 mg) was separated by CHIRALPAK™ IB manufactured by Daicel Chemical Industries, Ltd. (2 cm×25 cm; mobile phase: ethanol) to obtain a (+)-isomer of the title optically active compound with a retention time of 11 minutes (0.91 mg; >99% ee) and a (−)-isomer of the title optically active compound with a retention time of 17 minutes (0.89 mg; >99% ee).

The property values of the title optically active compound with a retention time of 11 minutes are as follows.

ESI-MS; m/z 443 [M$^+$+H].

$^1$H-NMR (acetone-d6) δ (ppm): 1.80-2.50 (m, 7H), 4.07 (s, 3H), 4.27-4.38 (m, 2H), 4.52-4.88 (m, 3H), 7.02-7.10 (m, 1H), 7.14-7.38 (m, 5H), 7.46-7.59 (m, 2H), 7.77 (d, J=7.6 Hz, 1H), 7.87 (brs, 1H).

The property values of the title optically active compound with a retention time of 17 minutes are as follows.

ESI-MS; m/z 443 [M$^+$+H].

$^1$H-NMR (acetone-d6) δ (ppm): 1.80-2.50 (m, 7H), 4.07 (s, 3H), 4.27-4.38 (m, 2H), 4.52-4.88 (m, 3H), 7.02-7.10 (m, 1H), 7.14-7.38 (m, 5H), 7.46-7.59 (m, 2H), 7.77 (d, J=7.6 Hz, 1H), 7.87 (brs, 1H).

Examples 324 and 325

Synthesis of (+) and (−)-8-(2-fluoromethylphenyl)-2-{(E)-2-[6-methoxy-5-(4-methyl-1H-imidazol-1-yl)-pyridin-2-yl]vinyl}-5,6,7,8-tetrahydro-[1,2,4]triazolo[1,5-a]pyridine

[Formula 184]

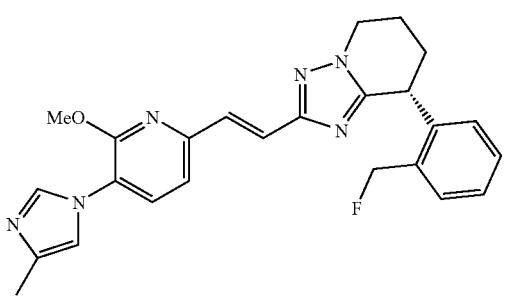

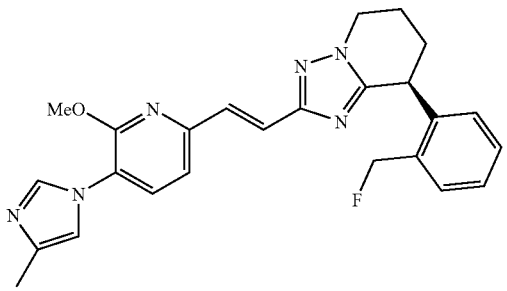

{2-{2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridin-8-yl}phenyl}methanol (350 mg) was dissolved in dichloromethane (40 mL). This was added dropwise to a solution of DAST (1.04 mL) in dichloromethane (6 mL) cooled to −78° C., and the reaction solution was stirred for one hour. Saturated sodium bicarbonate water was added to the reaction solution, followed by extraction with dichloromethane. The organic layer was dried over magnesium sulfate and concentrated under reduced pressure. The resulting residue was purified by silica gel chromatography (carrier: NH silica, elution solvent: ethyl acetate:methanol=9:1) to obtain a racemate of the title compound (70 mg). The resulting racemate was separated by CHIRALPAK™ IB manufactured by Daicel Chemical Industries, Ltd. (2 cm×25 cm, mobile phase: ethanol, flow rate: 10 mL/min) to obtain the title optically active compound with a retention time of 7 minutes and positive optical rotation (20 mg) and the title optically active compound with a retention time of 9 minutes and negative optical rotation (20 mg), where the retention time is an analysis result in CHIRALPAK™ IB manufactured by Daicel Chemical Industries, Ltd. (Lot. IB00CD-FD026, mobile phase: ethanol, flow rate: 0.5 mL/min).

The property values of the title optically active compound with a retention time of 7 minutes under the analysis conditions are as follows.

ESI-MS; m/z 455 [M$^+$+H]. $^1$H-NMR (CDCl$_3$) δ (ppm): 1.99-2.16 (m, 2H), 2.23-2.30 (m, 4H), 2.42 (m, 1H), 4.04 (s, 3H), 4.33 (m, 2H), 4.58 (m, 1H), 5.48 (dd, J=10.8, 108.8 Hz, 1H), 5.60 (m, 1H) 6.92-6.95 (m, 3H), 7.30-7.47 (m, 5H), 7.65 (d, J=15.6 Hz, 1H), 7.79 (m, 1H).

The property values of the title optically active compound with a retention time of 9 minutes under the analysis conditions are as follows.

ESI-MS; m/z 455 [M$^+$+H]. $^1$H-NMR (CDCl$_3$) δ (ppm): 1.99-2.16 (m, 2H), 2.23-2.30 (m, 4H), 2.42 (m, 1H), 4.04 (s, 3H), 4.33 (m, 2H), 4.58 (m, 1H), 5.48 (dd, J=10.8, 108.8 Hz, 1H), 5.60 (m, 1H) 6.92-6.95 (m, 3H), 7.30-7.47 (m, 5H), 7.65 (d, J=15.6 Hz, 1H), 7.79 (m, 1H).

Examples 326 and 327

Synthesis of (+) and (−)-8-(2-fluorophenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine

[Formula 185]

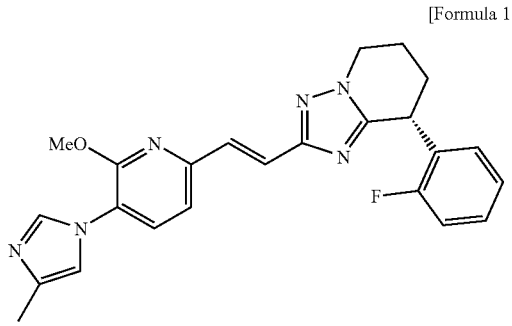

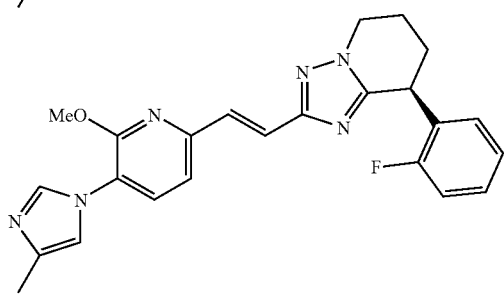

Synthesis of 1-amino-3-(2-fluorophenyl)piperidin-2-one 1.12 g of the title compound was obtained using 2-fluorophenylacetic acid (3.0 g) as a starting material according to the method in Examples 20 and 21. The property value of the compound is as follows.
ESI-MS; m/z 209 [$M^+ +H$].

Synthesis of (+) and (−)-8-(2-fluorophenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine A racemate of the title compound (21 mg) was obtained using 1-amino-3-(2-fluorophenyl)piperidin-2-one (300 mg) as a starting material according to the method in Examples 168 and 169. The resulting racemate (219 mg) was separated by CHIRALPAK™ IB manufactured by Daicel Chemical Industries, Ltd. (2 cm×25 cm, mobile phase: ethanol, flow rate: 10 mL/min) to obtain the title optically active compound with a retention time of 11.4 minutes and positive optical rotation (90 mg) and the title optically active compound with a retention time of 19 minutes and negative optical rotation (90 mg).

The property values of the title optically active compound with a retention time of 11.4 minutes are as follows.
$^1$H-NMR (CDCl$_3$) δ (ppm): 2.04-2.27 (m, 2H), 2.29 (s, 3H), 2.34-2.42 (m, 1H), 4.05 (s, 3H), 4.28-4.34 (m, 2H), 4.61 (dd, J=7.0, 7.0 Hz, 1H), 6.93 (d, J=9.4 Hz, 1H), 6.92-6.98 (m, 1H), 7.06-7.12 (m, 2H), 7.46 (d, J=15.6 Hz, 1H), 7.47 (d, J=9.4 Hz, 1H), 7.65 (d, J=15.6 Hz, 1H), 7.77 (d, J=1.2 Hz, 1H).

The property values of the title optically active compound with a retention time of 19 minutes are as follows.
$^1$H-NMR (CDCl$_3$) δ (ppm): 2.04-2.27 (m, 2H), 2.29 (s, 3H), 2.34-2.42 (m, 1H), 4.05 (s, 3H), 4.28-4.34 (m, 2H), 4.61 (dd, J=7.0, 7.0 Hz, 1H), 6.93 (d, J=9.4 Hz, 1H), 6.92-6.98 (m, 1H), 7.06-7.12 (m, 2H), 7.46 (d, J=15.6 Hz, 1H), 7.47 (d, J=9.4 Hz, 1H), 7.65 (d, J=15.6 Hz, 1H), 7.77 (d, J=1.2 Hz, 1H).

Examples 328 and 329

Synthesis of (+)-8-(5-fluoro-2-trifluoromethylphenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine and (−)-8-(5-fluoro-2-trifluoromethylphenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine

[Formula 186]

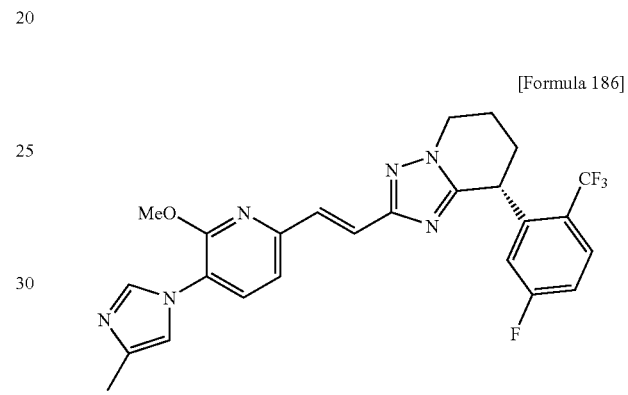

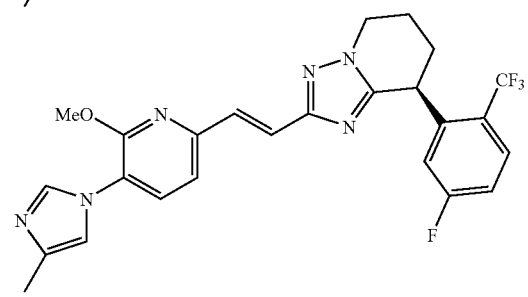

Synthesis of 1-amino-3-(5-fluoro-2-trifluoromethylphenyl)piperidin-2-one 890 mg of the title compound was obtained using 5-fluoro-2-trifluoromethylphenylacetic acid (1 g) as a starting material according to the method in Examples 194 and 195. The property value of the compound is as follows.
ESI-MS; m/z 277 [$M^+ +H$].

Synthesis of (+)-8-(5-fluoro-2-trifluoromethylphenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine and (−)-8-(5-fluoro-2-trifluoromethylphenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine A racemate of the title compound (132 mg) was obtained using (E)-3-[6-methoxy-5-(4-methyl-1H-imidazol-1-yl)pyridin-2-yl]acrylic acid trifluoroacetate (353 mg) and 1-amino-3-(5-fluoro-2-trifluoromethylphenyl)piperidin-2-one (200 mg) as starting materials according to the method in Examples 168 and 169. The resulting racemate (132 mg) was separated by CHIRALPAK™ IB manufactured by Daicel Chemical Industries, Ltd. (2 cm×25 cm, mobile phase; hexane:ethanol=7:3, flow rate: 11 mL/min) to obtain the title optically active compound with a retention time of 18 minutes and positive optical rotation (46 mg), and the title optically active compound with a retention time of 31 minutes and negative optical rotation (45 mg).

The property values of the title optically active compound with a retention time of 18 minutes are as follows.

$^1$H-NMR (CDCl$_3$) δ (ppm): 1.87-2.00 (m, 1H), 2.10-2.33 (m, 2H), 2.28 (s, 3H), 2.42-2.52 (m, 1H), 4.03 (s, 3H), 4.27-4.42 (m, 2H), 4.68 (dd, J=8.4, 6.4 Hz, 1H), 6.73 (dd, J=9.2, 2.4 Hz, 1H), 6.93 (d, J=7.6 Hz, 1H), 6.95 (d, J=1.2 Hz, 1H), 7.08 (ddd, J=8.8, 8.0, 2.4 Hz, 1H), 7.43 (d, J=15.6 Hz, 1H), 7.46 (d, J=7.6 Hz, 1H), 7.63 (d, J=15.6 Hz, 1H), 7.73 (dd, J=8.8, 5.6 Hz, 1H), 7.76 (d, J=1.2 Hz, 1H).

The property values of the title optically active compound with a retention time of 31 minutes are as follows.

$^1$H-NMR (CDCl$_3$) δ (ppm): 1.87-2.00 (m, 1H), 2.10-2.33 (m, 2H), 2.28 (s, 3H), 2.42-2.52 (m, 1H), 4.03 (s, 3H), 4.27-4.42 (m, 2H), 4.68 (dd, J=8.4, 6.4 Hz, 1H), 6.73 (dd, J=9.2, 2.4 Hz, 1H), 6.93 (d, J=7.6 Hz, 1H), 6.95 (d, J=1.2 Hz, 1H), 7.08 (ddd, J=8.8, 8.0, 2.4 Hz, 1H), 7.43 (d, J=15.6 Hz, 1H), 7.46 (d, J=7.6 Hz, 1H), 7.63 (d, J=15.6 Hz, 1H), 7.73 (dd, J=8.8, 5.6 Hz, 1H), 7.76 (d, J=1.2 Hz, 1H).

Examples 330 and 331

Synthesis of (+)-8-(6-fluoro-2-trifluoromethylphenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine and (−)-8-(6-fluoro-2-trifluoromethylphenyl)-2-{(E)-2-[6-methoxy-5-(4-methyl-1H-imidazol-1-yl)pyridin-2-yl]vinyl}-5,6,7, 8-tetrahydro-[1,2,4]triazolo[1,5-a]pyridine

[Formula 187]

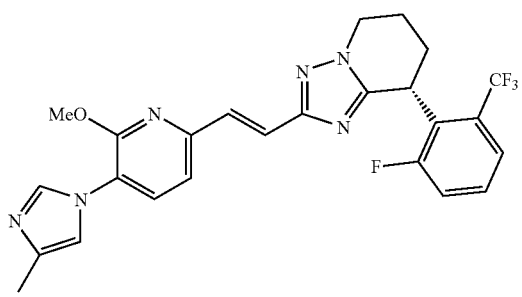

Synthesis of 1-amino-3-(6-fluoro-2-trifluoromethylphenyl)piperidin-2-one 381 mg of the title compound was obtained using 6-fluoro-2-trifluoromethylphenylacetic acid (1 g) as a starting material according to the method in Examples 20 and 21. The property value of the compound is as follows.

ESI-MS; m/z 277 [M$^+$+H].

Synthesis of (+)-8-(6-fluoro-2-trifluoromethylphenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine and (−)-8-(6-fluoro-2-trifluoromethylphenyl)-2-{(E)-2-[6-methoxy-5-(4-methyl-1H-imidazol-1-yl)pyridin-2-yl]vinyl}-5,6,7, 8-tetrahydro-[1,2,4]triazolo[1,5-a]pyridine A racemate of the title compound (181 mg) was obtained using (E)-3-[6-methoxy-5-(4-methyl-1H-imidazol-1-yl)pyridin-2-yl]acrylic acid (340 mg) and 1-amino-3-(6-fluoro-2-trifluoromethylphenyl)piperidin-2-one (200 mg) as starting materials according to the method in Examples 168 and 169. The resulting racemate (181 mg) was separated by CHIRALPAK™ IB manufactured by Daicel Chemical Industries, Ltd. (2 cm×25 cm, mobile phase: hexane:ethanol=7:3, flow rate: 12 mL/min) to obtain the title optically active compound with a retention time of 18 minutes and positive optical rotation (76 mg) and the title optically active compound with a retention time of 34 minutes and negative optical rotation (75 mg).

The property values of the title optically active compound with a retention time of 18 minutes are as follows.

$^1$H-NMR (CDCl$_3$) δ (ppm): 2.07-2.41 (m, 7H), 4.01 (s, 3H), 4.19-4.26 (m, 1H), 4.39-4.43 (m, 1H), 4.52-4.56 (m, 1H), 6.91 (d, J=6.9 Hz, 1H), 6.94 (s, 1H), 7.22 (t, J=8.8 Hz, 1H), 7.37-7.45 (m, 3H), 7.55 (d, J=7.6 Hz, 1H), 7.60 (d, J=15.6 Hz, 1H) 7.75 (s, 1H).

The property values of the title optically active compound with a retention time of 34 minutes are as follows.

$^1$H-NMR (CDCl$_3$) δ (ppm): 2.07-2.41 (m, 7H), 4.01 (s, 3H), 4.19-4.26 (m, 1H), 4.39-4.43 (m, 1H), 4.52-4.56 (m, 1H), 6.91 (d, J=6.9 Hz, 1H), 6.94 (s, 1H), 7.22 (t, J=8.8 Hz, 1H), 7.37-7.45 (m, 3H), 7.55 (d, J=7.6 Hz, 1H), 7.60 (d, J=15.6 Hz, 1H) 7.75 (s, 1H).

Examples 332 and 333

Synthesis of (+) and (−)-8-(3-fluoro-2-methylphenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine

[Formula 188]

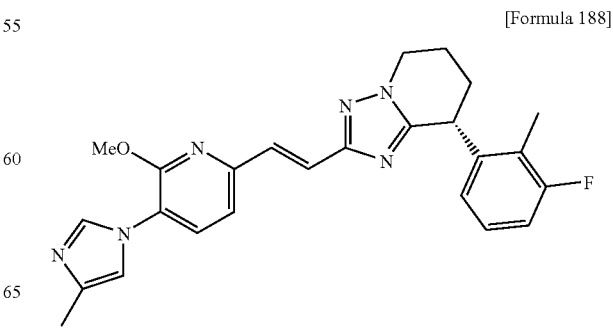

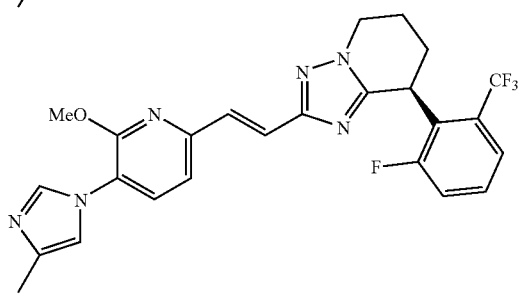

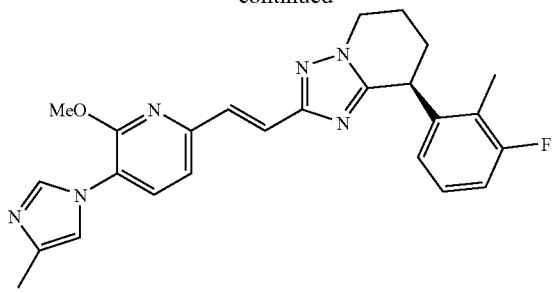

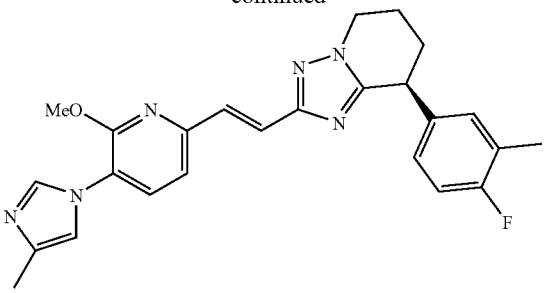

A racemate of the title compound (21 mg) was obtained using 1-amino-3-(3-fluoro-2-methylphenyl)piperidin-2-one (197 mg) as a starting material according to the method in Examples 168 and 169. The resulting racemate (21 mg) was separated by CHIRALPAK™ IB manufactured by Daicel Chemical Industries, Ltd. (2 cm×25 cm, mobile phase: ethanol, flow rate: 10 mL/min) to obtain the title optically active compound with a retention time of 12.5 minutes and positive optical rotation (8 mg) and the title optically active compound with a retention time of 27 minutes and negative optical rotation (8 mg).

The property values of the title optically active compound with a retention time of 12.5 minutes are as follows.

$^1$H-NMR (CDCl$_3$) δ (ppm): 1.90-2.27 (m, 3H), 2.28-2.38 (m, 1H), 2.29 (s, 3H), 2.30 (s, 3H) 4.04 (s, 3H), 4.24-4.38 (m, 2H), 4.53-4.60 (m, 1H), 6.53 (d, J=7.7 Hz, 1H), 6.91-6.98 (m, 2H), 6.93 (d, J=7.7 Hz, 1H), 7.05-7.12 (m, 1H) 7.46 (d, J=15.7 Hz, 1H), 7.47 (d, J=7.7 Hz, 1H), 7.65 (d, J=15.7 Hz, 1H), 7.77 (d, J=1.1 Hz, 1H).

The property values of the title optically active compound with a retention time of 27 minutes are as follows.

$^1$H-NMR (CDCl$_3$) δ (ppm): 1.90-2.27 (m, 3H), 2.28-2.38 (m, 1H), 2.29 (s, 3H), 2.30 (s, 3H) 4.04 (s, 3H), 4.24-4.38 (m, 2H), 4.53-4.60 (m, 1H), 6.53 (d, J=7.7 Hz, 1H), 6.91-6.98 (m, 2H), 6.93 (d, J=7.7 Hz, 1H), 7.05-7.12 (m, 1H) 7.46 (d, J=15.7 Hz, 1H), 7.47 (d, J=7.7 Hz, 1H), 7.65 (d, J=15.7 Hz, 1H), 7.77 (d, J=1.1 Hz, 1H).

Examples 334 and 335

Synthesis of (+) and (−)-8-(4-fluoro-3-methylphenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine

[Formula 189]

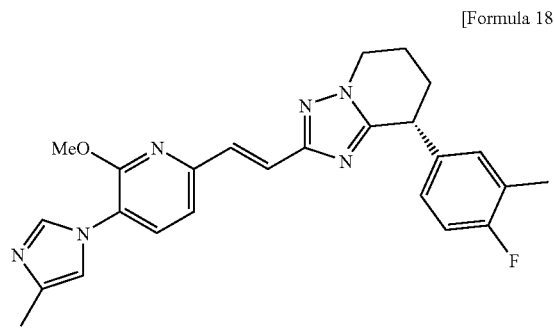

Synthesis of 2-(4-fluoro-3-methylphenyl)acetamide

4-Fluoro-3-methylphenylacetonitrile (1.1 g) was dissolved in toluene (35 ml), and trimethylsiloxypotassium (3.7 g) was added. After stirring at 110° C. for 2.5 hours, saturated sodium bicarbonate water was added, followed by separation with ethyl acetate. The organic layer was washed with brine, dried over magnesium sulfate and concentrated under reduced pressure to obtain 863 mg of the title compound. The property values of the compound are as follows.

$^1$H-NMR (CDCl$_3$) δ (ppm): 2.27 (s, 3H), 3.52 (s, 2H), 5.24-5.60 (m, 1H), 6.92-7.15 (m, 3H).

Synthesis of ethyl 2-(4-fluoro-3-methylphenyl)acetate 2-(4-Fluoro-3-methylphenyl)acetamide (863 mg) was dissolved in saturated hydrochloric acid/ethanol (20 ml), and the reaction solution was stirred at 85° C. for 10 hours. The reaction solution was concentrated under reduced pressure and then diluted with ethyl acetate, followed by separation with water. The organic layer was washed with saturated aqueous sodium bicarbonate and brine and then dried over magnesium sulfate. 919 mg of the title compound was obtained by concentration under reduced pressure. The property values of the compound are as follows.

$^1$H-NMR (CDCl$_3$) δ (ppm): 1.25 (t, J=8.4 Hz, 3H), 2.05 (s, 3H), 2.26 (s, 3H) 3.54 (s, 2H), 4.15 (q, J=8.4 Hz, 1H), 6.92-6.97 (m, 1H), 7.03-7.10 (m, 2H).

Synthesis of 1-amino-3-(4-fluoro-3-methylphenyl)piperidin-2-one 396 mg of the title compound was obtained using ethyl 2-(4-fluoro-3-methylphenyl)acetate (919 mg) as a starting material according to the method in Examples 20 and 21. The property value of the compound is as follows.

ESI-MS; m/z 223 [M$^+$+H].

Synthesis of (+) and (−)-8-(4-fluoro-3-methylphenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine A racemate of the title compound (44.5 mg) was obtained using 1-amino-3-(4-fluoro-3-methylphenyl)piperidin-2-one (135 mg) as a starting material according to the method in Examples 168 and 169. The resulting racemate (44.5 mg) was separated by CHIRALPAK™ IB manufactured by Daicel Chemical Industries, Ltd. (2 cm×25 cm, mobile phase: ethanol, flow rate: 10 mL/min) to obtain the title optically active compound with a retention time of 12.5 minutes and positive optical rotation (20 mg) and the title optically active compound with a retention time of 19 minutes and negative optical rotation (20 mg).

The property values of the title optically active compound with a retention time of 12.5 minutes are as follows.

$^1$H-NMR (CDCl$_3$) δ (ppm): 1.80-1.98 (m, 1H), 1.98-2.14 (m, 1H), 2.25 (s, 3H), 2.26-2.40 (m, 2H), 2.29 (s, 3H), 4.05 (s, 3H), 4.21-4.36 (m, 3H), 6.88-7.00 (m, 5H), 7.46 (d, J=7.7 Hz, 1H), 7.47 (d, J=15.7 Hz, 1H), 7.65 (d, J=15.7 Hz, 1H), 7.75-7.78 (m, 1H).

The property values of the title optically active compound with a retention time of 19 minutes are as follows.

$^1$H-NMR (CDCl$_3$) δ (ppm): 1.80-1.98 (m, 1H), 1.98-2.14 (m, 1H), 2.25 (s, 3H), 2.26-2.40 (m, 2H), 2.29 (s, 3H), 4.05 (s, 3H), 4.21-4.36 (m, 3H), 6.88-7.00 (m, 5H), 7.46 (d, J=7.7 Hz, 1H), 7.47 (d, J=15.7 Hz, 1H), 7.65 (d, J=15.7 Hz, 1H), 7.75-7.78 (m, 1H).

Examples 336 and 337

Synthesis of (+) and (−)-8-(3,5-difluorophenyl)-2-{(E)-2-[6-methoxy-5-(4-methyl-1H-imidazol-1-yl)pyridin-2-yl]vinyl}-5,6,7,8-tetrahydro[1,2,4]triazolo[1,5-a]pyridine

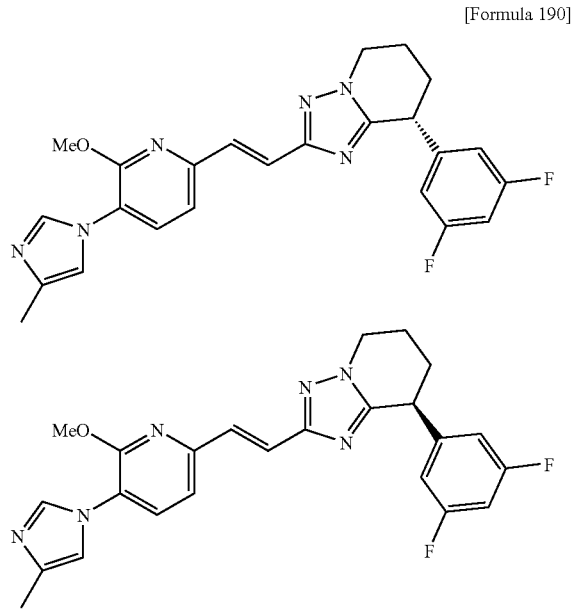

[Formula 190]

A racemate of the title compound was obtained from (E)-3-[6-methoxy-5-(4-methyl-1H-imidazol-1-yl)pyridin-2-yl] acrylic acid ditrifluoroacetate (800 mg) and 1-amino-3-(3,5-difluorophenyl)piperidin-2-one (445 mg) according to the method in Examples 168 and 169. The resulting racemate was separated by CHIRALCEL™ OD-H manufactured by Daicel Chemical Industries, Ltd. (2 cm×25 cm; mobile phase: ethanol) to obtain the title optically active compound with a retention time of 6.1 minutes and positive optical rotation (35.6 mg, >99% ee) and the title optically active compound with a retention time of 8.1 minutes and negative optical rotation (40.6 mg, >99% ee).

The property values of the title compound with positive optical rotation are as follows.

ESI-MS; m/z 449 [M$^+$+H]. $^1$H-NMR (CDCl$_3$) δ (ppm): 2.00-2.25 (m, 3H), 2.30 (s, 3H), 2.35-2.40 (m, 1H), 4.06 (s, 3H), 4.28-4.35 (m, 3H), 6.67-6.77 (m, 3H), 6.95 (d, J=8.0 Hz, 1H), 6.97 (s, 1H), 7.46 (d, J=8.0 Hz, 1H), 7.47 (d, J=16.0 Hz, 1H), 7.65 (d, J=16.0 Hz, 1H), 7.78 (s, 1H).

The property values of the title compound with negative optical rotation are as follows.

ESI-MS; m/z 449 [M$^+$+H]. 1H-NMR (CDCl$_3$) δ (ppm): 2.00-2.25 (m, 3H), 2.30 (s, 3H), 2.35-2.40 (m, 1H), 4.06 (s, 3H), 4.28-4.35 (m, 3H), 6.67-6.77 (m, 3H), 6.95 (d, J=8.0 Hz, 1H), 6.97 (s, 1H), 7.46 (d, J=8.0 Hz, 1H), 7.47 (d, J=16.0 Hz, 1H), 7.65 (d, J=16.0 Hz, 1H), 7.78 (s, 1H).

Examples 338 and 339

Synthesis of (R) and (S)-2-{(E)-3-[6-methoxy-5-(4-methyl-1H-imidazol-1-yl)pyridin-2-yl]vinyl}-8-(2,3,4-trifluorophenyl)-5,6,7,8-tetrahydro-[1,2,4]triazole[1,5-a]pyridine

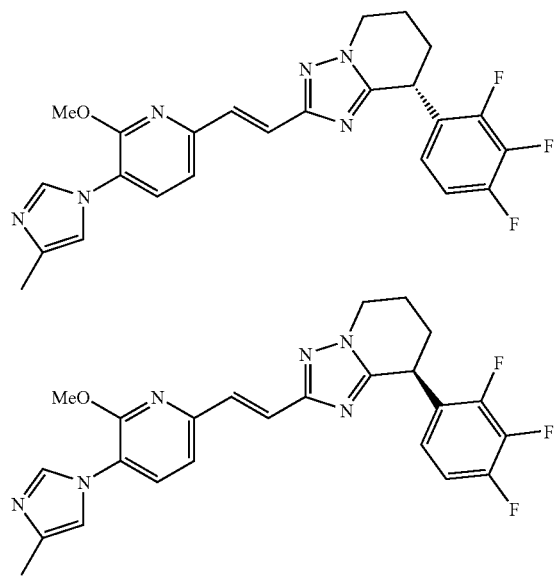

[Formula 191]

Synthesis of 1-amino-3-(2,3,4-trifluorophenyl)piperidin-2-one

The title compound (220 mg) was obtained from 2,3,4-trifluorophenylacetic acid (1.48 g) by the same method as in Examples 1 and 2. The property values of the compound are as follows.

ESI-MS; m/z 245 [M$^+$+H]. $^1$H-NMR (CDCl$_3$) δ (ppm): 1.90-2.04 (m, 3H), 2.11-2.17 (m, 1H), 3.56-3.70 (m, 2H), 3.81-3.86 (m, 1H), 4.58 (brs, 2H), 6.82-6.96 (m, 2H).

Synthesis of (R) and (S)-2-{(E)-3-[6-methoxy-5-(4-methylimidazol-1-yl)pyridin-2-yl]vinyl}-8-(2,3,4-trifluorophenyl)-5,6,7,8-tetrahydro-[1,2,4]triazole[1,5-a]pyridine The racemic title compound (100 mg) was obtained from 1-amino-3-(2,3,4-trifluorophenyl)piperidin-2-one (220 mg) by the same method as in Examples 168 and 169. The resulting racemic title compound (100 mg) was separated by CHIRALPAK™ IB manufactured by Daicel Chemical Industries, Ltd. (2 cm×25 cm; mobile phase: hexane:ethanol=7:3) to obtain the title optically active compound with positive optical rotation and a retention time of 53 minutes (19.5 mg) and the title optically active compound with negative optical rotation and a retention time of 90 minutes (13.5 mg). The property values of the compound are as follows. The title optically active compound with a retention time of 53 minutes ESI-MS; m/z 467 [M$^+$+H]. $^1$H-NMR (CDCl$_3$) δ (ppm): 1.99-2.08 (m, 1H), 2.09-2.25 (m, 2H), 2.29 (s, 3H), 2.35-2.43 (m, 1H), 4.05 (s, 3H), 4.25-4.35 (m, 2H), 4.53-4.57 (m, 1H), 6.68-6.74 (m, 1H), 6.90-6.96 (m, 3H), 7.44 (d, J=16.0 Hz, 1H), 7.47 (d, J=8.0 Hz, 1H), 7.64 (d, J=16.0 Hz, 1H), 7.78 (d, J=1.2 Hz, 1H).

The title optically active compound with a retention time of 90 minutes

ESI-MS; m/z 467 [M$^+$+H]. $^1$H-NMR (CDCl$_3$) δ (ppm): 1.99-2.08 (m, 1H), 2.09-2.25 (m, 2H), 2.29 (s, 3H), 2.35-2.43 (m, 1H), 4.05 (s, 3H), 4.25-4.35 (m, 2H), 4.53-4.57 (m, 1H), 6.68-6.74 (m, 1H), 6.90-6.96 (m, 3H), 7.44 (d, J=16.0 Hz, 1H), 7.47 (d, J=8.0 Hz, 1H), 7.64 (d, J=16.0 Hz, 1H), 7.78 (d, J=1.2 Hz, 1H).

Examples 340 and 341

Synthesis of (+) and (−)-8-benzo[1,3]dioxol-4-yl-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine

[Formula 192]

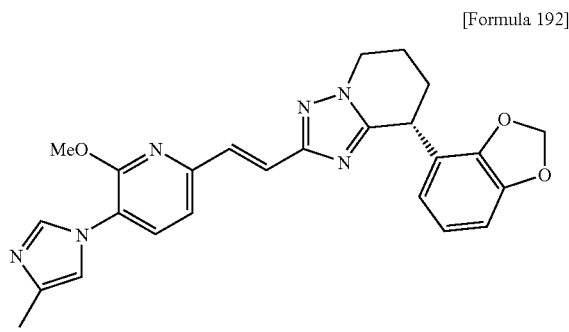

Synthesis of 1-amino-3-benzo[1,3]dioxol-4-yl-piperidin-2-one 1.19 g of the title compound was obtained using benzo[1,3]dioxol-4-carbaldehyde (5.0 g) as a starting material according to the method in Examples 293 and 294. The property value of the compound is as follows.

ESI-MS; m/z 235 [M$^+$+H].

Synthesis of (+) and (−)-8-benzo[1,3]dioxol-4-yl-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine A racemate of the title compound (810 mg) was obtained using 1-amino-3-benzo[1,3]dioxol-4-yl-piperidin-2-one (1.19 g) as a starting material according to the method in Examples 168 and 169. The resulting racemate (100 mg) was separated by CHIRALPAK™ IB manufactured by Daicel Chemical Industries, Ltd. (2 cm×25 cm, mobile phase: ethanol, flow rate: 10 mL/min) to obtain the title optically active compound with a retention time of 14.6 minutes and positive optical rotation (40 mg) and the title optically active compound with a retention time of 21 minutes and negative optical rotation (40 mg).

The property values of the title optically active compound with a retention time of 14.6 minutes are as follows.

$^1$H-NMR (CDCl$_3$) δ (ppm): 2.04-2.28 (m, 3H), 2.28-2.38 (m, 1H), 2.29 (s, 3H), 4.05 (s, 3H), 4.24-4.32 (m, 2H), 4.44 (dd, J=6.6, 5.6 Hz, 1H), 5.92 (s, 2H), 6.50 (dd, J=7.0, 1.6 Hz, 1H), 6.74-6.82 (m, 2H), 6.93 (d, J=7.8 Hz, 1H), 6.95-6.97 (m, 1H), 7.46 (d, J=7.8 Hz, 1H), 7.48 (d, J=15.6 Hz, 1H), 7.65 (d, J=15.6 Hz, 1H), 7.77 (d, J=1.2 Hz, 1H).

The property values of the title optically active compound with a retention time of 21 minutes are as follows.

$^1$H-NMR (CDCl$_3$) δ (ppm): 2.04-2.28 (m, 3H), 2.28-2.38 (m, 1H), 2.29 (s, 3H), 4.05 (s, 3H), 4.24-4.32 (m, 2H), 4.44 (dd, J=6.6, 5.6 Hz, 1H), 5.92 (s, 2H), 6.50 (dd, J=7.0, 1.6 Hz, 1H), 6.74-6.82 (m, 2H), 6.93 (d, J=7.8 Hz, 1H), 6.95-6.97 (m, 1H), 7.46 (d, J=7.8 Hz, 1H), 7.48 (d, J=15.6 Hz, 1H), 7.65 (d, J=15.6 Hz, 1H), 7.77 (d, J=1.2 Hz, 1H).

Examples 342 and 343

Synthesis of (+) and (−)-8-(2,2-difluoro-benzo[1,3]dioxol-4-yl)-2-{(E)-2-[6-methoxy-5-(4-methyl-1H-imidazol-1-yl)-pyridin-2-yl]-vinyl}-5,6,7,8-tetrahydro-[1,2,4]triazolo[1,5-a]pyridine

[Formula 193]

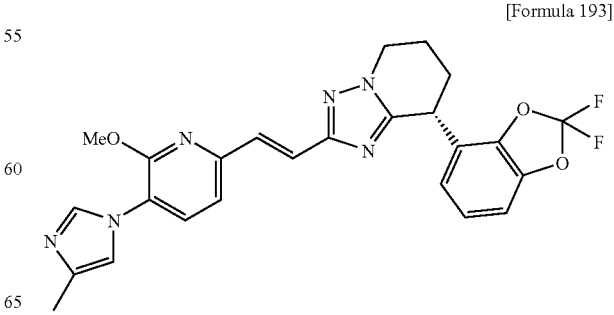

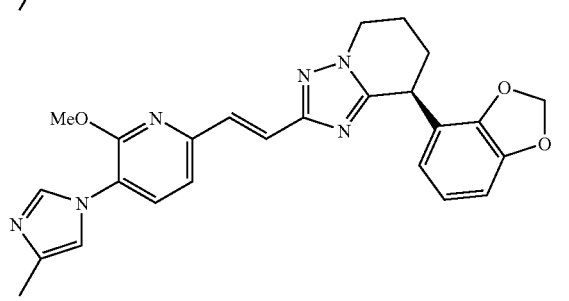

-continued

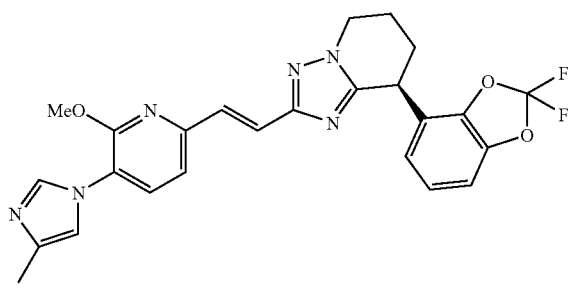

Synthesis of 5-chloro-2-(2,2-difluoro-benzo[1,3]dioxol-4-yl)valeric acid hydrazide 580 mg of the title compound was obtained using 2,2-difluoro-benzo[1,3]dioxol-4-carbaldehyde (1.8 g) as a starting material according to the method in Examples 293 and 294. The property value of the compound is as follows.

ESI-MS; m/z 307 [M$^+$+H].

Synthesis of (+) and (−)-8-(2,2-difluoro-benzo[1,3]dioxol-4-yl)-2-{(E)-2-[6-methoxy-5-(4-methyl-1H-imidazol-1-yl)-pyridin-2-yl]-vinyl}-5,6,7,8-tetrahydro-[1,2,4]triazolo[1,5-a]pyridine A racemate of the title compound (280 mg) was obtained using 5-chloro-2-(2,2-difluoro-benzo[1,3]dioxol-4-yl)valeric acid hydrazide (555 mg) and ethyl (E)-3-[6-methoxy-5-(4-methylimidazol-1-yl)-pyridin-2-yl]acrylimidate (482 mg) as starting materials according to the method in Examples 1 and 2. The resulting racemate (280 mg) was separated by CHIRALPAK™ IB manufactured by Daicel Chemical Industries, Ltd. (2 cm×25 cm, mobile phase: ethanol, flow rate: 10 mL/min) to obtain the title optically active compound with a retention time of 13 minutes and positive optical rotation (110 mg) and the title optically active compound with a retention time of 18 minutes and negative optical rotation (120 mg).

The property values of the title optically active compound with a retention time of 13 minutes are as follows.

$^1$H-NMR (CDCl$_3$) δ (ppm): 2.07-2.28 (m, 3H), 2.30 (s, 3H), 2.38-2.47 (m, 1H), 4.05 (s, 3H), 4.29-4.34 (m, 2H), 4.54 (dd, J=6.6, 5.8 Hz, 1H), 6.74 (dd, J=7.8, 1.4 Hz, 1H), 6.94 (d, J=7.6 Hz, 1H), 6.95-6.97 (m, 1H), 6.98-7.06 (m, 2H), 7.46 (d, J=15.7 Hz, 1H), 7.47 (d, J=7.6 Hz, 1H), 7.67 (d, J=15.7 Hz, 1H), 7.78 (d, J=1.2 Hz, 1H).

The property values of the title optically active compound with a retention time of 21 minutes are as follows.

$^1$H-NMR (CDCl$_3$) δ (ppm): 2.07-2.28 (m, 3H), 2.30 (s, 3H), 2.38-2.47 (m, 1H), 4.05 (s, 3H), 4.29-4.34 (m, 2H), 4.54 (dd, J=6.6, 5.8 Hz, 1H), 6.74 (dd, J=7.8, 1.4 Hz, 1H), 6.94 (d, J=7.6 Hz, 1H), 6.95-6.97 (m, 1H), 6.98-7.06 (m, 2H), 7.46 (d, J=15.7 Hz, 1H), 7.47 (d, J=7.6 Hz, 1H), 7.67 (d, J=15.7 Hz, 1H), 7.78 (d, J=1.2 Hz, 1H).

Example 344

Synthesis of 3-(4-methyl-1H-imidazol-1-yl)-6-{(E)-2-[(S)-8-(2-trifluoromethylphenyl)-5,6,7,8-tetrahydro-[1,2,4]triazolo[1,5-a]pyridin-2-yl]vinyl}pyridin-2-ol

[Formula 194]

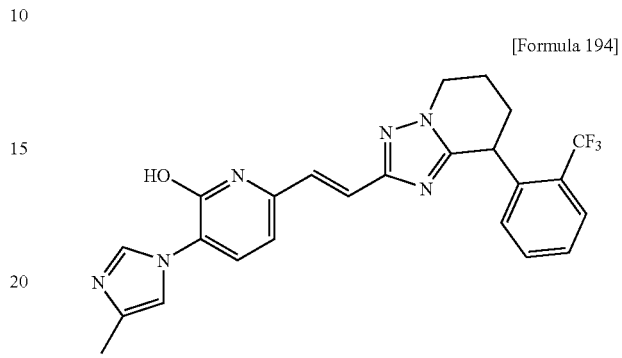

Reaction was carried out using 1-amino-3-(2-trifluoromethylphenyl)piperidin-2-one (2.0 g) as a starting material, and the resulting crude product was purified by silica gel column chromatography (amino silica, 40 μm, 53 g, ethyl acetate:heptane=0:1 to 1:0) to obtain 8-(2-trifluoromethylphenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine (739 mg) and a racemate of the title compound (88 mg) according to the method in Examples 194 and 195. The property values of the compound are as follows.

$^1$H-NMR (CDCl$_3$) δ (ppm): 1.90-2.00 (m, 1H), 2.10-2.23 (m, 1H), 2.23-2.30 (m, 1H), 2.28 (s, 3H), 2.40-2.51 (m, 1H) 4.30-4.42 (m, 2H), 4.68 (dd, J=8.8, 5.6 Hz, 1H), 6.34 (d, J=7.8 Hz, 1H), 7.00 (d, J=7.4 Hz, 1H), 7.13-7.23 (m, 3H), 7.37-7.42 (m, 2H), 7.46-7.52 (m, 1H), 7.73 (d, J=7.4 Hz, 1H), 8.14 (d, J=1.2 Hz, 1H).

Examples 345 and 346

Synthesis of (+) and (−)-2-{(E)-2-[6-chloro-5-(4-methyl-1H-imidazol-1-yl]vinyl}-8-(2-trifluoromethylphenyl)-5,6,7,8-tetrahydro[1,2,4]triazolo[1,5-a]pyridine

[Formula 195]

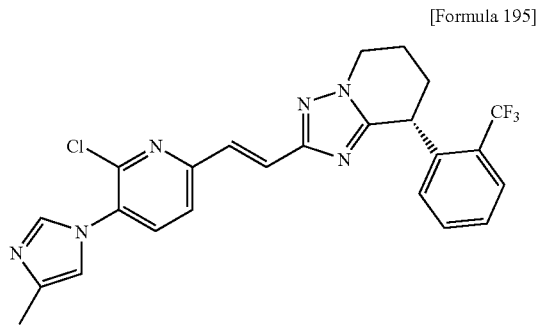

-continued

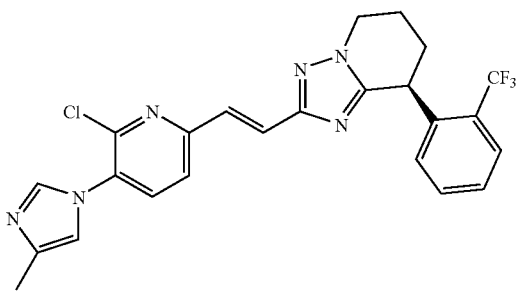

A solution of 3-(4-methyl-1H-imidazol-1-yl)-6-{(E)-2-[8-(2-trifluoromethylphenyl)-5,6,7,8-tetrahydro[1,2,4]triazolo[1,5-a]pyridin-2-yl]vinyl}pyridin-2-ol (500 mg) in phosphorus oxychloride (10 ml) was heated and stirred at 100° C. overnight. The reaction solution was concentrated under reduced pressure. Ethyl acetate and a saturated sodium bicarbonate solution were added and the organic layer was separated. The resulting organic layer was washed with brine and then dried over anhydrous sodium sulfate. The drying agent was separated by filtration, and then the organic layer was concentrated under reduced pressure. The residue was purified by silica gel column chromatography to obtain a racemate of the title compound (176 mg). The resulting racemate was separated by CHIRALPAK™ IB manufactured by Daicel Chemical Industries, Ltd. (2 cm×25 cm; mobile phase: hexane:ethanol=7:3) to obtain the title optically active compound with positive optical rotation (46 mg, >99% ee) and the title optically active compound with negative optical rotation (47 mg, >99% ee).

The property values of the title optically active compound with positive optical rotation are as follows.

$^1$H-NMR (CDCl$_3$) δ (ppm): 1.90-2.00 (m, 1H), 2.07-2.22 (m, 1H), 2.22-2.32 (m, 1H), 2.31 (s, 3H), 2.42-2.50 (m, 1H), 4.29-4.41 (m, 2H), 4.69 (dd, J=8.8, 6.0 Hz, 1H), 6.88 (d, J=1.6 Hz, 1H), 7.01 (d, J=7.6 Hz, 1H), 7.30 (d, J=7.6 Hz, 1H), 7.40 (t, J=7.6 Hz, 1H), 7.45-7.51 (m, 2H), 7.56 (d, J=8.0 Hz, 1H), 7.61 (d, J=1.6 Hz, 1H), 7.66 (d, J=15.6 Hz, 1H), 7.73 (d, J=7.6 Hz, 1H).

The property values of the title optically active compound with negative optical rotation are as follows.

$^1$H-NMR (CDCl$_3$) δ (ppm): 1.90-2.00 (m, 1H), 2.07-2.22 (m, 1H), 2.22-2.32 (m, 1H), 2.31 (s, 3H), 2.42-2.50 (m, 1H), 4.29-4.41 (m, 2H), 4.69 (dd, J=8.8, 6.0 Hz, 1H), 6.88 (d, J=1.6 Hz, 1H), 7.01 (d, J=7.6 Hz, 1H), 7.30 (d, J=7.6 Hz, 1H), 7.40 (t, J=7.6 Hz, 1H), 7.45-7.51 (m, 2H), 7.56 (d, J=8.0 Hz, 1H), 7.61 (d, J=1.6 Hz, 1H), 7.66 (d, J=15.6 Hz, 1H), 7.73 (d, J=7.6 Hz, 1H).

Examples 347 and 348

Synthesis of (+) and (−)-2-{(E)-2-[6-fluoro-5-(4-methyl-1H-imidazol-1-yl)pyridin-2-yl]vinyl}-8-(2-trifluoromethylphenyl)-5,6,7,8-tetrahydro[1,2,4]triazolo[1,5-a]pyridine

[Formula 196]

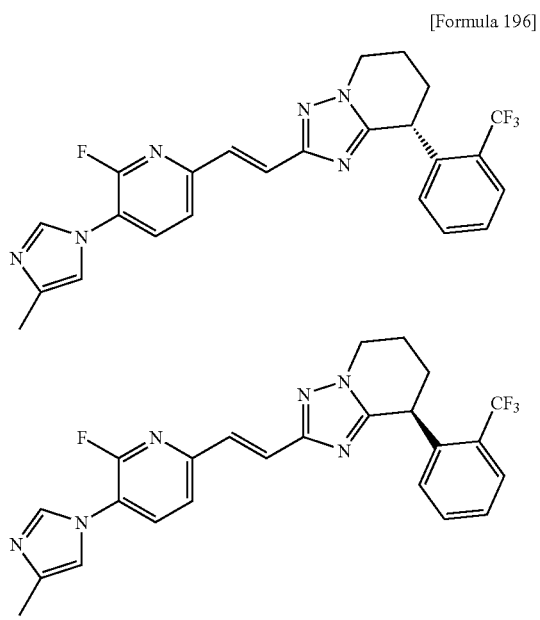

Synthesis of N-[2-oxo-3-(2-trifluoromethylphenyl)piperidin-1-yl]-3-p-tolylsulfanylpropionamide EDC (9.01 g), HOBT (6.34 g) and IPEA (21.8 ml) were added to a solution of 1-amino-3-(2-trifluoromethylphenyl)piperidin-2-one (8.08 g) and 3-[(4-methylphenyl)thio]propionic acid (7.37 g) in DMF (80 ml) under cooling in an ice water bath. The reaction solution was stirred at room temperature for four hours. Ethyl acetate and a sodium bicarbonate solution were added to the reaction solution, and the organic layer was separated. The resulting organic layer was washed with brine and then dried over anhydrous sodium sulfate. The drying agent was separated by filtration, and then the organic layer was concentrated under reduced pressure. The residue was purified by silica gel column chromatography to obtain the title compound (13.51 g). The property values of the compound are as follows.

$^1$H-NMR (CDCl$_3$) δ (ppm): 1.90-2.12 (m, 3H), 2.20-2.28 (m, 1H), 2.32 (s, 3H), 2.44-2.58 (m, 2H), 3.12-3.24 (m, 2H), 3.58-3.64 (m, 1H), 3.84-3.92 (m, 1H), 4.08-4.14 (m, 1H), 7.11 (d, J=8.0 Hz, 2H), 7.28 (d, J=8.0 Hz, 2H), 7.34 (dd, J=8.0, 7.6 Hz, 1H), 7.42 (d, J=7.6 Hz, 1H), 7.53 (dd, J=8.0, 7.6 Hz, 1H), 7.64 (d, J=8.0 Hz, 1H), 7.79 (brs, 1H).

Synthesis of 2-(2-p-tolylsulfanylethyl)-8-(2-trifluoromethylphenyl)-5,6,7,8-tetrahydro[1,2,4]triazolo[1,5-a]pyridine A solution of N-[2-oxo-3-(2-trifluoromethylphenyl)piperidin-1-yl]-3-p-tolylsulfanylpropionamide in phosphorus oxychloride (80 ml) was heated and stirred at 120° C. for one hour. The reaction solution was concentrated under reduced pressure, followed by addition of acetic acid (100 ml) and sodium acetate (23.8 g) heated and dried under reduced pressure. The reaction solution was heated and stirred at 150° C. for 1.5 hours. After leaving to cool, the reaction solution was concentrated under reduced pressure. Ethyl acetate and a saturated sodium bicarbonate solution were added and the organic layer was separated. The resulting organic layer was washed with brine and then dried over anhydrous sodium sulfate. The drying agent was separated by filtration, and then the organic layer was concentrated under reduced pressure. The residue was purified by NH silica gel column chromatography to obtain the title compound (8.8 g). The property values of the compound are as follows.

ESI-MS; m/z 419 [M$^+$+H]. $^1$H-NMR (CDCl$_3$) δ (ppm): 1.80-1.92 (m, 1H), 2.04-2.15 (m, 1H), 2.15-2.27 (m, 1H), 2.30 (s, 3H), 2.36-2.45 (m, 1H), 2.95-3.00 (m, 2H), 3.18-3.23 (m, 2H), 4.18-4.30 (m, 2H), 7.56 (dd, J=8.6, 6.2 Hz, 1H), 6.93 (d, J=7.6 Hz, 1H), 7.07 (d, J=8.0 Hz, 2H), 7.27 (d, J=8.0 Hz, 2H), 7.35 (dd, J=8.0, 7.6 Hz, 1H), 7.45 (dd, J=8.0, 7.6 Hz, 1H), 7.68 (d, J=8.0 Hz, 1H).

Synthesis of 2-[2-(toluene-4-sulfinyl)ethyl]-8-(2-trifluoromethylphenyl)-5,6,7,8-tetrahydro[1,2,4]triazolo[1,5-a]pyridine 2-(2-p-Tolylsulfanylethyl)-8-(2-trifluoromethylphenyl)-5,6,7,8-tetrahydro[1,2,4]triazolo[1,5-a]pyridine (8.8 g) was dissolved in a mixed solvent of methanol-water (2:1 v/v) (300 ml). Sodium periodide (6.78 g) was added under cooling with an ice water bath, and the reaction solution was stirred at room temperature overnight. Ethyl acetate and water were added to the reaction solution, and the organic layer was separated. The resulting organic layer was washed with brine and then dried over anhydrous sodium sulfate. The drying agent was separated by filtration and the organic layer was concentrated under reduced pressure to obtain the title compound (8.87 g). The property values of the compound are as follows.

$^1$H-NMR (CDCl$_3$) δ (ppm): 1.80-1.93 (m, 1H), 2.02-2.15 (m, 1H), 2.16-2.28 (m, 1H), 2.36-2.45 (m, 1H), 2.39 (s, 3H), 2.83-2.98 (m, 1H), 3.05-3.30 (m, 3H), 4.17-4.30 (m, 2H), 4.54-4.60 (m, 1H), 6.93 (d, J=7.6 Hz, 1H), 7.26-7.32 (m, 2H), 7.36 (dd, J=8.0, 7.6 Hz, 1H), 7.43-7.52 (m, 3H), 7.69 (d, J=7.6 Hz, 1H).

Synthesis of 8-(2-trifluoromethylphenyl)-2-vinyl-5,6,7,8-tetrahydro[1,2,4]triazolo[1,5-a]pyridine 2-[2-(Toluene-4-sulfinyl)ethyl]-8-(2-trifluoromethylphenyl)-5,6,7,8-tetrahydro[1,2,4]triazolo[1,5-a]pyridine (8.87 g) was dissolved in toluene (300 ml), and the reaction solution was heated under reflux for three days. After leaving to cool, the reaction solution was concentrated under reduced pressure. The residue was purified by silica gel column chromatography to obtain the title compound (4.27 g). The property values of the compound are as follows.

$^1$H-NMR (CDCl$_3$) δ (ppm): 1.87-1.97 (m, 1H), 2.08-2.16 (m, 1H), 2.18-2.28 (m, 1H), 2.38-2.48 (m, 1H), 4.22-4.34 (m, 2H), 4.66 (dd, J=8.2, 1.8 Hz, 1H), 5.43 (dd, J=11.2, 1.4 Hz, 1H), 6.13 (dd, J=17.6, 1.4 Hz, 1H), 6.65 (dd, J=17.6, 11.2 Hz, 1H), 6.97 (d, J=8.0 Hz, 1H), 7.37 (dd, J=8.0, 7.2 Hz, 1H), 7.46 (dd, J=7.6, 7.2 Hz, 1H), 7.70 (d, J=7.6 Hz, 1H).

Synthesis of 2,6-difluoro-3-nitropyridine

Tetramethylammonium nitride (4.5 g) was suspended in dichloromethane (10 ml), and a solution of trifluoromethanesulfonic anhydride (5.56 ml) in dichloromethane (5 ml) was added dropwise at room temperature. After stirring at room temperature for 1.5 hours, a solution of 2,6-difluoropyridine (2 ml) in dichloromethane (5 ml) was added at room temperature, and the reaction solution was heated under reflux overnight. After leaving to cool, the reaction solution was poured into an ice-cooled saturated sodium bicarbonate solution. Dichloromethane was added and the organic layer was separated. The resulting organic layer was washed with brine and then dried over anhydrous sodium sulfate. The drying agent was separated by filtration and the organic layer was concentrated under reduced pressure to obtain the title compound (3.84 g). The property values of the compound are as follows.

$^1$H-NMR (CDCl$_3$) δ (ppm): 7.03-7.07 (m, 1H), 8.66-8.73 (m, 1H).

Synthesis of 2,6-difluoro-3-aminopyridine 2,6-Difluoro-3-nitropyridine (3.84 g) was dissolved in ethanol (42 ml). A solution of iron powder (4.03 g) and ammonium chloride (2.57 g) in water (14 ml) was added, and the reaction solution was heated and stirred at 80° C. for one hour. After leaving to cool, the reaction solution was filtered through celite. Ethyl acetate and water were added and the organic layer was separated. The resulting organic layer was washed with brine and then dried over anhydrous sodium sulfate. The drying agent was separated by filtration, and then the organic layer was concentrated under reduced pressure. The residue was purified by silica gel column chromatography to obtain the title compound (2.06 g). The property values of the compound are as follows.

$^1$H-NMR (CDCl$_3$) δ (ppm): 3.66 (brs, 2H), 6.65 (dd, J=8.2, 3.0 Hz, 1H), 7.22 (ddd, 10.4, 8.2, 6.8 Hz, 1H).

Synthesis of N-(2,6-difluoropyridin-3-yl)formamide

Acetic anhydride (6 ml) was added to formic acid (6 ml), followed by stirring at room temperature for 20 minutes. Then, a solution of 2,6-difluoro-3-aminopyridine (2.06 g) in tert-butyl methyl ether (7 ml) was added so that the reaction solution was maintained at room temperature. The reaction solution was further stirred at room temperature for four hours. Ethyl acetate and a saturated sodium bicarbonate solution were added to the reaction solution, and the organic layer was separated. The resulting organic layer was washed with brine and then dried over anhydrous sodium sulfate. The drying agent was separated by filtration, and then the organic layer was concentrated under reduced pressure. The residue was purified by silica gel column chromatography to obtain the title compound (2.42 g). The property values of the compound are as follows.

$^1$H-NMR (CDCl$_3$) δ (ppm): 6.86 (dd, J=8.8, 2.8 Hz, 1H), 7.42 (brs, 1H), 8.49 (s, 1H), 8.83-8.90 (m, 1H).

Synthesis of N-(2,6-difluoropyridin-3-yl)-N-(2-oxopropyl)formamide

Chloroacetone (1.83 ml), cesium carbonate (7.99 g) and potassium iodide (254 mg) were added to a solution of N-(2,6-difluoropyridin-3-yl)formamide (2.42 g) in N,N-dimethylformamide (50 ml), and the reaction solution was stirred at room temperature for two hours. Ethyl acetate and water were added to the reaction solution, and the organic layer was separated. The resulting organic layer was washed with brine and then dried over anhydrous sodium sulfate. The drying agent was separated by filtration, and then the organic layer was concentrated under reduced pressure. The residue was purified by silica gel column chromatography to obtain the title compound (2.52 g). The property values of the compound are as follows.

$^1$H-NMR (CDCl$_3$) δ (ppm): 2.21 (s, 3H), 4.54 (s, 2H), 6.93 (dd, J=8.0, 3.2 Hz, 1H), 7.99 (ddd, J=9.6, 8.4, 7.2 Hz, 1H), 8.28 (s, 1H).

Synthesis of
2,6-difluoro-3-(4-methyl-1H-imidazol-1-yl)pyridine

Trifluoroacetic acid (1.08 ml) and ammonium acetate (1.08 g) were added to a solution of N-(2,6-difluoropyridin-3-yl)-N-(2-oxopropyl)formamide (2.52 g) in toluene (40 ml), and the reaction solution was heated under reflux in a nitrogen atmosphere for four hours. After leaving to cool, ethyl acetate and a saturated sodium bicarbonate solution were added to the reaction solution, and the organic layer was separated. The resulting organic layer was washed with brine and then dried over anhydrous sodium sulfate. The drying agent was separated by filtration, and then the organic layer was concentrated under reduced pressure. The residue was purified by silica gel column chromatography to obtain the title compound (2.19 g). The property values of the compound are as follows.

ESI-MS; m/z 196 [M$^+$+H]. $^1$H-NMR (CDCl$_3$) δ (ppm): 2.31 (s, 3H), 6.95-7.00 (m, 2H), 7.71-7.72 (m, 1H), 7.90 (ddd, J=9.2, 8.6, 6.8 Hz, 1H).

Synthesis of 2-amino-6-fluoro-5-(4-methyl-1H-imidazol-1-yl)pyridine

28% aqueous ammonia (5 ml) was added to 2,6-difluoro-3-(4-methyl-1H-imidazol-1-yl)pyridine (750 mg), and the reaction solution was heated and stirred at 125° C. for one hour using a microwave synthesizer. Ethyl acetate and water were added to the reaction solution, and the organic layer was separated. The resulting organic layer was washed with brine and then dried over anhydrous sodium sulfate. The drying agent was separated by filtration and then the organic layer was concentrated under reduced pressure. The residue was purified by NH silica gel column chromatography to obtain the title compound (92 mg), 6-amino-2-fluoro-5-(4-methyl-1H-imidazol-1-yl)pyridine (252 mg) and 2,6-diamino-5-(4-methyl-1H-imidazol-1-yl)pyridine (53 mg).

The property values of the title compound are as follows.
$^1$H-NMR (CDCl$_3$) δ (ppm): 2.28 (s, 3H), 4.67 (brs, 2H), 6.40 (dd, J=8.2, 1.2 Hz, 1H), 6.84 (d, J=1.0 Hz, 1H), 7.49 (dd, J=9.6, 8.2 Hz, 1H), 7.57 (d, J=1.0 Hz, 1H).

The property values of 6-amino-2-fluoro-5-(4-methyl-1H-imidazol-1-yl)pyridine are as follows.
$^1$H-NMR (CDCl$_3$) δ (ppm): 2.30 (s, 3H), 4.63 (brs, 2H), 6.352 (dd, J=8.2, 3.0 Hz, 1H), 6.79 (d, J=0.8 Hz, 1H), 7.44 (dd, J=8.2, 7.2 Hz, 1H), 7.49 (d, J=0.8 Hz, 1H).

The property values of 2,6-diamino-5-(4-methyl-1H-imidazol-1-yl)pyridine are as follows.
$^1$H-NMR (CDCl$_3$) δ (ppm): 2.28 (s, 3H), 4.25 (brs, 2H), 4.37 (brs, 2H), 5.91 (d, J=8.2 Hz, 1H), 6.73 (d, J=1.4 Hz, 1H), 7.13 (d, J=8.2 Hz, 1H), 7.43 (d, J=1.4 Hz, 1H).

Synthesis of 6-bromo-2-fluoro-3-(4-methyl-1H-imidazol-1-yl)pyridine

Copper sulfate pentahydrate (438 mg) and sodium bromide (289 mg) were dissolved in water (8 ml), and a solution sodium sulfite (176 mg) in water (6 ml) was added dropwise at room temperature. After stirring at room temperature for 15 minutes, the supernatant was removed and the resulting precipitate was washed with water. A 24% hydrobromic acid solution (5 ml) was added thereto to obtain a copper bromide solution. In another reaction vessel, 2-amino-6-fluoro-5-(4-methyl-1H-imidazol-1-yl)pyridine was dissolved in a 24% hydrobromic acid solution (5 ml), and a solution of sodium nitrite (105 mg) in water (6 ml) was added dropwise under ice-cooling. The resulting diazonium salt solution was added to the copper bromide solution prepared above, and the reaction solution was further stirred under ice-cooling for one hour. The reaction solution was neutralized with a 5 N sodium hydroxide solution. Aqueous ammonia and tert-butyl methyl ether were added and the organic layer was separated. The resulting organic layer was washed with brine and then dried over anhydrous sodium sulfate. The drying agent was separated by filtration, and then the organic layer was concentrated under reduced pressure. The residue was purified by silica gel column chromatography to obtain the title compound (115 mg). The property values of the compound are as follows.

$^1$H-NMR (CDCl$_3$) δ (ppm): 2.30 (s, 3H), 6.99 (s, 1H), 7.52 (d, J=8.0 Hz, 1H), 7.66 (dd, J=8.8, 8.0 Hz, 1H), 7.76 (s, 1H).

Synthesis of (+) and (−)-2-{(E)-2-[6-fluoro-5-(4-methyl-1H-imidazol-1-yl)pyridin-2-yl]vinyl}-8-(2-trifluoromethylphenyl)-5,6,7,8-tetrahydro[1,2,4]triazolo[1,5-a]pyridine 6-Bromo-2-fluoro-3-(4-methyl-1H-imidazol-1-yl)pyridine (156 mg) and 8-(2-trifluoromethylphenyl)-2-vinyl-5,6,7,8-tetrahydro[1,2,4]triazolo[1,5-a]pyridine (179 mg) were dissolved in toluene (5 ml). Tris(dibenzylideneacetone)dipalladium (167 mg), tri-o-tolylphosphine (111 mg) and triethylamine (340 ul) were added and the reaction solution was heated and stirred in a nitrogen atmosphere at 120° C. for 1.3 hours. After leaving to cool, ethyl acetate and water were added. The reaction solution was filtered through celite and the organic layer was separated. The resulting organic layer was washed with brine and then dried over anhydrous sodium sulfate. The drying agent was separated by filtration, and then the organic layer was concentrated under reduced pressure. The residue was purified by NH silica gel column chromatography to obtain a racemate of the title compound (65 mg). The resulting racemate was separated by CHIRALPAK™ IB manufactured by Daicel Chemical Industries, Ltd. (2 cm×25 cm; mobile phase: hexane:ethanol=6:4) to obtain the title optically active compound with positive optical rotation (20 mg, >99% ee) and the title optically active compound with negative optical rotation (20 mg, >99% ee).

The property values of the title optically active compound with positive optical rotation are as follows.

ESI-MS; m/z 469 [M$^+$+H]. $^1$H-NMR (CDCl$_3$) δ (ppm): 1.90-2.00 (m, 1H), 2.10-2.21 (m, 1H), 2.21-2.35 (m, 1H), 2.30 (s, 3H), 2.40-2.51 (m, 1H), 4.28-4.40 (m, 2H), 4.70 (dd, J=7.6, 5.6 Hz, 1H), 6.97-7.03 (m, 2H), 7.22-7.28 (m, 1H), 7.37-7.52 (m, 3H), 7.57-7.77 (m, 4H).

The property values of the title optically active compound with negative optical rotation are as follows.

ESI-MS; m/z 469 [M$^+$+H]. $^1$H-NMR (CDCl$_3$) δ (ppm): 1.90-2.00 (m, 1H), 2.10-2.21 (m, 1H), 2.21-2.35 (m, 1H), 2.30 (s, 3H), 2.40-2.51 (m, 1H), 4.28-4.40 (m, 2H), 4.70 (dd, J=7.6, 5.6 Hz, 1H), 6.97-7.03 (m, 2H), 7.22-7.28 (m, 1H), 7.37-7.52 (m, 3H), 7.57-7.77 (m, 4H).

Examples 349 and 350

Synthesis of (+) and (−)-2-{(E)-2-[5-(4-methyl-1H-imidazol-1-yl)-pyridin-2-yl]vinyl}-8-(2-trifluoromethylphenyl)-5,6,7,8-tetrahydro-[1,2,4]triazolo[1,5-a]pyridine

[Formula 197]

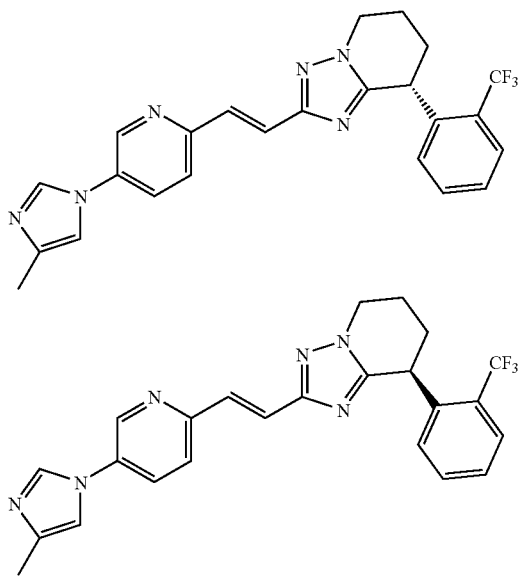

Synthesis of 3-(4-methyl-1H-imidazol-1-yl)-6-{(E)-2-[8-(2-trifluoromethylphenyl)-5,6,7,8-tetrahydro-[1,2,4]triazolo[1,5-a]pyridin-2-yl]vinyl}pyridin-2-yl trifluoromethanesulfonate Pyridine (200 µL) was added to a solution of 3-(4-methyl-1H-imidazol-1-yl)-6-{(E)-2-[8-(2-trifluoromethylphenyl)-5,6,7,8-tetrahydro-[1,2,4]triazolo[1,5-a]pyridin-2-yl]vinyl}pyridin-2-ol synthesized in Example 344 (200 mg) in dichloromethane (2 mL), and trifluoromethanesulfonic anhydride (78.3 µL) was added dropwise under ice-cooling. The reaction solution was stirred at room temperature for one hour. Water was added to the reaction solution under ice-cooling, followed by separatory extraction with ethyl acetate. The resulting organic layer was dried over magnesium sulfate and concentrated under reduced pressure. The resulting residue was purified by silica gel chromatography (carrier: Chromatorex NH; elution solvent: heptane:ethyl acetate=2:1→ethyl acetate) to obtain the title compound (64 mg).
The property value of the compound is as follows.
ESI-MS; m/z 599 [M⁺+H].

Synthesis of (+) and (−)-2-{(E)-2-[5-(4-methyl-1H-imidazol-1-yl)pyridin-2-yl]vinyl}-8-(2-trifluoromethylphenyl)-5,6,7,8-tetrahydro-[1,2,4]triazolo[1,5-a]pyridine Triethylsilane (40.9 µL) and a 1,1'-bis(diphenylphosphino) ferrocene palladium (II) dichloride-dichloromethane complex (4.37 mg) were added to a solution of 3-(4-methyl-1H-imidazol-1-yl)-6-{(E)-2-[8-(2-trifluoromethylphenyl)-5,6,7,8-tetrahydro-[1,2,4]triazolo[1,5-a]pyridin-2-yl]vinyl}pyridin-2-yl trifluoromethanesulfonate (64 mg) in DMF (2 mL). The reaction solution was stirred at 70° C. for five hours. The reaction solution was concentrated under reduced pressure. The resulting residue was purified by silica gel chromatography (carrier: Chromatorex NH; elution solvent: heptane:ethyl acetate=4:1→ethyl acetate) to obtain a racemate of the title compound (25 mg). The resulting racemate (25 mg) was separated by CHIRALPAK™ IB manufactured by Daicel Chemical Industries, Ltd. (2 cm×25 cm, mobile phase: ethanol, flow rate: 11 mL/min) to obtain the title optically active compound with a retention time of 21 minutes and positive optical rotation (10 mg) and the title optically active compound with a retention time of 30 minutes and negative optical rotation (10 mg).
The property values of the title optically active compound with a retention time of 21 minutes are as follows.
¹H-NMR (CDCl₃) δ (ppm): 1.90-2.49 (m, 7H), 4.28-4.39 (m, 2H), 4.70 (dd, J=7.6, 6.4 Hz, 1H), 7.00-7.02 (m, 2H), 7.37-7.61 (m, 6H), 7.72 (d, J=7.6 Hz, 1H), 7.76 (s, 1H), 8.67 (d, J=2.8 Hz, 1H).
The property values of the title optically active compound with a retention time of 30 minutes are as follows.
¹H-NMR (CDCl₃) δ (ppm): 1.90-2.49 (m, 7H), 4.28-4.39 (m, 2H), 4.70 (dd, J=7.6, 6.4 Hz, 1H), 7.00-7.02 (m, 2H), 7.37-7.61 (m, 6H), 7.72 (d, J=7.6 Hz, 1H), 7.76 (s, 1H), 8.67 (d, J=2.8 Hz, 1H).

Examples 351 and 352

Synthesis of (+) and (−)-2-{(E)-2-[5-(4-methyl-1H-imidazol-1-yl)-6-(2,2,2-trifluoroethoxy)pyridin-2-yl]vinyl}-8-(2-trifluoromethylphenyl)-5,6,7,8-tetrahydro-[1,2,4]triazolo[1,5-a]pyridine

[Formula 198]

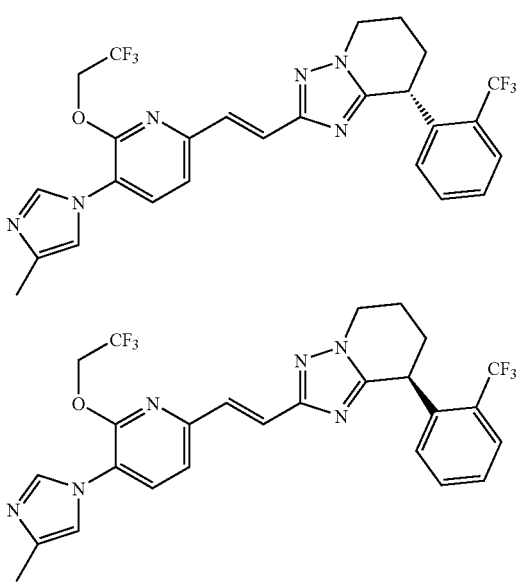

Cesium carbonate (83.7 mg) and 2,2,2-trifluoroethyl trifluoromethanesulfonate (35.7 µL) were added to a mixture of 3-(4-methyl-1H-imidazol-1-yl)-6-{(E)-2-[8-(2-trifluoromethylphenyl)-5,6,7,8-tetrahydro-[1,2,4]triazolo[1,5-a]pyridin-2-yl]vinyl}pyridin-2-ol synthesized in Example 344 (100 mg) and DMF (1.2 mL), and the reaction solution was stirred at room temperature for four hours. Water and ethyl acetate were added to the reaction solution, and the organic layer was separated. The organic layer was dried over magnesium sulfate and concentrated under reduced pressure. The residue was purified by silica gel chromatography (carrier: Chromatorex NH; elution solvent: heptane:ethyl acetate=4:1→ethyl acetate) to obtain a racemate of the title compound (110 mg). The resulting racemate (110 mg) was separated by CHIRALPAK™ IB manufactured by Daicel Chemical Industries, Ltd. (2 cm×25 cm, mobile phase: hexane:ethanol=5:5, flow rate: 11 mL/min) to obtain the title optically active compound with a retention time of 13 minutes and positive optical rotation (51 mg) and the title optically active compound with a retention time of 18 minutes and negative optical rotation (53 mg).

The property values of the title optically active compound with a retention time of 13 minutes are as follows.

$^1$H-NMR (CDCl$_3$) δ (ppm): 1.90-2.49 (m, 7H), 4.30-4.40 (m, 2H), 4.70 (dd, J=8.4, 6.0 Hz, 2H), 4.84-4.93 (m, 2H), 6.96-7.04 (m, 3H), 7.37-7.58 (m, 5H), 7.25 (d, J=7.6 Hz, 1H), 7.78 (d, J=1.2 Hz, 1H).

The property values of the title optically active compound with a retention time of 18 minutes are as follows.

$^1$H-NMR (CDCl$_3$) δ (ppm): 1.90-2.49 (m, 7H), 4.30-4.40 (m, 2H), 4.70 (dd, J=8.4, 6.0 Hz, 2H), 4.84-4.93 (m, 2H), 6.96-7.04 (m, 3H), 7.37-7.58 (m, 5H), 7.25 (d, J=7.6 Hz, 1H), 7.78 (d, J=1.2 Hz, 1H).

Examples 353 and 354

Synthesis of (+) and (−)-2-{(E)-2-[5-(4-methyl-1H-imidazol-1-yl)-6-(2,2-difluoroethoxy)pyridin-2-yl]vinyl}-8-(2-trifluoromethylphenyl)-5,6,7,8-tetrahydro-[1,2,4]triazolo[1,5-a]pyridine vinyl}pyridin-2-ol synthesized in Example 344 (100 mg) and DMF (1.2 mL), and the reaction solution was stirred at room temperature for 48 hours. Water and ethyl acetate were added to the reaction solution, and the organic layer was separated. The organic layer was dried over magnesium sulfate and concentrated under reduced pressure. The residue was purified by silica gel chromatography (carrier: Chromatorex NH; elution solvent: heptane:ethyl acetate=4:1→ethyl acetate) to obtain a racemate of the title compound (80 mg). The resulting racemate (80 mg) was separated by CHIRALPAK™ IB manufactured by Daicel Chemical Industries, Ltd. (2 cm×25 cm, mobile phase: hexane:ethanol=4:6, flow rate: 11 mL/min) to obtain the title optically active compound with a retention time of 14 minutes and positive optical rotation (33 mg) and the title optically active compound with a retention time of 25 minutes and negative optical rotation (35 mg).

The property values of the title optically active compound with a retention time of 14 minutes are as follows.

$^1$H-NMR (CDCl$_3$) δ (ppm): 1.90-2.49 (m, 7H), 4.31-4.40 (m, 2H), 4.62-4.72 (m, 3H), 5.99-6.92 (m, 1H), 6.96 (s, 1H), 6.96-7.02 (m, 3H) 7.26-7.57 (m, 5H), 7.25 (d, J=7.2 Hz, 1H), 7.77 (d, J=1.2 Hz, 1H).

The property values of the title optically active compound with a retention time of 25 minutes are as follows.

$^1$H-NMR (CDCl$_3$) δ (ppm): 1.90-2.49 (m, 7H), 4.31-4.40 (m, 2H), 4.62-4.72 (m, 3H), 5.99-6.92 (m, 1H), 6.96 (s, 1H), 6.96-7.02 (m, 3H) 7.26-7.57 (m, 5H), 7.25 (d, J=7.2 Hz, 1H), 7.77 (d, J=1.2 Hz, 1H).

Examples 355 and 356

Synthesis of (+) and (−)-2-{(E)-2-[5-(1H-imidazol-1-yl)-6-methoxypyridin-2-yl]vinyl}-8-(2-trifluorophenyl)-5,6,7,8-tetrahydro-[1,2,4]triazolo[1,5-a]pyridine

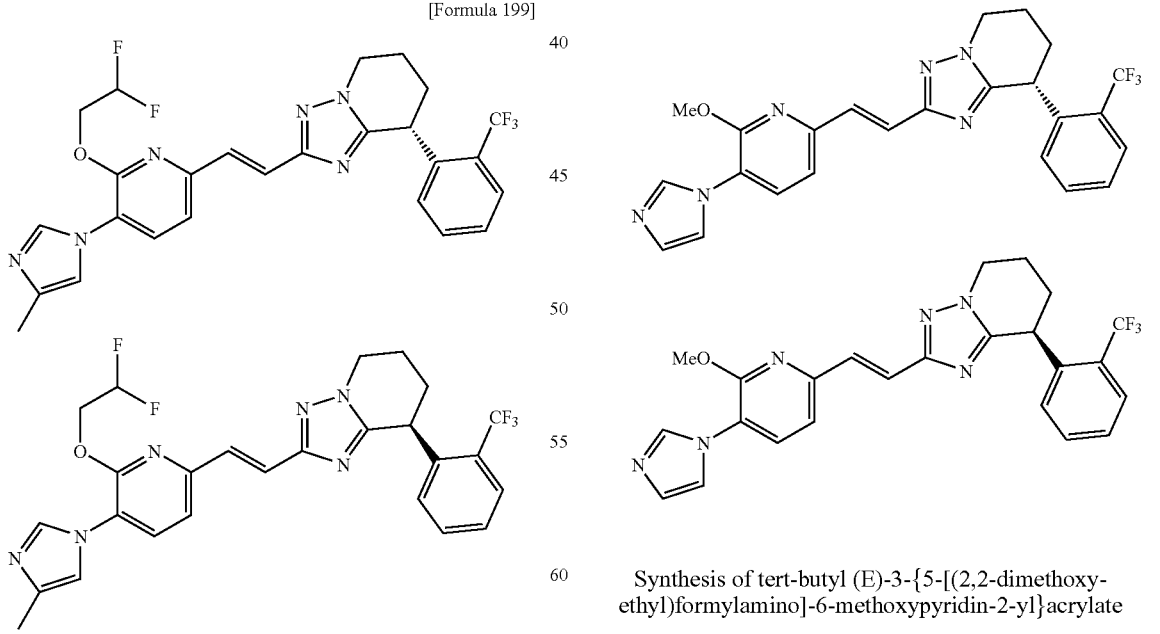

[Formula 199]

[Formula 200]

Cesium carbonate (83.7 mg) and 2-bromo-1,1-difluoroethane (34.1 mg) were added to a mixture of 3-(4-methyl-1H-imidazol-1-yl)-6-{(E)-2-[8-(2-trifluoromethylphenyl)-5,6,7,8-tetrahydro-[1,2,4]triazolo[1,5-a]pyridin-2-yl]

Synthesis of tert-butyl (E)-3-{5-[(2,2-dimethoxyethyl)formylamino]-6-methoxypyridin-2-yl}acrylate tert-Butyl (E)-3-(5-formylamino-6-methoxypyridin-2-yl)acrylate synthesized according to the method in Examples 168 and 169 (4 g) was dissolved in DMF (60 mL). Cesium carbonate (9.38 g) was added and the reaction solution was heated to 60° C. Bromoacetaldehyde dimethylacetal (2.08 mL) was added to the reaction solution. The reaction solution was stirred for two hours, heated to 110° C. and stirred for 10 hours. The reaction solution was left to cool. Ice water was added under ice-cooling, followed by extraction with ethyl acetate. The organic layer was dried over magnesium sulfate and concentrated under reduced pressure. The residue was purified by silica gel chromatography (carrier: Chromatorex Si; elution solvent: heptane:ethyl acetate=7:1→heptane:ethyl acetate=1:2) to obtain the title compound (3.99 g). The property values of the compound are as follows.

$^1$H-NMR (CDCl$_3$) δ (ppm): 1.54 (s, 9H), 3.30 (s, 6H), 3.83 (d, J=5.2 Hz, 2H), 4.01 (s, 3H), 4.53 (t, J=5.2 Hz, 1H), 6.84 (d, J=15.6 Hz, 1H), 7.00 (d, J=8.0 Hz, 1H), 7.46 (d, J=15.2 Hz, 1H), 7.46 (d, J=7.2 Hz, 1H), 8.17 (s, 1H).

Synthesis of tert-butyl (E)-3-[5-(1H-imidazol-1-yl)-6-methoxypyridin-2-yl]acrylate tert-Butyl (E)-3-{5-[(2,2-dimethoxyethyl)formylamino]-6-methoxypyridin-2-yl}acrylate (3.7 g) was dissolved in acetic acid (36 mL). Ammonium acetate (7 g) was added and the reaction solution was stirred at 135° C. for two hours. The reaction solution was concentrated under reduced pressure. A saturated sodium bicarbonate solution and ethyl acetate were added and the organic layer was separated. The organic layer was dried over magnesium sulfate and concentrated under reduced pressure. The residue was purified by silica gel chromatography (carrier: Chromatorex NH; elution solvent: heptane:ethyl acetate=9:1→heptane:ethyl acetate=1:2) to obtain the title compound (490 mg).

The property value of the compound is as follows.
ESI-MS; m/z 302 [M$^+$+H].

Synthesis of (E)-3-[5-(1H-imidazol-1-yl)-6-methoxypyridin-2-yl]acrylic acid

A solution of trifluoroacetic acid (3 mL) in dichloromethane (1.5 mL) was added to tert-butyl (E)-3-[5-(1H-imidazol-1-yl)-6-methoxypyridin-2-yl]acrylate (490 mg) under ice-cooling, and the reaction solution was stirred at room temperature for one hour. The reaction solution was concentrated under reduced pressure, diluted with chloroform and then concentrated under reduced pressure. Diethyl ether was added to the residue, and the precipitated solid was collected by filtration. The solid was washed with diethyl ether to obtain the title compound as a solid (345 mg). The property values of the compound are as follows.

$^1$H-NMR (CDCl$_3$) δ (ppm): 4.00 (s, 3H), 6.88 (d, J=15.6 Hz, 1H), 7.52-7.70 (m, 4H), 7.90 (s, 1H), 8.10 (d, J=8.0 Hz, 1H), 9.18 (s, 1H).

Synthesis of (E)-3-[5-(1H-imidazol-1-yl)-6-methoxypyridin-2-yl]-N-[2-oxo-3-(2-trifluoromethylphenyl)piperidin-1-yl]acrylamide IPEA (742 μL), EDC (206 mg) and HOBT (146 mg) were added to a mixture of 1-amino-3-(2-trifluoromethylphenyl)piperidin-2-one (185 mg), (E)-3-[5-(1H-imidazol-1-yl)-6-methoxypyridin-2-yl]acrylic acid (340 mg) and DMF (5 mL), and the reaction solution was stirred at room temperature for 14 hours. A saturated sodium bicarbonate solution was added to the reaction solution, followed by extraction with ethyl acetate. The organic layer was dried over magnesium sulfate and concentrated under reduced pressure. The residue was purified by silica gel chromatography (carrier: Chromatorex NH; elution solvent: ethyl acetate→ethyl acetate:methanol=9:1) to obtain the title compound (453 mg). The property value of the compound is as follows.
ESI-MS; m/z 486 [M$^+$+H].

Synthesis of (+) and (−)-2-{(E)-2-[5-(1H-imidazol-1-yl)-6-methoxypyridin-2-yl]vinyl}-8-(2-trifluorophenyl)-5,6,7,8-tetrahydro-[1,2,4]triazolo[1,5-a]pyridine Phosphorus oxychloride (9 mL) was added to (E)-3-[5-(1H-imidazol-1-yl)-6-methoxypyridin-2-yl]-N-[2-oxo-3-(2-trifluoromethylphenyl)piperidin-1-yl]acrylamide (340 mg), and the reaction solution was stirred at 100° C. for 35 minutes. The reaction solution was concentrated under reduced pressure. The resulting residue was diluted with acetic acid (5 mL). Then, ammonium acetate (1.43 g) was added and the reaction solution was stirred at 140° C. for one hour and 15 minutes. The reaction solution was concentrated under reduced pressure. Ethyl acetate and a saturated sodium bicarbonate solution were added to the residue, and the organic layer was separated. The organic layer was dried over magnesium sulfate and concentrated under reduced pressure. The residue was purified by silica gel chromatography (carrier: Chromatorex NH; elution solvent: heptane:ethyl acetate=2:1→ethyl acetate) to obtain a racemate of the title compound (200 mg). The racemate (200 mg) was separated by CHIRALPAK™ IB manufactured by Daicel Chemical Industries, Ltd. (2 cm×25 cm, mobile phase: hexane:ethanol=5:5, flow rate: 11 mL/min) to obtain the title optically active compound with a retention time of 16 minutes and positive optical rotation (70 mg) and the title optically active compound with a retention time of 34 minutes and negative optical rotation (75 mg).

The property values of the title optically active compound with a retention time of 16 minutes are as follows.

$^1$H-NMR (CDCl$_3$) δ (ppm): 1.90-2.50 (m, 4H), 4.03 (s, 3H), 4.29-4.40 (m, 2H), 4.69 (dd, J=6.4, 6.0 Hz, 1H), 6.94 (d, J=7.2 Hz, 1H), 7.01 (d, J=7.6 Hz, 1H), 7.17 (brm, 1H), 7.23-7.24 (m, 1H), 7.37-7.50 (m, 4H), 7.65 (d, J=15.6 Hz, 1H), 7.72 (d, J=8.0 Hz, 1H), 7.85 (m, 1H).

The property values of the title optically active compound with a retention time of 34 minutes are as follows.

$^1$H-NMR (CDCl$_3$) δ (ppm): 1.90-2.50 (m, 4H), 4.03 (s, 3H), 4.29-4.40 (m, 2H), 4.69 (dd, J=6.4, 6.0 Hz, 1H), 6.94 (d, J=7.2 Hz, 1H), 7.01 (d, J=7.6 Hz, 1H), 7.17 (brm, 1H), 7.23-7.24 (m, 1H), 7.37-7.50 (m, 4H), 7.65 (d, J=15.6 Hz, 1H), 7.72 (d, J=8.0 Hz, 1H), 7.85 (m, 1H).

Examples 357 and 358

Synthesis of (+) and (−)-8-(4-fluorophenyl)-2-{(E)-2-[6-methoxy-5-(4-methyl-1H-imidazol-1-yl)pyridin-2-yl]propenyl}-5,6,7,8-tetrahydro-[1,2,4]triazolo[1,5-a]pyridine

[Formula 201]

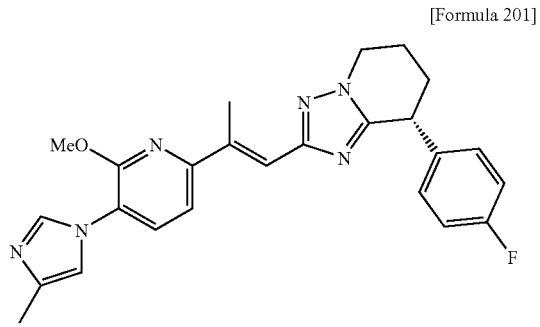

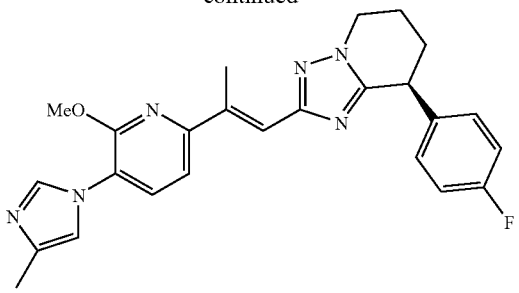

Synthesis of (E)-3-[6-methoxy-5-(4-methyl-1H-imidazol-1-yl)pyridin-2-yl]-2-butenoic acid ditrifluoroacetate Sodium hydride (401 mg; containing 60 wt % of mineral oil) was added to a solution of tert-butyl (E)-3-[6-methoxy-5-(4-methyl-1H-imidazol-1-yl)pyridin-2-yl]acrylate (1.58 g) and trimethylsulfonium iodide (2.21 g) in DMSO (15 mL) at 0° C. Then, the reaction solution was stirred at room temperature for one hour. Ice water and ethyl acetate were added to the reaction solution, and the organic layer was separated. The resulting organic layer was washed with brine and then dried over anhydrous magnesium sulfate. The organic layer was concentrated under reduced pressure. The residue was purified by NH-silica gel column chromatography (elution solvent: heptane-ethyl acetate system) to obtain a crude product. Trifluoroacetic acid (6 mL) was added to a solution of the crude product in methylene chloride (3 mL) at room temperature, and the reaction solution was stirred at room temperature for two hours. The reaction solvent was removed under reduced pressure, followed by azeotropic distillation with chloroform. Then, the resulting solid was filtered, washed with diethyl ether and dried to obtain 1.05 g of the title compound. The property value of the compound is as follows.

ESI-MS; m/z 274 [M$^+$+H].

Synthesis of (+) and (−)-8-(4-fluorophenyl)-2-{(E)-2-[6-methoxy-5-(4-methyl-1H-imidazol-1-yl)pyridin-2-yl]propenyl}-5,6,7,8-tetrahydro-[1,2,4]triazolo[1,5-a]pyridine A racemate of the title compound (125 mg) was obtained from (E)-3-[6-methoxy-5-(4-methyl-1H-imidazol-1-yl)pyridin-2-yl]-2-butenoic acid ditrifluoroacetate (300 mg) and 1-amino-3-(4-fluorophenyl)piperidin-2-one (163 mg) according to the method in Examples 168 and 169. The resulting racemate was separated by CHIRALPAK™ IB manufactured by Daicel Chemical Industries, Ltd. (2 cm×25 cm; mobile phase: hexane-ethanol system) to obtain the title optically active compound with a retention time of 18.7 minutes and positive optical rotation (41.7 mg, >99% ee) and the title optically active compound with a retention time of 27.9 minutes and negative optical rotation (41.8 mg, >99% ee).

The property values of the title compound with positive optical rotation are as follows.

ESI-MS; m/z 464 [M$^+$+H]. $^1$H-NMR (CDCl$_3$) δ (ppm): 2.00-2.18 (m, 2H), 2.18-2.28 (m, 1H), 2.30 (s, 3H), 2.30-2.40 (m, 1H), 2.63 (s, 3H), 4.05 (s, 3H), 4.30-4.36 (m, 3H), 6.97 (s, 1H), 7.00-7.05 (m, 2H), 7.10-7.14 (m, 2H), 7.22 (d, J=8.0 Hz, 1H), 7.52 (d, J=8.0 Hz, 1H), 7.57 (d, J=1.2 Hz, 1H), 7.79 (d, J=1.2 Hz, 1H).

The property values of the title compound with negative optical rotation are as follows.

ESI-MS; m/z 464 [M$^+$+H]. $^1$H-NMR (CDCl$_3$) δ (ppm): 2.00-2.18 (m, 2H), 2.18-2.28 (m, 1H), 2.30 (s, 3H), 2.30-2.40 (m, 1H), 2.63 (s, 3H), 4.05 (s, 3H), 4.30-4.36 (m, 3H), 6.97 (s, 1H), 7.00-7.05 (m, 2H), 7.10-7.14 (m, 2H), 7.22 (d, J=8.0 Hz, 1H), 7.52 (d, J=8.0 Hz, 1H), 7.57 (d, J=1.2 Hz, 1H), 7.79 (d, J=1.2 Hz, 1H).

Examples 359, 360, 361 and 362

Synthesis of (5R,8R), (5S,8S), (5R,8S) and (5S,8R)-2-{(E)-2-[6-methoxy-5-(4-methyl-1H-imidazol-1-yl)pyridin-2-yl]vinyl}-5-methyl-8-(2-trifluoromethylphenyl)-5,6,7,8-tetrahydro-[1,2,4]triazolo[1,5-a]pyridine

[Formula 202]

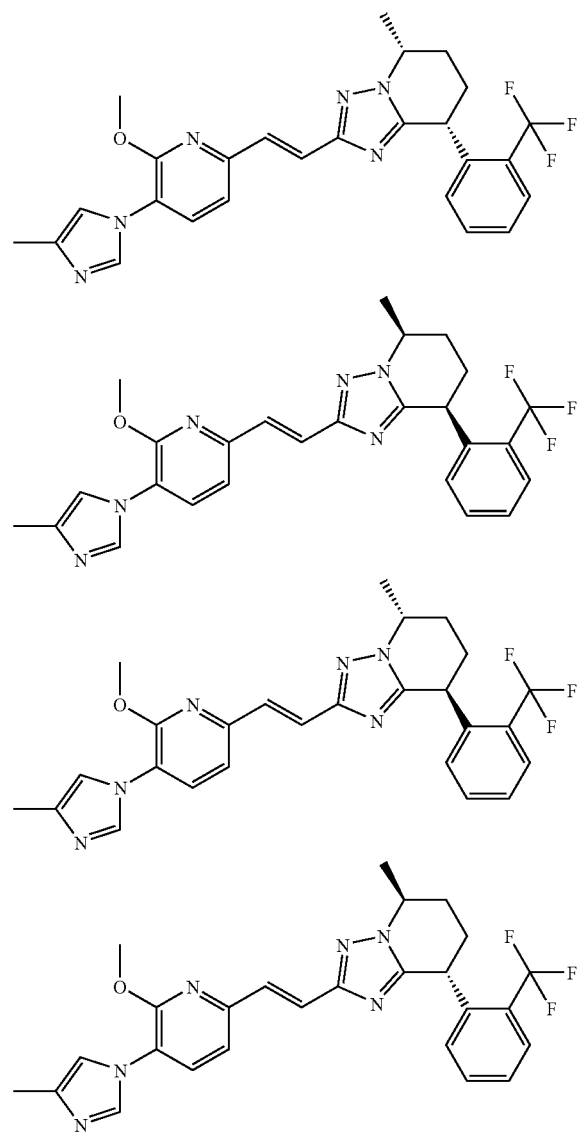

Synthesis of 2-(2-trifluoromethylphenyl)pentanedioic acid 5-tert-butyl ester 1-methyl ester Methyl 2-trifluoromethylphenylacetate (5 g) was dissolved in THF (75 mL). Potassium tert-butoxide (2.71 g) was added under ice-cooling, and the reaction solution was stirred for 30 minutes. tert-Butyl 3-bromopropionate (3.83 mL) was added to the reaction solution. The reaction solution was gradually heated until room temperature and stirred for four hours. A 1 N hydrochloric acid aqueous solution was added to the reaction solution, followed by extraction with ethyl acetate. The organic layer was dried over magnesium sulfate and concentrated under reduced pressure. The resulting residue was purified by silica gel chromatography (carrier: Chromatorex Si; elution solvent: heptane:ethyl acetate=19:1→heptane:ethyl acetate=1:1) to obtain the title compound (6 g). The property values of the compound are as follows.

$^1$H-NMR (CDCl$_3$) δ (ppm): 1.42 (s, 9H), 2.02-2.43 (m, 4H), 3.66 (s, 3H), 4.06 (dd, J=7.2, 7.2 Hz, 1H), 7.35-7.41 (m, 1H), 7.50-7.67 (m, 3H).

Synthesis of methyl 5-oxo-2-(2-trifluoromethylphenyl)hexanoate 2-(2-Trifluoromethylphenyl)pentanedioic acid 5-tert-butyl ester 1-methyl ester (3 g) was dissolved in dichloromethane (30 mL). Trifluoroacetic acid (12 mL) was added and the reaction solution was stirred at room temperature for one hour. The reaction solution was concentrated under reduced pressure, and the resulting residue was dissolved in toluene (60 mL). Thionyl chloride (1.89 mL) was added and the reaction solution was stirred at 80° C. for three hours. The reaction solution was concentrated under reduced pressure and diluted with THF (50 mL). Then, tributylphosphine (2.37 mL) was added at −20° C. and the reaction solution was stirred for 20 minutes. A 0.97 M solution of methylmagnesium bromide in THF (9.78 mL) was added dropwise to the reaction solution, and the reaction solution was stirred for 15 minutes. Then, a 1 N hydrochloric acid aqueous solution was added, followed by extraction with ethyl acetate. The organic layer was dried over magnesium sulfate and concentrated under reduced pressure. The residue was purified by silica gel chromatography (carrier: Chromatorex Si; elution solvent: heptane:ethyl acetate=19:1→heptane:ethyl acetate=1:1) to obtain the title compound (728 mg). The property values of the compound are as follows.

$^1$H-NMR (CDCl$_3$) δ (ppm): 2.01-2.51 (m, 7H), 3.65 (s, 3H), 3.98-4.02 (m, 1H), 7.35-7.38 (m, 1H), 7.51-7.57 (m, 2H), 7.56 (d, J=8.0 Hz, 1H).

Synthesis of 1-amino-6-methyl-3-(2-trifluoromethylphenyl)piperidin-2-one

Methyl 5-oxo-2-(2-trifluoromethylphenyl)hexanoate (728 mg) was dissolved in methanol (15.2 mL). Sodium borohydride (47.8 mg) was added under ice-cooling, and the reaction solution was stirred at the same temperature for 30 minutes. A 1 N hydrochloric acid aqueous solution was added to the reaction solution, followed by extraction with ethyl acetate. The resulting organic layer was dried over magnesium sulfate and then concentrated under reduced pressure. The resulting residue was dissolved in chloroform (15 mL). Thionyl chloride (576 μL) was added and the reaction solution was stirred at 50° C. for three hours. The reaction solution was concentrated under reduced pressure. The resulting residue was purified by silica gel chromatography (carrier: Chromatorex Si; elution solvent: heptane:ethyl acetate=19:1→heptane:ethyl acetate=1:1) to obtain methyl 5-chloro-2-(2-trifluoromethylphenyl)hexanoate (380 mg) as a diastereomer mixture. The mixture (320 mg) was dissolved in ethanol (7.8 mL). Hydrazine monohydrate (1.5 mL) was added and the reaction solution was stirred at 100° C. for 14 hours. The reaction solution was concentrated under reduced pressure. A saturated sodium bicarbonate solution was added to the residue, followed by extraction with ethyl acetate. The organic layer was dried over magnesium sulfate and concentrated under reduced pressure. The resulting residue was purified by silica gel chromatography (carrier: Chromatorex Si; elution solvent: heptane:ethyl acetate=19:1→heptane:ethyl acetate=1:1) to obtain the title compound (380 mg).

The property values of the compound are as follows.
ESI-MS; m/z 273 [M$^+$+H].

Synthesis of (5R,8R), (5S,8S), (5R,8S) and (5S,8R)-2-{(E)-2-[6-methoxy-5-(4-methyl-1H-imidazol-1-yl)pyridin-2-yl]vinyl}-5-methyl-8-(2-trifluoromethylphenyl)-5,6,7,8-tetrahydro-[1,2,4]triazolo[1,5-a]pyridine A racemate of the title compound (140 mg) was obtained using 1-amino-6-methyl-3-(2-trifluoromethylphenyl)piperidin-2-one (210 mg) as a starting material according to the method in Examples 168 and 169. The resulting racemate (140 mg) was separated by CHIRALPAK™ IB manufactured by Daicel Chemical Industries, Ltd. (2 cm×25 cm, mobile phase; hexane:ethanol=8:2, flow rate: 10 mL/min) to obtain the title optically active compound with a retention time of 30 minutes and positive optical rotation (18 mg), the title optically active compound with a retention time of 33 minutes and positive optical rotation (10 mg), the title optically active compound with a retention time of 43 minutes and negative optical rotation (15 mg) and the title optically active compound with a retention time of 71 minutes and negative optical rotation (14 mg).

The property values of the title optically active compound with a retention time of 30 minutes are as follows.

$^1$H-NMR (CDCl$_3$) δ (ppm): 1.70-2.34 (m, 10H), 4.03 (s, 3H), 4.49-4.55 (m, 1H), 4.73 (dd, J=6.8, 6.8 Hz, 1H), 6.91-6.94 (m, 3H), 7.37-7.50 (m, 4H), 7.66 (d, J=15.6 Hz, 1H), 7.73 (d, J=7.6 Hz, 1H), 7.76 (s, 1H).

The property values of the title optically active compound with a retention time of 33 minutes are as follows.

$^1$H-NMR (CDCl$_3$) δ (ppm): 1.63-1.93 (m, 5H), 2.29-2.48 (m, 5H), 4.03 (s, 3H), 4.42-4.50 (m, 1H), 4.63-4.67 (m, 1H), 6.91-6.95 (m, 2H), 7.03-7.06 (d, J=7.6 Hz, 1H), 7.36-7.50 (m, 4H), 7.64 (d, J=15.6 Hz, 1H), 7.72 (d, J=7.6 Hz, 1H), 7.76 (s, 1H).

The property values of the title optically active compound with a retention time of 43 minutes are as follows.

$^1$H-NMR (CDCl$_3$) δ (ppm): 1.63-1.93 (m, 5H), 2.29-2.48 (m, 5H), 4.03 (s, 3H), 4.42-4.50 (m, 1H), 4.63-4.67 (m, 1H), 6.91-6.95 (m, 2H), 7.03-7.06 (d, J=7.6 Hz, 1H), 7.36-7.50 (m, 4H), 7.64 (d, J=15.6 Hz, 1H), 7.72 (d, J=7.6 Hz, 1H), 7.76 (s, 1H).

The property values of the title optically active compound with a retention time of 71 minutes are as follows.

$^1$H-NMR (CDCl$_3$) δ (ppm): 1.70-2.34 (m, 10H), 4.03 (s, 3H), 4.49-4.55 (m, 1H), 4.73 (dd, J=6.8, 6.8 Hz, 1H), 6.91-6.94 (m, 3H), 7.37-7.50 (m, 4H), 7.66 (d, J=15.6 Hz, 1H), 7.73 (d, J=7.6 Hz, 1H), 7.76 (s, 1H).

Example 363

Synthesis of 2-{(E)-2-[6-methoxy-5-(4-methyl-1H-imidazol-1-yl)pyridin-2-yl]vinyl}-8-(2-trifluoromethylphenyl)-5,6,7,8-tetrahydro-[1,2,4]triazolo[1,5-a]pyridin-8-ol

[Formula 203]

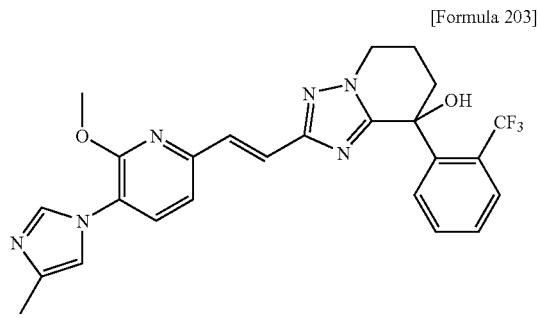

2-{(E)-2-[6-methoxy-5-(4-methyl-1H-imidazol-1-yl)pyridin-2-yl]vinyl}-8-(2-Trifluoromethylphenyl)-5,6,7,8-tetrahydro-[1,2,4]triazolo[1,5-a]pyridine (50 mg) was dissolved in DMF (3 mL). Sodium hydride (containing 40% of mineral oil, 8.3 mg) was added and the reaction solution was stirred at room temperature for 10 minutes. The reaction solution was internally replaced with oxygen. The reaction solution was bubbled with oxygen and stirred for two hours. A sodium thiosulfate solution was added to the reaction solution, and the reaction solution was stirred at room temperature for 30 minutes. Ethyl acetate was added to the reaction solution and the organic layer was separated. The organic layer was dried over magnesium sulfate and concentrated under reduced pressure. The resulting residue was purified by silica gel chromatography (carrier: Chromatorex Si; elution solvent: heptane:ethyl acetate=1:1→ethyl acetate→ethyl acetate:methanol=9:1) to obtain the title compound (10 mg). The property values of the compound are as follows.

ESI-MS; m/z 497 [M$^+$+H].

$^1$H-NMR (CDCl$_3$) δ (ppm): 2.05-2.62 (m, 7H), 3.97 (s, 3H), 4.16-4.41 (m, 2H), 6.74 (d, J=7.6 Hz, 1H), 6.91 (s, 1H), 7.29-7.60 (m, 5H), 7.72-7.75 (m, 2H), 7.86 (s, 1H).

Examples 364 and 365

Synthesis of (+) and (−)-8-(3,5-difluorophenyl)-2-{(E)-2-[6-methoxy-5-(4-methyl-1H-imidazol-1-yl)pyridin-2-yl]vinyl}-5,6,7,8-tetrahydro-[1,2,4]triazolo[1,5-a]pyridine

[Formula 204]

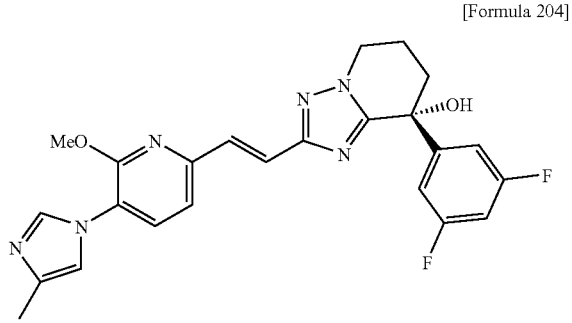

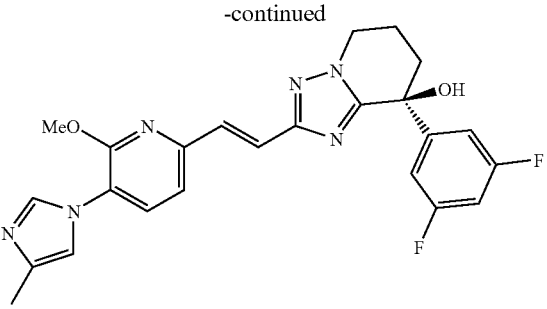

A racemate of the title compound was obtained from 8-(3,5-difluorophenyl)-2-{(E)-2-[6-methoxy-5-(4-methyl-1H-imidazol-1-yl)pyridin-2-yl]vinyl}-5,6,7,8-tetrahydro[1,2,4]triazolo[1,5-a]pyridine (133 mg) according to the method in Examples 53 and 54. The resulting racemate was separated by CHIRALPAK™ IC manufactured by Daicel Chemical Industries, Ltd. (2 cm×25 cm; mobile phase: ethanol) to obtain the title optically active compound with a retention time of 6.1 minutes and positive optical rotation (28.7 mg, >99% ee) and the title optically active compound with a retention time of 7.0 minutes and negative optical rotation (25.5 mg, >99% ee).

The property values of the title compound with positive optical rotation are as follows.

ESI-MS; m/z 465 [M$^+$+H]. $^1$H-NMR (CDCl$_3$) δ (ppm): 2.01-2.12 (m, 1H), 2.14-2.21 (m, 1H), 2.29 (s, 3H), 2.30-2.50 (m, 2H), 4.00 (s, 3H), 4.23-4.37 (m, 2H), 6.75 (m, 1H), 6.79 (d, J=8.0 Hz, 1H), 6.90-6.94 (m, 3H), 7.38 (d, J=15.6 Hz, 1H), 7.41 (d, J=8.0 Hz, 1H), 7.62 (d, J=15.6 Hz, 1H), 7.80 (s, 1H).

The property values of the title compound with negative optical rotation are as follows.

ESI-MS; m/z 465 [M$^+$+H]. $^1$H-NMR (CDCl$_3$) δ (ppm): 2.01-2.12 (m, 1H), 2.14-2.21 (m, 1H), 2.29 (s, 3H), 2.30-2.50 (m, 2H), 4.00 (s, 3H), 4.23-4.37 (m, 2H), 6.75 (m, 1H), 6.79 (d, J=8.0 Hz, 1H), 6.90-6.94 (m, 3H), 7.38 (d, J=15.6 Hz, 1H), 7.41 (d, J=8.0 Hz, 1H), 7.62 (d, J=15.6 Hz, 1H), 7.80 (s, 1H).

Example 366

Synthesis of 2-{(E)-2-[6-methoxy-5-(4-methyl-1H-imidazol-1-yl)pyridin-2-yl]vinyl}-8-(2-trifluoromethylphenyl)-5,6-dihydro[1,2,4]triazolo[1,5-a]pyridine

[Formula 205]

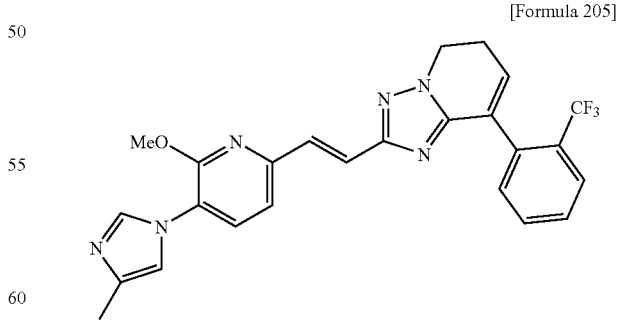

2-{(E)-2-[6-Methoxy-5-(4-methyl-1H-imidazol-1-yl)pyridin-2-yl]vinyl}-8-(2-trifluoromethylphenyl)-5,6,7,8-tetrahydro-[1,2,4]triazolo[1,5-a]pyridin-8-ol (56 mg) was dissolved in dichloromethane (2 ml). Diethylaminosulfur trifluoride (45 ul) was added under ice-cooling, and the reaction solution was stirred at room temperature for three hours. Thereafter, diethylaminosulfur trifluoride (45 ul) was added again at room temperature, and the reaction solution was further stirred at room temperature overnight. Ethyl acetate and water were added to the reaction solution, and the organic layer was separated. The resulting organic layer was washed with brine and then dried over anhydrous sodium sulfate. The drying agent was separated by filtration and then the organic layer was concentrated under reduced pressure. The residue was separated by CHIRALPAK™ IB manufactured by Daicel Chemical Industries, Ltd. (2 cm×25 cm; mobile phase: hexane:ethanol=1:1) to obtain the title compound (20 mg). The property values of the compound are as follows.

ESI-MS; m/z 479 [M++H]. $^1$H-NMR (CDCl$_3$) δ (ppm): 2.29 (s, 3H), 2.93 (td, J=8.2, 4.4 Hz, 2H), 4.03 (s, 3H), 4.44 (t, J=8.2 Hz, 2H), 6.27 (t, J=4.4 Hz, 1H), 6.91-6.96 (m, 2H), 7.39-7.55 (m, 4H), 7.60-7.66 (m, 2H), 7.74-7.78 (m, 2H).

Examples 367 and 368

Synthesis of (+) and (−)-2-{(E)-2-[6-methoxy-5-(4-methyl-1H-imidazol-1-yl)pyridin-2-yl]vinyl}-8-(2-trifluoromethylphenyl)-5,6-dihydro-8H-[1,2,4]triazolo[5,1-c][1,4]oxazine

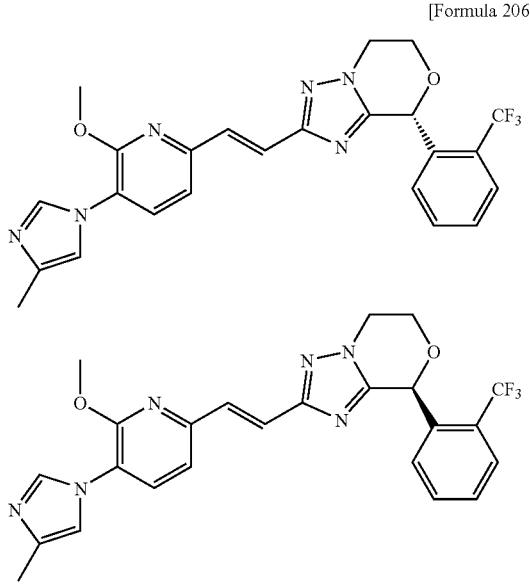

[Formula 206]

A racemate of the title compound (190 mg) was obtained using 2-(trifluoromethyl)benzaldehyde (3 g) as a starting material according to the method in Examples 257 and 258. The resulting racemate (190 mg) was separated by CHIRALPAK™ IB manufactured by Daicel Chemical Industries, Ltd. (2 cm×25 cm, mobile phase: hexane:ethanol=1:1, flow rate: 11 mL/min) to obtain the title optically active compound with a retention time of 27 minutes and positive optical rotation (38 mg) and the title optically active compound with a retention time of 41 minutes and negative optical rotation (37 mg).

The property values of the title optically active compound with a retention time of 27 minutes are as follows.

$^1$H-NMR (CDCl$_3$) δ (ppm): 2.29 (s, 3H), 4.04 (s, 3H), 4.17-4.53 (m, 4H), 6.26 (s, 1H), 6.93-6.95 (m, 2H), 7.30 (d, J=7.6 Hz, 1H), 7.43-7.58 (m, 4H), 7.64 (d, J=15.6 Hz, 1H), 7.77-7.80 (m, 2H).

The property values of the title optically active compound with a retention time of 41 minutes are as follows.

$^1$H-NMR (CDCl$_3$) δ (ppm): 2.29 (s, 3H), 4.04 (s, 3H), 4.17-4.53 (m, 4H), 6.26 (s, 1H), 6.93-6.95 (m, 2H), 7.30 (d, J=7.6 Hz, 1H), 7.43-7.58 (m, 4H), 7.64 (d, J=15.6 Hz, 1H), 7.77-7.80 (m, 2H).

Example 369

Synthesis of 4-(4-fluorophenyl)-2-{(E)-2-[6-methoxy-5-(4-methyl-1H-imidazol-1-yl)pyridin-2-yl]vinyl}-4,5,6,7-tetrahydro-[1,2,4]triazolo[1,5-a]pyrimidine

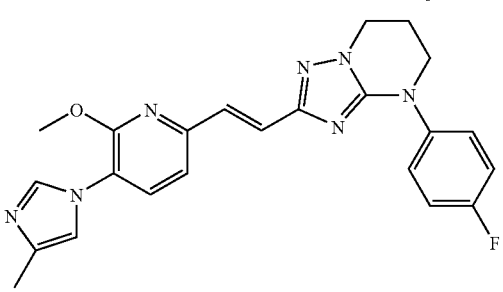

[Formula 207]

146 mg of the racemic title compound was obtained from (E)-N-[3-(4-fluorophenyl)-2-oxo-tetrahydropyrimidin-1-yl]-3-[6-methoxy-5-(4-methyl-1H-imidazol-1-yl)pyridin-2-yl]acrylamide (240 mg) by the same method as in Example 232. The property values of the compound are as follows.

ESI-MS; m/z 432 [M++H]. $^1$H-NMR (CDCl$_3$) δ (ppm): 2.30 (d, J=0.8 Hz, 3H), 2.33-2.42 (m, 2H), 3.83 (t, J=5.6 Hz, 2H), 4.05 (s, 3H), 4.24 (t, J=6.0 Hz, 2H), 6.93-6.98 (m, 2H), 7.07-7.14 (m, 2H), 7.38 (d, J=15.6 Hz, 1H), 7.45-7.56 (m, 4H), 7.77 (d, J=1.2 Hz, 1H).

Example 370

Synthesis of 2-{(E)-2-[6-methoxy-5-(4-methyl-1H-imidazol-1-yl)pyridin-2-yl]vinyl}-4-(2-trifluoromethylphenyl)-4,5,6,7-tetrahydro-[1,2,4]triazolo[1,5-a]pyrimidine

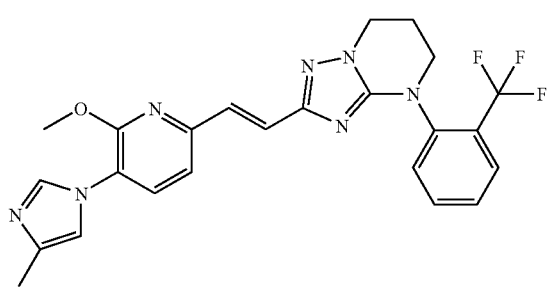

[Formula 208]

320 mg of the title compound was obtained from (E)-3-[6-methoxy-5-(4-methyl-1H-imidazol-1-yl)pyridin-2-yl]-N-[2-oxo-3-(2-trifluoromethylphenyl)-tetrahydropyrimidin-1-yl] acrylamide (474 mg) by the same method as in Example 232. The property values of the compound are as follows.

ESI-MS; m/z 482 [M++H]. ¹H-NMR (CDCl₃) δ (ppm): 2.25-2.55 (m, 2H), 2.29 (d, J=0.8 Hz, 3H), 3.57-3.73 (m, 2H), 4.01 (s, 3H), 4.20-4.34 (m, 2H), 6.88 (d, J=8.0 Hz, 1H), 6.93-6.96 (m, 1H), 7.26-7.32 (m, 1H), 7.43 (d, J=8.0 Hz, 1H), 7.46-7.54 (m, 3H), 7.64-7.70 (m, 1H), 7.74 (d, J=1.2 Hz, 1H), 7.77-7.82 (m, 1H).

Examples 371 and 372

Synthesis of (R) and (S)-4-(2,4-difluorophenyl)-2-{(E)-2-[6-methoxy-5-(4-methyl-1H-imidazol-1-yl)pyridin-2-yl]vinyl}-5-methyl-4,5,6,7-tetrahydro-[1,2,4]triazolo[1,5-a]pyrimidine

[Formula 209]

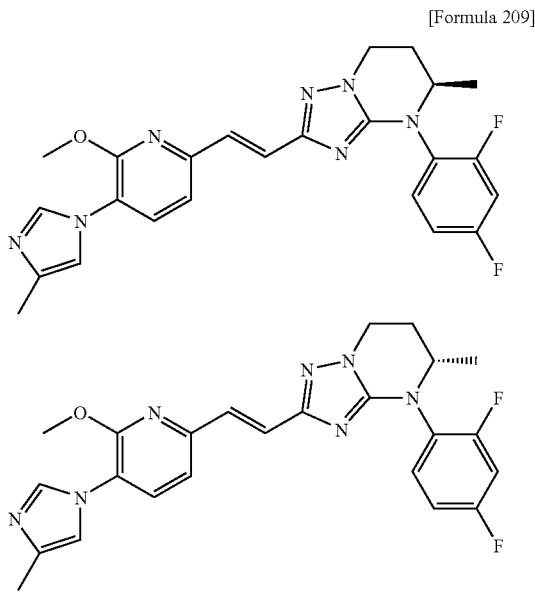

374 mg of the racemic title compound was obtained from (E)-N-[3-(2,4-difluorophenyl)-4-methyl-2-oxo-tetrahydropyrimidin-1-yl]-3-[6-methoxy-5-(4-methyl-1H-imidazol-1-yl)pyridin-2-yl]acrylamide (500 mg) by the same method as in Example 232. The racemic title compound (250 mg) was separated by CHIRALPAK™ IC manufactured by Daicel Chemical Industries, Ltd. (2 cm×25 cm; mobile phase: ethyl acetate:methanol=2:3) to obtain the title optically active compound with a retention time of 16 minutes (110 mg) and the title optically active compound with a retention time of 19 minutes (110 mg).

The property values of the title optically active compound with a retention time of 16 minutes are as follows.

ESI-MS; m/z 464 [M++H]. ¹H-NMR (CDCl₃) δ (ppm): 1.23 (d, J=6.4 Hz, 3H), 2.11-2.20 (m, 1H), 2.29 (s, 3H), 2.38-2.48 (m, 1H), 3.93-4.02 (m, 1H), 4.03 (s, 3H), 4.26 (t, J=6.4 Hz, 2H), 6.90 (d, J=8.0 Hz, 1H), 6.92-7.00 (m, 3H), 7.29 (d, J=15.6 Hz, 1H), 7.39-7.47 (m, 2H), 7.49 (d, J=15.6 Hz, 1H), 7.76 (brs, 1H).

The property values of the title optically active compound with a retention time of 19 minutes are as follows.

ESI-MS; m/z 464 [M++H]. ¹H-NMR (CDCl₃) δ (ppm): 1.23 (d, J=6.4 Hz, 3H), 2.11-2.20 (m, 1H), 2.29 (s, 3H), 2.38-2.48 (m, 1H), 3.93-4.02 (m, 1H), 4.03 (s, 3H), 4.26 (t, J=6.4 Hz, 2H), 6.90 (d, J=8.0 Hz, 1H), 6.92-7.00 (m, 3H), 7.29 (d, J=15.6 Hz, 1H), 7.39-7.47 (m, 2H), 7.49 (d, J=15.6 Hz, 1H), 7.76 (brs, 1H).

Examples 373 and 374

Synthesis of (+) and (−)-2-{(E)-2-[6-methoxy-5-(4-methyl-1H-imidazol-1-yl)pyridin-2-yl]vinyl}-5-methyl-4-(2-trifluoromethylphenyl)-4,5,6,7-tetrahydro-[1,2,4]triazolo[1,5-a]pyrimidine

[Formula 210]

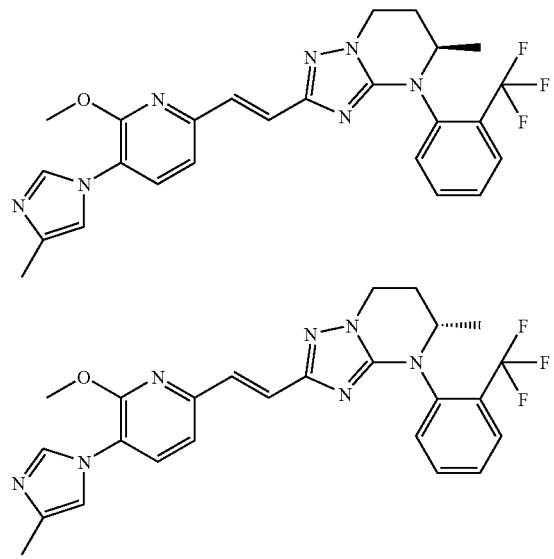

374 mg of the racemic title compound was obtained from (E)-3-[6-methoxy-5-(4-methyl-1H-imidazol-1-yl)pyridin-2-yl]-N-[4-methyl-2-oxo-3-(2-trifluoromethylphenyl)-tetrahydropyrimidin-1-yl]acrylamide (494 mg) by the same method as in Example 232. The racemic title compound (220 mg) was separated by CHIRALPAK™ IC manufactured by Daicel Chemical Industries, Ltd. (2 cm×25 cm; mobile phase: ethyl acetate:methanol=1:1) and solidified with ethyl acetate and heptane to obtain the title optically active compound with positive optical rotation and a retention time of 2 minutes (97 mg) and the title optically active compound with negative optical rotation and a retention time of 5 minutes (92 mg).

The property values of the title optically active compound with a retention time of 2 minutes are as follows.

ESI-MS; m/z 496 [M++H]. ¹H-NMR (CDCl₃) δ (ppm): 1.25-1.34 (m, 3H), 2.04-2.15 (m, 1H), 2.28 (s, 3H), 2.46-2.60 (m, 1H), 3.91-4.03 (m, 1H), 4.01 (s, 3H), 4.20-4.36 (m, 2H), 6.88 (d, J=7.6 Hz, 1H), 6.94 (brs, 1H), 7.23-7.30 (m, 1H), 7.42 (d, J=7.6 Hz, 1H), 7.44-7.56 (m, 3H), 7.65-7.71 (m, 1H), 7.73-7.76 (m, 1H), 7.79-7.84 (m, 1H).

The property values of the title optically active compound with a retention time of 5 minutes are as follows.

ESI-MS; m/z 496 [M++H]. ¹H-NMR (CDCl₃) δ (ppm): 1.25-1.34 (m, 3H), 2.04-2.15 (m, 1H), 2.28 (s, 3H), 2.46-2.60 (m, 1H), 3.91-4.03 (m, 1H), 4.01 (s, 3H), 4.20-4.36 (m, 2H), 6.88 (d, J=7.6 Hz, 1H), 6.94 (brs, 1H), 7.23-7.30 (m, 1H), 7.42 (d, J=7.6 Hz, 1H), 7.44-7.56 (m, 3H), 7.65-7.71 (m, 1H), 7.73-7.76 (m, 1H), 7.79-7.84 (m, 1H).

Examples 375 and 376

Synthesis of (R) and (S)-2-{(E)-2-[6-methoxy-5-(4-methyl-1H-imidazol-1-yl)pyridin-2-yl]vinyl}-7-phenyl-6,7-dihydro-5H-pyrrolo[1,2-b][1,2,4]triazole

[Formula 211]

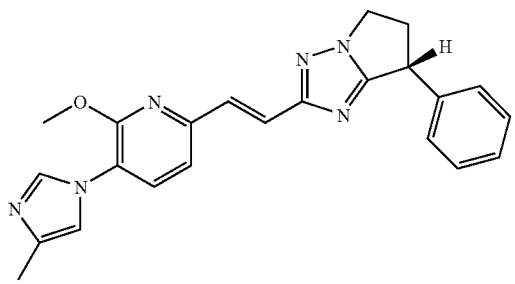

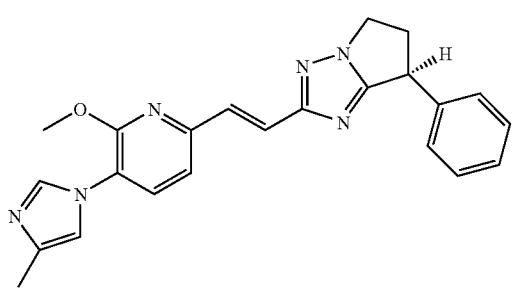

60 mg of the racemic title compound was obtained from ethyl (E)-3-[6-methoxy-5-(4-methyl-1H-imidazol-1-yl)pyridin-2-yl]acrylimidate dihydrochloride (250 mg) and 4-chloro-2-phenylbutyric acid hydrazide hydrochloride (191 mg) by the same method as in Examples 253 and 254. The racemic title compound (60 mg) was separated by CHIRALPAK™ IB manufactured by Daicel Chemical Industries, Ltd. (2 cm×25 cm; mobile phase: hexane:ethanol=1:1) to obtain the title optically active compound with a retention time of 13 minutes (13 mg) and the title optically active compound with a retention time of 23 minutes (15 mg).

The property values of the title optically active compound with a retention time of 13 minutes are as follows.

ESI-MS; m/z 399 [M$^+$+H]. $^1$H-NMR (CDCl$_3$) δ (ppm): 2.30 (d, J=0.8 Hz, 3H), 2.66-2.78 (m, 1H), 3.20-3.32 (m, 1H), 4.07 (s, 3H), 4.17-4.27 (m, 1H), 4.30-4.40 (m, 1H), 4.46 (dd, J=6.4, 8.4 Hz, 1H), 6.93-6.98 (m, 2H), 7.23-7.44 (m, 5H), 7.48 (d, J=8.0 Hz, 1H), 7.52 (d, J=15.6 Hz, 1H), 7.67 (d, J=15.6 Hz, 1H), 7.78 (d, J=1.2 Hz, 1H).

The property values of the title optically active compound with a retention time of 23 minutes are as follows.

ESI-MS; m/z 399 [M$^+$+H]. $^1$H-NMR (CDCl$_3$) δ (ppm): 2.30 (d, J=0.8 Hz, 3H), 2.66-2.78 (m, 1H), 3.20-3.32 (m, 1H), 4.07 (s, 3H), 4.17-4.27 (m, 1H), 4.30-4.40 (m, 1H), 4.46 (dd, J=6.4, 8.4 Hz, 1H), 6.93-6.98 (m, 2H), 7.23-7.44 (m, 5H), 7.48 (d, J=8.0 Hz, 1H), 7.52 (d, J=15.6 Hz, 1H), 7.67 (d, J=15.6 Hz, 1H), 7.78 (d, J=1.2 Hz, 1H).

Examples 377 and 378

Synthesis of (+) and (−)-7-(4-fluorophenyl)-2-{(E)-2-[6-methoxy-5-(4-methyl-1H-imidazol-1-yl)pyridin-2-yl]vinyl}-6,7-dihydro-5H-pyrrolo[1,2-b][1,2,4]triazole

[Formula 212]

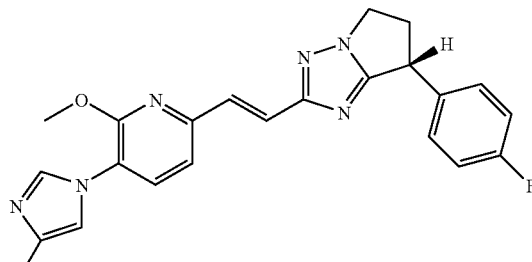

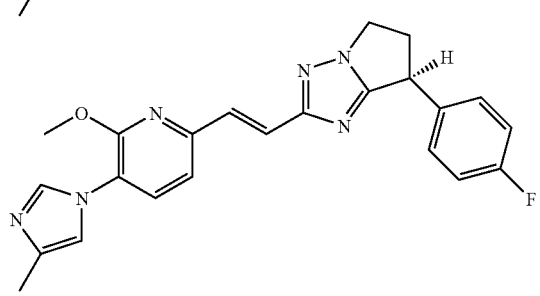

264 mg of the racemic title compound was obtained from ethyl (E)-3-[6-methoxy-5-(4-methyl-1H-imidazol-1-yl)pyridin-2-yl]acrylimidate (800 mg) and 4-chloro-2-(4-fluorophenyl)butyric acid hydrazide hydrochloride (807 mg) by the same method as in Examples 253 and 254. The racemic title compound (264 mg) was separated by CHIRALPAK™ IB manufactured by Daicel Chemical Industries, Ltd. (2 cm×25 cm; mobile phase: hexane:ethanol=1:1) to obtain the title optically active compound with positive optical rotation and a retention time of 11 minutes (87 mg) and the title optically active compound with negative optical rotation and a retention time of 22 minutes (88 mg).

The property values of the title optically active compound with a retention time of 11 minutes are as follows.

ESI-MS; m/z 417 [M$^+$+H]. $^1$H-NMR (CDCl$_3$) δ (ppm): 2.30 (d, J=0.8 Hz, 3H), 2.62-2.73 (m, 1H), 3.20-3.31 (m, 1H), 4.07 (s, 3H), 4.18-4.26 (m, 1H), 4.31-4.38 (m, 1H), 4.46 (dd, J=6.8, 8.4 Hz, 1H), 6.94-6.98 (m, 2H), 7.03-7.10 (m, 2H), 7.22-7.28 (m, 2H), 7.48 (d, J=7.6 Hz, 1H), 7.52 (d, J=15.6 Hz, 1H), 7.66 (d, J=15.6 Hz, 1H), 7.78 (d, J=0.8 Hz, 1H).

The property values of the title optically active compound with a retention time of 22 minutes are as follows.

ESI-MS; m/z 417 [M$^+$+H]. $^1$H-NMR (CDCl$_3$) δ (ppm): 2.30 (d, J=0.8 Hz, 3H), 2.62-2.73 (m, 1H), 3.20-3.31 (m, 1H), 4.07 (s, 3H), 4.18-4.26 (m, 1H), 4.31-4.38 (m, 1H), 4.46 (dd, J=6.8, 8.4 Hz, 1H), 6.94-6.98 (m, 2H), 7.03-7.10 (m, 2H), 7.22-7.28 (m, 2H), 7.48 (d, J=7.6 Hz, 1H), 7.52 (d, J=15.6 Hz, 1H), 7.66 (d, J=15.6 Hz, 1H), 7.78 (d, J=0.8 Hz, 1H).

Examples 379 and 380

Synthesis of (R) and (S)-7-(3,4-difluorophenyl)-2-{(E)-2-[6-methoxy-5-(4-methyl-1H-imidazol-1-yl)pyridin-2-yl]vinyl}-6,7-dihydro-5H-pyrrolo[1,2-b][1,2,4]triazole 2H), 7.49 (d, J=7.6 Hz, 1H), 7.52 (d, J=15.6 Hz, 1H), 7.66 (d, J=15.6 Hz, 1H), 7.78 (d, J=1.2 Hz, 1H).

Examples 381 and 382

Synthesis of (+) and (−)-7-(2,3-difluorophenyl)-2-{(E)-2-[6-methoxy-5-(4-methyl-1H-imidazol-1-yl)pyridin-2-yl]vinyl}-6,7-dihydro-5H-pyrrolo[1,2-b][1,2,4]triazole

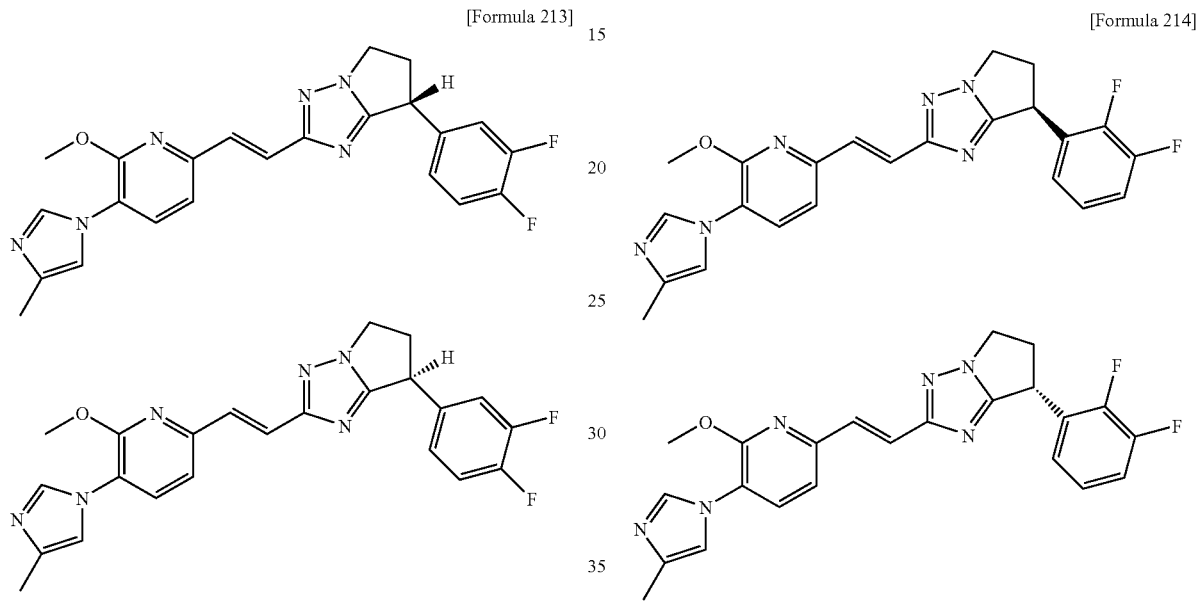

[Formula 213]

[Formula 214]

71 mg of the racemic title compound was obtained from ethyl (E)-3-[6-methoxy-5-(4-methyl-1H-imidazol-1-yl)pyridin-2-yl]acrylimidate dihydrochloride (500 mg) and 4-chloro-2-(3,4-difluorophenyl)butyric acid hydrazide hydrochloride (500 mg) by the same method as in Examples 253 and 254. The racemic title compound (71 mg) was separated by CHIRALPAK™ IB manufactured by Daicel Chemical Industries, Ltd. (2 cm×25 cm; mobile phase: hexane:ethanol=1:1) to obtain the title optically active compound with a retention time of 11 minutes (20 mg) and the title optically active compound with a retention time of 24 minutes (19 mg).

The property values of the title optically active compound with a retention time of 11 minutes are as follows.

ESI-MS; m/z 435 [M$^+$+H]. $^1$H-NMR (CDCl$_3$) δ (ppm): 2.30 (s, 3H), 2.62-2.74 (m, 1H), 3.21-3.32 (m, 1H), 4.07 (s, 3H), 4.18-4.27 (m, 1H), 4.31-4.40 (m, 1H), 4.41-4.48 (m, 1H), 6.94-7.00 (m, 2H), 7.01-7.07 (m, 1H), 7.10-7.21 (m, 2H), 7.49 (d, J=7.6 Hz, 1H), 7.52 (d, J=15.6 Hz, 1H), 7.66 (d, J=15.6 Hz, 1H), 7.78 (d, J=1.2 Hz, 1H).

The property values of the title optically active compound with a retention time of 24 minutes are as follows.

ESI-MS; m/z 435 [M$^+$+H]. $^1$H-NMR (CDCl$_3$) δ (ppm): 2.30 (s, 3H), 2.62-2.74 (m, 1H), 3.21-3.32 (m, 1H), 4.07 (s, 3H), 4.18-4.27 (m, 1H), 4.31-4.40 (m, 1H), 4.41-4.48 (m, 1H), 6.94-7.00 (m, 2H), 7.01-7.07 (m, 1H), 7.10-7.21 (m, 266 mg of the racemic title compound was obtained from ethyl (E)-3-[6-methoxy-5-(4-methyl-1H-imidazol-1-yl)pyridin-2-yl]acrylimidate (1.0 g) and 4-chloro-2-(2,3-difluorophenyl)butyric acid hydrazide hydrochloride (1.05 g) by the same method as in Examples 253 and 254. The racemic title compound (266 mg) was separated by CHIRALPAK™ IB manufactured by Daicel Chemical Industries, Ltd. (2 cm×25 cm; mobile phase: hexane:ethanol=1:1) to obtain the title optically active compound with positive optical rotation and a retention time of 13 minutes (60 mg) and the title optically active compound with negative optical rotation and a retention time of 27 minutes (83 mg).

The property values of the title optically active compound with a retention time of 13 minutes are as follows.

ESI-MS; m/z 435 [M$^+$+H]. $^1$H-NMR (CDCl$_3$) δ (ppm): 2.30 (s, 3H), 2.63-2.74 (m, 1H), 3.28-3.40 (m, 1H), 4.07 (s, 3H), 4.22-4.31 (m, 1H), 4.33-4.41 (m, 1H), 4.71 (dd, J=6.8, 8.8 Hz, 1H), 6.94-7.02 (m, 3H), 7.04-7.18 (m, 2H), 7.49 (d, J=7.6 Hz, 1H), 7.52 (d, J=15.6 Hz, 1H), 7.67 (d, J=15.6 Hz, 1H), 7.78 (d, J=1.2 Hz, 1H).

The property values of the title optically active compound with a retention time of 27 minutes are as follows.

ESI-MS; m/z 435 [M$^+$+H]. $^1$H-NMR (CDCl$_3$) δ (ppm): 2.30 (s, 3H), 2.63-2.74 (m, 1H), 3.28-3.40 (m, 1H), 4.07 (s, 3H), 4.22-4.31 (m, 1H), 4.33-4.41 (m, 1H), 4.71 (dd, J=6.8, 8.8 Hz, 1H), 6.94-7.02 (m, 3H), 7.04-7.18 (m, 2H), 7.49 (d, J=7.6 Hz, 1H), 7.52 (d, J=15.6 Hz, 1H), 7.67 (d, J=15.6 Hz, 1H), 7.78 (d, J=1.2 Hz, 1H).

Examples 383 and 384

Synthesis of (+) and (−)-7-(3,5-difluorophenyl)-2-{(E)-2-[6-methoxy-5-(4-methyl-1H-imidazol-1-yl)pyridin-2-yl]vinyl}-6,7-dihydro-5H-pyrrolo[1,2-b][1,2,4]triazole Examples 385 and 386

Synthesis of (R) and (S)-2-{(E)-2-[6-methoxy-5-(4-methyl-1H-imidazol-1-yl)pyridin-2-yl]vinyl}-7-(2,4,5-trifluorophenyl)-6,7-dihydro-5H-pyrrolo[1,2-b][1,2,4]triazole

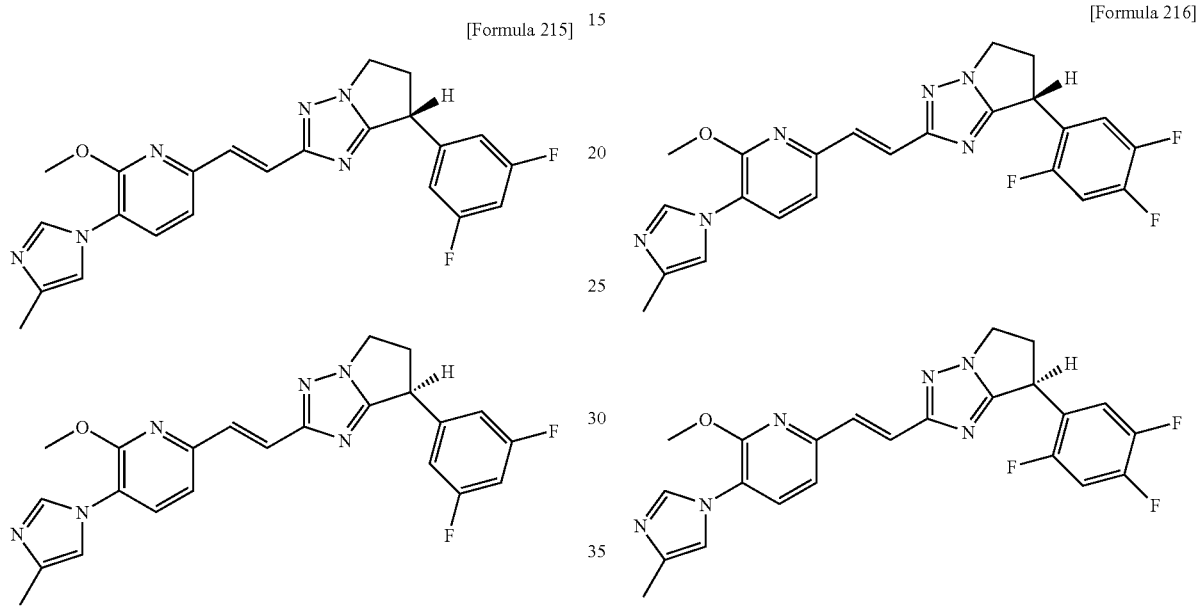

[Formula 215]

[Formula 216]

371 mg of the racemic title compound was obtained from ethyl (E)-3-[6-methoxy-5-(4-methyl-1H-imidazol-1-yl)pyridin-2-yl]acrylimidate dihydrochloride (2.2 g) and 4-chloro-2-(3,5-difluorophenyl)butyric acid hydrazide hydrochloride (1.7 g) by the same method as in Examples 253 and 254. The racemic title compound (371 mg) was separated by CHIRALPAK™ IB manufactured by Daicel Chemical Industries, Ltd. (2 cm×25 cm; mobile phase: hexane:ethanol=1:1) to obtain the title optically active compound with positive optical rotation and a retention time of 14 minutes (125 mg) and the title optically active compound with negative optical rotation and a retention time of 35 minutes (134 mg).

The property values of the title optically active compound with a retention time of 14 minutes are as follows.

ESI-MS; m/z 435 [M+ +H]. $^1$H-NMR (CDCl$_3$) δ (ppm): 2.30 (d, J=1.2 Hz, 3H), 2.65-2.75 (m, 1H), 3.23-3.33 (m, 1H), 4.08 (s, 3H), 4.18-4.27 (m, 1H), 4.32-4.40 (m, 1H), 4.42-4.49 (m, 1H), 6.73-6.80 (m, 1H), 6.81-6.89 (m, 2H), 6.95-7.01 (m, 2H), 7.49 (d, J=7.6 Hz, 1H), 7.53 (d, J=15.6 Hz, 1H), 7.66 (d, J=15.6 Hz, 1H), 7.79 (d, J=1.2 Hz, 1H).

The property values of the title optically active compound with a retention time of 35 minutes are as follows.

ESI-MS; m/z 435 [M+ +H]. $^1$H-NMR (CDCl$_3$) δ (ppm): 2.30 (d, J=1.2 Hz, 3H), 2.65-2.75 (m, 1H), 3.23-3.33 (m, 1H), 4.08 (s, 3H), 4.18-4.27 (m, 1H), 4.32-4.40 (m, 1H), 4.42-4.49 (m, 1H), 6.73-6.80 (m, 1H), 6.81-6.89 (m, 2H), 6.95-7.01 (m, 120 mg of the racemic title compound was obtained from ethyl (E)-3-[6-methoxy-5-(4-methyl-1H-imidazol-1-yl)pyridin-2-yl]acrylimidate dihydrochloride (500 mg) and 4-chloro-2-(2,4,5-trifluorophenyl)butyric acid hydrazide hydrochloride (500 mg) by the same method as in Examples 253 and 254. The racemic title compound (120 mg) was separated by CHIRALPAK™ IB manufactured by Daicel Chemical Industries, Ltd. (2 cm×25 cm; mobile phase: hexane:ethanol=1:1) to obtain the title optically active compound with a retention time of 9 minutes (30 mg) and the title optically active compound with a retention time of 22 minutes (28 mg).

The property values of the title optically active compound with a retention time of 9 minutes are as follows.

ESI-MS; m/z 453 [M+ +H]. $^1$H-NMR (CDCl$_3$) δ (ppm): 2.30 (d, J=0.8 Hz, 3H), 2.58-2.70 (m, 1H), 3.27-3.38 (m, 1H), 4.08 (s, 3H), 4.20-4.30 (m, 1H), 4.31-4.39 (m, 1H), 4.59-4.66 (m, 1H), 6.94-7.04 (m, 3H), 7.09-7.17 (m, 1H), 7.49 (d, J=7.6 Hz, 1H), 7.52 (d, J=15.6 Hz, 1H), 7.67 (d, J=15.6 Hz, 1H), 7.79 (d, J=1.2 Hz, 1H).

The property values of the title optically active compound with a retention time of 22 minutes are as follows.

ESI-MS; m/z 453 [M+ +H]. $^1$H-NMR (CDCl$_3$) δ (ppm): 2.30 (d, J=0.8 Hz, 3H), 2.58-2.70 (m, 1H), 3.27-3.38 (m, 1H), 4.08 (s, 3H), 4.20-4.30 (m, 1H), 4.31-4.39 (m, 1H), 4.59-4.66

(m, 1H), 6.94-7.04 (m, 3H), 7.09-7.17 (m, 1H), 7.49 (d, J=7.6 Hz, 1H), 7.52 (d, J=15.6 Hz, 1H), 7.67 (d, J=15.6 Hz, 1H), 7.79 (d, J=1.2 Hz, 1H).

Examples 387 and 388

Synthesis of (+) and (−)-2-{(E)-2-[6-methoxy-5-(4-methyl-1H-imidazol-1-yl)pyridin-2-yl]vinyl}-7-(2,3,4-trifluorophenyl)-6,7-dihydro-5H-pyrrolo[1,2-b][1,2,4]triazole 226 mg of the racemic title compound was obtained from ethyl (E)-3-[6-methoxy-5-(4-methyl-1H-imidazol-1-yl)pyridin-2-yl]acrylimidate (730 mg) and 4-chloro-2-(2,3,4-trifluorophenyl)butyric acid hydrazide hydrochloride (794 mg) by the same method as in Examples 253 and 254. The racemic title compound (226 mg) was separated by CHIRALPAK™ IB manufactured by Daicel Chemical Industries, Ltd. (2 cm×25 cm; mobile phase: hexane:ethanol=1:1) to obtain the title optically active compound with positive optical rotation and a retention time of 14 minutes (52 mg) and the title optically active compound with negative optical rotation and a retention time of 25 minutes (78 mg).

The property values of the title optically active compound with a retention time of 14 minutes are as follows.

ESI-MS; m/z 453 [M++H]. 1H-NMR (CDCl3) δ (ppm): 2.30 (s, 3H), 2.60-2.71 (m, 1H), 3.28-3.39 (m, 1H), 4.07 (s, 3H), 4.22-4.30 (m, 1H), 4.32-4.40 (m, 1H), 4.66 (dd, J=6.8, 8.8 Hz, 1H), 6.94-7.02 (m, 4H), 7.49 (d, J=7.6 Hz, 1H), 7.51 (d, J=15.6 Hz, 1H), 7.66 (d, J=15.6 Hz, 1H), 7.79 (d, J=1.2 Hz, 1H).

The property values of the title optically active compound with a retention time of 25 minutes are as follows.

ESI-MS; m/z 453 [M++H]. 1H-NMR (CDCl3) δ (ppm): 2.30 (s, 3H), 2.60-2.71 (m, 1H), 3.28-3.39 (m, 1H), 4.07 (s, 3H), 4.22-4.30 (m, 1H), 4.32-4.40 (m, 1H), 4.66 (dd, J=6.8, 8.8 Hz, 1H), 6.94-7.02 (m, 4H), 7.49 (d, J=7.6 Hz, 1H), 7.51 (d, J=15.6 Hz, 1H), 7.66 (d, J=15.6 Hz, 1H), 7.79 (d, J=1.2 Hz, 1H).

Examples 389 and 390

Synthesis of (R) and (S)-2-{(E)-2-[6-methoxy-5-(4-methyl-1H-imidazol-1-yl)pyridin-2-yl]vinyl}-7-(2-trifluoromethylphenyl)-6,7-dihydro-5H-pyrrolo[1,2-b][1,2,4]triazole

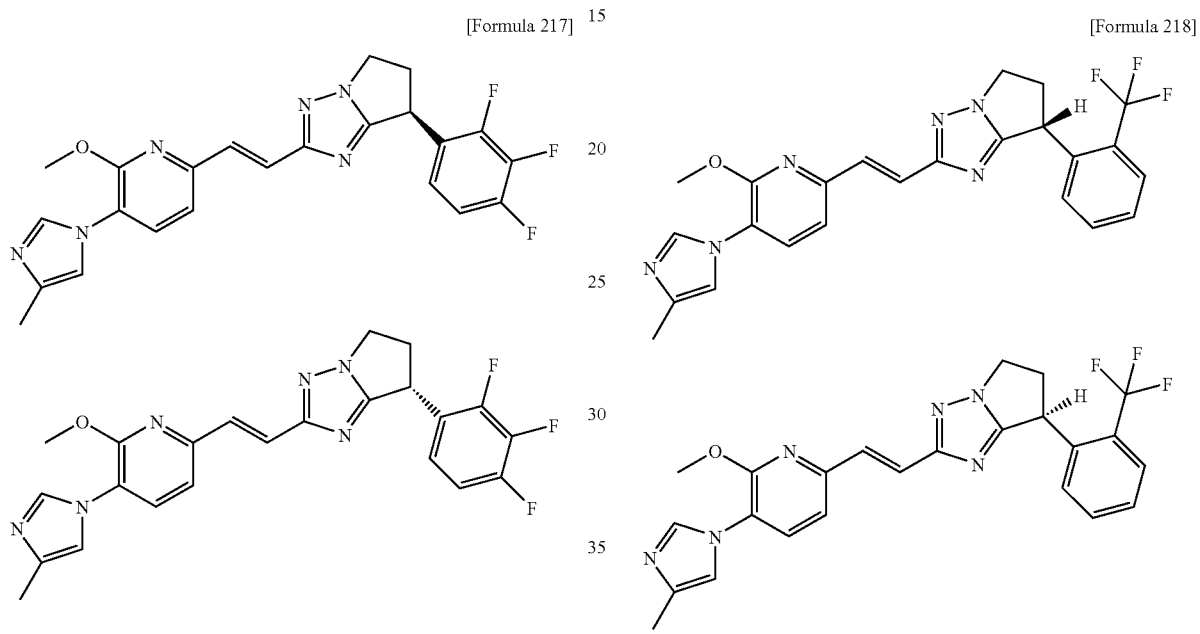

55 mg of the racemic title compound was obtained from ethyl (E)-3-[6-methoxy-5-(4-methyl-1H-imidazol-1-yl)pyridin-2-yl]acrylimidate dihydrochloride (250 mg) and 4-chloro-2-(2-trifluoromethylphenyl)butyric acid hydrazide hydrochloride (212 mg) synthesized from (2-trifluoromethylphenyl)acetic acid by the same method as in Examples 253 and 254. The racemic title compound (55 mg) was separated by CHIRALPAK™ IB manufactured by Daicel Chemical Industries, Ltd. (2 cm×25 cm; mobile phase: hexane:ethanol=4:1) to obtain the title optically active compound with a retention time of 16 minutes (12 mg) and the title optically active compound with a retention time of 28 minutes (11 mg).

The property values of the title optically active compound with a retention time of 16 minutes are as follows.

ESI-MS; m/z 467 [M++H]. 1H-NMR (CDCl3) δ (ppm): 2.30 (s, 3H), 2.54-2.65 (m, 1H), 3.27-3.38 (m, 1H), 4.07 (s, 3H), 4.20-4.30 (m, 1H), 4.31-4.40 (m, 1H), 4.87 (dd, J=8.0, 8.0 Hz, 1H), 6.93-6.99 (m, 2H), 7.09 (d, J=7.6 Hz, 1H), 7.39-7.45 (m, 1H), 7.46-7.57 (m, 3H), 7.65-7.75 (m, 2H), 7.79 (s, 1H).

The property values of the title optically active compound with a retention time of 28 minutes are as follows.

ESI-MS; m/z 467 [M++H]. 1H-NMR (CDCl3) δ (ppm): 2.30 (s, 3H), 2.54-2.65 (m, 1H), 3.27-3.38 (m, 1H), 4.07 (s, 3H), 4.20-4.30 (m, 1H), 4.31-4.40 (m, 1H), 4.87 (dd, J=8.0, 8.0 Hz, 1H), 6.93-6.99 (m, 2H), 7.09 (d, J=7.6 Hz, 1H), 7.39-7.45 (m, 1H), 7.46-7.57 (m, 3H), 7.65-7.75 (m, 2H), 7.79 (s, 1H).

Examples 391 and 392

Synthesis of (R) and (S)-7-(5-fluoro-2-trifluoromethylphenyl)-2-{(E)-2-[6-methoxy-5-(4-methyl-1H-imidazol-1-yl)pyridin-2-yl]vinyl}-6,7-dihydro-5H-pyrrolo[1,2-b][1,2,4]triazole

[Formula 219]

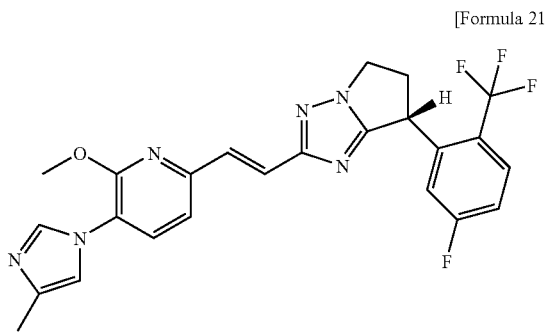

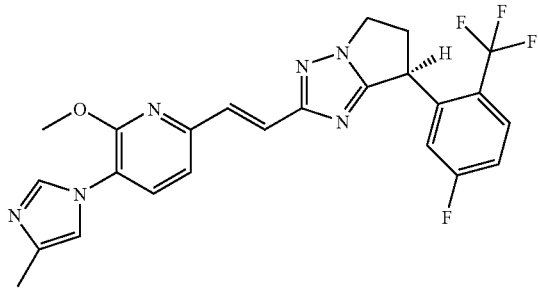

151 mg of the racemic title compound was obtained from ethyl (E)-3-[6-methoxy-5-(4-methyl-1H-imidazol-1-yl)pyridin-2-yl]acrylimidate (550 mg) and 4-chloro-2-(5-fluoro-2-trifluoromethylphenyl)butyric acid hydrazide hydrochloride (680 mg) by the same method as in Examples 253 and 254. The racemic title compound (151 mg) was separated by CHIRALPAK™ IB manufactured by Daicel Chemical Industries, Ltd. (2 cm×25 cm; mobile phase: hexane:ethanol=4:1) to obtain the title optically active compound with a retention time of 18 minutes (46 mg) and the title optically active compound with a retention time of 34 minutes (34 mg).

The property value of the title optically active compound with a retention time of 18 minutes is as follows.

ESI-MS; m/z 485 [M$^+$+H].

The property values of the title optically active compound with a retention time of 34 minutes are as follows.

ESI-MS; m/z 485 [M$^+$+H]. $^1$H-NMR (CDCl$_3$) δ (ppm): 2.30 (s, 3H), 2.54-2.65 (m, 1H), 3.28-3.40 (m, 1H), 4.08 (s, 3H), 4.20-4.30 (m, 1H), 4.32-4.41 (m, 1H), 4.87 (t, J=7.6 Hz, 1H), 6.78-6.84 (m, 1H), 6.94-7.01 (m, 2H), 7.07-7.14 (m, 1H), 7.47-7.56 (m, 2H), 7.68 (d, J=15.6 Hz, 1H), 7.74 (dd, J=5.6, 8.8 Hz, 1H), 7.79 (brs, 1H).

Example 393

Synthesis of 2-{(E)-2-[6-methoxy-5-(4-methyl-1H-imidazol-1-yl)pyridin-2-yl]vinyl}-7-phenyl-6,7-dihydro-5H-pyrrolo[1,2-b][1,2,4]triazol-7-ol

[Formula 220]

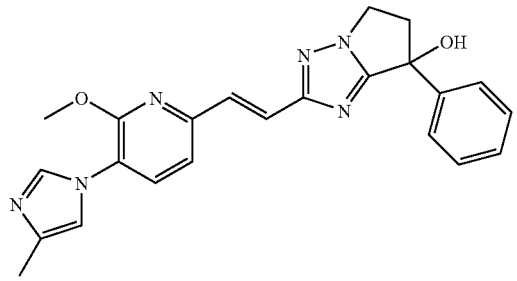

50 mg of the title compound was obtained by the same method as in Examples 53 and 54 from the optically active compound synthesized by the method in Examples 375 and 376 with a retention time of 13 minutes, 2-{(E)-2-[6-methoxy-5-(4-methyl-1H-imidazol-1-yl)pyridin-2-yl]vinyl}-7-phenyl-6,7-dihydro-5H-pyrrolo[1,2-b][1,2,4]triazole (112 mg). The property value of the compound is as follows.

ESI-MS; m/z 415 [M$^+$+H].

Examples 394 and 395

Synthesis of (+) and (−)-2-{(E)-2-[5-methoxy-6-(4-methyl-1H-imidazol-1-yl)pyridin-3-yl]vinyl}-8-(2-trifluoromethylphenyl)-5,6,7,8-tetrahydro-[1,2,4]triazolo[1,5-a]pyridine

[Formula 221]

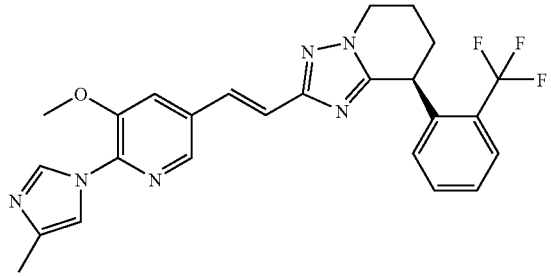

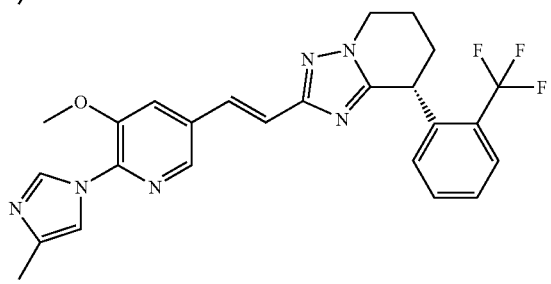

230 mg of the racemic title compound was obtained from 1-amino-3-(2-trifluoromethylphenyl)piperidin-2-one (343 mg) and (E)-3-[5-methoxy-6-(4-methyl-1H-imidazol-1-yl)pyridin-3-yl]acrylic acid (500 mg) by the same method as in Examples 194 and 195. The racemic title compound (220 mg) was separated by CHIRALPAK™ IC manufactured by Daicel Chemical Industries, Ltd. (2 cm×25 cm; mobile phase: methanol) to obtain the title optically active compound with positive optical rotation and a retention time of 16 minutes (92 mg) and the title optically active compound with negative optical rotation and a retention time of 19 minutes (79 mg).

The property value of the title optically active compound with a retention time of 16 minutes is as follows.

ESI-MS; m/z 481 [M$^+$+H].

The property values of the title optically active compound with a retention time of 19 minutes are as follows.

ESI-MS; m/z 481 [M$^+$+H]. $^1$H-NMR (CDCl$_3$) δ (ppm): 1.90-2.01 (m, 1H), 2.10-2.35 (m, 2H), 2.29 (s, 3H), 2.43-2.52 (m, 1H), 3.95 (s, 3H), 4.27-4.41 (m, 2H), 4.69 (dd, J=6.0, 8.4 Hz, 1H), 7.02 (d, J=8.0 Hz, 1H), 7.08 (d, J=16.4 Hz, 1H), 7.40 (dd, J=7.6, 7.6 Hz, 1H), 7.44-7.53 (m, 4H), 7.73 (d, J=8.0 Hz, 1H), 8.13 (d, J=1.6 Hz, 1H), 8.34 (s, 1H).

Examples 396 and 397

Synthesis of (+) and (−)-2-{(E)-2-[5-methoxy-6-(4-methyl-1H-imidazol-1-yl)pyridin-3-yl]vinyl}-7-phenyl-6,7-dihydro-5H-pyrrolo[1,2-b][1,2,4]triazole

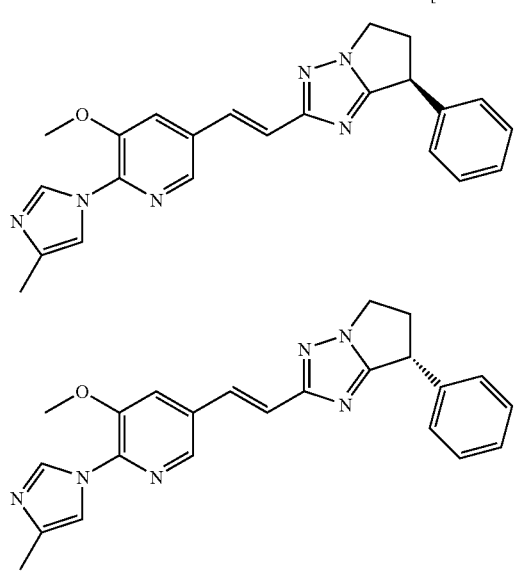

[Formula 222]

167 mg of the racemic title compound was obtained from ethyl (E)-3-[5-methoxy-6-(4-methyl-1H-imidazol-1-yl)pyridin-3-yl]acrylimidate dihydrochloride (1.0 g) and 4-chloro-2-phenylbutyric acid hydrazide hydrochloride (965 mg) by the same method as in Examples 255 and 256. The racemic title compound (167 mg) was separated by CHIRALPAK™ AD-H manufactured by Daicel Chemical Industries, Ltd. (2 cm×25 cm; mobile phase: ethanol) to obtain the title optically active compound with positive optical rotation and a retention time of 28 minutes (50 mg) and the title optically active compound with negative optical rotation and a retention time of 42 minutes (47 mg).

The property values of the title optically active compound with a retention time of 28 minutes are as follows.

ESI-MS; m/z 399 [M$^+$+H]. $^1$H-NMR (CDCl$_3$) δ (ppm): 2.30 (s, 3H), 2.67-2.78 (m, 1H), 3.21-3.32 (m, 1H), 3.99 (s, 3H), 4.18-4.27 (m, 1H), 4.32-4.40 (m, 1H), 4.46 (dd, J=6.8, 8.8 Hz, 1H), 7.12 (d, J=16.0 Hz, 1H), 7.22-7.34 (m, 3H), 7.34-7.41 (m, 2H), 7.47-7.56 (m, 2H), 7.58 (d, J=16.0 Hz, 1H), 8.16 (d, J=1.6 Hz, 1H), 8.36 (s, 1H).

The property values of the title optically active compound with a retention time of 42 minutes are as follows.

ESI-MS; m/z 399 [M$^+$+H]. $^1$H-NMR (CDCl$_3$) δ (ppm): 2.30 (s, 3H), 2.67-2.78 (m, 1H), 3.21-3.32 (m, 1H), 3.99 (s, 3H), 4.18-4.27 (m, 1H), 4.32-4.40 (m, 1H), 4.46 (dd, J=6.8, 8.8 Hz, 1H), 7.12 (d, J=16.0 Hz, 1H), 7.22-7.34 (m, 3H), 7.34-7.41 (m, 2H), 7.47-7.56 (m, 2H), 7.58 (d, J=16.0 Hz, 1H), 8.16 (d, J=1.6 Hz, 1H), 8.36 (s, 1H).

Examples 398 and 399

Synthesis of (+) and (−)-2-{(E)-2-[5-methoxy-6-(4-methyl-1H-imidazol-1-yl)pyridin-3-yl]vinyl}-7-(2-trifluoromethylphenyl)-6,7-dihydro-5H-pyrrolo[1,2-b][1,2,4]triazole

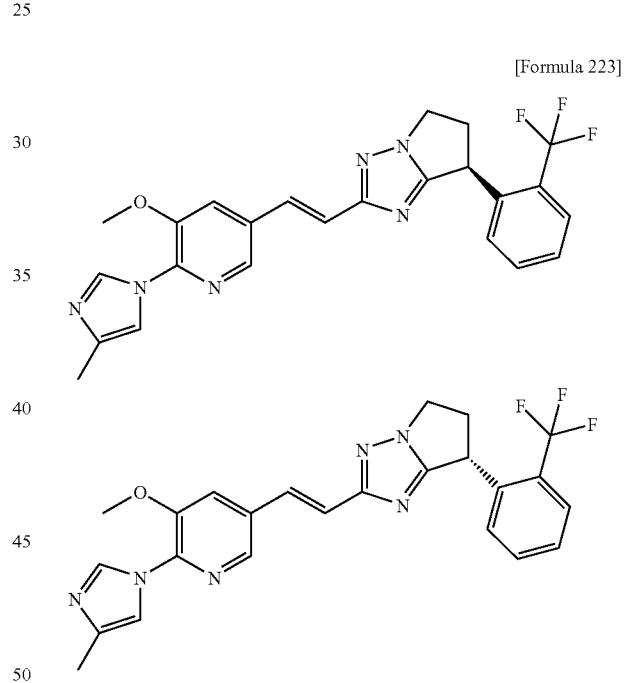

[Formula 223]

230 mg of the racemic title compound was obtained from ethyl (E)-3-[5-methoxy-6-(4-methyl-1H-imidazol-1-yl)pyridin-3-yl]acrylimidate dihydrochloride (1.0 g) and 4-chloro-2-(2-trifluoromethylphenyl)butyric acid hydrazide hydrochloride (1.17 g) by the same method as in Examples 255 and 256. The racemic title compound (230 mg) was separated by CHIRALCEL™ OD-H manufactured by Daicel Chemical Industries, Ltd. (2 cm×25 cm; mobile phase: hexane:ethanol=4:1) to obtain the title optically active compound with positive optical rotation and a retention time of 29 minutes (41 mg) and the title optically active compound with negative optical rotation and a retention time of 33 minutes (43 mg).

The property values of the title optically active compound with a retention time of 29 minutes are as follows.

ESI-MS; m/z 467 [M$^+$+H]. $^1$H-NMR (CDCl$_3$) δ (ppm): 2.30 (d, J=1.2 Hz, 3H), 2.54-2.65 (m, 1H), 3.28-3.38 (m, 1H), 3.99 (s, 3H), 4.20-4.29 (m, 1H), 4.32-4.40 (m, 1H), 4.87 (t, J=7.8 Hz, 1H), 7.09 (d, J=8.0 Hz, 1H), 7.13 (d, J=16.4 Hz, 1H), 7.42 (dd, J=7.6, 7.6 Hz, 1H), 7.47-7.55 (m, 3H), 7.57 (d, J=16.4 Hz, 1H), 7.73 (d, J=8.0 Hz, 1H), 8.17 (d, J=1.6 Hz, 1H), 8.36 (d, J=1.2 Hz, 1H).

The property values of the title optically active compound with a retention time of 33 minutes are as follows.

ESI-MS; m/z 467 [M$^+$+H]. $^1$H-NMR (CDCl$_3$) δ (ppm): 2.30 (d, J=1.2 Hz, 3H), 2.54-2.65 (m, 1H), 3.28-3.38 (m, 1H), 3.99 (s, 3H), 4.20-4.29 (m, 1H), 4.32-4.40 (m, 1H), 4.87 (t, J=7.8 Hz, 1H), 7.09 (d, J=8.0 Hz, 1H), 7.13 (d, J=16.4 Hz, 1H), 7.42 (dd, J=7.6, 7.6 Hz, 1H), 7.47-7.55 (m, 3H), 7.57 (d, J=16.4 Hz, 1H), 7.73 (d, J=8.0 Hz, 1H), 8.17 (d, J=1.6 Hz, 1H), 8.36 (d, J=1.2 Hz, 1H).

Reference Example 5

Another Example of Method for Preparation of the Compound of the Example 195

Synthesis of 5-Chloro-2-(2-trifluoromethylphenyl)pentanenitrile

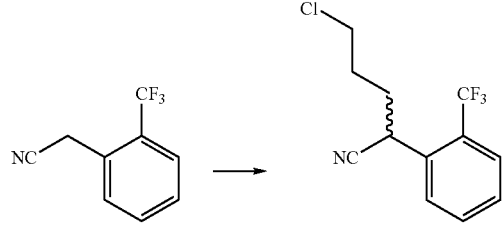

[Formula 224]

(2-Trifluoromethylphenyl)acetonitrile (12.47 g, 67.3 mmol) was dissolved in THF (87.3 mL) at room temperature under nitrogen atmosphere. The reaction solution was cooled to –10° C. Then, potassium tert-butoxide (7.93 g, 70.7 mmol) was added to the reaction solution and the reaction mixture was stirred at –10° C. for 10 minutes. 1-Bromo-3-chloropropane (6.99 mL, 70.7 mmol) was added dropwise to the reaction mixture over 14 minutes, and the reaction mixture was stirred at 0° C. for 2 hours. The reaction was quenched with 10% NH$_4$Cl aq. (8.6 mL). After the mixture was stirred, the aqueous layer was separated. The organic layer was concentrated under the reduced pressure to obtain the title compound (23.24 g). The yield was calculated as over 99% by HPLC external standard method.

$^1$H-NMR (400 MHz, CDCl$_3$) δ (ppm): 2.18-1.88 (m, 4H), 3.58 (m, 2H), 4.18 (m, 1H), 7.47 (t, 1H, J=7.6 Hz), 7.65 (t, 1H, J=7.6 Hz), 7.71 (m, 2H).

Synthesis of Ethyl 5-chloro-2-(2-trifluoromethylphenyl)pentanimidoate hydrochloride

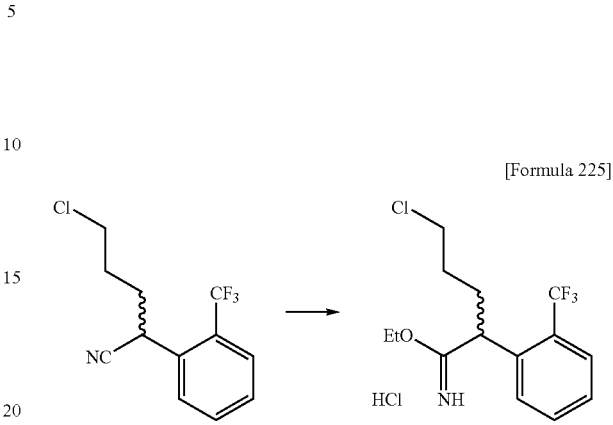

[Formula 225]

5-Chloro-2-(2-trifluoromethylphenyl)pentanenitrile (2.0 g, 7.64 mmol) was dissolved in ethanol (5.36 mL, 91.72 mmol) at room temperature under nitrogen atmosphere. Then, the solution was cooled to 0° C. Acetyl chloride (4.34 mL, 61.14 mmol) was added dropwise to the solution, and the reaction mixture was stirred at room temperature for 67 hours. The reaction mixture was cooled to 10° C. Traces of seed crystal of the title compound which was obtained by the method similar to this step and tert-butylmethylether (hereinafter referred to as "MTBE") (40 mL) were added to the reaction mixture and the reaction mixture was stirred. The solid was collected by filtration, washed with MTBE to obtain the title compound (2.14 g, 81.6% yield).

$^1$H-NMR (400 MHz, CDCl$_3$) δ (ppm): 1.38 (t, 3H, J=7.2 Hz), 1.78-1.65 (m, 1H), 1.95-1.83 (m, 1H), 2.43-2.32 (m, 1H), 2.65-2.50 (m, 1H), 3.62-3.55 (m, 2H), 4.47 (t, 1H, J=8 Hz), 4.65 (q, 2H, J=7.2 Hz), 7.47 (t, 1H, J=8.0 Hz), 7.66 (t, 1H, J=8.0 Hz), 7.71 (d, 1H, J=8.0 Hz), 7.85 (d, 1H, J=8.0 Hz), 12.05 (brs, 1H), 12.58 (brs, 1H).

Synthesis of tert-Butyl 2-{(2E)-3-[6-methoxy-5-(4-methyl-1H-imidazol-1-yl)pyridin-2-yl]prop-2-enoyl}hydrazinecarboxylate

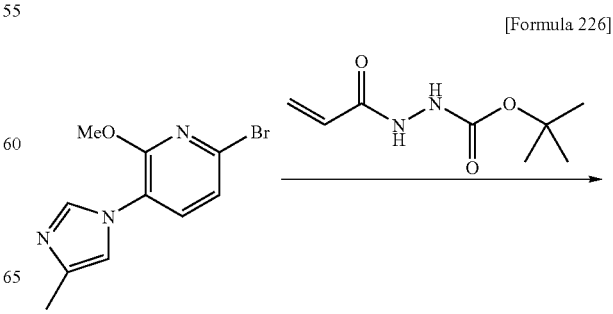

[Formula 226]

-continued

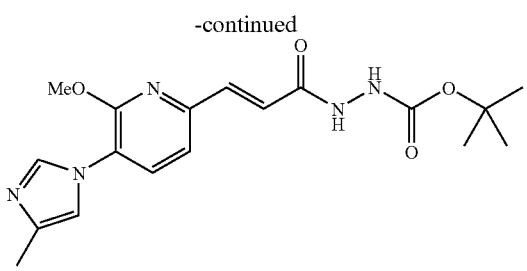

DMF (52 mL) was added to the 6-Bromo-2-methoxy-3-(4-methyl-1H-imidazol-1-yl)pyridine (13.0 g, 48.5 mmol) and the tert-Butyl 2-acryloylhydrazinecarboxylate (9.9 g, 53.3 mmol) at room temperature under nitrogen atmosphere, And the mixture was stirred at 50° C. for 10 minutes. Tri(o-tolyl)phosphine (885 mg, 2.90 mmol), Palladium (II) acetate (327 mg, 1.45 mmol) and N,N-diisopropylethylamine (12.7 mL, 72.7 mmol) were added to the mixture, and the reaction mixture was stirred at 100° C. for 4 hours. The reaction mixture was cooled to room temperature and filtrated through Celite. The residue was washed twice with DMF (6 mL). Water (104 mL) was added dropwise to the filtrate at room temperature over 10 minutes. The mixture was stirred at room temperature for 15 hours. After the mixture was filtrated, the residue was washed with water/DMF=2:1 (30 mL) and MTBE (30 mL). The obtained solid was suspended in MTBE (50 mL) at room temperature for 2 hours, filtrated and dried under the reduced pressure to obtain the title compound (15.8 g, 87% yield).

$^1$H-NMR (400 MHz, CDCl$_3$) δ (ppm): 1.50 (s, 9H), 2.28 (d, J=1.2 Hz, 3H), 4.03 (s, 3H), 6.83 (brs, 1H), 6.97-7.02 (m, 3H), 7.51 (d, J=8.0 Hz, 1H), 7.59 (d, J=15.2 Hz, 1H), 7.82 (s, 1H), 8.01 (br s, 1H).

Synthesis of (2E)-3-[6-Methoxy-5-(4-methyl-1H-imidazol-1-yl)pyridin-2-yl]acrylohydrazide dihydrochloride

[Formula 227]

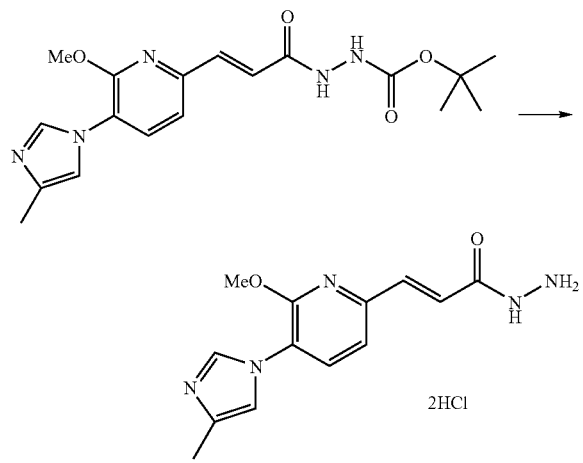

Conc. HCl (5.85 mL) was added to the suspension of tert-Butyl 2-{(2E)-3-[6-methoxy-5-(4-methyl-1H-imidazol-1-yl)pyridin-2-yl]prop-2-enoyl}hydrazinecarboxylate (1.17 g, 3.13 mmol) in methanol (5.85 mL) with an ice-bath cooling. The reaction mixture was stirred at room temperature for 30 minutes. 1-Butanol (5.85 mL) and MTBE (5.85 mL) were added to the reaction mixture, and the mixture was stirred for 20 minutes with an ice-bath cooling. The mixture was filtrated, and the residue was washed with 1-butanol-MTBE (2:8) (5.85 mL) and dried under the reduced pressure to obtain the title compound (937 mg, 78.2% yield).

$^1$H NMR (100 MHz, d$_6$-DMSO) δ (ppm): 2.36 (d, J=0.8 Hz, 3H), 3.82 (brs, 2H), 4.04 (s, 3H), 7.28 (d, J=15.2 Hz, 1H), 7.54 (d, J=8.0 Hz, 1H), 7.70 (d, J=15.2 Hz, 1H), 7.83 (d, J=1.6 Hz, 1H), 8.15 (d, J=7.6 Hz), 9.44 (d, J=1.6 Hz, 1H), 11.56 (s, 1H).

Synthesis of 2-{(E)-2-[6-Methoxy-5-(4-methyl-1H-imidazol-1-yl)pyridin-2-yl]vinyl}-8-[2-(trifluoromethyl)phenyl]-5,6,7,8-tetrahydro[1,2,4]triazolo[1,5-a]pyridine

[Formula 228]

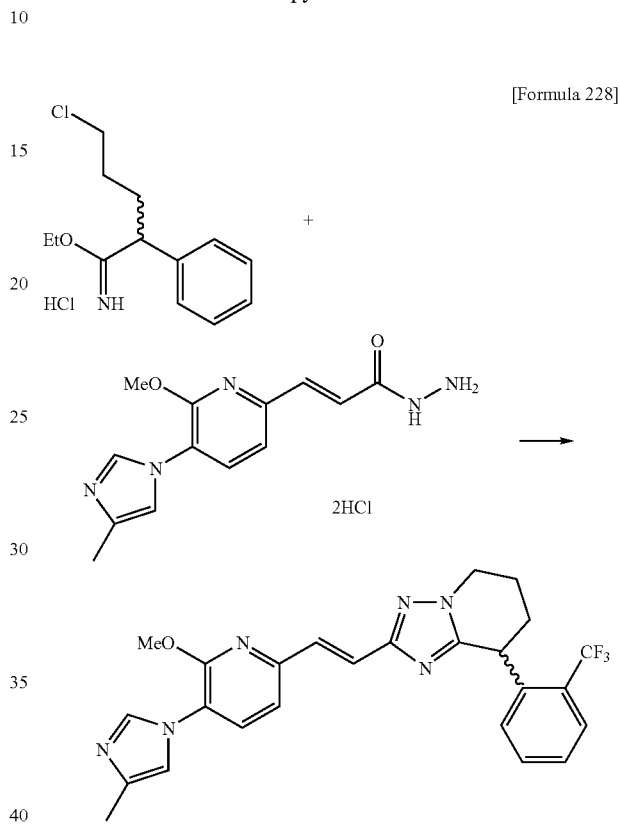

Imidazole (4.75 g, 69.7 mmol) and Ethyl 5-chloro-2-(2-trifluoromethylphenyl)pentanimidoate hydrochloride (2.00 g, 5.81 mmol) were added the solution of (2E)-3-[6-Methoxy-5-(4-methyl-1H-imidazol-1-yl)pyridin-2-yl]acrylohydrazide dihydrochloride in methanol (10 mL) at 0° C. under nitrogen atmosphere. The reaction mixture was stirred at 30° C. for 40 hours. The reaction mixture was adjusted to the pH6.5 with 5N HCl aq., and extracted with ethyl acetate (22 mL). The organic layer was washed with water (4 mL), concentrated under the reduced pressure and azeotroped with 2-propanol under the reduced pressure to obtain the title compound (2.4 g, 86% yield). Traces of seed crystal of the title compound which was obtained by the method similar to this step was added to the solution of the crude title compound in 2-propanol (10 mL), and the mixture was stirred at room temperature for 13.5 hours. The suspension was stirred for 2 hours with an ice-bath cooling. The solids were collected by filtration and washed with 2-propanol and dried under the reduced pressure to obtain the title compound (1.55 g, 56% yield).

$^1$H-NMR (CDCl$_3$) δ (ppm): 1.90-2.01 (m, 1H), 2.10-2.35 (m, 2H), 2.29 (d, J=1.2 Hz, 3H), 2.42-2.51 (m, 1H), 4.03 (s, 3H), 4.28-4.41 (m, 2H), 4.70 (dd, J=8.4, 6.0 Hz, 1H), 6.92 (d, J=8.0 Hz, 1H), 6.95 (t, J=1.2 Hz, 1H), 7.01 (d, J=7.6 Hz, 1H), 7.39 (t, J=7.6 Hz, 1H), 7.44 (d, J=16.0 Hz, 1H), 7.45 (d, J=8.0 Hz, 1H), 7.49 (t, J=7.6 Hz, 1H), 7.63 (d, J=16.0 Hz, 1H), 7.72 (d, J=7.6 Hz, 1H), 7.76 (d, J=1.2 Hz, 1H).

Synthesis of (8S)-2-{(E)-2-[6-Methoxy-5-(4-methyl-1H-imidazol-1-yl)pyridin-2-yl]vinyl}-8-[2-(trifluoromethyl)phenyl]-5,6,7,8-tetrahydro[1,2,4]triazolo[1,5-a]pyridine (2S,3S)-2,3-bis(benzoyloxy)succinate (1/1)

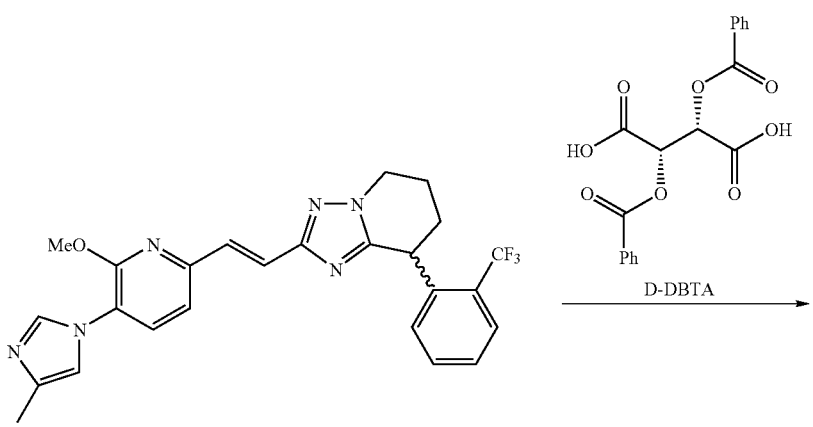

[Formula 229]

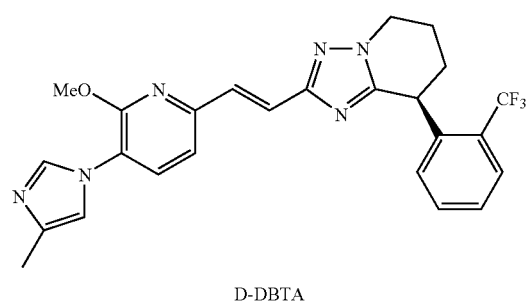

D-DBTA

2-{(E)-2-[6-Methoxy-5-(4-methyl-1H-imidazol-1-yl)pyridin-2-yl]vinyl}-8-[2-(trifluoromethyl)phenyl]-5,6,7,8-tetrahydro[1,2,4]triazolo[1,5-a]pyridine (100 mg, 0.208 mmol) was dissolved in the mixture of 2-propanol (1.6 mL) and acetonitrile (2.0 mL) at 45° C., and the solution of (2S,3S)-2,3-bis(benzoyloxy)succinic acid (D-DBTA) (89.5 mg, 0.250 mmol) in acetonitrile (1.6 mL) was added. Traces of seed crystal of the title compound which was obtained by the method similar to this step was added to the solution at 33° C., and the mixture was stirred at room temperature for 18 hours. The solids were collected by filtration, washed with acecotonitrile/2-propanol=2/1 (0.5 mL) and dried at 50° C. under the reduced pressure to obtain the title compound (62.3 mg, 35.7% yield, 90.7% de). The title compound (50.7 mg, 90.7% de) was suspended in acecotonitrile/2-propanol=1/1 (0.5 mL), and the mixture was stirred at 80° C. for 25 minutes, and then stirred at room temperature for 15 hours. The solids were collected by filtration and dried at 50° C. under the reduced pressure to obtain the title compound (35.9 mg, 70.8% yield, 98.1% de)

$^1$H NMR (400 MHz, CDCl3) δ (ppm): 1.90-2.00 (1H, m), 2.12-2.20 (1H, m), 2.15 (3H, s), 2.27-2.32 (2H, m), 3.98 (3H, s), 4.27-4.31 (2H, m), 4.48-4.52 (1H, dd, J=5.9, 9.5 Hz), 5.84 (2H, s), 7.24-7.34 (4H, m), 7.44-7.51 (2H, m), 7.56-7.63 (5H, m), 7.69-7.80 (4H, m), 7.96-8.00 (5H, m).

Synthesis of (8S)-2-{(E)-2-[6-Methoxy-5-(4-methyl-1H-imidazol-1-yl)pyridin-2-yl]vinyl}-8-[2-(trifluoromethyl)phenyl]-5,6,7,8-tetrahydro[1,2,4]triazolo[1,5-a]pyridine

[Formula 230]

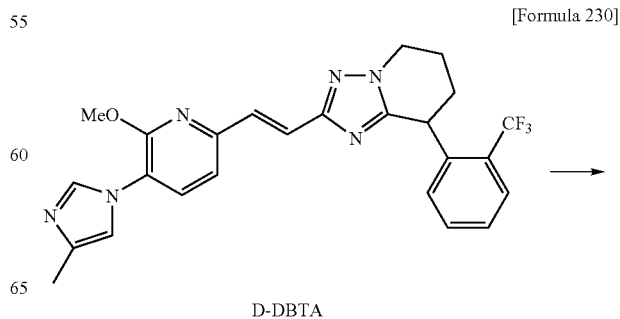

D-DBTA

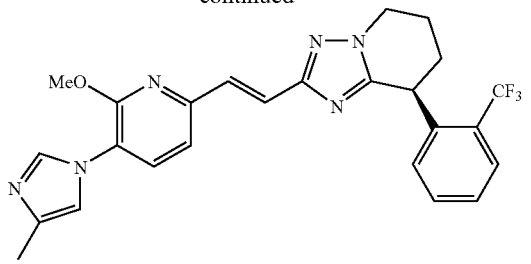

(8S)-2-{(E)-2-[6-Methoxy-5-(4-methyl-1H-imidazol-1-yl)pyridin-2-yl]vinyl}-8-[2-(trifluoromethyl)phenyl]-5,6,7,8-tetrahydro[1,2,4]triazolo[1,5-a]pyridine (2S,3S)-2,3-bis(benzoyloxy)succinate (1/1) (20 mg, 0.024 mmol) was added to the mixed solution of ethyl acetate (0.1 mL) and 5N HCl aq. (0.1 mL), and the organic layer was separated. Ethyl acetate (0.2 mL) and 5N sodium hydrate aq. (0.1 mL) were added to the aqueous layer, and the organic layer was separated. The organic layer was washed twice with water (0.1 mL), and dried under the reduced pressure to obtain the title compound (11.5 mg, 99.9% yield).

Synthesis of (8S)-2-{(E)-2-[6-Methoxy-5-(4-methyl-1H-imidazol-1-yl)pyridin-2-yl]vinyl}-8-[2-(trifluoromethyl)phenyl]-5,6,7,8-tetrahydro[1,2,4]triazolo[1,5-a]pyridine (2S,3S)-tartarate (2/3)

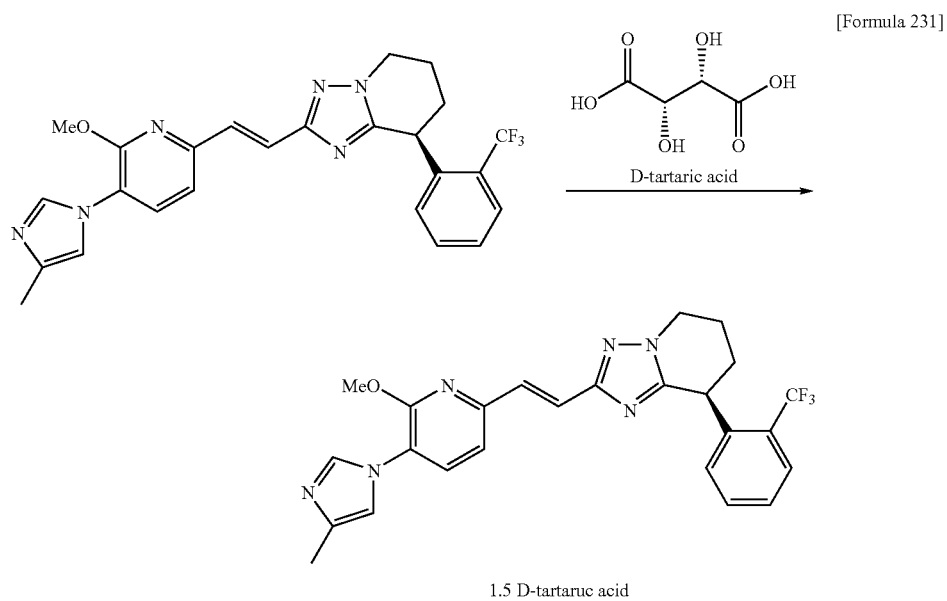

[Formula 231]

1.5 D-tartaric acid (8S)-2-{(E)-2-[6-Methoxy-5-(4-methyl-1H-imidazol-1-yl)pyridin-2-yl]vinyl}-8-[2-(trifluoromethyl)phenyl]-5,6,7,8-tetrahydro[1,2,4]triazolo[1,5-a]pyridine and D-tartaric acid (48.4 mg, 0.323 mmol) were solved in 1-butanol (2.0 mL) at 70° C. The solution was cooled to 60° C., and then 1-butanol (1.0 mL) was added. The mixture was stirred at 8° C. for 11 hours. The solids were collected by filtration, washed with 1-butanol/n-heptan=1/2 (5.0 mL) and dried at 50° C. for 3 hours to obtain the title compound (127.1 mg, 86.6% yield).

$^1$H-NMR (400 MHz, DMSO-$d_6$) δ (ppm): 1.94-1.99 (1H, m), 2.14 (3H, d, J=1.0 Hz), 2.14-2.17 (2H, m), 2.27-2.32 (1H, m), 3.98 (3H, s), 4.26-4.31 (2H, m), 4.29 (3H, s), 4.48-4.52 (1H, m), 7.22-7.33 (4H, m), 7.43-7.51 (2H, m), 7.59-7.63 (1H, m), 7.56-7.79 (2H, m), 7.90 (1H, d, J=1.0 Hz).

Test Example 1

Quantification of Aβ Peptide in Culture of Neurons from Rat Fetus Brain

The present inventors performed the following tests in order to exhibit utility of the compound of the general formula (I) of the present invention.
(1) Rat Primary Neuronal Culture Primary neuronal cultures were prepared from the cerebral cortex of embryonic day 18 Wistar rats (Charles River Japan, Yokohama, Japan). Specifically, the embryos were aseptically removed from pregnant rats under ether anesthesia. The brain was isolated from the embryo and immersed in an ice-cold L-15 medium (Invitrogen Corp. Cat #11415-064, Carlsbad, Calif., USA, or SIGMA L1518, for example). The cerebral cortex was collected from the isolated brain under a stereoscopic microscope. The cerebral cortex fragments collected were enzymatically treated in an enzyme solution containing 0.25% trypsin (Invitrogen Corp. Cat #15050-065, Carlsbad, Calif., USA) and 0.01% DNase (Sigma D5025, St. Louis, Mo., USA) at 37° C. for 30 minutes to disperse the cells. Here, the enzymatic reaction was stopped by adding inactivated horse serum to the solution. The enzymatically treated solution was centrifuged at 1,500 rpm for five minutes to remove the supernatant. 5 to 10 ml of a medium was added to the resulting cell mass. Neurobasal medium (Invitrogen Corp. Cat #21103-049, Carlsbad, Calif., USA) supplemented with 2% B27 supplement (Invitrogen Corp. Cat #17504-044, Carlsbad, Calif., USA), 25 μM 2-mercaptoethanol (2-ME, WAKO Cat #139-06861, Osaka, Japan), 0.5 mM L-glutamine (Invitrogen Corp. Cat #25030-081, Carlsbad, Calif., USA), and Antibiotics-Antimycotics (Invitrogen Corp. Cat #15240-062, Carlsbad, Calif., USA) was used as the medium (Neurobasal/B27/2-ME). However, the above Neurobasal medium not supplemented with 2-ME (Neurobasal/B27) was used for the assay. The cells were redispersed by mild pipetting of the cell mass to which the medium was added. The cell dispersion was filtered through a 40-μm nylon mesh (Cell Strainer, Cat #35-2340, Becton Dickinson Labware, Franklin Lakes, N.J., USA) to remove the remaining cell mass, and thus a neuronal cell suspension was obtained. The neuronal cell suspension was diluted with the medium and then plated in a volume of 100 μl/well at an initial cell density of $5 \times 10^5$ cells/cm$^2$ in a 96-well polystyrene culture plate pre-coated with poly-L or D-lysine (Falcon Cat #35-3075, Becton Dickinson Labware, Franklin Lakes, N.J., USA coated with poly-L-lysine using the method shown below, or BIOCOAT™ cell environments Poly-D-lysine cell ware 96-well plate, Cat #35-6461, Becton Dickinson Labware, Franklin Lakes, N.J., USA). Poly-L-lysine coating was carried out as follows. 100 μg/ml of a poly-L-lysine (SIGMA P2636, St. Louis, Mo., USA) solution was aseptically prepared with a 0.15 M borate buffer (pH 8.5). 100 μl/well of the solution was added to the 96-well polystyrene culture plate and incubated at room temperature for one or more hours or at 4° C. overnight or longer. The coated 96-well polystyrene culture plate was washed with sterile water four or more times, and then dried or rinsed with, for example, sterile PBS or medium, and used for cell plating. The plated cells were cultured in the culture plate at 37° C. in 5% $CO_2$-95% air for one day. Then, the total amount of the medium was replaced with a fresh Neurobasal™/B27/2-ME medium, and then the cells were cultured for further three days.

Addition of Compounds

The drug was added to the culture plate on Day 4 of culture as follows. The total amount of the medium was removed from the wells, and 180 μl/well of Neurobasal medium not containing 2-ME and containing 2% B-27 (Neurobasal/B27) was added thereto. A solution of the test compound in dimethyl sulfoxide (hereinafter abbreviated as DMSO) was diluted with Neurobasal/B27 at 10-fold of the final concentration. 20 μl/well of the dilution was added to and sufficiently mixed with the medium. The final DMSO concentration was 1% or less. Only DMSO was added to the control group.

Sampling

The cells were cultured for three days after addition of the compound, and the total amount of the medium was collected. The resulting medium was used as an ELISA sample. The sample was not diluted for ELISA measurement of Aβx-42 and diluted to 5-fold with a diluent supplied with an ELISA kit for ELISA measurement of Aβx-40.

Evaluation of Cell Survival

Cell survival was evaluated by an MTT assay according to the following procedure. After collecting the medium, 100 μl/well of a pre-warmed medium was added to the wells. Further, 8 μl/well of a solution of 8 mg/ml of MTT (SIGMA M2128, St. Louis, Mo., USA) in D-PBS(-) (Dulbecco's phosphate buffered Saline, SIGMA D8537, St. Louis, Mo., USA) was added to the wells. The 96-well polystyrene culture plate was incubated in an incubator at 37° C. in 5% $CO_2$-95% air for 20 minutes. 100 μl/well of an MTT lysis buffer was added thereto, and MTT formazan crystals were sufficiently dissolved in the buffer in the incubator at 37° C. in 5% $CO_2$-95% air. Then, the absorbance at 550 nm in each well was measured. The MTT lysis buffer was prepared as follows. 100 g of SDS (sodium dodecyl sulfate (sodium lauryl sulfate), WAKO 191-07145, Osaka, Japan) was dissolved in a mixed solution of 250 mL of N,N-dimethylformamide (WAKO 045-02916, Osaka, Japan) with 250 mL of distilled water. 350 μl each of concentrated hydrochloric acid and concentrated acetic acid were further added to the solution to allow the solution to have a final pH of about 4.7.

Upon measurement, wells having no cells plated and containing only the medium and MTT solution were set as background (bkg). The measured values were respectively applied to the following formula including subtracting bkg values from them. Thus, the proportion against the control group (group not treated with the drug, CTRL) (% of CTRL) was calculated to compare and evaluate cell survival activities.

% of CTRL=(($A550\_sample-A550\_bkg$)/($A550\_CTRL-bkg$))×100

(A550_sample: absorbance at 550 nm of sample well, A550_bkg: absorbance at 550 nm of background well, A550_CTRL: absorbance at 550 nm of control group well)

Aβ ELISA

For Aβ ELISA, Human/Rat β Amyloid (42) ELISA Kit Wako (#290-62601) from Wako Pure Chemical Industries, Ltd. or Human Amyloid beta (1-42) Assay Kit (#27711) from IBL Co., Ltd. was used. Aβ ELISA was carried out according to the protocols recommended by the manufacturers (methods described in the attached documents). However, the Aβ calibration curve was created using beta-amyloid peptide 1-42, rat (Calbiochem, #171596 [Aβ$_{42}$]) The results are shown in Table 1 as percentage to the Aβ concentration in the medium of the control group (% of CTRL).

(2) The measurement results are shown in Tables 9, 10, 11 and 12 as percentage to the Aβ concentration in the medium of the control group (% of CTRL).

TABLE 9

| Test compound | Aβ42 production reducing effect IC50 (nM) |
|---|---|
| Example 2 | 28 |
| Example 3 | 48 |
| Example 5 | 21 |
| Example 7 | 30 |
| Example 10 | 33 |
| Example 12 | 135 |
| Example 19 | 43 |
| Example 20 | 30 |
| Example 22 | 25 |
| Example 24 | 12 |
| Example 45 | 30 |
| Example 55 | 28 |
| Example 59 | 45 |
| Example 61 | 31 |
| Example 72 | 26 |
| Example 80 | 29 |
| Example 94 | 52 |
| Example 96 | 63 |
| Example 97 | 38 |
| Example 99 | 20 |
| Example 102 | 20 |
| Example 103 | 32 |
| Example 106 | 39 |
| Example 108 | 29 |
| Example 110 | 33 |
| Example 114 | 51 |
| Example 116 | 173 |
| Example 133 | 65 |
| Example 141 | 36 |
| Example 143 | 41 |
| Example 150 | 41 |

TABLE 10

| Test compound | Aβ42 production reducing effect IC50 (nM) |
|---|---|
| Example 156 | 48 |
| Example 165 | 115 |
| Example 169 | 22 |

TABLE 10-continued

| Test compound | Aβ42 production reducing effect IC50 (nM) |
|---|---|
| Example 171 | 17 |
| Example 173 | 37 |
| Example 175 | 38 |
| Example 179 | 22 |
| Example 183 | 48 |
| Example 185 | 34 |
| Example 187 | 38 |
| Example 189 | 43 |
| Example 193 | 80 |
| Example 195 | 17 |
| Example 199 | 23 |
| Example 207 | 28 |
| Example 209 | 20 |
| Example 212 | 100 |
| Example 215 | 74 |
| Example 218 | 69 |
| Example 229 | 169 |
| Example 232 | 33 |
| Example 233 | 42 |
| Example 236 | 39 |
| Example 243 | 50 |
| Example 246 | 39 |
| Example 247 | 45 |
| Example 250 | 44 |
| Example 252 | 146 |
| Example 254 | 50 |
| Example 262 | 74 |
| Example 271 | 57 |

TABLE 11

| Test compound | Aβ42 production reducing effect IC50 (nM) |
|---|---|
| Example 280 | 18 |
| Example 282 | 29 |
| Example 283 | 27 |
| Example 286 | 8 |
| Example 287 | 24 |
| Example 290 | 16 |
| Example 294 | 26 |

TABLE 12

| Test compound | Aβ42 production reducing effect IC50(nM) |
|---|---|
| Example 311 | 11 |
| Example 317 | 25 |
| Example 319 | 15 |
| Example 321 | 23 |
| Example 327 | 20 |
| Example 329 | 17 |
| Example 331 | 22 |
| Example 333 | 10 |
| Example 337 | 13 |
| Example 339 | 21 |
| Example 354 | 37 |
| Example 361 | 12 |
| Example 362 | 9 |
| Example 365 | 21 |
| Example 368 | 25 |
| Example 371 | 27 |
| Example 373 | 29 |
| Example 376 | 28 |
| Example 380 | 29 |
| Example 384 | 36 |
| Example 390 | 26 |
| Example 392 | 22 |

The results from Tables 9, 10, 11 and 12 confirmed that the compound of the present invention has an Aβ42 production reducing effect.

Accordingly, the compound of the general formula (I) or pharmaceutically acceptable salt thereof according to the present invention have an Aβ42 production reducing effect. Thus, the present invention can particularly provide a prophylactic or therapeutic agent for a neurodegenerative disease caused by Aβ such as Alzheimer's disease or Down's syndrome.

The compound of the general formula (I) of the present invention has an Aβ40 and Aβ42 production reducing effect, and thus is particularly useful as a prophylactic or therapeutic agent for a neurodegenerative disease caused by Aβ such as Alzheimer's disease or Down's syndrome.

The invention claimed is:

1. A compound represented by formula (I-1), (I-2) or (1-3):

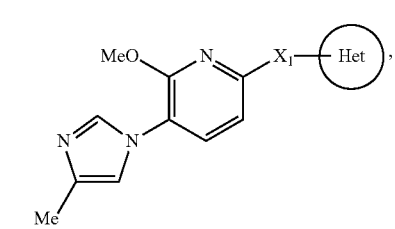

(I-1)

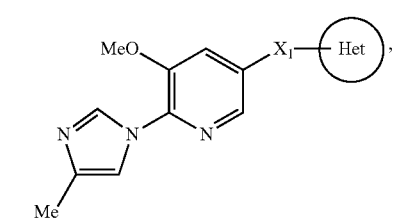

(I-2)

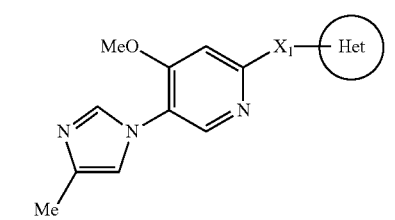

(I-3)

or a pharmacologically acceptable salt thereof,
wherein
$X_1$ represents —$CR^1$=$CR^2$— (wherein $R^1$ and $R^2$ are the same or different and each represents (1) a hydrogen atom, (2) a C1-6 alkyl group or (3) a halogen atom), and
Het represents a group which may be substituted with 1 to 3 substituents selected from Substituent Group A1 and is represented by the following formula:

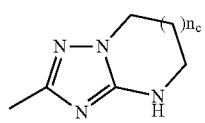

wherein $n_c$ represents an integer of 0 to 3;
Substituent Group A1:
(1) a hydrogen atom, (2) a halogen atom, (3) a hydroxyl group, (4) a cyano group, (5) a nitro group, (6) a C3-8 cycloalkyl group which may be substituted with 1 to 3 substituents selected from Substituent Group A2, (7) a C2-6 alkenyl group which may be substituted with 1 to 3 substituents selected from Substituent Group A2, (8) a C2-6 alkynyl group which may be substituted with 1 to 3 substituents selected from Substituent Group A2, (9) a C3-8 cycloalkoxy group, (10) a C3-8 cycloalkylthio group, (11) a formyl group, (12) a C1-6 alkylcarbonyl group which may be substituted with 1 to 3 substituents selected from Substituent Group A2, (13) a C1-6 alkylthio group which may be substituted with 1 to 3 substituents selected from Substituent Group A2, (14) a C1-6 alkylsulfinyl group which may be substituted with 1 to 3 substituents selected from Substituent Group A2, (15) a C1-6 alkylsulfonyl group which may be substituted with 1 to 3 substituents selected from Substituent Group A2, (16) a hydroxyimino group, (17) a C1-6 alkoxyimino group, (18) a C1-6 alkyl group which may be substituted with 1 to 3 substituents selected from Substituent Group A2, (19) a C1-6 alkoxy group which may be substituted with 1 to 3 substituents selected from Substituent Group A2, (20) an amino group which may be substituted with 1 or 2 substituents selected from Substituent Group A2, (21) a carbamoyl group which may be substituted with 1 or 2 substituents selected from Substituent Group A2, (22) A* (wherein A* represents an aromatic hydrocarbon ring selected from a phenyl group, an indenyl group, a naphthyl group, an azulenyl group, a heptalenyl group, a fluorenyl group, a phenalenyl group, a phenanthrenyl group and an anthracenyl group, an aromatic heterocycle selected from a pyrrolyl group, a pyridyl group, a pyridazinyl group, a pyrimidinyl group, a pyrazinyl group, a pyrazolinyl group, an imidazolyl group, an indolyl group, an isoindolyl group, an indolizinyl group, a purinyl group, an indazolyl group, a quinolyl group, an isoquinolyl group, a quinolizinyl group, a phthalazinyl group, a naphthyridinyl group, a quinoxalinyl group, a quinazolinyl group, a cinnolinyl group, a pteridinyl group, an imidazotriazinyl group, a pyrazinopyridazinyl group, an acridinyl group, a phenanthridinyl group, a carbazolyl group, a perimidinyl group, a phenanthrolinyl group, a thienyl group and a benzothienyl group, a furyl group, a pyranyl group, a cyclopentapyranyl group, a benzofuranyl group and an isobenzofuranyl group, a thiazolyl group, an isothiazolyl group, a benzothiazolinyl group, a benzothiadiazolyl group, a phenothiazinyl group, an isoxazolyl group, a furazanyl group, a phenoxazinyl group, a pyrazoloxazolyl group, an imidazothiazolyl group, a thienofuryl group, a furopyrrolyl group and a pyridooxazinyl group), which may be substituted with 1 to 3 substituents selected from Substituent Group A2, (23) a 6- to 14-membered non-aromatic hydrocarbon ring which may be substituted with 1 to 3 substituents selected from Substituent Group A2, (24) a 5- to 14-membered non-aromatic heterocycle, which may be substituted with 1 to 3 substituents selected from Substituent Group A2, (25) a C2-6 alkenyloxy group, (26) a C2-6 alkynyloxy group, (27) a C3-8 cycloalkylsulfinyl group, (28) a C3-8 cycloalkylsulfonyl group, (29) —X-A* (wherein X represents an imino group, —O— or —S— and A* is as defined above, wherein A* may be substituted with 1 to 3 substituents selected from Substituent Group A2), (30) —CO-A* (wherein A* is as defined above, which may be substituted with 1 to 3 substituents selected from Substituent Group A2), (31) =CH-A* (wherein A* is as defined above, which may be substituted with 1 to 3 substituents selected from Substituent Group A2), (32) a carboxyl group, (33) a C1-6 alkoxycarbonyl group and (34) an azido group;

Substituent Group A2:

(1) a hydrogen atom, (2) a halogen atom, (3) a hydroxyl group, (4) a cyano group, (5) a nitro group, (6) a C3-8 cycloalkyl group, (7) a C2-6 alkenyl group, (8) a C2-6 alkynyl group, (9) a C3-8 cycloalkoxy group, (10) a C3-8 cycloalkylthio group, (11) a formyl group, (12) a C1-6 alkylcarbonyl group, (13) a C1-6 alkylthio group, (14) a C1-6 alkylsulfinyl group, (15) a C1-6 alkylsulfonyl group, (16) a hydroxyimino group, (17) a C1-6 alkoxyimino group, (18) a C1-6 alkyl group (wherein the C1-6 alkyl group may be substituted with 1 to 3 substituents selected from the group consisting of a halogen atom, a hydroxyl group, a C1-6 alkoxy group, a phenyl group which may be substituted with 1 to 3 halogen atoms and a pyridinyl group which may be substituted with 1 to 3 halogen atoms), (19) a C1-6 alkoxy group (wherein the C1-6 alkoxy group may be substituted with 1 to 3 substituents selected from the group consisting of a halogen atom, a hydroxyl group, a C1-6 alkoxy group, a phenyl group which may be substituted with 1 to 3 halogen atoms and a pyridinyl group which may be substituted with 1 to 3 halogen atoms), (20) an amino group which may be substituted with 1 or 2 C1-6 alkyl groups or C1-6 alkylcarbonyl groups, (21) a carbamoyl group which may be substituted with 1 or 2 C1-6 alkyl groups, (22) A* (wherein A* is as defined above), (23) a 6- to 14-membered non-aromatic hydrocarbon ring, (24) a 5- to 14-membered non-aromatic heterocycle, (25) a C2-6 alkenyloxy group, (26) a C2-6 alkynyloxy group, (27) a C3-8 cycloalkylsulfinyl group, (28) a C3-8 cycloalkylsulfonyl group, (29) —X-A* (wherein X represents an imino group, —O—, —S— or —SO2- and A* is as defined above, wherein A* may be substituted with 1 to 3 halogen atoms), (30) —CO-A* (wherein A* is as defined above, which may be substituted with 1 to 3 halogen atoms) and (31) =CH-A* (wherein A* is as defined above, which may be substituted with 1 to 3 halogen atoms).

2. The compound or pharmacologically acceptable salt thereof according to claim 1, wherein Substituent Group A1 is selected from the group consisting of (1) a hydrogen atom, (2) a halogen atom, (3) a hydroxyl group, (4) a cyano group, (5) a C3-8 cycloalkyl group which may be substituted with 1 to 3 substituents selected from Substituent Group A2, (6) a C1-6 alkyl group which may be substituted with 1 to 3 substituents selected from Substituent Group A2, (7) A*, wherein A is as defined in claim 2, which may be substituted with 1 to 3 substituents selected from Substituent Group A2, (8) a 6- to 14-membered non-aromatic hydrocarbon ring group which may be substituted with 1 to 3 substituents selected from Substituent Group A2, (9) a 5- to 14-membered non-aromatic heterocycle which may be substituted with 1 to 3 substituents selected from Substituent Group A2, (10) —X-A*, wherein X represents an imino group, —O— or —S— and A* is as defined in claim 2, wherein A* may be substituted with 1 to 3 substituents selected from Substituent Group A2, (11) =CH-A*, wherein A* is as defined in claim 1, which may be substituted with 1 to 3 substituents selected from Substituent Group A2) and (12) an azido group.

3. The compound or pharmacologically acceptable salt thereof according to claim 1, wherein Substituent Group A2 is selected from the group consisting of (1) a hydrogen atom, (2) a halogen atom, (3) a C1-6 alkyl group, wherein the C1-6 alkyl group may be substituted with 1 to 3 substituents selected from the group consisting of a halogen atom and a C1-6 alkoxy group, and (4) a C1-6 alkoxy group, wherein the C1-6 alkoxy group may be substituted with a halogen atom.

4. The compound or pharmacologically acceptable salt thereof according to claim 1, wherein the (23) a 6- to 14-membered non-aromatic hydrocarbon ring of Substituent Group A2 is selected from the group consisting of a cyclopropyl group, a cyclobutyl group, a cyclopentyl group, a cyclohexyl group, a cycloheptyl group, a cyclooctyl group, a spiro[3.4]octanyl group, a decanyl group, an indanyl group, a 1-acenaphthenyl group, a cyclopentacyclooctenyl group, a benzocyclooctenyl group, an indenyl group, a tetrahydronaphthyl group, a 6,7,8,9-tetrahydro-5H-benzocycloheptenyl group and a 1,4-dihydronaphthalenyl group.

5. The compound or pharmacologically acceptable salt thereof according to claim 1, wherein the (24) a 5- to 14-membered non-aromatic heterocycle of Substituent Group A2 is selected from the group consisting of an azetidinyl ring, a pyrrolidinyl ring, a piperidinyl ring, an azepanyl ring, an azocanyl ring, a tetrahydrofuranyl ring, a tetrahydropyranyl ring, a morpholinyl ring, a thiomorpholinyl ring, a piperazinyl ring, a thiazolidinyl ring, a dioxanyl ring, an imidazolinyl ring, a thiazolinyl ring, a 1,2-benzopyranyl ring, an isochromanyl ring, a chromanyl ring, an indolinyl ring, an isoindolinyl ring, an azaindanyl group, an azatetrahydronaphthyl group, an azachromanyl group, a tetrahydrobenzofuranyl group, a tetrahydrobenzothienyl group, a 2,3,4,5-tetrahydrobenzo[b]thienyl group, a 3,4-dihydro-2H-benzo[b][1,4]dioxepinyl group, an indan-1-onyl group, a 6,7-dihydro-5H-cyclopentapyrazinyl group, a 6,7-dihydro-5H-[1]pyridinyl group, a 6,7-dihydro-5H-[1]pyridinyl group, a 5,6-dihydro-4H-cyclopenta[b]thienyl group, a 4,5,6,7-tetrahydro-benzo[b]thienyl group, a 3,4-dihydro-2H-naphthale-1-onyl group, a 2,3-dihydro-isoindol-1-onyl group, a 3,4-dihydro-2H-isoquinolin-1-onyl group and a 3,4-dihydro-2H-benzo[1,4]oxapinyl group.

6. The compound or pharmacologically acceptable salt thereof according to claim 1, wherein the compound is selected from the group consisting of:
1) 4-(4-chlorophenyl)-2-{(E)-2-[6-methoxy-5-(4-methyl-1H-imidazol-1-yl)pyridin-2-yl]vinyl}-4,5,6,7-tetrahydro-[1,2,4]triazolo[1,5-a]pyrimidine,
2) 2-{(E)-2-[6-methoxy-5-(4-methyl-1H-imidazol-1-yl)pyridin-2-yl]vinyl}-4-phenyl-4,5,6,7-tetrahydro-[1,2,4]triazolo[1,5-a]pyrimidine,
3) 2-{(E)-2-[6-methoxy-5-(4-methyl-1H-imidazol-1-yl)pyridin-2-yl]vinyl}-4-(3,4,5-trifluorophenyl)-4,5,6,7-tetrahydro-[1,2,4]triazolo[1,5-a]pyrimidine,
4) (R)-4-(4-fluorophenyl)-2-{(E)-2-[6-methoxy-5-(4-methyl-1H-imidazol-1-yl)pyridin-2-yl]vinyl}-5-methyl-4,5,6,7-tetrahydro-[1,2,4]triazolo[1,5-a]pyrimidine,
5) (S)-4-(4-fluorophenyl)-2-{(E)-2-[6-methoxy-5-(4-methyl-1H-imidazol-1-yl)pyridin-2-yl]vinyl}-5-methyl-4,5,6,7-tetrahydro-[1,2,4]triazolo[1,5-a]pyrimidine,
6) 2-{(E)-2-[5-methoxy-6-(4-methyl-1H-imidazol-1-yl)pyridin-3-yl]vinyl}-4-phenyl-4,5,6,7-tetrahydro-[1,2,4]triazolo[1,5-a]pyrimidine,
7) 4-(4-chlorophenyl)-2-{(E)-2-[5-methoxy-6-(4-methyl-1H-imidazol-1-yl)pyridin-3-yl]vinyl}-4,5,6,7-tetrahydro-[1,2,4]triazolo[1,5-a]pyrimidine,
8) 2-{(E)-2-[5-methoxy-6-(4-methyl-1H-imidazol-1-yl)pyridin-3-yl]vinyl}-4-(3,4,5-trifluorophenyl)-4,5,6,7-tetrahydro-[1,2,4]triazolo[1,5-a]pyrimidine,
9) (R)-4-(4-fluorophenyl)-2-{(E)-2-[5-methoxy-6-(4-methyl-1H-imidazol-1-yl)pyridin-3-yl]vinyl}-5-methyl-4,5,6,7-tetrahydro-[1,2,4]triazolo[1,5-a]pyrimidine,
10) (S)-4-(4-fluorophenyl)-2-{(E)-2-[5-methoxy-6-(4-methyl-1H-imidazol-1-yl)pyridin-3-yl]vinyl}-5-methyl-4,5,6,7-tetrahydro-[1,2,4]triazolo[1,5-a]pyrimidine,
11) 4-cyclohexyl-2-{(E)-2-[6-methoxy-5-(4-methyl-1H-imidazol-1-yl)pyridin-2-yl]vinyl}-4,5,6,7-tetrahydro-[1,2,4]triazolo[1,5-a]pyrimidine,
12) 4-(4-fluorophenyl)-2-{(E)-2-[6-methoxy-5-(4-methyl-1H-imidazol-1-yl)pyridin-2-yl]vinyl}-4,5,6,7-tetrahydro-[1,2,4]triazolo[1,5-a]pyrimidine,
13) 2-{(E)-2-[6-methoxy-5-(4-methyl-1H-imidazol-1-yl)pyridin-2-yl]vinyl}-4-(2-trifluoromethylphenyl)-4,5,6,7-tetrahydro-[1,2,4]triazolo[1,5-a]pyrimidine,
14) (R)-4-(2,4-difluorophenyl)-2-{(E)-2-[6-methoxy-5-(4-methyl-1H-imidazol-1-yl)pyridin-2-yl]vinyl}-5-methyl-4,5,6,7-tetrahydro-[1,2,4]triazolo[1,5-a]pyrimidine,
15) (S)-4-(2,4-difluorophenyl)-2-{(E)-2-[6-methoxy-5-(4-methyl-1H-imidazol-1-yl)pyridin-2-yl]vinyl}-5-methyl-4,5,6,7-tetrahydro-[1,2,4]triazolo[1,5-a]pyrimidine,
16) (+)-2-{(E)-2-[6-methoxy-5-(4-methyl-1H-imidazol-1-yl)pyridin-2-yl]vinyl}-5-methyl-4-(2-trifluoromethylphenyl)-4,5,6,7-tetrahydro-[1,2,4]triazolo[1,5-a]pyrimidine, and
17) (−)-2-{(E)-2-[6-methoxy-5-(4-methyl-1H-imidazol-1-yl)pyridin-2-yl]vinyl}-5-methyl-4-(2-trifluoromethylphenyl)-4,5,6,7-tetrahydro-[1,2,4]triazolo[1,5-a]pyrimidine.

7. A pharmaceutical composition comprising:
the compound or pharmacologically acceptable salt thereof according to claim 1 as an active ingredient; and
a pharmaceutically acceptable carrier.

* * * * *